(12) United States Patent
Wuest

(10) Patent No.: US 10,647,671 B2
(45) Date of Patent: May 12, 2020

(54) PROMYSALIN ANALOGUES AND METHODS OF USE THEREOF

(71) Applicant: Temple University—Of The Commonwealth System of Higher Education, Philadelphia, PA (US)

(72) Inventor: William M. Wuest, Wallingford, PA (US)

(73) Assignee: Temple University—Of The Commonwealth System of Higher Education, Philadelphia, PA (US)

( * ) Notice: Subject to any disclaimer, the term of this patent is extended or adjusted under 35 U.S.C. 154(b) by 0 days.

(21) Appl. No.: 16/091,685

(22) PCT Filed: Apr. 18, 2017

(86) PCT No.: PCT/US2017/028057
§ 371 (c)(1),
(2) Date: Oct. 5, 2018

(87) PCT Pub. No.: WO2017/184558
PCT Pub. Date: Oct. 26, 2017

(65) Prior Publication Data
US 2019/0161444 A1  May 30, 2019

Related U.S. Application Data

(60) Provisional application No. 62/324,068, filed on Apr. 18, 2016.

(51) Int. Cl.
| | | |
|---|---|---|
| C07D 207/12 | (2006.01) |
| A61K 31/40 | (2006.01) |
| C07D 207/24 | (2006.01) |
| A61P 31/04 | (2006.01) |
| A61K 45/06 | (2006.01) |
| A61K 31/401 | (2006.01) |

(52) U.S. Cl.
CPC ............ *C07D 207/24* (2013.01); *A61K 31/40* (2013.01); *A61K 31/401* (2013.01); *A61K 45/06* (2013.01); *A61P 31/04* (2018.01)

(58) Field of Classification Search
CPC .... C07D 207/12; C07D 211/40; A61K 31/40; A61K 31/445
USPC ................... 548/533; 546/326; 514/423, 354
See application file for complete search history.

(56) References Cited

U.S. PATENT DOCUMENTS 6,316,488 B1  11/2001 Bernard-King

OTHER PUBLICATIONS

Anthoni U. et al., "Pseudomonine, an Isoxazolidone with Siderophoric Activity from Pseudomonas fluorescens AH2 Isolated from Lake Victorian Nile Perch", 1995, J. Nat. Prod., 58:1786-1789.
Butler, M. S. et al., "Antibiotics in the clinical pipeline at the end of 2015", 2017, J. Antibiot., 70:3-24.
Cox, Laura. M. et al., "Altering the Intestinal Microbiota during a Critical Developmental Window Has Lasting Metabolic Consequences", 2014, Cell, 158:705-721.
De Carvalho, C. C. C. R. et al., "Phenotypic Modifications in *Staphylococcus aureus* Cells Exposed to High Concentrations of Vancomycin and Teicoplanin", 2016, Front. Microbiol.,.
Delden, C. V. et al., "Involvement of Fe uptake systems and AmpC β-lactamase in susceptibility to the siderophore monosulfactam BAL30072 in Pseudomonas aeruginosa", 2013, Antimicrob. Agents Chemother., 57:2095-2102.
Fahnoe, K. C. et al., "Non-Traditional Antibacterial Screening Approaches for the Identification of Novel Inhibitors of the Glyoxylate Shunt in Gram-Negative Pathogens", 2012, Plos One, 7:e51732.
Fair, R. J., et al., "Antibiotics and bacterial resistance in the 21st century", 2014, Perspect. Medicin. Chem., 6:25-64.
Gellatly, S. L. et al. "Pseudomonas aeruginosa: new insights into pathogenesis and host defenses", 2013, Pathogens and Disease, 67:159-173.
Giglio, Krista M. et al., "Transcriptomic Profiling Suggests that Promysalin Alters the Metabolic Flux, Motility, and Iron Regulation in Pseudomonas putida KT2440", 2018, ACS Infect. Dis, 4:1179-1187.
Gorska, A. et al., "Siderophore—drug complexes: potential medicinal applications of the 'Trojan horse' strategy", 2014, Trends Pharmacol. Sci., 35:442-449.
Hermann, J. et al., "Natural products from myxobacteria: novel metabolites and bioactivities", 2017, Nat. Prod. Rep., 34:135-160.
Hunter, R. et al., "Application of a pH-sensitive fluoroprobe (C-SNARF-4) for pH microenvironment analysis in Pseudomonas aeruginosa biofilms", 2005, Appl. Environ. Microbiol., 2501-2510.
Katayama, N. et al., "Ferrocins, new iron-containing peptide antibiotics produced by bacteria", 1993, J. Antibiotics, 46:65-70.
Keohane, C. E. et al., "Promysalin Elicits Species-Selective Inhibition of Pseudomonas aeruginosa by Targeting Succinate Dehydrogenase", 2018, J. Am. Chem. Soc., 140:1774-1782.
Keohane, Colleen E. et al., "The Rhizosphere Microbiome: A Playground for Natural Product Chemists", 2015, Synlett, 26:2739-2744.
Knouse, K. et al., "The enantioselective synthesis and biological evaluation of chimeric promysalin analogs facilitated by diverted total synthesis", 2016, J. Antibiotics, 69:337-339.
Lee, S. A. et al., "General and condition-specific essential functions of Pseudomonas aeruginosa", 2015, Proc. Natl. Acad. Sci., 112:5189-5194.
Li, W. et al., "Promysalin, a salicylate-containing Pseudomonas putida antibiotic, promotes surface colonization and selectively targets other Pseudomonas", 2011, Chem. Biol., 18:1320-1330.
Maxson, Tucker et al., "Targeted Treatment for Bacterial Infections: Prospects for Pathogen-Specific Antibiotics Coupled with Rapid Diagnostics", 2016, Tetrahedron, 72:3609-3624.
Meylan, S. et al., "Carbon sources tune antibiotic susceptibility in Pseudomonas aeruginosa via tricarboxylic acid cycle control", 2017, Cell Chem. Biol. 24:195-206.

(Continued)

*Primary Examiner* — Charanjit Aulakh
(74) *Attorney, Agent, or Firm* — Riverside Law LLP

(57) ABSTRACT

The present invention includes novel analogs of promysalin useful in preventing or treating a microbial infection. The present invention also includes methods preventing or treating a microbial infection in a subject in need thereof, the method comprising administering to the subject an effective amount of a compound of the invention.

20 Claims, 130 Drawing Sheets

(56) References Cited

OTHER PUBLICATIONS

Mogi, T. et al, "Siccanin Rediscovered as a Species-Selective Succinate Dehydrogenase Inhibitor", 2009, J. Biochem., 146:383-387.

Moynie, L. et al., "Structure and Function of the PiuA and PirA Siderophore-Drug Receptors from Pseudomonas aeruginosa and Acinetobacter baumannii", 2017, Antimicrob. Agents Chemother., 61:1-16.

Noinaj, N. et al., "TonB-dependent transporters: regulation, structure, and function", 2010, Annu. Rev. Microbiol., 64:43-60.

Overhage, J. et al., "Swarming of Pseudomonas aeruginosa is a complex adaptation leading to increased production of virulence factors and antibiotic resistance", 2008, J. Bacteriol., 190:2671-2679.

Philippot, L. et al., "Going back to the roots: the microbial ecology of the rhizosphere", 2013, Nat. Rev. Microbiol., 11:789-799.

Schlegel, K. et al., "The X-Ray Structure of the Pyochelin $Fe^{3+}$ Complex", 2006, Z. Naturforsch., 61:263-266.

Sierotzki, H. et al., "A review of current knowledge of resistance aspects for the next-generation succinate dehydrogenase inhibitor fungicides", 2013, Phytopath., 103:880-887.

Steele, A. D. et al., "Total synthesis and biological investigation of (−)-promysalin", 2015, J. Am. Chem. Soc., 137:7314-7317.

The Human Microbiome Project Consortium, "Structure, function and diversity of the healthy human microbiome", 2012, Nature, 486:207-214.

Vlassak, K. et al., "Isolation and characterization of fluorescent Pseudomonas associated with the roots of rice and banana grown in Sri Lanka", 1992, Plant Soil, 145:51-63.

Walsh, Christopher "Molecular mechanisms that confer antibacterial drug resistance", 2000, Nature, 406:775-781.

Wencewicz, T. A. et al., "Biscatecholate-Monohydroxamate Mixed Ligand Siderophore-Carbacephalosporin Conjugates are Selective Sideromycin Antibiotics that Target Acinetobacter baumannii", 2013, J. Med. Chem., 56:4044-4052.

Wu, M. et al., "The Pseudomonas aeruginosa proteome during anaerobic growth", 2005, J. Bacteriol., 187:8185-8190.

Wuest, W.M. et al, "Three Siderophores from One Bacterial Enzymatic Assembly Line", 2009, J. Am. Chem. Soc., 131:5056-5057.

A

B

A

PA14

B

Plot 1
$R^2 = 0.975$
EC50 = 0.103

| Parameter | Estimated Value |
|---|---|
| A | 0.868 |
| B | 0.430 |
| C | 0.103 |
| D | 0.106 |

Plot 1
$R^2 = 0.974$
EC50 = 0.021

| Parameter | Estimated Value |
|---|---|
| A | 0.596 |
| B | 0.730 |
| C | 0.021 |
| D | 0.177 |

Plot 1
$R^2 = 0.948$
EC50 = 0.079

| Parameter | Estimated Value |
|---|---|
| A | 0.435 |
| B | 0.940 |
| C | 0.079 |
| D | 0.135 |

PROMYSALIN ANALOGUES AND METHODS OF USE THEREOF

CROSS-REFERENCE TO RELATED APPLICATIONS

The present application is a 35 U.S.C. § 371 national stage patent application of International Patent Application No. PCT/US2017/028057, filed Apr. 18, 2017, which claims priority under 35 U.S.C. § 119(e) to U.S. Provisional Application Ser. No. 62/324,068, filed Apr. 18, 2016, all of which are incorporated by reference herein in their entireties.

STATEMENT REGARDING FEDERALLY SPONSORED RESEARCH OR DEVELOPMENT

This invention was made with government support under contract numbers CHE-1454116, awarded by the National Science Foundation, and R35 GM119426, awarded by the National Institute of General Medical Studies. The government has certain rights in the invention.

BACKGROUND OF THE INVENTION

Over the past century, groundbreaking discoveries in the field of antibiotics have resulted in the saving of countless lives. This can be primarily attributed to their broad-spectrum activity that is ideal for the treatment of a wide range of bacterial infections but can also result in significant misuse and unintended side effects Cox et al., 2014, Cell 158:705). For example, recent work from the Blaser lab strongly suggests that prolonged broad-spectrum antibiotic exposure early in life can lead to an increased likelihood of obesity, allergies, and inflammatory diseases (Cox et al., 2014, Cell 158:705). These findings highlight the effect that certain antimicrobials have on one's commensal population, resulting in an altered community dynamic and leading to undesired outcomes lending credence to the recent call for the development of narrow-spectrum therapies.

To date very few options currently exist for pathogen-specific treatments (Maxson and Mitchell, 2016, Tetrahedron). Furthermore, with species-specific compounds in hand one would also have access to tool compounds to aid in deconvoluting the complex multispecies environments present. The recent advances in genetic sequencing, as exemplified by the human microbiome project, would allow for the probing of these environments if the appropriate tools were available (the Human Microbiome Project Consortium, 2012, Nature 486:207).

It is well documented that there is a general lack of diversity amongst cellular targets of approved antibiotics with recent reports estimating that fewer than twenty-five targets are represented (Fair and Tor, 2014, Perspect. Medicin. Chem. 6:25-64). Most of these compounds are non-discriminatory (broad-spectrum), and target essential pathways such as cell wall or protein synthesis (Walsh, 2000, Nature 406:775-781). Although some "narrow-spectrum" therapies are available, they target large subsets of bacteria (anaerobes vs. aerobes, Gram-positive vs. Gram-negative) instead of focusing on particular pathogenic species. The latter method of treatment would be preferred in an effort to reduce adverse side effects to the host and microbiome communities and to minimize the development of resistance; however, both financial and technical limitations have thwarted such efforts to date (Maxson and Mitchell, 2016, Tetrahedron 72:3609-3624). Furthermore, the identification of either 1) unique targets that would permit selective killing or 2) compounds that discriminate species is not trivial; this presents a clear unmet need that is ripe for discovery.

The combination of microbial diversity and evolutionary pressure has incentivized bacteria to create natural products with extraordinary selectivity and bioactivity. It should be noted that these scaffolds serve with distinction as antibacterial agents; an estimated 70% of marketed antibiotics are derived from natural products. One specific example exists within the rhizosphere where predominantly Gram-negative bacteria, particularly the *Pseudomonads*, utilize chemical warfare to both colonize the environment (quorum sensing) and defend themselves (antibiotics) (Keohane et al., 2015, Synlett 26:2739-2744; Philippot et al., 2013, Nat. Rev. Microbiol. 11:789-799). Of particular health interest is the bacterial species *Pseudomonas aeruginosa* (PA), an opportunistic environmental pathogen inherently resistant to many antibiotics yet rarely infective to healthy individuals (Gellatly and Hancock, 2013, Pathogens and Disease 67:159-173). However, those with compromised immune systems (i.e. burn victims, chemotherapy patients, and the chronically hospitalized) or cystic fibrosis are especially susceptible to a fatal infection. In 2013, the Centers for Disease Control listed Multi-drug resistant PA one of the top fifteen urgent/serious microbial threats facing society demonstrating a pressing need to develop new therapeutics which target this pathogen of interest (Antibiotic Resistance Threats in the United States, 2013. https://www.cdc.gov/drugresistance/threat-report-2013/(accessed Mar. 27, 2017)).

Recent efforts by both the De Mot (Vlassak et al., 1992, Plant Soil 145:51-63) and Muller (Hermann et al., 2017, Nat. Prod. Rep. 34:135-160) labs have focused on this call by targeting untapped resources within the soil, which are rich in diversity. Thorough work by both groups has revealed natural products with complex chemical architecture and unique bioactivity providing inspiration for organic chemists as platforms for further discovery. One such example is the *Pseudomonad* secondary metabolite promysalin, which is, as the name alludes to, derived from proline, myristate, and salicylate, which possesses species-specific inhibitory activity against PA, while inducing swarming and biofilm formation in a related species, *P. putida* (Li et al., 2011, Chem. Biol. 18:320-1330). In 2015, the first total synthesis of the natural product was completed, which elucidated the relative and absolute stereochemistry and also confirmed the reported biological activity (Steele et al., 2015, J. Am. Chem. Soc. 137, 7314-7317). It was also shown for the first time that promysalin repressed fluorescence of *P. putida* KT2440, which is presumably attributed to the inhibition of pyoverdine production by the bacterium.

Other *Pseudomonad* siderophores include pyochelin (Cox et al., 1981, proc. Natl. Acad. Sci. USA 78:4256; Schlegel et al., 2006, Natuforsch C. 61:263), pseudomonine (Anthoni et al., 1995, J. Nat. Prod. 58:1786; Sanely and Walsh, 2008, J. Am. Chem. Soc. 130:12282, Wuest, et al., 2009, J. Am. Chem. Soc. 131:5056), and ferrocin (Katayama et al., 1993, J. Antibiotics 46:65.

There is an interest in developing narrow-spectrum agents to combat *Pseudomonas aeruginosa* (PA) infections. PA is a Gram-negative pathogen that is typically found in people with weakened immune systems and/or hospital settings accounting for an estimated 51,000 infections/year in the United States alone (seudomonas aeruginosa in Healthcare Settings. (2014). Retrieved Mar. 19, 2016, from http://www.cdc.gov/hai/organisms/pseudomonas.html). The community has postulated that the rhizosphere, which is defined as the immediate area of soil that is directly influenced by microorganisms and root secretions, is an ideal environment to discover such compounds as the soil is teeming with *Pseudomonads* competing to establish their own (Keohane et al., 2015, Synlett 26:2739).

There is a need in the art for novel compounds with activity against PA infections. The present invention addresses this unmet need in the art.

BRIEF SUMMARY OF THE INVENTION

The present invention includes a compound of formula I, or a salt or solvate thereof:

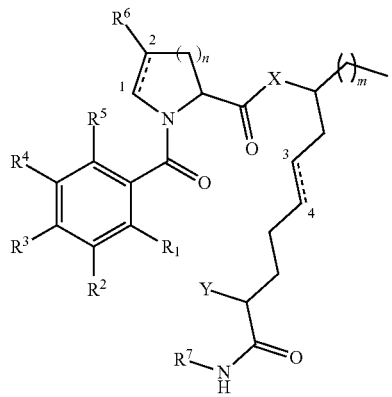

wherein in formula I:

$R^1$, $R^2$, $R^3$, $R^4$, $R^5$, and $R^6$ are each independently selected from the group consisting of H, —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, —$OR^7$, —$S(=O)R^7$, —$S(=O)_2R^7$, —$NHS(=O)_2R^7$, —$C(=O)R^7$, —$OC(=O)R^7$, —$CO_2R^7$, —$OCO_2R^7$, —$CH(R^7)_2$, —$N(R^7)_2$, —$C(=O)N(R^7)_2$, —$OC(=O)N(R^7)_2$, —$NHC(=O)NH(R^7)$, —$NHC(=O)R^7$, —$NHC(=O)OR^7$, —$C(OH)(R^7)_2$, and —$C(NH_2)(R^7)_2$, wherein the alkyl, aryl, heteroaryl, cycloalkyl, heterocycloalkyl, and $C_1$-$C_6$ heteroalkyl group is optionally substituted;

each occurrence of $R^7$ is independently selected from the group consisting of H and —$C_1$-$C_6$ alkyl, wherein the alkyl group is optionally substituted;

the bond between carbons 1 and 2 and the bond between carbons 3 and 4 each independently represents a single or double bond;

X is O or $NR^7$;

Y is selected from the group consisting of H, $OR^7$, halogen, and —$NHR^7$;

n is 1 or 2; and m is an integer from 0 to 8;

with the proviso that the compound of formula I is not:

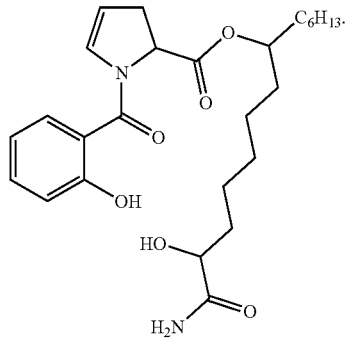

In one embodiment, the compound of formula I is a compound of formula II, or a salt or solvate thereof:
wherein in formula II:

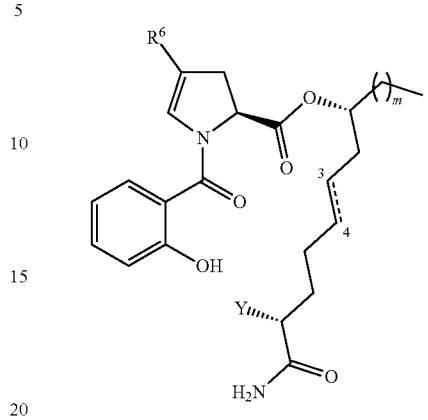

$R^6$ is selected from the group consisting of H, —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, —$SR^7$, —$S(=O)R^7$, —$S(=O)_2R^7$, —$NHS(=O)_2R^7$, —$C(=O)R^7$, —$OC(=O)R^7$, —$CO_2R^7$, —$OCO_2R^7$, —$CH(R^7)_2$, —$N(R^7)_2$, —$C(=O)N(R^7)_2$, —$OC(=O)N(R^7)_2$, —$NHC(=O)NH(R^7)$, —$NHC(=O)R^7$, —$NHC(=O)OR^7$, —$C(OH)(R^7)_2$, and —$C(NH_2)(R^7)_2$, wherein the alkyl, aryl, heteroaryl, cycloalkyl, heterocycloalkyl, and $C_1$-$C_6$ heteroalkyl group is optionally substituted;

each occurrence of $R^7$ is independently selected from the group consisting of H and —$C_1$-$C_6$ alkyl, wherein the alkyl group is optionally substituted;

the bond between carbons 3 and 4 represents a single or double bond;

Y is H or $OR^7$; and m is an integer from 4 to 6;

with the proviso that the compound of formula II is not:

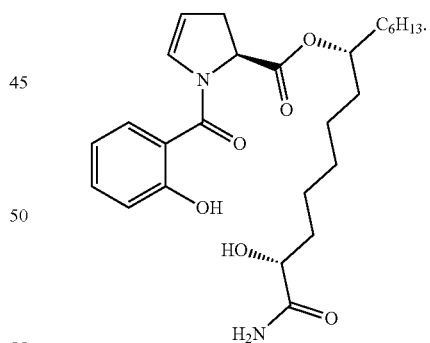

In one embodiment, $R^1$, is —OH. In one embodiment, $R^2$ is H. In one embodiment, $R^3$ is H. In one embodiment, $R^4$ is H. In one embodiment, $R^5$ is H. In one embodiment, $R^6$ is F. In one embodiment, the bond between carbons 1 and 2 represents a single bond. In one embodiment, the bond between carbons 3 and 4 represents a single bond. In one embodiment, the bond between carbons 3 and 4 represents a double bond. In one embodiment, X is O. In one embodiment, Y is H. In one embodiment, Y is $OR^7$. In one embodiment, n is 1. In one embodiment, n is 2. In one embodiment, m is 5.

In one embodiment, the compound is selected from the group consisting of (1R,7R)-1-carbamoyl-1-hydroxytridecan-7-yl (2S)-1-(2-hydroxybenzoyl)pyrrolidine-2-carboxylate, (1R,7R)-1-carbamoyl-1-hydroxytridecan-7-yl (2S)-1-(2-hydroxybenzoyl)piperidine-2-carboxylate, (1R,7R)-1-carbamoyl-1-hydroxytridecan-7-yl (2S,4R)-4-hydroxy-1-(2-hydroxybenzoyl)pyrrolidine-2-carboxylate, (7R,13R)-14-amino-13-hydroxy-14-oxotetradecan-7-yl (S)-4-fluoro-1-(2-hydroxybenzoyl)-2,3-dihydro-1H-pyrrole-2-carboxylate, (7R,13R)-14-amino-13-hydroxy-14-oxotetradecan-7-yl (S)-1-(2-hydroxybenzoyl)-4-methyl-2,3-dihydro-1H-pyrrole-2-carboxylate, (1R,7R)-1-carbamoyl-1-hydroxytridecan-7-yl (2S)-1-(2-methoxybenzoyl)-2,3-dihydro-1H-pyrrole-2-carboxylate, (7R,13R)-14-amino-13-hydroxy-14-oxotetradecan-7-yl (S)-1-(3-hydroxybenzoyl)-2,3-dihydro-1H-pyrrole-2-carboxylate, (1R,7R)-1-carbamoyl-1-hydroxytridecan-7-yl (2S)-1-(4-hydroxybenzoyl)-2,3-dihydro-1H-pyrrole-2-carboxylate, (1R,7R)-1-carbamoyl-1-hydroxytridecan-7-yl (2S)-1-benzoyl-2,3-dihydro-1H-pyrrole-2-carboxylate, (7R,13R)-14-amino-13-hydroxy-14-oxotetradecan-7-yl (S)-1-(2-hydroxy-6-methoxybenzoyl)-2,3-dihydro-1H-pyrrole-2-carboxylate, (1R,7R)-1-carbamoyl-1-hydroxytridecan-7-yl (2S)-1-(3,4,5-trimethoxybenzoyl)-2,3-dihydro-1H-pyrrole-2-carboxylate, (7R,13R)-14-amino-13-hydroxy-14-oxotetradecan-7-yl (S)-1-(2-nitrobenzoyl)-2,3-dihydro-1H-pyrrole-2-carboxylate, (R)-14-amino-14-oxotetradecan-7-yl(S)-1-(2-hydroxybenzoyl)-2,3-dihydro-1H-pyrrole-2-carboxylate, (7R,13R)-14-amino-13-methoxy-14-oxotetradecan-7-yl (S)-1-(2-hydroxybenzoyl)-2,3-dihydro-1H-pyrrole-2-carboxylate, (S)—N-((7R,13R)-14-amino-13-hydroxy-14-oxotetradecan-7-yl)-1-(2-hydroxybenzoyl)-2,3-dihydro-1H-pyrrole-2-carboxamide, and (7R,13R,E)-14-amino-13-hydroxy-14-oxotetradec-9-en-7-yl(S)-1-(2-hydroxybenzoyl)-2,3-dihydro-1H-pyrrole-2-carboxylate, or a salt or solvate thereof.

In one embodiment, the compound is selected from the group consisting of (7R,13R)-14-amino-13-hydroxy-14-oxotetradecan-7-yl(S)-4-fluoro-1-(2-hydroxybenzoyl)-2,3-dihydro-1H-pyrrole-2-carboxylate, (R)-14-amino-14-oxotetradecan-7-yl(S)-1-(2-hydroxybenzoyl)-2,3-dihydro-1H-pyrrole-2-carboxylate, and (7R,13R,E)-14-amino-13-hydroxy-14-oxotetradec-9-en-7-yl(S)-1-(2-hydroxybenzoyl)-2,3-dihydro-1H-pyrrole-2-carboxylate, or a salt or solvate thereof.

The present invention also includes a pharmaceutical composition comprising a pharmaceutically acceptable carrier and at least one compound of formula I.

The present invention also includes a method of preventing or treating a microbial infection in a subject in need thereof. In one embodiment, the method includes administering to the subject an effective amount of a therapeutic composition comprising at least one compound of formula I, or a salt or solvate thereof:

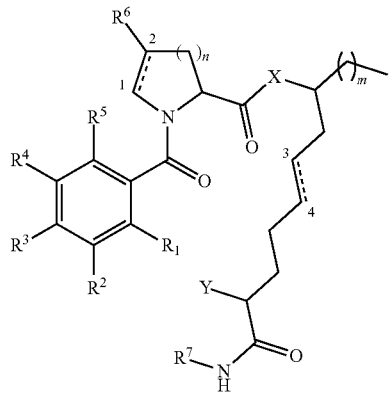

wherein in formula I:
$R^1$, $R^2$, $R^3$, $R^4$, $R^5$, and $R^6$ are each independently selected from the group consisting of H, —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, —$SR^7$, —S(=O)$R^7$, —S(=O)$_2R^7$, —NHS(=O)$_2R^7$, —C(=O)$R^7$, —OC(=O)$R^7$, —$CO_2R^7$, —$OCO_2R^7$, —CH($R^7$)$_2$, —N($R^7$)$_2$, —C(=O)N($R^7$)$_2$, —OC(=O)N($R^7$)$_2$, —NHC(=O)NH($R^7$), —NHC(=O)$R^7$, —NHC(=O)O$R^7$, —C(OH)($R^7$)$_2$, and —C($NH_2$)($R^7$)$_2$, wherein the alkyl, aryl, heteroaryl, cycloalkyl, heterocycloalkyl, and $C_1$-$C_6$ heteroalkyl group is optionally substituted;

each occurrence of $R^7$ is independently selected from the group consisting of H and —$C_1$-$C_6$ alkyl, wherein the alkyl group is optionally substituted;

the bond between carbons 1 and 2 and the bond between carbons 3 and 4 each independently represents a single or double bond;

X is O or $NR^7$;

Y is selected from the group consisting of H, $OR^7$, halogen, and —$NHR^7$;

n is 1 or 2; and m is an integer from 0 to 8;

with the proviso that the compound of formula I is not:

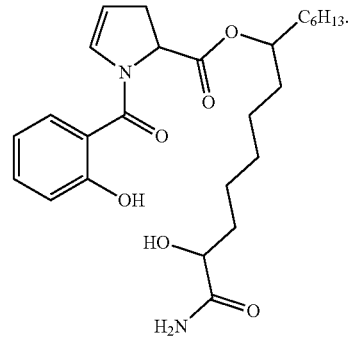

In one embodiment, the compound is selected from the group consisting of (1R,7R)-1-carbamoyl-1-hydroxytridecan-7-yl(2S)-1-(2-hydroxybenzoyl)pyrrolidine-2-carboxylate, (1R,7R)-1-carbamoyl-1-hydroxytridecan-7-yl (2S)-1-(2-hydroxybenzoyl)piperidine-2-carboxylate, (1R,7R)-1-carbamoyl-1-hydroxytridecan-7-yl (2S,4R)-4-hydroxy-1-(2-hydroxybenzoyl)pyrrolidine-2-carboxylate, (7R,13R)-14-amino-13-hydroxy-14-oxotetradecan-7-yl (S)-4-fluoro-1-(2-hydroxybenzoyl)-2,3-dihydro-1H-pyrrole-2-carboxylate, (7R,13R)-14-amino-13-hydroxy-14-oxotetradecan-7-yl (S)-1-(2-hydroxybenzoyl)-4-methyl-2,3-dihydro-1H-pyrrole-2-carboxylate, (1R,7R)-1-carbamoyl-1-hydroxytridecan-7-yl (2S)-1-(2-methoxybenzoyl)-2,3-dihydro-1H-pyrrole-2-carboxylate, (7R,13R)-14-amino-13-hydroxy-14-oxotetradecan-7-yl (S)-1-(3-hydroxybenzoyl)-2,3-dihydro-1H-pyrrole-2-carboxylate, (1R,7R)-1-carbamoyl-1-hydroxytridecan-7-yl (2S)-1-(4-hydroxybenzoyl)-2,3-dihydro-1H-pyrrole-2-carboxylate, (1R,7R)-1-carbamoyl-1-hydroxytridecan-7-yl (2S)-1-benzoyl-2,3-dihydro-1H-pyrrole-2-carboxylate, (7R,13R)-14-amino-13-hydroxy-14-oxotetradecan-7-yl (S)-1-(2-hydroxy-6-methoxybenzoyl)-2,3-dihydro-1H-pyrrole-2-carboxylate, (1R,7R)-1-carbamoyl-1-hydroxytridecan-7-yl (2S)-1-(3,4,5-trimethoxybenzoyl)-2,3-dihydro-1H-pyrrole-2-carboxylate, (7R,13R)-14-amino-13-hydroxy-14-oxotetradecan-7-yl (S)-1-(2-nitrobenzoyl)-2,3-dihydro-1H-pyrrole-2-carboxylate, (R)-14-amino-14-oxotetradecan-7-yl(S)-1-(2-hydroxybenzoyl)-2,3-dihydro- 1H-pyrrole-2-carboxylate, (7R,13R)-14-amino-13-methoxy-14-oxotetradecan-7-yl (S)-1-(2-hydroxybenzoyl)-2,3-dihydro-1H-pyrrole-2-carboxylate, (S)—N-((7R,13R)-14-amino-13-hydroxy-14-oxotetradecan-7-yl)-1-(2-hydroxybenzoyl)-2,3-dihydro-1H-pyrrole-2-carboxamide, and (7R,13R,E)-14-amino-13-hydroxy-14-oxotetradec-9-en-7-yl(S)-1-(2-hydroxybenzoyl)-2,3-dihydro-1H-pyrrole-2-carboxylate, or a salt or solvate thereof.

In one embodiment, the microbial infection is a *Psuedomonas aeruginosa* (PA) infection. In one embodiment, the compound is species-specific. In one embodiment, the compound is administered in combination with an additional therapeutic agent. In one embodiment, the therapeutic agent is an antibiotic. In one embodiment, the compound and the therapeutic agent are co-administered to the subject. In one embodiment, the compound of the invention and the therapeutic agent are co-formulated to the subject. In one embodiment, the subject is human.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 4A-4B, depicts the structures of various siderophores. FIG. 4A depicts the structures of PA siderophores pyochelin and pseudomonine, and antimicrobial siderophore ferrocin. Putative iron-binding atoms are colored red and fatty acid tails in blue. FIG. 4B depicts the structure of promysalin with proposed iron contacts shown in red (left), minimized calculated structure (middle), CAS agar plate (right). Numbers refer to the concentration (mM) of 10 μL of promysalin used. EDTA (10 μL of 6 mM) and DMSO (10%) are used as controls.

FIGS. 6A-6D, depicts the growth curves and inhibition of two strains of *P. aeruginosa*, PA01 and PA14. FIG. 6A is a plot of the PA01 growth curve from $OD_{595}$ readings over a period of 6 hours. FIG. 6B is a plot of the PA14 growth curve from $OD_{595}$ readings over a period of 6 hours. FIG. 6C is a graphical summary of compiled $IC_{50}$ values for 11 active analogs against PA01. FIG. 6D is a graphical summary of compiled $IC_{50}$ values for 11 active analogs against PA14.

FIGS. 7A and 7B, depicts the $IC_{50}$ data from the promysalin analog (−)-1(2R,8R) against PA01. FIG. 7A is the structure of the promysalin analog. FIG. 7B is the $IC_{50}$ data.

FIGS. 8A and 8B, depicts the $IC_{50}$ data from the promysalin analog (−)-1(2R,8R) against PA14. FIG. 8A is the structure of the promysalin analog. FIG. 8B is the $IC_{50}$ data.

FIGS. 9A and 9B, depicts the $IC_{50}$ data from the promysalin analog (−)-1b(2R,8S) against PA01. FIG. 9A is the structure of the promysalin analog. FIG. 9B is the $IC_{50}$ data.

FIGS. 10A and 10B, depicts the $IC_{50}$ data from the promysalin analog (−)-1b(2R,8S) against PA14. FIG. 10A is the structure of the promysalin analog. FIG. 10B is the $IC_{50}$ data.

FIGS. 11A and 11B, depicts the $IC_{50}$ data from the promysalin analog (−)-1c(2R,8S) against PA01. FIG. 11A is the structure of the promysalin analog. FIG. 11B is the $IC_{50}$ data.

FIGS. 12A and 12B, depicts the $IC_{50}$ data from the promysalin analog (−)-1c(2R,8S) against PA14. FIG. 12A is the structure of the promysalin analog. FIG. 12B is the $IC_{50}$ data.

FIGS. 13A and 13B, depicts the $IC_{50}$ data from the promysalin analog (−)-1d(2S,8R) against PA01. FIG. 13A is the structure of the promysalin analog. FIG. 13B is the $IC_{50}$ data.

FIGS. 14A and 14B, depicts the $IC_{50}$ data from the promysalin analog (−)-1d(2S,8R) against PA14. FIG. 14A is the structure of the promysalin analog. FIG. 14B is the $IC_{50}$ data.

FIGS. 15A and 15B, depicts the $IC_{50}$ data from the promysalin analog (−)-6 against PA14. FIG. 15A is the structure of the promysalin analog. FIG. 15B is the $IC_{50}$ data.

FIGS. 16A and 16B, depicts the $IC_{50}$ data from the promysalin analog (+)-9 against PA01. FIG. 16A is the structure of the promysalin analog. FIG. 16B is the $IC_{50}$ data.

FIGS. 17A and 17B, depicts the $IC_{50}$ data from the promysalin analog (+)-9 against PA14. FIG. 17A is the structure of the promysalin analog. FIG. 17B is the $IC_{50}$ data.

FIGS. 18A and 18B, depicts the $IC_{50}$ data from the promysalin analog (−)-10 against PA01. FIG. 18A is the structure of the promysalin analog. FIG. 18B is the $IC_{50}$ data.

FIGS. 19A and 19B, depicts the $IC_{50}$ data from the promysalin analog (−)-10 against PA14. FIG. 19A is the structure of the promysalin analog. FIG. 19B is the $IC_{50}$ data.

FIGS. 20A and 20B, depicts the $IC_{50}$ data from the promysalin analog (−)-11 against PA01. FIG. 20A is the structure of the promysalin analog. FIG. 20B is the $IC_{50}$ data.

FIGS. 21A and 21B, depicts the $IC_{50}$ data from the promysalin analog (−)-11 against PA14. FIG. 21A is the structure of the promysalin analog. FIG. 21B is the $IC_{50}$ data.

FIGS. 22A and 22B, depicts the $IC_{50}$ data from the promysalin analog (−)-18 against PA01. FIG. 22A is the structure of the promysalin analog. FIG. 22B is the $IC_{50}$ data.

FIGS. 23A and 23B, depicts the $IC_{50}$ data from the promysalin analog (−)-18 against PA14. FIG. 23A is the structure of the promysalin analog. FIG. 23B is the $IC_{50}$ data.

FIGS. 24A and 24B, depicts the $IC_{50}$ data from the promysalin analog (−)-19 against PA01. FIG. 24A is the structure of the promysalin analog. FIG. 24B is the $IC_{50}$ data.

FIGS. 25A and 25B, depicts the $IC_{50}$ data from the promysalin analog (−)-19 against PA14. FIG. 25A is the structure of the promysalin analog. FIG. 25B is the $IC_{50}$ data.

FIGS. 26A and 26B, depicts the $IC_{50}$ data from the promysalin analog (−)-21 against PA01. FIG. 26A is the structure of the promysalin analog. FIG. 26B is the $IC_{50}$ data.

FIGS. 27A and 27B, depicts the $IC_{50}$ data from the promysalin analog (−)-21 against PA14. FIG. 27A is the structure of the promysalin analog. FIG. 27B is the $IC_{50}$ data.

FIGS. 114A-114C, depicts the ABPP workflow and results. FIG. 114A is a schematic of the general ABPP workflow. Bacteria are incubated with probe and irradiated. Biotin-azide click chemistry permits pull down and subsequent digestion and labeling allows for the identification of enriched proteins. FIG. 114B is a volcano plot of significantly enriched proteins in PA14 comparing the differential in selectivity with an inactive probe. FIG. 114C is a volcano plot of significantly enriched proteins in PA14 comparing the differential in selectivity with a competitive inhibitor.

FIGS. 115A-115F, depicts structures known to interact with Sdh, as well as a model of the interaction between promysalin and Sdh. FIG. 115A depicts the terminal electron acceptor of Sdh, ubiquinone, alongside several known inhibitors of the complex that also engage the ubiquinone-binding site. Moieties that exhibit similarity to promysalin are highlighted. FIG. 115B depicts a model of P. aeruginosa Sdh built from the closely related E. coli structure; promysalin (brown) is shown at the ubiquinone-binding site, using a modeled binding mode. The subunits of SdhA, SdhB, SdhC, and SdhD are colored orange, green, cyan, and pink, respectively. Redox centers involved in the electron transport pathway are shown in yellow. FIG. 115C depicts the binding conformation of promysalin, which includes an intramolecular hydrogen bond between the amide tail and the ester linker, consistent with previous SAR pointing to the importance of this ester. FIG. 115D shows an intermolecular hydrogen bond involving the salicylate hydroxyl group, further consistent with previous SAR. FIG. 115E shows that the dehydroproline ring faces outwards in the model, consistent with previous SAR. FIG. 115F shows that the model of promysalin binding includes interactions with all three subunits that surround the ubiquinone-binding site, which explains additional experimental observations that were not used in developing the model.

FIGS. 116A and 116B, depicts the proposed mechanism of action against the TCA Cycle and Glyoxylate shunt pathway. FIG. 116A is a schematic of the TCA Cycle and Glyoxylate shunt pathway. Promysalin inhibits SdhC, which in turn inhibits the TCA pathway (Bottom left). FIG. 116B depicts the results of zone of inhibition assays in TSB (nutrient rich media, left) and M9 minimal media (with succinate as sole carbon source, right) against PA14, PA01, PP KT2440, and PP RW10S (producing strain) when treated with Promysalin (P), Gentamicin (G) and DMSO (D).

Figure 119:
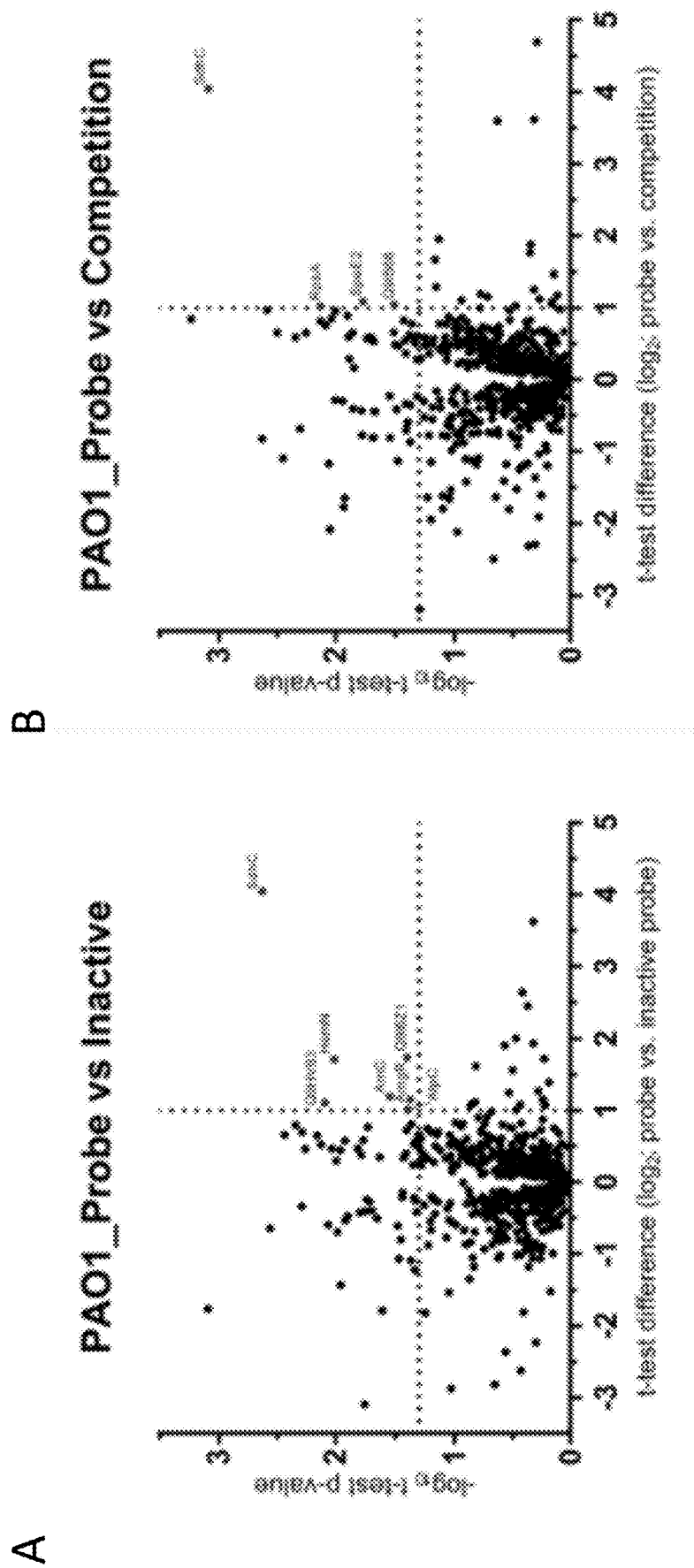

FIG. 119, comprising FIGS. 119A-119B, depicts a series of tables of experimental data of ABPP volcano plots for PAO1. FIG. 119A depicts the ABPP volcano plot for PAO1 of the probe versus inactive. FIG. 119B depicts the ABPP volcano plot for PAO1 of the probe versus competition.

Figure 120:
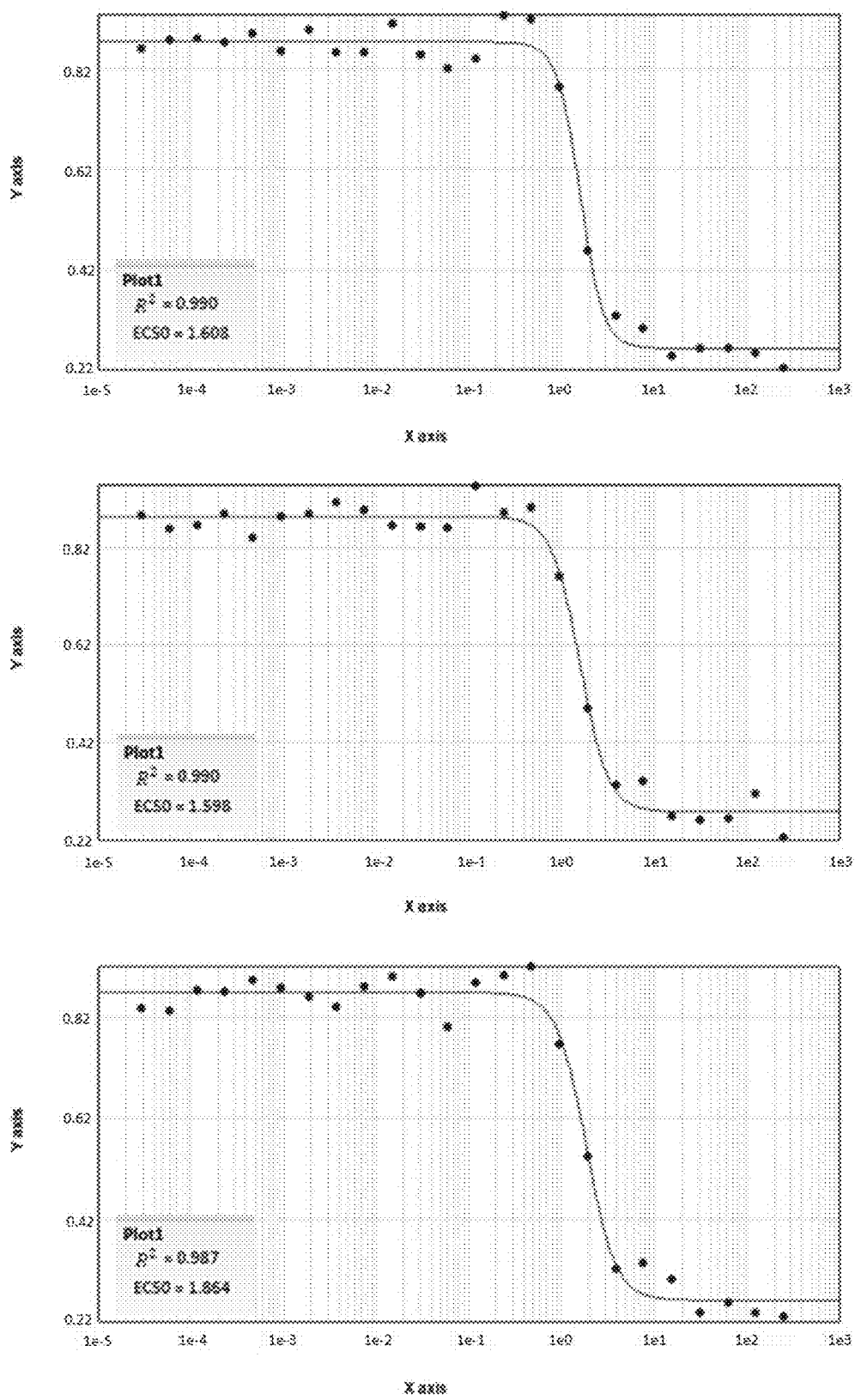

FIG. 120 depicts a series of tables of experimental data demonstrating $IC_{50}$ curves for the probe compound.

Figure 121:
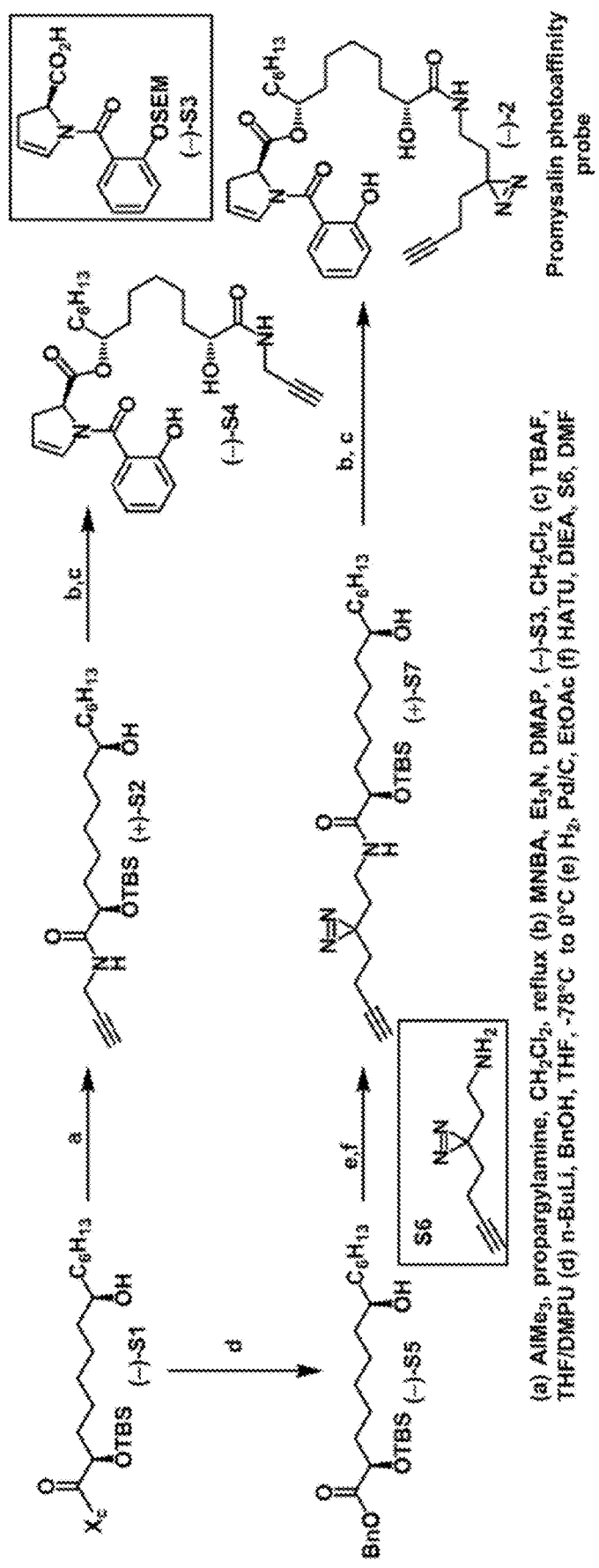

FIG. 121 depicts a scheme for a synthesis of promysalin photoaffinity probe (−)-2.

Figure 122:
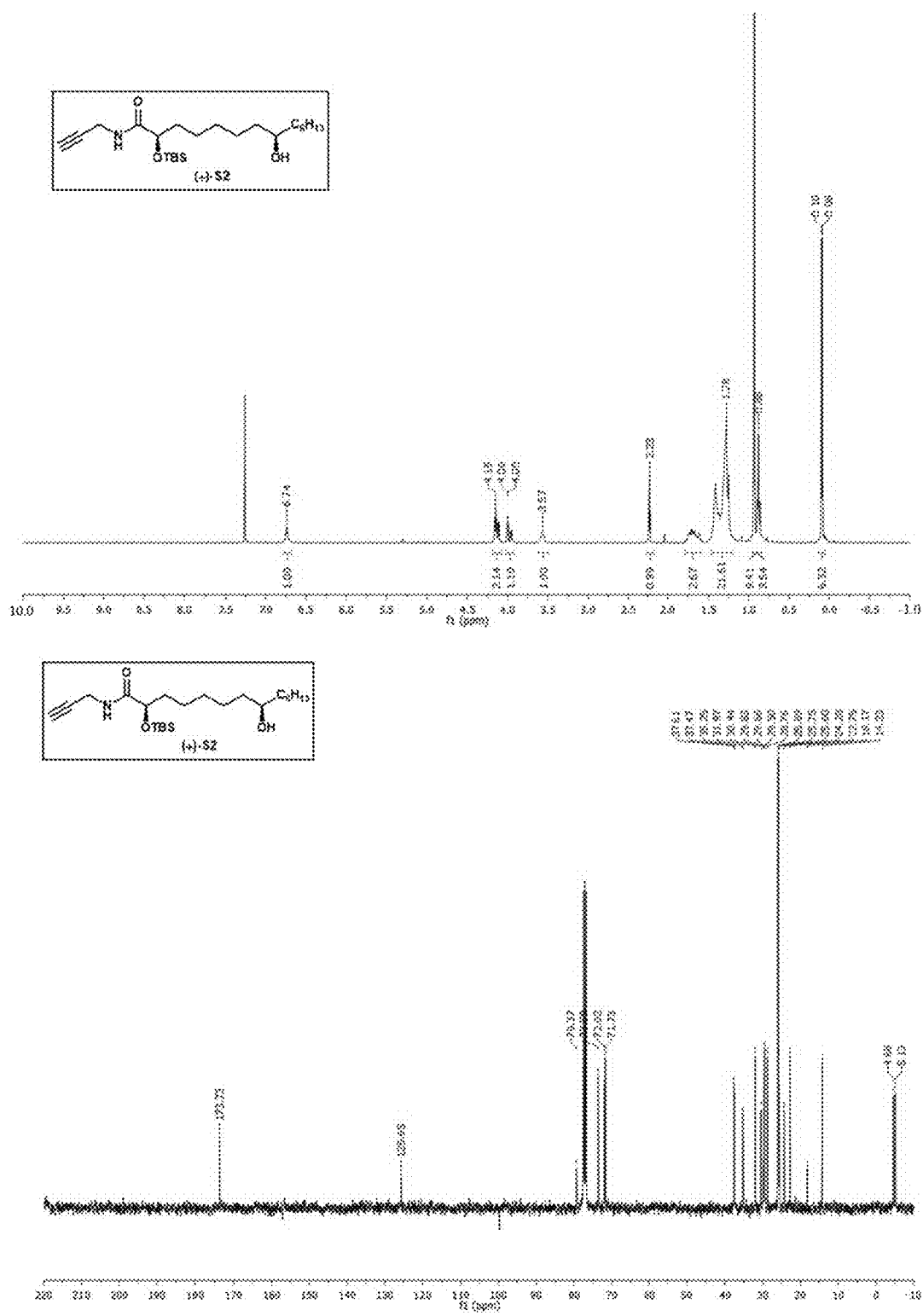

FIG. 122 depicts the proton ($^1$H) and carbon ($^{13}$C) NMR spectra of promysalin photoaffinity probe intermediate (+)-S2.

Figure 123:
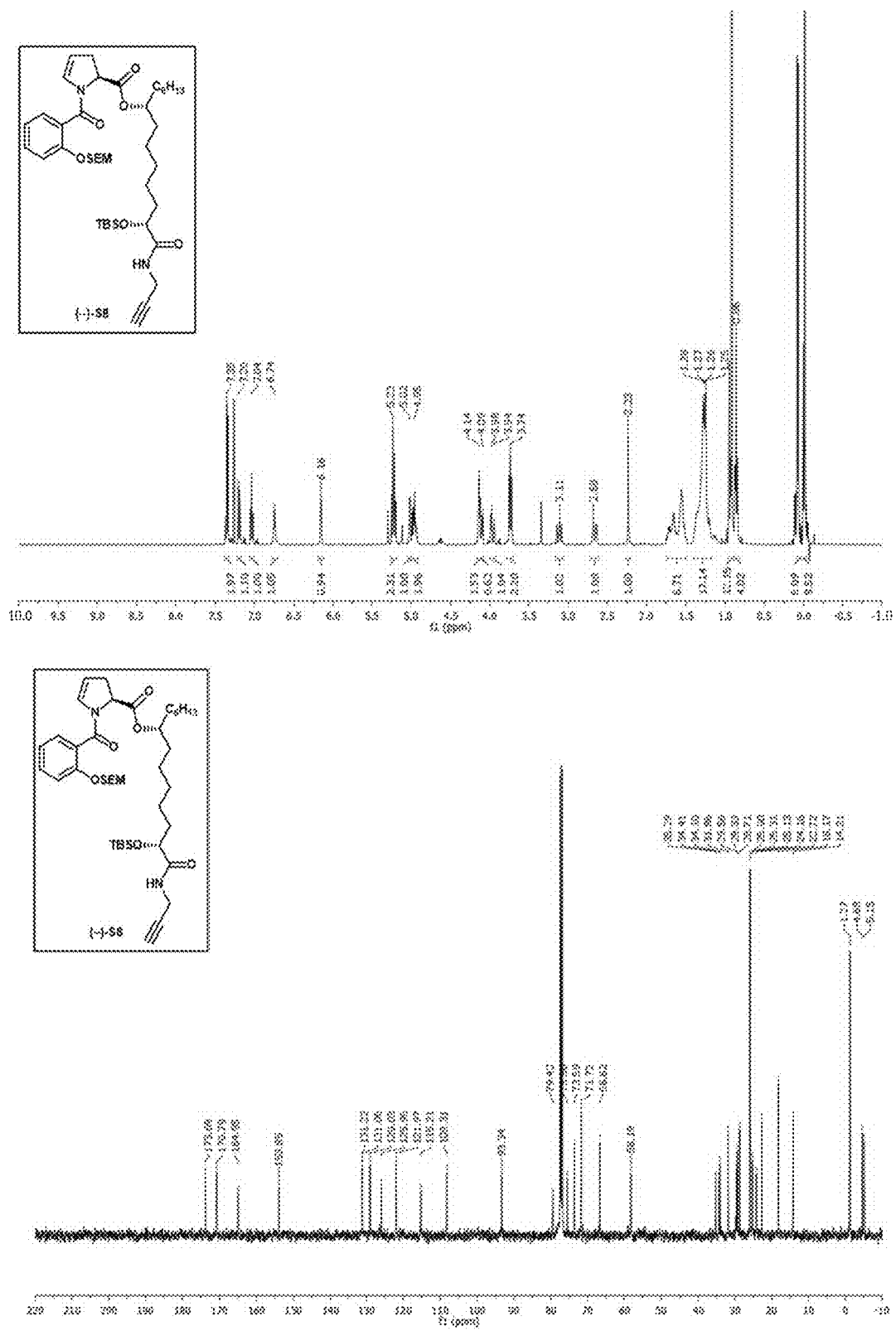

FIG. 123 depicts the proton ($^1$H) and carbon ($^{13}$C) NMR spectra of promysalin photoaffinity probe intermediate (−)-S8.

Figure 124:
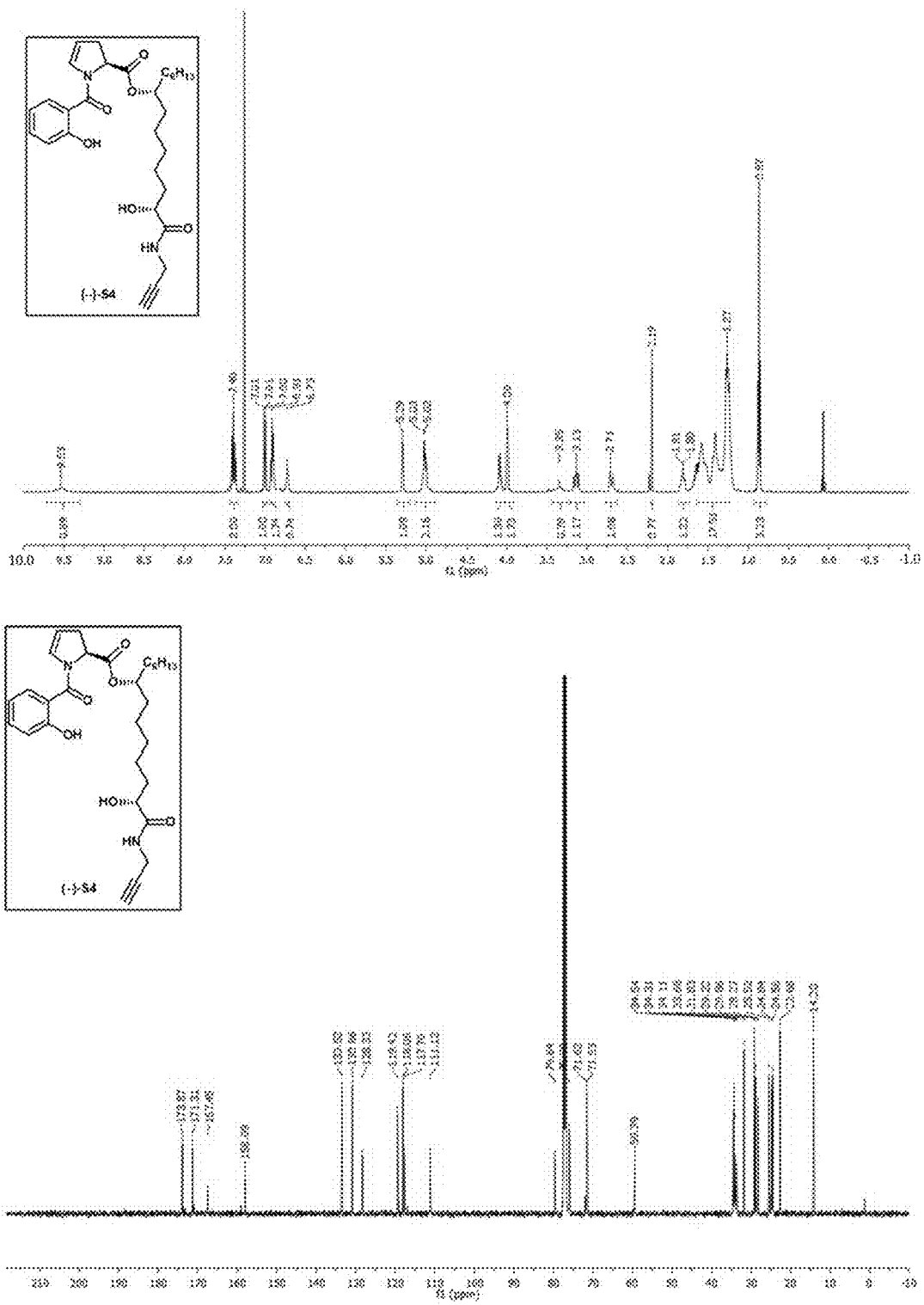

FIG. 124 depicts the proton ($^1$H) and carbon ($^{13}$C) NMR spectra of promysalin photoaffinity probe intermediate (−)-S4.

Figure 125:
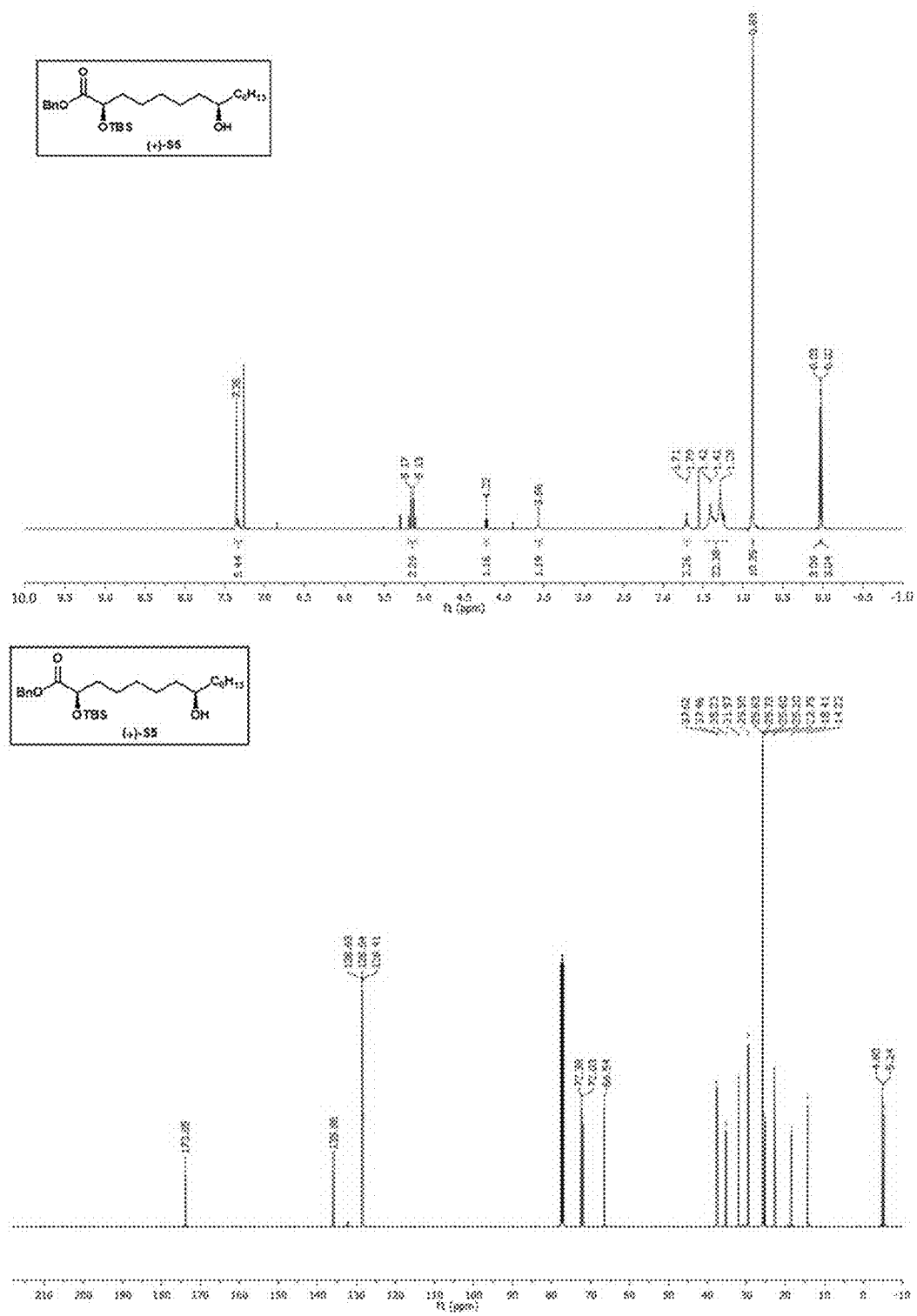

FIG. 125 depicts the proton ($^1$H) and carbon ($^{13}$C) NMR spectra of promysalin photoaffinity probe intermediate (+)-S5.

Figure 126:
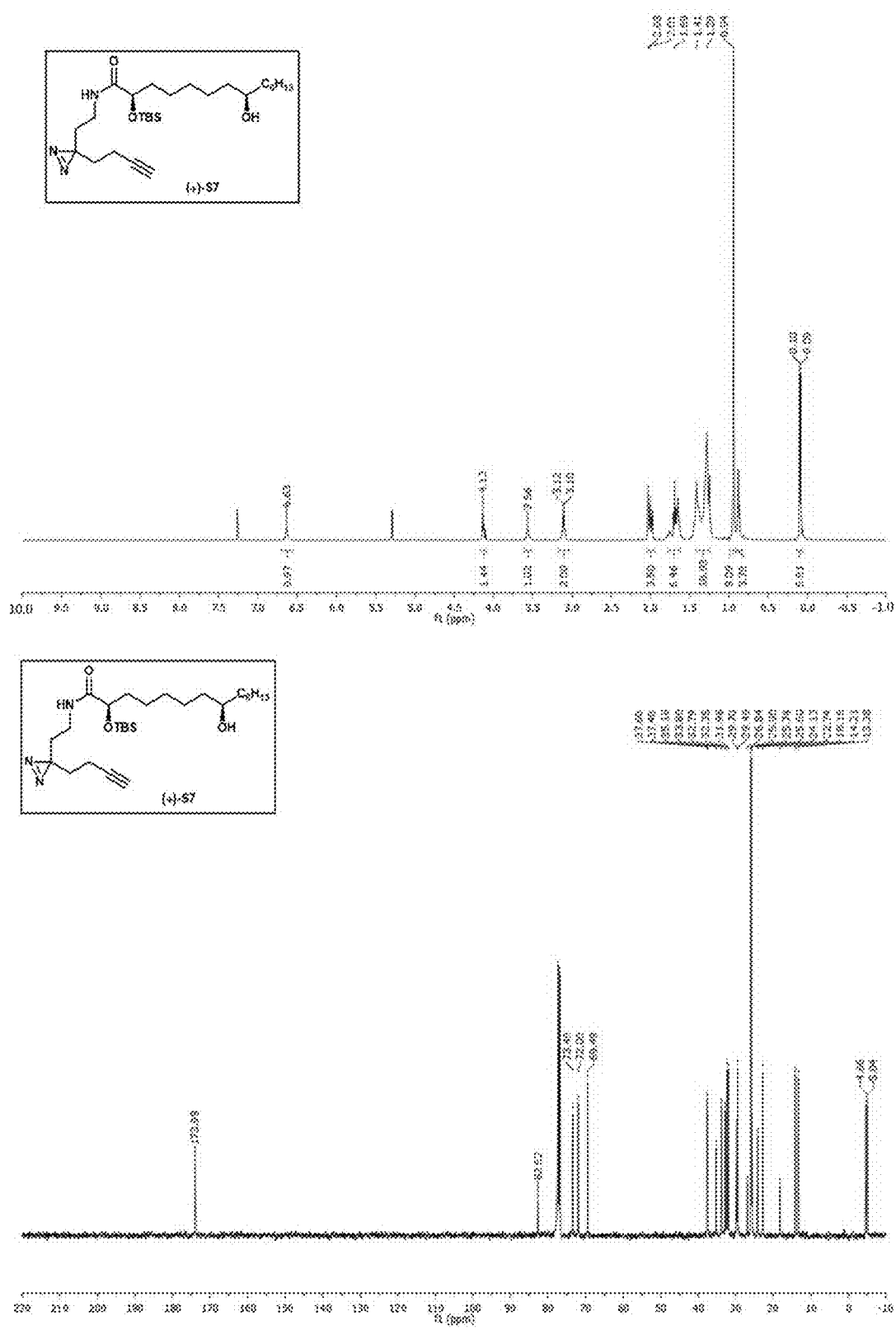

FIG. 126 depicts the proton ($^1$H) and carbon ($^{13}$C) NMR spectra of promysalin photoaffinity probe intermediate (+)-S7.

Figure 127:
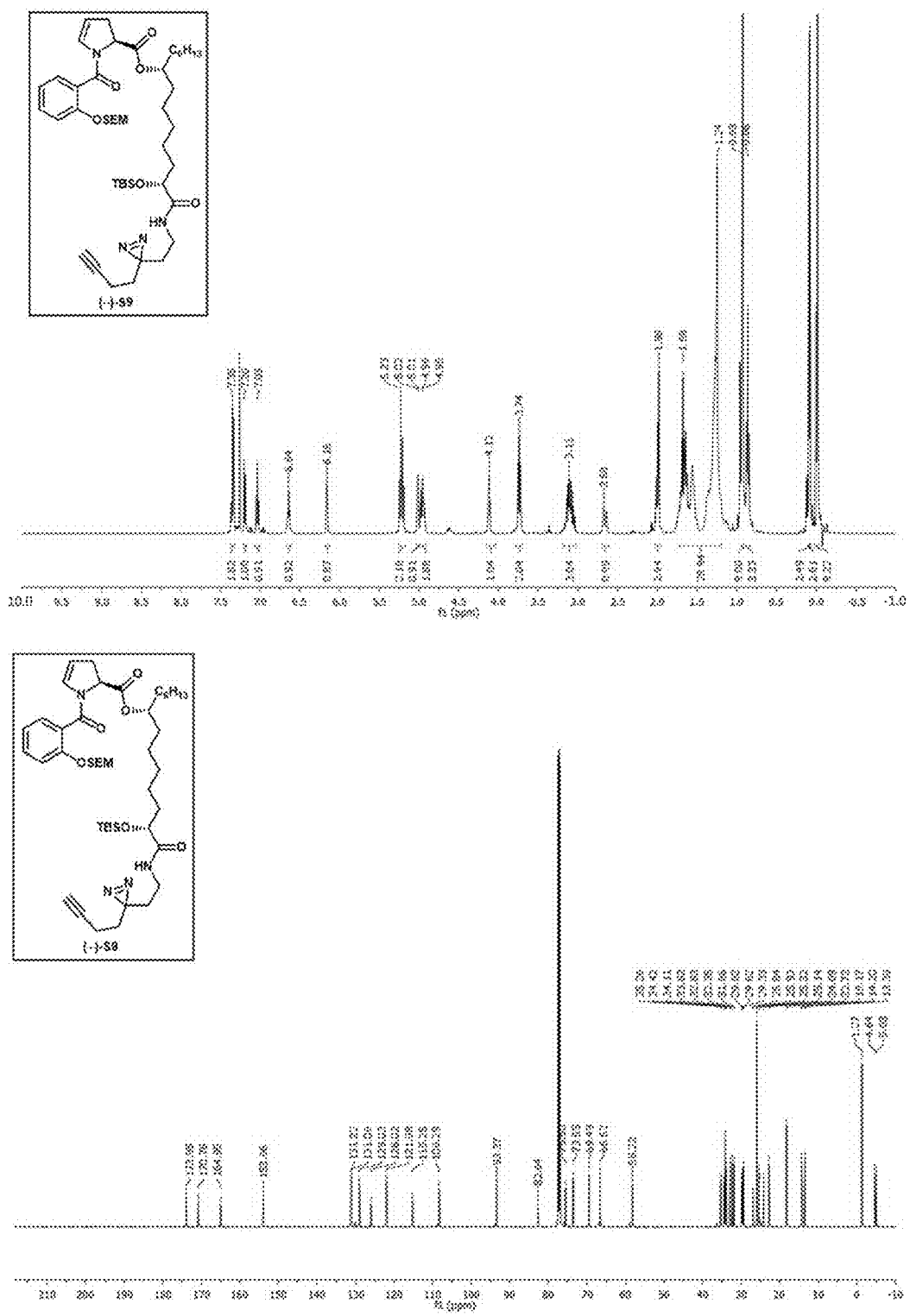

FIG. 127 depicts the proton ($^1$H) and carbon ($^{13}$C) NMR spectra of promysalin photoaffinity probe intermediate (−)-S9.

Figure 128:
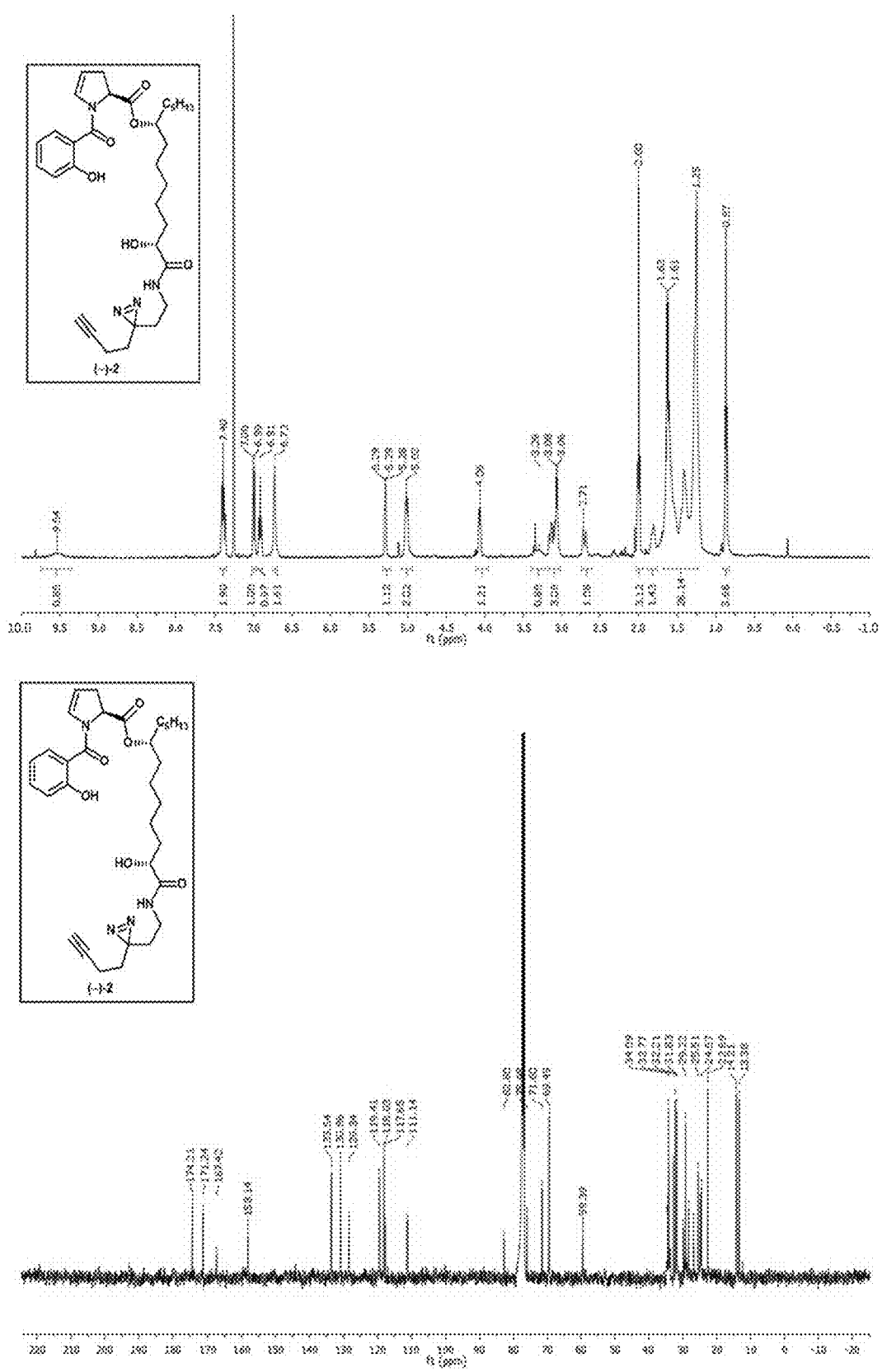

FIG. 128 depicts the proton ($^1$H) and carbon ($^{13}$C) NMR spectra of promysalin photoaffinity probe (−)-2.

Figure 129:
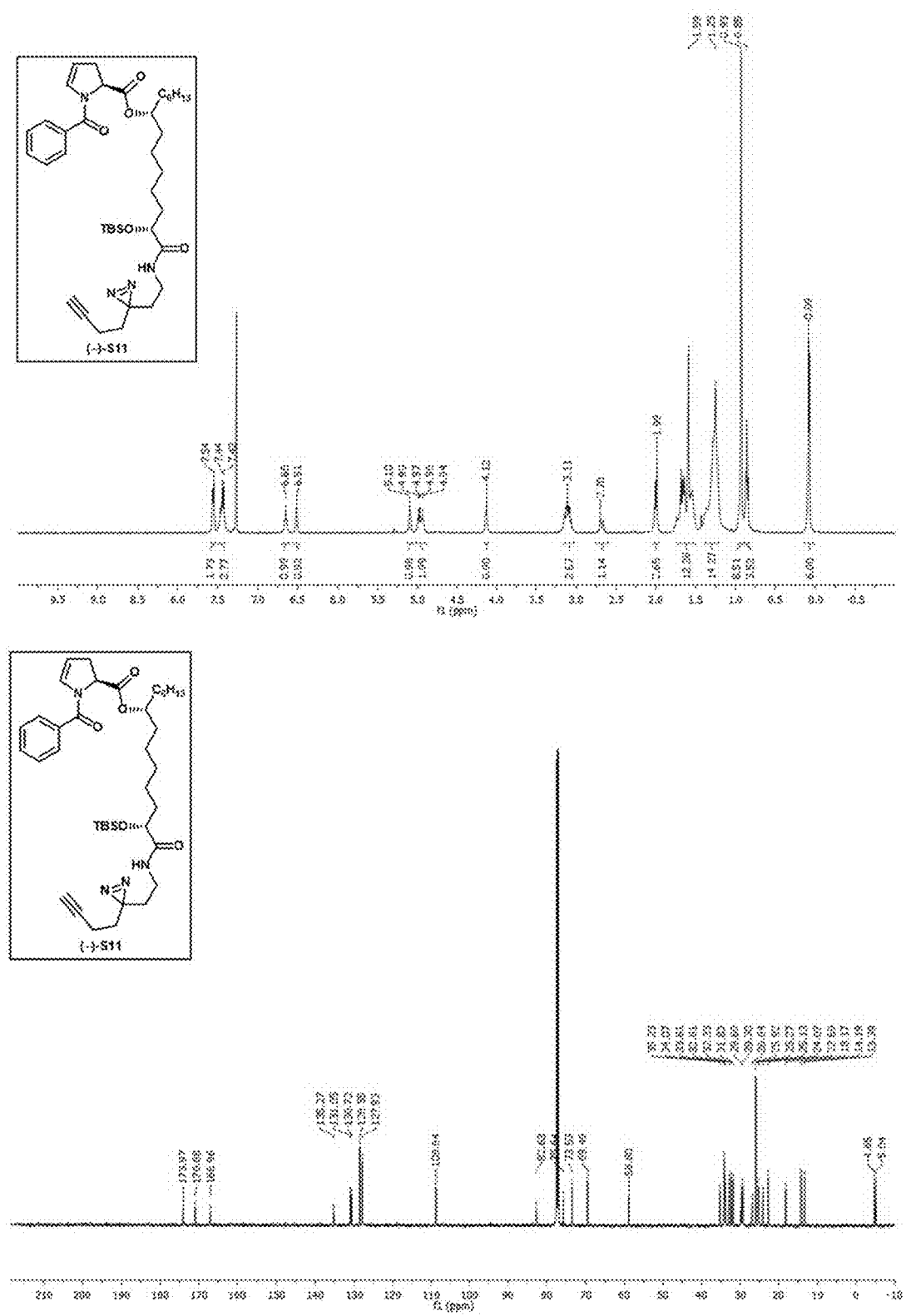

FIG. 129 depicts the proton ($^1$H) and carbon ($^{13}$C) NMR spectra of promysalin photoaffinity probe intermediate (−)-S11.

Figure 130:
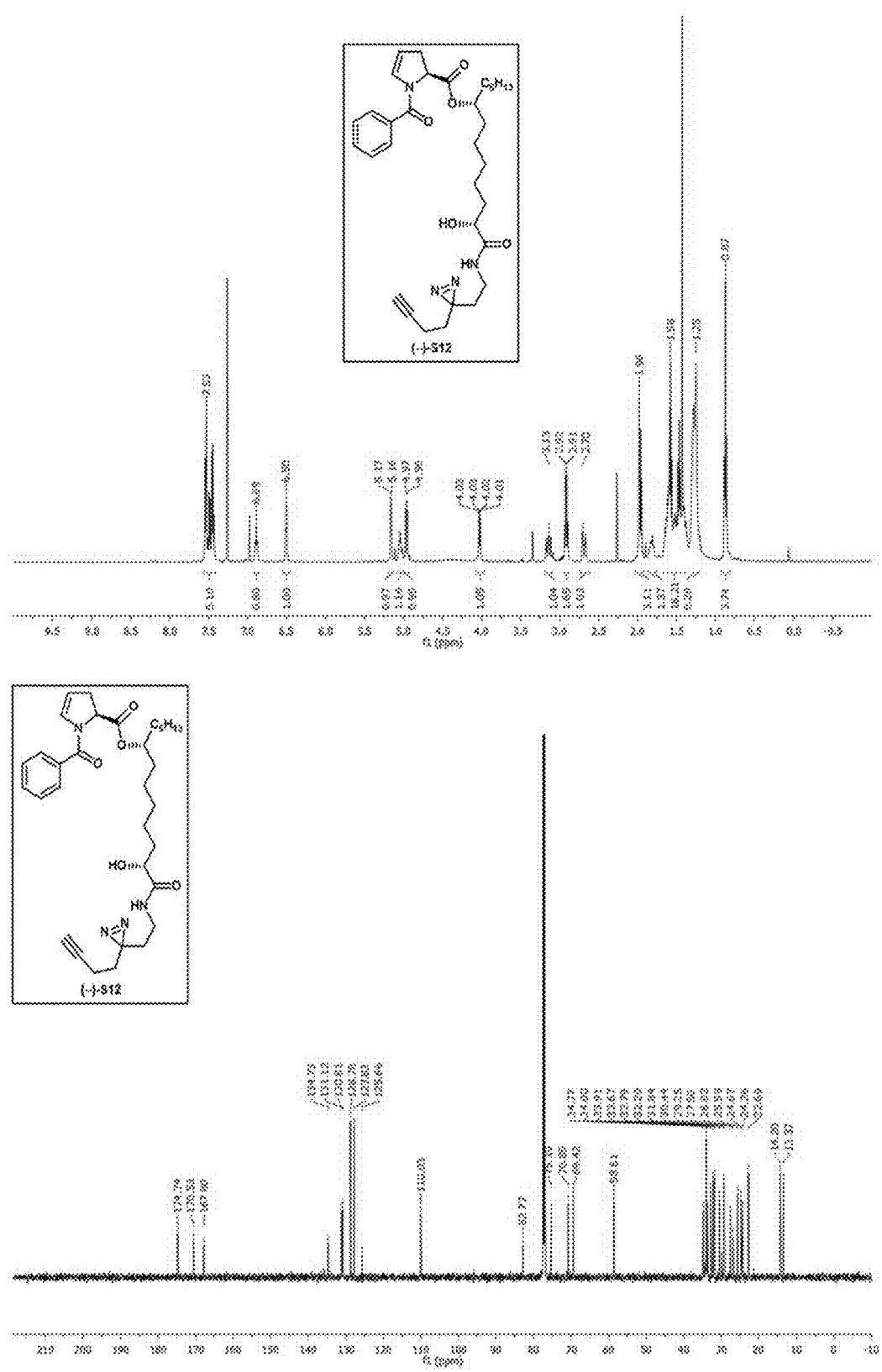

FIG. 130 depicts the proton ($^1$H) and carbon ($^{13}$C) NMR spectra of promysalin photoaffinity probe (−)-S12.

DETAILED DESCRIPTION OF THE INVENTION

It is to be understood that the figures and descriptions of the present invention have been simplified to illustrate elements that are relevant for a clear understanding of the present invention, while eliminating, for the purpose of clarity, many other elements found in the art related to organic chemistry and methods of treating microbial infections. Those of ordinary skill in the art may recognize that other elements and/or steps are desirable and/or required in implementing the present invention. However, because such elements and steps are well known in the art, and because they do not facilitate a better understanding of the present invention, a discussion of such elements and steps is not provided herein. The disclosure herein is directed to all such variations and modifications to such elements and methods known to those skilled in the art. Although any methods, materials and components similar or equivalent to those described herein can be used in the practice or testing of the present invention, the preferred methods and materials are described.

Definitions

Unless defined otherwise, all technical and scientific terms used herein have the same meaning as commonly understood by one of ordinary skill in the art to which this invention belongs. Although any methods, materials and components similar or equivalent to those described herein can be used in the practice or testing of the present invention, the preferred methods and materials are described.

As used herein, each of the following terms has the meaning associated with it in this section.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

A "disease" is a state of health of an animal wherein the animal cannot maintain homeostasis, and wherein if the disease is not ameliorated then the animal's health continues to deteriorate.

In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

A disease or disorder is "alleviated" if the severity of a sign or symptom of the disease or disorder, the frequency with which such a sign or symptom is experienced by a patient, or both, is reduced.

The terms "patient," "subject," or "individual" are used interchangeably herein, and refer to any animal, or cells thereof whether in vitro or in situ, amenable to the methods described herein. In a non-limiting embodiment, the patient, subject or individual is a human.

As used herein, the term "pharmaceutical composition" refers to a mixture of at least one compound useful within the invention with a pharmaceutically acceptable carrier. The pharmaceutical composition facilitates administration of the compound to a patient or subject. Multiple techniques of administering a compound exist in the art including, but not limited to, intravenous, oral, aerosol, parenteral, ophthalmic, pulmonary and topical administration.

A "therapeutic" treatment is a treatment administered to a subject who exhibits signs of pathology, for the purpose of diminishing or eliminating those signs.

As used herein, the term "treatment" or "treating" is defined as the application or administration of a therapeutic agent, i.e., a compound of the invention (alone or in combination with another pharmaceutical agent), to a patient, or application or administration of a therapeutic agent to an isolated tissue or cell line from a patient (e.g., for diagnosis or ex vivo applications), who has a condition contemplated herein, a sign or symptom of a condition contemplated herein or the potential to develop a condition contemplated herein, with the purpose to cure, heal, alleviate, relieve, alter, remedy, ameliorate, improve or affect a condition contemplated herein, at least one sign or symptom of a condition contemplated herein or the potential to develop a condition contemplated herein. Such treatments may be specifically tailored or modified, based on knowledge obtained from the field of pharmacogenomics.

As used herein, the terms "effective amount," "pharmaceutically effective amount" and "therapeutically effective amount" refer to a nontoxic but sufficient amount of an agent to provide the desired biological result. That result may be reduction and/or alleviation of a sign, a symptom, or a cause of a disease or disorder, or any other desired alteration of a biological system. An appropriate therapeutic amount in any individual case may be determined by one of ordinary skill in the art using routine experimentation.

As used herein, the term "pharmaceutically acceptable" refers to a material, such as a carrier or diluent, which does not abrogate the biological activity or properties of the compound, and is relatively non-toxic, i.e., the material may be administered to an individual without causing an undesirable biological effect or interacting in a deleterious manner with any of the components of the composition in which it is contained.

As used herein, the language "pharmaceutically acceptable salt" refers to a salt of the administered compound prepared from pharmaceutically acceptable non-toxic acids, including inorganic acids, organic acids, solvates, hydrates, or clathrates thereof. Examples of such inorganic acids are hydrochloric, hydrobromic, hydroiodic, nitric, sulfuric, phosphoric, acetic, hexafluorophosphoric, citric, gluconic, benzoic, propionic, butyric, sulfosalicylic, maleic, lauric, malic, fumaric, succinic, tartaric, amsonic, pamoic, p-tolunenesulfonic, and mesylic. Appropriate organic acids may be selected, for example, from aliphatic, aromatic, carboxylic and sulfonic classes of organic acids, examples of which are formic, acetic, propionic, succinic, camphorsulfonic, citric, fumaric, gluconic, isethionic, lactic, malic, mucic, tartaric, para-toluenesulfonic, glycolic, glucuronic, maleic, furoic, glutamic, benzoic, anthranilic, salicylic, phenylacetic, mandelic, embonic (pamoic), methanesulfonic, ethanesulfonic, pantothenic, benzenesulfonic (besylate), stearic, sulfanilic, alginic, galacturonic, and the like. Furthermore, pharmaceutically acceptable salts include, by way of non-limiting example, alkaline earth metal salts (e.g., calcium or magnesium), alkali metal salts (e.g., sodium-dependent or potassium), and ammonium salts.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

An "effective amount" of a delivery vehicle is that amount sufficient to effectively bind or deliver a compound.

As used herein, the term "potency" refers to the dose needed to produce half the maximal response ($ED_{50}$).

As used herein, the term "efficacy" refers to the maximal effect ($E_{max}$) achieved within an assay.

As used herein, the term "alkyl," by itself or as part of another substituent means, unless otherwise stated, a straight or branched chain hydrocarbon having the number of carbon atoms designated (i.e. $C_{1-6}$ means one to six carbon atoms) and including straight, branched chain, or cyclic substituent groups. Examples include methyl, ethyl, propyl, isopropyl, butyl, isobutyl, tert-butyl, pentyl, neopentyl, hexyl, and cyclopropylmethyl.

As used herein, the term "substituted alkyl" means alkyl as defined above, substituted by one, two or three substituents selected from the group consisting of halogen, —OH, alkoxy, —NH$_2$, amino, azido, —N(CH$_3$)$_2$, —C(═O)OH, trifluoromethyl, —C≡N, —C(═O)O(C$_1$-C$_4$)alkyl, —C(═O)NH$_2$, —SO$_2$NH$_2$, —C(═NH)NH$_2$, and —NO$_2$. Examples of substituted alkyls include, but are not limited to, 2,2-difluoropropyl, 2-carboxycyclopentyl and 3-chloropropyl.

As used herein, the term "heteroalkyl" by itself or in combination with another term means, unless otherwise stated, a stable straight or branched chain alkyl group consisting of the stated number of carbon atoms and one or two heteroatoms selected from the group consisting of O, N, and S, and wherein the nitrogen and sulfur atoms may be optionally oxidized and the nitrogen heteroatom may be optionally quaternized. The heteroatom(s) may be placed at any position of the heteroalkyl group, including between the rest of the heteroalkyl group and the fragment to which it is attached, as well as attached to the most distal carbon atom in the heteroalkyl group. Examples include: —O—CH$_2$—CH$_2$—CH$_3$, —CH$_2$—CH$_2$—CH$_2$—OH, —CH$_2$—CH$_2$—NH—CH$_3$, —CH$_2$—S—CH$_2$—CH$_3$, and —CH$_2$CH$_2$—S(═O)—CH$_3$. Up to two heteroatoms may be consecutive, such as, for example, —CH$_2$—NH—OCH$_3$, or —CH$_2$—CH$_2$—S—S—CH$_3$ As used herein, the term "alkoxy" employed alone or in combination with other terms means, unless otherwise stated, an alkyl group having the designated number of carbon atoms, as defined above, connected to the rest of the molecule via an oxygen atom, such as, for example, methoxy, ethoxy, 1-propoxy, 2-propoxy (isopropoxy) and the higher homologs and isomers.

As used herein, the term "halo" or "halogen" alone or as part of another substituent means, unless otherwise stated, a fluorine, chlorine, bromine, or iodine atom.

As used herein, the term "cycloalkyl" refers to a mono cyclic or polycyclic non-aromatic radical, wherein each of the atoms forming the ring (i.e. skeletal atoms) is a carbon atom. In one embodiment, the cycloalkyl group is saturated or partially unsaturated. In another embodiment, the cycloalkyl group is fused with an aromatic ring. Cycloalkyl groups include groups having from 3 to 10 ring atoms. Illustrative examples of cycloalkyl groups include, but are not limited to, the following moieties:

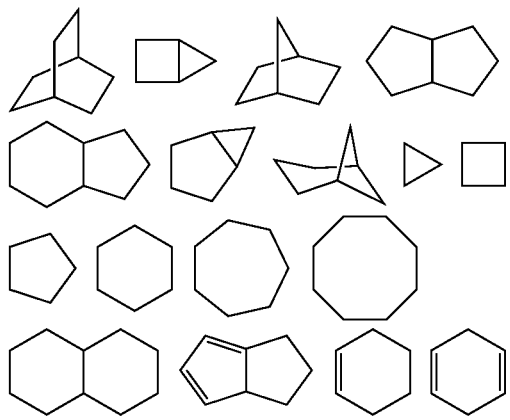

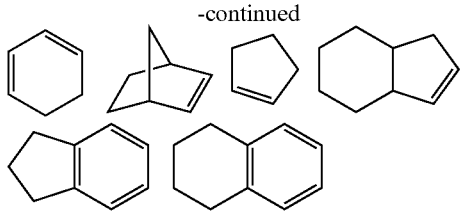

Monocyclic cycloalkyls include, but are not limited to, cyclopropyl, cyclobutyl, cyclopentyl, cyclohexyl, cycloheptyl, and cyclooctyl. Dicyclic cycloalkyls include, but are not limited to, tetrahydronaphthyl, indanyl, and tetrahydropentalene. Polycyclic cycloalkyls include adamantine and norbornane. The term cycloalkyl includes "unsaturated nonaromatic carbocyclyl" or "nonaromatic unsaturated carbocyclyl" groups, both of which refer to a nonaromatic carbocycle as defined herein, which contains at least one carbon double bond or one carbon triple bond.

As used herein, the term "heterocycloalkyl" or "heterocyclyl" refers to a heteroalicyclic group containing one to four ring heteroatoms each selected from O, S and N. In one embodiment, each heterocycloalkyl group has from 4 to 10 atoms in its ring system, with the proviso that the ring of said group does not contain two adjacent O or S atoms. In another embodiment, the heterocycloalkyl group is fused with an aromatic ring. In one embodiment, the nitrogen and sulfur heteroatoms may be optionally oxidized, and the nitrogen atom may be optionally quaternized. The heterocyclic system may be attached, unless otherwise stated, at any heteroatom or carbon atom that affords a stable structure. A heterocycle may be aromatic or non-aromatic in nature. In one embodiment, the heterocycle is a heteroaryl.

An example of a 3-membered heterocycloalkyl group includes, and is not limited to, aziridine. Examples of 4-membered heterocycloalkyl groups include, and are not limited to, azetidine and a beta lactam. Examples of 5-membered heterocycloalkyl groups include, and are not limited to, pyrrolidine, oxazolidine and thiazolidinedione. Examples of 6-membered heterocycloalkyl groups include, and are not limited to, piperidine, morpholine and piperazine. Other non-limiting examples of heterocycloalkyl groups are:

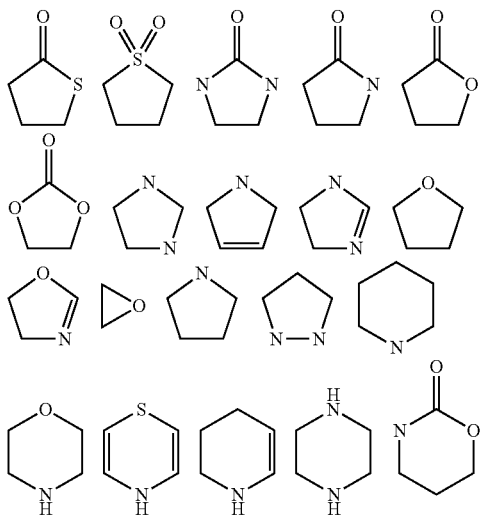

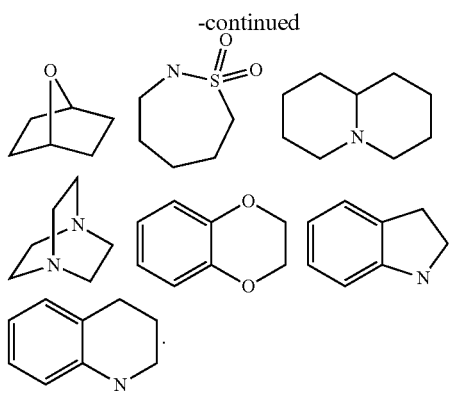

Examples of non-aromatic heterocycles include monocyclic groups such as aziridine, oxirane, thiirane, azetidine, oxetane, thietane, pyrrolidine, pyrroline, pyrazolidine, imidazoline, dioxolane, sulfolane, 2,3-dihydrofuran, 2,5-dihydrofuran, tetrahydrofuran, thiophane, piperidine, 1,2,3,6-tetrahydropyridine, 1,4-dihydropyridine, piperazine, morpholine, thiomorpholine, pyran, 2,3-dihydropyran, tetrahydropyran, 1,4-dioxane, 1,3-dioxane, homopiperazine, homopiperidine, 1,3-dioxepane, 4,7-dihydro-1,3-dioxepin, and hexamethyleneoxide.

As used herein, the term "aromatic" refers to a carbocycle or heterocycle with one or more polyunsaturated rings and having aromatic character, i.e. having (4n+2) delocalized π (pi) electrons, where n is an integer.

As used herein, the term "aryl," employed alone or in combination with other terms, means, unless otherwise stated, a carbocyclic aromatic system containing one or more rings (typically one, two or three rings), wherein such rings may be attached together in a pendent manner, such as a biphenyl, or may be fused, such as naphthalene. Examples of aryl groups include phenyl, anthracyl, and naphthyl.

As used herein, the term "aryl-($C_1$-$C_3$)alkyl" means a functional group wherein a one- to three-carbon alkylene chain is attached to an aryl group, e.g., —$CH_2CH_2$-phenyl. Preferred is aryl-$CH_2$— and aryl-$CH(CH_3)$—. The term "substituted aryl-($C_1$-$C_3$)alkyl" means an aryl-($C_1$-$C_3$)alkyl functional group in which the aryl group is substituted. Similarly, the term "heteroaryl-($C_1$-$C_3$)alkyl" means a functional group wherein a one to three carbon alkylene chain is attached to a heteroaryl group, e.g., —$CH_2CH_2$-pyridyl. The term "substituted heteroaryl-($C_1$-$C_3$)alkyl" means a heteroaryl-($C_1$-$C_3$)alkyl functional group in which the heteroaryl group is substituted.

As used herein, the term "heteroaryl" or "heteroaromatic" refers to a heterocycle having aromatic character. A polycyclic heteroaryl may include one or more rings that are partially saturated. Examples include the following moieties:

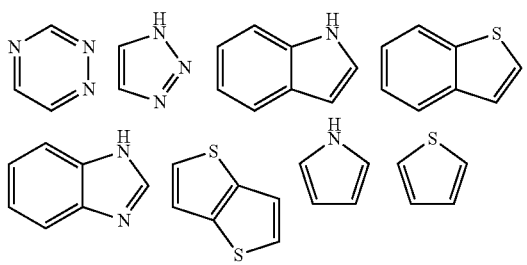

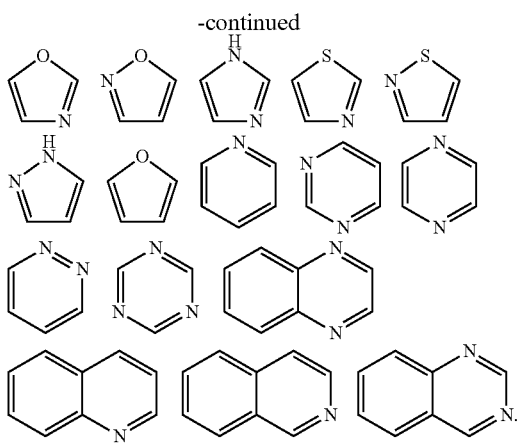

Examples of heteroaryl groups also include pyridyl, pyrazinyl, pyrimidinyl (particularly 2- and 4-pyrimidinyl), pyridazinyl, thienyl, furyl, pyrrolyl (particularly 2-pyrrolyl), imidazolyl, thiazolyl, oxazolyl, pyrazolyl (particularly 3- and 5-pyrazolyl), isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl. Examples of polycyclic heterocycles and heteroaryls include indolyl (particularly 3-, 4-, 5-, 6- and 7-indolyl), indolinyl, quinolyl, tetrahydroquinolyl, isoquinolyl (particularly 1- and 5-isoquinolyl), 1,2,3,4-tetrahydroisoquinolyl, cinnolinyl, quinoxalinyl (particularly 2- and 5-quinoxalinyl), quinazolinyl, phthalazinyl, 1,8-naphthyridinyl, 1,4-benzodioxanyl, coumarin, dihydrocoumarin, 1,5-naphthyridinyl, benzofuryl (particularly 3-, 4-, 5-, 6- and 7-benzofuryl), 2,3-dihydrobenzofuryl, 1,2-benzisoxazolyl, benzothienyl (particularly 3-, 4-, 5-, 6-, and 7-benzothienyl), benzoxazolyl, benzothiazolyl (particularly 2-benzothiazolyl and 5-benzothiazolyl), purinyl, benzimidazolyl (particularly 2-benzimidazolyl), benzotriazolyl, thioxanthinyl, carbazolyl, carbolinyl, acridinyl, pyrrolizidinyl, and quinolizidinyl.

As used herein, the term "substituted" means that an atom or group of atoms has replaced hydrogen as the substituent attached to another group. The term "substituted" further refers to any level of substitution, namely mono-, di-, tri-, tetra-, or penta-substitution, where such substitution is permitted. The substituents are independently selected, and substitution may be at any chemically accessible position. In one embodiment, the substituents vary in number between one and four. In another embodiment, the substituents vary in number between one and three. In yet another embodiment, the substituents vary in number between one and two.

As used herein, the term "optionally substituted" means that the referenced group may be substituted or unsubstituted. In one embodiment, the referenced group is optionally substituted with zero substituents, i.e., the referenced group is unsubstituted. In another embodiment, the referenced group is optionally substituted with one or more additional group(s) individually and independently selected from groups described herein.

In one embodiment, the substituents are independently selected from the group consisting of oxo, halogen, —CN, —NH$_2$, —OH, —NH(CH$_3$), —N(CH$_3$)$_2$, alkyl (including straight chain, branched and/or unsaturated alkyl), substituted or unsubstituted cycloalkyl, substituted or unsubstituted heterocycloalkyl, fluoro alkyl, substituted or unsubstituted heteroalkyl, substituted or unsubstituted alkoxy, fluoroalkoxy, —S-alkyl, S(=O)$_2$alkyl, —C(=O)NH[substituted or unsubstituted alkyl, or substituted or unsubstituted phenyl], —C(=O)N[H or alkyl]$_2$, —OC(=O)N[substituted or unsubstituted alkyl]$_2$, —NHC(=O)NH [substituted or unsubstituted alkyl, or substituted or unsubstituted phenyl], —NHC(=O)alkyl, —N[substituted or unsubstituted alkyl]C(=O)[substituted or unsubstituted alkyl], —NHC(=O)[substituted or unsubstituted alkyl], —C(OH)[substituted or unsubstituted alkyl]$_2$, and —C(NH$_2$)[substituted or unsubstituted alkyl]$_2$. In another embodiment, by way of example, an optional substituent is selected from oxo, fluorine, chlorine, bromine, iodine, —CN, —NH$_2$, —OH, —NH(CH$_3$), —N(CH$_3$)$_2$, —CH$_3$, —CH$_2$CH$_3$, —CH(CH$_3$)$_2$, —CF$_3$, —CH$_2$CF$_3$, —OCH$_3$, —OCH$_2$CH$_3$, —OCH(CH$_3$)$_2$, —OCF$_3$, —OCH$_2$CF$_3$, —S(=O)$_2$—CH$_3$, —C(=O)NH$_2$, —C(=O)—NHCH$_3$, —NHC(=O)NHCH$_3$, —C(=O)CH$_3$, —ON(O)$_2$, and —C(=O)OH. In yet one embodiment, the substituents are independently selected from the group consisting of C$_{1-6}$ alkyl, —OH, C$_{1-6}$ alkoxy, halo, amino, acetamido, oxo and nitro. In yet another embodiment, the substituents are independently selected from the group consisting of C$_{1-6}$ alkyl, C$_{1-6}$ alkoxy, halo, acetamido, and nitro. As used herein, where a substituent is an alkyl or alkoxy group, the carbon chain may be branched, straight or cyclic, with straight being preferred.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

Description

This invention includes the unexpected identification of novel analogs of promysalin that are useful for the treatment of microbial infections. In one embodiment, the microbial infection is a *Psuedomonas aeruginosa* (PA) infection. As demonstrated herein, the compounds of the present invention have been shown to be effective against multiple PA strains.

In one aspect, the compounds of the invention may be useful as species-specific antibiotics. As opposed to broad-spectrum antibiotics, species-specific antibiotics would permit targeting only one microbe in a multispecies environment, and would reduce the misuse and unintended side effects observed with the use of broad-spectrum antibiotics. Thus, in one embodiment, the compounds of the invention are species-specific.

The present invention also includes novel methods of treating or preventing a microbial infection using the compounds of the invention. In one embodiment, the microbial infection is a bacterial infection. In one embodiment, the bacterial infection is a *Psuedomonas aeruginosa* (PA) infection.

The present invention includes a composition comprising at least one compound of the invention. The present invention also includes a pharmaceutical composition comprising at least one compound of the invention.

Compounds

The compounds of the present invention may be synthesized using techniques well-known in the art of organic synthesis. The starting materials and intermediates required for the synthesis may be obtained from commercial sources or synthesized according to methods known to those skilled in the art.

In one aspect, the compound of the invention is a compound of formula I, or a salt or solvate thereof:

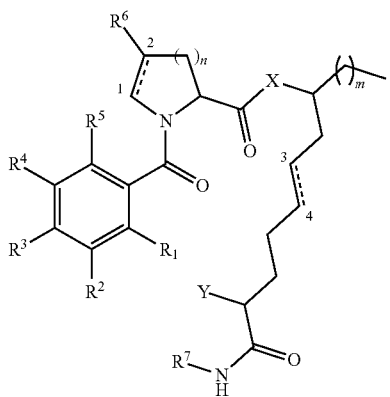

wherein in formula I:

$R^1$, $R^2$, $R^3$, $R^4$, $R^5$, and $R^6$ are each independently selected from the group consisting of H, —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, —$OR^7$, —$SR^7$, —S(=O)$R^7$, —S(=O)$_2R^7$, —NHS(=O)$_2R^7$, —C(=O)$R^7$, —OC(=O)$R^7$, —$CO_2R^7$, —$OCO_2R^7$, —CH($R^7$)$_2$, —N($R^7$)$_2$, —C(=O)N($R^7$)$_2$, —OC(=O)N($R^7$)$_2$, —NHC(=O)NH($R^7$), —NHC(=O)$R^7$, —NHC(=O)$OR^7$, —C(OH)($R^7$)$_2$, and —C($NH_2$)($R^7$)$_2$, wherein the alkyl, aryl, heteroaryl, cycloalkyl, heterocycloalkyl, and $C_1$-$C_6$ heteroalkyl group is optionally substituted;

each occurrence of $R^7$ is independently selected from the group consisting of H and —$C_1$-$C_6$ alkyl, wherein the alkyl group is optionally substituted;

the bond between carbons 1 and 2 and the bond between carbons 3 and 4 each independently represents a single or double bond;

X is O or $NR^7$;

Y is selected from the group consisting of H, $OR^7$, halogen, and —$NHR^7$;

n is 1 or 2; and m is an integer from 0 to 8.

In one embodiment, the compound of formula I is not:

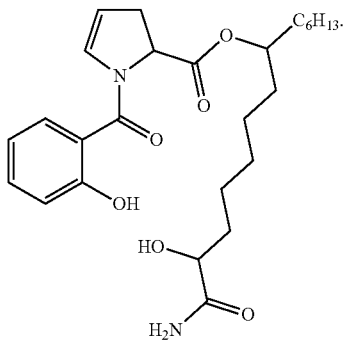

In another aspect, the compound of the invention is a compound of formula II, or a salt or solvate thereof:

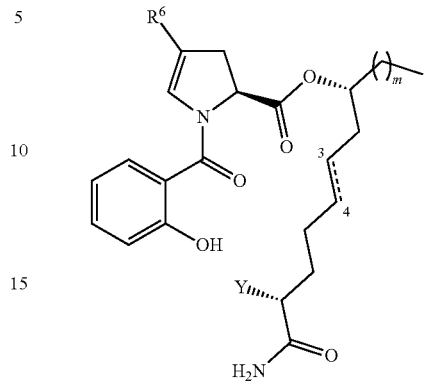

wherein in formula II:

$R^6$ is selected from the group consisting of H, —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, —$OR^7$, —$SR^7$, —S(=O)$R^7$, —S(=O)$_2R^7$, —NHS(=O)$_2R^7$, —C(=O)$R^7$, —OC(=O)$R^7$, —$CO_2R^7$, —$OCO_2R^7$, —CH($R^7$)$_2$, —N($R^7$)$_2$, —C(=O)N($R^7$)$_2$, —OC(=O)N($R^7$)$_2$, —NHC(=O)NH($R^7$), —NHC(=O)$R^7$, —NHC(=O)$OR^7$, —C(OH)($R^7$)$_2$, and —C($NH_2$)($R^7$)$_2$, wherein the alkyl, aryl, heteroaryl, cycloalkyl, heterocycloalkyl, and $C_1$-$C_6$ heteroalkyl group is optionally substituted;

each occurrence of $R^7$ is independently selected from the group consisting of H and —$C_1$-$C_6$ alkyl, wherein the alkyl group is optionally substituted;

the bond between carbons 3 and 4 represents a single or double bond;

Y is H or $OR^7$; and m is an integer from 4 to 6.

In one embodiment, the compound of formula II is not:

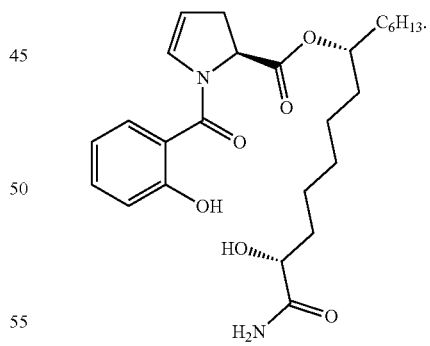

In one embodiment, $R^1$, is —OH. In one embodiment, $R^1$ is —$OR^7$.

In one embodiment, $R^2$ is H. In one embodiment, $R^2$ is —OH. In one embodiment, $R^2$ is —$OR^7$.

In one embodiment, $R^3$ is H. In one embodiment, $R^3$ is —OH. In one embodiment, $R^3$ is —$OR^7$.

In one embodiment, $R^4$ is H. In one embodiment, $R^4$ is —OH. In one embodiment, $R^4$ is —$OR^7$.

In one embodiment, $R^5$ is H. In one embodiment, $R^5$ is —OH. In one embodiment, $R^5$ is —$OR^7$.

In one embodiment, R⁶ is H. In one embodiment, R⁶ is F. In one embodiment, R⁶ is —C₁-C₆ alkyl.

In one embodiment, R⁷ is H. In one embodiment, R⁷ is —C₁-C₆ alkyl. In one embodiment, R⁷ is methyl.

In one embodiment, the bond between carbons 1 and 2 represents a single bond. In one embodiment, the bond between carbons 1 and 2 represents a double bond.

In one embodiment, the bond between carbons 3 and 4 represents a single bond. In one embodiment, the bond between carbons 3 and 4 represents a double bond.

In one embodiment, X is O. In one embodiment, X is NR⁷.

In one embodiment, Y is H. In one embodiment, Y is OR⁷.

In one embodiment, n is 1. In one embodiment, n is 2.

In one embodiment, m is 5.

In one embodiment, the compound is selected from the group consisting of (1R,7R)-1-carbamoyl-1-hydroxytridecan-7-yl(2S)-1-(2-hydroxybenzoyl)pyrrolidine-2-carboxylate, (1R,7R)-1-carbamoyl-1-hydroxytridecan-7-yl (2S)-1-(2-hydroxybenzoyl)piperidine-2-carboxylate, (1R,7R)-1-carbamoyl-1-hydroxytridecan-7-yl (2S,4R)-4-hydroxy-1-(2-hydroxybenzoyl)pyrrolidine-2-carboxylate, (7R,13R)-14-amino-13-hydroxy-14-oxotetradecan-7-yl (S)-4-fluoro-1-(2-hydroxybenzoyl)-2,3-dihydro-1H-pyrrole-2-carboxylate, (7R,13R)-14-amino-13-hydroxy-14-oxotetradecan-7-yl (S)-1-(2-hydroxybenzoyl)-4-methyl-2,3-dihydro-1H-pyrrole-2-carboxylate, (1R,7R)-1-carbamoyl-1-hydroxytridecan-7-yl (2S)-1-(2-methoxybenzoyl)-2,3-dihydro-1H-pyrrole-2-carboxylate, (7R,13R)-14-amino-13-hydroxy-14-oxotetradecan-7-yl (S)-1-(3-hydroxybenzoyl)-2,3-dihydro-1H-pyrrole-2-carboxylate, (1R,7R)-1-carbamoyl-1-hydroxytridecan-7-yl (2S)-1-(4-hydroxybenzoyl)-2,3-dihydro-1H-pyrrole-2-carboxylate, (1R,7R)-1-carbamoyl-1-hydroxytridecan-7-yl (2S)-1-benzoyl-2,3-dihydro-1H-pyrrole-2-carboxylate, (7R,13R)-14-amino-13-hydroxy-14-oxotetradecan-7-yl (S)-1-(2-hydroxy-6-methoxybenzoyl)-2,3-dihydro-1H-pyrrole-2-carboxylate, (1R,7R)-1-carbamoyl-1-hydroxytridecan-7-yl (2S)-1-(3,4,5-trimethoxybenzoyl)-2,3-dihydro-1H-pyrrole-2-carboxylate, (7R,13R)-14-amino-13-hydroxy-14-oxotetradecan-7-yl (S)-1-(2-nitrobenzoyl)-2,3-dihydro-1H-pyrrole-2-carboxylate, (R)-14-amino-14-oxotetradecan-7-yl(S)-1-(2-hydroxybenzoyl)-2,3-dihydro-1H-pyrrole-2-carboxylate, (7R,13R)-14-amino-13-methoxy-14-oxotetradecan-7-yl (S)-1-(2-hydroxybenzoyl)-2,3-dihydro-1H-pyrrole-2-carboxylate, (S)—N-((7R,13R)-14-amino-13-hydroxy-14-oxotetradecan-7-yl)-1-(2-hydroxybenzoyl)-2,3-dihydro-1H-pyrrole-2-carboxamide, and (7R,13R,E)-14-amino-13-hydroxy-14-oxotetradec-9-en-7-yl(S)-1-(2-hydroxybenzoyl)-2,3-dihydro-1H-pyrrole-2-carboxylate, or a salt or solvate thereof.

In one embodiment, the compound is selected from the group consisting of (7R,13R)-14-amino-13-hydroxy-14-oxotetradecan-7-yl(S)-4-fluoro-1-(2-hydroxybenzoyl)-2,3-dihydro-1H-pyrrole-2-carboxylate, (R)-14-amino-14-oxotetradecan-7-yl(S)-1-(2-hydroxybenzoyl)-2,3-dihydro-1H-pyrrole-2-carboxylate, and (7R,13R,E)-14-amino-13-hydroxy-14-oxotetradec-9-en-7-yl(S)-1-(2-hydroxybenzoyl)-2,3-dihydro-1H-pyrrole-2-carboxylate, or a salt or solvate thereof.

The structures and corresponding names of the compounds are illustrated in Table A.

TABLE A

| | Compounds of the present invention | |
|---|---|---|
| Structure | Name | Compound Name |
| | (1R,7R)-1-carbamoyl-1-hydroxytridecan-7-yl (2S)-1-(2-hydroxybenzoyl)pyrrolidine-2-carboxylate | (−)-6 |

TABLE A-continued

Compounds of the present invention

| Structure | Name | Compound Name |
|---|---|---|
| 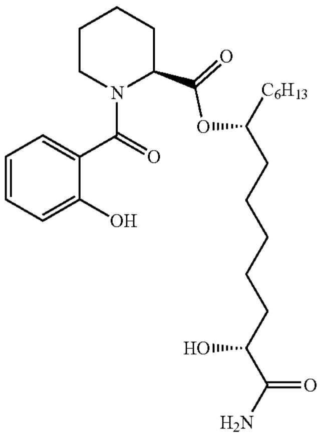 | (1R,7R)-1-carbamoyl-1-hydroxytridecan-7-yl (2S)-1-(2-hydroxybenzoyl)piperidine-2-carboxylate | (+)-7 |
| 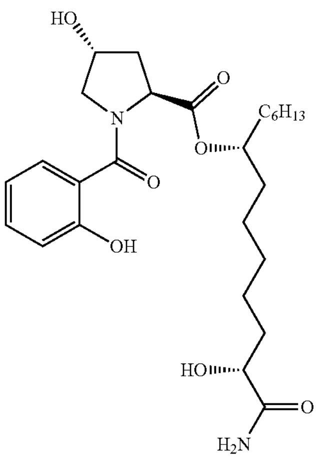 | (1R,7R)-1-carbamoyl-1-hydroxytridecan-7-yl (2S,4R)-4-hydroxy-1-(2-hydroxybenzoyl)pyrrolidine-2-carboxylate | (−)-8 |
| 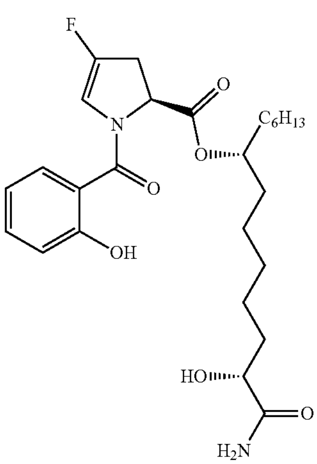 | (7R,13R)-14-amino-13-hydroxy-14-oxotetradecan-7-yl (S)-4-fluoro-1-(2-hydroxybenzoyl)-2,3-dihydro-1H-pyrrole-2-carboxylate | (+)-9 |

TABLE A-continued

Compounds of the present invention

| Structure | Name | Compound Name |
|---|---|---|
| 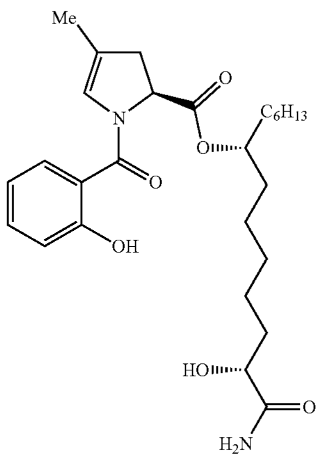 | (7R,13R)-14-amino-13-hydroxy-14-oxotetradecan-7-yl (S)-1-(2-hydroxybenzoyl)-4-methyl-2,3-dihydro-1H-pyrrole-2-carboxylate | (−)-10 |
| 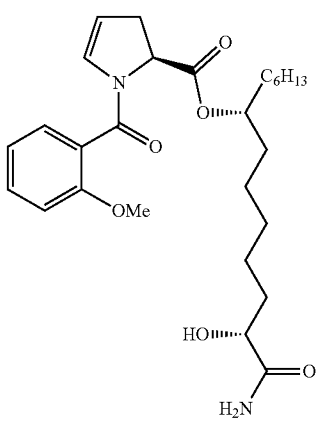 | (1R,7R)-1-carbamoyl-1-hydroxytridecan-7-yl (2S)-1-(2-methoxybenzoyl)-2,3-dihydro-1H-pyrrole-2-carboxylate | (−)-11 |
| 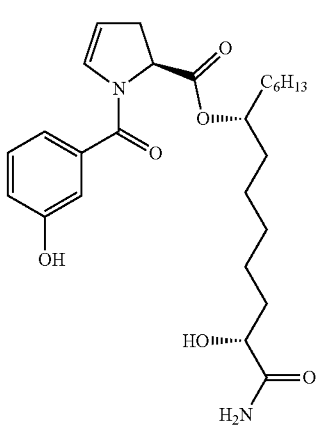 | (7R,13R)-14-amino-13-hydroxy-14-oxotetradecan-7-yl (S)-1-(3-hydroxybenzoyl)-2,3-dihydro-1H-pyrrole-2-carboxylate | (−)-12 |

TABLE A-continued

Compounds of the present invention

| Structure | Name | Compound Name |
|---|---|---|
| 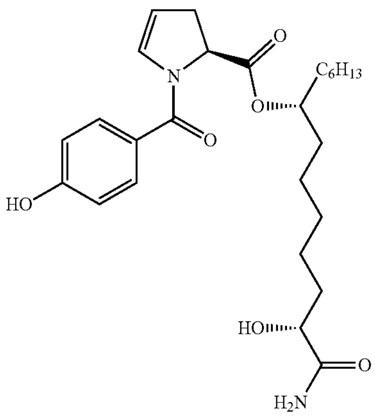 | (1R,7R)-1-carbamoyl-1-hydroxytridecan-7-yl (2S)-1-(4-hydroxybenzoyl)-2,3-dihydro-1H-pyrrole-2-carboxylate | (−)-13 |
| 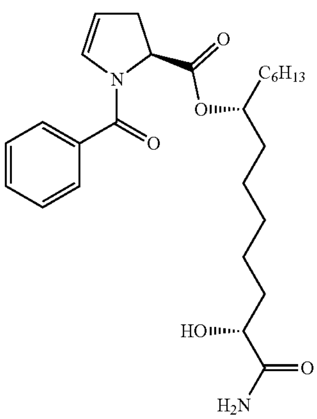 | (1R,7R)-1-carbamoyl-1-hydroxytridecan-7-yl (2S)-1-benzoyl-2,3-dihydro-1H-pyrrole-2-carboxylate | (−)-14 |
| 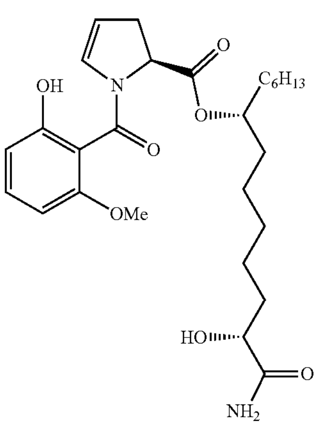 | (7R,13R)-14-amino-13-hydroxy-14-oxotetradecan-7-yl (S)-1-(2-hydroxy-6-methoxybenzoyl)-2,3-dihydro-1H-pyrrole-2-carboxylate | (−)-15 |

TABLE A-continued

Compounds of the present invention

| Structure | Name | Compound Name |
|---|---|---|
| 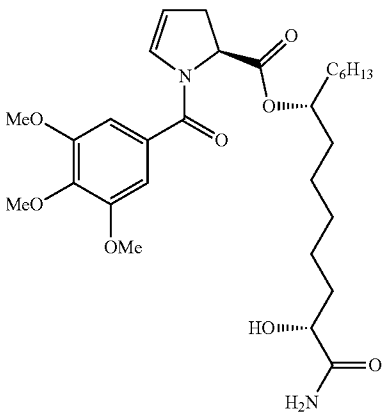 | (1R,7R)-1-carbamoyl-1-hydroxytridecan-7-yl (2S)-1-(3,4,5-trimethoxybenzoyl)-2,3-dihydro-1H-pyrrole-2-carboxylate | (−)-16 |
| 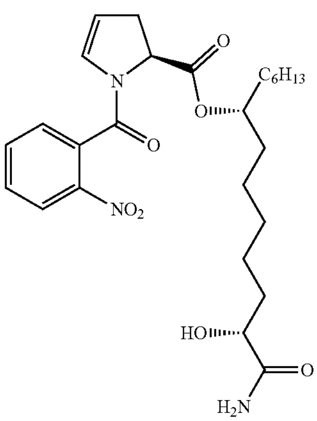 | (7R,13R)-14-amino-13-hydroxy-14-oxotetradecan-7-yl (S)-1-(2-nitrobenzoyl)-2,3-dihydro-1H-pyrrole-2-carboxylate | (−)-17 |
| 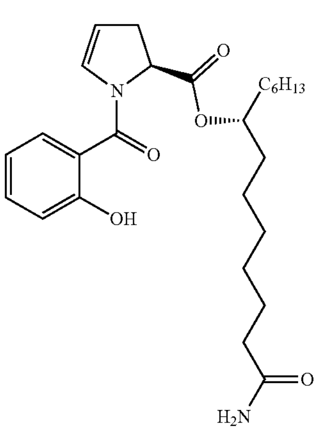 | (R)-14-amino-14-oxotetradecan-7-yl (S)-1-(2-hydroxybenzoyl)-2,3-dihydro-1H-pyrrole-2-carboxylate | (−)-18 |

TABLE A-continued

Compounds of the present invention

| Structure | Name | Compound Name |
|---|---|---|
| 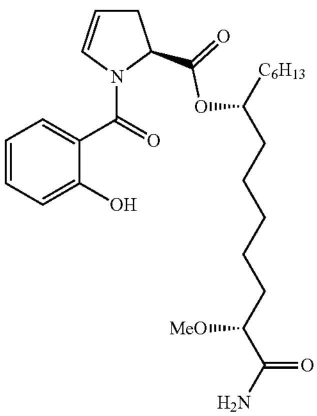 | (7R,13R)-14-amino-13-methoxy-14-oxotetradecan-7-yl (S)-1-(2-hydroxybenzoyl)-2,3-dihydro-1H-pyrrole-2-carboxylate | (−)-19 |
| 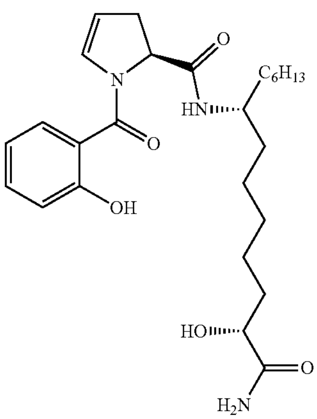 | (S)-N-((7R,13R)-14-amino-13-hydroxy-14-oxotetradecan-7-yl)-1-(2-hydroxybenzoyl)-2,3-dihydro-1H-pyrrole-2-carboxamide | (−)-20 |
| 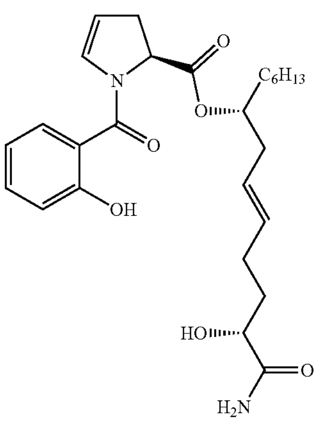 | (7R,13R,E)-14-amino-13-hydroxy-14-oxotetradec-9-en-7-yl (S)-1-(2-hydroxybenzoyl)-2,3-dihydro-1H-pyrrole-2-carboxylate | (−)-21 |

Preparation of the Compounds of the Invention

Compounds of formula I-II may be prepared by the general schemes described herein, using the synthetic method known by those skilled in the art. The following examples illustrate non-limiting embodiments of the invention.

The compounds of the invention may possess one or more stereocenters, and each stereocenter may exist independently in either the R or S configuration. In one embodiment, compounds described herein are present in optically active or racemic forms. It is to be understood that the compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In one embodiment, a mixture of one or more isomer is utilized as the therapeutic compound described herein. In another embodiment, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In one embodiment, the compounds described herein exist in solvated forms with pharmaceutically acceptable solvents such as water, and ethanol. In another embodiment, the compounds described herein exist in unsolvated form.

In one embodiment, the compounds of the invention may exist as tautomers. All tautomers are included within the scope of the compounds presented herein.

In one embodiment, compounds described herein are prepared as prodrugs. A "prodrug" refers to an agent that is converted into the parent drug in vivo. In one embodiment, upon in vivo administration, a prodrug is chemically converted to the biologically, pharmaceutically or therapeutically active form of the compound. In another embodiment, a prodrug is enzymatically metabolized by one or more steps or processes to the biologically, pharmaceutically or therapeutically active form of the compound.

In one embodiment, sites on, for example, the aromatic ring portion of compounds of the invention are susceptible to various metabolic reactions. Incorporation of appropriate substituents on the aromatic ring structures may reduce, minimize or eliminate this metabolic pathway. In one embodiment, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In one embodiment, isotopically-labeled compounds are useful in drug and/or substrate tissue distribution studies. In another embodiment, substitution with heavier isotopes such as deuterium affords greater metabolic stability (for example, increased in vivo half-life or reduced dosage requirements). In yet another embodiment, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In one embodiment, the compounds described herein are labeled by other means, including, but not limited to, the use of chromophores or fluorescent moieties, bioluminescent labels, or chemiluminescent labels.

The compounds described herein, and other related compounds having different substituents are synthesized using techniques and materials described herein and as described, for example, in Fieser & Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), Larock's Comprehensive Organic Transformations (VCH Publishers Inc., 1989), March, Advanced Organic Chemistry 4th Ed., (Wiley 1992); Carey & Sundberg, Advanced Organic Chemistry 4th Ed., Vols. A and B (Plenum 2000, 2001), and Green & Wuts, Protective Groups in Organic Synthesis 3rd Ed., (Wiley 1999) (all of which are incorporated by reference for such disclosure). General methods for the preparation of compound as described herein are modified by the use of appropriate reagents and conditions, for the introduction of the various moieties found in the formula as provided herein.

Compounds described herein are synthesized using any suitable procedures starting from compounds that are available from commercial sources, or are prepared using procedures described herein.

In one embodiment, reactive functional groups, such as hydroxyl, amino, imino, thio or carboxy groups, are protected in order to avoid their unwanted participation in reactions. Protecting groups are used to block some or all of the reactive moieties and prevent such groups from participating in chemical reactions until the protective group is removed. In another embodiment, each protective group is removable by a different means. Protective groups that are cleaved under totally disparate reaction conditions fulfill the requirement of differential removal.

In one embodiment, protective groups are removed by acid, base, reducing conditions (such as, for example, hydrogenolysis), and/or oxidative conditions. Groups such as trityl, dimethoxytrityl, acetal and t-butyldimethylsilyl are acid labile and are used to protect carboxy and hydroxy reactive moieties in the presence of amino groups protected with Cbz groups, which are removable by hydrogenolysis, and Fmoc groups, which are base labile. Carboxylic acid and hydroxy reactive moieties are blocked with base labile groups such as, but not limited to, methyl, ethyl, and acetyl, in the presence of amines that are blocked with acid labile groups, such as t-butyl carbamate, or with carbamates that are both acid and base stable but hydrolytically removable.

In one embodiment, carboxylic acid and hydroxy reactive moieties are blocked with hydrolytically removable protective groups such as the benzyl group, while amine groups capable of hydrogen bonding with acids are blocked with base labile groups such as Fmoc. Carboxylic acid reactive moieties are protected by conversion to simple ester compounds as exemplified herein, which include conversion to alkyl esters, or are blocked with oxidatively-removable protective groups such as 2,4-dimethoxybenzyl, while co-existing amino groups are blocked with fluoride labile silyl carbamates.

Allyl blocking groups are useful in the presence of acid- and base-protecting groups since the former are stable and are subsequently removed by metal or pi-acid catalysts. For example, an allyl-blocked carboxylic acid is deprotected with a palladium-catalyzed reaction in the presence of acid labile t-butyl carbamate or base-labile acetate amine protecting groups. Yet another form of protecting group is a resin to which a compound or intermediate is attached. As long as the residue is attached to the resin, that functional group is blocked and does not react. Once released from the resin, the functional group is available to react.

Typically blocking/protecting groups may be selected from:

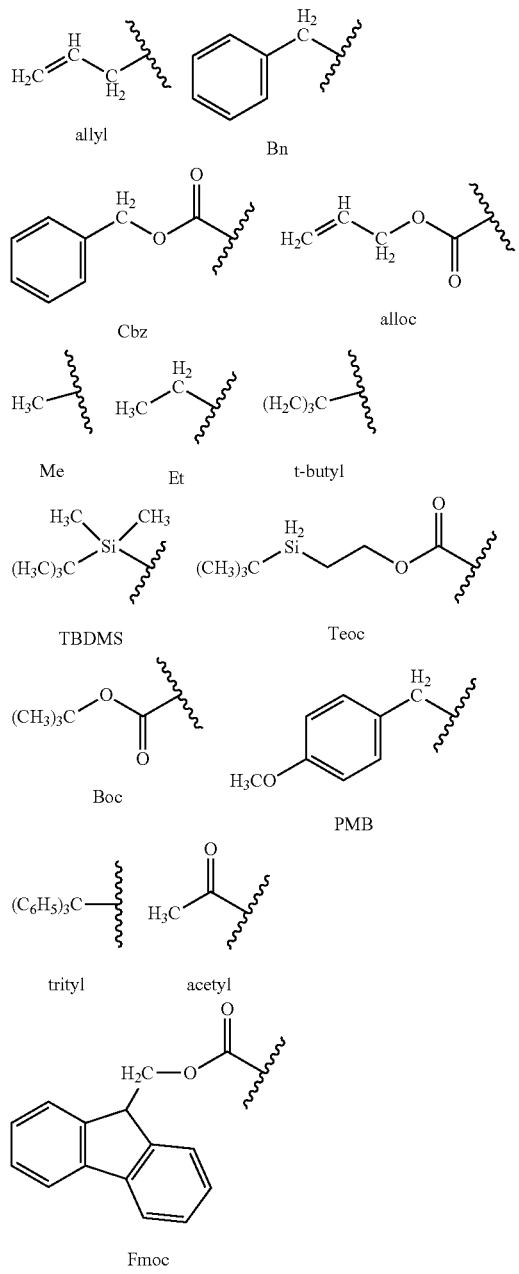

Other protecting groups, plus a detailed description of techniques applicable to the creation of protecting groups and their removal are described in Greene & Wuts, Protective Groups in Organic Synthesis, 3rd Ed., John Wiley & Sons, New York, N.Y., 1999, and Kocienski, Protective Groups, Thieme Verlag, New York, N.Y., 1994, which are incorporated herein by reference for such disclosure.

Methods of the Invention

The present invention includes a method of treating a microbial infection in a subject in need thereof. The method comprises administering to the subject an effective amount of a therapeutic composition comprising a compound of the invention. The microbial infection can be a variety of microbial infections, such as a bacterial infection, a viral infection, or a protozoan infection. In one embodiment, the microbial infection is a bacterial infection. In one embodiment, the bacterial infection is caused by a Gram positive bacterium. In another embodiment, the bacterial infection is caused by a Gram negative bacterium.

Gram-positive bacterial infections that can be treated include, without limitation, infections of *M. tuberculosis* (including multi drug resistant TB and extensively drug resistant TB), *M. bovis*, *M. typhimurium*, *M. bovis* strain BCG, BCG substrains, *M. avium*, *M. intracellulare*, *M. africanum*, *M. kansasii*, *M. marinum*, *M. ulcerans*, *M. avium* subspecies *paratuberculosis*, *Staphylococcus aureus*, *Staphylococcus epidermidis*, *Staphylococcus equi*, *Streptococcus pyogenes*, *Streptococcus agalactiae*, *Listeria monocytogenes*, *Listeria ivanovii*, *Bacillus anthraces*, *B. subtilis*, *Nocardia asteroides*, and other *Nocardia* species, *Streptococcus viridans* group, *Peptococcus* species, *Peptostreptococcus* species, *Actinomyces israelii* and other *Actinomyces* species, *Propionibacterium acnes*, *Clostridium tetani*, *Clostridium perfringens*, *Clostridium botulinum*, other *Clostridium* species, and *Enterococcus* species.

Infections of gram-negative bacteria that can be treated include, without limitation, infections of *Pseudomonas aeruginosa*, other *Pseudomonas* species, *Campylobacter* species, *Vibrio cholerae*, *Ehrlichia* species, *Actinobacillus pleuropneumoniae*, *Pasteurella haemolytica*, *Pasteurella multocida*, other *Pasteurella* species, *Legionella pneumophila*, other *Legionella* species, *Salmonella typhi*, other *Salmonella* species, *Shigella* species, *Brucella abortus*, other *Brucella* species, *Chlamydi trachomatis*, *Chlamydia psittaci*, *Coxiella burnetti*, *Escherichia coli*, *Neiserria meningitidis*, *Neiserria gonorrhea*, *Haemophilus influenzae*, *Haemophilus ducreyi*, other *Hemophilus* species, *Yersinia pestis*, *Yersinia enterolitica*, other *Yersinia* species, *Escherichia coli*, *Escherichia hirae*, and other *Escherichia* species, as well as other *Enterobacteriacae*, *Burkholderia cepacia*, *Burkholderia pseudomallei*, *Francisella tularensis*, *Bacteroides fragilis*, *Fusobascterium nucleatum*, *Provetella* species, *Cowdria ruminantium*, *Klebsiella* species, and *Proteus* species. In one embodiment, the infection is a *Psuedomonas* infection. In one embodiment, the infection is a *Psuedomonas aeruginosa* (PA) infection.

The above examples of bacterial infections are not intended to be limiting, but are intended to be representative of a larger population including all bacterial infections that affect public health, as well as non-Gram test responsive bacterial infections. Examples of other bacterial infections include, but are not limited to, infections of *Abiotrophia*, *Achromobacter*, *Acidaminococcus*, *Acidovorax*, *Acinetobacter*, *Actinobacillus*, *Actinobaculum*, *Actinomadura*, *Actinomyces*, *Aerococcus*, *Aeromonas*, *Afipia*, *Agrobacterium*, *Alcaligenes*, *Alloiococcus*, *Alteromonas*, *Amycolata*, *Amycolatopsis*, *Anaerobospirillum*, *Anaerorhabdus*, *Arachnia*, *Arcanobacterium*, *Arcobacter*, *Arthrobacter*, *Atopobium*, *Aureobacterium*, *Bacteroides*, *Balneatrix*, *Bartonella*, *Bergeyella*, *Bifidobacterium*, *Bilophila Branhamella*, *Borrelia*, *Bordetella*, *Brachyspira*, *Brevibacillus*, *Brevibacterium*, *Brevundimonas*, *Brucella*, *Burkholderia*, *Buttiauxella*, *Butyrivibrio*, *Calymmatobacterium*, *Campylobacter*, *Capnocytophaga*, *Cardiobacterium*, *Catonella*, *Cedecea*, *Cellulomonas*, *Centipeda*, *Chlamydia*, *Chlamydophila*, *Chromobacterium*, *Chyseobacterium*, *Chryseomonas*, *Citrobacter*, *Clostridium*, *Collinsella*, *Comamonas*, *Corynebacterium*, *Coxiella*, *Cryptobacterium*, *Delftia*, *Dermabacter*, *Dermatophilus*, *Desulfomonas*, *Desulfovibrio*, *Dialister*, *Dich-*

*elobacter, Dolosicoccus, Dolosigranulum, Edwardsiella, Eggerthella, Ehrlichia, Eikenella, Empedobacter, Enterobacter, Enterococcus, Erwinia, Erysipelothrix, Escherichia, Eubacterium, Ewingella, Exiguobacterium, Facklamia, Filifactor, Flavimonas, Flavobacterium, Francisella, Fusobacterium, Gardnerella, Globicatella, Gemella, Gordona, Haemophilus, Hafnia, Helicobacter, Helococcus, Holdemania Ignavigranum, Johnsonella, Kingella, Klebsiella, Kocuria, Koserella, Kurthia, Kytococcus, Lactobacillus, Lactococcus, Lautropia, Leclercia, Legionella, Leminorella, Leptospira, Leptotrichia, Leuconostoc, Listeria, Listonella, Megasphaera, Methylobacterium, Microbacterium, Micrococcus, Mitsuokella, Mobiluncus, Moellerella, Moraxella, Morganella, Mycobacterium, Mycoplasma, Myroides, Neisseria, Nocardia, Nocardiopsis, Ochrobactrum, Oeskovia, Oligella, Orientia, Paenibacillus, Pantoea, Parachlamydia, Pasteurella, Pediococcus, Peptococcus, Peptostreptococcus, Photobacterium, Photorhabdus, Plesiomonas, Porphyrimonas, Prevotella, Propionibacterium, Proteus, Providencia, Pseudomonas, Pseudonocardia, Pseudoramibacter, Psychrobacter, Rahnella, Ralstonia, Rhodococcus, Rickettsia Rochalimaea, Roseomonas, Rothia, Ruminococcus, Salmonella, Selenomonas, Serpulina, Serratia, Shewenella, Shigella, Simkania, Slackia, Sphingobacterium, Sphingomonas, Spirillum, Staphylococcus, Stenotrophomonas, Stomatococcus, Streptobacillus, Streptococcus, Streptomyces, Succinivibrio, Sutterella, Suttonella, Tatumella, Tissierella, Trabulsiella, Treponema, Tropheryma, Tsakamurella, Turicella, Ureaplasma, Vagococcus, Veillonella, Vibrio, Weeksella, Wolinella, Xanthomonas, Xenorhabdus, Yersinia,* and *Yokenella.*

Specific examples of bacterial infections include, without limitation, infections of *M. smegmatis* or *B. subtilis, M. tuberculosis,* or multidrug resistant or extensively drug resistant *M. tuberculosis.* Other specific examples include *Salmonella typhimurium, Aeromonas hydrophila, Arcobacter butzleri, Bacillus cereus, Campylobacter jejuni, Escherichia coli, Listeria monocytogenes, Staphylococcus aureus, Pseudomonas fluorescens, Enterococcus* sp., *Clostridium difficile* and *Shewanella putrefaciens.*

In one embodiment, the subject is a mammal. In another embodiment, the mammal is a human.

Combination Therapies

The compounds of the present invention are intended to be useful in combination with one or more additional compounds. In certain embodiments, these additional compounds may comprise compounds of the present invention or therapeutic agents known to treat or reduce the symptoms or effects of a microbial infection.

In one embodiment, administering the compound of the invention to the subject allows for administering a lower dose of the therapeutic agent compared to the dose of the therapeutic agent alone that is required to achieve similar results in treating or preventing cancer in the subject. For example, in one embodiment, the compound of the invention enhances the antibiotic activity of the additional therapeutic compound, thereby allowing for a lower dose of the therapeutic compound to provide the same effect. In another embodiment, administering the compound of the invention to the subject allows for administering a lower dose of the therapeutic agent compared to the dose of the therapeutic agent alone that is required to achieve similar results in treating or preventing pain or inflammation in the subject.

In one embodiment, the compound of the invention and the therapeutic agent are co-administered to the subject. In another embodiment, the compound of the invention and the therapeutic agent are co-formulated and co-administered to the subject.

In certain embodiments, the additional therapeutic agent is an antibiotic. Examples of antibiotics, include, but are not limited to, amoxicillin, ampicillin, arsphenamine, azithromycin, aztreonam, azlocillin, bacitracin, carbenicillin, cefaclor, cefadroxil, cefamandole, cefazolin, cephalexin, cefdinir, cefditoren, cefepime, cefixime, cefoperazone, cefotaxime, cefoxitin, cefpodoxime, cefprozil, ceftazidime, ceftibuten, ceftizoxime, ceftriaxone, cefuroxime, chloramphenicol, cilastin, ciprofloxacin, clarithromycin, clindamycin, clofazimine, cloxacillin, colistin, dalfopristan, demeclocycline, dicloxacillin, dirithromycin, doxycycline, erythromycin, enafloxacin, enviomycin, ertepenem, ethambutol, flucloxacillin, fosfomycin, furazolidone, gatifloxacin, geldanamycin, gentamicin, herbimicin, imipenem, linezolid, lomefloxacin, loracarbef, mafenide, moxifloxacin, meropenem, metronidazole, mezlocillin, minocycline, mupirozin, nafcillin, neomycin, netilmicin, nitrofurantoin, norfloxacin, oxytetracycline, penicillin, piperacillin, platensimycin, polymixin B, prochlorperazine, prontocil, quinupristine, rifabutin, roxithromycin, spectinomycin, sulfacetamide, sulfamethizole, sulfamethoxazole, teicoplanin, telithromycin, tetracycline, thioacetazone, thioridazine, ticarcillin, tobramycin, trimethoprim, troleandomycin, trovafloxacin, and vancomycin.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

The regimen of administration may affect what constitutes an effective amount. The therapeutic formulations may be administered to the subject either before or after the onset of the microbial infection. Further, several divided dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, such as a mammal, (e.g., human), may be carried out using known procedures, at dosages and for periods of time effective to treat a microbial infection in the patient. An effective amount of the therapeutic compound necessary to achieve a therapeutic effect may vary according to factors such as the state of the disease or disorder in the patient; the age, sex, and weight of the patient; and the ability of the therapeutic compound to treat a microbial infection in the patient. Dosage regimens may be adjusted to provide the optimum therapeutic response. For example, several divided doses may be administered daily. In another example, the dose may be proportionally reduced as indicated by the exigencies of the therapeutic situation. A non-limiting example of an effective dose range for a therapeutic compound of the invention is from about 1 mg/kg to about 5,000 mg/kg of body weight/per day. One of ordinary skill in the art would be able to assess the relevant factors and make the determination regarding the effective amount of the therapeutic compound without undue experimentation.

Actual dosage levels of the active ingredients in the pharmaceutical compositions of this invention may be varied to obtain an amount of the active ingredient that is effective to achieve the desired therapeutic response for a particular patient, composition, and mode of administration, without generating excessive side effects in the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well, known in the medical arts.

A medical professional, e.g., physician or veterinarian, having ordinary skill in the art may readily determine and prescribe the effective amount of the pharmaceutical composition required. For example, the physician or veterinarian could start with a dosage of the compound of the invention in the pharmaceutical composition at a level that is lower than the level required to achieve the desired therapeutic effect, and then increase the dosage over time until the desired effect is achieved.

In particular embodiments, it is advantageous to formulate the compound in dosage unit form for ease of administration and uniformity of dosage. "Dosage unit form" as used herein refers to a physically discrete unit containing a predetermined quantity of therapeutic compound calculated to produce the desired therapeutic effect, in association with the required pharmaceutical vehicle. The dosage unit forms of the invention can be selected based upon (a) the unique characteristics of the therapeutic compound and the particular therapeutic effect to be achieved, and (b) the limitations inherent in the art of compounding/formulating such a therapeutic compound for the treatment of a microbial infection in a patient.

In one embodiment, the compositions of the invention are formulated using one or more pharmaceutically acceptable excipients or carriers. In one embodiment, the pharmaceutical compositions of the invention comprise a therapeutically effective amount of a compound of the invention and a pharmaceutically acceptable carrier.

The carrier may be a solvent or dispersion medium containing, for example, water, ethanol, polyol (for example, glycerol, propylene glycol, and liquid polyethylene glycol, and the like), vegetable oils, and suitable mixtures thereof. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In some embodiments, it is useful to include isotonic agents, for example, sugars, sodium chloride, or polyalcohols such as mannitol and sorbitol, in the composition. Prolonged absorption of the injectable compositions can be achieved by including in the composition an agent which delays absorption, for example, aluminum monostearate or gelatin. In one embodiment, the pharmaceutically acceptable carrier is DMSO, alone or in combination with other carriers.

The therapeutically effective amount or dose of a compound of the present invention depends on the age, sex and weight of the patient, the current medical condition of the patient and the severity of the microbial infection in the patient being treated. The skilled artisan is able to determine appropriate doses depending on these and other factors.

The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

Doses of the compound of the invention for administration may be in the range of from about 1 µg to about 10,000 mg, from about 20 µg to about 9,500 mg, from about 40 µg to about 9,000 mg, from about 75 µg to about 8,500 mg, from about 150 µg to about 7,500 mg, from about 200 µg to about 7,000 mg, from about 3050 µg to about 6,000 mg, from about 500 µg to about 5,000 mg, from about 750 µg to about 4,000 mg, from about 1 mg to about 3,000 mg, from about 10 mg to about 2,500 mg, from about 20 mg to about 2,000 mg, from about 25 mg to about 1,500 mg, from about 30 mg to about 1,000 mg, from about 40 mg to about 900 mg, from about 50 mg to about 800 mg, from about 60 mg to about 750 mg, from about 70 mg to about 600 mg, from about 80 mg to about 500 mg, and any and all whole or partial increments therebetween.

In some embodiments, the dose of a compound of the invention is from about 1 mg to about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, the dosage of a second compound as described elsewhere herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

In one embodiment, the compositions of the invention are administered to the patient from about one to about five times per day or more. In various embodiments, the compositions of the invention are administered to the patient, 1-7 times per day, 1-7 times every two days, 1-7 times every 3 days, 1-7 times every week, 1-7 times every two weeks, and 1-7 times per month. It is readily apparent to one skilled in the art that the frequency of administration of the various combination compositions of the invention will vary from individual to individual depending on many factors including, but not limited to, age, the disease or disorder to be treated, the severity of the disease or disorder to be treated, gender, overall health, and other factors. Thus, the invention should not be construed to be limited to any particular dosing regime and the precise dosage and composition to be administered to any patient is determined by the medical professional taking all other factors about the patient into account.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's condition has occurred, a maintenance dose is administered if necessary. Subsequently, the dosage or the frequency of administration, or both, may be reduced to a level at which the improved disease is retained. In some embodiments, a patient may require intermittent treatment on a long-term basis, or upon any recurrence of the disease or disorder.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

In one embodiment, the present invention is directed to a packaged pharmaceutical composition comprising a container holding a therapeutically effective amount of a compound of the invention, alone or in combination with a second pharmaceutical agent; and instructions for using the compound to treat or prevent a microbial infection in a patient.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

Routes of administration of any of the compositions of the invention include oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans) buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration

For oral administration, suitable forms include tablets, dragees, liquids, drops, suppositories, or capsules, caplets and gelcaps. The compositions formulated for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

For oral administration, the compounds of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY-P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation involves the use of materials that are solid or semi-solid at room temperature (i.e., having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e., drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) melt.

The present invention also includes a multi-layer tablet comprising a layer providing for the delayed release of one or more compounds of the invention, and a further layer providing for the immediate release of a medication for treatment of G-protein receptor-related diseases or disorders. Using a wax/pH-sensitive polymer mix, a gastric insoluble composition may be obtained in which the active ingredient is entrapped, ensuring its delayed release.

Parenteral Administration

For parenteral administration, the compounds of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475; 6,488,962; 6,451,808; 5,972,389; 5,582,837; and 5,007,790. Additional dosage forms of this invention also include dosage forms as described in U.S. Patent Applications Nos. 20030147952; 20030104062; 20030104053; 20030044466; 20030039688; and 20020051820. Additional dosage forms of this invention also include dosage forms as described in PCT Applications Nos. WO 03/35041; WO 03/35040; WO 03/35029; WO 03/35177; WO 03/35039; WO 02/96404; WO 02/32416; WO 01/97783; WO 01/56544; WO 01/32217; WO 98/55107; WO 98/11879; WO 97/47285; WO 93/18755; and WO 90/11757.

Controlled Release Formulations and Drug Delivery Systems

In one embodiment, the formulations of the present invention may be, but are not limited to, short-term, rapid-offset, as well as controlled, for example, sustained release, delayed release and pulsatile release formulations.

The term sustained release refers to a drug formulation that provides for gradual release of a drug over an extended period of time, and that may, although not necessarily, result in substantially constant blood levels of a drug over an extended time period. The period of time may be as long as a day, a week, or a month or more and should be a release which is longer that the same amount of agent administered in bolus form. The term delayed release is used herein in its conventional sense to refer to a drug formulation that provides for an initial release of the drug after some delay following drug administration and that mat, although not necessarily, includes a delay of from about 10 minutes up to about 12 hours.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In one embodiment of the invention, the compounds of the invention are administered to a patient, alone or in combination with another pharmaceutical agent, using a sustained release formulation.

The term pulsatile release refers to a drug formulation that provides release of the drug in such a way as to produce pulsed plasma profiles of the drug after drug administration.

The term immediate release refers to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Those skilled in the art recognize, or are able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that wherever values and ranges are provided herein, all values and ranges encompassed by these values and ranges, are meant to be encompassed within the scope of the present invention. Moreover, all values that fall within these ranges, as well as the upper or lower limits of a range of values, are also contemplated by the present application.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

The materials and methods employed in the experiments and the results of the experiments presented in this Example are now described.

Example 1: Diverted Total Synthesis of Promysalin Analogs Demonstrates that an Iron-Binding Motif is Responsible for its Narrow-Spectrum Antibacterial Activity Materials and Methods NMR spectra were recorded using the following spectrometers: Bruker Advance 500 (500/125 MHz) or Bruker Advance 400 (400/100 MHz). Chemical shifts are quoted in ppm relative to tetramethylsilane and with the indicated solvent as an internal reference. The following abbreviations are used to describe signal multiplicities: s (singlet), d (doublet), t (triplet), q (quartet), m (multiplet), br (broad), dd (doublet of doublets), dt (doublet of triplets), etc. Accurate mass spectra were recorded on an Agilent 6520 Accurate-Mass Q-TOF LC/MS, infrared spectra were obtained using a Thermo Nicolet Nexus 670 FTIR spectrophotometer and specific rotation measurements were made with a 1 dm path length using a Perkin Elmer 341 Polarimeter.

Non-aqueous reactions were performed under an atmosphere of argon, in flame-dried glassware, with HPLC-grade solvents dried by passage through activated alumina. 2,6-lutidine, triethylamine, and diisopropylethylamine were freshly distilled from $CaH_2$ prior to use. Brine refers to a saturated aqueous solution of sodium chloride, sat. $NaHCO_3$ refers to a saturated aqueous solution of sodium bicarbonate, sat. $NH_4Cl$ refers to a saturated aqueous solution of ammonium chloride, etc. 3 Å molecular sieves were activated in a round-bottom flask under vacuum heating at 120° C. in an oil bath overnight. "Column chromatography", unless otherwise indicated, refers to purification in a gradient of increasing EtOAc concentration in hexanes, on a Biotage® flash chromatography purification system. Metathesis catalysts were obtained as generous gifts from Materia, Inc. All other chemicals were used as received from Oakwood, TCI America, Sigma-Aldrich, Alfa Aesar, or AK Scientific.

General Procedure A: SEM Protection of Methyl Hydroxybenzoates.

To a methyl hydroxybenzoate (1 eq) dissolved in $CH_2Cl_2$ (2M) was added SEMCl (2 eq) and then cooled to 0° C. Diisopropylethylamine (4 eq) was added dropwise and the solution was allowed to warm to room temperature while stirring overnight. The following day, the mixture was poured into water and extracted with $Et_2O$ 3×. The combined organic layers were washed with brine, dried over $MgSO_4$, filtered, concentrated, and purified by column chromatography.

General Procedure B: Hydrolysis of Methyl Esters.

Methyl ester (1.0 eq) was dissolved in 3:1:1 THF:MeOH:$H_2O$ (1M) and $LiOH \cdot H_2O$ (5 eq) was added as a solution in a minimal volume of water. The reaction was monitored by TLC and carefully acidified by addition of 1M HCl or 5% AcOH (pH 5-6). The solution was extracted with $CH_2Cl_2$ 3×, washed with brine, dried over $MgSO_4$, filtered, concentrated, and used directly in the next step.

General Procedure C: HATU-Mediated Amide Coupling of SEM-Benzoic Acids and Hydroxyproline Methyl Ester.

Acid (1.0 eq) was dissolved in DMF (0.2 M) with HATU (1.2 eq) to which a solution of amine hydrochloride (1.2 eq) and diisopropylethylamine (1.5 eq) in an equal volume of DMF was added. Another portion of diisopropylethylamine (3 eq) was added and the reaction was allowed to stir overnight, then was poured into water and extracted with ethyl acetate 3×. The combined organic layers were washed with sat. $NH_4Cl$, sat. $NaHCO_3$, water 2× and brine 2×, then dried over $MgSO_4$, filtered, concentrated, and purified by column chromatography (0→50% EtOAc/$CH_2Cl_2$).

General Procedure D: DMP Oxidation.

An acylated trans-L-hydroxyproline derivative (1 eq) was dissolved in dry $CH_2Cl_2$ (0.05 M), and to the resulting solution was added $NaHCO_3$ (20 eq) and Dess-Martin periodinane (2 eq), and the reaction was allowed to stir overnight. The next day, the reaction was quenched with 2:1:1 $H_2O$:sat. $NaHCO_3$:sat. $Na_2S_2O_3$ allowed to stir for an hour. The mixture was then extracted with $CH_2Cl_2$ 3× and the combined organic layers were washed with sat. $Na_2S_2O_3$, sat. $NaHCO_3$, water, and brine, then dried over $MgSO_4$, filtered, concentrated, and purified by column chromatography.

General procedure E: Synthesis of Enol Triflates from Ketones.

The ketone (1 eq) was dissolved in $CH_2Cl_2$ (0.1 M) and cooled to −50° C. 2,6-Lutidine (4 eq) was added, and trifluoromethanesulfonic anhydride (2 eq) was added dropwise. The reaction was allowed to warm to −35° C. After 30 minutes the reaction was quenched with sat. $NaHCO_3$ and extracted with $CH_2Cl_2$ 3×. The combined organic layers were washed with sat. $NaHCO_3$, brine, dried over $MgSO_4$, concentrated, and purified by column chromatography (0→5% EtOAc/hexanes held at 5% until 2,6-lutidine finishes eluting, then 5→20% EtOAc/hexanes).

General Procedure F: Reductive Cleavage of Enol Triflates.

The enol triflate was dissolved in THF (0.1 M), to which solution was added $PPh_3$ (0.3 eq), $Pd(OAc)_2$ (0.1 eq), and flame-dried LiCl (1.5 eq). Tributyltin hydride (1 eq) was added dropwise. The reactions turned orange or brown upon completion, then were quenched with a solution of KF (1M) and extracted with $Et_2O$ 3×. The combined organic layers were washed with 1M KF, water, and brine, dried over $Na_2SO_4$, filtered, concentrated, and purified by column chromatography (0→30% EtOAc/hexanes, load in $CH_2Cl_2$).

General Procedure G: EDC Esterification.

An acid (1.4 eq) was dissolved in $CH_2Cl_2$ (0.2 M) was cooled to 0° C. and EDC (2 eq) was added. A solution of alcohol (+)-S1[1] (1 eq) and DMAP (0.5 eq) were dissolved in an equal volume of dry $CH_2Cl_2$, added to the first solution, and allowed to stir overnight. The resulting mixture was poured into water and extracted with $CH_2Cl_2$ 3×. The combined organic layers were washed with brine, dried over $MgSO_4$, concentrated, and purified by column chromatography (0→30% $Et_2O$/$CH_2Cl_2$).

General Procedure H: Shiina Esterification.

To a solution of acid (1.4 eq) dissolved in $CH_2Cl_2$ (0.2 M) was added MNBA (2.6 eq) and $Et_3N$ (3.3 eq), and the solution was stirred for 10 minutes. Then alcohol 16 (1 eq) and DMAP (0.1 eq) were added to the acid solution in an equal volume of $CH_2Cl_2$, and the reaction was stirred overnight. The reaction was poured into sat. $NH_4Cl$, extracted with $CH_2Cl_2$ 3×, washed with brine, dried over $MgSO_4$, filtered, concentrated, and purified by column chromatography (0→30% $Et_2O$/$CH_2Cl_2$).

General Procedure I: Global Deprotection.

The protected ester was dissolved in DMPU (0.05 M, dried over 3 Å molecular sieves). Tetrabutylammonium fluoride (20 eq, 1M solution in THF, recently dried over 3 Å molecular sieves) was added dropwise. The reaction was monitored by LC/MS and quenched with sat. $NH_4Cl$ after 30 minutes. The deprotections could be monitored by LC/MS, but never proceeded any further after this time. The mixture was extracted with Et$_2$O (3-5 times, TLC analysis of aqueous layer to confirm full extraction), and the combined organic layers were washed with aq. 1M NH$_4$Cl 5× followed by brine, dried over Na$_2$SO$_4$, concentrated, and purified by column chromatography (0→5% MeOH/CH$_2$Cl$_2$).

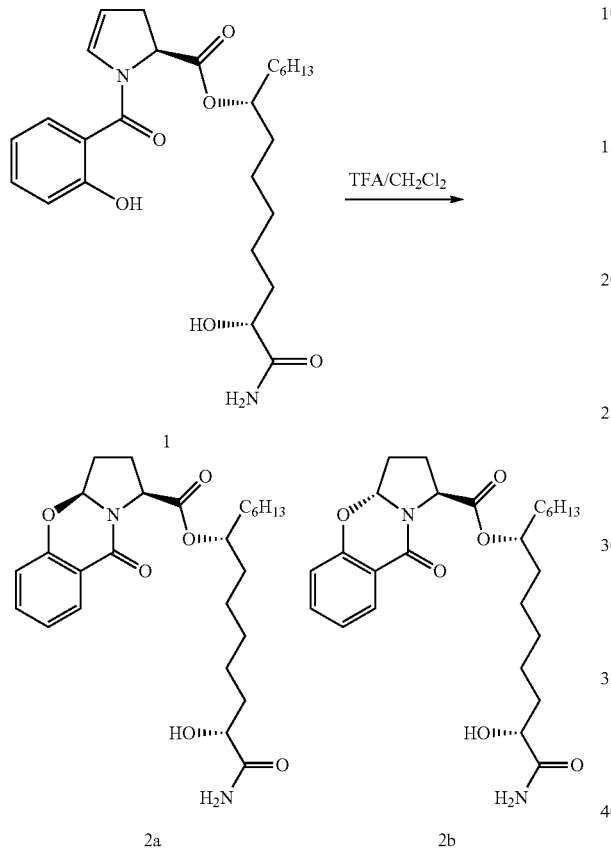

(7R,13R)-14-amino-13-hydroxy-14-oxotetradecan-7-yl (1S,3aS)-9-oxo-1,2,3,3a-tetrahydro-9H-benzo[e]pyrrolo[2,1-b][1,3]oxazine-1-carboxylate (2a), (7R,13R)-14-amino-13-hydroxy-14-oxotetradecan-7-yl (1S,3aR)-9-oxo-1,2,3,3a-tetrahydro-9H-benzo[e]pyrrolo[2,1-b][1,3]oxazine-1-carboxylate (2b). To a solution of 1 (12 mg, 0.025 mmol) dissolved in CH$_2$Cl$_2$ (1 mL) was added trifluoroacetic acid (1 mL), and the reaction was stirred for 30 minutes at room temperature. The reaction was slowly quenched with sat. Na$_2$CO$_3$ solution until the pH was greater than 8, then extracted with CH$_2$Cl$_2$ 3×, washed with brine, dried over MgSO$_4$, filtered, concentrated, and purified by preparative TLC (2% MeOH/EtOAc), yielding diastereomeric compounds 2a and 2b (configurations were not assigned). Less polar isomer: $^1$H NMR (500 MHz, CDCl$_3$) δ 7.88-7.81 (m, 1H), 7.49-7.43 (m, 1H), 7.12 (td, J=7.7, 0.9 Hz, 1H), 7.01-6.70 (m, 2H), 5.78-5.73 (m, 1H), 5.42 (s, 1H), 5.04-4.97 (m, 1H), 4.82-4.71 (m, 1H), 4.28-4.17 (m, 2H), 2.59-2.46 (m, 2H), 2.36-2.27 (m, 1H), 2.03-1.96 (m, 1H), 1.95-1.87 (m, 1H), 1.80-1.70 (m, 1H), 1.68-1.43 (m, 7H), 1.42-1.20 (m, 12H), 0.88 (t, J=6.9 Hz, 3H); $^{13}$C NMR (125 MHz, CDCl$_3$) δ 177.48, 171.59, 171.49, 161.36, 157.42, 134.64, 128.18, 128.04, 123.12, 119.04, 116.94, 88.82, 75.73, 71.17, 58.31, 34.64, 33.98, 33.86, 31.87, 30.96, 29.84, 29.22, 27.73, 26.36, 25.56, 24.62, 24.28, 22.70, 14.21; [α]$^{25}_D$ +63.8 (c=0.13 in CHCl$_3$) IR (film) 3326 (br, O—H), 2928, 2858, 2360, 1733 (C=O), 1660 (C=O), 1597, 1507, 1468, 1431, 1351, 1197, 1166, 1099, 1019, 959, 860, 822, 788, 758, 651, 608, 585; HRMS Accurate mass (ES$^+$): Found 475.2781 (−5.7 ppm), C$_{26}$H$_{39}$N$_2$O$_6$ (M+H$^+$) requires 475.2808; R$_f$ (2% MeOH/EtOAc)=0.37 More polar isomer: $^1$H NMR (500 MHz, CDCl$_3$) δ 7.91-7.79 (m, 1H), 7.49-7.44 (m, 1H), 7.12 (td, J=7.7, 1.0 Hz, 1H), 7.01 (dd, J=8.2, 4.2 Hz, 1H), 6.94-6.73 (m, 1H), 5.58 (dt, J=9.8, 4.9 Hz, 1H), 5.39 (s, 1H), 5.05-4.94 (m, 1H), 4.68-4.59 (m, 1H), 4.28 (d, J=17.5 Hz, 1H), 4.17-4.09 (m, 1H), 2.53-2.47 (m, 1H), 2.44-2.25 (m, 2H), 2.19 (dd, J=13.4, 7.8 Hz, 1H), 1.87-1.79 (m, 1H), 1.77-1.68 (m, 1H), 1.59-1.35 (m, 7H), 1.30-1.20 (m, 12H), 0.87 (t, J=7.0 Hz, 3H); $^{13}$C NMR (100 MHz, CDCl$_3$) δ 177.36, 170.73, 161.68, 158.00, 134.67, 127.96, 123.01, 119.04, 117.12, 88.70, 75.62, 71.05, 57.27, 34.68, 33.93, 33.71, 31.85, 30.33, 29.84, 29.21, 27.61, 26.19, 25.57, 24.60, 24.05, 22.69, 14.22; [α]$^{25}_D$ −28.1 (c=0.11 in CHCl$_3$) IR (film) 3326 (br, O—H), 2927, 2856, 2360, 1734 (C=O), 1659 (C=O), 1613, 1578, 1469, 1432, 1351, 1225, 1196, 1079, 1024, 954, 907, 856, 785, 759, 732, 700, 652, 606, 584; HRMS Accurate mass (ES$^+$): Found 475.2783 (−5.3 ppm), C$_{26}$H$_{39}$N$_2$O$_6$ (M+H$^+$) requires 475.2808; R$_f$ (2% MeOH/EtOAc)=0.29.

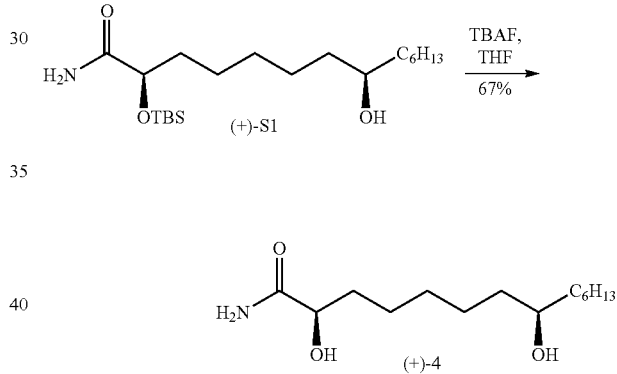

(2R,8R)-2,8-dihydroxytetradecanamide (+)-4. To a solution of silyl ether (+)-S1 (Steele et al., J. Am. Chem. Soc. 2015, 137, 7314) (25 mg, 0.069 mmol) in THF (0.5 mL) was added TBAF (1M in THF, 0.34 mL, 0.34 mmol), and the reaction was stirred for 30 minutes, poured into sat. NH$_4$Cl, and extracted with Et$_2$O 3×. The combined organic layers were washed with 1M NH$_4$Cl 5×, dried over MgSO$_4$, filtered, concentrated, and purified by column chromatography (2:1 CH$_2$Cl$_2$:Et$_2$O) yielding the title compound as a white solid (12 mg, 67% yield). $^1$H NMR (500 MHz, MeOD) δ 3.98 (dd, J=7.9, 3.9 Hz, 1H), 3.53-3.46 (m, 1H), 1.80-1.72 (m, 1H), 1.64-1.55 (m, 1H), 1.50-1.26 (m, 18H), 0.91 (t, J=7.0 Hz, 3H); $^{13}$C NMR (125 MHz, MeOD) δ 180.66, 72.68, 72.42, 38.47, 38.36, 35.64, 33.07, 30.63, 30.57, 26.80, 26.72, 26.13, 23.71, 14.43; [α]$^{25}_D$ +14.8 (c=0.59 in MeOH); IR (film) 3232 (br, O—H), 2953, 2922, 2852, 2545, 2410, 2361, 2342, 2159, 2027, 1978, 1734, 1622 (C=O), 1591, 1558, 1465, 1452, 1436, 1378, 1363, 1345, 1227, 1169, 1133, 1090, 1065, 1024, 957, 923, 906, 857, 803, 721, 668, 609; HRMS Accurate mass (ES$^+$): Found 282.2041 (−1.4 ppm), C$_{14}$H$_{29}$NO$_3$Na (M+Na$^+$) requires 282.2045

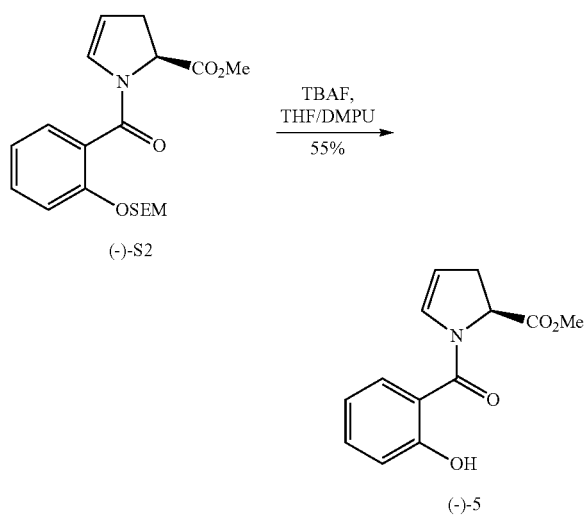

Methyl (2S)-1-(2-hydroxybenzoyl)-2,3-dihydro-1H-pyrrole-2-carboxylate (−)-5. Using modified procedure I (10 eq TBAF, 0.10 M DMPU), SEM-ether S2 (Steele et al., *J. Am. Chem. Soc.* 2015, 137, 7314) (23 mg, 0.061 mmol) yielded the title compound as a clear oil (8.2 mg, 55% yield). $^1$H NMR (500 MHz, CDCl$_3$) δ 9.80 (s, 1H), 7.43 (dd, J=7.8, 1.5 Hz, 1H), 7.41-7.35 (m, 1H), 7.01 (dd, J=8.3, 0.8 Hz, 1H), 6.89 (td, J=7.8, 1.1 Hz, 1H), 6.83 (s, 1H), 5.28 (dt, J=4.4, 2.7 Hz, 1H), 5.04 (dd, J=11.3, 5.2 Hz, 1H), 3.80 (s, 3H), 3.11 (ddt, J=16.4, 11.3, 2.4 Hz, 1H), 2.73 (ddt, J=17.1, 5.0, 2.5 Hz, 1H); $^{13}$C NMR (100 MHz, CDCl$_3$) δ 171.45, 167.75, 159.36, 133.70, 130.99, 128.49, 118.98, 118.15, 110.85, 77.16, 59.29, 52.85, 33.49, 29.83. [α]$^{25}_D$ −104.5 (c=1.00 in CHCl$_3$); IR (film) 3119 (br, O—H), 2954, 2918, 2850, 2360, 2341, 2160, 2031, 1979, 1746 (C=O), 1616, 1590 (C=O), 1487, 1434, 1362, 1295, 1250, 1202, 1179, 1153, 1098, 1017, 984, 944, 855, 817, 757, 721, 667; HRMS Accurate mass (ES$^+$): Found 270.0751 (+3.3 ppm), C$_{13}$H$_{13}$NO$_4$Na (M+Na$^+$) requires 270.0742.

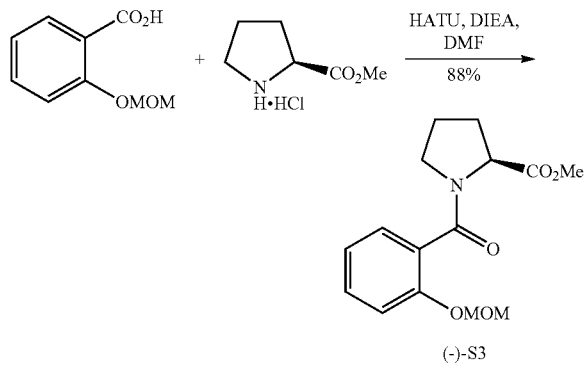

Methyl (2S)-1-[2-(methoxymethoxy)benzoyl]pyrrolidine-2-carboxylate (−)-S3. Using general procedure C, 2-methoxymethyloxybenzoic acid (248 mg, 1.364 mmol) and proline methyl ester hydrochloride (271 mg, 1.636 mmol) yielded the title compound as a clear oil (352 mg, 88% yield). $^1$H NMR (400 MHz, MeOD, mixture of rotamers/conformers) δ 7.43-7.34 (m, 1H), 7.28 (dd, J=7.5, 1.7 Hz, 0.73H), 7.23 (d, J=8.4 Hz, 0.71H), 7.20 (d, J=8.3 Hz, 0.30H), 7.15 (d, J=7.6 Hz, 0.26H), 7.09 (td, J=7.5, 0.9 Hz, 0.74H), 7.04 (dd, J=11.2, 3.8 Hz, 0.29H), 5.26-5.20 (m, 2H), 4.59 (dd, J=8.7, 4.7 Hz, 0.72H), 4.30 (dd, J=8.6, 2.8 Hz, 0.28H), 3.77 (s, 1.52H), 3.75-3.69 (m, 0.54H), 3.48 (s, 0.63H), 3.47 (s, 1.88H), 3.46 (s, 1.18H), 3.41 (dt, J=17.4, 5.3 Hz, 1.40H), 3.35 (s, 1.28H), 2.44-2.25 (m, 1H), 2.09-1.86 (m, 3H); $^{13}$C NMR (100 MHz, MeOD) δ 173.83, 170.08, 169.82, 154.26, 131.97, 129.18, 128.65, 128.30, 127.93, 123.08, 122.81, 116.41, 116.07, 95.98, 61.55, 59.94, 56.67, 52.73, 49.54, 47.42, 31.87, 30.48, 25.55, 23.76; [α]$^{25}_D$ −18.3 (c=0.66 in CHCl$_3$) IR (film) 2054, 2359, 1741 (C=O), 1625 (C=O), 1601, 1489, 1455, 1418, 1362, 1281, 1234, 1198, 1152, 1107, 1078, 1041, 989, 922, 844, 747, 666; HRMS Accurate mass (ES$^+$): Found 316.1134 (−8.6 ppm), C$_{15}$H$_{19}$NO$_5$Na (M+Na$^+$) requires 316.1161.

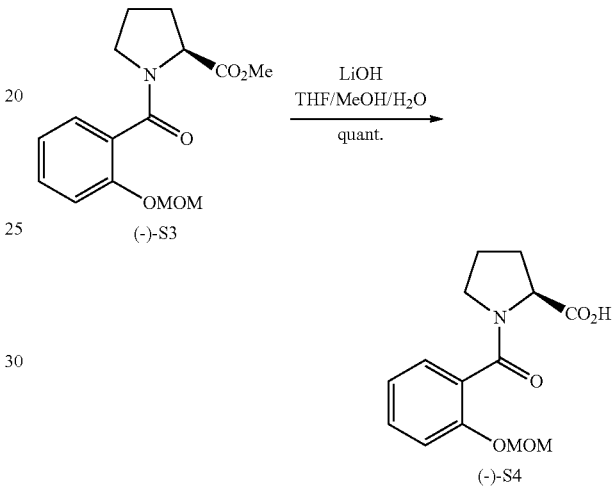

(2S)-1-[2-(methoxymethoxy)benzoyl]pyrrolidine-2-carboxylic acid (−)-S4. Using general procedure B, methyl ester (−)-S3 (117 mg, 0.399 mmol) yielded the title compound as a clear oil (115 mg, quant. yield). $^1$H NMR (400 MHz, MeOD, mixture of rotamers/conformers) δ 7.91 (s, 0.55H), 7.43-7.34 (m, 1.06H), 7.31 (dd, J=7.5, 1.6 Hz, 0.66H), 7.26-7.18 (m, 1.29H), 7.09 (td, J=7.5, 0.9 Hz, 0.64H), 7.03 (t, J=7.5 Hz, 0.31H), 5.26-5.19 (m, 2H), 4.57 (dd, J=8.5, 4.5 Hz, 0.60H), 4.23 (d, J=6.6 Hz, 0.31H), 3.80-3.67 (m, 0.66H), 3.47 (s, 3H), 3.45-3.35 (m, 1H), 2.44-2.22 (m, 1H), 2.14-1.84 (m, 3H); $^{13}$C NMR (100 MHz, MeOD) δ 175.57, 170.59, 170.23, 154.43, 132.01, 128.76, 128.55, 123.19, 122.97, 116.54, 116.05, 96.13, 96.01, 79.48, 56.66, 49.74, 47.41, 32.11, 30.81, 25.64, 23.78; [α]$^{25}_D$ −71.4 (c=1.28 in CHCl$_3$); IR (film) 2956, 2359, 1733 (C=O), 1592 (C=O), 1490, 1456, 1234, 1198, 1152, 1107, 1078, 1042, 979, 921, 845, 748, 665; HRMS Accurate mass (ES$^+$): Found 302.1012 (+2.6 ppm), C$_{14}$H$_{17}$NO$_5$ (M+Na$^+$) requires 302.1004.

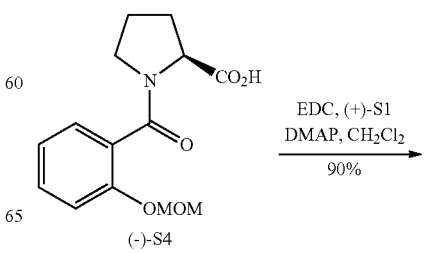

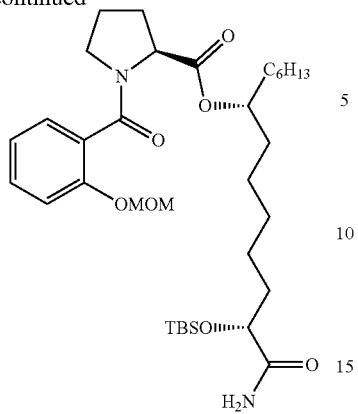

(−)-S5

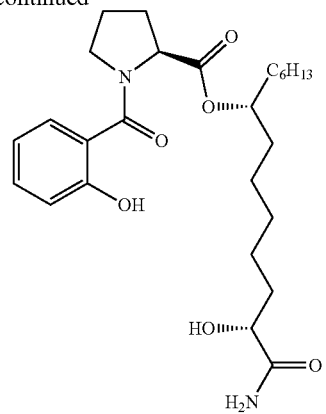

(−)-6

(1R,7R)-1-[(tert-butyldimethylsilyl)oxy]-1-carbamoyltridecan-7-yl (2S)-1-[2-(methoxymethoxy)benzoyl]pyrrolidine-2-carboxylate (−)-S5. Using modified general procedure G (2 eq acid, 2 eq EDC, 1 eq alcohol, 0.1 eq DMAP), acid (−)-S4 (43 mg, 0.154 mmol) yielded the title compound as a clear oil (43 mg, 90% yield). $^1$H NMR (500 MHz, CDCl$_3$, mixture of rotamers/conformers) δ 7.29 (tdd, J=9.8, 8.2, 1.4 Hz, 1.36H), 7.25-7.20 (m, 0.86H), 7.14 (d, J=8.2 Hz, 0.69H), 7.08 (d, J=8.4 Hz, 0.41H), 7.03 (t, J=7.4 Hz, 0.68H), 6.94 (t, J=7.5 Hz, 0.39H), 6.53 (dd, J=10.1, 4.3 Hz, 1H), 5.77 (s, 0.39H), 5.74 (s, 0.58H), 5.21-5.14 (m, 2H), 4.92 (dt, J=12.2, 6.2 Hz, 0.62H), 4.69-4.60 (m, 1H), 4.27-4.21 (m, 0.34H), 4.12 (dt, J=10.4, 5.0 Hz, 1H), 3.81-3.73 (m, 0.63H), 3.50-3.38 (m, 3.66H), 3.33 (dt, J=10.6, 6.7 Hz, 1H), 2.34-2.17 (m, 1H), 2.06-1.79 (m, 4H), 1.79-1.47 (m, 5H), 1.42-1.16 (m, 18H), 0.94-0.88 (m, 9H), 0.85 (t, J=6.8 Hz, 3H), 0.10 (d, J=5.6 Hz, 1.78H), 0.06 (d, J=6.1 Hz, 3.81H); $^{13}$C NMR (125 MHz, CDCl$_3$) δ 177.06, 172.01, 167.68, 153.19, 130.57, 128.16, 127.98, 122.31, 115.60, 95.22, 95.09, 75.56, 75.15, 73.54, 60.47, 58.90, 56.36, 48.31, 46.18, 35.23, 35.11, 34.10, 33.98, 33.77, 31.85, 31.78, 31.43, 29.92, 29.49, 29.29, 29.18, 25.85, 25.31, 25.11, 24.86, 24.10, 22.89, 22.69, 22.64, 18.12, 14.17, −4.73, −5.16; $[α]^{25}_D$ −21.4 (c=0.95 in CHCl$_3$); IR (film) 3477 (N—H), 3307 (br O—H); 2927, 2856, 1738 (C=O), 1683 (C=O), 1626, 1601, 1558, 1489, 1456, 1417, 1338, 1281, 1235, 1194, 1153, 1079, 1042, 989, 922, 837, 755, 652; HRMS Accurate mass (ES$^+$): Found 635.4109 (+2.7 ppm), C$_{34}$H$_{59}$N$_2$O$_7$Si (M+H$^+$) requires 635.4092.

(1R,7R)-1-carbamoyl-1-hydroxytridecan-7-yl (2S)-1-(2-hydroxybenzoyl)pyrrolidine-2-carboxylate (−)-6. To a solution of protected ester (−)-S5 (43 mg, 0.068 mmol) in MeOH (1 mL) was added acetyl chloride (ca. 1 μL, 1 drop) at room temperature. After 1 hour, the reaction was quenched with sat. NaHCO$_3$ and extracted with CH$_2$Cl$_2$ 3×. The combined organic layers were washed with water, dried over Na$_2$SO$_4$, filtered, concentrated, and purified by column chromatography (0→10% MeOH/CH$_2$Cl$_2$), yielding the title compound as a clear oil (16 mg, 50% yield). $^1$H NMR (500 MHz, CDCl$_3$) δ 10.64 (s, 1H), 7.49 (d, J=6.9 Hz, 1H), 7.33 (t, J=7.6 Hz, 1H), 6.96 (t, J=8.6 Hz, 1H), 6.86 (t, J=7.3 Hz, 1H), 6.66 (s, 1H), 5.52 (s, 1H), 4.98 (s, 1H), 4.71-4.60 (m, 1H), 4.08 (s, J=19.6 Hz, 1H), 3.93-3.83 (m, 1H), 3.83-3.73 (m, 1H), 3.66 (s, 1H), 2.40-2.28 (m, 1H), 2.15-2.05 (m, 1H), 2.05-1.90 (m, 2H), 1.87-1.76 (m, 3H), 1.68-1.48 (m, 5H), 1.48-1.33 (m, 6H), 1.33-1.16 (m, 11H), 0.86 (t, J=7.0 Hz, 3H); $^{13}$C NMR (125 MHz, CDCl$_3$) δ 177.22, 172.37, 170.30, 159.04, 133.20, 128.10, 118.83, 117.85, 117.73, 75.42, 71.48, 60.56, 50.78, 34.58, 34.39, 34.29, 31.84, 29.21, 28.52, 25.82, 25.49, 24.87, 24.65, 22.67, 14.19; $[α]^{25}_D$ −28.0 (c=1.51 in CHCl$_3$); IR (film) 3189 (br O—H), 2928, 2857, 2360, 1736 (C=O), 1667 (C=O), 1583 (C=O), 1434, 1374, 1186, 1089, 1025, 877, 754, 651, 609, 563; HRMS Accurate mass (ES$^+$): Found 477.2935 (−6.3 ppm), C$_{26}$H$_{41}$N$_2$O$_6$ (M+H$^+$) requires 477.2965.

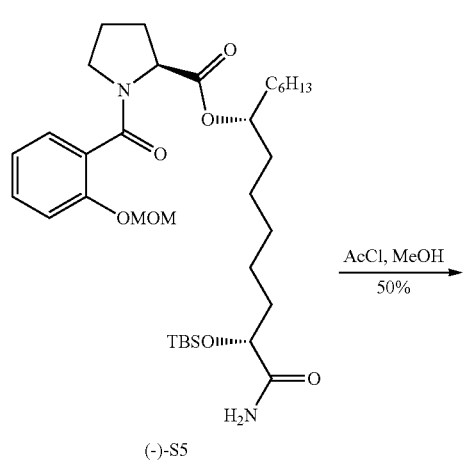

(−)-S5

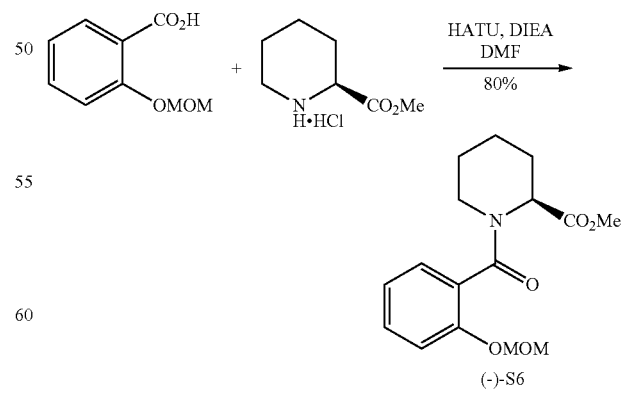

(−)-S6

Methyl (2S)-1-[2-(methoxymethoxy)benzoyl]piperidine-2-carboxylate (−)-S6. Using general procedure C, 2-methoxymethyloxybenzoic acid (200 mg, 1.101 mmol)

and methyl 2-piperidinecarboxylate hydrochloride (237 mg, 1.321 mmol) yielded the title compound as a clear oil (248 mg, 80% yield). $^1$H NMR (500 MHz, CDCl$_3$, mixture of rotamers/conformers) δ 7.42-7.26 (m, 2.67H), 7.25-7.17 (m, 1.16H), 7.14-7.03 (m, 1.23H), 5.67 (s, 0.73H), 5.27 (dt, J=11.7, 6.9 Hz, 2H), 5.15 (dd, J=39.3, 6.6 Hz, 0.32H), 4.81 (d, J=13.7 Hz, 0.31H), 4.43 (d, J=5.1 Hz, 0.08H), 4.36 (d, J=4.3 Hz, 0.22H), 3.85 (s, 2.22H), 3.76 (s, J=4.4 Hz, 1.08H), 3.59-3.46 (m, 4.22H), 3.41-3.33 (m, 0.55H), 3.18 (td, J=13.0, 2.4 Hz, 0.57H), 2.92-2.84 (m, 0.23H), 2.41 (t, J=13.5 Hz, 0.75H), 2.28 (d, J=12.8 Hz, 0.32H), 1.87-1.73 (m, 2.52H), 1.68-1.51 (m, 2.08H), 1.51-1.35 (m, 1.49H); $^{13}$C NMR (125 MHz, CDCl$_3$) δ 171.53, 171.34, 171.26, 168.93, 168.85, 168.72, 153.19, 152.82, 152.62, 130.27, 130.24, 127.98, 127.81, 127.42, 126.70, 126.65, 126.53, 122.28, 122.11, 122.05, 115.15, 114.77, 114.72, 94.85, 94.78, 94.70, 77.36, 60.27, 57.86, 56.17, 56.11, 52.28, 52.24, 52.07, 51.82, 51.60, 45.34, 44.53, 39.40, 39.05, 27.38, 26.87, 26.59, 25.49, 25.33, 24.64, 21.16, 21.10, 20.95, 14.12; $[α]^{25}_D$ -28.6 (c=2.15 in CHCl$_3$); IR (film) 1076, 2945, 1737 (C=O), 1633 (C=O), 1599, 1488, 1452, 1422, 1339, 1286, 1232, 1199, 1143, 985, 921, 756, 645; HRMS Accurate mass (ES$^+$): Found 308.1502 (+1.3 ppm), C$_{16}$H$_{21}$NO$_5$Na (M+Na$^+$) requires 308.1498.

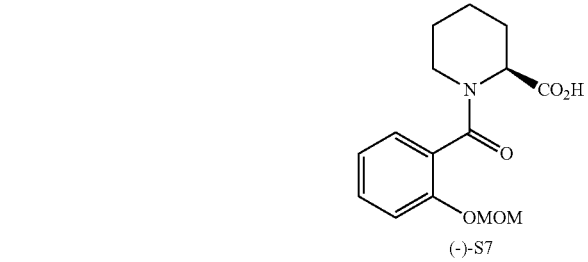

(2S)-1-[2-(methoxymethoxy)benzoyl]piperidine-2-carboxylic acid (−)-S7. Using general procedure B, compound (−)-S6 (215 mg, 0.700 mmol) yielded the title compound as a clear oil (200 mg, 98% yield). $^1$H NMR (500 MHz, CDCl$_3$, mixture of rotamers/conformers) δ 9.53 (br s, 1H), 7.36-7.23 (m, 2.16H), 7.16 (dt, J=18.2, 8.0 Hz, 1.56H), 7.04 (t, J=7.3 Hz, 0.91H), 6.99 (t, J=7.6 Hz, 0.37H), 5.64-5.56 (m, 0.75H), 5.18 (ddd, J=14.8, 13.8, 7.3 Hz, 2H), 5.06 (dd, J=40.1, 6.7 Hz, 0.40H), 4.72 (d, J=10.5 Hz, 0.31H), 4.35 (d, J=4.9 Hz, 0.09H), 4.27 (d, J=4.0 Hz, 0.20H), 3.76 (t, J=6.0 Hz, 0.60H), 3.49-3.40 (m, 3.74H), 3.32-3.22 (m, 0.61H), 3.12 (t, J=12.0 Hz, 0.57H), 2.86-2.77 (m, 0.28H), 2.37 (d, J=13.2 Hz, 0.77H), 2.19 (d, J=13.3 Hz, 0.26H), 2.07 (d, J=11.4 Hz, 0.12H), 1.89-1.82 (m, 0.62H), 1.82-1.63 (m, 2.67H), 1.56 (dd, J=32.8, 13.9 Hz, 1.35H), 1.51-1.32 (m, 2.57H); $^{13}$C NMR (125 MHz, CDCl$_3$) δ 175.19, 174.99, 174.14, 169.79, 169.58, 169.27, 153.31, 152.97, 152.77, 130.68, 130.58, 128.22, 128.01, 127.59, 126.13, 122.40, 122.18, 115.15, 114.79, 94.92, 94.78, 67.95, 57.89, 56.29, 56.26, 52.02, 51.92, 45.59, 44.84, 39.64, 27.51, 26.73, 26.55, 25.61, 25.53, 25.36, 24.75, 21.17; $[α]^{25}_D$ −59.8 (c=0.85 in CHCl$_3$); IR (film) 2941, 1731 (C=O), 1587 (C=O), 1442, 1286, 1233, 1199, 1151, 1077, 1041, 983, 921, 864, 755, 732, 700, 641; HRMS Accurate mass (ES$^+$): Found 316.1173 (+3.8 ppm), C$_{15}$H$_{19}$NO$_5$Na (M+Na$^+$) requires 316.1161.

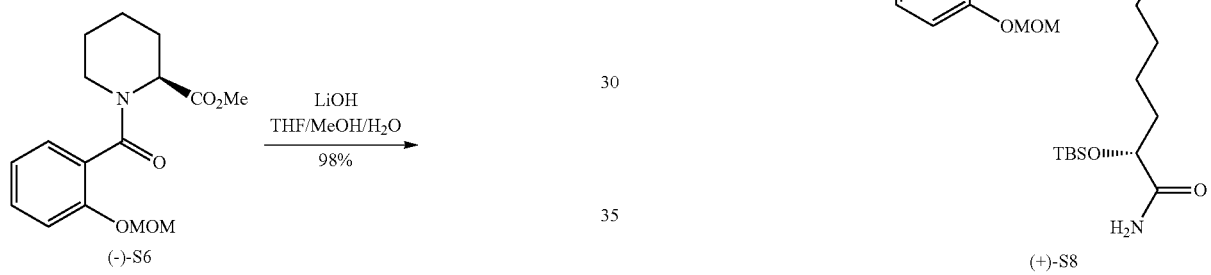

(1R,7R)-1-[(tert-butyldimethylsilyl)oxy]-1-carbamoyltridecan-7-yl (2S)-1-[2-(methoxymethoxy)benzoyl]piperidine-2-carboxylate (+)-S8. Using modified general procedure G (1.5 eq acid, 1.7 eq EDC, 0.5 eq DMAP, 1.0 eq alcohol); acid (−)-S7 (85 mg, 0.291 mmol) yielded the title compound as a clear oil (94 mg, 75% yield). $^1$H NMR (500 MHz, CDCl$_3$, mixture of rotamers/conformers) δ 7.34-7.27 (m, 1.42H), 7.25-7.10 (m, 2.47H), 7.04 (t, J=7.5 Hz, 0.82H), 6.96 (t, J=6.9 Hz, 0.45H), 6.52 (s, 1.13H), 5.56 (s, 0.88H), 5.49-5.33 (m, 1.49H), 5.25-5.16 (m, 2.13H), 4.94 (s, 0.77H), 4.75 (d, J=13.9 Hz, 0.71H), 4.16-4.07 (m, 1.93H), 3.48 (d, J=3.8 Hz, 3H), 3.45-3.37 (m, 1.45H), 3.12 (t, J=12.7 Hz, 0.59H), 2.90-2.80 (m, 0.48H), 2.39-2.29 (m, 0.81H), 2.23-2.15 (m, 0.51H), 1.82-1.68 (m, 4.11H), 1.60-1.45 (m, 9.21H), 1.45-1.11 (m, 17.89H), 0.93 (d, J=6.7 Hz, 9.57H), 0.87 (t, J=7.0 Hz, 4.95H), 0.11-0.06 (m, 6H); $^{13}$C NMR (100 MHz, CDCl$_3$) δ 176.93, 170.95, 170.77, 168.84, 153.37, 152.84, 130.34, 128.13, 127.04, 125.65, 122.31, 114.92, 94.96, 75.69, 73.53, 58.07, 56.43, 56.32, 52.06, 45.55, 35.20, 34.05, 31.83, 30.43, 29.55, 29.31, 25.86, 25.43, 25.32, 24.19, 22.70, 21.39, 18.14, 14.20, −4.71, −5.12; $[α]^{25}_D$ +13.9 (c=2.42 in CHCl$_3$); IR (film) 3480, 2928, 2857, 1732 (C=O), 1687 (C=O), 1634 (C=O), 1600, 1489, 1455, 1424, 1286, 1251, 1233, 1198, 1153, 1096, 1078, 1042, 991, 922, 836, 778, 755, 730, 668, 645; HRMS Accurate mass (ES$^+$): Found 649.4264 (+2.3 ppm), C$_{35}$H$_{61}$N$_2$O$_7$Si (M+H$^+$) requires 649.4249.

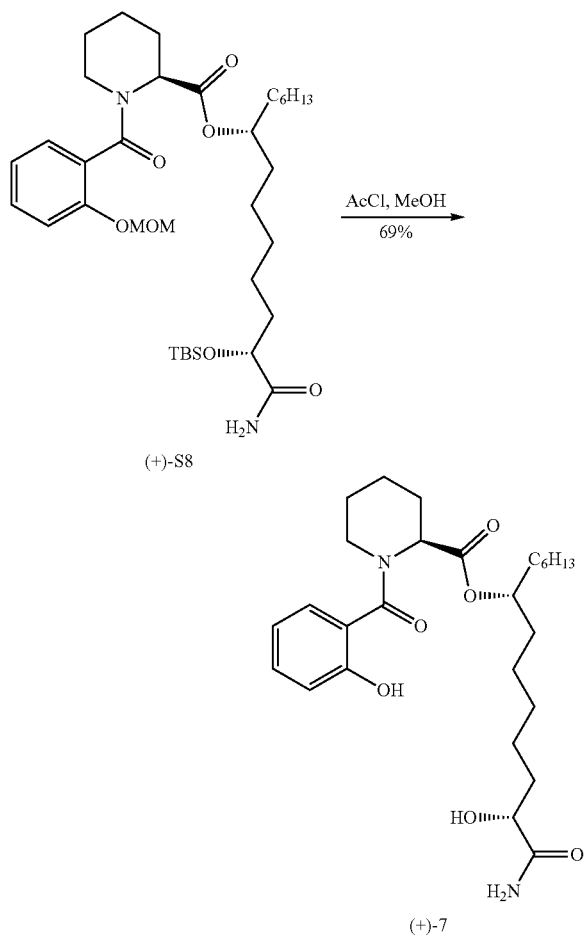

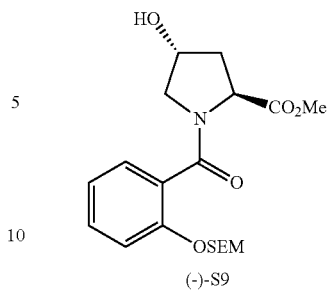

(1R,7R)-1-carbamoyl-1-hydroxytridecan-7-yl (2S)-1-(2-hydroxybenzoyl)piperidine-2-carboxylate (+)-7. To a solution of protected ester (+)-S8 (25 mg, 0.038 mmol) dissolved in MeOH (1 mL) was added acetyl chloride (5 µL, 0.006 mmol) at 0° C. The reaction was stirred at this temperature for 45 minutes then warmed to room temperature and stirred for 2 hours. The reaction was quenched with sat. NaHCO₃, and extracted with CH₂Cl₂ 3×. The combined organic layers were washed with brine, dried over MgSO₄, filtered, concentrated, and purified by preparative TLC (100% EtOAc), yielding the title compound as a clear oil (12 mg, 69% yield). Note: High temperature proton NMR was possible, but extended heating times caused decomposition. ¹H NMR (500 MHz, CDCl₃, 328K) δ 8.67 (br s, 0.39H), 8.54 (br s, 0.47H), 7.37-7.27 (m, 1H), 6.99 (d, J=8.1 Hz, 1H), 6.87 (s, 1H), 5.21 (d, J=34.3 Hz, 1H), 5.05-4.96 (m, 1H), 4.16-3.98 (m, 2H), 3.36-3.22 (m, 1H), 2.39-2.26 (m, 1H), 1.80 (d, J=11.5 Hz, 3H), 1.60 (s, 10H), 1.30 (s, 15H), 0.90 (t, J=6.6 Hz, 3H); ¹³C NMR (125 MHz, CDCl₃, room temp) δ 171.55, 171.12, 157.86, 132.52, 132.41, 130.70, 128.11, 128.03, 119.41, 119.26, 118.08, 118.01, 60.41, 34.83, 34.56, 34.46, 34.23, 34.10, 31.88, 29.86, 29.29, 29.24, 29.03, 28.80, 26.95, 26.79, 25.58, 25.54, 25.36, 25.21, 25.14, 24.80, 22.66, 21.38, 21.24, 14.33, 14.03; [α]²⁵_D +21.5 (c=1.3 in CHCl₃); IR (film) 3291 (br O—H), 2928, 2857, 1731 (C=O), 1692 (C=O), 1624 (C=O), 1454, 1373, 1207, 1142, 1007, 935, 911, 847, 827, 753, 645, 602; HRMS Accurate mass (ES⁺): Found 491.3097 (−4.9 ppm) C₂₇H₄₃N₂O₆ (M+H⁺) requires 491.3121.

Methyl (2S,4R)-4-hydroxy-1-(2-((2-(trimethylsilyl)ethoxy)methoxy)benzoyl)pyrrolidine-2-carboxylate (−)-S9. Prepared as previously described (Steele et al., *J. Am. Chem. Soc.* 2015, 137, 7314) with an additional purification by preparative TLC (2:1:1 EtOAc:CH₂Cl₂:Et₂O) yielded a pure sample of the title compound. ¹H NMR (500 MHz, CDCl₃, mixture of rotamers/conformers) δ 7.34 (ddt, J=7.6, 3.2, 1.8 Hz, 1.50H), 7.32-7.29 (m, 0.25H), 7.20 (dd, J=7.5, 1.7 Hz, 0.25H), 7.16 (d, J=7.9 Hz, 1H), 7.05 (td, J=7.5, 0.9 Hz, 0.75H), 6.99 (td, J=7.5, 0.9 Hz, 0.25H), 5.24 (dt, J=13.7, 5.1 Hz, 2H), 4.80 (t, J=8.2 Hz, 0.75H), 4.56 (br s, 0.25H), 4.48-4.41 (m, 1H), 3.99 (d, J=12.9 Hz, 0.25H), 3.82-3.72 (m, 4.50H), 3.62 (d, J=8.4 Hz, 0.75H), 3.42 (s, 0.75H), 3.39-3.31 (m, 1H), 2.44-2.28 (m, 1H), 2.17-2.09 (m, 2H), 1.62 (br s, 1H), 0.95 (ddd, J=8.3, 7.5, 4.2 Hz, 2H), 0.01-0.01 (m, 9H); ¹³C NMR (100 MHz, CDCl₃) δ 172.74, 168.37, 153.34, 130.99, 130.93, 128.36, 127.03, 126.18, 122.23, 121.82, 115.72, 115.10, 93.87, 69.94, 68.81, 66.74, 60.52, 58.73, 57.31, 56.22, 54.71, 52.38, 52.14, 39.49, 38.17, 18.07, 14.25, −1.33; [α]²⁵_D −62.5 (c=2.14 in CHCl₃); IR (film) 3390 (br, O—H), 2951, 2944, 2360, 2160, 2028, 1979, 1747 (C=O), 1616 (C=O), 1601, 1491, 1455, 1432, 1359, 1248, 1229, 1248, 1201, 1175, 1148, 1084, 1042, 984, 916, 857, 834, 755; HRMS Accurate mass (ES⁺): Found 418.1656 (−1.4 ppm), C₂₉H₂₉NO₆SiNa (M+Na⁺) requires 418.1662.

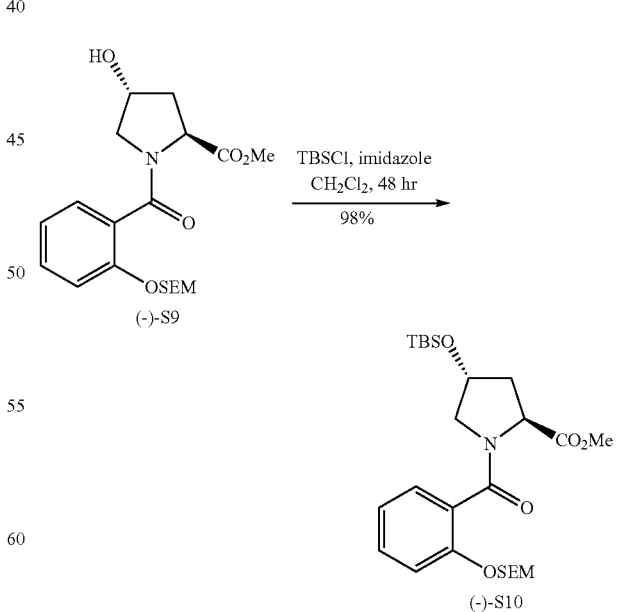

Methyl (2S,4R)-4-[(tert-butyldimethylsily)oxy]-1-(2-{[2-(trimethylsilyl)ethoxy]methoxy}benzoyl)pyrrolidine-2-carboxylate (−)-S10. To a solution of compound 17 (64 mg, 0.162 mmol) in CH$_2$Cl$_2$ (1 mL) was added imidazole (22 mg, 0.324 mmol) followed by TBSCl (49 mg, 0.324 mmol), and the reaction was stirred for 24 hours, after which time TLC analysis indicated the reaction was incomplete. Another portion of imidazole (22 mg, 0.324 mmol) and TBSCl (49 mg, 0.324) was added, and the reaction was stirred at room temperature for an additional 24 hours, after which time TLC analysis indicated the consumption of starting material. The reaction was quenched with water and extracted with CH$_2$Cl$_2$ 3×. The combined organic layers were washed with water and brine, dried over MgSO$_4$, filtered, concentrated and purified by column chromatography, yielding the title compound as a clear oil (80 mg, 98% yield). $^1$H NMR (500 MHz, CDCl$_3$, mixture of rotamers/conformers) δ 7.36-7.27 (m, 1.36H), 7.20-7.17 (m, 1.31H), 7.03 (td, J=7.5, 1.0 Hz, 0.68H), 6.98 (td, J=7.5, 0.9 Hz, 0.33H), 5.25-5.19 (m, 2H), 4.75 (t, J=7.8 Hz, 0.67H), 4.52-4.44 (m, 0.59H), 4.43-4.38 (m, 0.69H), 3.82-3.72 (m, 4.53H), 3.59 (dd, J=10.9, 4.5 Hz, 0.68H), 3.37 (s, 0.89H), 3.18 (dd, J=11.0, 1.7 Hz, 0.68H), 2.28-2.19 (m, 1H), 2.14-2.05 (m, 1H), 0.95 (td, J=8.3, 2.5 Hz, 2H), 0.90 (s, J=2.9 Hz, 2.84H), 0.82 (s, J=2.9 Hz, 6H), 0.10 (s, J=3.1 Hz, 0.85H), 0.09 (s, J=3.0 Hz, 0.86H), 0.02 (s, J=2.8 Hz, 1.79H), 0.00-0.01 (m, 8.25H), —0.04 (s, 2H); $^{13}$C NMR (125 MHz, CDCl$_3$) δ 172.74, 168.16, 153.74, 130.77, 130.73, 128.24, 127.33, 122.04, 121.71, 115.89, 93.86, 93.47, 70.45, 69.40, 66.47, 57.47, 56.28, 54.78, 52.26, 51.98, 40.39, 38.58, 25.78, 25.65, 18.12, 18.02, 17.87, −1.32, −1.36, −4.81, −4.92; [α]$^{25}_D$ −65.9 (c=0.72 in CHCl$_3$); IR (film) 2952, 2924, 2893, 2856, 1746 (C=O), 1644 (C=O), 1601 (C=O), 1489, 1455, 1412, 1359, 1317, 1249, 1227, 1197, 1175, 1144, 1086, 1023, 986, 920, 833, 775, 753, 693, 653; HRMS Accurate mass (ES$^+$): Found 532.2485 (−7.9 ppm), C$_{25}$H$_{43}$NO$_6$Si$_2$Na (M+Na$^+$) requires 532.2527.

(t, J=7.7 Hz, 1H), 4.36 (s, 1H), 3.49 (dd, J=11.2, 4.1 Hz, 1H), 3.20 (t, J=17.9 Hz, 1H), 2.53-2.44 (m, 1H), 2.25-2.12 (m, 1H), 0.98-0.87 (m, 3H), 0.82 (s, 9H), 0.03 (s, 3H), —0.01 (s, 9H), −0.06 (s, 3H); $^{13}$C NMR (125 MHz, CDCl$_3$) δ 172.72, 171.48, 153.73, 131.57, 128.02, 125.78, 122.12, 115.57, 93.64, 69.84, 66.80, 58.79, 57.12, 37.22, 25.72, 18.10, 17.95, −1.27, −4.73, −4.89; [α]$^{25}_D$ −86.6 (c=1.75 in CHCl$_3$); IR (film) 2952, 2856, 2359, 2341, 1743 (C=O), 1595 (C=O), 1489, 1462, 1434, 1361, 1249, 1024, 988, 921, 754, 693, 667, 611; HRMS Accurate mass (ES$^+$): Found 518.2330 (−7.7 ppm), C$_{24}$H$_{41}$NO$_6$Si$_2$Na (M+Na$^+$) requires 518.2370.

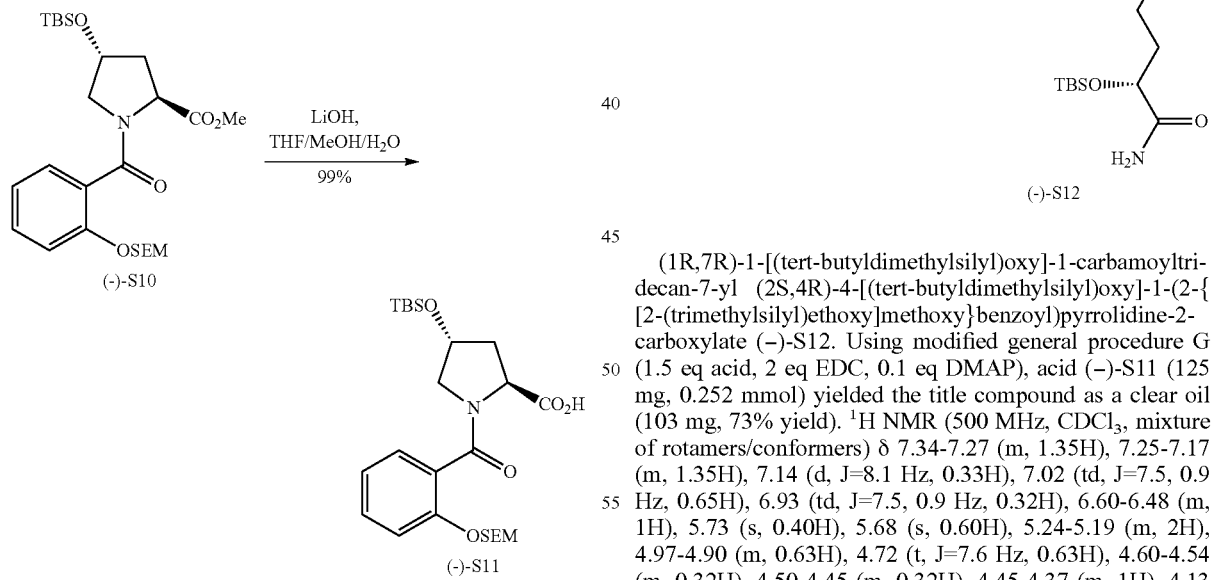

(1R,7R)-1-[(tert-butyldimethylsilyl)oxy]-1-carbamoyltridecan-7-yl (2S,4R)-4-[(tert-butyldimethylsilyl)oxy]-1-(2-{[2-(trimethylsilyl)ethoxy]methoxy}benzoyl)pyrrolidine-2-carboxylate (−)-S12. Using modified general procedure G (1.5 eq acid, 2 eq EDC, 0.1 eq DMAP), acid (−)-S11 (125 mg, 0.252 mmol) yielded the title compound as a clear oil (103 mg, 73% yield). $^1$H NMR (500 MHz, CDCl$_3$, mixture of rotamers/conformers) δ 7.34-7.27 (m, 1.35H), 7.25-7.17 (m, 1.35H), 7.14 (d, J=8.1 Hz, 0.33H), 7.02 (td, J=7.5, 0.9 Hz, 0.65H), 6.93 (td, J=7.5, 0.9 Hz, 0.32H), 6.60-6.48 (m, 1H), 5.73 (s, 0.40H), 5.68 (s, 0.60H), 5.24-5.19 (m, 2H), 4.97-4.90 (m, 0.63H), 4.72 (t, J=7.6 Hz, 0.63H), 4.60-4.54 (m, 0.32H), 4.50-4.45 (m, 0.32H), 4.45-4.37 (m, 1H), 4.13 (dt, J=13.1, 5.2 Hz, 1H), 3.87-3.69 (m, 2.72H), 3.57 (dd, J=10.7, 4.3 Hz, 0.63H), 3.16 (dd, J=10.9, 2.7 Hz, 0.63H), 2.24 (ddd, J=12.8, 8.2, 4.7 Hz, 1H), 2.14-2.03 (m, 1H), 1.81-1.70 (m, 1H), 1.70-1.46 (m, 4H), 1.46-1.09 (m, 16H), 0.95-0.93 (m, 4H), 0.91-0.89 (m, 8.54H), 0.83-0.81 (m, 5.72H), 0.12-0.06 (m, 8.34H), 0.01-−0.02 (m, 10.78H), —0.05 (s, 1.77H); $^{13}$C NMR (125 MHz, CDCl$_3$) δ 177.18, 171.97, 168.48, 168.01, 153.83, 130.67, 128.29, 127.45, 126.67, 122.04, 121.88, 115.88, 93.92, 93.43, 75.48, 75.11, 73.49, 70.42, 69.34, 66.48, 58.74, 57.83, 56.18, 54.35, 40.40, 38.72, 35.25, 35.12, 34.09, 33.74, 33.69, 31.82, 31.75, 29.55, 29.49, 29.24, 29.13, 25.82, 25.71, 25.31, 25.24, 25.10, 24.79, 24.08, 22.66, 22.61, 18.20, 18.08, 17.93, 14.15, −1.27, −4.76, −4.80, −4.90, −5.19; [α]$^{25}_D$ −20.8 (c=0.86 in CHCl$_3$); IR (film) 3480 (N–H), 2927, 2856, 1739 (C=O), 1691 (C=O), 1644 (C=O), 1455, 1412, 1250, 1189, 1088, 991, 937, 897, 834, 754, 574; HRMS Accurate mass (ES$^+$): Found 873.5226 (−5.8 ppm), C$_{44}$H$_{82}$N$_2$O$_8$Si$_3$Na (M+Na$^+$) requires 873.5277.

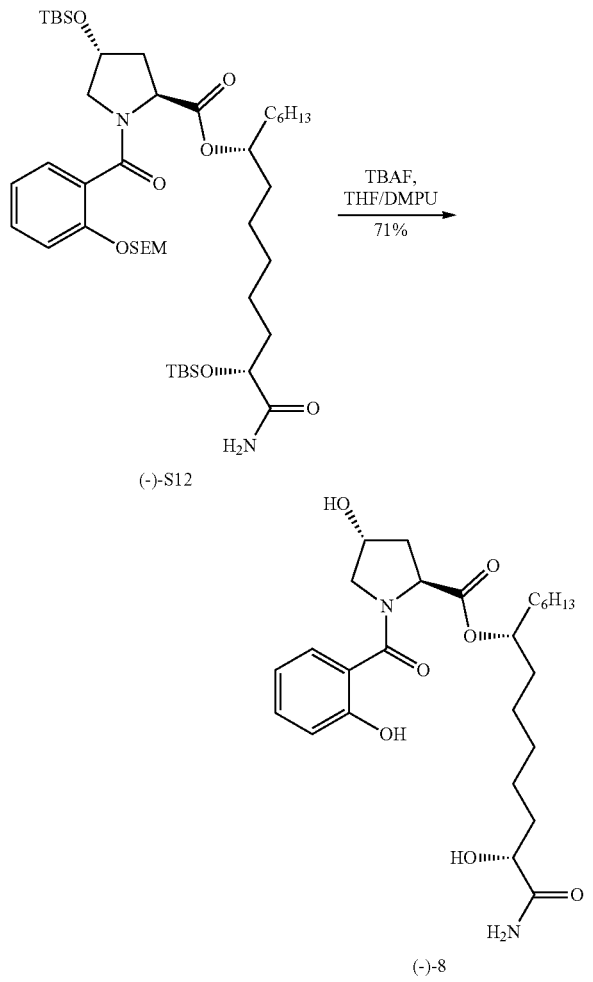

(1R,7R)-1-carbamoyl-1-hydroxytridecan-7-yl (2S,4R)-4-hydroxy-1-(2-hydroxybenzoyl)pyrrolidine-2-carboxylate (−)-8. Using modified general procedure I (25 eq. TBAF, 0.040M DMPU), silyl ether (−)-S12 (25 mg, 0.029 mmol) with column chromatography eluting in 0→5% MeOH/CH$_2$Cl$_2$ yielded the title compound as a clear oil (10 mg, 71% yield). $^1$H NMR (500 MHz, CDCl$_3$) δ 10.50 (br s, 1H), 7.41 (d, J=7.2 Hz, 1H), 7.32 (t, J=7.7 Hz, 1H), 6.93 (d, J=8.3 Hz, 1H), 6.86 (t, J=7.5 Hz, 1H), 6.74 (br s, 1H), 5.69 (br s, 1H), 4.97 (br s, 1H), 4.81 (t, J=8.2 Hz, 1H), 4.53 (s, 1H), 4.05 (dd, J=7.7, 3.4 Hz, 1H), 3.95 (d, J=8.7 Hz, 1H), 3.82-3.61 (m, 2H), 3.15 (br s, 1H), 2.43-2.30 (m, 1H), 2.09 (ddd, J=13.0, 8.7, 4.4 Hz, 1H), 1.85-1.72 (m, 1H), 1.65-1.32 (m, 9H), 1.30-1.12 (m, 10H), 0.86 (t, J=7.1 Hz, 3H); $^{13}$C NMR (125 MHz, CDCl$_3$) δ 177.57, 172.31, 170.88, 158.86, 133.28, 128.30, 118.98, 117.88, 75.73, 71.58, 70.44, 59.12, 58.36, 37.40, 34.48, 34.17, 34.04, 31.84, 29.23, 28.42, 25.46, 24.70, 24.50, 22.69, 14.21; [α]$^{25}_D$ −43.4 (c=0.71 in CHCl$_3$); IR (film) 3303 (br O–H), 2928, 2857, 1732 (C=O), 1666 (C=O), 1586 (C=O), 1434, 1376, 1298, 1193, 1082, 1001, 958, 911, 878, 754, 728, 651, 609; HRMS Accurate mass (ES$^+$): Found 515.2691 (−8.2 ppm), C$_{26}$H$_{40}$N$_2$O$_7$Na (M+Na$^+$) requires 515.2733; R$_f$ (9:1 CH$_2$Cl$_2$:MeOH)=0.34.

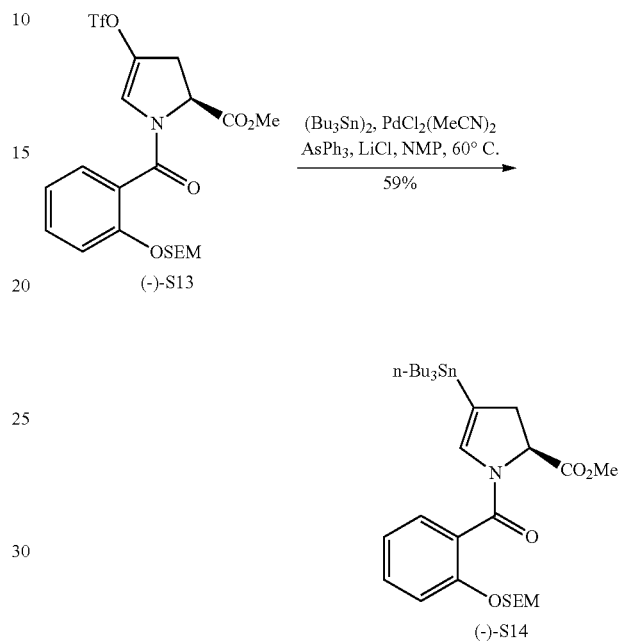

Methyl (S)-4-(tributylstannyl)-1-(2-((2-(trimethylsilyl)ethoxy)methoxy)benzoyl)-2,3-dihydro-1H-pyrrole-2-carboxylate (−)-S14. To a solution of triflate (−)-S13 (Steele et al., J. Am. Chem. Soc. 2015, 137, 7314) (559 mg, 1.064 mmol) in NMP (6 mL) was added PdCl$_2$(MeCN)$_2$ (14 mg, 0.053 mmol), AsPh$_3$ (65 mg, 0.213 mmol), LiCl (135 mg, 3.191 mmol), and bis(tributyltin) (0.56 mL, 1.117 mmol). The solution was heated to 60° C. for 1 hour, after which time the reaction turned from orange to brown/black. The reaction was cooled to room temperature, quenched with 1M aq. KF, and extracted 2× with Et$_2$O. The combined organic layers were washed with 1M aq. KF, and brine 2×, then dried over MgSO$_4$, filtered, concentrated and purified by column chromatography, yielding the title compound as a yellow oil (416 mg, 59% yield). $^1$H NMR (400 MHz, CDCl$_3$) δ 7.41-7.35 (m, 2H), 7.22 (dd, J=8.8, 0.9 Hz, 1H), 7.09-7.03 (m, 1H), 5.97 (t, J=2.1 Hz, 1H), 5.26-5.19 (m, 2H), 4.96 (dd, J=11.4, 5.0 Hz, 1H), 3.84-3.72 (m, 5H), 3.15 (ddd, J=16.8, 11.3, 2.3 Hz, 1H), 2.76 (ddd, J=16.8, 5.0, 1.9 Hz, 1H), 1.52-1.38 (m, 6H), 1.33-1.20 (m, 8H), 0.98-0.82 (m, 18H), 0.00 (s, 9H); $^{13}$C NMR (125 MHz, CDCl$_3$) δ 171.83, 164.19, 154.01, 135.61, 131.09, 128.90, 126.25, 121.93, 118.43, 93.64, 66.39, 58.29, 52.28, 40.55, 29.08, 29.00, 27.24, 27.16, 17.92, 13.67, 13.63, 9.52 (J=309 Hz, $^{13}$C-$^{117}$Sn; J=355 Hz, $^{13}$C-$^{119}$Sn), −1.36; [α]$^{25}_D$ −41.5 (c=1.63 in CHCl$_3$); IR (film) 2953, 2923, 2869, 2852, 1754 (C=O), 1651 (C=O), 1584, 1488, 1454, 1399, 1283, 1247, 1228, 1198, 1176, 1152, 1087, 1019, 989, 917, 856, 834, 753, 731, 692, 658, 599, 561; HRMS Accurate mass (ES$^+$): Found 668.2798 (+0.7 ppm), C$_{31}$H$_{54}$NO$_5$SiSn (M+H$^+$) requires 668.2793.

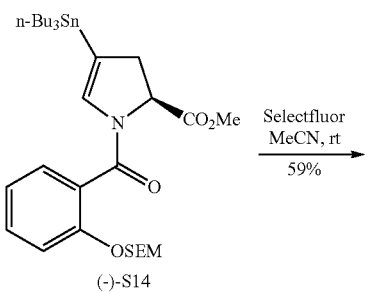

(-)-S14

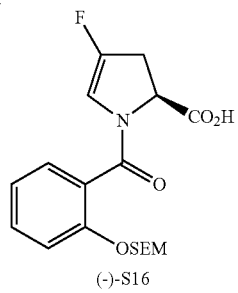

(-)-S16

(S)-4-fluoro-1-(2-((2-(trimethylsilyl)ethoxy)methoxy)benzoyl)-2,3-dihydro-1H-pyrrole-2-carboxylic acid (−)-S16. To a solution of methyl ester (−)-S15 (128 mg, 0.3236 mmol) in 3:1:1 THF:MeOH:H$_2$O (3 mL) was added LiOH.H$_2$O (14 mg) dissolved in water (0.5 mL) at 0° C. The reaction was stirred for 15 minutes then warmed to room temperature and stirred for 2 hours. The reaction was acidified (pH~5-6) with 5% aq. AcOH, and extracted with CH$_2$Cl$_2$ 3×. The combined organic layers were washed with brine, dried over MgSO$_4$, filtered, concentrated and purified by column chromatography (0→5% MeOH/0.1% AcOH/CH$_2$Cl$_2$), yielding the title compound as a clear oil (116 mg, 94% yield). Note: While the acids in this study prepared by ester hydrolysis generally did not require chromatography, this one in particular required purification for acceptable yields in the next step. $^1$H NMR (400 MHz, CDCl$_3$) δ 7.47-7.42 (m, 1H), 7.36 (dd, J=7.5, 1.5 Hz, 1H), 7.24 (d, J=8.5 Hz, 1H), 7.09 (td, J=7.5, 0.7 Hz, 1H), 5.96 (d, J=1.9 Hz, 1H), 5.28-5.20 (m, 3H), 3.76-3.70 (m, 2H), 3.62-3.54 (m, 1H), 3.27-3.14 (m, 1H), 0.97-0.91 (m, 2H), 0.00 (s, 9H); $^{13}$C NMR (100 MHz, CDCl$_3$) δ 171.19, 167.47, 153.70, 153.26, 150.58, 132.17, 129.05, 123.85, 122.08, 115.05, 110.80 (d, J=31 Hz, $^{13}$C-$^{19}$F), 93.26, 66.93, 57.71, 18.13, −1.39; [α]$^{25}_D$ −62.7 (c=0.72 in CHCl$_3$); IR (film) 2954, 2923, 2853, 1742 (C=O), 1600 (C=O), 1458, 1425, 1354, 1315, 1248, 1231, 1144, 1086, 983, 916, 857, 834, 753, 693, 658 HRMS Accurate mass (ES$^+$): Found 404.1291 (−3.5 ppm), C$_{18}$H$_{24}$FNO$_5$SiNa (M+Na$^+$) requires 404.1305; R$_f$ (10% MeOH/0.1% AcOH/CH$_2$Cl$_2$)=0.29.

Methyl (S)-4-fluoro-1-(2-((2-(trimethylsilyl)ethoxy)methoxy)benzoyl)-2,3-dihydro-1H-pyrrole-2-carboxylate (−)-S15. To a solution of stannane (−)-S14 (400 mg, 0.6001 mmol) in acetonitrile (5 mL) was added Selectfluor® (234 mg, 0.6601 mmol). After 5 minutes, solids crashed out and the solution was filtered into water. The layers were separated and the aqueous layer was extracted with CH$_2$Cl$_2$ 2×. The combined organic layers were washed with brine, dried over MgSO$_4$, filtered, concentrated, and purified by column chromatography, yielding the title compound as a clear oil (140 mg, 59%). $^1$H NMR (500 MHz, CDCl$_3$) δ 7.40-7.34 (m, 2H), 7.21 (t, J=7.2 Hz, 1H), 7.05 (td, J=7.5, 0.9 Hz, 1H), 6.06 (dd, J=4.1, 2.2 Hz, 1H), 5.24 (q, J=7.1 Hz, 2H), 5.05 (dd, J=11.7, 4.7 Hz, 1H), 3.83 (s, 3H), 3.79-3.73 (m, 2H), 3.32 (dddd, J=16.4, 11.8, 4.3, 2.3 Hz, 1H), 2.89-2.83 (m, 1H), 0.99-0.91 (m, 2H), −0.01 (s, 9H); $^{13}$C NMR (125 MHz, CDCl$_3$) δ 170.10, 165.21, 153.60, 151.05, 148.92, 131.45, 128.93, 124.94, 121.95, 115.07, 111.54 (d, J=30 Hz $^{13}$C-$^{19}$F), 93.20, 66.66, 56.30, 56.26, 52.70, 32.07, 31.91, 18.04, −1.47; [α]$^{25}_D$ −56.1 (c=1.08 in CHCl$_3$; IR (film) 2953, 2924, 1749 (C=O), 1644 (C=O), 1600, 1488, 1456, 1417, 1356, 1229, 1306, 1247, 1231, 1201, 1179, 1144, 1086, 1028, 982, 934, 914, 857, 834, 754, 693, 658, 577; HRMS Accurate mass (ES$^+$): Found 418.1427 (−8.4 ppm), C$_{19}$H$_{26}$FNO$_5$SiNa (M+Na$^+$) requires 418.1462.

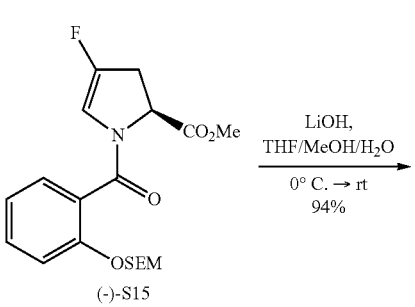

(-)-S15

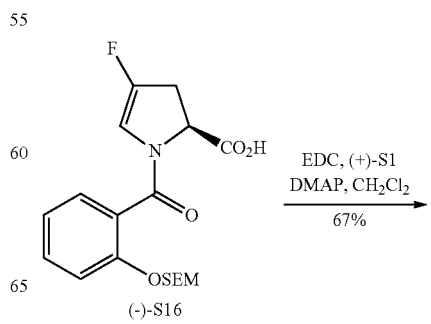

(-)-S16

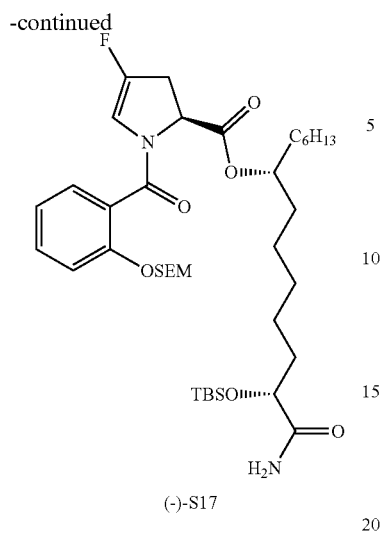

(−)-S17

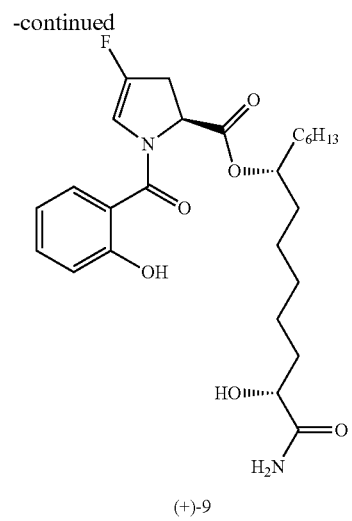

(+)-9

(7R,13R)-14-amino-13-((tert-butyldimethylsilyl)oxy)-14-oxotetradecan-7-yl (S)-4-fluoro-1-(2-((2-(trimethylsilyl)ethoxy)methoxy)benzoyl)-2,3-dihydro-1H-pyrrole-2-carboxylate (S9). Using general procedure G, acid (−)-S16 (39 mg, 0.102 mmol) yielded the title compound as a clear oil (36 mg, 67% yield). $^1$H NMR (400 MHz, CDCl$_3$) δ 7.40-7.30 (m, 2H), 7.20 (d, J=8.2 Hz, 1H), 7.04 (t, J=7.1 Hz, 1H), 6.57-6.48 (m, 1H), 6.05 (d, J=1.8 Hz, 1H), 5.57-5.43 (m, 1H), 5.24 (q, J=7.1 Hz, 2H), 5.08-4.91 (m, 2H), 4.13 (t, J=5.1 Hz, 1H), 3.80-3.71 (m, 2H), 3.38-3.27 (m, 1H), 2.85-2.75 (m, 1H), 1.82-1.70 (m, 1H), 1.69-1.50 (m, 6H), 1.41-1.19 (m, 20H), 0.97-0.89 (m, 12H), 0.89-0.85 (m, 3H), 0.13-0.06 (m, 6H), −0.01 (s, 9H); $^{13}$C NMR (125 MHz, CDCl$_3$) δ 177.10, 169.48, 165.13, 153.75, 151.09, 148.97, 131.45, 129.02, 125.18, 122.02, 115.20, 111.72 (d, J=31 Hz, $^{13}$C-$^{19}$F), 93.33, 76.00, 73.52, 66.76, 56.71, 35.16, 35.06, 34.00, 33.95, 32.39, 32.23, 31.81, 29.80, 29.44, 29.27, 25.84, 25.31, 25.19, 25.00, 24.14, 24.07, 22.68, 18.17, 18.11, 14.16, −1.30, −1.35, −4.74, −5.16; $[α]^{25}_D$ −12.5 (c=1.18 in CHCl$_3$) IR (film) 3480, 2951, 2927, 2856, 2242, 1742 (C=O), 1688 (C=O), 1645 (C=O), 1601, 1488, 1456, 1419, 1353, 1249, 1189, 1142, 1088, 988, 916, 835, 778, 754, 730, 659, 577; HRMS Accurate mass (ES$^+$): Found 759.4182 (−4.0 ppm), C$_{38}$H$_{65}$FN$_2$O$_7$Si$_2$Na (M+Na$^+$) requires 759.4212; R$_f$ (2:1 CH$_2$Cl$_2$:Et$_2$O)=0.60.

(7R,13R)-14-amino-13-hydroxy-14-oxotetradecan-7-yl (S)-4-fluoro-1-(2-hydroxybenzoyl)-2,3-dihydro-1H-pyrrole-2-carboxylate (+)-9. Using general procedure I, silyl ether (−)-S17 (21 mg, 0.029 mmol) yielded the title compound as a clear oil (8.1 mg, 58% yield). $^1$H NMR (500 MHz, CDCl$_3$) δ 9.67 (br d, 1H), 7.41-7.33 (m, 2H), 7.02-6.96 (m, 1H), 6.91 (t, J=7.6 Hz, 1H), 6.70 (d, J=38.0 Hz, 1H), 6.55 (d, J=28.6 Hz, 1H), 5.49 (d, J=44.7 Hz, 1H), 5.07-4.92 (m, 2H), 4.09 (dd, J=7.9, 3.5 Hz, 1H), 3.35 (t, J=14.0 Hz, 1H), 3.03 (br s, 1H), 2.88-2.80 (m, 1H), 1.84-1.72 (m, 1H), 1.72-1.50 (m, 6H), 1.50-1.18 (m, 14H), 0.87 (t, J=7.0 Hz, 3H); $^{13}$C NMR (125 MHz, CDCl$_3$) δ 176.96, 176.73, 169.87, 169.56, 167.43, 159.01, 158.10, 152.93, 152.82, 150.67, 133.80, 133.63, 127.97, 119.49, 119.28, 118.22, 118.13, 117.08, 116.43, 112.12, 111.87, 76.58, 71.68, 71.48, 58.34, 57.83, 34.53, 34.45, 34.37, 34.14, 33.86, 31.82, 29.21, 28.81, 28.43, 25.52, 25.27, 24.95, 24.84, 24.61, 22.68, 14.19; $[α]^{25}_D$ +12.0 (c=0.45 in CHCl$_3$); IR (film) 3308 (br, O—H), 2929, 2858, 1734 (C=O), 1669 (C=O), 1653, 1623, 1594, 1521, 1457, 1436, 1354, 1337, 1300, 1192, 1142, 1097, 1037, 1004, 919, 859, 804, 755, 655; HRMS Accurate mass (ES$^+$): Found 493.2738 (+4.9 ppm), C$_{26}$H$_{38}$FN$_2$O$_6$ (M+H$^+$) requires 493.2714.

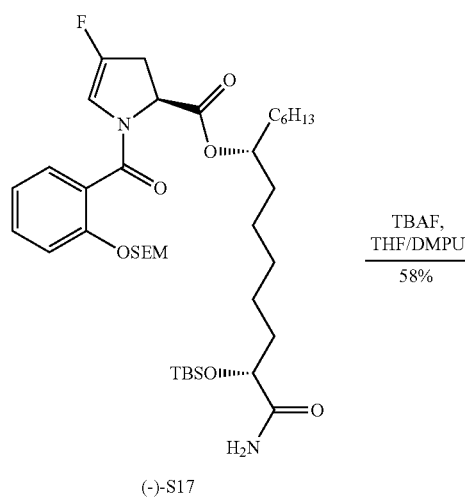

(−)-S17

$\xrightarrow[\text{58%}]{\text{TBAF, THF/DMPU}}$

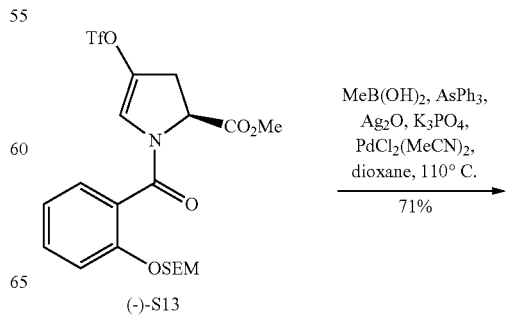

(−)-S13

$\xrightarrow[\text{71%}]{\text{MeB(OH)}_2\text{, AsPh}_3\text{, Ag}_2\text{O, K}_3\text{PO}_4\text{, PdCl}_2\text{(MeCN)}_2\text{, dioxane, 110° C.}}$

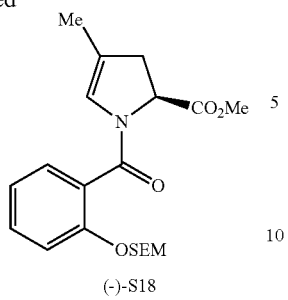

(-)-S18

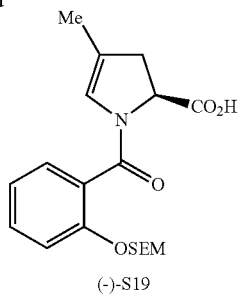

(-)-S19

Methyl (S)-4-methyl-1-(2-((2-(trimethylsilyl)ethoxy)methoxy)benzoyl)-2,3-dihydro-1H-pyrrole-2-carboxylate (−)-S18. Triflate (−)-S13 (Steele et al., *J. Am. Chem. Soc.* 2015, 137, 7314) (75 mg, 0.143 mmol) was dissolved in dioxane (1.5 mL), and triphenylarsine (18 mg, 0.057 mmol), methylboronic acid (30 mg, 0.501 mmol), silver oxide (133 mg, 0.572 mmol) and K$_3$PO$_4$ (182 mg, 0.858 mmol) were added, and the reaction flask was covered in foil. The flask was vacuumed and backfilled with argon 3×, then PdCl$_2$(MeCN)$_2$ (4 mg, 0.014 mmol) was added, and the reaction was heated to 110° C. Upon heating, the reaction turned from green to dark red, and TLC analysis indicated the starting material was consumed. The reaction was filtered through Celite, concentrated, and purified by column chromatography, yielding the title compound as an orange oil (39 mg, 71% yield). $^1$H NMR (400 MHz, CDCl$_3$, mixture of rotamers/conformers) δ 7.39-7.28 (m, 2H), 7.20 (d, J=8.1 Hz, 0.91H), 7.15 (d, J=7.9 Hz, 0.15H), 7.04 (td, J=7.5, 1.0 Hz, 0.92H), 6.99 (td, J=7.5, 1.0 Hz, 0.14H), 5.88 (dd, J=3.5, 1.7 Hz, 1H), 5.26-5.19 (m, 2H), 5.01 (dd, J=11.6, 4.9 Hz, 1H), 3.80 (s, 3H), 3.78-3.71 (m, 2H), 3.06-2.96 (m, 1H), 2.61-2.53 (m, 1H), 1.64 (d, J=1.4 Hz, 3H), 0.98-0.89 (m, 2H), 0.01-0.03 (m, 9H); $^{13}$C NMR (100 MHz, CDCl$_3$) δ 171.70, 164.44, 153.83, 131.11, 128.90, 126.23, 125.30, 122.04, 119.42, 115.48, 93.48, 66.58, 58.32, 52.59, 38.23, 18.16, 13.54, −1.27; [α]$^{25}_D$ −18.5 (c=0.43 in CHCl$_3$); IR (film) 2951, 2919, 2850, 2102, 1747 (C=O), 1670 (C=O), 1600, 1486, 1454, 1409, 1345, 1247, 1230, 1144, 1088, 1052, 976, 916, 857, 834, 755, 694, 664, 605; HRMS Accurate mass (ES$^+$): Found 414.1684 (−7.0 ppm), C$_{20}$H$_{29}$NO$_5$SiNa (M+Na$^+$) requires 414.1713.

(S)-4-methyl-1-(2-((2-(trimethylsilyl)ethoxy)methoxy)benzoyl)-2,3-dihydro-1H-pyrrole-2-carboxylic acid (−)-S19. Using general procedure B, methyl ester (−)-S18 (19 mg, 0.049 mmol) yielded the title compound as a clear oil (20 mg, quant. yield). $^1$H NMR (500 MHz, CDCl$_3$) δ 7.41 (t, J=7.7 Hz, 1H), 7.33 (d, J=6.5 Hz, 1H), 7.23 (d, J=8.3 Hz, 1H), 7.07 (t, J=7.5 Hz, 1H), 5.78 (s, 1H), 5.22 (s, 2H), 5.20-5.11 (m, 1H), 3.75-3.69 (m, 2H), 3.22 (d, J=16.4 Hz, 1H), 2.97-2.85 (m, 1H), 1.70 (s, 3H), 0.99-0.87 (m, 2H), −0.01 (s, 9H); $^{13}$C NMR (100 MHz, CDCl$_3$) δ 170.97, 167.90, 153.86, 132.11, 124.43, 124.15, 123.55, 122.09, 115.25, 93.38, 66.87, 60.45, 36.19, 18.17, 13.61, −1.27; [α]$^{25}_D$ −80.6 (c=0.70 in CHCl$_3$); IR (film) 2954, 2921, 2857, 1743, 1598, 1489, 1457, 1427, 1378, 1303, 1232, 1143, 1086, 1043, 983, 916, 856, 834, 754, 694, 658; HRMS Accurate mass (ES$^+$): Found 400.1573 (+4.2 ppm), C$_{19}$H$_{27}$NO$_5$SiNa (M+Na$^+$) requires 400.1556.

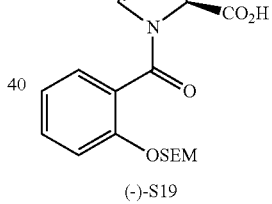

(-)-S19

EDC, (+)-S1
DMAP, CH$_2$Cl$_2$

59%

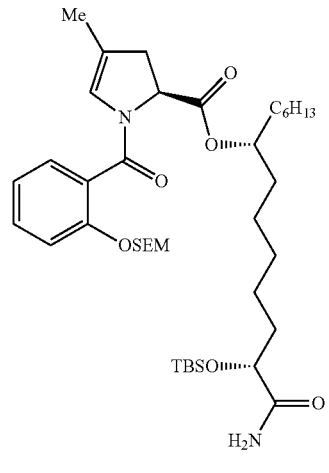

(-)-S20

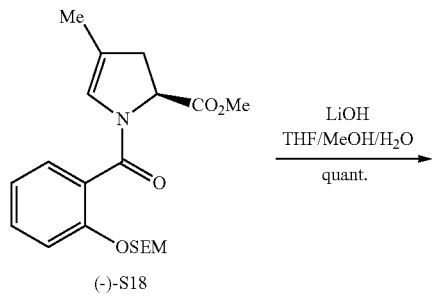

(-)-S18

LiOH
THF/MeOH/H$_2$O
quant.

(7R,13R)-14-amino-13-((tert-butyldimethylsilyl)oxy)-14-oxotetradecan-7-yl (S)-4-methyl-1-(2-((2-(trimethylsilyl)ethoxy)methoxy)benzoyl)-2,3-dihydro-1H-pyrrole-2- carboxylate (−)-S20). Using modified general procedure H (1.2 eq acid, 1.2 eq MNBA, 1.0 eq alcohol, 0.1 eq DMAP), acid (−)-S19 (25 mg, 0.066 mmol) after purification by column chromatography eluting in 0→30% Et$_2$O/CH$_2$Cl$_2$, yielded the title compound as a yellow oil (24 mg, 59% yield). $^1$H NMR (500 MHz, CDCl$_3$) δ 7.37-7.31 (m, 2H), 7.19 (t, J=9.5 Hz, 1H), 7.03 (td, J=7.5, 0.9 Hz, 1H), 6.53 (t, J=8.5 Hz, 1H), 5.87 (d, J=1.6 Hz, 1H), 5.58-5.46 (m, 1H), 5.22 (dd, J=17.5, 7.1 Hz, 2H), 5.03-4.91 (m, 2H), 4.16-4.09 (m, 1H), 3.79-3.70 (m, 2H), 3.08-2.96 (m, 1H), 2.51 (dd, J=16.7, 4.8 Hz, 1H), 1.79-1.66 (m, 3H), 1.64 (s, 3H), 1.60-1.51 (m, 4H), 1.41-1.19 (m, 18H), 0.96-0.89 (m, 12H), 0.88-0.84 (m, 3H), 0.09-0.05 (m, 6H), 0.01--0.03 (m, 9H); $^{13}$C NMR (100 MHz, CDCl$_3$) δ 176.96, 170.93, 164.26, 153.87, 131.01, 128.89, 126.36, 125.41, 121.99, 119.19, 115.47, 93.48, 75.41, 73.57, 66.56, 58.63, 38.46, 35.12, 34.08, 31.87, 29.52, 29.32, 25.88, 25.34, 25.05, 24.12, 22.73, 18.17, 14.22, 13.58, −1.26, −4.69, −5.13; [α]$^{25}_D$ −18.3 (c=0.69 in CHCl$_3$); IR (film) 2927, 2856, 2359, 2341, 1733 (C=O), 1683 (C=O), 1645 (C=O), 1601, 1506, 1488, 1456, 1419, 1377, 1248, 1188, 1141, 1086, 989, 834, 778, 754, 692, 667, 561; HRMS Accurate mass (ES$^+$): Found 733.4666 (+3.1 ppm), C$_{39}$H$_{69}$N$_2$O$_7$Si$_2$ (M+H$^+$) requires 733.4643.

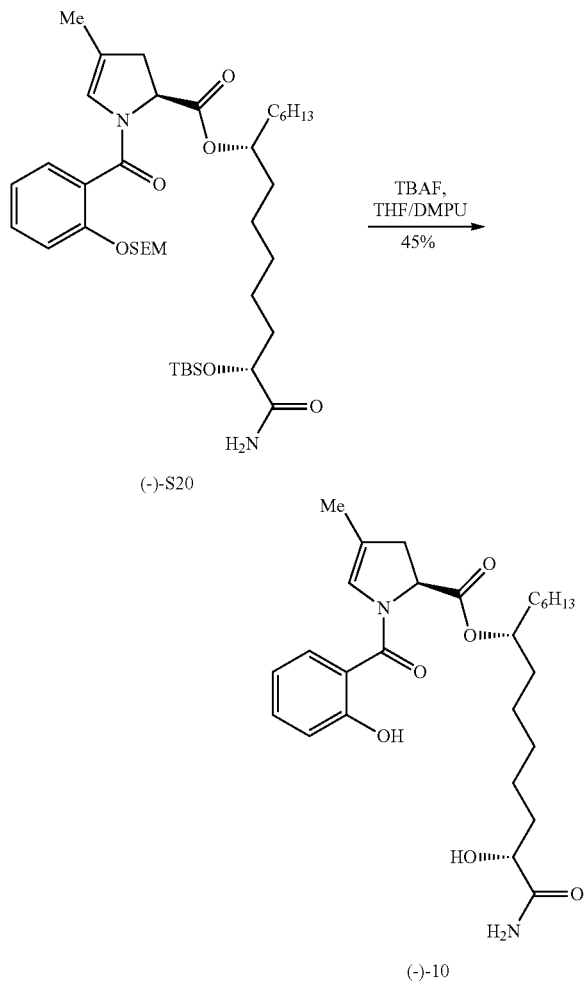

(−)-S20

(−)-10

(7R,13R)-14-amino-13-hydroxy-14-oxotetradecan-7-yl (S)-1-(2-hydroxybenzoyl)-4-methyl-2,3-dihydro-1H-pyr-role-2-carboxylate (−)-10. Using general procedure I, silyl ether (−)-S20 (10.7 mg, 0.0146 mmol) yielded the title compound as a clear oil (3.2 mg, 45% yield). $^1$H NMR (500 MHz, CDCl$_3$) δ 9.53 (s, 1H), 7.44-7.32 (m, 2H), 7.01-6.96 (m, 1H), 6.90 (t, J=7.4 Hz, 1H), 6.61 (s, 0.68H), 6.55 (s, 0.46H), 6.44 (s, 1H), 5.32 (s, 1H), 5.05-4.94 (m, 2H), 4.13-4.05 (m, 1H), 3.47 (s, 1H), 3.09-3.00 (m, 1H), 2.59-2.51 (m, 1H), 1.84-1.77 (m, 1H), 1.75 (s, J=8.0 Hz, 3H), 1.68-1.49 (m, 12H), 1.48-1.36 (m, 4H), 1.36-1.22 (m, 12H), 0.87 (t, J=7.0 Hz, 3H); $^{13}$C NMR (125 MHz, CDCl$_3$) δ 176.97, 171.46, 166.42, 157.88, 133.25, 128.21, 125.19, 122.31, 119.35, 117.98, 117.92, 75.91, 71.33, 59.76, 56.13, 37.72, 34.59, 34.27, 34.20, 31.84, 29.85, 29.22, 28.26, 25.53, 24.81, 24.54, 22.69, 14.20, 13.70; [α]$^{25}_D$ −21.8 (c=0.27 in CHCl$_3$); IR (film) 3306 (br O—H), 2921, 2855, 2493, 2361, 2159, 2031, 1978, 1734 (C=O), 1669 (C=O), 1591 (C=O), 1457, 1378, 1298, 1202, 1157, 1096, 1020, 867, 806, 756, 667; HRMS Accurate mass (ES$^+$): Found 489.2937 (−5.7 ppm), C$_{27}$H$_{41}$N$_2$O$_6$ (M+H$^+$) requires 489.2965.

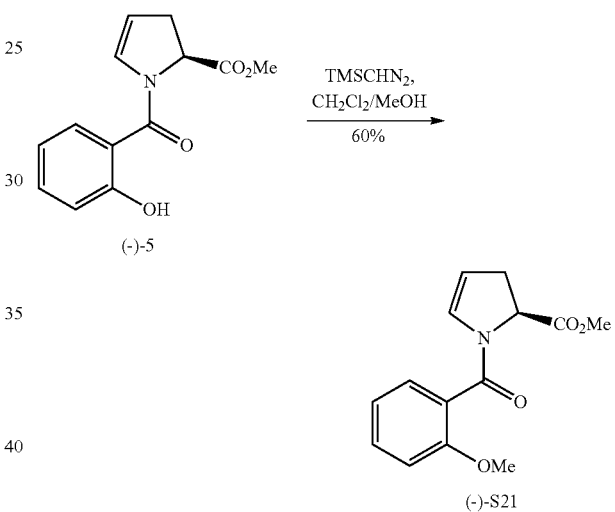

(−)-5

(−)-S21

Methyl (2S)-1-(2-methoxybenzoyl)-2,3-dihydro-1H-pyr-role-2-carboxylate (−)-S21. To a solution of phenol (−)-5 (45 mg, 0.182 mmol) in 3:1 CH$_2$Cl$_2$:MeOH (2 mL) was added TMSCHN$_2$ (0.46 mL, 2M in hexanes, 0.920 mmol), and the reaction went from a clear to yellow color, with effervescence. After 2 hours, TLC analysis indicated remaining starting material, and more MeOH (0.5 mL) was added, after another 30 minutes the starting material was consumed. The reaction was concentrated and purified by column chromatography, yielding the title compound as a yellow oil (28 mg, 60% yield). $^1$H NMR (500 MHz, CDCl$_3$) δ 7.41-7.34 (m, 2H), 7.00 (t, J=7.5 Hz, 1H), 6.94 (d, J=8.3 Hz, 1H), 6.17-6.13 (m, 1H), 5.07-5.00 (m, 2H), 3.84 (s, 3H), 3.81 (s, 3H), 3.16-3.07 (m, 1H), 2.75-2.67 (m, 1H); $^{13}$C NMR (100 MHz, CDCl$_3$) δ 171.61, 165.22, 155.94, 131.42, 130.91, 129.11, 124.94, 120.92, 111.44, 108.60, 57.88, 55.90, 52.59, 34.17; [α]$^{25}_D$ −85.9 (c=1.27 in CHCl$_3$); IR (film) 2951, 2923, 2851, 2160, 2032, 1979, 1746 (C=O), 1643 (C=O), 1618, 1600, 1491, 1461, 1436, 1406, 1363, 1280, 1249, 1201, 1179, 1103, 1046, 1016, 843, 754, 654; HRMS Accurate mass (ES$^+$): Found 284.0875 (−8.4 ppm), C$_{14}$H$_{15}$NO$_4$Na (M+Na$^+$) requires 284.0899.

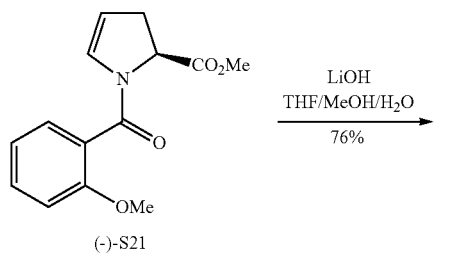

(-)-S21

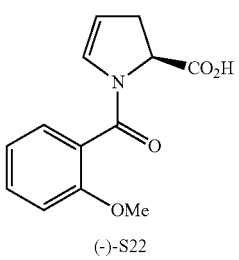

(-)-S22

(2S)-1-(2-methoxybenzoyl)-2,3-dihydro-1H-pyrrole-2-carboxylic acid (-)-S22. Using general procedure B, methyl ester (-)-S21 (27 mg, 0.103 mmol) yielded the title compound as a yellow oil (19 mg, 76% yield). $^1$H NMR (500 MHz, CDCl$_3$) δ 8.03 (s, 1H), 7.46-7.41 (m, 1H), 7.38 (d, J=7.5 Hz, 1H), 7.03 (t, J=7.5 Hz, 1H), 6.96 (d, J=8.4 Hz, 1H), 6.06 (dt, J=4.3, 2.2 Hz, 1H), 5.23 (dd, J=4.3, 2.4 Hz, 1H), 5.13 (dd, J=11.0, 4.2 Hz, 1H), 3.84 (s, 3H), 3.19 (d, J=17.1 Hz, 1H), 3.09-3.00 (m, 1H); $^{13}$C NMR (125 MHz, CDCl$_3$) δ 172.39, 167.64, 155.96, 132.16, 129.76, 129.23, 123.82, 121.07, 111.58, 111.51, 59.25, 55.89, 32.89, 29.82; $[α]^{25}_D$ −82.1 (c=1.80 in CHCl$_3$); IR (film) 3444 (br, CO$_2$—H), 2930, 1738 (C=O), 1598 (C=O), 1492, 1464, 1437, 1412, 1356, 1282, 1249, 1185, 1163, 1104, 1047, 1018, 941, 848, 754, 723, 652; HRMS Accurate mass (ES$^+$): Found 270.0721 (−7.8 ppm), C$_{13}$H$_{13}$NO$_4$Na (M+Na$^+$) requires 270.0742.

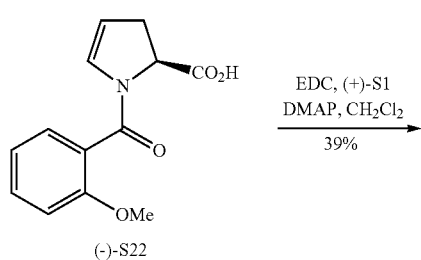

(-)-S22

EDC, (+)-S1
DMAP, CH$_2$Cl$_2$
───────→
39%

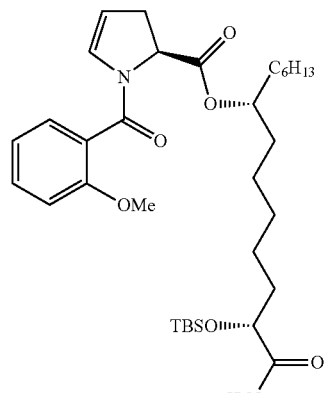

(-)-S23

(1R,7R)-1-[(tert-butyldimethylsilyl)oxy]-1-carbamoyltridecan-7-yl (2S)-1-(2-methoxybenzoyl)-2,3-dihydro-1H-pyrrole-2-carboxylate (-)-S23. Using modified general procedure G (1.2 eq acid, 1.5 eq EDC, 1.0 eq alcohol, 0.1 eq DMAP), acid (-)—S22 (18 mg, 0.073 mmol), after purification by column chromatography eluting with 0→2% MeOH/CH$_2$Cl$_2$, yielded the title compound as a clear oil (14 mg, 39% yield). $^1$H NMR (500 MHz, CDCl$_3$) δ 7.40-7.31 (m, 2H), 7.17 (d, J=7.2 Hz, 1H), 6.99 (s, 1H), 6.93 (d, J=8.2 Hz, 1H), 6.54 (s, 1H), 6.14 (dd, J=4.1, 1.9 Hz, 1H), 5.71-5.59 (m, 1H), 5.05-4.95 (m, 2H), 4.17-4.06 (m, 2H), 3.83 (s, 3H), 3.12 (ddd, J=14.1, 11.6, 2.0 Hz, 1H), 2.91-2.85 (m, 1H), 2.66 (ddd, J=17.1, 4.3, 2.1 Hz, 1H), 1.76-1.54 (m, 6H), 1.39-1.19 (m, 20H), 0.91 (s, 9H), 0.89-0.83 (m, 3H), 0.08 (d, J=6.2 Hz, 6H); $^{13}$C NMR (100 MHz, CDCl$_3$) δ 177.11, 170.92, 165.02, 155.98, 131.32, 131.01, 129.17, 129.11, 127.43, 125.11, 120.89, 111.42, 108.46, 75.50, 73.55, 69.78, 58.23, 55.86, 53.93, 41.65, 35.11, 34.39, 34.08, 34.02, 31.85, 29.83, 29.51, 29.33, 25.87, 25.31, 25.05, 24.11, 22.72, 18.15, 14.21, −4.70, −5.13; $[α]^{25}_D$ −27.2 (c=1.11 in CHCl$_3$); IR (film) 3481, 2927, 2856, 1745, 1683, 1646, 1619, 1601, 1491, 1463, 1437, 1406, 1360, 1280, 1251, 1194, 1101, 1048, 1019, 939, 837, 778, 754, 701, 655; HRMS Accurate mass (ES$^+$): Found 603.3802 (−4.5 ppm), C$_{33}$H$_{55}$N$_2$O$_6$Si (M+H$^+$) requires 603.3829; R$_f$ (2:1 CH$_2$Cl$_2$: Et$_2$O)=0.60.

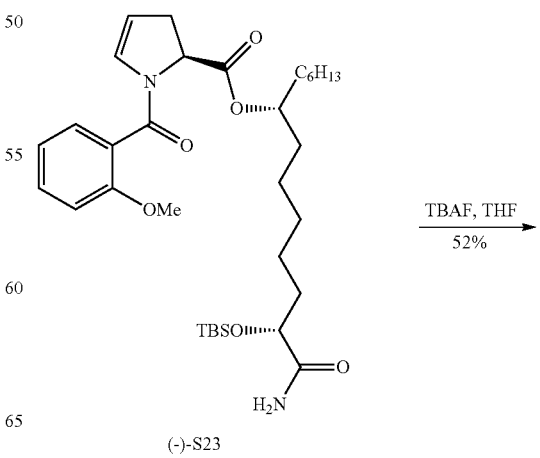

(-)-S23

TBAF, THF
───────→
52%

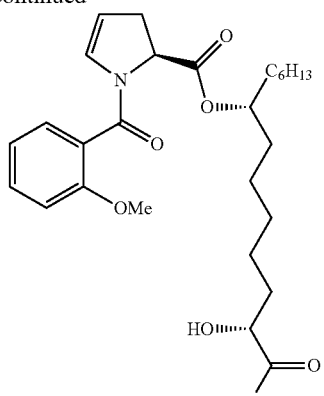

(−)-11

(1R,7R)-1-carbamoyl-1-hydroxytridecan-7-yl (2S)-1-(2-methoxybenzoyl)-2,3-dihydro-1H-pyrrole-2-carboxylate (−)-11. To a solution of protected ester (−)-S23 (11 mg, 0.018 mmol) dissolved in THF (0.5 mL) was added TBAF (0.18 mL, 1M in THF, 0.180 mmol). After 5 minutes the reaction was poured into 1M aq. NH$_4$Cl and extracted with Et$_2$O 3×. The combined organic layers were washed with brine, dried over Na$_2$SO$_4$, filtered, concentrated and purified by preparative TLC (2% MeOH/EtOAc), yielding the title compound as a clear oil (4.6 mg, 52% yield). $^1$H NMR (500 MHz, CDCl$_3$) δ 7.43-7.38 (m, 1H), 7.33 (d, J=7.3 Hz, 1H), 7.00 (t, J=7.5 Hz, 1H), 6.97-6.91 (m, 2H), 6.19-6.12 (m, 1H), 5.15-5.02 (m, 3H), 4.95 (dd, J=11.6, 4.8 Hz, 1H), 4.43 (s, 1H), 4.06 (d, J=4.4 Hz, 1H), 3.83 (s, 3H), 3.18-3.09 (m, 1H), 2.68 (ddd, J=14.7, 4.5, 2.2 Hz, 1H), 1.87-1.77 (m, 1H), 1.69-1.35 (m, 17H), 1.35-1.16 (m, 21H), 0.88 (t, J=6.8 Hz, 4H); $^{13}$C NMR (100 MHz, CDCl$_3$) δ 177.75, 170.61, 165.90, 155.96, 131.80, 130.74, 128.96, 124.24, 120.99, 111.52, 109.73, 74.99, 70.35, 58.07, 55.92, 34.99, 34.27, 33.52, 31.86, 29.85, 29.26, 27.29, 25.65, 24.65, 24.22, 22.71, 14.22; [α]$^{25}_D$ −8.9 (c=0.45 in CHCl$_3$); IR (film) 2920, 2850, 1740 (C=O), 1668 (C=O), 1618 (C=O), 1492, 1463, 1439, 1412, 1377, 1280, 1253, 1196, 1102, 1047, 1021, 847, 803, 755, 720; HRMS Accurate mass (ES$^+$): Found 489.2941 (−4.9 ppm), C$_{27}$H$_{41}$N$_2$O$_6$ (M+H$^+$) requires 489.2965; R$_f$ (2% MeOH/EtOAc)=0.45.

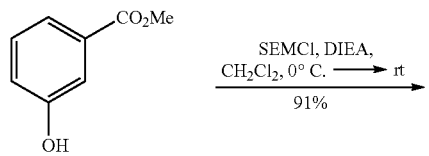

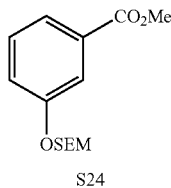

S24

Methyl 3-((2-(trimethylsilyl)ethoxy)methoxy)benzoate S24. Using general procedure A, methyl 3-hydroxybenzoate (250 mg, 1.640 mmol) yielded the title compound as a clear oil (421 mg, 91% yield). $^1$H NMR (500 MHz, CDCl$_3$) δ 7.71-7.66 (m, 2H), 7.34 (dd, J=11.9, 4.2 Hz, 1H), 7.23 (ddd, J=8.2, 2.6, 1.1 Hz, 1H), 5.26 (s, 2H), 3.91 (s, J=2.9 Hz, 3H), 3.80-3.73 (m, 2H), 0.98-0.93 (m, 2H), −0.01 (s, J=3.3 Hz, 9H); $^{13}$C NMR (125 MHz, CDCl$_3$) δ 166.58, 157.34, 131.42, 129.27, 122.79, 120.89, 116.93, 92.73, 77.16, 66.22, 51.93, 17.91, −1.51; IR (film) 2952, 2897, 1723 (C=O), 1586, 1488, 1447, 1380, 1274, 1248, 1211, 1153, 1106, 1083, 1009, 994, 918, 857, 833, 783, 755, 683; HRMS Accurate mass (ES$^+$): Found 305.1195 (+3.3 ppm), C$_{14}$H$_{22}$O$_4$SiNa (M+Na$^+$) requires 305.1185.

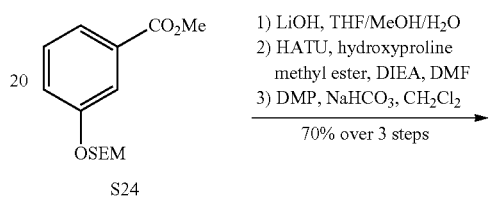

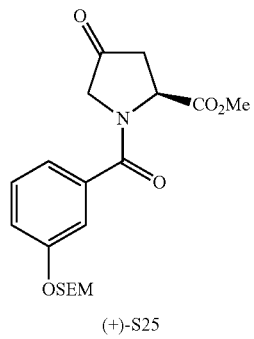

(+)-S25

Methyl (S)-4-oxo-1-(3-((2-(trimethylsilyl)ethoxy)methoxy)benzoyl)pyrrolidine-2-carboxylate (+)-S25. Using general procedure B, methyl ester S24 (264 mg, 0.934 mmol) yielded the corresponding acid, which was used directly in the next step. Using general procedure C, the acid yielded the corresponding acylhydroxyproline methyl ester compound, whose purity made it unsuitable for characterization. Using general procedure D, the alcohol intermediate yielded the title compound as a yellow oil (254 mg, 70% over 3 steps). $^1$H NMR (500 MHz, CDCl$_3$) δ 7.37-7.32 (m, 1H), 7.19-7.11 (m, 3H), 5.37-5.27 (m, 1H), 5.24 (s, 2H), 3.85-3.70 (m, 5H), 2.97 (dd, J=18.8, 10.6 Hz, 1H), 2.70 (d, J=20.3 Hz, 1H), 0.98-0.91 (m, 2H), −0.00 (s, J=3.4 Hz, 9H); $^{13}$C NMR (100 MHz, CDCl$_3$) δ 207.21, 171.60, 170.18, 157.50, 136.18, 129.90, 120.19, 118.61, 114.92, 92.81, 66.44, 55.37, 52.90, 40.02, 18.04, −1.39; [α]$^{25}_D$ +25.3 (c=0.91 in CHCl$_3$); IR (film) 2950, 2395, 2342, 1757 (C=O), 1635 (C=O), 1575 (C=O), 1445, 1393, 1296, 1264, 1250, 1228, 1186, 1151, 1122, 1078, 1030, 1008, 990, 950, 862, 833, 817, 774, 753, 694, 600, 562; HRMS Accurate mass (ES$^+$): Found 394.1700 (+3.6 ppm), C$_{19}$H$_{28}$NO$_6$Si (M+H$^+$) requires 394.1686.

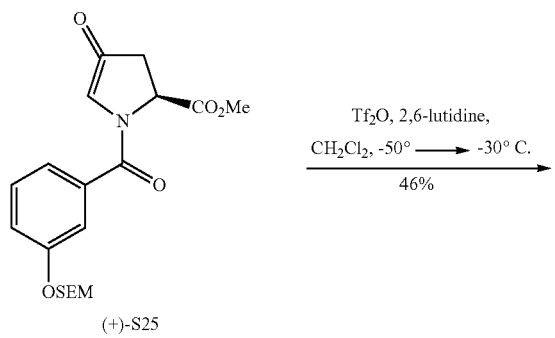

(+)-S25

Tf₂O, 2,6-lutidine,
CH₂Cl₂, -50° ⟶ -30° C.
─────────────
46%

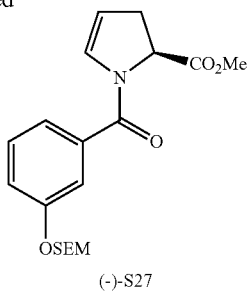

(-)-S27

Methyl (S)-1-(3-((2-(trimethylsilyl)ethoxy)methoxy)benzoyl)-2,3-dihydro-1H-pyrrole-2-carboxylate (−)-S27. Using general procedure F, triflate (−)-S26 (90 mg, 0.171 mmol) yielded the title compound as a yellow oil (47 mg, 73% yield). ¹H NMR (500 MHz, CDCl₃) δ 7.33 (t, J=7.9 Hz, 1H), 7.23 (s, 1H), 7.18 (d, J=7.6 Hz, 1H), 7.14 (d, J=8.4 Hz, 1H), 6.58-6.52 (m, 1H), 5.23 (s, 2H), 5.11 (d, J=5.1 Hz, 1H), 5.01 (dd, J=11.6, 5.0 Hz, 1H), 3.80 (s, 3H), 3.77-3.72 (m, 2H), 3.15-3.06 (m, 1H), 2.76-2.67 (m, 1H), 0.98-0.93 (m, 2H), 0.00 (s, 9H); ¹³C NMR (100 MHz, CDCl₃) δ 171.56, 166.75, 157.46, 136.25, 130.97, 129.71, 121.15, 118.65, 115.86, 109.05, 92.95, 66.49, 58.51, 52.64, 33.87, 18.14, −1.31; [α]$^{25}_D$ −44.0 (c=0.31 in CHCl₃); IR (film) 2953, 2359, 2341, 1749 (C=O), 1646, 1617, 1488, 1446, 1398, 1362, 1317, 1086, 1005, 989, 858, 834, 694, 668; HRMS Accurate mass (ES⁺): Found 378.1706 (−8.2 ppm), C₁₉H₂₈NO₅Si (M+H⁺) requires 378.1737.

Methyl (S)-4-(((trifluoromethyl)sulfonyl)oxy)-1-(3-((2-(trimethylsilyl)ethoxy)methoxy)benzoyl)-2,3-dihydro-1H-pyrrole-2-carboxylate (−)-S26. Using general procedure E, ketone (+)-S25 (150 mg, 0.388 mmol) yielded the title compound as an orange oil (95 mg, 46% yield). ¹H NMR (500 MHz, CDCl₃) δ 7.37 (t, J=7.9 Hz, 1H), 7.18 (dt, J=24.8, 8.2 Hz, 3H), 6.81 (s, 1H), 5.24 (s, 2H), 5.08 (d, J=6.5 Hz, 1H), 3.83 (s, 3H), 3.78-3.72 (m, 2H), 3.46-3.36 (m, 1H), 2.97 (ddd, J=16.4, 4.8, 1.5 Hz, 1H), 0.99-0.92 (m, 2H), 0.00 (s, 9H); ¹³C NMR (125 MHz, CDCl₃) δ 169.70, 167.12, 159.69, 157.65, 144.29, 137.47, 134.65, 134.45, 130.04, 124.14, 123.29, 123.07, 120.90, 119.79, 119.45, 117.23, 115.61, 92.84, 66.56, 58.33, 57.60, 53.02, 33.18, 24.36, 18.09, −1.42; [α]$^{25}_D$ −56.4 (c=0.45 in CHCl₃); IR (film) 2954, 2359, 2341, 1749 (C=O), 1652 (C=O), 1581 (C=O), 1488, 1427, 1398, 1207, 1137, 1086, 1005, 990, 917, 857, 832, 744, 693, 667, 605; HRMS Accurate mass (ES⁺): Found 548.1028 (+5.5 ppm), C₂₀H₂₆NO₈SSiNa (M+Na⁺) requires 548.0998.

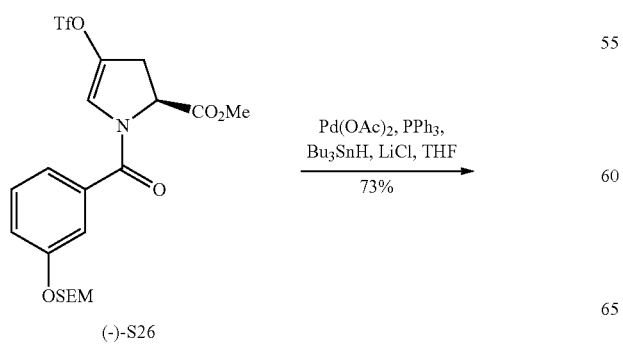

(-)-S26

Pd(OAc)₂, PPh₃,
Bu₃SnH, LiCl, THF
─────────────
73%

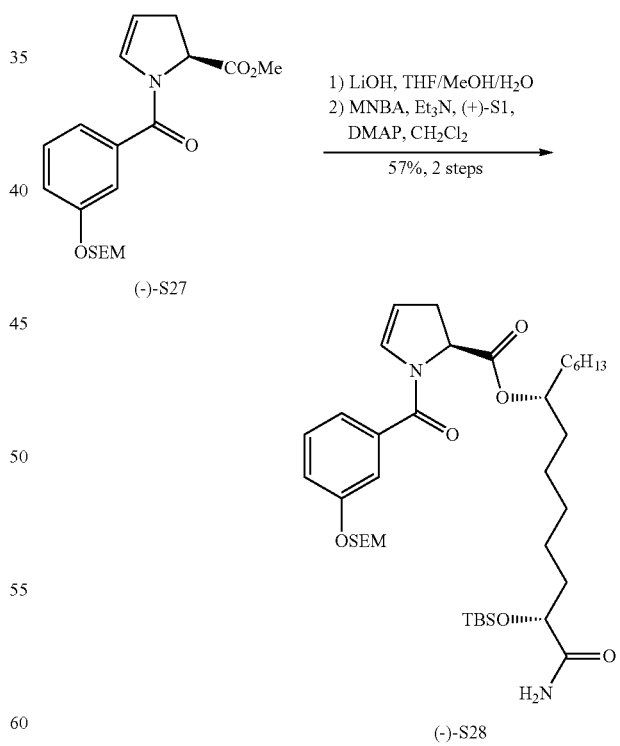

(-)-S27

1) LiOH, THF/MeOH/H₂O
2) MNBA, Et₃N, (+)-S1,
   DMAP, CH₂Cl₂
─────────────
57%, 2 steps (-)-S28

(7R,13R)-14-amino-13-((tert-butyldimethylsilyl)oxy)-14-oxotetradecan-7-yl (S)-1-(3-((2-(trimethylsilyl)ethoxy)methoxy)benzoyl)-2,3-dihydro-1H-pyrrole-2-carboxylate (−)-S28. Using general procedure B, methyl ester (−)-S27 (26 mg, 0.069 mmol) yielded the acid intermediate as a yellow oil. This compound was not of sufficient purity for characterization. Next, using modified general procedure H (1.2 eq acid and MNBA), acid intermediate (25 mg, 0.069 mmol) yielded the title compound as a yellow oil (24 mg, 57% yield, 2 steps). $^1$H NMR (500 MHz, CDCl$_3$) δ 7.32 (q, J=7.8 Hz, 1H), 7.20 (s, J=11.1 Hz, 1H), 7.15 (dd, J=15.5, 7.9 Hz, 2H), 6.52 (s, 2H), 5.54-5.44 (m, 1H), 5.23 (s, 2H), 5.08 (d, J=1.9 Hz, 1H), 5.01-4.90 (m, 2H), 4.17-4.08 (m, 1H), 3.80-3.67 (m, 2H), 3.15-3.06 (m, 1H), 2.67 (d, J=16.9 Hz, 1H), 1.81-1.70 (m, 1H), 1.69-1.47 (m, 7H), 1.26 (dd, J=14.1, 6.9 Hz, 17H), 0.97-0.89 (m, 12H), 0.85 (t, J=6.9 Hz, 3H), 0.10-0.06 (m, 6H), −0.01 (s, J=3.2 Hz, 9H); 13C NMR (100 MHz, CDCl$_3$) δ 176.94, 170.86, 166.62, 157.49, 136.52, 131.08, 129.70, 121.13, 118.46, 115.85, 108.87, 92.97, 75.62, 73.60, 66.51, 58.80, 35.13, 34.05, 31.85, 29.85, 29.51, 29.32, 25.89, 25.31, 25.08, 24.11, 22.72, 18.17, 14.22, −1.28, −4.68, −5.12; $[α]^{25}_D$ −16.1 (c=1.18 in CHCl$_3$); IR (film) 3480, 2927, 2867, 1739 (C=O), 1689 (C=O), 1651 (C=O), 1618, 1579, 1488, 1446, 1397, 1248, 1192, 1088, 1029, 1005, 991, 938, 857, 834, 778, 745, 694, 668; HRMS Accurate mass (ES$^+$): Found 719.4445 (−5.8 ppm), $C_{38}H_{67}N_2O_7Si_2$ (M+H$^+$) requires 719.4487.

5H), 6.57 (s, 1H), 5.91 (s, 1H), 5.16 (s, 1H), 5.09-5.01 (m, 1H), 4.93 (dd, J=11.4, 5.1 Hz, 1H), 4.12-4.02 (m, 1H), 3.18-3.07 (m, 1H), 2.67 (d, J=17.3 Hz, 1H), 1.87-1.76 (m, 1H), 1.61-1.23 (m, 27H) 0.88 (t, J=5.6 Hz, 3H); $^{13}$C NMR (100 MHz, CDCl$_3$) δ 178.78, 171.03, 167.83, 167.38, 157.46, 157.32, 135.46, 130.94, 129.78, 118.82, 115.06, 110.10, 75.42, 71.04, 58.70, 34.90, 34.43, 33.97, 33.75, 31.85, 29.84, 29.24, 27.91, 25.63, 24.83, 24.60, 22.70, 14.21; $[α]^{25}_D$ +14.4 (c=0.90 in CHCl$_3$); IR (film) 3195 (br, O—H), 2925, 2856, 1732 (C=O), 1662 (C=O), 1579, 1416, 1273, 1196, 998, 880, 746; HRMS Accurate mass (ES$^+$): Found 475.2838 (+6.3 ppm), $C_{26}H_{39}N_2O_6$ (M+H$^+$) requires 475.2808.

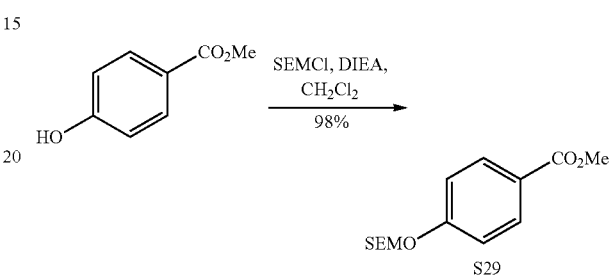

Methyl 4-((2-(trimethylsilyl)ethoxy)methoxy)benzoate S29. Using general procedure A, methyl 4-hydroxybenzoate (250 mg, 1.640 mmol) yielded the title compound as a clear oil (454 mg, 98% yield). $^1$H NMR (500 MHz, CDCl$_3$) δ 7.99 (dd, J=8.9, 1.9 Hz, 2H), 7.05 (dd, J=8.8, 1.9 Hz, 2H), 5.27 (s, J=1.8 Hz, 2H), 3.89 (s, 3H), 3.78-3.73 (m, 2H), 0.95 (s, 2H), −0.01 (s, 9H); $^{13}$C NMR (125 MHz, CDCl$_3$) δ 166.96, 161.32, 131.63, 123.55, 115.75, 92.71, 66.73, 52.02, 18.17, −1.28, −1.31; IR (film) 2952, 2896, 1717 (C=O), 1605, 1580, 1510, 1435, 1381, 1315, 1276, 1234, 1191, 1168, 1090, 1013, 986, 938, 917, 851, 834, 770, 696, 668, 610; HRMS Accurate mass (ES$^+$): Found 283.1373 (+2.5 ppm), $C_{14}H_{23}O_4Si$ (M+H$^+$) requires 283.1366.

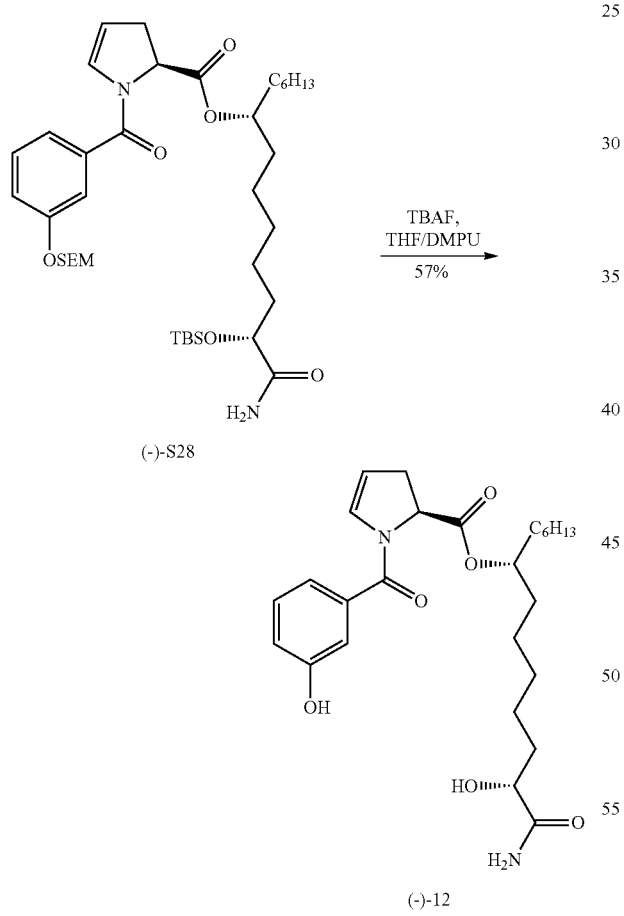

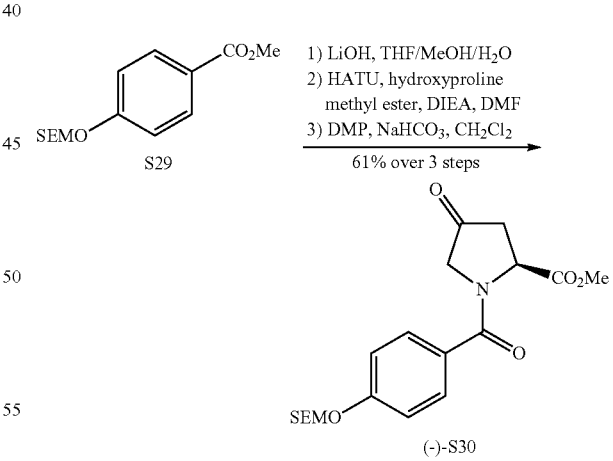

(7R,13R)-14-amino-13-hydroxy-14-oxotetradecan-7-yl (S)-1-(3-hydroxybenzoyl)-2,3-dihydro-1H-pyrrole-2-carboxylate (−)-12. Using general procedure I, silyl ether (−)-S28 (24 mg, 0.033 mmol) yielded the title compound as a clear oil (9 mg, 57% yield) after purification by column chromatography (50→100% EtOAc/hexanes). $^1$H NMR (400 MHz, CDCl$_3$) δ 7.22 (d, J=7.8 Hz, 1H), 7.05-6.87 (m, Methyl (2S)-4-oxo-1-(4-{[2-(trimethylsilyl)ethoxy]methoxy}benzoyl)pyrrolidine-2-carboxylate (−)-S30. Using general procedure B, methyl ester S29 (445 mg, 1.577 mmol) yielded the corresponding acid, which was used directly in the next step. Using general procedure C, the acid yielded the corresponding acylhydroxyproline methyl ester compound, whose purity made it unsuitable for characterization. Using general procedure D, the alcohol intermediate yielded the title compound as a yellow oil (394 mg, 61% over 3 steps). $^1$H NMR (500 MHz, CDCl$_3$) δ 7.49 (br s, J=12.1 Hz, 2H), 7.12-7.06 (m, 2H), 5.25 (s, 2H), 3.83-3.72 (m, 5H), 2.96 (dd, J=18.8, 10.5 Hz, 1H), 2.69 (dd, J=18.8, 2.2 Hz, 1H), 1.03-0.91 (m, 2H), —0.00 (s, J=3.3 Hz, 9H); $^{13}$C NMR (100 MHz, CDCl$_3$) δ 207.52, 207.36, 171.78, 171.05, 170.65, 159.54, 129.46, 129.22, 127.41, 125.35, 116.02, 115.53, 92.59, 66.57, 65.02, 52.91, 18.00, −1.42; [α]$^{25}_D$ −24.2 (c=1.39 in CHCl$_3$); IR (film) 2953, 1764 (C=O), 1745 (C=O), 1606 (C=O), 1513, 1404, 1230, 1168, 1090, 1025, 986, 918, 834, 764, 692, 612; HRMS Accurate mass (ES$^+$): Found 394.1698 (+3.0 ppm), C$_{19}$H$_{28}$NO$_6$Si (M+H$^+$) requires 394.1686.

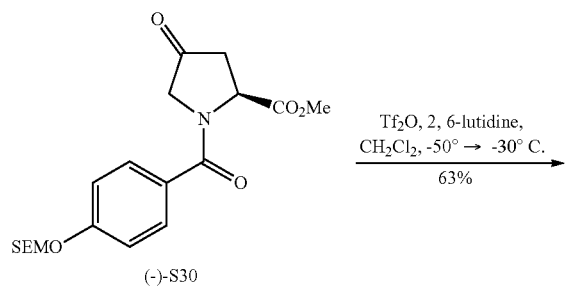

Methyl (2S)-4-(trifluoromethanesulfonyloxy)-1-(4-{[2-(trimethylsilyl)ethoxy]methoxyl}benzoyl)-2,3-dihydro-1H-pyrrole-2-carboxylate (−)-S31. Using general procedure E, ketone (−)-S30 (100 mg, 0.254 mmol) yielded the title compound as a yellow oil (85 mg, 63% yield). $^1$H NMR (400 MHz, CDCl$_3$) δ 7.52 (d, J=8.7 Hz, 2H), 7.10 (d, J=8.7 Hz, 2H), 6.87 (s, 1H), 5.27 (s, 2H), 5.08 (dd, J=11.6, 5.1 Hz, 1H), 3.82 (s, 3H), 3.80-3.72 (m, 2H), 3.44-3.35 (m, 1H), 2.97 (ddd, J=16.4, 5.1, 1.6 Hz, 1H), 1.00-0.91 (m, 2H), 0.00 (s, 9H); $^{13}$C NMR (125 MHz, CDCl$_3$) δ 169.86, 167.25, 160.10, 134.28, 129.89, 126.40, 123.58, 119.82, 117.26, 116.24, 92.72, 66.71, 57.83, 53.01, 33.25, 29.79, 18.12, −1.36; [α]$^{25}_D$ −18.5 (c=0.20 in 2:1 CHCl$_3$/MeOH); IR (film) 2954, 2899, 1750 (C=O), 1644, 1606, 1512, 1424, 1398, 1306, 1280, 1208, 1170, 1136, 1091, 1027, 987, 935, 910, 833, 759, 694, 644, 607; HRMS Accurate mass (ES$^+$): Found 526.1148 (−5.9 ppm), C$_{20}$H$_{27}$F$_3$NO$_8$SSi (M+H$^+$) requires 526.1179.

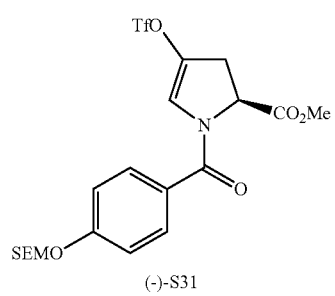

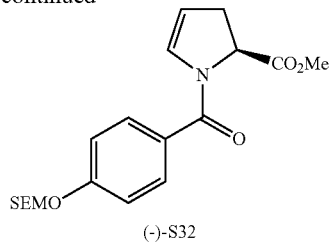

Methyl (2S)-1-(4-{[2-(trimethylsilyl)ethoxy]meth oxy}benzoyl)-2,3-dihydro-1H-pyrrole-2-carboxylate (−)-S32. Using general procedure F, triflate (−)-S31 (62 mg, 0.117 mmol) yielded the title compound as a yellow oil (47 mg, quant. yield). $^1$H NMR (400 MHz, CDCl$_3$) δ 7.53 (d, J=8.5 Hz, 2H), 7.08-7.03 (m, 2H), 6.60 (s, 1H), 5.25 (s, 2H), 5.11 (s, 1H), 5.04-4.95 (m, 1H), 3.84-3.71 (m, 5H), 3.17-3.03 (m, 1H), 2.77-2.66 (m, 1H), 0.97-0.90 (m, 2H), −0.01 (s, J=3.3 Hz, 9H); $^{13}$C NMR (125 MHz, CDCl$_3$) δ 171.72, 166.83, 159.49, 131.22, 129.91, 128.10, 115.94, 108.69, 92.76, 66.60, 58.70, 52.59, 33.82, 18.16, −1.31; [α]$^{25}_D$ −60.2 (c=1.22 in MeOH); IR (film) 2952, 2924, 2872, 1749 (C=O), 1644 (C=O), 1606, 1574, 1511, 1396, 1362, 1291, 1231, 1201, 1170, 1089, 1023, 985, 917, 834, 759, 694, 582; HRMS Accurate mass (ES$^+$): Found 378.1710 (−7.1 ppm), C$_{19}$H$_{28}$NO$_5$Si (M+H$^+$) requires 378.1737; R$_f$ (3:1 hexanes: EtOAc)=0.20.

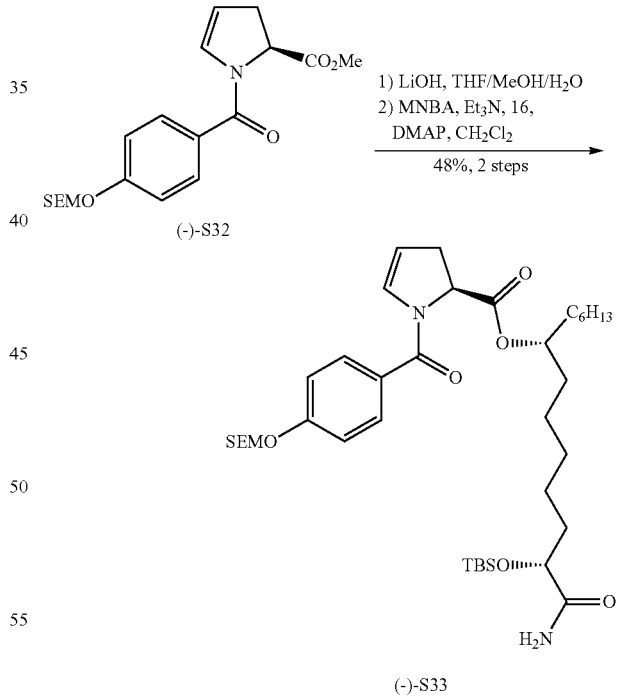

(1R,7R)-1-[(tert-butyldimethylsilyl)oxy]-1-carbamoyltridecan-7-yl (2S)-1-(4-{[2-(trimethylsilyl)ethoxy]methoxy}benzoyl)-2,3-dihydro-1H-pyrrole-2-carboxylate (−)-S33. Using general procedure B, methyl ester (−)-S32 (22 mg, 0.055 mmol) was converted to the corresponding acid, which was not of sufficient purity for characterization. Next, using modified general procedure H (1.2 eq acid, 1.2 eq MNBA), the acid intermediate yielded the title compound as

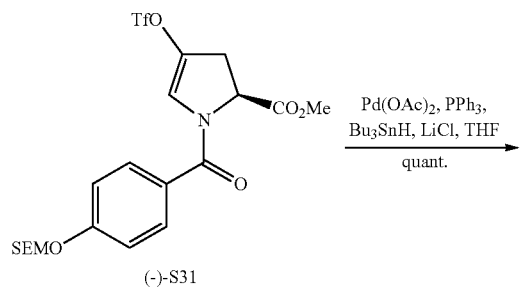

a yellow oil (19 mg, 48% yield). $^1$H NMR (500 MHz, CDCl$_3$) δ 7.52 (d, J=8.6 Hz, 2H), 7.05 (d, J=8.6 Hz, 2H), 6.60-6.51 (m, 2H), 5.45 (m, 2H), 5.25 (s, 2H), 5.09 (s, 1H), 5.01-4.89 (m, 2H), 4.88-4.81 (m, 1H), 4.15-4.12 (m, 2H), 3.78-3.72 (m, 2H), 3.14-3.06 (m, 1H), 2.71-2.64 (m, 1H), 1.80-1.70 (m, 1H), 1.69-1.65 (m, 1H), 1.61-1.47 (m, 7H), 1.40-1.17 (m, 27H), 0.91 (s, 9H), 0.86 (t, J=8.0 Hz, 3H), 0.08 (d, J=6.0 Hz, 6H), −0.00 (s, 9H); $^{13}$C NMR (125 MHz, CDCl$_3$) δ 176.97, 171.07, 166.70, 159.41, 131.32, 129.85, 128.40, 115.93, 108.50, 92.80, 75.56, 74.45, 73.60, 66.61, 58.98, 35.20, 35.15, 34.26, 34.18, 34.02, 31.84, 29.56, 29.51, 29.32, 25.88, 25.40, 25.33, 25.28, 25.07, 24.18, 24.12, 22.71, 21.42, 18.18, 14.20, −1.30, −4.69, −5.12; $[\alpha]^{25}_D$ −1645 (c=0.95 in CHCl$_3$); IR (film) 2926, 2856, 1733 (C=O), 1688 (C=O), 1645 (C=O), 1607, 1510, 1463, 1396, 1248, 1195, 1169, 1089, 991, 939, 760, 713, 580; HRMS Accurate mass (ES$^+$): Found 719.4447 (−5.6 ppm), C$_{38}$H$_{67}$N$_2$O$_7$Si$_2$ (M+H$^+$) requires 719.4487.

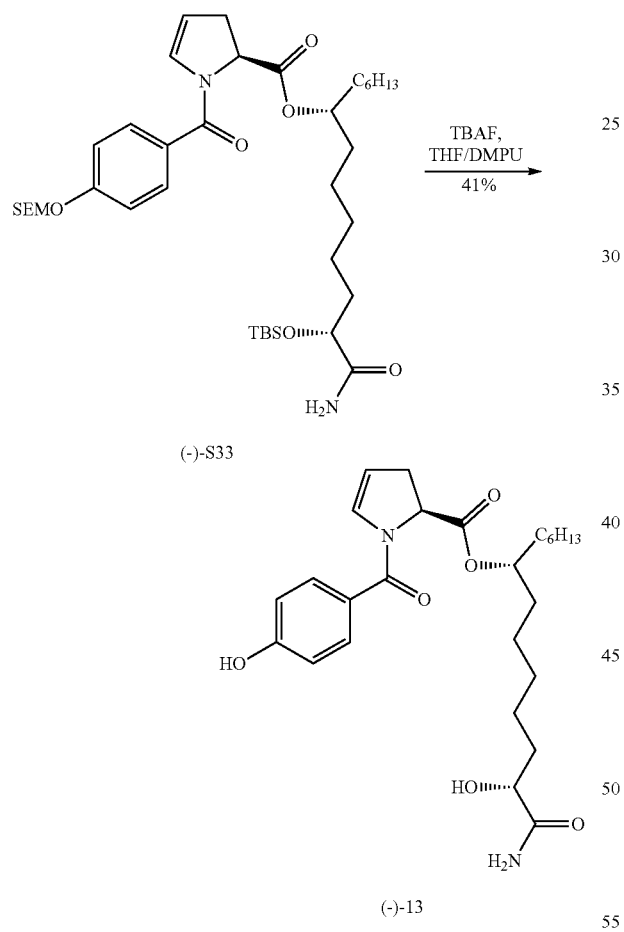

(1R,7R)-1-carbamoyl-1-hydroxytridecan-7-yl (2S)-1-(4-hydroxybenzoyl)-2,3-dihydro-1H-pyrrole-2-carboxylate (−)-13. Using general procedure I, silyl ether (−)-S33 (18.9 mg, 0.026 mmol) yielded the title compound as a clear oil (5.3 mg, 41% yield). $^1$H NMR (500 MHz, CDCl$_3$) δ 8.11 (s, 1H), 7.38 (d, J=7.9 Hz, 2H), 6.94 (s, 1H), 6.79 (d, J=8.1 Hz, 2H), 6.53 (d, J=45.0 Hz, 1H), 5.63 (s, 1H), 5.17 (s, 1H), 4.96 (s, 2H), 4.03 (s, 2H), 3.18-3.09 (m, 1H), 2.69 (d, J=16.8 Hz, 1H), 1.77-1.12 (m, 37H), 0.87 (t, J=6.8 Hz, 3H); $^{13}$C NMR (125 MHz, CDCl$_3$) δ 171.12, 168.20, 159.37, 131.12, 129.98, 115.68, 109.85, 74.51, 70.77, 60.57, 58.82, 34.80, 34.27, 34.21, 34.06, 31.85, 29.85, 29.32, 29.25, 28.97, 27.62, 25.60, 25.45, 25.23, 24.78, 24.32, 22.70, 21.47, 14.34, 14.21; $[\alpha]^{25}_D$ +17.9 (c=0.24 in CHCl$_3$); IR (film) 3300 (br O—H), 2956, 2923, 2853, 2361, 2341, 2159, 2028, 1976, 1733, 1669, 1653, 1609, 1558, 1516, 1507, 1467, 1436, 1378, 1260, 1198, 1165, 1093, 1021, 948, 847, 798, 761, 721, 667; HRMS Accurate mass (ES$^+$): Found 475.2804 (−0.8 ppm), C$_{26}$H$_{39}$N$_2$O$_6$ (M+H$^+$) requires 475.2808.

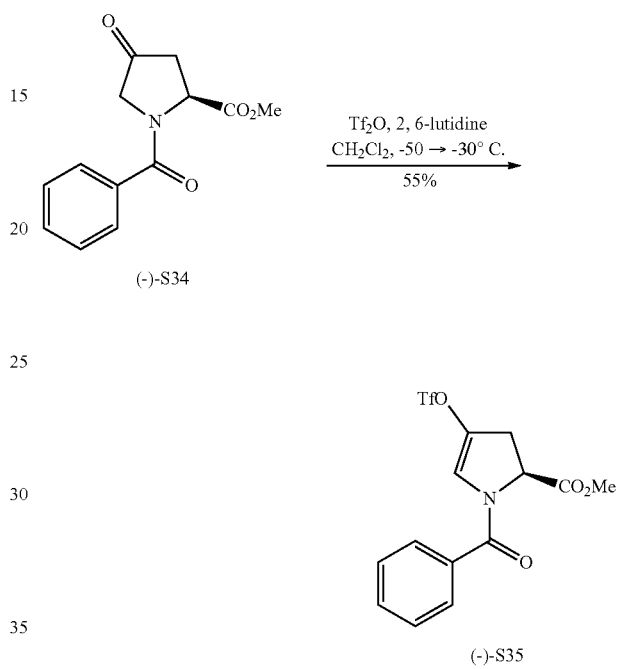

Methyl (2S)-1-benzoyl-4-(trifluoromethanesulfonyloxy)-2,3-dihydro-1H-pyrrole-2-carboxylate (−)-S35. Using general procedure E, ketone (−)-S34$^2$ (50 mg, 0.202 mmol) yielded the title compound as an orange oil (44 mg, 55% yield). $^1$H NMR (500 MHz, CDCl$_3$) δ 7.59-7.43 (m, 5H), 6.79 (s, 1H), 5.16-5.05 (m, 1H), 3.83 (s, 3H), 3.45-3.37 (m, 1H), 2.98 (ddd, J=16.5, 4.9, 1.6 Hz, 1H); $^{13}$C NMR (100 MHz, CDCl$_3$) δ 169.78, 167.56, 134.52, 133.50, 131.67, 128.95, 127.93, 123.31, 120.14, 116.95, 77.16, 57.65, 53.12, 33.26; $[\alpha]^{25}_D$ −47.6 (c=1.49 in CHCl$_3$); IR (film) 2957, 2921, 2851, 2361, 2160, 2031, 1979, 1749 (C=O), 1648 (C=O), 1578, 1495, 1448, 1426, 1404, 1306, 1208, 1135, 1029, 937, 909, 843, 752, 721, 702, 669; HRMS Accurate mass (ES$^+$): Found 402.0244 (+2.2 ppm), C$_{14}$H$_{12}$F$_3$NO$_6$SNa (M+Na$^+$) requires 402.0235.

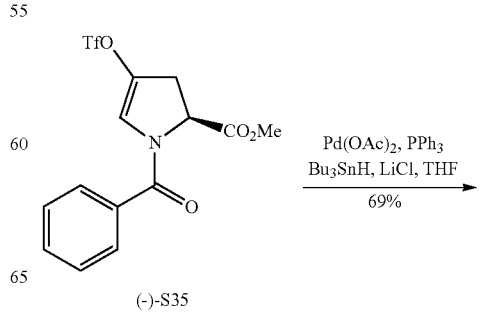

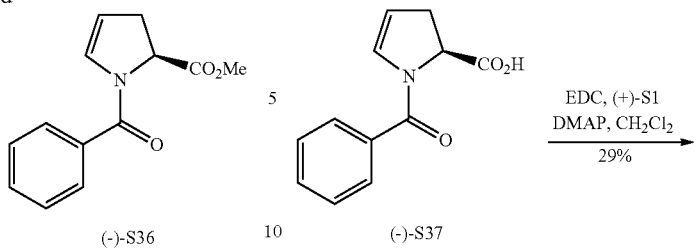

Methyl (2S)-1-benzoyl-2,3-dihydro-1H-pyrrole-2-carboxylate (−)-S36. Using general procedure F, triflate (−)-S35 (100 mg, 0.252 mmol) yielded the title compound as a yellow oil (40 mg, 69% yield). $^1$H NMR (500 MHz, CDCl$_3$) δ 7.57 (d, J=7.3 Hz, 2H), 7.50-7.37 (m, 3H), 6.53 (s, 1H), 5.12 (s, 1H), 5.02 (dd, J=11.5, 5.0 Hz, 1H), 3.81 (s, 3H), 3.15-3.07 (m, 1H), 2.72 (d, J=16.9 Hz, 1H); $^{13}$C NMR (125 MHz, CDCl$_3$) δ 171.6, 167.2, 135.1, 131.0, 130.9, 128.6, 128.0, 109.1, 58.5, 52.7, 33.9; $[α]^{25}_D$ −110.8 (c=1.00 in CHCl$_3$); IR (film) 2953, 2923, 2160, 2029, 1979, 1747 (C=O), 1641, 1615, 1576, 1496, 1447, 1403, 1362, 1290, 1201, 1179, 1106, 1016, 936, 841, 790, 724, 700, 662; HRMS Accurate mass (ES$^+$): Found 254.0813 (+7.9 ppm), C$_{13}$H$_{13}$NO$_3$Na (M+Na$^+$) requires 254.0793.

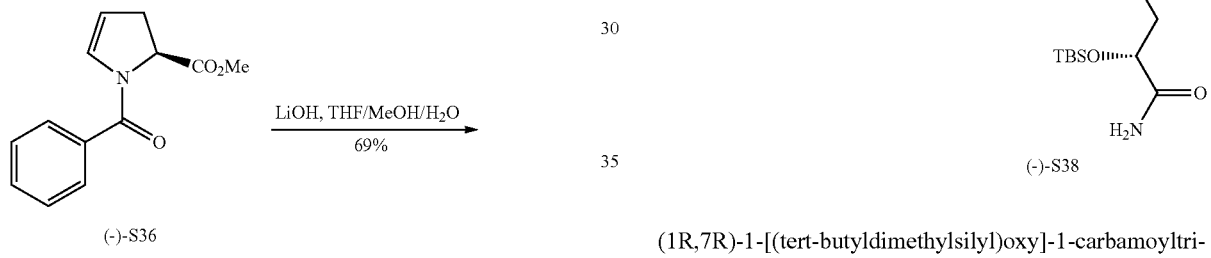

(2S)-1-benzoyl-2,3-dihydro-1H-pyrrole-2-carboxylic acid (−)-S37. Using general procedure B, methyl ester (−)-S36 (37 mg, 0.160 mmol) yielded the title compound as a yellow oil (24 mg, 69% yield). $^1$H NMR (500 MHz, CDCl$_3$) δ 7.61-7.43 (m, 5H), 6.47 (s, 1H), 5.30 (s, 1H), 5.12 (d, J=7.5 Hz, 1H), 3.19 (d, J=17.1 Hz, 1H), 3.10-3.02 (m, 1H); 13C NMR (100 MHz, CDCl$_3$) δ 173.24, 168.67, 131.41, 130.06, 128.71, 128.56, 128.23, 111.50, 59.52, 32.97, 29.83; $[α]^{25}_D$ −85.3 (c=1.20 in CHCl$_3$); IR (film) 3061 (br, CO$_2$—H), 2953, 2924, 2918, 1716 (C=O), 1596 (C=O), 1573, 1497, 1448, 1408, 1352, 1315, 1289, 1195, 1106, 1017, 941, 846, 787, 753, 719, 700, 660; HRMS Accurate mass (ES$^+$): Found 218.0825 (+3.2 ppm), C$_{12}$H$_{12}$NO$_3$ (M+H$^+$) requires 218.0818.

(1R,7R)-1-[(tert-butyldimethylsilyl)oxy]-1-carbamoyltridecan-7-yl (2S)-1-benzoyl-2,3-dihydro-1H-pyrrole-2-carboxylate (−)-S38. Using modified general procedure G (1.2 eq acid, 1.5 eq EDC, 1.0 eq alcohol, 0.5 eq DMAP), acid (−)-S37 (24 mg, 0.111 mmol) after purification by preparative TLC (2:1 CH$_2$Cl$_2$:Et$_2$O), yielded the title compound as a clear oil (15 mg, 29% yield). $^1$H NMR (500 MHz, CDCl3) δ 7.57 (d, J=7.5 Hz, 2H), 7.45 (dt, J=14.5, 7.1 Hz, 3H), 6.53 (s, 2H), 5.58 (s, 1H), 5.02 (dd, J=11.5, 4.7 Hz, 1H), 4.98-4.94 (m, 1H), 3.18-3.08 (m, 1H), 2.70 (d, J=17.1 Hz, 1H), 1.85-1.16 (m, 10H), 0.92 (s, 9H), 0.87 (t, J=6.6 Hz, 3H), 0.10 (s, 3H), 0.09 (s, 3H); $^{13}$C NMR (100 MHz, CDCl$_3$) δ 177.0, 170.9, 167.0, 135.3, 131.1, 130.7, 128.6, 127.9, 108.9, 75.6, 73.6, 58.8, 35.1, 34.0, 31.8, 29.8, 29.5, 29.3, 25.9, 25.3, 25.1, 24.1, 22.7, 18.2, 14.2, −4.7, −5.1; $[α]^{25}_D$ −38.6 (c=1.43 in CHCl$_3$); IR (film) 3480, 2927, 2856, 1738 (C=O), 1688 (C=O), 1645 (C=O), 1618, 1577, 1463, 1495, 1402, 1360, 1253, 1195, 1100, 1004, 940, 836, 779, 723, 699, 666; HRMS Accurate mass (ES$^+$): Found 573.3695 (−5.1 ppm), C$_{32}$H$_{53}$N$_2$O$_5$Si (M+H$^+$) requires 573.3724; R$_f$ (2:1 CH$_2$Cl$_2$:Et$_2$O)=0.70.

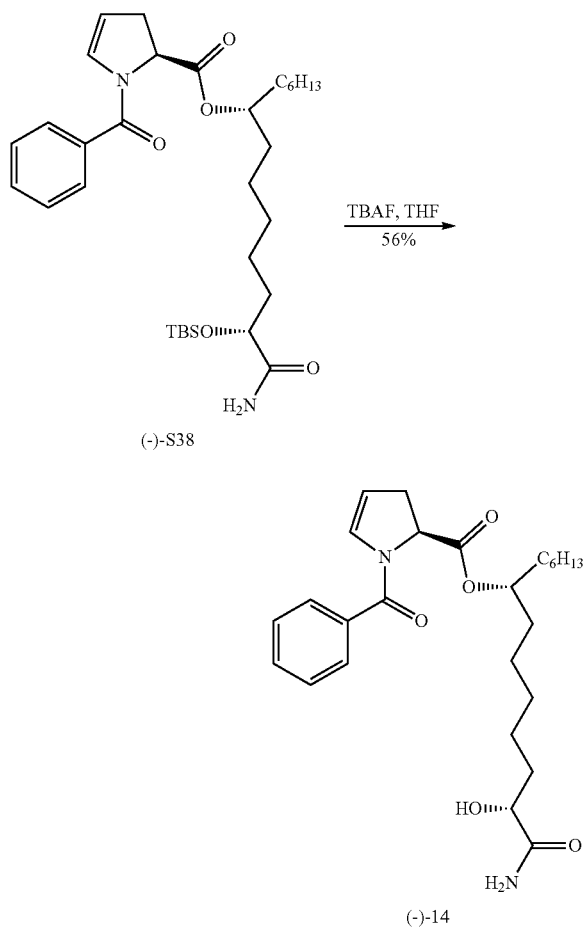

(−)-S38

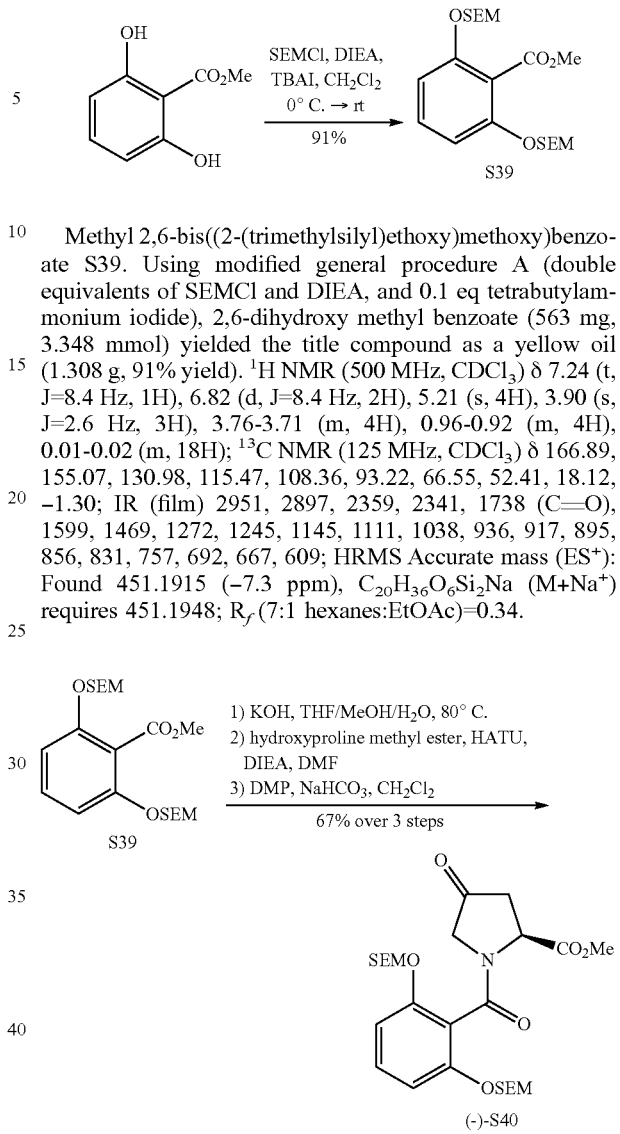

(1R,7R)-1-carbamoyl-1-hydroxytridecan-7-yl (2S)-1-benzoyl-2,3-dihydro-1H-pyrrole-2-carboxylate (−)-14. To a solution of silyl ether (−)-S38 (14 mg, 0.025 mmol) dissolved in THF (0.5 mL) was added TBAF (0.25 mL, 1M in THF, 0.250 mmol) at room temperature. After 5 minutes, the reaction was quenched with 1M aq. NH$_4$Cl and extracted with Et$_2$O 3×. The combined organic layers were washed with brine, dried over Na$_2$SO$_4$, filtered, concentrated, and purified by preparative TLC (2% MeOH/EtOAc), yielding the title compound as a clear oil (6.4 mg, 56% yield). $^1$H NMR (500 MHz, CDCl$_3$) δ 7.61-7.36 (m, 5H), 6.95 (s, 0.16H), 6.91 (s, 0.45H), 6.83 (s, 0.67H), 6.52-6.47 (m, 1H), 5.47 (s, 0.37H), 5.27 (s, 1H), 5.16 (d, J=4.0 Hz, 1H), 5.08-5.02 (m, 1H), 5.02-4.94 (m, 1H), 4.35 (s, 0.55H), 4.14-3.99 (m, 1H), 3.18-3.08 (m, 1H), 2.76-2.66 (m, 1H), 1.87-1.79 (m, 1H), 1.77-1.48 (m, 11H), 1.48-1.16 (m, 22H), 0.87 (t, J=6.8 Hz, 3H); $^{13}$C NMR (125 MHz, CDCl$_3$) δ 177.59, 170.92, 170.62, 167.88, 167.49, 134.93, 134.69, 131.09, 130.80, 128.81, 128.76, 127.78, 127.69, 110.01, 109.84, 75.54, 75.24, 70.64, 59.14, 58.60, 34.84, 34.53, 34.39, 34.15, 34.02, 33.78, 33.61, 31.85, 29.84, 29.25, 27.73, 27.49, 25.60, 25.31, 24.68, 24.50, 24.24, 24.00, 22.70, 14.20; [α]$^{25}_D$ −5.3 (c=0.62 in CHCl$_3$); IR (film) 3325 (br, O—H), 2925, 2856, 2360, 1733 (C=O), 1668 (C=O), 1615 (C=O), 1576, 1496, 1448, 1406, 1197, 1153, 1082, 1017, 1001, 944, 844, 788, 724, 699, 660; HRMS Accurate mass (ES$^+$): Found 481.2650 (−5.8 ppm), C$_{26}$H$_{38}$N$_2$O$_5$Na (M+Na$^+$) requires 481.2678; R$_f$ (2% MeOH/EtOAc)=0.50.

Methyl 2,6-bis((2-(trimethylsilyl)ethoxy)methoxy)benzoate S39. Using modified general procedure A (double equivalents of SEMCl and DIEA, and 0.1 eq tetrabutylammonium iodide), 2,6-dihydroxy methyl benzoate (563 mg, 3.348 mmol) yielded the title compound as a yellow oil (1.308 g, 91% yield). $^1$H NMR (500 MHz, CDCl$_3$) δ 7.24 (t, J=8.4 Hz, 1H), 6.82 (d, J=8.4 Hz, 2H), 5.21 (s, 4H), 3.90 (s, J=2.6 Hz, 3H), 3.76-3.71 (m, 4H), 0.96-0.92 (m, 4H), 0.01-0.02 (m, 18H); $^{13}$C NMR (125 MHz, CDCl$_3$) δ 166.89, 155.07, 130.98, 115.47, 108.36, 93.22, 66.55, 52.41, 18.12, −1.30; IR (film) 2951, 2897, 2359, 2341, 1738 (C=O), 1599, 1469, 1272, 1245, 1145, 1111, 1038, 936, 917, 895, 856, 831, 757, 692, 667, 609; HRMS Accurate mass (ES$^+$): Found 451.1915 (−7.3 ppm), C$_{20}$H$_{36}$O$_6$Si$_2$Na (M+Na$^+$) requires 451.1948; R$_f$ (7:1 hexanes:EtOAc)=0.34.

Methyl (S)-1-(2,6-bis((2-(trimethylsilyl)ethoxy)methoxy)benzoyl)-4-oxopyrrolidine-2-carboxylate (−)-S40. Methyl ester S39 (1.283 g, 2.993 mmol) was dissolved in 9:1:1 MeOH:THF:H$_2$O (11 mL), and KOH (1.914 g, 34.117 mmol) was added as a solid. The reaction was heated to reflux (80° C.) overnight. The following day, the reaction was cooled to room temperature, acidified (pH 5-6) with 5% aq. AcOH, and extracted with CH$_2$Cl$_2$ 3×. The combined organic layers were washed with brine, dried over MgSO$_4$, filtered and concentrated. The crude acid was unstable and used directly in the next step. Using general procedure C, the acid yielded the corresponding acylhydroxyproline methyl ester compound, whose purity made it unsuitable for characterization. Using general procedure D, the alcohol intermediate yielded the title compound as a yellow oil (1.075 g, 67% over 3 steps). $^1$H NMR (500 MHz, CDCl$_3$, mixture of rotamers/conformers) δ 7.29-7.24 (m, 1H), 6.86 (tt, J=7.4, 4.3 Hz, 2H), 5.32-5.15 (m, 4.56H), 5.11 (t, J=5.8 Hz, 0.35H), 4.64-4.59 (m, 0.33H), 4.43 (d, J=19.7 Hz, 0.34H), 4.07-4.03 (m, 0.18H), 4.03-3.99 (m, 0.16), 3.93-3.90 (m, 0.30), 3.90-3.86 (m, 0.41H), 3.82-3.66 (m, 6.48H), 3.63-3.59 (m, 0.83H), 3.03-2.93 (m, 0.73H), 2.90-2.82 (m, 0.38H), 2.72-

2.62 (m, 0.73H), 2.57 (d, J=18.1 Hz, 0.35H), 0.98-0.88 (m, 4H), 0.05--0.06 (m, 18H); $^{13}$C NMR (125 MHz, CDCl$_3$) δ 207.70, 170.94, 165.99, 154.92, 154.16, 131.50, 131.17, 116.27, 109.11, 108.75, 108.54, 108.23, 93.81, 93.63, 93.47, 93.31, 66.84, 66.73, 66.68, 57.33, 54.73, 52.69, 52.55, 51.82, 41.95, 40.69, 18.10, 14.31, −1.27, −1.30, −1.31; [α]$^{25}_D$ −1.8 (c=1.41 in CHCl$_3$); IR (film) 2952, 2896, 1765 (C=O), 1747 (C=O), 1658 (C=O), 1596, 1467, 1404, 1245, 1177, 1142, 1094, 1035, 918, 893, 856, 832, 790, 751, 693, 664; HRMS Accurate mass (ES$^+$): Found 562.2232 (−6.4 ppm), C$_{25}$H$_{41}$NO$_8$Si$_2$Na (M+Na$^+$) requires 562.2268; R$_f$ (3:1 hexanes:EtOAc)=0.25.

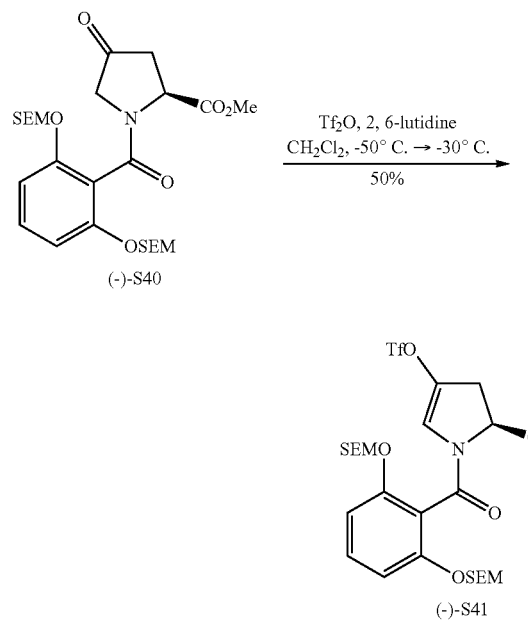

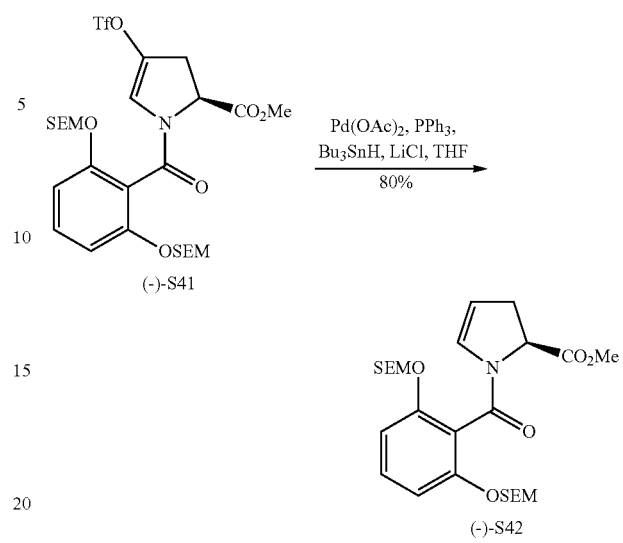

Methyl (S)-1-(2,6-bis((2-(trimethylsilyl)ethoxy)methoxy)benzoyl)-2,3-dihydro-1H-pyrrole-2-carboxylate (−)-S42. Using general procedure F, triflate (−)-S41 (130 mg, 0.194 mmol) yielded the title compound as a yellow oil (82 mg, 80% yield). $^1$H NMR (500 MHz, CDCl$_3$) δ 7.25-7.20 (m, 1H), 6.83 (dt, J=12.5, 6.2 Hz, 2H), 6.11 (dt, J=4.4, 2.2 Hz, 1H), 5.29 (d, J=7.1 Hz, 1H), 5.24-5.13 (m, 3H), 5.01 (ddd, J=8.3, 6.9, 3.8 Hz, 2H), 3.86-3.64 (m, 7H), 3.12 (ddt, J=16.7, 11.6, 2.3 Hz, 1H), 2.74-2.68 (m, 1H), 0.99-0.87 (m, 4H), 0.02--0.06 (m, 18H); $^{13}$C NMR (100 MHz, CDCl$_3$) δ 171.27, 162.64, 154.96, 154.81, 130.92, 130.58, 115.96, 108.57, 108.29, 108.10, 93.02, 92.96, 66.43, 57.50, 52.35, 34.42, 18.05, −1.36; [α]$^{25}_D$ −55.9 (c=1.49 in CHCl$_3$); IR (film) 2952, 2921, 2899, 1744 (C=O), 1656 (C=O), 1620, 1596, 1468, 1404, 1245, 1199, 1178, 1151, 1094, 1038, 917, 895, 857, 832, 741, 694, 608; HRMS Accurate mass (ES$^+$): Found 546.2288 (−5.7 ppm), C$_{25}$H$_{41}$NO$_7$Si$_2$Na (M+Na$^+$) requires 546.2319.

Methyl (S)-1-(2,6-bis((2-(trimethylsilyl)ethoxy)methoxy)benzoyl)-4-(((trifluoromethyl)sulfonyl)oxy)-2,3-dihydro-1H-pyrrole-2-carboxylate (−)-S41. Using general procedure E, ketone (−)-S40 (238 mg, 0.440 mmol) yielded the title compound as an orange oil (149 mg, 50% yield). $^1$H NMR (400 MHz, CDCl$_3$) δ 7.37-7.28 (m, 1H), 6.87 (t, J=8.2 Hz, 2H), 6.35 (s, 1H), 5.28-5.16 (m, 4H), 5.10 (dd, J=11.8, 5.0 Hz, 1H), 3.82 (s, 3H), 3.74 (dt, J=21.8, 8.0 Hz, 4H), 3.45-3.34 (m, 1H), 2.95 (dd, J=16.5, 4.9 Hz, 1H), 0.93 (dd, J=16.0, 7.7 Hz, 4H), −0.01 (s, J=7.4 Hz, 18H); $^{13}$C NMR (125 MHz, CDCl$_3$) δ 169.52, 163.25, 155.19, 133.94, 131.84, 123.14, 114.23, 108.67, 108.37, 93.48, 93.16, 66.69, 66.64, 56.77, 52.81, 33.66, 18.04, −1.34, −1.38; [α]$^{25}_D$ −41.3 (c=1.04 in CHCl$_3$); IR (film) 3269, 2954, 2899, 1747 (C=O), 1605 (C=O), 1425, 1363, 1311, 1208, 1136, 1028, 912, 833, 755, 693, 605; HRMS Accurate mass (ES$^+$): Found 694.1727 (−4.9 ppm), C$_{26}$H$_{40}$F$_3$NO$_{10}$SSi$_2$Na (M+Na$^+$) requires 694.1761; R$_f$ (3:1 hexanes:EtOAc)=0.48.

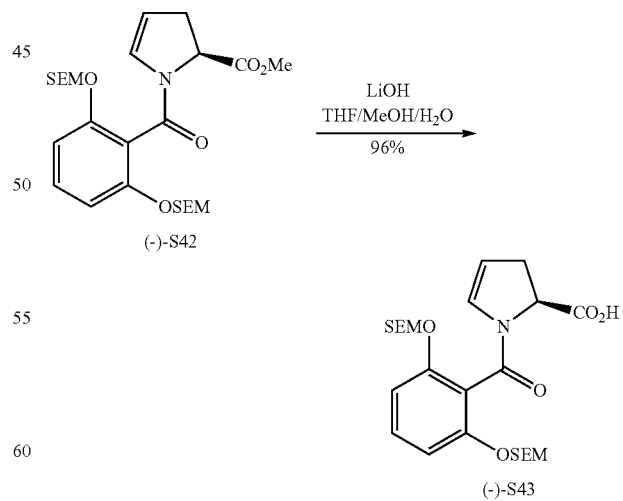

(S)-1-(2,6-bis((2-(trimethylsilyl)ethoxy)methoxy)benzoyl)-2,3-dihydro-1H-pyrrole-2-carboxylic acid (−)-S43. Using general procedure B, methyl ester (−)-S42 (73 mg, 0.139 mmol) yielded the title compound as a yellow oil (68 mg, 96% yield). $^1$H NMR (400 MHz, CDCl$_3$) δ 7.31 (t, J=8.4 Hz, 1H), 6.85 (dd, J=8.5, 0.8 Hz, 2H), 6.02 (dt, J=4.4, 2.2 Hz, 1H), 5.28-5.16 (m, 6H), 3.74-3.67 (m, 4H), 3.48-3.40 (m, 1H), 2.98 (ddt, J=17.4, 11.0, 2.5 Hz, 1H), 0.95-0.89 (m, 4H), −0.01 (d, J=1.7 Hz, 18H); $^{13}$C NMR (100 MHz, CDCl$_3$) δ 171.36, 166.43, 154.97, 154.62, 131.84, 129.07, 114.45, 112.17, 108.27, 107.97, 93.08, 92.94, 77.36, 66.75, 66.67, 59.24, 32.64, 30.43, 29.81, 18.10, −1.30, −1.33; [α]$^{25}_D$ −66.4 (c=1.38 in CHCl$_3$); IR (film) 2952, 2924, 2896, 1748 (C=O), 1652 (C=O), 1619, 1595, 1468, 1405, 1245, 1183, 1150, 1093, 1039, 832, 738, 693, 664; HRMS Accurate mass (ES$^+$): Found 532.2130 (−6.2 ppm), C$_{24}$H$_{39}$NO$_7$Si$_2$Na (M+Na$^+$) requires 532.2163.

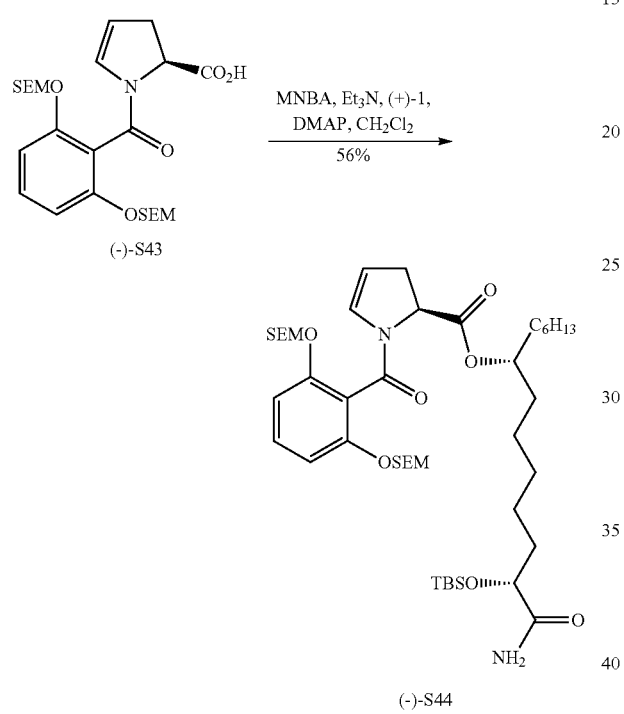

(7R,13R)-14-amino-13-((tert-butyldimethylsilyl)oxy)-14-oxotetradecan-7-yl (S)-1-(2,6-bis((2-(trimethylsilyl)ethoxy)methoxy)benzoyl)-2,3-dihydro-1H-pyrrole-2-carboxylate (−)-S44. Using general procedure H, acid (−)-S43 (81 mg, 0.158 mmol) yielded the title compound as a yellow oil (55 mg, 56% yield). $^1$H NMR (500 MHz, CDCl$_3$) δ 7.23 (d, J=8.4 Hz, 1H), 6.92-6.75 (m, 2H), 6.57-6.48 (m, 1H), 6.10 (dt, J=4.2, 2.0 Hz, 1H), 5.46-5.35 (m, 1H), 5.30-5.12 (m, 5H), 4.98 (dt, J=8.7, 5.3 Hz, 2H), 4.13 (t, J=5.1 Hz, 1H), 3.83-3.64 (m, 4H), 3.17-3.07 (m, 1H), 2.70-2.62 (m, 1H), 1.81-1.70 (m, 1H), 1.70-1.62 (m, 1H), 1.43-1.17 (m, 16H), 0.98-0.89 (m, 12H), 0.87 (t, J=6.3 Hz, 3H), 0.14-0.04 (m, 6H), 0.03-0.06 (m, 18H); $^{13}$C NMR (125 MHz, CDCl$_3$) δ 177.02, 170.41, 162.48, 155.04, 154.97, 130.87, 130.79, 116.20, 108.76, 108.22, 108.10, 93.11, 93.03, 75.01, 73.54, 66.43, 57.85, 35.10, 34.67, 34.07, 34.02, 31.85, 29.48, 29.30, 25.85, 25.28, 25.06, 24.11, 22.68, 18.16, 18.10, 14.17, −1.30, −4.73, −5.15; [α]$^{25}_D$ −25.4 (c=1.27 in CHCl$_3$); IR (film) 2927, 2857, 1749 (C=O), 1689 (C=O), 1657 (C=O), 1621, 1596, 1467, 1404, 1247, 1188, 1151, 1095, 1040, 937, 896, 833, 778, 751, 694, 665, 580, 554; HRMS Accurate mass (ES$^+$): Found 865.5290 (+4.6 ppm), C$_{44}$H$_{81}$N$_2$O$_9$Si$_3$ (M+H$^+$) requires 865.5250; R$_f$ (4:1 CH$_2$Cl$_2$:Et$_2$O)=0.67.

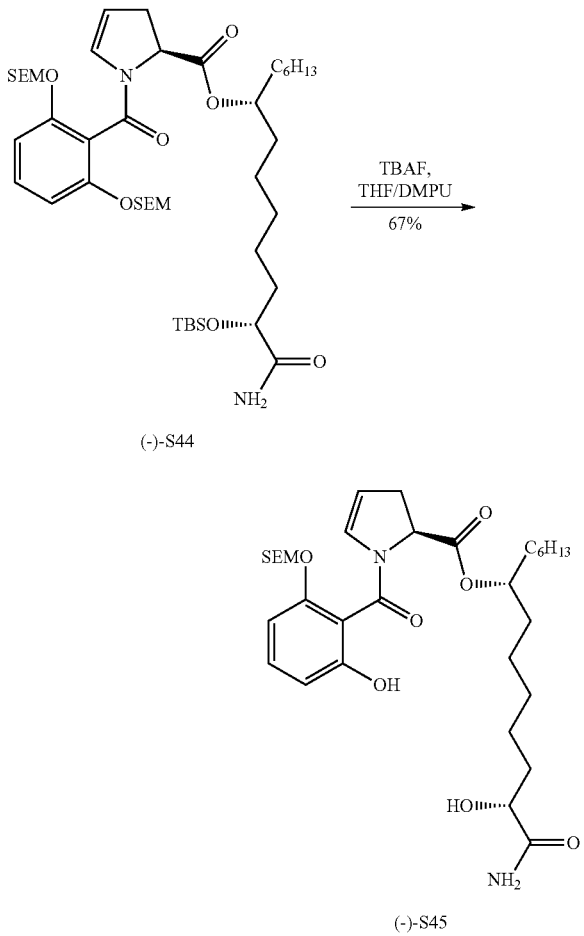

(7R,13R)-14-amino-13-hydroxy-14-oxotetradecan-7-yl (S)-1-(2-hydroxy-6-((2-(trimethylsilyl)ethoxy)methoxy)benzoyl)-2,3-dihydro-1H-pyrrole-2-carboxylate (−)-S45. Using general procedure I, compound (−)-S44 (37 mg, 0.043 mmol) yielded the title compound, after purification by preparative TLC (4% MeOH/EtOAc), as a yellow oil (18 mg, 67% yield). $^1$H NMR (400 MHz, CDCl$_3$) δ 8.13-7.89 (m, 1H), 7.22 (t, J=8.3 Hz, 1H), 6.81 (s, 1H), 6.71 (t, J=7.2 Hz, 1H), 6.62 (d, J=8.3 Hz, 1H), 6.31-6.25 (m, 1H), 5.33-5.02 (m, 6H), 4.14-3.99 (m, 2H), 3.77-3.68 (m, 2H), 3.23-3.10 (m, 1H), 2.70 (d, J=17.5 Hz, 1H), 1.86-1.74 (m, 1H), 1.73-1.15 (m, 22H), 0.99-0.81 (m, 5H), −0.01 (d, J=2.9 Hz, 9H); $^{13}$C NMR (125 MHz, CDCl$_3$) δ 177.79, 172.11, 164.33, 155.46, 154.76, 132.20, 130.96, 130.57, 111.63, 110.73, 110.27, 106.20, 93.42, 76.45, 70.80, 66.78, 58.28, 34.75, 34.29, 34.13, 33.84, 31.81, 29.17, 27.77, 25.59, 24.78, 24.40, 22.66, 18.13, 14.18, −1.29; [α]$^{25}_D$ −1.7 (c=0.93 in CHCl$_3$); IR (film) 3338 (br, O—H), 2927, 2858, 1748 (C=O), 1661, 1616, 1601, 1466, 1432, 1378, 1292, 1247, 1193, 1153, 1102, 1038, 941, 835, 792, 721; HRMS Accurate mass (ES$^+$): Found 643.3417 (+4.0 ppm), C$_{32}$H$_{52}$N$_2$O$_8$SiNa (M+Na$^+$) requires 643.3391.

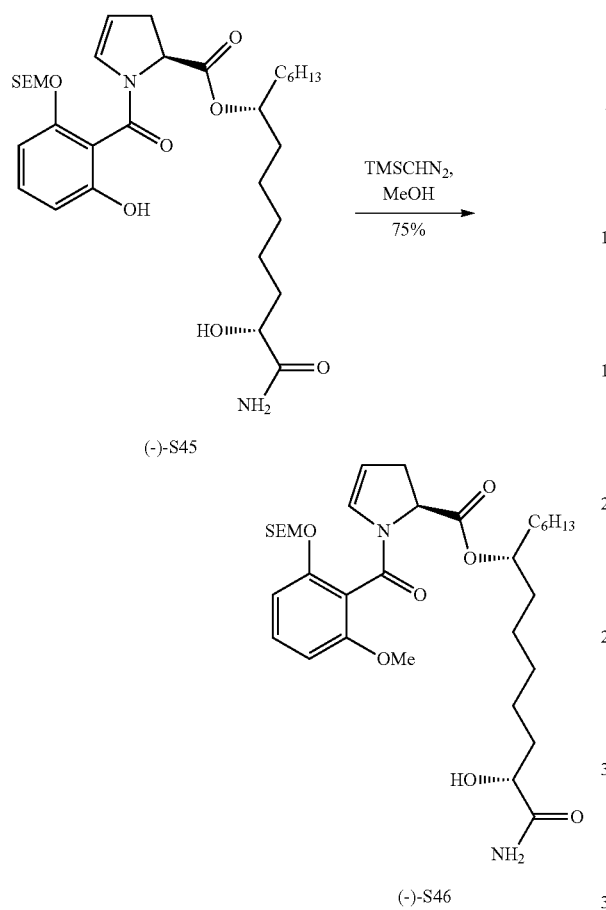

3329 (br, O—H), 2924, 2854, 1721, 1658, 1619, 1595, 1472, 1409, 1379, 1291, 1247, 1190, 1107, 1073, 1002, 951, 898, 858, 835, 789, 716; 668, 604; HRMS Accurate mass (ES$^+$): Found 657.3570 (+3.5 ppm), $C_{33}H_{54}N_2O_8SiNa$ (M+Na$^+$) requires 657.3547.

(7R,13R)-14-amino-13-hydroxy-14-oxotetradecan-7-yl (S)-1-(2-methoxy-6-((2-(trimethylsilyl)ethoxy)methoxy)benzoyl)-2,3-dihydro-1H-pyrrole-2-carboxylate (−)-S46. To a solution of compound (−)-S45 (19 mg, 0.031 mmol) in MeOH (1 mL) was added TMSCHN$_2$ (0.07 mL, 2M in hexanes, 0.035 mmol). The reaction was stirred overnight at room temperature, over which time the reaction turned from yellow to clear. The reaction was concentrated and purified by preparative TLC (5% MeOH/EtOAc), yielding the title compound as a yellow oil (15 mg, 75% yield). $^1$H NMR (500 MHz, CDCl$_3$, mixture of rotamers/conformers) δ 8.00 (dd, J=8.3, 1.3 Hz, 1H), 7.61-7.56 (m, 0.39H), 7.45 (t, J=7.8 Hz, 1H), 7.28 (td, J=8.0, 1.9 Hz, 1H), 6.97 (d, J=26.7 Hz, 1H), 6.78 (dd, J=8.2, 6.7 Hz, 1H), 6.58 (dd, J=8.3, 2.7 Hz, 1H), 6.43 (s, 0.37H), 6.10 (ddq, J=12.7, 6.4, 2.2 Hz, 1H), 5.32-5.03 (m, 5H), 4.98-4.88 (m, 2H), 4.26 (dd, J=7.0, 3.2 Hz, 0.38H), 4.16-4.11 (m, 0.42H), 4.06 (d, J=6.6 Hz, 0.62H), 3.84-3.80 (m, 1.84H), 3.80-3.76 (m, 2.25H), 3.75-3.66 (m, 1.59H), 3.18-3.08 (m, 1H), 2.74-2.63 (m, 1H), 1.89-1.68 (m, 2H), 1.68-1.37 (m, 12H), 1.36-1.14 (m, 24H), 0.98-0.77 (m, 9H), −0.02 (d, J=5.9 Hz, 9H); $^{13}$C NMR (100 MHz, CDCl$_3$) δ 178.21, 178.09, 170.41, 170.07, 165.15, 163.64, 157.65, 157.10, 155.01, 154.80, 133.70, 131.56, 131.47, 130.53, 129.95, 128.63, 113.96, 113.59, 109.58, 107.87, 107.12, 104.95, 104.55, 101.07, 93.07, 92.78, 82.51, 79.60, 77.16, 74.43, 74.34, 70.81, 70.12, 69.95, 66.72, 66.65, 63.15, 57.71, 56.30, 56.06, 35.11, 34.57, 34.35, 33.50, 32.06, 31.87, 29.84, 29.50, 29.29, 27.22, 27.04, 26.15, 25.66, 24.80, 24.63, 24.23, 24.15, 22.83, 22.71, 18.15, 18.10, 14.22, −1.28; [α]$^{25}_D$ −19.8 (c=1.72 in CHCl$_3$); IR (film)

(7R,13R)-14-amino-13-hydroxy-14-oxotetradecan-7-yl (S)-1-(2-hydroxy-6-methoxybenzoyl)-2,3-dihydro-1H-pyrrole-2-carboxylate (−)-15. Using modified general procedure I (10 eq TBAF, 0.1M DMPU), silyl ether (−)-S46 (17 mg, 0.027 mmol) after purification by column chromatography (0→3% MeOH/CH$_2$Cl$_2$), yielded the title compound as a clear oil (5.6 mg, 41% yield). $^1$H NMR (500 MHz, CDCl$_3$) δ 7.98 (s, 1H), 7.28-7.23 (m, 1H), 6.83 (s, 1H), 6.60 (dd, J=8.3, 4.8 Hz, 1H), 6.47 (t, J=8.7 Hz, 1H), 6.25 (dt, J=4.4, 2.2 Hz, 1H), 5.19 (dt, J=4.6, 2.4 Hz, 1H), 5.14-5.04 (m, 2H), 4.60 (d, J=5.9 Hz, 1H), 4.08-4.00 (m, 1H), 3.83-3.79 (m, 3H), 3.21-3.12 (m, 1H), 2.69 (d, J=18.6 Hz, 1H), 1.84-1.74 (m, 1H), 1.71-1.19 (m, 22H), 0.88 (t, J=6.9 Hz, 3H); $^{13}$C NMR (125 MHz, CDCl$_3$) δ 177.47, 176.57, 172.39, 172.24, 164.48, 164.39, 157.00, 155.68, 132.38, 130.55, 110.52, 110.44, 110.14, 110.10, 102.72, 102.63, 76.66, 76.46, 70.77, 70.70, 64.51, 58.37, 58.33, 56.07, 56.02, 34.79, 34.35, 34.21, 34.07, 33.81, 33.58, 31.83, 29.84, 29.18, 27.72, 27.53, 25.63, 24.75, 24.69, 24.33, 24.14, 22.68, 14.20; [α]$^{25}_D$ −10.5 (c=0.56 in CHCl$_3$); IR (film) 3307 (br, O—H), 2926, 2856, 1733 (C=O), 1653, 1592, 1470, 1435, 1250, 1194, 1088, 1016, 947, 847, 791, 720, 601; HRMS Accurate mass (ES$^+$): Found 527.2751 (+3.4 ppm), $C_{27}H_{40}N_2O_7Na$ (M+Na$^+$) requires 527.2733.

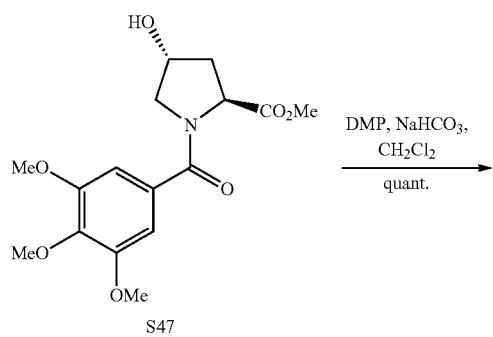

S47

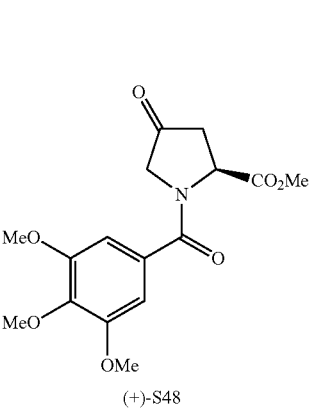

(+)-S48

Methyl (2S)-4-oxo-1-(3,4,5-trimethoxybenzoyl)pyrrolidine-2-carboxylate (+)-S48. Using general procedure D, alcohol S47[3] (1.340 g, 3.950 mmol) yielded the title compound as a white foam (1.33 g, quant. yield). $^1$H NMR (400 MHz, CDCl$_3$) δ 6.66 (s, 2H), 5.19 (br s, 1H), 3.97 (br s, 1H), 3.83-3.67 (m, 12H), 2.91 (dd, J=18.8, 10.5 Hz, 1H), 2.59 (d, J=18.6 Hz, 1H); $^{13}$C NMR (100 MHz, CDCl$_3$) δ 207.11, 171.59, 170.16, 153.24, 139.94, 129.95, 104.43, 77.36, 60.80, 56.19, 52.80; $[α]^{25}_D$ +4.4 (c=0.45 in 2:1 CHCl$_3$/MeOH); IR (film) 3451, 2953, 2360, 1728 (C=O), 1633 (C=O), 1580, 1506, 1448, 1414, 1324, 1238, 1179, 1119, 998, 922, 879, 840, 763, 723, 691, 603; HRMS Accurate mass (ES$^+$): Found 360.1072 (+3.6 ppm), C$_{16}$H$_{19}$NO$_7$Na (M+Na$^+$) requires 360.1059.

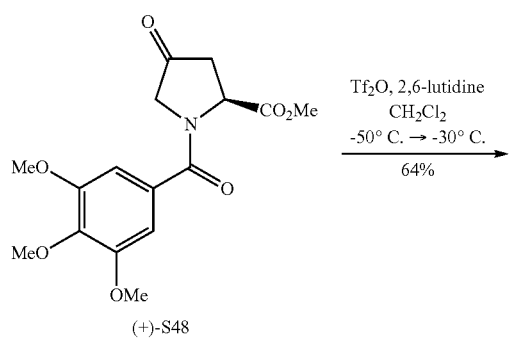

(+)-S48

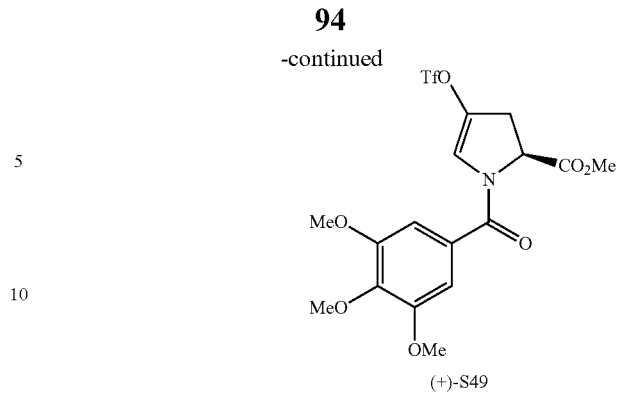

(+)-S49

Methyl (2S)-4-(trifluoromethanesulfonyloxy)-1-(3,4,5-trimethoxybenzoyl)-2,3-dihydro-1H-pyrrole-2-carboxylate (+)-S49. Using general procedure E, ketone (+)-S48 (145 mg, 0.431 mmol) yielded the title compound as an orange oil (129 mg, 64% yield). $^1$H NMR (500 MHz, CDCl$_3$) δ 6.90 (s, 1H), 6.75 (s, 2H), 5.10-5.00 (m, 1H), 3.88-3.78 (m, 12H), 3.40 (dd, J=15.2, 13.1 Hz, 1H), 3.00-2.90 (m, 1H); $^{13}$C NMR (125 MHz, CDCl$_3$) δ 169.72, 167.22, 153.49, 140.84, 134.51, 128.35, 123.32, 105.35, 61.03, 56.37, 53.10; $[α]^{25}_D$ +7.3 (c=0.26 in CHCl$_3$); IR (film) 2953, 2359, 1745 (C=O), 1636 (C=O), 1582, 1413, 1326, 1234, 1120, 999, 924, 819, 760, 725, 637, 605; HRMS Accurate mass (ES$^+$): Found 470.0756 (+4.9 ppm), C$_{17}$H$_{19}$F$_3$NO$_9$S (M+H$^+$) requires 470.0733.

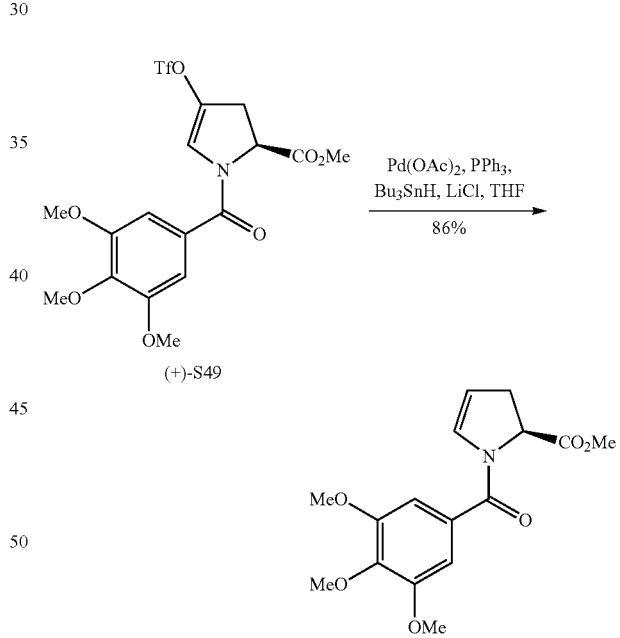

Methyl (2S)-1-(3,4,5-trimethoxybenzoyl)-2,3-dihydro-1H-pyrrole-2-carboxylate (−)-S50. Using general procedure F, triflate (+)-S49 (110 mg, 0.234 mmol) yielded the title compound as a yellow oil (61 mg, 86% yield). $^1$H NMR (500 MHz, CDCl$_3$) δ 6.78 (s, 2H), 6.60 (s, 1H), 5.13 (s, 1H), 4.98 (dd, J=11.2, 4.6 Hz, 1H), 3.91-3.76 (m, 12H), 3.16-3.07 (m, 1H), 2.71 (ddd, J=17.0, 4.7, 2.3 Hz, 1H); $[α]^{25}_D$ −48.3 (c=0.40 in CHCl$_3$); $^{13}$C NMR (125 MHz, CDCl$_3$) δ 171.56, 166.79, 153.30, 140.20, 131.00, 130.21, 109.13, 105.39, 61.02, 58.61, 56.43, 52.65, 33.81; IR (film) 2997, 2950, 2832, 1751 (C=O), 1642 (C=O), 1619, 1582, 1506, 1462, 1404, 1361, 1315, 1235, 1196, 1177, 1143, 1119, 1000, 964, 895, 850, 810, 754, 734, 675, 570; HRMS Accurate mass (ES⁺): Found 344.1087(−6.7 ppm), $C_{16}H_{19}NO_6Na$ (M+Na⁺) requires 344.1110.

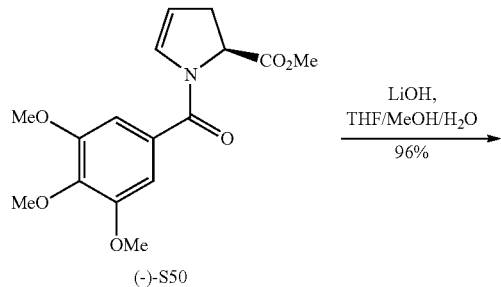

(−)-S50

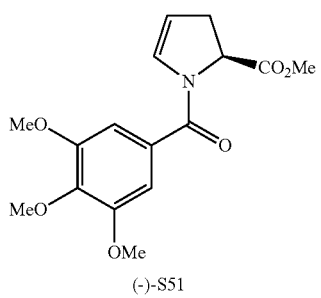

(−)-S51

(2S)-1-(3,4,5-trimethoxybenzoyl)-2,3-dihydro-1H-pyrrole-2-carboxylic acid (−)-S51. Using general procedure B, methyl ester (−)-S50 (55 mg, 0.180 mmol) yielded the title compound as a yellow oil (50 mg, 96% yield). ¹H NMR (400 MHz, CDCl₃) δ 6.83-6.76 (m, 2H), 6.55 (s, 1H), 5.28 (d, J=11.1 Hz, 1H), 5.06 (d, J=6.1 Hz, 1H), 3.92-3.83 (m, 12H), 3.14-3.00 (m, 2H); ¹³C NMR (100 MHz, CDCl₃) δ 173.49, 167.90, 153.29, 140.45, 132.30, 132.20, 130.28, 129.39, 128.76, 128.64, 110.99, 105.54, 68.02, 61.02, 59.25, 56.42; $[α]^{25}_D$ −104.3 (c=0.29 in CHCl₃); IR (film) 3269, 2954, 2899, 1747 (C=O), 1631 (C=O), 1605, 1467, 1425, 1363, 1311, 1208, 1136, 1028, 912, 833, 755, 693, 665, 605; HRMS Accurate mass (ES⁺): Found 308.1148 (+4.5 ppm), $C_{15}H_{18}NO_6$ (M+H⁺) requires 308.1134.

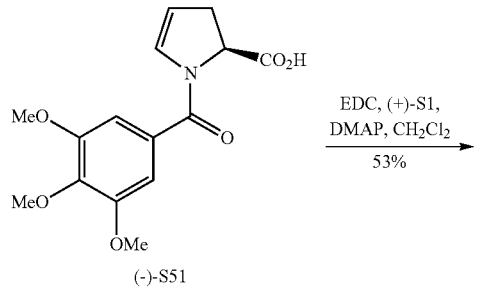

(−)-S51

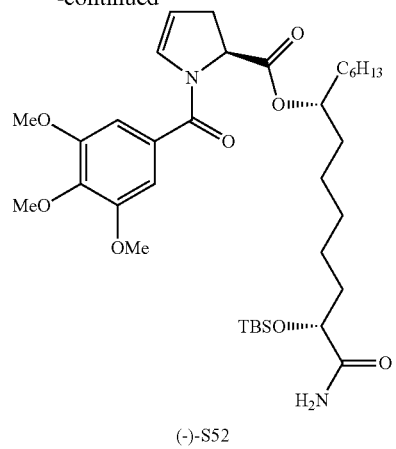

(−)-S52

(1R,7R)-1-[(tert-butyldimethylsilyl)oxy]-1-carbamoyltridecan-7-yl (2S)-1-(3,4,5-trimethoxybenzoyl)-2,3-dihydro-1H-pyrrole-2-carboxylate (−)-S52. Using general procedure G, acid (−)-S51 (26 mg, 0.085 mmol) yielded the title compound as a yellow oil (21 mg, 53% yield). ¹H NMR (500 MHz, CDCl₃) δ 6.78 (s, 2H), 6.58 (s, 1H), 6.53 (d, J=4.1 Hz, 1H), 5.47 (d, J=4.1 Hz, 1H), 5.12 (s, 1H), 5.01-4.91 (m, 2H), 4.13 (t, J=5.1 Hz, 1H), 3.87 (s, 9H), 3.16-3.06 (m, 1H), 2.68 (d, J=16.5 Hz, 1H), 1.80-1.71 (m, 1H), 1.68-1.46 (m, 10H), 1.39-1.16 (m, 20H), 0.91 (s, J=6.5 Hz, 9H), 0.86 (t, J=7.0 Hz, 3H), 0.08 (d, J=5.8 Hz, 6H); ¹³C NMR (100 MHz, CDCl₃) δ 177.02, 170.84, 166.66, 153.28, 140.01, 131.08, 130.50, 129.10, 108.95, 105.25, 75.67, 73.52, 61.03, 58.84, 56.39, 35.10, 34.01, 31.83, 29.49, 29.31, 25.85, 25.30, 25.03, 24.06, 22.69, 18.13, 14.18, −4.72, −5.15; $[α]^{25}_D$ −34.7 (c=0.86 in CHCl₃); IR (film) 3480, 2927, 2856, 1738 (C=O), 1687 (C=O), 1645 (C=O), 1616, 1582, 1506, 1456, 1414, 1358, 1236, 1192, 1126, 1004, 951, 836, 810, 778, 720, 671; HRMS Accurate mass (ES⁺): Found 663.4066 (+3.8 ppm), $C_{35}H_{59}N_2O_8Si$ (M+H⁺) requires 663.4041.

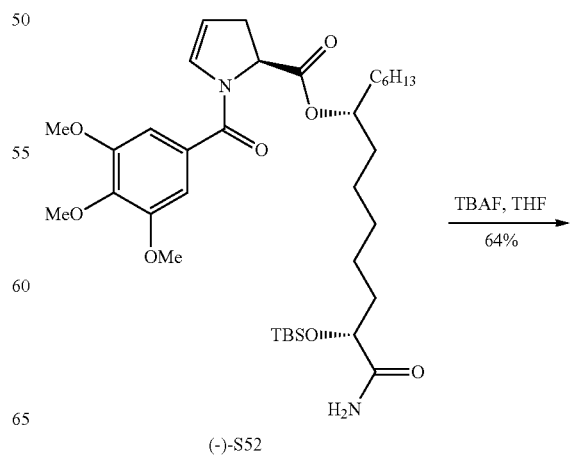

(−)-S52

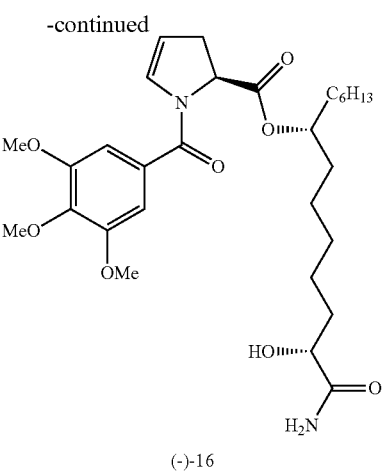

(-)-16

(1R,7R)-1-carbamoyl-1-hydroxytridecan-7-yl (2S)-1-(3,4,5-trimethoxybenzoyl)-2,3-dihydro-1H-pyrrole-2-carboxylate (-)-16. To a solution of silyl ether (-)-S52 (12.5 mg, 0.0189 mmol) dissolved in THF (0.5 mL) was added TBAF (0.094 mL, 1M in THF, 0.094 mmol). After 20 minutes, the reaction was diluted with Et$_2$O, and washed with sat. NH$_4$Cl 4×, dried over Na$_2$SO$_4$, filtered, concentrated, and purified by preparative TLC (100% EtOAc), yielding the title compound as a clear oil (6.7 mg, 64% yield). $^1$H NMR (500 MHz, CDCl$_3$) δ 6.96-6.66 (t, J=14.9 Hz, 2H), 6.57 (s, 1H), 5.20 (dd, J=64.4, 27.8 Hz, 2H), 5.11-4.96 (m, 1H), 4.96-4.85 (m, 1H), 4.28 (d, J=25.3 Hz, 1H), 4.05 (d, J=39.2 Hz, 1H), 3.87 (s, J=6.2 Hz, 9H), 3.13 (s, 1H), 2.69 (d, J=16.0 Hz, 1H), 1.82 (s, 1H), 1.75-1.40 (m, 12H), 1.35-1.16 (m, 10H), 0.87 (s, J=6.3 Hz, 3H); $^{13}$C NMR (125 MHz, CDCl$_3$) δ 177.45, 170.66, 167.47, 153.39, 140.28, 130.92, 129.85, 110.16, 109.95, 105.18, 75.30, 70.81, 61.09, 58.71, 56.48, 34.77, 34.04, 33.98, 33.81, 31.85, 29.25, 27.53, 25.59, 24.67, 24.28, 22.69, 14.20; [α]$^{25}_D$ -32.4 (c=0.67 in CHCl$_3$); IR (film) 3337 (br O—H), 2927, 2856, 1733 (C═O), 1668 (C═O), 1614 (C═O), 1581, 1506, 1414, 1318, 1236, 1194, 1124, 1002, 951, 853, 810, 756, 722, 674; HRMS Accurate mass (ES$^+$): Found 549.3152 (-4.4 ppm), C$_{29}$H$_{45}$N$_2$O$_8$ (M+H$^+$) requires 283.1366.

NaH (60% in mineral oil, 74 mg, 1.852 mmol) and KI (307 mg, 1.852 mmol) in THF (4 mL) at 0° C. was added a solution of (S)-5-(((tert-butyldimethylsilyl)oxy)methyl)pyrrolidin-2-one$^4$ (386 mg, 1.683 mmol) dropwise in THF (2 mL). The solution was allowed to warm to room temperature and stir for 90 minutes. Then 2-nitrobenzoyl chloride (0.27 mL, 2.020 mmol) was added as a solution in THF (2 mL). After 10 minutes, the reaction was quenched with sat. NH$_4$Cl (10 mL) and extracted 3× with EtOAc. The combined organic layers were washed 2× with sat. Na$_2$CO$_3$, water, and brine, dried over MgSO$_4$, filtered, concentrated, and filtered through a plug of silica gel, which was washed with 3:1 hexanes:EtOAc. The filtrate was concentrated then triturated with MeOH, yielding the title compound as a white solid (609 mg, 96% yield). $^1$H NMR (500 MHz, CDCl$_3$) δ 8.23 (dd, J=8.3, 0.9 Hz, 1H), 7.71 (td, J=7.5, 1.2 Hz, 1H), 7.58 (ddd, J=8.3, 7.5, 1.4 Hz, 1H), 7.32 (dt, J=6.7, 3.4 Hz, 1H), 4.69-4.62 (m, 1H), 4.14 (dd, J=10.4, 3.7 Hz, 1H), 3.85 (d, J=10.6 Hz, 1H), 2.75 (dt, J=17.8, 10.3 Hz, 1H), 2.36 (ddd, J=17.8, 9.8, 2.0 Hz, 1H), 2.21 (ddd, J=34.5, 22.6, 11.4 Hz, 2H), 0.90 (s, 9H), 0.11 (s, 3H), 0.11 (s, 3H); $^{13}$C NMR (125 MHz, CDCl$_3$) δ 175.70, 166.50, 145.21, 134.37, 133.47, 129.94, 127.72, 124.17, 63.52, 58.18, 32.27, 25.94, 21.33, 18.29, -5.39, -5.50; [α]$^{25}_D$ -76.1 (c=0.77 in CHCl$_3$); IR (film) 2925, 2891, 2853, 1743 (C═O), 1668 (C═O), 1533, 1471, 1353, 1319, 1264, 1226, 1193, 1104, 1087, 1028, 1005, 986, 967, 872, 837, 776, 744, 703, 640, 560; HRMS Accurate mass (ES$^+$): Found 401.1536 (+6.7 ppm), C$_{18}$H$_{26}$N$_2$O$_5$SiNa (M+Na$^+$) requires 401.1509; MP 121.5-124.0° C.

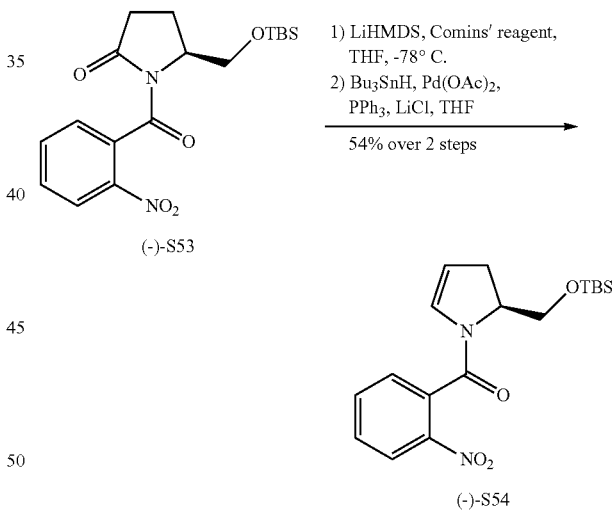

(S)-(2-(((tert-butyldimethylsilyl)oxy)methyl)-2,3-dihydro-1H-pyrrol-1-yl)(2-nitrophenyl)methanone (-)-S54. LiHMDS (1M in THF, 2.83 mL, 2.83 mmol) was diluted with THF (12 mL) and cooled to -78° C. A solution of compound (-)-S53 (713 mg, 1.884 mmol) was added dropwise as a solution in THF (6 mL), and the reaction turned a deep purple color. After 1 hour, Comins' reagent (1.849 g, 4.710 mmol) was added dropwise as a solution in THF (5 mL), and the reaction was stirred for 2 hours at -78° C., quenched with sat. NH$_4$Cl, warmed to room temperature, and extracted 3× with EtOAc. The combined organic layers were washed with sat NaHCO$_3$ and brine, then purified by column chromatography [OTf R$_f$ (4:1 hexanes:EtOAc)= 0.49], which yielded the triflate intermediate as a yellow oil, which was highly unstable (decomposed overnight in a freezer). The triflate was immediately taken up in THF (15 mL) and to the resulting solution was added LiCl (240 mg, 5.651 mmol), Pd(OAc)$_2$ (42 mg, 0.188 mmol), PPh$_3$ (148 mg, 0.565 mmol), and Bu$_3$SnH (0.40 mL, 1.484 mmol) dropwise; during addition of the stannane the solution turned from a yellow suspension to a clear orange/brown solution. After 10 minutes, the reaction was quenched with aqueous 1M KF and extracted 3× with EtOAc. The combined organic layers were washed with aqueous 1M KF, water, and brine, dried over MgSO$_4$, filtered, concentrated, and purified by column chromatography, yielding the title compound as a yellow solid (366 mg, 54% over two steps). $^1$H NMR (500 MHz, CDCl$_3$) δ 8.20 (dd, J=8.3, 1.0 Hz, 1H), 7.72 (td, J=7.5, 1.2 Hz, 1H), 7.63-7.57 (m, 1H), 7.45 (dd, J=7.6, 1.4 Hz, 1H), 5.87-5.83 (m, 1H), 5.15-5.10 (m, 1H), 4.70 (qd, J=7.1, 3.7 Hz, 1H), 4.09-3.95 (m, 1H), 3.90-3.80 (m, 1H), 2.86 (ddt, J=12.3, 9.9, 2.6 Hz, 1H), 2.73 (ddd, J=17.0, 5.0, 3.3 Hz, 1H), 0.91 (s, J=2.8 Hz, 9H), 0.11 (s, 3H), 0.10 (s, 3H); $^{13}$C NMR (125 MHz, CDCl$_3$) δ 163.35, 145.47, 134.47, 132.51, 130.27, 128.78, 128.71, 124.75, 112.36, 58.64, 32.34, 25.86, 18.23, −5.31, −5.32; [α]$^{25}_D$ −144.6 (c=0.81 in CHCl$_3$); IR (film) 2952, 2929, 2856, 1633 (C=O), 1615, 1571, 1528, 1480, 1471, 1422, 1388, 1345, 1286, 1248, 1205, 1179, 1104, 1077, 1060, 1006, 969, 941, 832, 775, 763, 740, 723, 701, 687, 666, 642, 607; HRMS Accurate mass (ES$^+$): Found 363.1754 (+3.9 ppm), C$_{18}$H$_{27}$N$_2$O$_4$Si (M+H$^+$) requires 363.1740. MP 90.1-94.7° C.

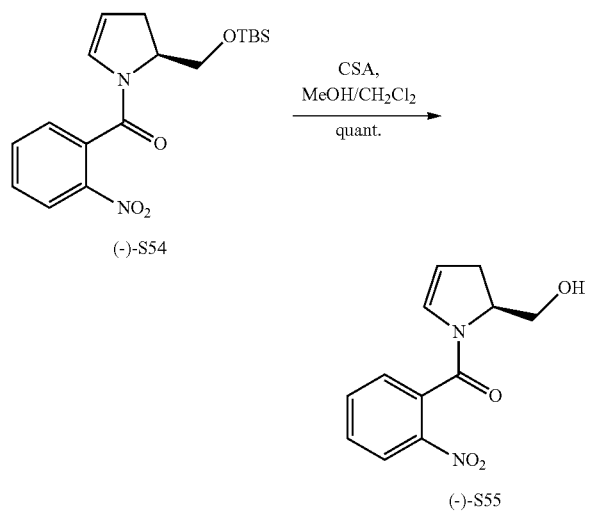

(S)-(2-(hydroxymethyl)-2,3-dihydro-1H-pyrrol-1-yl)(2-nitrophenyl)methanone (−)-S55. To a solution of compound (−)-S54 (285 mg, 0.786 mmol) in 1:1 MeOH:CH$_2$Cl$_2$ (8 mL) was added CSA (183 mg, 0.7862 mmol). The reaction was stirred for 1 hour at rt then quenched with sat. NaHCO$_3$ and extracted 3× with CH$_2$Cl$_2$.

The combined organic layers were washed with water and brine, dried over MgSO$_4$, filtered, concentrated, and purified by column chromatography, yielding the title compound as a yellow oil (209 mg, quant. yield). $^1$H NMR (500 MHz, CDCl$_3$) δ 8.24 (dd, J=8.3, 0.9 Hz, 1H), 7.77 (td, J=7.5, 1.1 Hz, 1H), 7.67-7.62 (m, 1H), 7.52-7.49 (m, 1H), 5.88 (dt, J=4.4, 2.2 Hz, 1H), 5.18 (dt, J=4.4, 2.7 Hz, 1H), 4.78 (td, J=10.0, 4.9 Hz, 1H), 3.92 (d, J=4.5 Hz, 2H), 3.01 (ddt, J=17.1, 10.5, 2.5 Hz, 1H), 2.44 (d, J=16.8 Hz, 1H); $^{13}$C NMR (100 MHz, CDCl$_3$) δ 165.39, 145.33, 134.82, 132.02, 130.72, 128.81, 128.69, 124.98, 113.00, 66.05, 61.30, 33.25; [α]$^{25}_D$ −105.2 (c=1.23 in CHCl$_3$); IR (film) 3392 (br O—H), 2928, 2359, 2341, 1610 (C=O), 1574, 1526, 1482, 1418, 1343, 1240, 1046, 967, 789, 761, 687, 668, 643; HRMS Accurate mass (ES$^+$): Found 271.0715 (+7.4 ppm), C$_{12}$H$_{12}$N$_2$O$_4$Na (M+Na$^+$) requires 271.0695.

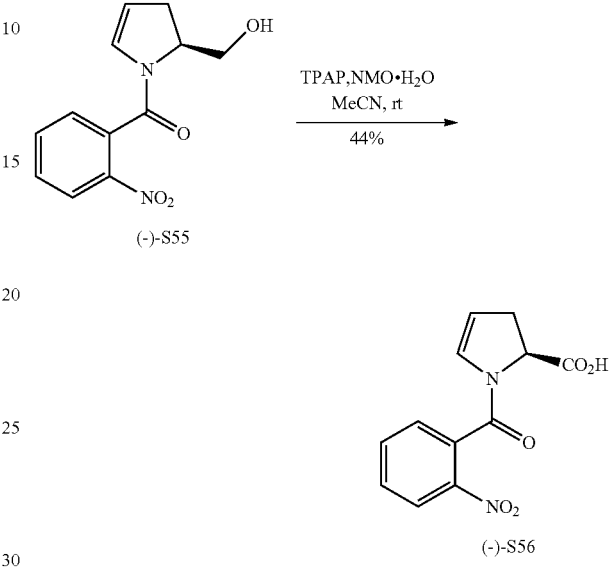

(S)-1-(2-nitrobenzoyl)-2,3-dihydro-1H-pyrrole-2-carboxylic acid (−)-S56. To a solution of compound (−)-S55 (52 mg, 0.210 mmol) in MeCN (2 mL) was added NMO.H2O (294 mg, 2.096 mmol), and the solution was stirred until complete dissolution. Then TPAP (7 mg, 0.021 mmol) was added, and the reaction was stirred for 1 hour, quenched with IPA, concentrated, and filtered over a plug of silica gel, which was washed with 1% AcOH/MeCN. The filtrate was concentrated and purified by column chromatography, eluting with 0→3% MeOH/0.1% AcOH/CH$_2$Cl$_2$, yielding the title compound as a brown residue (24 mg, 44% yield). 1H NMR (400 MHz, CDCl$_3$) δ 8.15 (d, J=8.1 Hz, 1H), 7.73 (t, J=7.0 Hz, 1H), 7.64-7.55 (m, 2H), 5.92 (s, 1H), 5.17 (s, 1H), 5.02 (s, 1H), 3.17-3.01 (m, 1H), 2.97-2.85 (m, 1H); $^{13}$C NMR (100 MHz, CDCl$_3$) δ 174.39, 164.60, 145.33, 134.98, 131.34, 130.80, 129.52, 128.51, 124.76, 112.48, 99.77, 59.21, 53.58, 33.98; [α]$^{25}_D$ −127.8 (c=0.94 in CHCl$_3$); IR (film) 3446, 3098, 2921, 2851, 1733 (C=O), 1615 (C=O), 1526, 1485, 1417, 1344, 1200, 1119, 1080, 1018, 941, 860, 840, 790, 762, 737, 704, 642; HRMS Accurate mass (ES$^+$): Found 263.683 (+5.7 ppm), C$_{12}$H$_{11}$N$_2$O$_5$ (M+H$^+$) requires 263.0668.

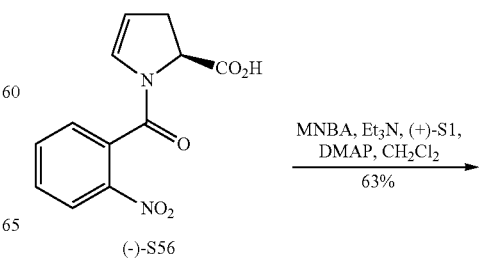

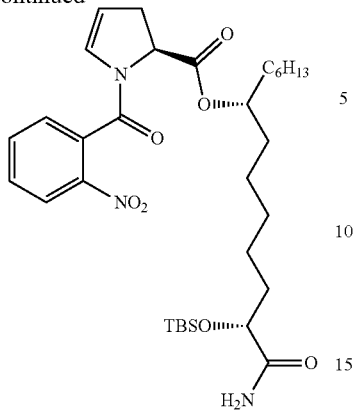

(-)-S57

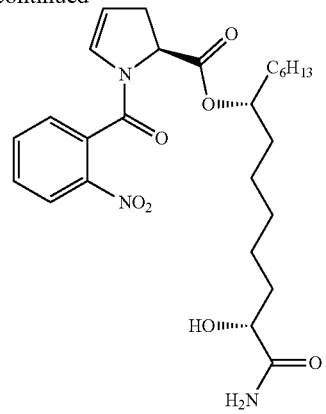

(-)-17

(7R,13R)-14-amino-13-((tert-butyldimethylsilyl)oxy)-14-oxotetradecan-7-yl (S)-1-(2-nitrobenzoyl)-2,3-dihydro-1H-pyrrole-2-carboxylate (xx). Using general procedure H, acid (−)-S56 (19 mg, 0.073 mmol), after purification by preparative TLC (2:1 CH$_2$Cl$_2$: Et$_2$O) yielded the title compound as a clear oil (24 mg, 63% yield). $^1$H NMR (500 MHz, CDCl$_3$) δ 8.20 (d, J=8.2 Hz, 1H), 7.74 (td, J=7.5, 1.0 Hz, 1H), 7.64-7.55 (m, 2H), 6.52 (d, J=3.9 Hz, 1H), 6.01 (dt, J=4.2, 2.1 Hz, 1H), 5.49 (s, 1H), 5.14-5.11 (m, 1H), 5.07 (dd, J=11.7, 5.0 Hz, 1H), 5.02-4.95 (m, 1H), 4.14-4.09 (m, 1H), 3.23-3.15 (m, 1H), 2.72 (ddd, J=19.5, 4.8, 2.4 Hz, 1H), 1.74 (dd, J=14.9, 9.5 Hz, 1H), 1.69-1.51 (m, 6H), 1.37-1.21 (m, 16H), 0.90 (s, J=3.0 Hz, 9H), 0.87 (t, J=6.8 Hz, 3H), 0.12-0.04 (m, 9H); $^{13}$C NMR (125 MHz, CDCl$_3$) δ 177.07, 170.65, 163.28, 145.61, 134.56, 131.99, 130.59, 129.38, 129.26, 124.80, 110.35, 75.99, 73.59, 58.19, 35.15, 34.45, 34.14, 34.09, 31.86, 29.48, 29.29, 25.87, 25.41, 25.08, 24.11, 22.71, 18.14, 14.20, −4.70, −5.14; $[α]^{25}_D$ −71.1 (c=1.21 in CHCl$_3$); IR (film) 3480, 2927, 2856, 1739 (C=O), 1658 (C=O), 1622 (C=O), 1574, 1531, 1463, 1413, 1347, 1252, 1198, 1098, 1005, 940, 836, 779, 739, 705, 669, 642, 582; HRMS Accurate mass (ES$^+$): Found 618.3548 (−4.4 ppm), C$_{32}$H$_{52}$N$_3$O$_7$Si (M+H$^+$) requires 618.3575.

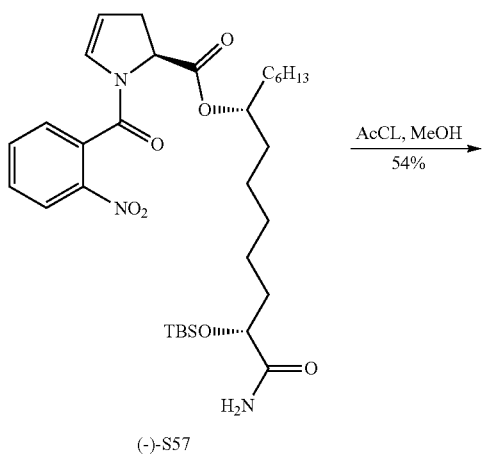

(-)-S57

(7R,13R)-14-amino-13-hydroxy-14-oxotetradecan-7-yl (S)-1-(2-nitrobenzoyl)-2,3-dihydro-1H-pyrrole-2-carboxylate (−)-17. To a solution of silyl ether (−)-S57 (13 mg, 0.021 mmol) dissolved in MeOH (0.5 mL) was added acetyl chloride (ca. 1 μL, 1 drop). After 10 minutes, the reaction was diluted with EtOAc and quenched with sat. NaHCO$_3$, then extracted with EtOAc 3×. The combined organic layers were washed with water and brine, dried over MgSO$_4$, filtered, concentrated, and purified by preparative TLC (10% MeOH/CH$_2$Cl$_2$), yielding the title compound as a yellow oil (7.0 mg, 54% yield). $^1$H NMR (500 MHz, CDCl$_3$) δ 8.21 (dd, J=8.3, 0.9 Hz, 1H), 7.76 (tt, J=4.0, 2.0 Hz, 1H), 7.67-7.60 (m, 2H), 6.64 (s, 1H), 6.03 (dt, J=4.4, 2.2 Hz, 1H), 5.26-5.21 (m, 1H), 5.20-5.17 (m, 1H), 5.11-5.02 (m, 2H), 4.04-3.99 (m, 1H), 3.90 (t, J=7.0 Hz, 1H), 3.21 (ddt, J=16.8, 11.7, 2.4 Hz, 1H), 2.76-2.69 (m, 1H), 1.85-1.76 (m, 1H), 1.68-1.36 (m, 16H), 1.36-1.20 (m, 14H), 0.88 (t, J=7.0 Hz, 3H); $[α]^{25}_D$ −64.6 (c=0.22 in CHCl$_3$); IR (film) 3350 (br, O—H), 2926, 2856, 1733 (C=O), 1652 (C=O), 1621, 1530, 1483, 1417, 1346, 1197, 1079, 840, 791, 763, 740, 705; HRMS Accurate mass (ES$^+$): Found 526.2540 (+2.1 ppm), C$_{26}$H$_{37}$N$_3$O$_7$Na (M+Na$^+$) requires 526.2529.

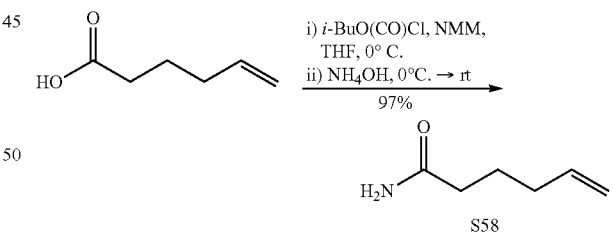

S58

Hex-5-enamide S58. To a solution of 5-hexenoic acid (0.44 mL, 3.701 mmol) dissolved in THF (5 mL) was added N-methylmorpholine (0.45 mL, 4.071 mmol) and the solution was cooled to 0° C. Isobutyl chloroformate (0.53 mL, 4.071 mmol) was added dropwise and the reaction was stirred at 0° C. for 30 minutes, then ammonium hydroxide (28% NH$_3$ in H$_2$O, 0.64 mL) was added and the reaction was allowed to warm to room temperature and stir overnight. The reaction was quenched with sat. NH$_4$Cl and extracted with EtOAc 3×. The combined organic layers were washed with 1M HCl and brine, dried over MgSO$_4$, filtered and concentrated, yielding the title compound as a white solid (407 mg, 97% yield). $^1$H NMR (400 MHz, CDCl$_3$) δ 5.79

(ddt, J=17.0, 10.2, 6.7 Hz, 1H), 5.34 (br s, 2H), 5.10-4.95 (m, 2H), 2.28-2.21 (m, 1H), 2.12 (dd, J=14.2, 7.1 Hz, 2H), 1.82-1.70 (m, 1H); $^{13}$C NMR (101 MHz, CDCl$_3$) δ 175.73, 137.90, 115.51, 35.16, 33.16, 24.57; IR (film) 3361 (br N–H), 3184 (br N—H), 2944, 2359, 2342, 1633 (C=O), 1415, 1229, 1135, 1077, 991, 908, 775, 667; HRMS Accurate mass (ES$^+$): Found 114.0917 (−1.8 ppm), C$_6$H$_{12}$NO (M+H$^+$) requires 114.0919; MP 70.0-75.1° C.

2.27-2.16 (m, 2H), 1.69-1.60 (m, 2H), 1.48-1.21 (m, 18H), 0.90-0.85 (m, 3H); $^{13}$C NMR (100 MHz, CDCl$_3$) δ 175.89, 72.02, 37.65, 37.46, 35.99, 35.87, 31.96, 29.49, 29.45, 29.27, 25.75, 25.56, 22.74, 14.22; [α]$^{25}_D$ +7.0 (c=1.34 in CHCl$_3$); IR (film) 3207 (br O—H), 2922, 2849, 1651 (C=O), 1614, 1467, 1413, 1129, 1066, 1012, 913, 850, 793, 720, 655; HRMS Accurate mass (ES$^+$): Found 266.2102 (+2.3 ppm), C$_{14}$H$_{29}$NO$_2$Na (M+Na$^+$) requires 266.2096.

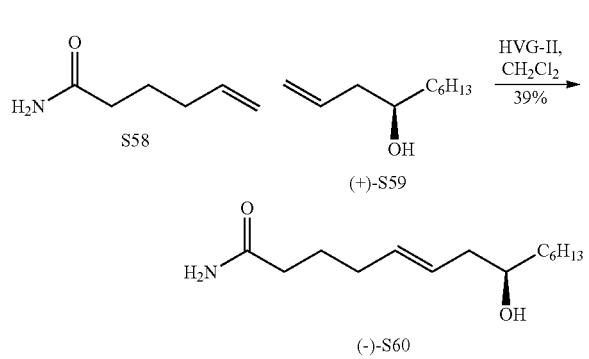

(R,E)-8-hydroxytetradec-5-enamide (−)-S60. To a solution of S58 (173 mg, 0.429 mmol) and alcohol (+)-S59$^5$ (335 mg, 2.143 mmol) in CH$_2$Cl$_2$ (1 mL) was added Hoveyda-Grubbs II (13 mg, 0.021 mmol). The reaction was stirred for 3 hours at room temperature, concentrated and purified by column chromatography (0→5% MeOH/CH$_2$Cl$_2$) yielding the title compound as a yellow oil (89 mg, 39% yield). $^1$H NMR (400 MHz, CDCl$_3$) δ 5.52-5.44 (m, 2H), 5.30 (br s, 1H), 3.59 (br s, 1H), 2.23 (dd, J=13.6, 6.1 Hz, 2H), 2.08 (dt, J=14.3, 6.8 Hz, 2H), 1.74 (dt, J=14.3, 7.2 Hz, 2H), 1.66-1.54 (m, 3H), 1.50-1.38 (m, 3H), 1.29 (t, J=15.3 Hz, 7H), 0.93-0.84 (m, 10H); $^{13}$C NMR (100 MHz, CDCl$_3$) δ 176.13, 132.67, 127.69, 71.13, 40.68, 37.00, 35.02, 31.95, 31.90, 29.41, 25.83, 25.76, 24.93, 22.67, 14.15; [α]$^{25}_D$ −1.8 (c=1.69 in CHCl$_3$); IR (film) 3361, 3183, 2954, 2921, 2850, 2359, 1650 (C=O), 1416, 1349, 1268, 1202, 1126, 1068, 1040, 1008, 966, 940, 863, 647, 598, 559; HRMS Accurate mass (ES$^+$): Found 264.1950 (+3.8 ppm), C$_{14}$H$_{27}$NO$_2$Na (M+Na$^+$) requires 264.1940.

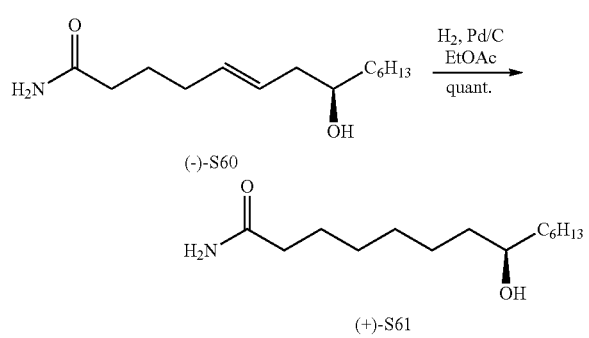

(R)-8-hydroxytetradecanamide (+)-S61. To a solution of alkene (−)-S60 (89 mg, 0.168 mmol) dissolved in EtOAc (5 mL) was added 10% Pd/C (50 mg), then the reaction flask was vacuum and backfilled with H$_2$ 5× and stirred under a H$_2$ balloon overnight. The reaction was filtered over Celite and concentrated, yielding the title compound as a clear oil (91 mg, quant. yield). $^1$H NMR (400 MHz, CDCl$_3$) δ 5.24 (br d, 2H), 3.58 (br s, 1H), 2.38 (td, J=7.4, 4.2 Hz, 1H),

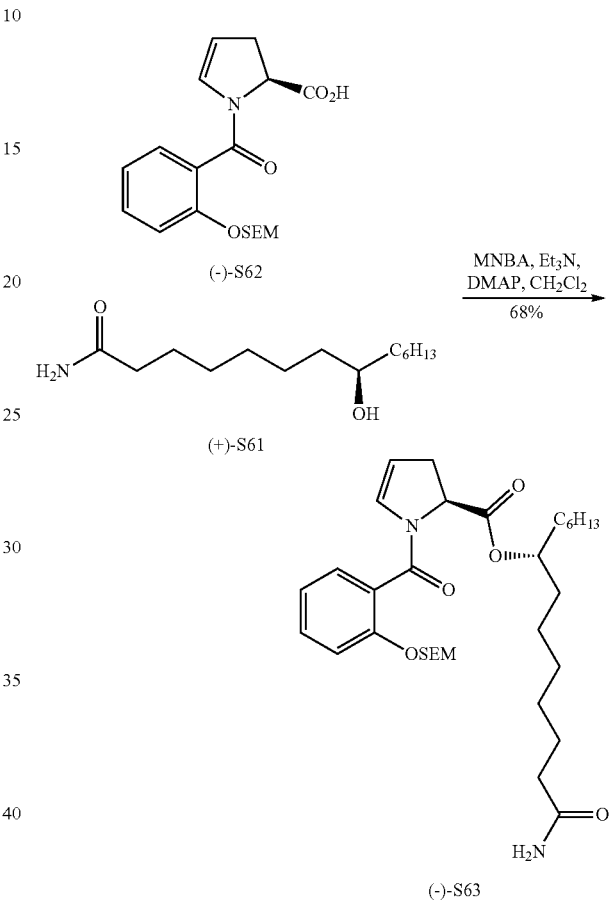

(R)-14-amino-14-oxotetradecan-7-yl (S)-1-(2-((2-(trimethylsilyl)ethoxy)methoxy)benzoyl)-2,3-dihydro-1H-pyrrole-2-carboxylate (−)-S63. Using modified general procedure H (1.2 eq acid, 1.2 eq MNBA), acid (−)-S62 (Steele et al., J. Am. Chem. Soc. 2015, 137, 7314) (18 mg, 0.050 mmol) and alcohol (+)-S61 (9.7 mg, 0.040 mmol) yielded the title compound as a yellow oil (16 mg, 68% yield). $^1$H NMR (500 MHz, CDCl$_3$) δ 7.40-7.28 (m, 2H), 7.19 (t, J=8.0 Hz, 1H), 7.04 (td, J=7.5, 0.8 Hz, 1H), 6.31 (s, 1H), 6.19-6.12 (m, 1H), 5.22 (ddd, J=16.3, 7.1, 2.9 Hz, 2H), 5.11 (s, 1H), 5.04 (td, J=5.4, 2.9 Hz, 1H), 5.03-4.93 (m, 2H), 3.79-3.69 (m, 2H), 3.19-3.10 (m, 1H), 2.72-2.64 (m, 1H), 2.23-2.11 (m, 1H), 1.66-1.52 (m, 6H), 1.45-1.16 (m, 16H), 0.97-0.90 (m, 2H), 0.90-0.83 (m, 3H), 0.03-0.05 (m, 9H); $^{13}$C NMR (125 MHz, CDCl$_3$) δ 170.73, 165.29, 153.74, 131.43, 130.96, 128.89, 125.67, 122.05, 115.33, 108.77, 93.34, 75.35, 66.70, 58.08, 35.99, 34.60, 34.37, 31.85, 29.27, 28.83, 28.55, 25.48, 25.09, 24.70, 22.70, 18.15, 14.19, −1.28; [α]$^{25}_D$ −27.2 (c=0.79 in CHCl$_3$); IR (film) 2925, 2856, 1738 (C=O), 1645 (C=O), 1618 (C=O), 1600, 1487, 1455, 1406, 1355, 1277, 1229, 1193, 1150, 1085, 1043, 987, 938, 917, 857, 834, 754, 696, 655; HRMS Accurate mass (ES+): Found 611.3533 (+6.7 ppm), $C_{32}H_{52}N_2O_6SiNa$ (M+Na+) requires 611.3492.

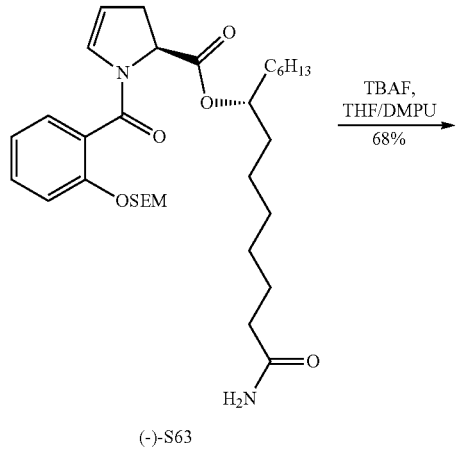

(-)-S63

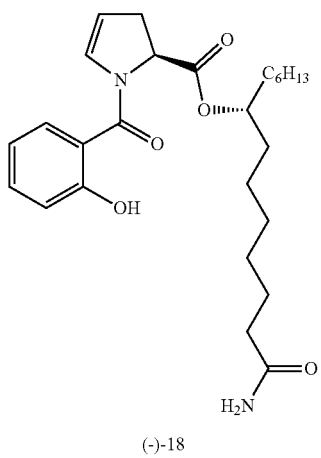

(-)-18

(R)-14-amino-14-oxotetradecan-7-yl (S)-1-(2-hydroxybenzoyl)-2,3-dihydro-1H-pyrrole-2-carboxylate (−)-18. Using modified general procedure I (10 eq TBAF, 0.1M DMPU), SEM ether (−)-S63 (7.5 mg, 0.013 mmol) yielded the title compound as a clear oil (4.1 mg, 68% yield) $^1$H NMR (500 MHz, CDCl$_3$) δ 9.83 (d, J=46.9 Hz, 1H), 7.44-7.34 (m, 2H), 6.99 (dd, J=7.4, 3.5 Hz, 1H), 6.89 (t, J=7.8 Hz, 1H), 6.79 (s, 1H), 5.60 (br d, 1H), 5.29 (d, J=10.2 Hz, 2H), 5.05-4.90 (m, 2H), 3.17-3.08 (m, 1H), 2.70 (d, J=18.0 Hz, 1H), 2.23-2.16 (m, 2H), 1.66-1.48 (m, 8H), 1.39-1.16 (m, 15H), 0.86 (t, J=7.0 Hz, 3H); $^{13}$C NMR (125 MHz, CDCl$_3$) δ 175.77, 171.03, 167.50, 159.30, 158.93, 133.56, 131.00, 128.41, 119.11, 118.06, 110.79, 75.99, 74.40, 59.54, 36.00, 35.90, 34.33, 34.19, 31.82, 29.25, 29.08, 29.02, 28.91, 25.41, 25.24, 24.90, 22.69, 14.20; $[\alpha]^{25}_D$ −20.8 (c=0.24 in CHCl$_3$); IR (film) 3190 (br O—H), 2926, 2856, 1733 (C=O), 1660 (C=O), 1593, 1456, 1414, 1294, 1252, 1194, 1152, 1098, 1016, 945, 912, 859, 816, 755, 723, 654, 617, 567; HRMS Accurate mass (ES+): Found 481.2700 (+4.6 ppm), $C_{26}H_{38}N_2O_5Na$ (M+Na+) requires 481.2678.

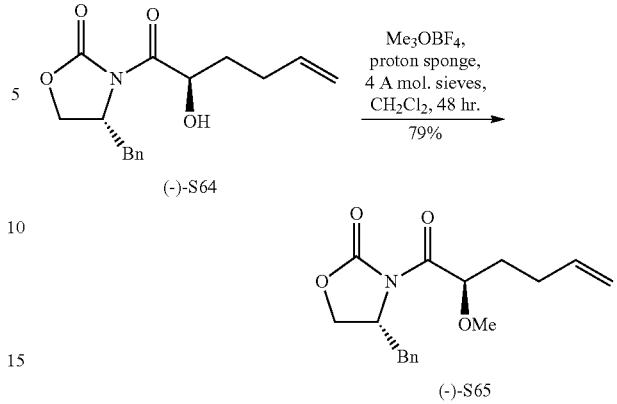

(R)-4-benzyl-3-((R)-2-methoxyhex-5-enoyl)oxazolidin-2-one (−)-S65. 4 Å molecular sieves were flame-dried in a round-bottom flask, and alcohol (−)-S64 (Steele et al., *J. Am. Chem. Soc.* 2015, 137, 7314) (121 mg, 0.418 mmol) was added to the flask as a solution in CH$_2$Cl$_2$ (2 mL) followed by trimethyloxonium tetrafluoroborate (493 mg, 3.333 mmol) and 1,8-Bis(dimethylamino)naphthalene (714 mg, 3.333 mmol). The reaction was stirred at room temperature for 48 hours, then quenched with isopropanol and filtered. The solution was diluted with Et$_2$O and washed with 1M HCl, sat. NaHCO$_3$, and brine, dried over Na$_2$SO$_4$, filtered, concentrated, and purified by column chromatography (4:1 hexanes:EtOAc) yielding the title compound as a yellow oil. $^1$H NMR (400 MHz, CDCl$_3$) δ 7.38-7.27 (m, 3H), 7.25-7.20 (m, 2H), 5.82 (ddt, J=16.9, 10.1, 6.7 Hz, 1H), 5.09-4.97 (m, 2H), 4.91 (dd, J=8.3, 3.5 Hz, 1H), 4.68 (ddt, J=10.1, 6.7, 3.3 Hz, 1H), 4.28-4.21 (m, 2H), 3.42 (s, 3H), 3.36 (dd, J=13.3, 3.1 Hz, 1H), 2.87-2.80 (m, 1H), 2.26 (dt, J=14.0, 6.9 Hz, 2H), 1.88-1.68 (m, 2H); $^{13}$C NMR (100 MHz, CDCl$_3$) δ 173.15, 153.22, 137.59, 135.13, 129.54, 129.11, 127.57, 115.42, 79.27, 66.87, 58.17, 55.61, 37.93, 32.13, 29.67; $[\alpha]^{25}_D$ −6.0 (c=0.63 in CHCl$_3$); IR (film) 2923, 2854, 1723 (C=O), 1583, 1452, 1376, 1313, 1271, 1109, 1070, 1028, 967, 817, 743, 710; HRMS Accurate mass (ES+): Found 326.1381 (+4.0 ppm), $C_{17}H_{21}NO_4Na$ (M+Na+) requires 326.1368.

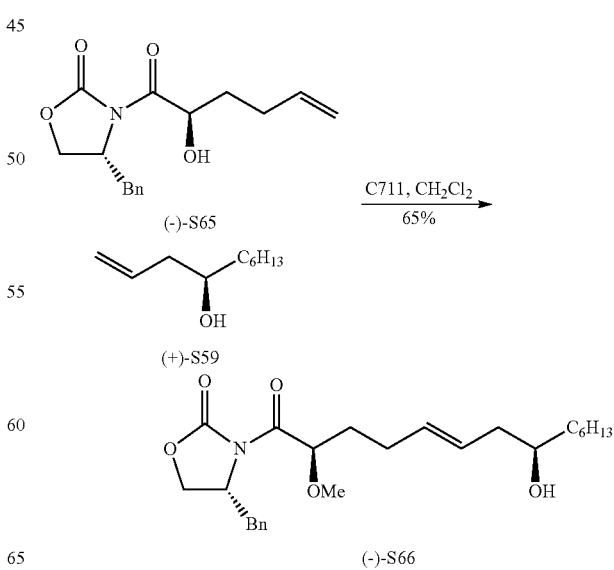

(R)-4-benzyl-3-((2R,8R,E)-8-hydroxy-2-methoxytetradec-5-enoyl)oxazolidin-2-one (−)-S66. Catalyst C711 (13 mg, 0.017 mmol-CAS #635679-24-2) was added to a solution of alcohol (+)-S59 (258 mg, 1.651 mmol) and methyl ether (−)-S65 (100 mg, 0.330 mmol) dissolved in CH$_2$Cl$_2$ (2 mL) and stirred at room temperature overnight. The reaction was concentrated and purified by column chromatography (4:1 hexanes:EtOAc), yielding the title compound as a yellow oil (95 mg, 65% yield). $^1$H NMR (400 MHz, CDCl$_3$) δ 7.37-7.27 (m, 3H), 7.23 (d, J=6.9 Hz, 2H), 5.52 (dt, J=13.2, 8.3 Hz, 3H), 4.91 (dd, J=8.1, 3.6 Hz, 1H), 4.73-4.65 (m, 1H), 4.27-4.20 (m, 2H), 3.60 (br s, 2H), 3.41 (s, J=3.4 Hz, 3H), 3.39-3.33 (m, 1H), 2.87-2.78 (m, 1H), 2.32-2.20 (m, 3H), 2.14-2.07 (m, 1H), 1.85-1.70 (m, 2H), 1.64-1.56 (m, 2H), 1.51-1.39 (m, 6H), 1.34-1.24 (m, 14H), 0.88 (t, J=6.4 Hz, 3H); $^{13}$C NMR (100 MHz, CDCl$_3$) δ 173.25, 153.23, 135.11, 132.69, 130.09, 129.53, 129.11, 127.56, 79.13, 70.95, 70.84, 66.91, 58.18, 55.61, 40.85, 40.72, 37.94, 37.03, 36.86, 32.68, 31.93, 29.44, 28.51, 25.80, 25.76, 22.72, 14.19; $[\alpha]^{25}_D$ −17.5 (c=0.83 in CHCl$_3$); IR (film) 3500 (br, O—H), 2925, 2854, 1778 (C=O), 1705 (C=O), 1455, 1387, 1349, 1290, 1252, 1211, 1113, 1073, 1049, 971, 814, 761, 732, 700; HRMS Accurate mass (ES$^+$): Found 454.2585 (+3.5 ppm), C$_{25}$H$_{37}$NO$_5$Na (M+Na$^+$) requires 454.2569.

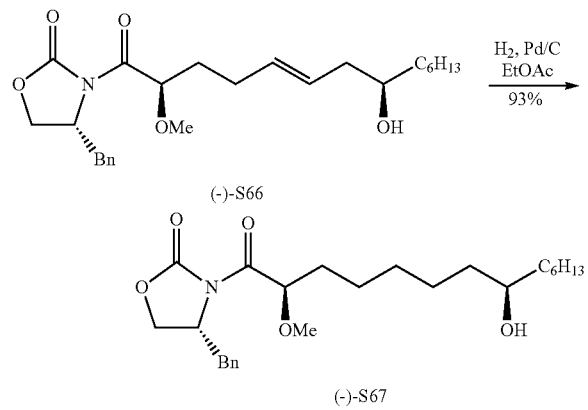

(R)-4-benzyl-3-((2R,8R)-8-hydroxy-2-methoxytetradecanoyl)oxazolidin-2-one (−)-S67. To a solution of alkene (−)-S66 (95 mg, 0.220 mmol) dissolved in EtOAc (10 mL) in a round-bottom flask was added 10% Pd/C (50 mg), and the flask was vacuum and backfilled with H$_2$ 5× then stirred under a balloon of H$_2$ overnight. The reaction was filtered over Celite and concentrated, yielding the title compound as a clear oil (89 mg, 93% yield). $^1$H NMR (400 MHz, CDCl$_3$) δ 7.36-7.27 (m, 3H), 7.24-7.20 (m, 2H), 4.90 (dd, J=7.9, 3.5 Hz, 1H), 4.72-4.66 (m, 1H), 4.28-4.22 (m, 2H), 3.59 (br s, 2H), 3.41 (s, 3H), 3.34 (dd, J=7.3, 4.2 Hz, 1H), 2.83 (dd, J=13.4, 9.5 Hz, 1H), 2.39 (dt, J=10.8, 7.4 Hz, 1H), 1.70-1.59 (m, 2H), 1.50-1.37 (m, 10H), 1.32-1.23 (m, 12H), 0.88-0.85 (m, 3H); $^{13}$C NMR (100 MHz, CDCl$_3$) δ 173.14, 153.17, 135.05, 129.43, 128.97, 127.42, 79.81, 71.80, 71.69, 66.76, 58.04, 55.46, 37.80, 37.52, 37.47, 37.35, 37.31, 32.79, 31.85, 29.39, 29.24, 25.62, 25.39, 22.62, 14.10; $[\alpha]^{25}_D$ −12.0 (c=0.93 in CHCl$_3$); IR (film) 2924, 2855, 1781 (C=O), 1705, 1456, 1387, 1349, 1211, 1107, 1019, 814, 754, 700, 667; HRMS Accurate mass (ES$^+$): Found 434.2911 (+1.2 ppm), C$_{25}$H$_{40}$NO$_5$ (M+H$^+$) requires 434.2906.

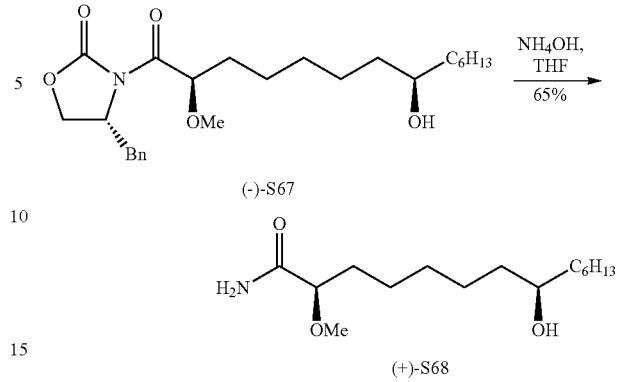

(2R,8R)-8-hydroxy-2-methoxytetradecanamide (+)-S68. To a solution of oxazolidinone (−)-S67 (88 mg, 0.203 mmol) in THF (3 mL) was added ammonium hydroxide (28% NH$_3$ in H$_2$O, 2 mL), and the reaction was tightly sealed and stirred for 48 hours. The reaction was diluted with MeOH and concentrated, and this process was repeated 2×. Purification by column chromatography (0→8% MeOH/CH$_2$Cl$_2$) yielded the title compound as a white solid (36 mg, 65% yield). $^1$H NMR (500 MHz, CDCl$_3$) δ 6.46 (br s, 1H), 5.57 (br s, 1H), 3.62 (dd, J=6.9, 4.4 Hz, 1H), 3.57 (br s, 1H), 3.41 (s, 3H), 1.82-1.74 (m, 1H), 1.73-1.63 (m, 2H), 1.47-1.35 (m, 9H), 1.35-1.22 (m, 10H), 0.88 (t, J=6.9 Hz, 3H); $^{13}$C NMR (100 MHz, CDCl$_3$) δ 175.75, 99.78, 82.49, 72.06, 58.47, 37.62, 37.47, 32.44, 31.99, 29.58, 29.51, 25.76, 25.59, 24.85, 22.76, 14.24; $[\alpha]^{25}_D$ +21.0 (c=0.67 in CHCl$_3$); IR (film) 3366 (br, N–H), 3189 (br, N–H), 2916, 2852, 1636 (C=O), 1532, 1462, 1431, 1340, 1221, 1207, 1133, 1112, 1067, 1050, 1001, 926, 859, 806, 726, 682, 617; HRMS Accurate mass (ES$^+$): Found 274.2385 (+1.1 ppm), C$_{15}$H$_{32}$NO$_3$ (M+H$^+$) requires 274.2382; MP 106-110° C., R$_f$ (8% MeOH/CH$_2$Cl$_2$)=0.36.

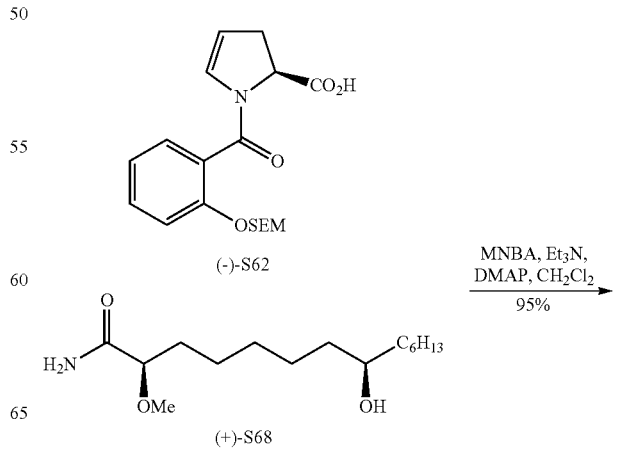

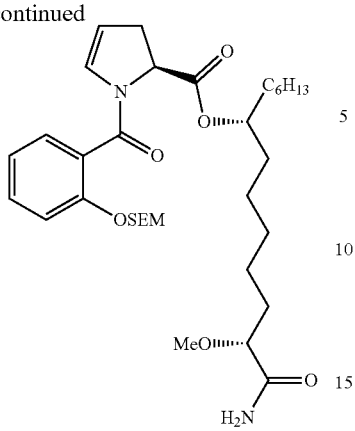

(−)-S69

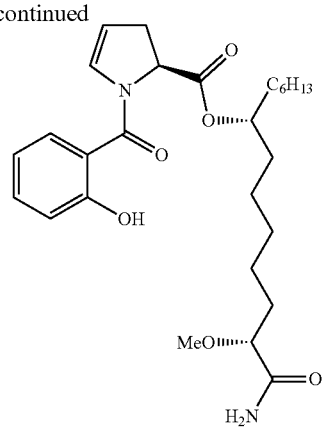

(−)-19

(7R,13R)-14-amino-13-methoxy-14-oxotetradecan-7-yl (S)-1-(2-((2-(trimethylsilyl)ethoxy)methoxy)benzoyl)-2,3-dihydro-1H-pyrrole-2-carboxylate (−)-S69. Using general procedure H, alcohol (+)-S68 (9 mg, 0.033 mmol) and acid (−)-S62 (Steele et al., *J. Am. Chem. Soc.* 2015, 137, 7314) (17 mg, 0.047 mmol) yielded the title compound as a yellow oil (19 mg, 95% yield). $^1$H NMR (400 MHz, CDCl$_3$) δ 7.40-7.28 (m, 2H), 7.21-7.16 (m, 1H), 7.03 (td, J=7.5, 0.8 Hz, 1H), 6.52 (br s, 1H), 6.20-6.11 (m, 1H), 5.60 (br s, 1H), 5.25-5.18 (m, 1H), 5.04-5.00 (m, 1H), 5.01-4.93 (m, 2H), 3.74 (dd, J=16.0, 7.6 Hz, 2H), 3.60 (dd, J=6.8, 4.5 Hz, 1H), 3.37 (s, 3H), 3.12 (ddd, J=14.2, 10.4, 5.8 Hz, 1H), 2.70-2.62 (m, 1H), 1.77-1.64 (m, 2H), 1.62-1.48 (m, 4H), 1.41-1.17 (m, 17H), 0.93 (dd, J=10.6, 6.2 Hz, 2H), 0.85 (t, J=5.8 Hz, 3H), −0.02 (s, 9H); $^{13}$C NMR (100 MHz, CDCl$_3$) δ 175.79, 170.79, 165.03, 153.82, 131.26, 131.02, 129.01, 125.91, 121.98, 115.24, 108.45, 99.74, 93.34, 82.37, 75.46, 66.63, 58.33, 58.16, 34.40, 34.18, 34.09, 32.33, 31.85, 29.30, 25.35, 25.01, 24.68, 22.71, 18.15, 14.20, −1.28; $[α]^{25}_D$ −10.0 (c=0.24 in CHCl$_3$); IR (film) 2927, 2858, 1733 (C=O), 1652 (C=O), 1619, 1601, 1488, 1456, 1278, 1407, 1248, 1230, 1194, 1153, 1087, 988, 836, 754, 697, 656, 609; HRMS Accurate mass (ES$^+$): Found 641.3621 (+3.6 ppm), C$_{33}$H$_{54}$N$_2$O$_7$SiNa (M+Na$^+$) requires 641.3598.

(7R,13R)-14-amino-13-methoxy-14-oxotetradecan-7-yl (S)-1-(2-hydroxybenzoyl)-2,3-dihydro-1H-pyrrole-2-carboxylate (−)-19. Using modified general procedure I (10 eq TBAF, 0.1M DMPU), SEM-ether (−)-S69 (13.7 mg, 0.022 mmol) yielded the title compound as a clear oil (8.1 mg, 75% yield). $^1$H NMR (400 MHz, CDCl$_3$) δ 9.87 (s, 1H), 7.42 (dd, J=7.8, 1.4 Hz, 1H), 7.39-7.34 (m, 1H), 6.99 (dd, J=8.3, 0.9 Hz, 1H), 6.93-6.86 (m, 1H), 6.81 (br s, 1H), 6.47 (br s, 1H), 5.40 (br s, 1H), 5.27 (d, J=4.2 Hz, 1H), 5.06-4.91 (m, 2H), 3.61 (dd, J=6.7, 4.5 Hz, 1H), 3.38 (s, 3H), 3.18-3.07 (m, 1H), 2.70 (d, J=17.0 Hz, 1H), 1.79-1.62 (m, 2H), 1.61-1.46 (m, 5H), 1.43-1.17 (m, 15H), 0.85 (t, J=6.9 Hz, 3H); $^{13}$C NMR (100 MHz, CDCl$_3$) δ 175.68, 170.88, 167.53, 159.28, 133.54, 131.05, 128.48, 118.96, 118.09, 117.03, 110.68, 82.44, 75.98, 59.61, 58.39, 34.16, 34.09, 33.66, 32.34, 31.82, 29.27, 25.35, 25.05, 24.71, 22.69, 14.21; $[α]^{25}_D$ −21.3 (c=0.39 in CHCl$_3$); IR (film) 3386 (N–H), 3348 (N–H), 3144 (br, O—H), 2927, 2858, 1719 (C=O), 1688 (C=O), 1672, 1619, 1567, 1487, 1445, 1431, 1355, 1303, 1281, 1252, 1230, 1191, 1147, 1120, 1095, 1070, 1039, 1020, 1003, 992, 954, 943, 905, 857, 822, 796, 759, 730, 699, 667, 643; HRMS Accurate mass (ES$^+$): Found 489.2979 (+2.9 ppm), C$_{27}$H$_{41}$N$_2$O$_6$ (M+H$^+$) requires 308.1498.

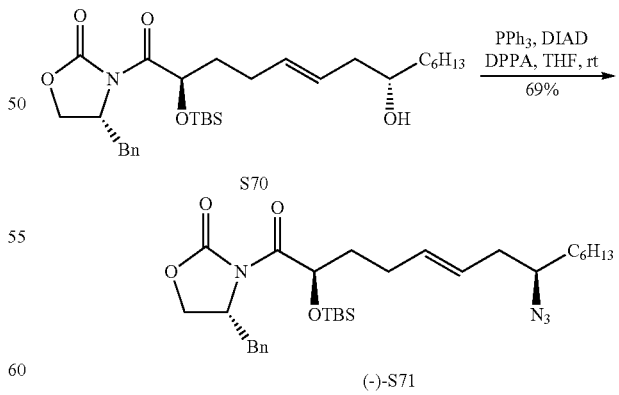

S70

(−)-S71

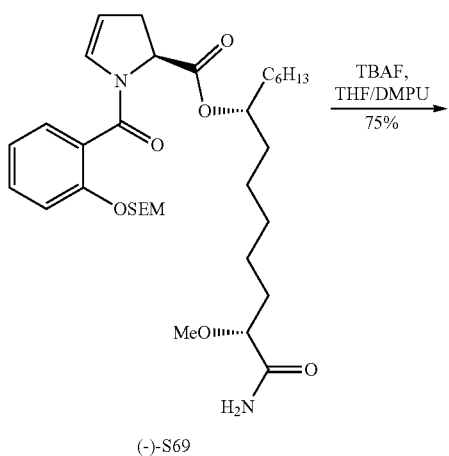

(−)-S69

(R)-3-((2R,8R,E)-8-azido-2-((tert-butyldimethylsilyl)oxy)tetradec-5-enoyl)-4-benzyloxazolidin-2-one (−)-S71. To a solution of compound S70 (Steele et al., *J. Am. Chem. Soc.* 2015, 137, 7314) (153 mg, 0.288 mmol) in THF (2 mL) was added PPh$_3$ (302 mg, 1.153 mmol), DIAD (0.23 mL, 1.153 mmol), and DPPA (0.25 mL, 1.153 mmol). After 30 minutes, the reaction was concentrated and purified by prep TLC (neat $CH_2Cl_2$), yielding the title compound as a yellow oil (111 mg, 69% yield). $^1$H NMR (400 MHz, CDCl$_3$) δ 7.26-7.16 (m, 3H), 7.15-7.11 (m, 2H), 5.48-5.29 (m, 2H), 5.27 (dd, J=8.2, 3.4 Hz, 1H), 4.55-4.47 (m, 1H), 4.12-4.04 (m, 2H), 3.30 (dd, J=13.3, 3.0 Hz, 1H), 2.58 (dd, J=13.2, 10.2 Hz, 1H), 2.19-2.01 (m, 2H), 1.72-1.52 (m, 2H), 1.42-1.26 (m, 3H), 1.26-1.10 (m, 8H), 0.86-0.82 (m, 9H), 0.77 (t, J=6.7 Hz, 3H), 0.02--0.03 (m, 6H); $^{13}$C NMR (125 MHz, CDCl$_3$) δ 174.33, 153.18, 135.34, 132.97, 129.56, 129.11, 127.51, 126.26, 71.01, 66.62, 62.84, 55.71, 37.79, 35.00, 33.98, 31.82, 29.17, 28.68, 26.15, 25.93, 22.69, 18.44, 14.18, 1.13, −4.49, −4.95; $[α]^{25}_D$ −5.0 (c=0.42 in CHCl$_3$); IR (film) 2927, 2856, 2097, 1780 (C=O), 1712 (C=O), 1455, 1386, 1347, 1249, 1209, 1194, 1106, 1012, 969, 835, 777, 749, 700, 663, 593; HRMS Accurate mass (ES$^+$): Found 579.3367 (+4.1 ppm), $C_{30}H_{48}N_4O_4SiNa$ (M+Na$^+$) requires 579.3343.

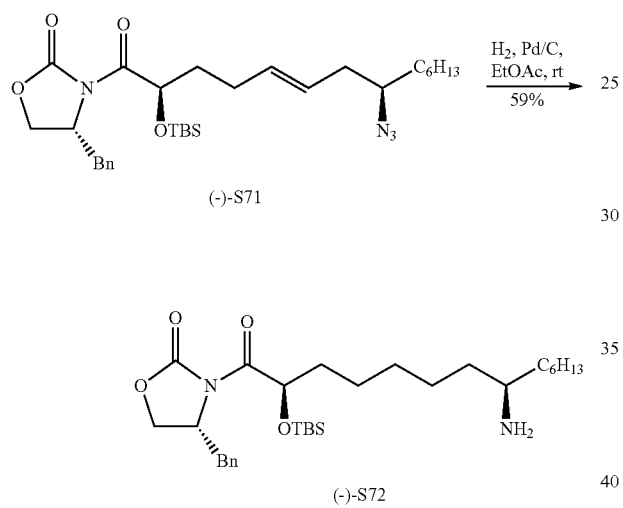

(-)-S71

(-)-S72

(R)-3-((2R,8R)-8-amino-2-((tert-butyldimethylsilyl)oxy)tetradecanoyl)-4-benzyloxazolidin-2-one (−)-S72. To a solution of compound (−)-S71 (111 mg, 0.199 mmol) in EtOAc (10 mL) was added Pd/C (10% by wt., 100 mg), and stirred for 16 hours under a balloon of H$_2$. The reaction was filtered through Celite and purified by column chromatography, eluting in 50%→0% hexanes/CH$_2$Cl$_2$ then 0→20% MeOH/CH$_2$Cl$_2$, yielding the title compound as a clear oil (63 mg, 59% yield). $^1$H NMR (400 MHz, CDCl$_3$) δ 7.36-7.29 (m, 3H), 7.25-7.22 (m, 2H), 5.40-5.34 (m, 1H), 4.70-4.59 (m, 1H), 4.32-4.24 (m, 1H), 4.15 (dd, J=9.0, 2.2 Hz, 1H), 3.42-3.35 (m, 1H), 3.15-3.07 (m, 1H), 2.70 (dd, J=13.3, 10.1 Hz, 1H), 1.74-1.57 (m, 10H), 1.52-1.19 (m, 20H), 0.93 (s, 9H), 0.86 (t, J=6.1 Hz, 3H), 0.10 (s, 3H), 0.08 (s, 3H); $^{13}$C NMR (125 MHz, CDCl$_3$) δ 174.56, 153.26, 135.40, 129.58, 129.12, 127.51, 71.45, 66.64, 55.72, 37.83, 35.33, 31.98, 29.58, 29.48, 26.15, 26.04, 25.95, 25.63, 22.77, 18.48, 14.22, −4.50, −4.95; $[α]^{25}_D$ −9.3 (c=0.45 in CHCl$_3$); IR (film) 2927, 2856, 1779 (C=O), 1711 (C=O), 1605, 1519, 1455, 1387, 1348, 1248, 1210, 1145, 1109, 1051, 1007, 977, 939, 835, 776, 762, 700, 663, 593; HRMS Accurate mass (ES$^+$): Found 533.3745 (−5.6 ppm), $C_{30}H_{53}N_2O_4Si$ (M+H$^+$) requires 533.3775; R$_f$ (9:1 CH$_2$Cl$_2$:MeOH)=0.18, stains brown in ninhydrin).

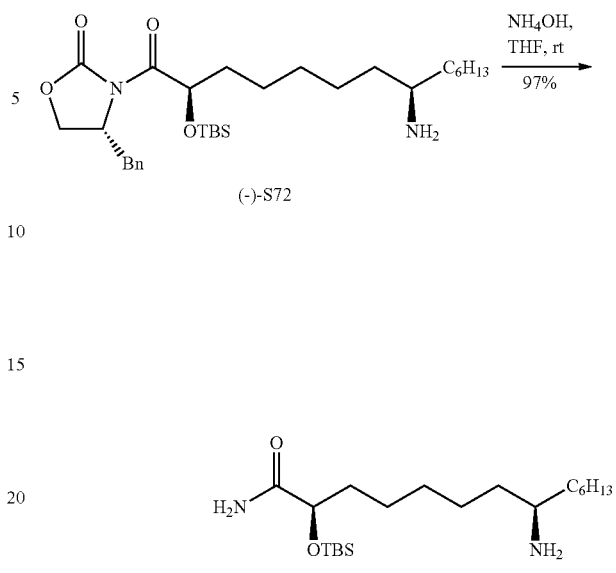

(-)-S72

(+)-S73

(2R,8R)-8-amino-2-((tert-butyldimethylsilyl)oxy)tetradecanamide (+)-S73. Compound (−)-S72 (44 mg, 0.083 mmol) was dissolved in THF (3 mL) and 28% ammonium hydroxide (2 mL), sealed tightly and stirred at rt for 48 hours. MeOH was added and the reaction was concentrated, and this process was repeated two more times. The resulting mixture was purified by column chromatography, eluting in 0→15% MeOH/0.1% NH$_4$OH/CH$_2$Cl$_2$, yielding the title compound as a clear oil (29 mg, 97% yield). $^1$H NMR (500 MHz, CDCl$_3$) δ 6.64-6.50 (m, 2H), 4.15-4.09 (m, 1H), 3.12 (dt, J=14.7, 7.4 Hz, 2H), 1.79 (ddd, J=15.1, 10.2, 4.9 Hz, 1H), 1.75-1.57 (m, 6H), 1.45-1.23 (m, 22H), 0.91 (s, 9H), 0.86 (t, J=6.6 Hz, 3H), 0.09 (s, 3H), 0.08 (s, 3H); $^{13}$C NMR (125 MHz, CDCl$_3$) δ 177.56, 73.20, 52.12, 34.60, 33.25, 32.94, 31.71, 29.78, 29.20, 29.04, 25.84, 25.40, 24.94, 23.51, 22.68, 18.11, 14.16, −4.73, −5.16; $[α]^{25}_D$ +5.8 (c=1.47 in CHCl$_3$); IR (film) 3477, 2925, 2854, 1672 (C=O), 1557, 1462, 1388, 1361, 1337, 1252, 1101, 1005, 938, 836, 778, 721, 668, 588; HRMS Accurate mass (ES$^+$): Found 373.3264 (+3.8 ppm), $C_{20}H_{45}N_2O_2Si$ (M+H$^+$) requires 373.3250; R$_f$ (0.1% NH$_4$OH/10% MeOH/90% CH$_2$Cl$_2$)=0.18.

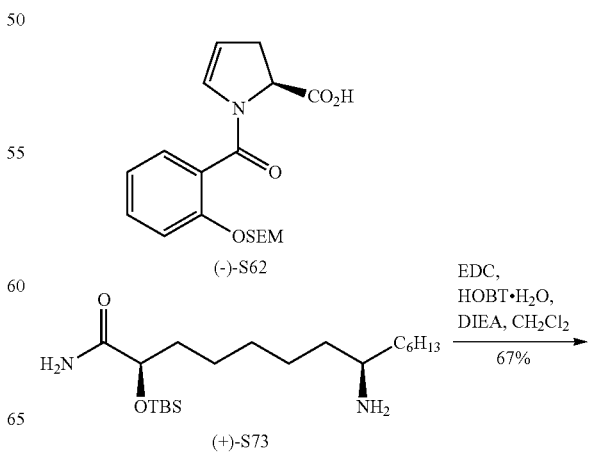

(-)-S62

(+)-S73

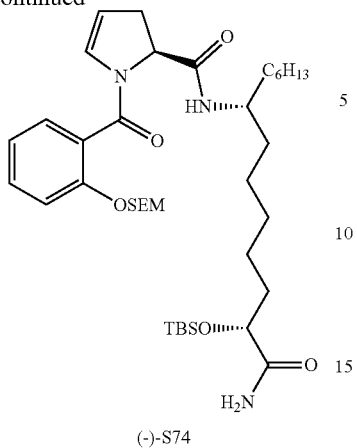

(-)-S74

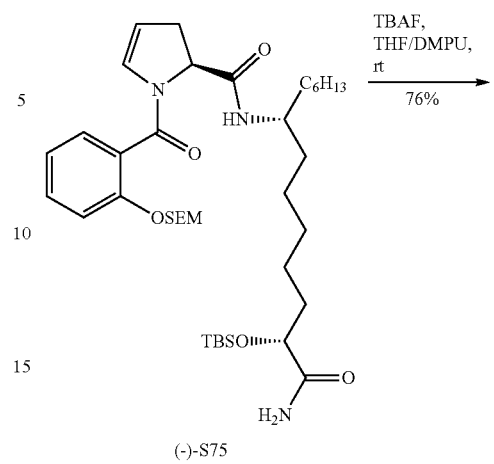

(-)-S75

(S)—N-((7R,13R)-14-amino-13-((tert-butyldimethylsilyl)oxy)-14-oxotetradecan-7-yl)-1-(2-((2-(trimethylsilyl)ethoxy)methoxy)benzoyl)-2,3-dihydro-1H-pyrrole-2-carboxamide (−)-S74. To a solution of acid (−)-S62 (Steele et al., *J. Am. Chem. Soc.* 2015, 137, 7314) (19 mg, 0.053 mmol) dissolved in CH$_2$Cl$_2$ (1 mL), was added EDC (9 mg, 0.056 mmol), HOBt.H$_2$O (9 mg, 0.056 mmol), DIEA (0.02 mL, 0.113 mmol), and amine (+)-S73 (14 mg, 0.038 mmol) dissolved in CH$_2$Cl$_2$ (1 mL). The reaction was stirred overnight, then poured into water, extracted 3× with CH$_2$Cl$_2$, washed with water and brine, dried over MgSO$_4$ and purified by column chromatography, eluting in 0→20% Et$_2$O/CH$_2$Cl$_2$, yielding the title compound as a yellow oil (18 mg, 67% yield). $^1$H NMR (500 MHz, CDCl$_3$) δ 7.41-7.36 (m, 1H), 7.25 (d, J=8.5 Hz, 1H), 7.07 (t, J=7.5 Hz, 1H), 6.98 (s, 1H), 6.52 (d, J=4.3 Hz, 1H), 6.11-6.02 (m, 1H), 5.52 (s, 1H), 5.23 (t, J=7.2 Hz, 2H), 5.19-5.14 (m, 1H), 5.09 (dd, J=15.0, 5.4 Hz, 1H), 4.18-4.08 (m, 1H), 3.93 (s, 1H), 3.77-3.69 (m, 2H), 3.18-2.89 (m, 2H), 1.80-1.45 (m, 6H), 1.40-1.17 (m, 22H), 0.96-0.89 (m, 12H), 0.88-0.81 (m, 3H), 0.08 (s, 3H), 0.08 (s, 3H), −0.01 (s, 9H); $^{13}$C NMR (100 MHz, CDCl$_3$) δ 176.95, 169.89, 153.58, 131.57, 129.66, 128.59, 125.53, 122.27, 114.83, 111.81, 93.28, 73.55, 66.95, 59.47, 56.12, 49.30, 35.34, 35.07, 31.87, 29.84, 29.58, 29.36, 25.87, 24.17, 22.74, 18.22, 18.15, 14.21, 1.16, −1.25, −4.69, −5.12; $[\alpha]^{25}_D$ −46.4 (c=0.74 in CHCl$_3$); IR (film) 3480, 3295, 2926, 2855, 1662, 1618, 1551, 1487, 1455, 1404, 1249, 1228, 1087, 985, 938, 778, 754, 730, 667, 506; HRMS Accurate mass (ES$^+$): Found 740.4447 (−2.6 ppm), C$_{38}$H$_{67}$N$_3$O$_6$Si$_2$Na (M+Na$^+$) requires 740.4466; R$_f$ (1:1 Et$_2$O:CH$_2$Cl$_2$)=0.51.

(-)-20

(S)—N-((7R,13R)-14-amino-13-hydroxy-14-oxotetradecan-7-yl)-1-(2-hydroxybenzoyl)-2,3-dihydro-1H-pyrrole-2-carboxamide (−)-20. Using general procedure I, silyl ether (−)-S75 (15 mg, 0.021 mmol) yielded the title compound (7.6 mg, 76% yield) as a white residue $^1$H NMR (500 MHz, CDCl$_3$) δ 9.68 (s, 1H), 7.33 (t, J=7.2 Hz, 2H), 6.97 (d, J=8.2 Hz, 1H), 6.89 (t, J=7.3 Hz, 1H), 6.82 (s, 1H), 6.61 (s, 1H), 6.45 (s, 1H), 5.74 (s, 1H), 5.26 (s, 1H), 5.08-4.99 (m, 1H), 4.14 (s, 1H), 4.03 (s, 1H), 3.92 (s, 1H), 3.07-2.96 (m, 1H), 2.90 (d, J=15.2 Hz, 1H), 1.81 (d, J=69.1 Hz, 2H), 1.64-1.11 (m, 22H), 0.86 (t, J=6.5 Hz, 3H); $^{13}$C NMR (100 MHz, CDCl$_3$) δ 177.87, 170.68, 167.49, 156.12, 132.93, 130.44, 128.40, 119.71, 117.58, 112.13, 71.27, 60.12, 49.71, 35.65, 34.89, 33.89, 31.89, 29.32, 28.13, 26.13, 25.18, 24.29, 22.73, 14.22; $[\alpha]^{25}_D$ −57.5 (c=0.76 in CHCl$_3$); IR (film) 3287 (br, O—H), 2927, 2856, 1653 (C=O), 1616 (C=O), 1558, 1540, 1507, 1489, 1457, 1398, 1295, 1235, 1155, 1096, 1016, 944, 855, 817, 754, 723, 653, 620, 566; HRMS Accurate mass (ES$^+$): Found 496.2817 (+6.0 ppm), C$_{26}$H$_{39}$N$_3$O$_5$Na (M+Na$^+$) requires 496.2787; R$_f$ (5% MeOH/95% CH$_2$Cl$_2$)=0.23.

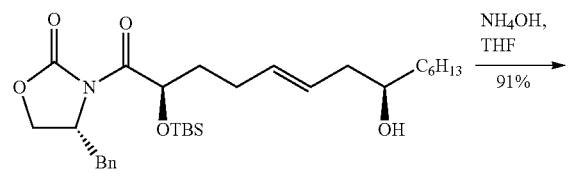

S76

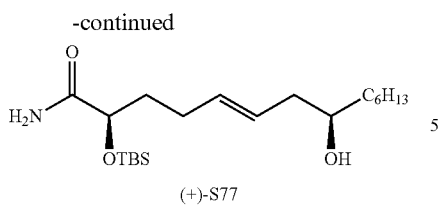

(+)-S77

(2R,8R,E)-2-((tert-butyldimethylsilyl)oxy)-8-hydroxytetradec-5-enamide (+)-S77. To a solution of oxazolidinone S76 (Steele et al., *J. Am. Chem. Soc.* 2015, 137, 7314) (50 mg, 0.094 mmol) dissolved in THF (3 mL) was added ammonium hydroxide (28% in H$_2$O, 2 mL). The reaction was tightly sealed and stirred for 24 hours. Another portion of ammonium hydroxide (1 mL) was added after this time, and the reaction was stirred for another 24 hours. The reaction was diluted with MeOH and concentrated. This process was repeated another 2×, and the crude product was purified by column chromatography (0→30% Et$_2$O/CH$_2$Cl$_2$→5% MeOH/30% Et$_2$O/65% CH$_2$Cl$_2$), yielding the title compound as a yellow oil (32 mg, 91% yield). $^1$H NMR (400 MHz, CDCl$_3$) δ 6.63-6.46 (m, 1H), 5.60-5.40 (m, 3H), 4.21-4.12 (m, 1H), 3.55 (d, J=16.1 Hz, 1H), 2.28-1.99 (m, 4H), 1.95-1.80 (m, 1H), 1.80-1.71 (m, 3H), 1.47-1.39 (m, 2H), 1.33-1.23 (m, 6H), 0.93 (s, J=2.9 Hz, 9H), 0.88 (t, J=6.7 Hz, 3H), 0.13-0.07 (m, 6H); $^{13}$C NMR (100 MHz, CDCl$_3$) δ 177.15, 133.16, 126.95, 72.95, 71.03, 56.05, 40.79, 36.87, 34.91, 31.92, 29.44, 27.36, 25.82, 22.70, 18.09, 14.18, −4.73, −5.15; [α]$^{25}_D$ +9.3 (c=1.64 in CHCl$_3$); IR (film) 3479, 2954, 2927, 2855, 1682 (C=O), 1556, 1463, 1388, 1361, 1253, 1101, 1005, 967, 912, 836, 778, 722, 669, 578; HRMS Accurate mass (ES$^+$): Found 394.2757 (+1.0 ppm), C$_{20}$H$_{41}$NO$_3$SiNa (M+Na$^+$) requires 394.2753; R$_f$ (2:1 CH$_2$Cl$_2$:Et$_2$O)=0.25.

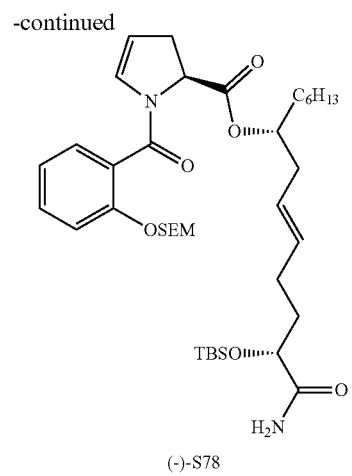

(−)-S78

(7R,13R,E)-14-amino-13-((tert-butyldimethylsilyl)oxy)-14-oxotetradec-9-en-7-yl (S)-1-(2-((2-(trimethylsilyl)ethoxy)methoxy)benzoyl)-2,3-dihydro-1H-pyrrole-2-carboxylate (−)-S78. Using general procedure H, acid (−)-S62 (22 mg, 0.060 mmol) and alcohol (+)-S77 (16 mg, 0.043 mmol) yielded the title compound as a yellow oil (24 mg, 77% yield). $^1$H NMR (500 MHz, CDCl$_3$) δ 7.38-7.31 (m, 2H), 7.20 (d, J=8.2 Hz, 1H), 7.03 (td, J=7.5, 0.8 Hz, 1H), 7.00-6.92 (m, 1H), 6.53 (d, J=4.2 Hz, 1H), 6.15 (dd, J=4.2, 2.1 Hz, 1H), 5.70 (s, 1H), 5.44 (dtd, J=22.1, 15.3, 6.6 Hz, 2H), 5.27-5.19 (m, 2H), 5.06-4.90 (m, 3H), 4.19-4.09 (m, 1H), 3.79-3.69 (m, 2H), 3.16-3.06 (m, 1H), 2.70-2.63 (m, 1H), 2.33-2.26 (m, 2H), 2.14-2.02 (m, 3H), 1.89-1.78 (m, 2H), 1.77-1.68 (m, 2H), 1.61-1.51 (m, 3H), 1.35-1.17 (m, 12H), 0.96-0.89 (m, 9H), 0.86 (t, J=6.9 Hz, 3H), 0.11-0.06 (m, 6H), −0.02 (s, 9H); $^{13}$C NMR (100 MHz, CDCl$_3$) δ 176.80, 170.68, 164.99, 153.84, 132.90, 131.25, 131.00, 128.99, 125.92, 125.52, 121.97, 115.21, 108.43, 93.33, 74.91, 73.13, 66.63, 58.24, 37.36, 34.89, 34.39, 33.45, 31.84, 30.43, 29.82, 29.26, 27.44, 25.86, 25.28, 22.70, 18.15, 14.19, −1.28, −4.70, −5.12; [α]$^{25}_D$ −19.8 (c=1.20 in CHCl$_3$); IR (film) 3479, 2952, 2926, 2856, 1736 (C=O), 1689, 1650, 1619, 1600, 1488, 1455, 1406, 1359, 1249, 1230, 1191, 1151, 1087, 1043, 988, 917, 778, 754; HRMS Accurate mass (ES$^+$): Found 717.4299 (−4.3 ppm), C$_{38}$H$_{65}$N$_2$O$_7$Si$_2$ (M+H$^+$) requires 717.4330; R$_f$ (2:1 CH$_2$Cl$_2$:Et$_2$O)=0.76.

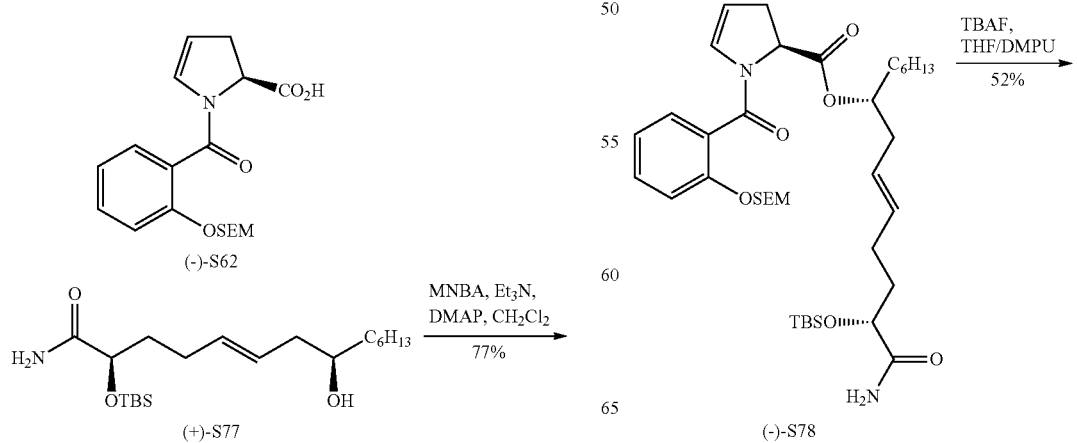

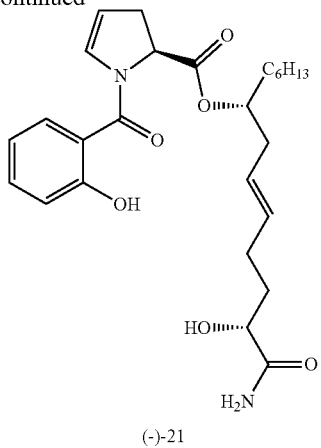

(-)-21

(7R,13R,E)-14-amino-13-hydroxy-14-oxotetradec-9-en-7-yl (S)-1-(2-hydroxybenzoyl)-2,3-dihydro-1H-pyrrole-2-carboxylate (−)-21. Using general procedure I, silyl ether (−)-S78 (24 mg, 0.034 mmol) yielded the title compound as a clear oil (8.3 mg, 52% yield). $^1$H NMR (500 MHz, CDCl$_3$) δ 9.06 (s, 1H), 7.42-7.34 (m, 2H), 7.03-6.95 (m, 1H), 6.95-6.87 (m, 1H), 6.62 (d, J=17.8 Hz, 2H), 5.52 (s, 2H), 5.35-5.29 (m, 1H), 5.29-5.23 (m, 1H), 5.03 (dd, J=11.5, 4.6 Hz, 2H), 4.08-4.00 (m, 1H), 3.90 (s, 1H), 3.20-3.08 (m, 1H), 2.70 (d, J=17.2 Hz, 1H), 2.34-2.11 (m, 2H), 1.96-1.87 (m, 1H), 1.72-1.49 (m, 5H), 1.34-1.18 (m, 10H), 0.87 (t, J=7.0 Hz, 3H); $^{13}$C NMR (100 MHz, CDCl$_3$) δ 177.53, 171.32, 167.40, 157.36, 133.41, 132.37, 130.76, 128.36, 126.87, 119.55, 118.26, 118.03, 111.07, 70.14, 59.13, 37.82, 34.65, 33.75, 33.34, 31.79, 29.16, 27.87, 25.45, 22.66, 14.20; $[\alpha]^{25}_D$ −40.3 (c=0.83 in CHCl$_3$); IR (film) 3200 (br, O—H), 2926, 2855, 1733 (C=O), 1662 (C=O), 1592, 1487, 1430, 1194, 1152, 1097, 1017, 969, 860, 755; HRMS Accurate mass (ES$^+$): Found 473.2689 (+7.8 ppm), C$_{26}$H$_{37}$N$_2$O$_6$ (M+H$^+$) requires 473.2652.

Bacterial Strains and Culture Conditions

Figure 6:
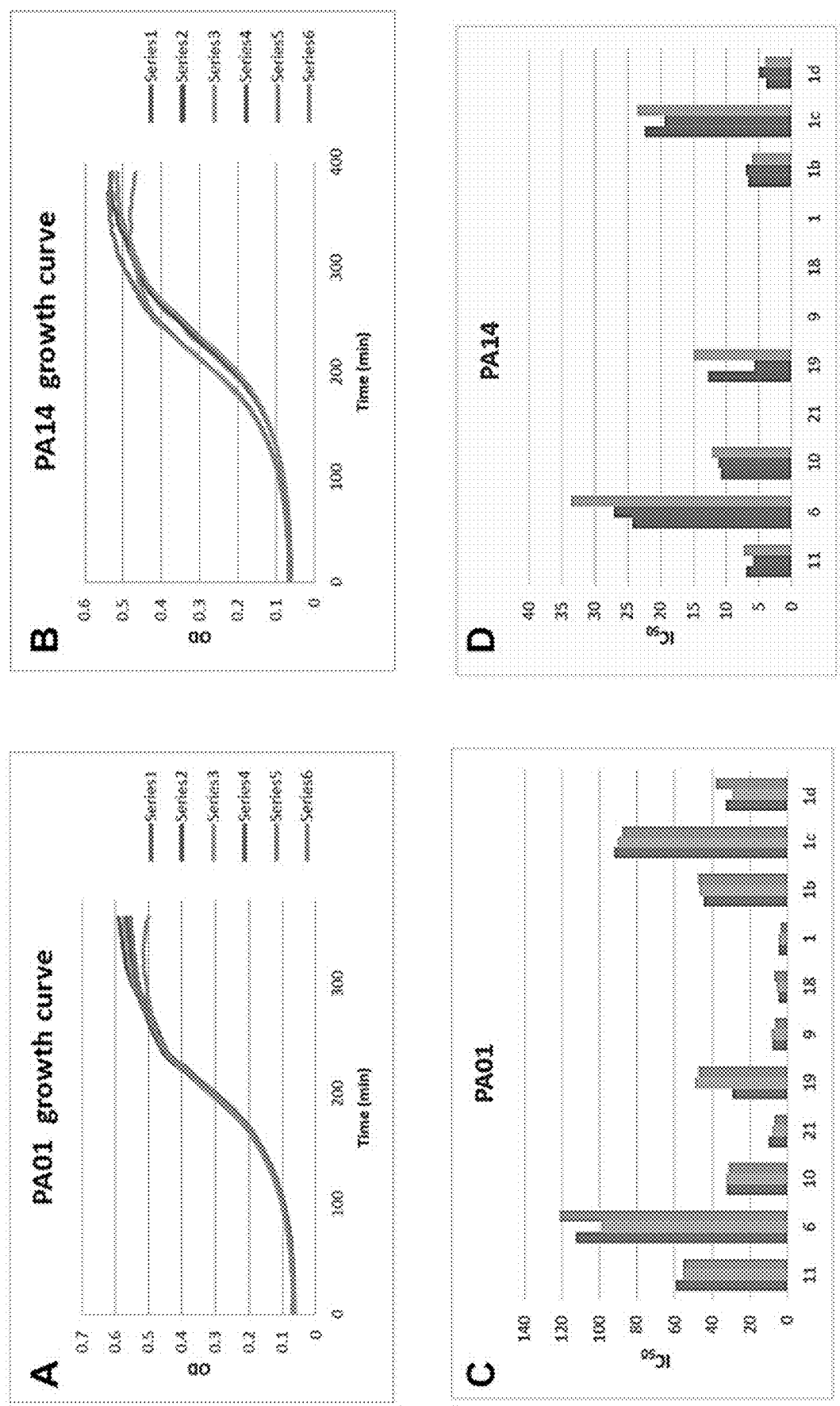
FIG. 6, comprising
Figure 7:
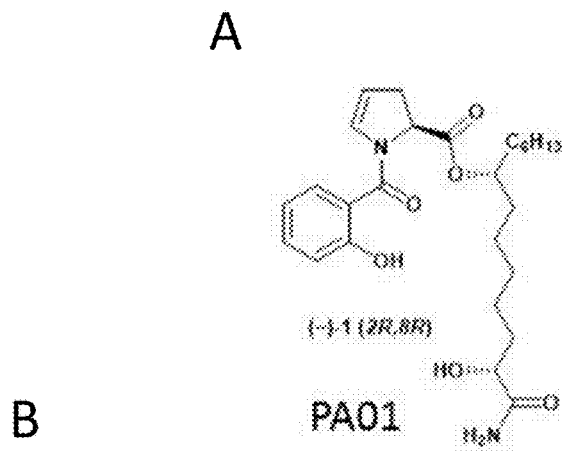
FIG. 7, comprising
Figure 7:
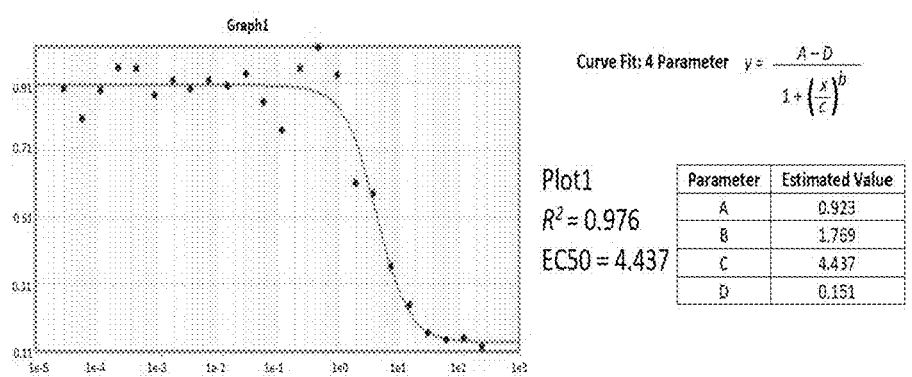
Figure 7:
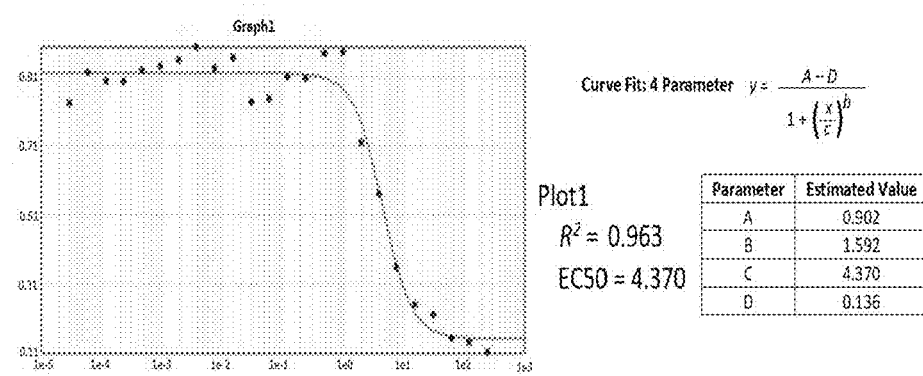
Figure 7:
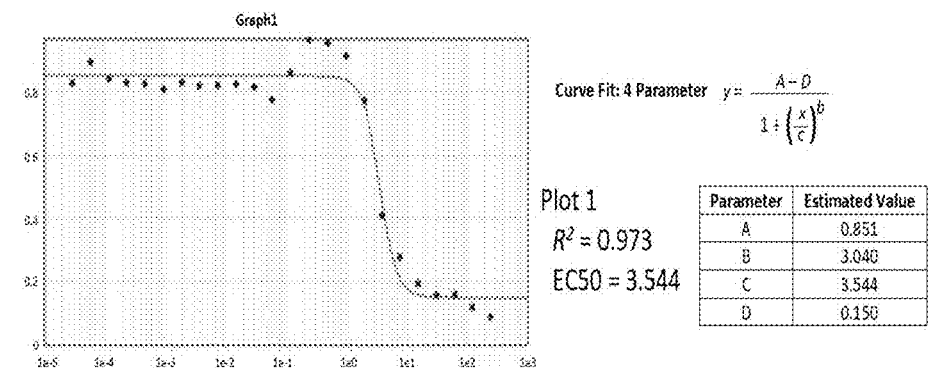
Figure 8:
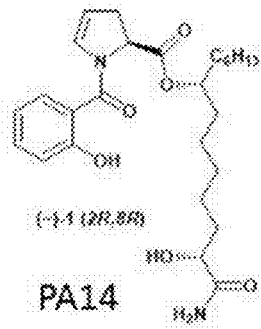
FIG. 8, comprising
Figure 8:
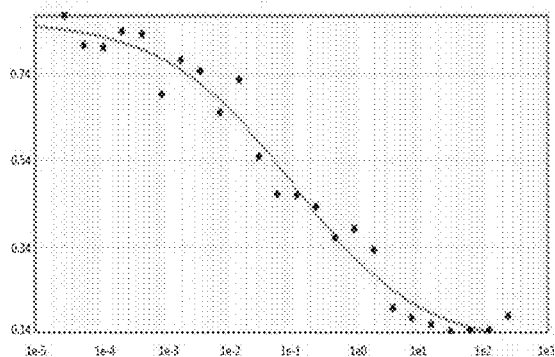
Figure 8:
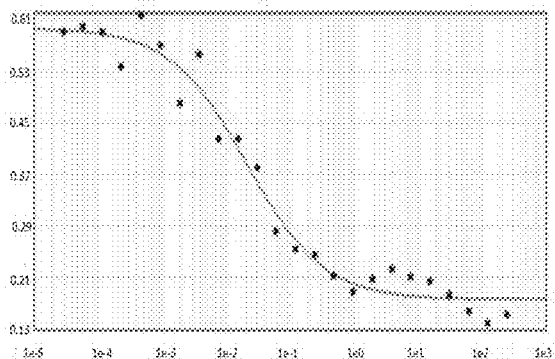
Figure 8:
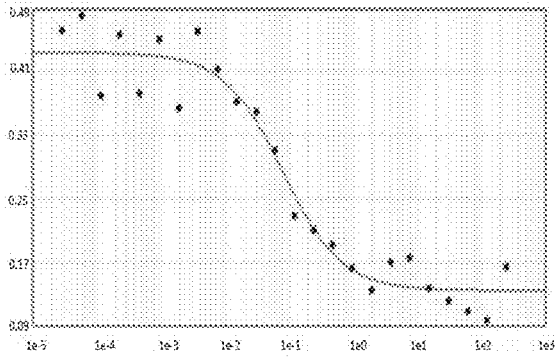
Figure 9:
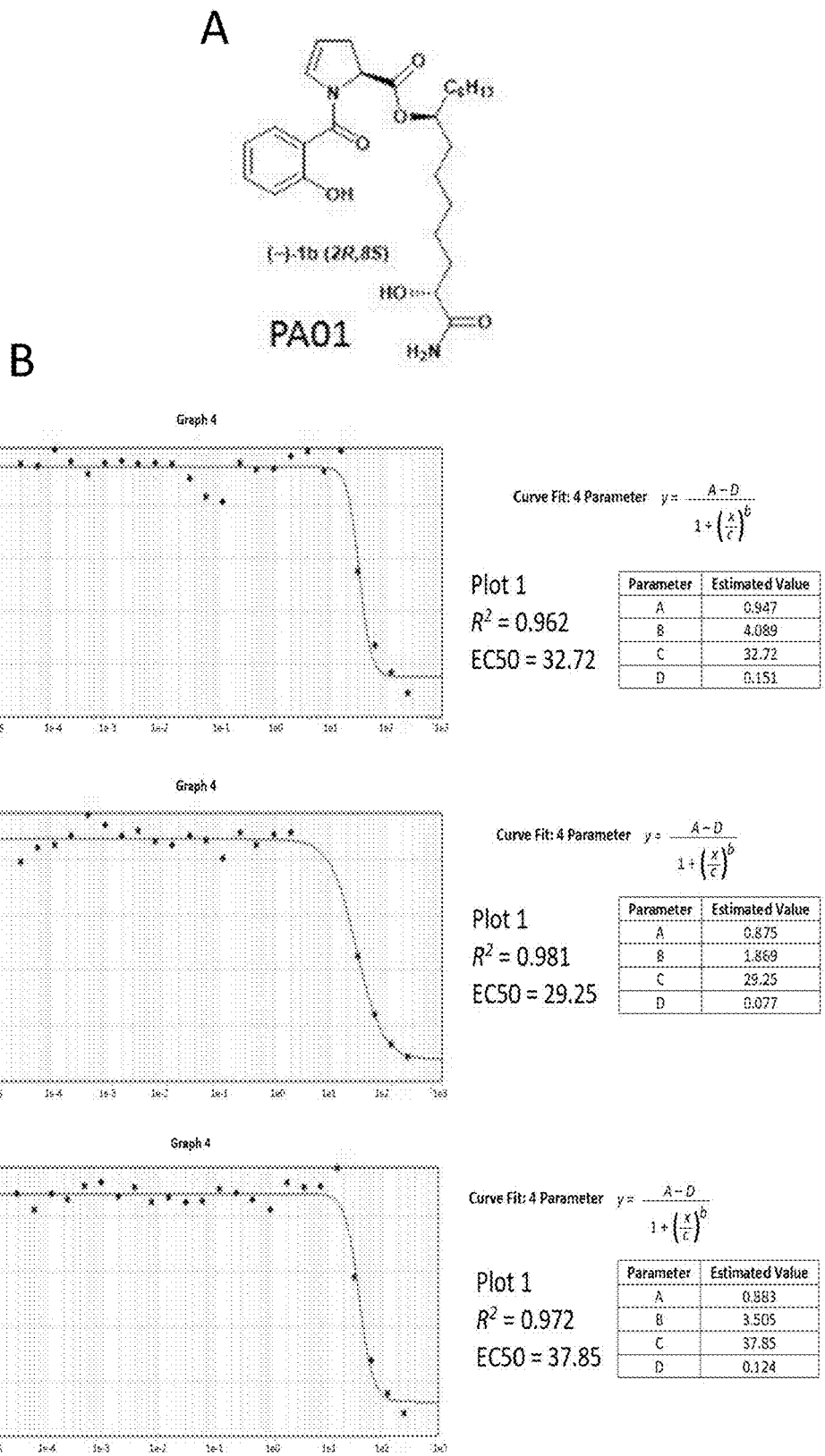
FIG. 9, comprising
Figure 10:
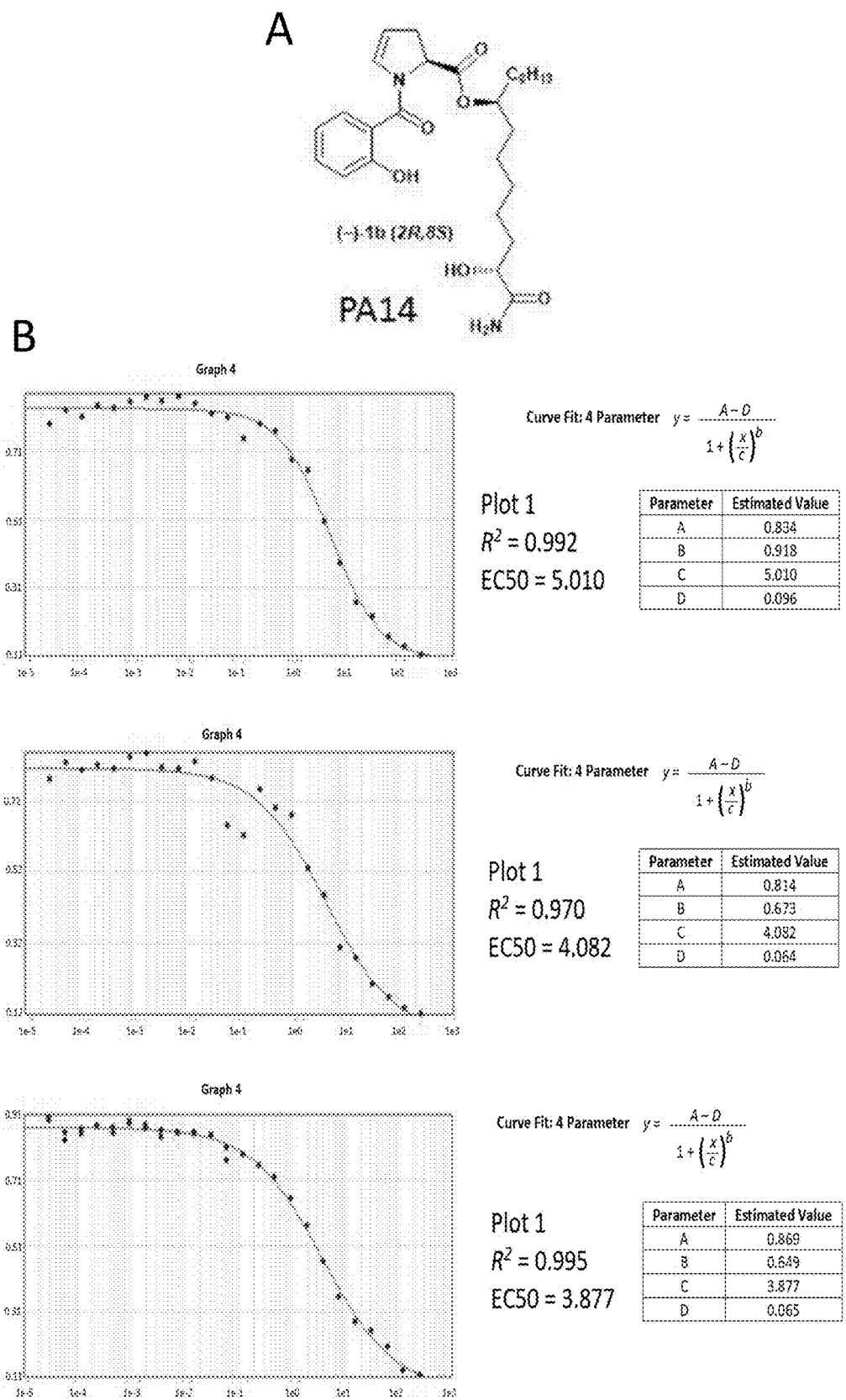
FIG. 10, comprising
Figure 11:
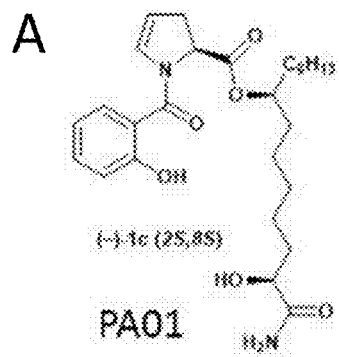
FIG. 11, comprising
Figure 11:
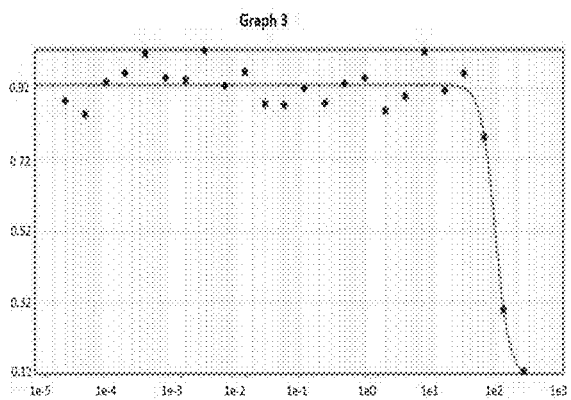
Figure 11:
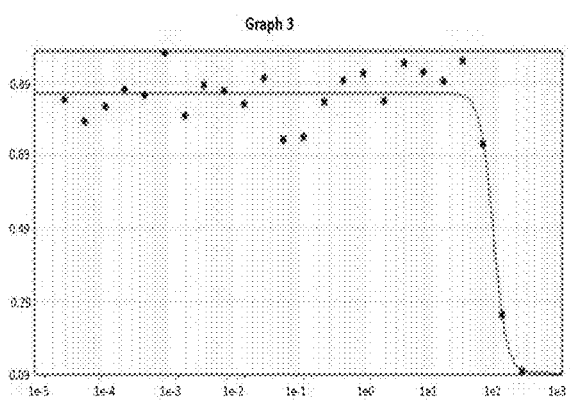
Figure 11:
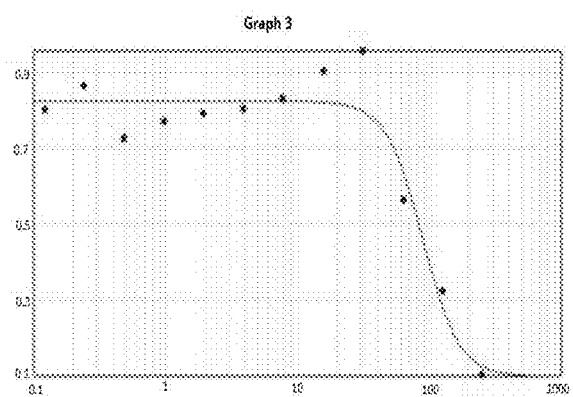
Figure 12:
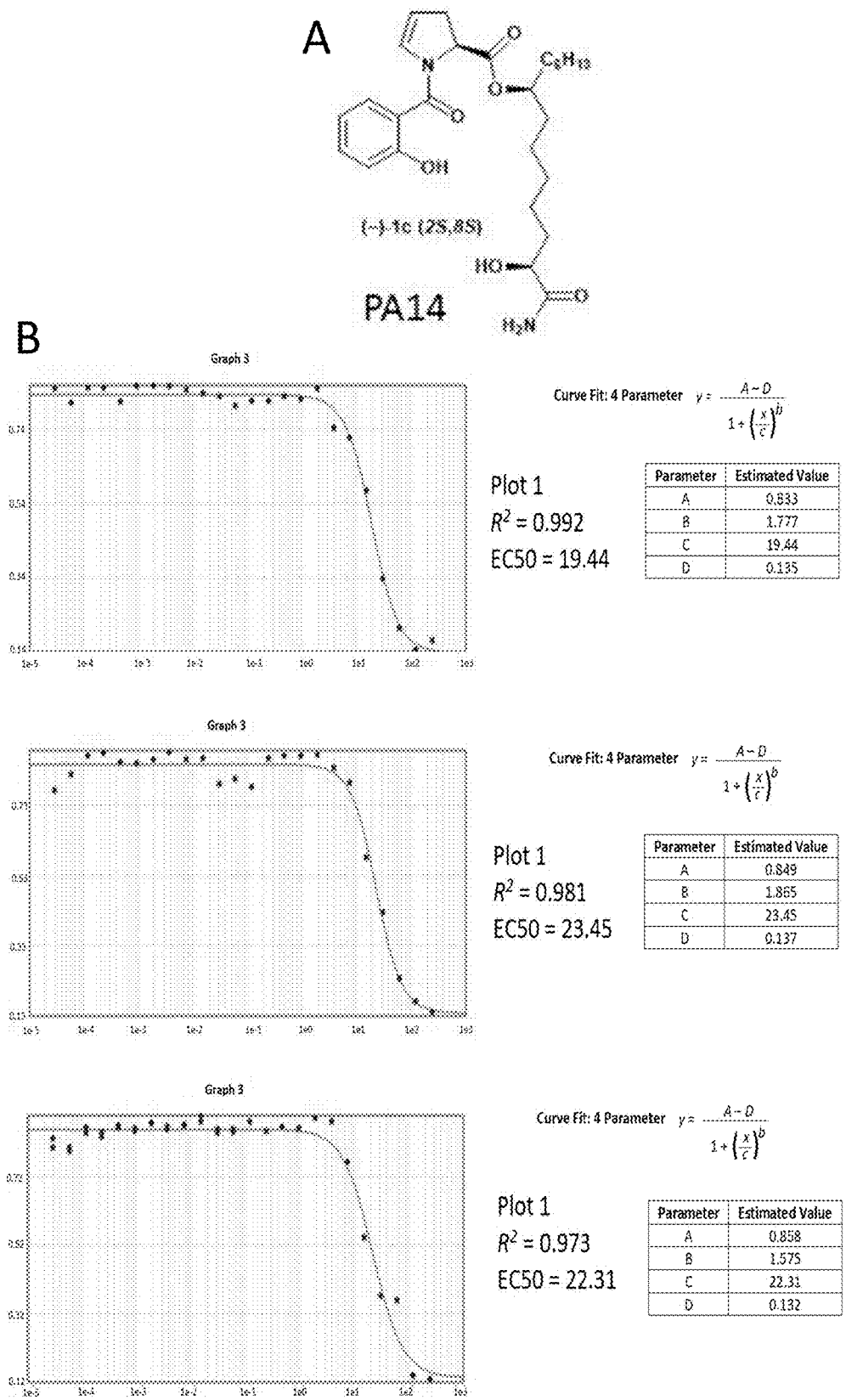
FIG. 12, comprising
Figure 13:
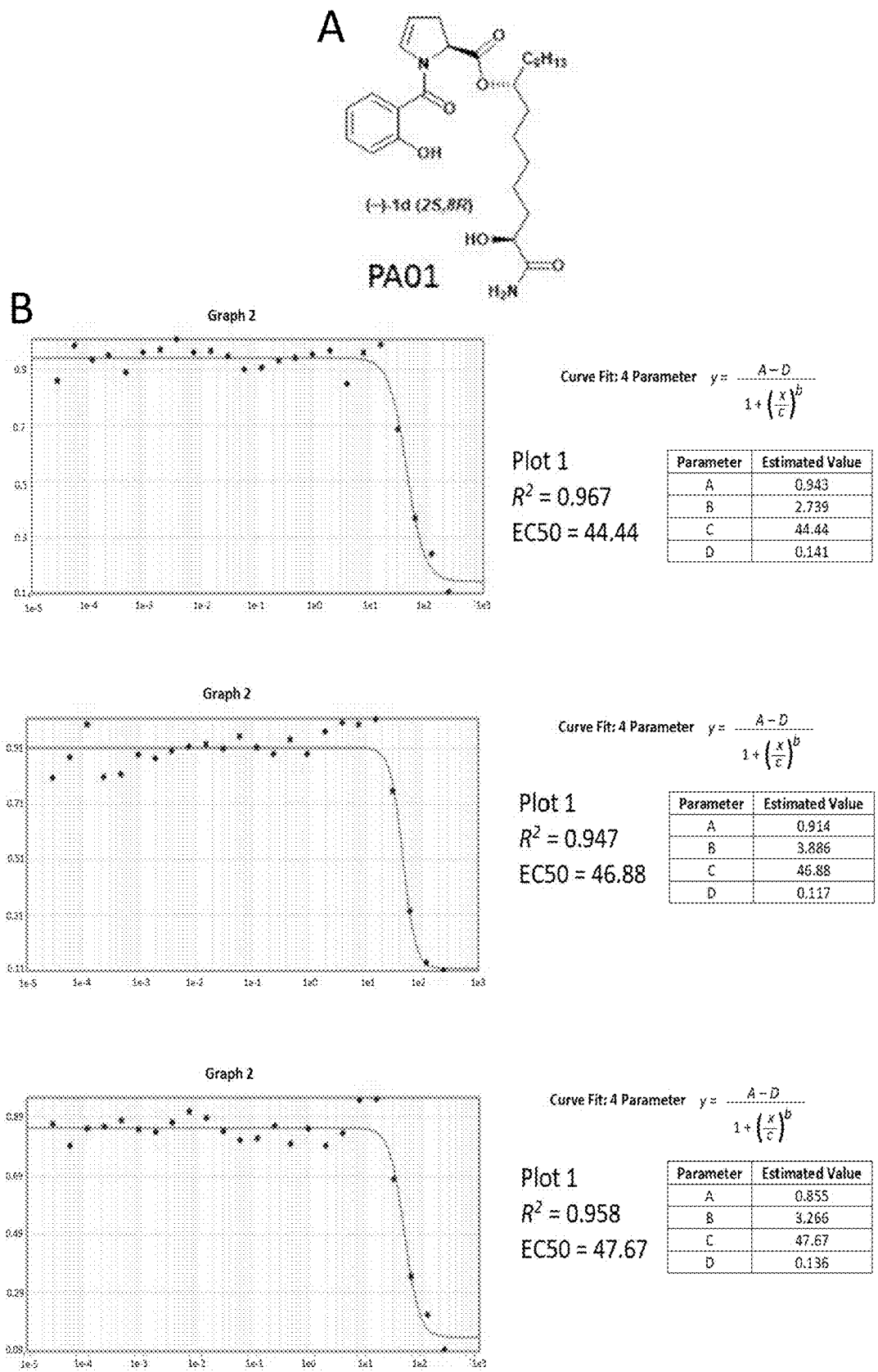
FIG. 13, comprising
Figure 14:
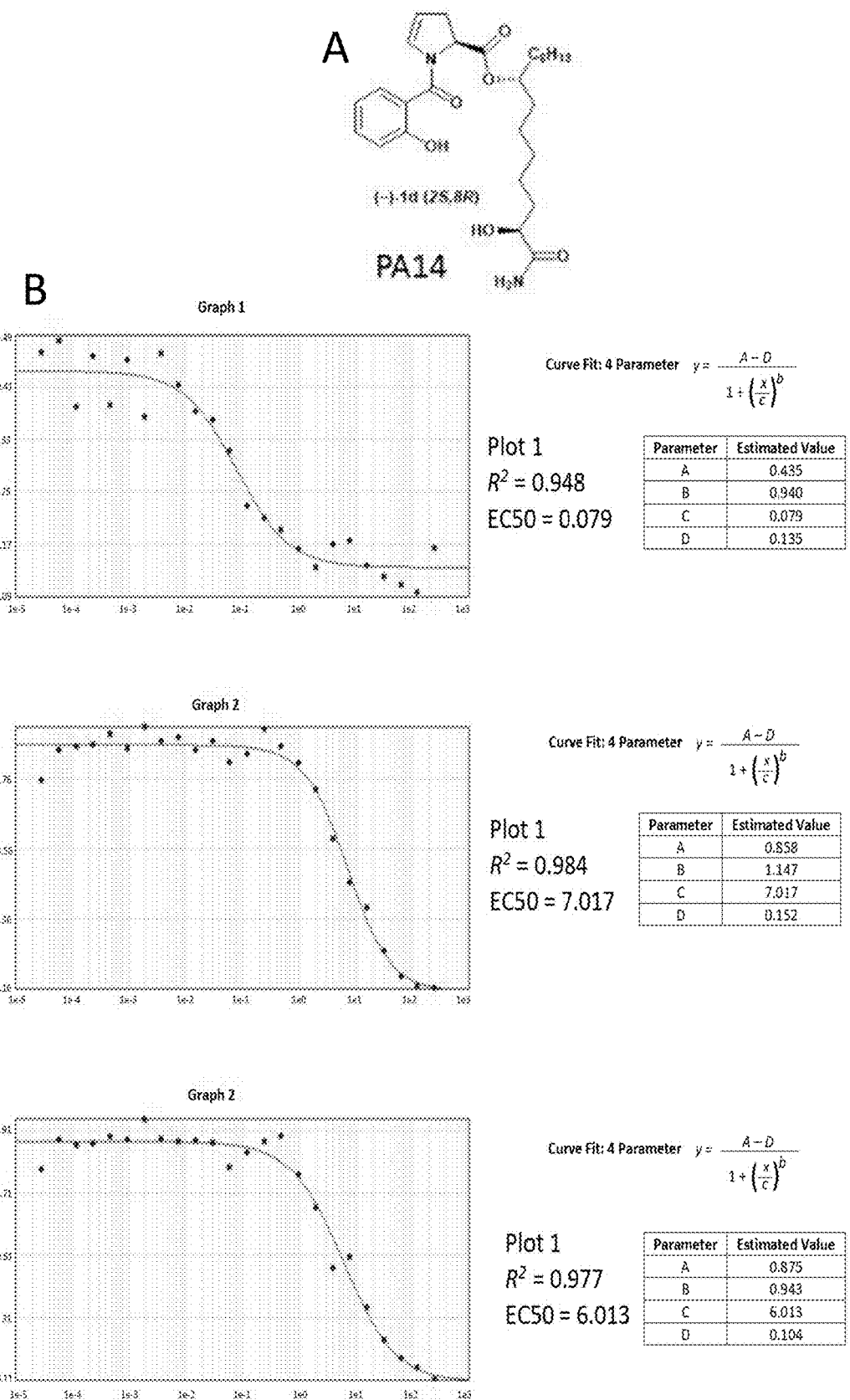
FIG. 14, comprising
Figure 15:
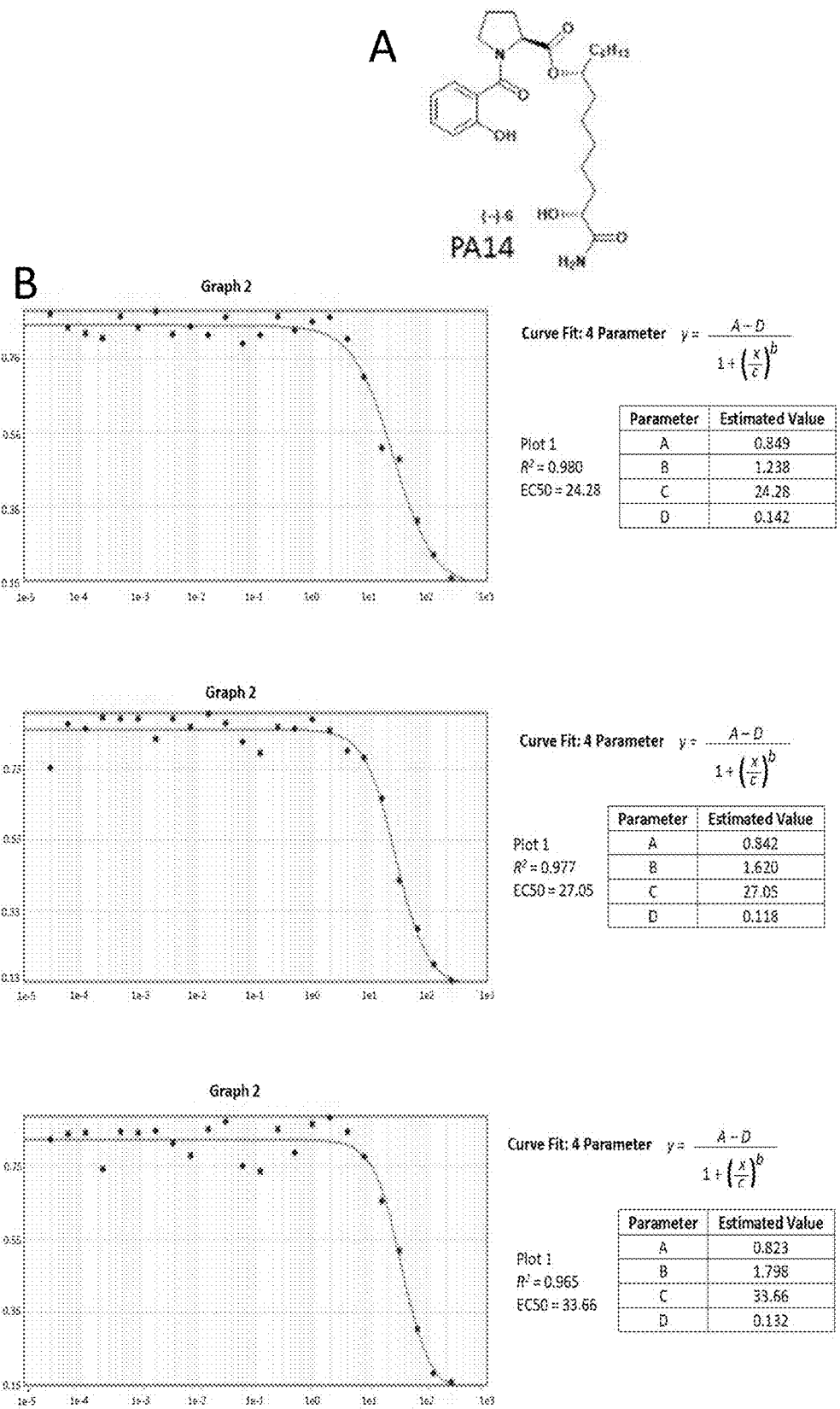
FIG. 15, comprising
Figure 16:
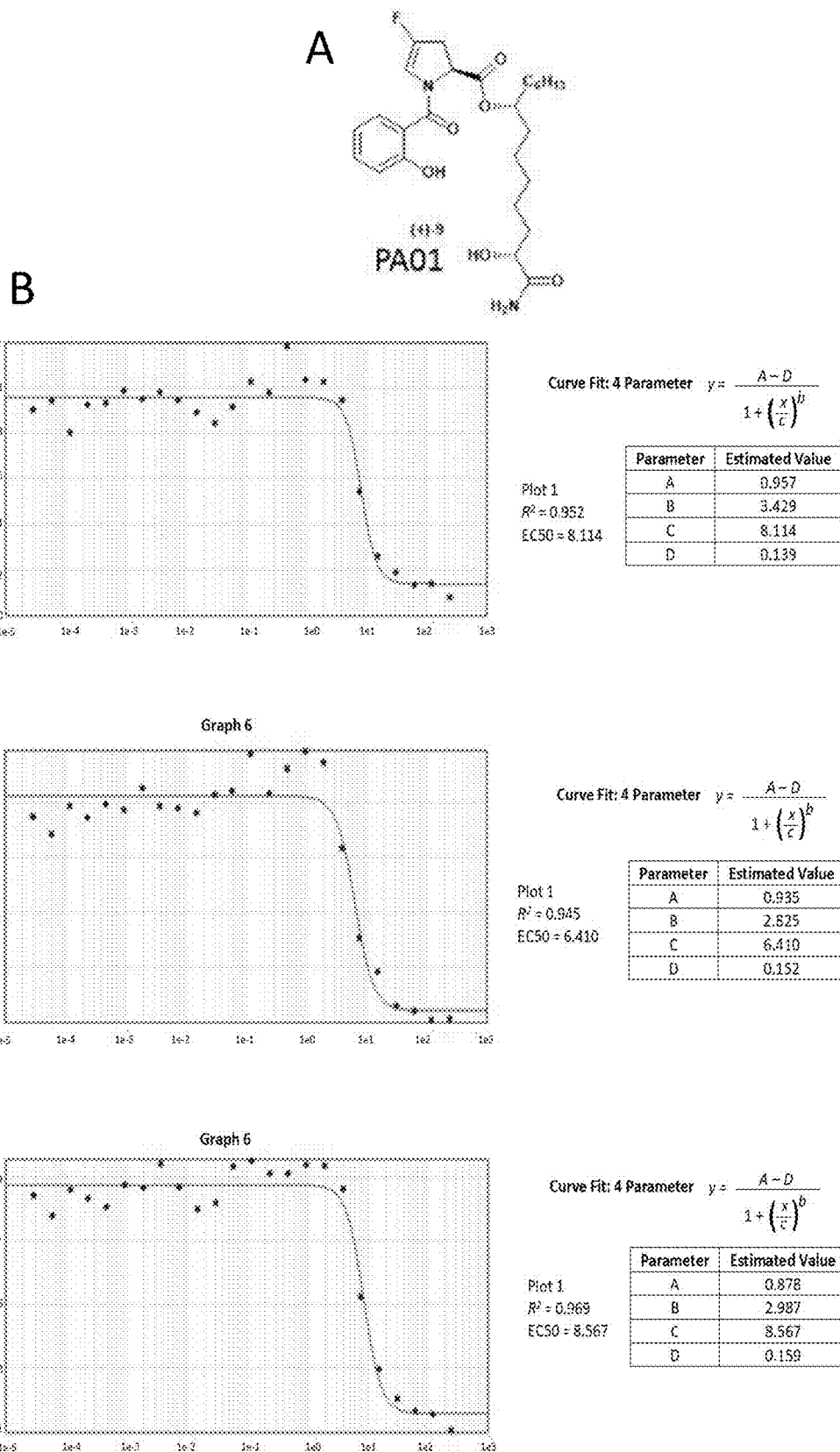
FIG. 16, comprising
Figure 17:
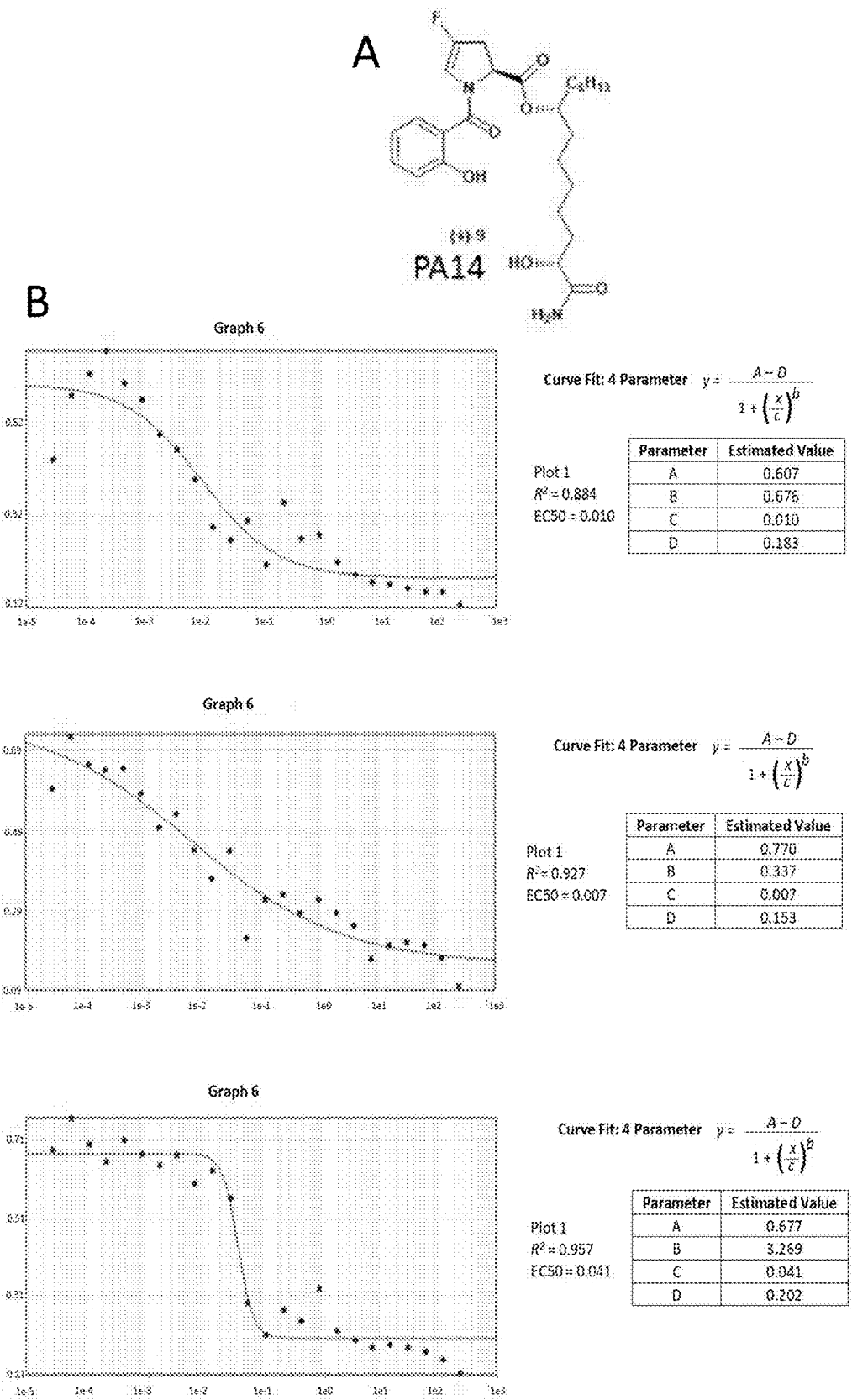
FIG. 17, comprising
Figure 18:
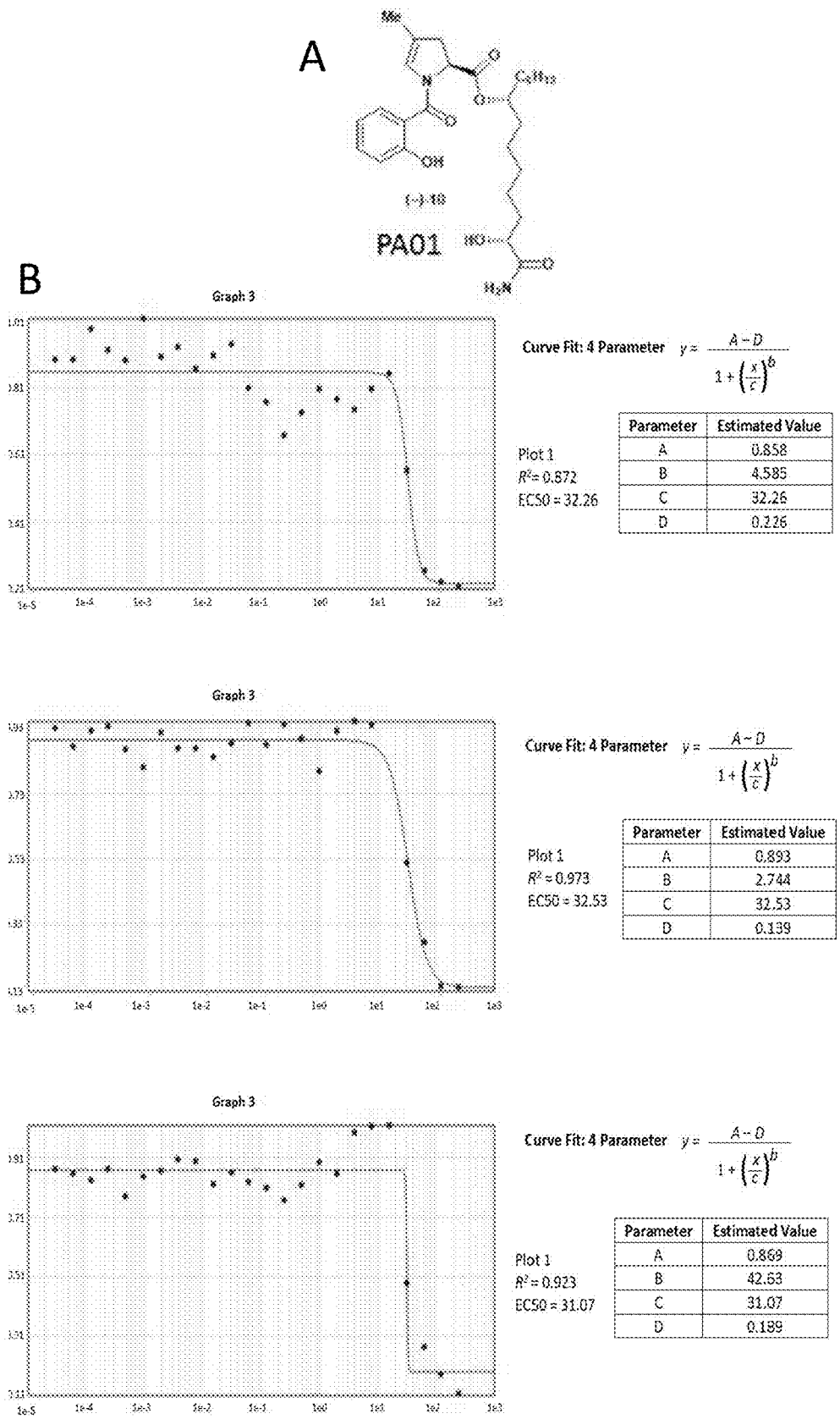
FIG. 18, comprising
Figure 19:
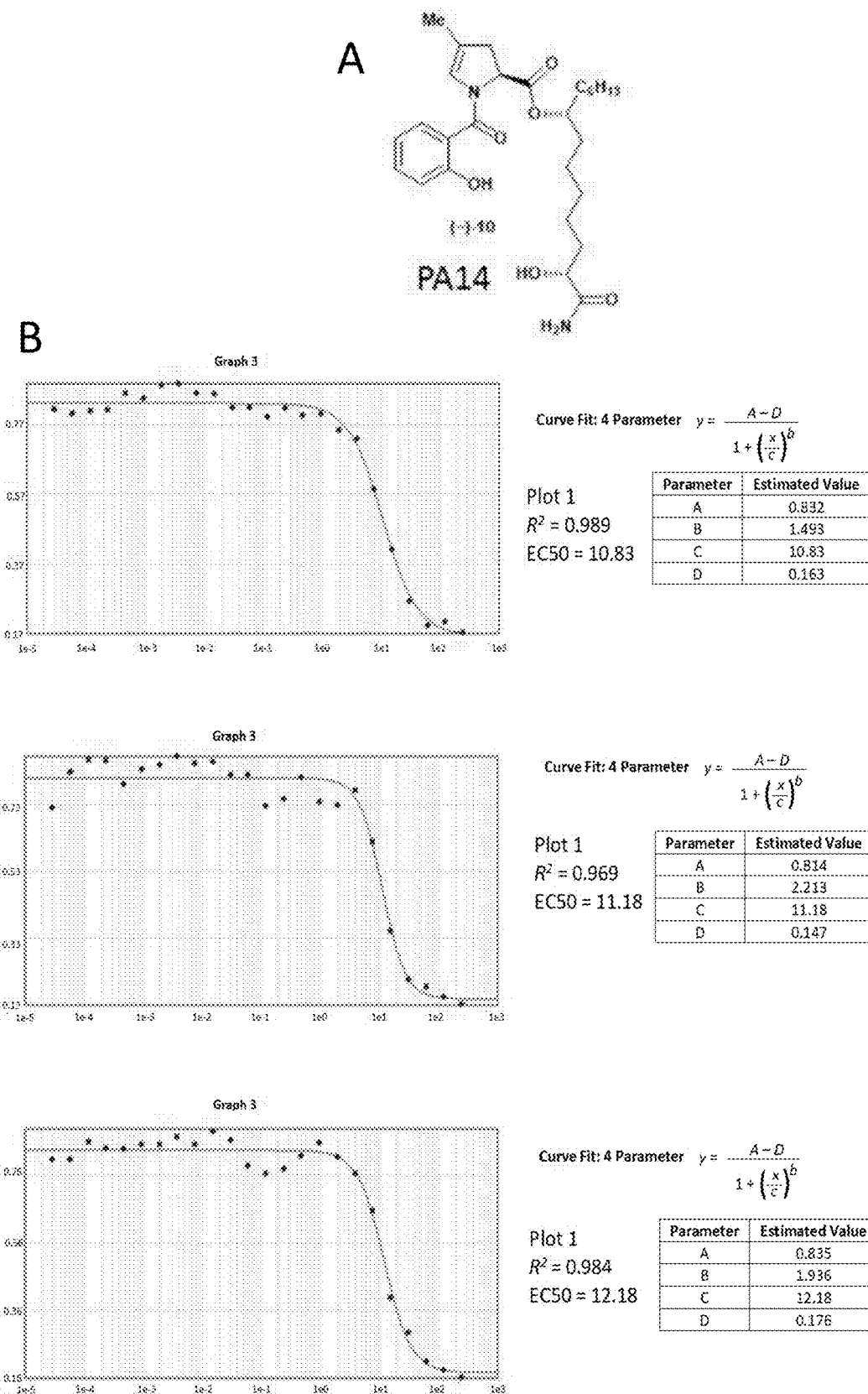
FIG. 19, comprising
Figure 20:
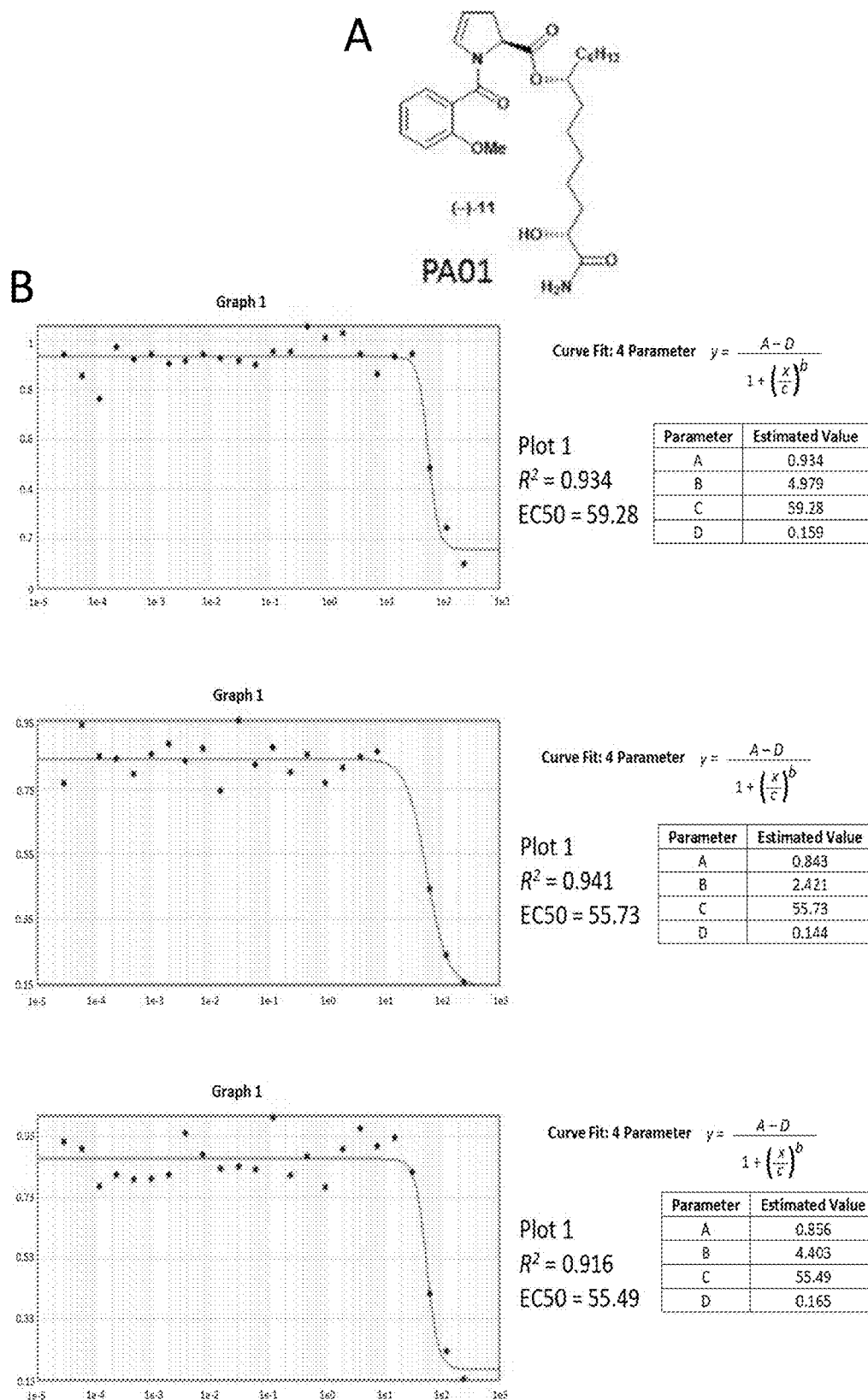
FIG. 20, comprising
Figure 21:
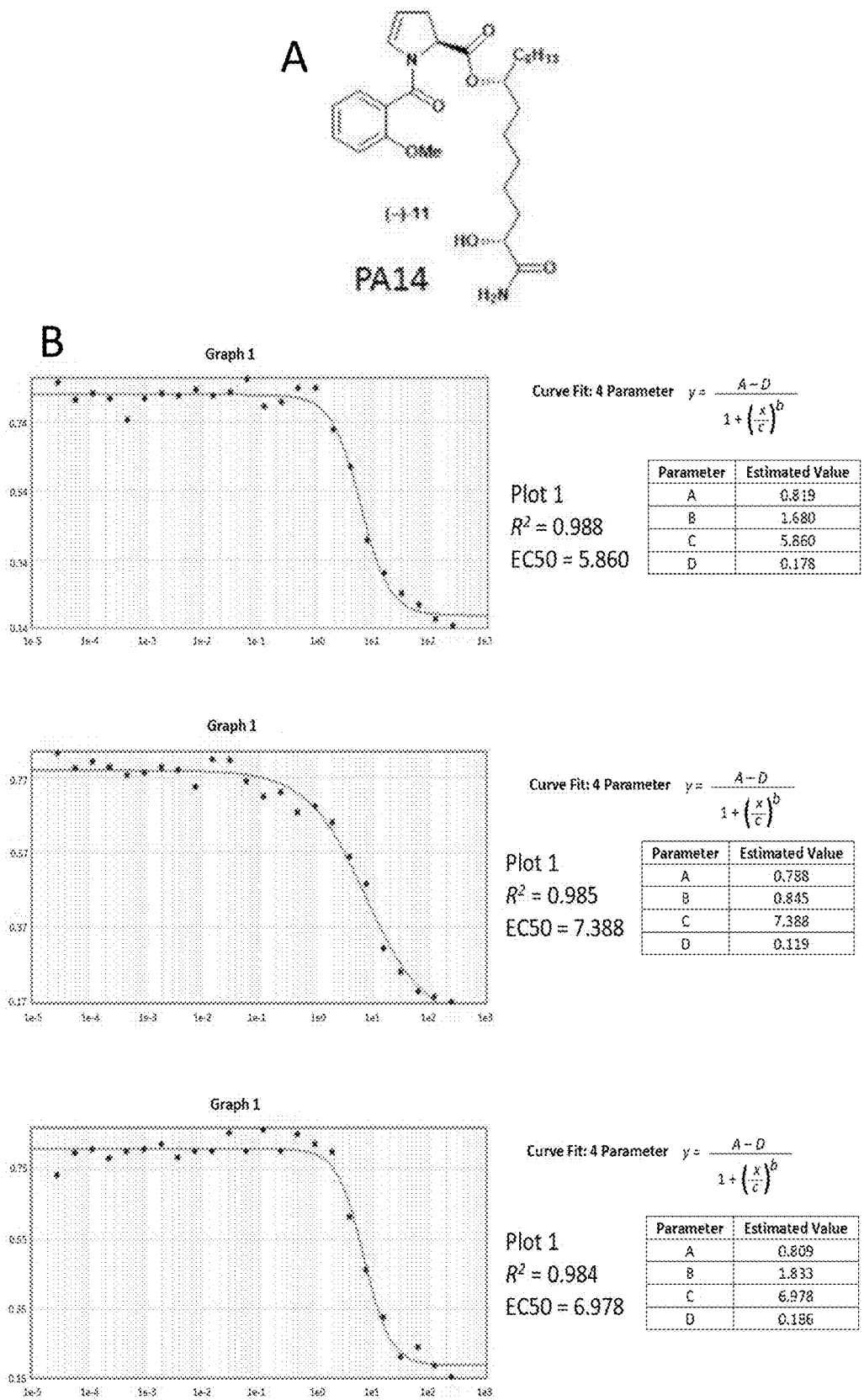
FIG. 21, comprising
Figure 22:
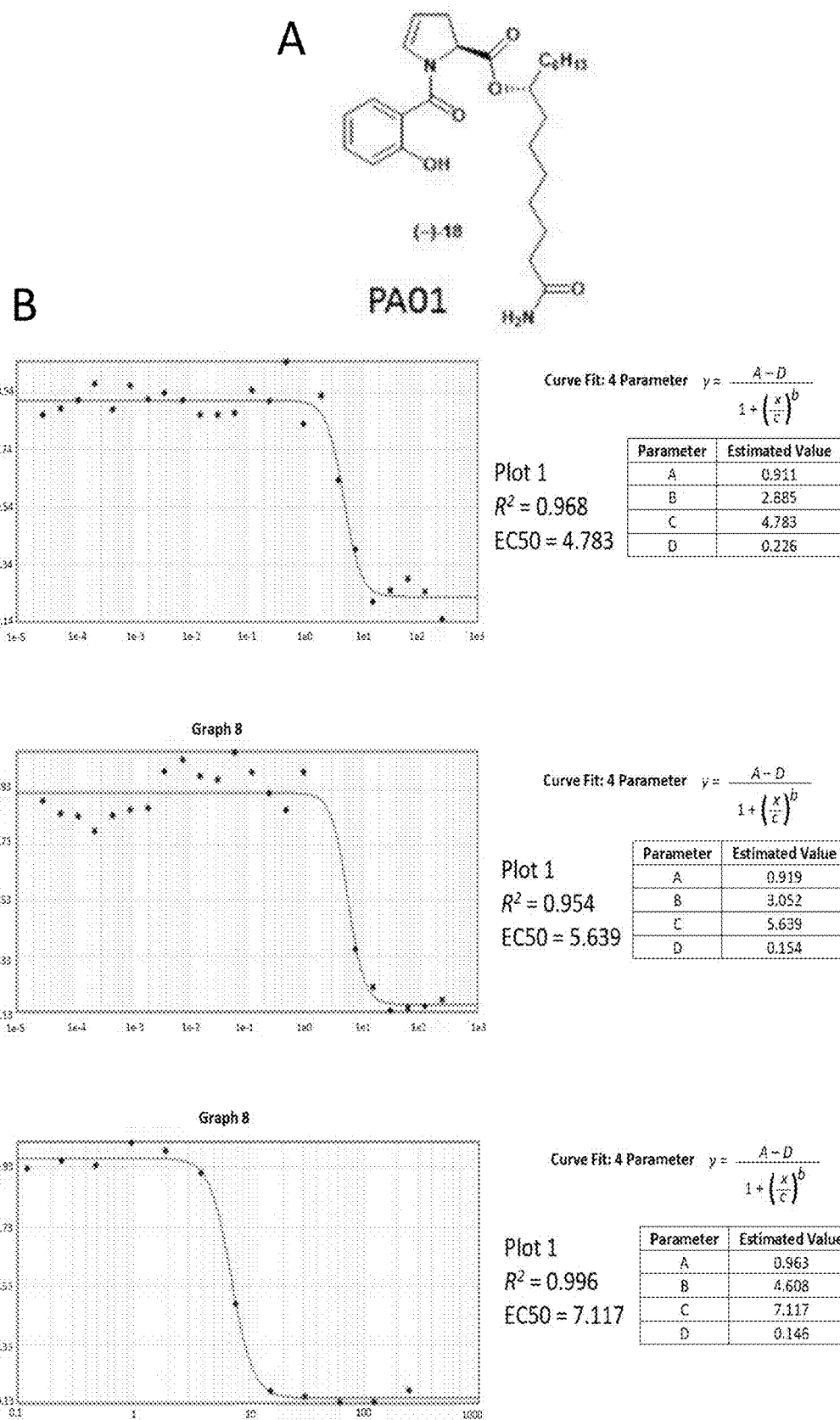
FIG. 22, comprising
Figure 23:
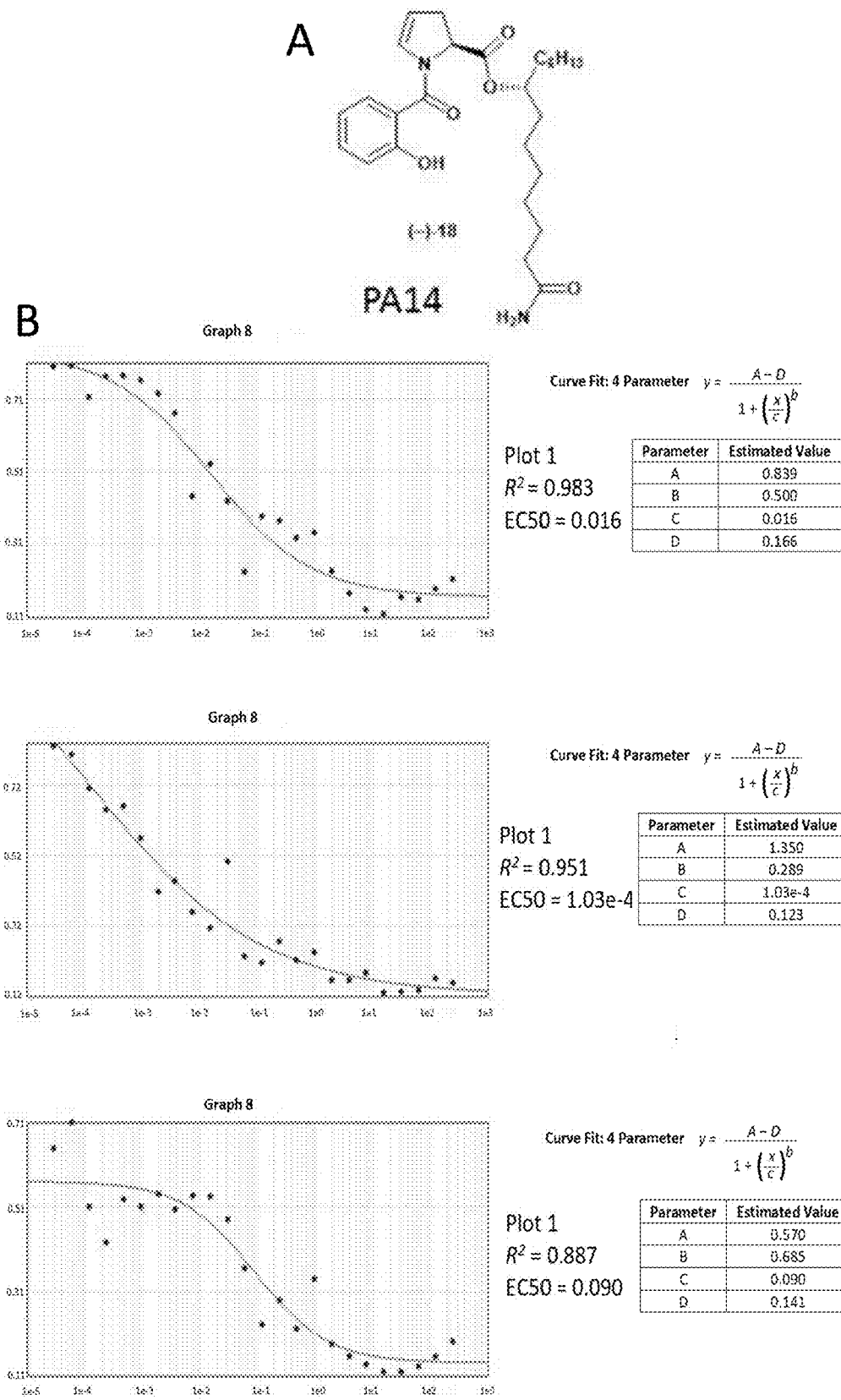
FIG. 23, comprising
Figure 24:
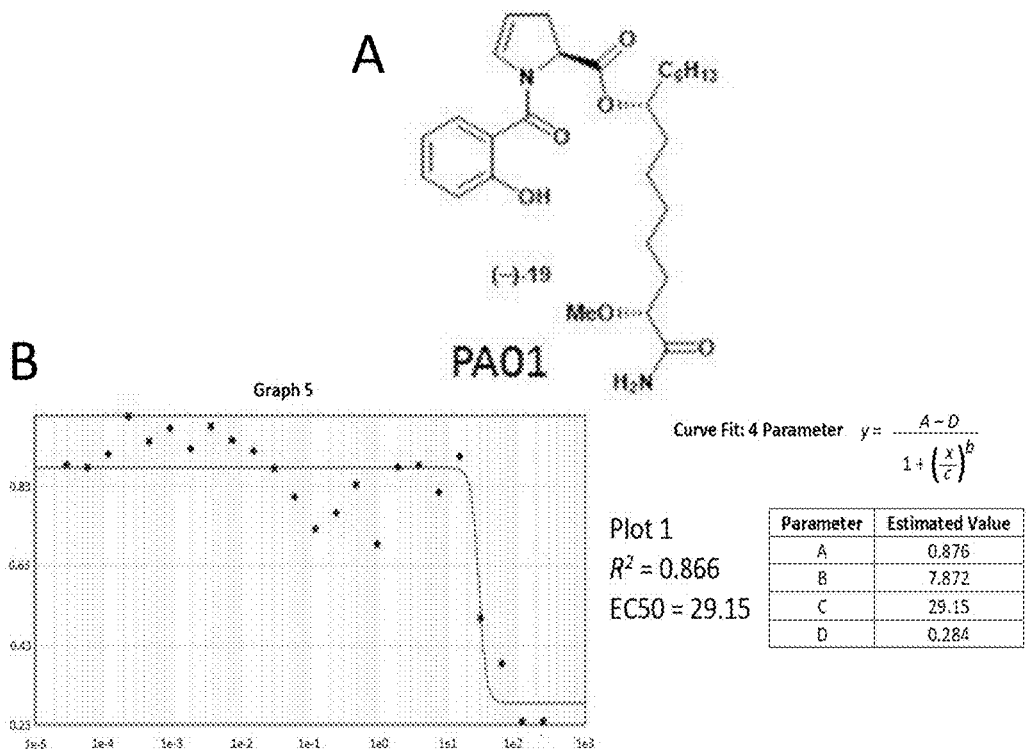
FIG. 24, comprising
Figure 24:
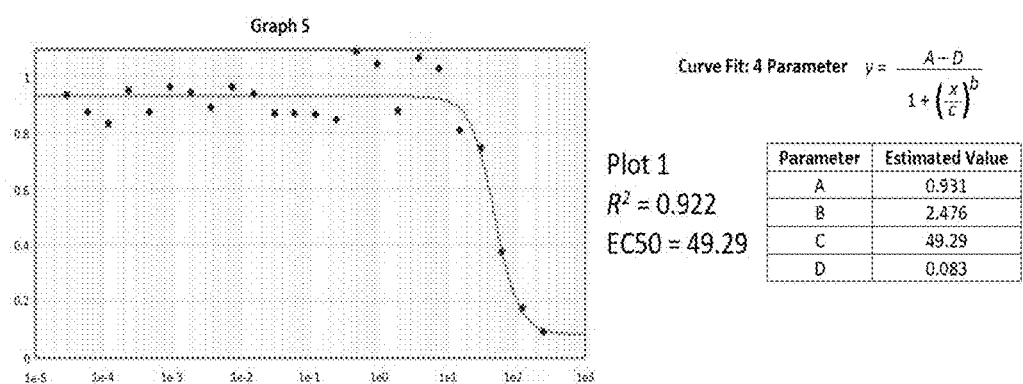
Figure 24:
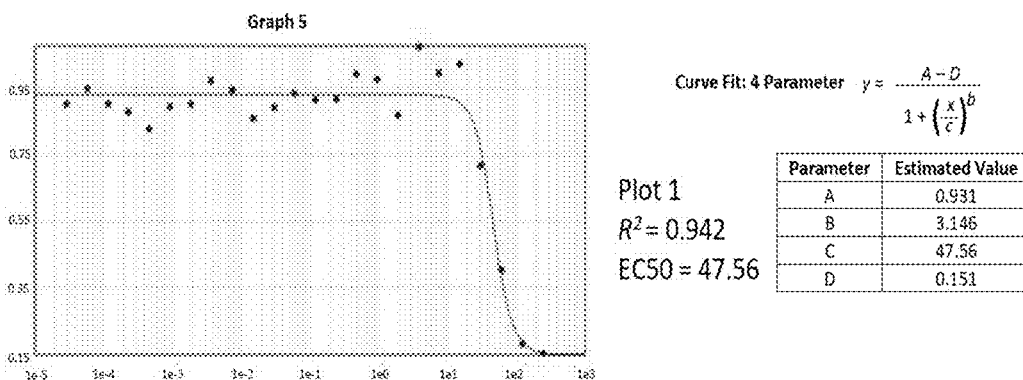
Figure 25:
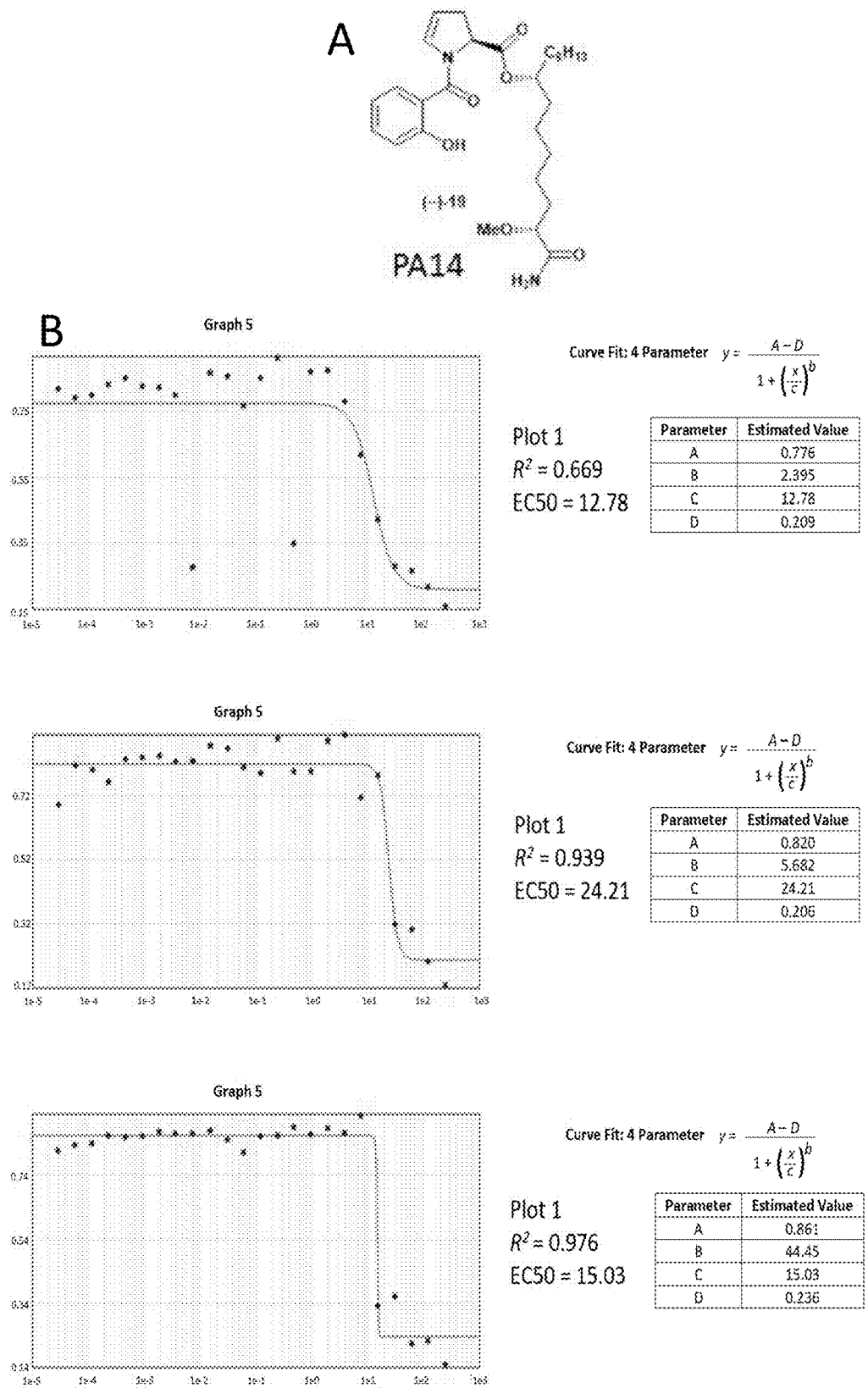
FIG. 25, comprising
Figure 26:
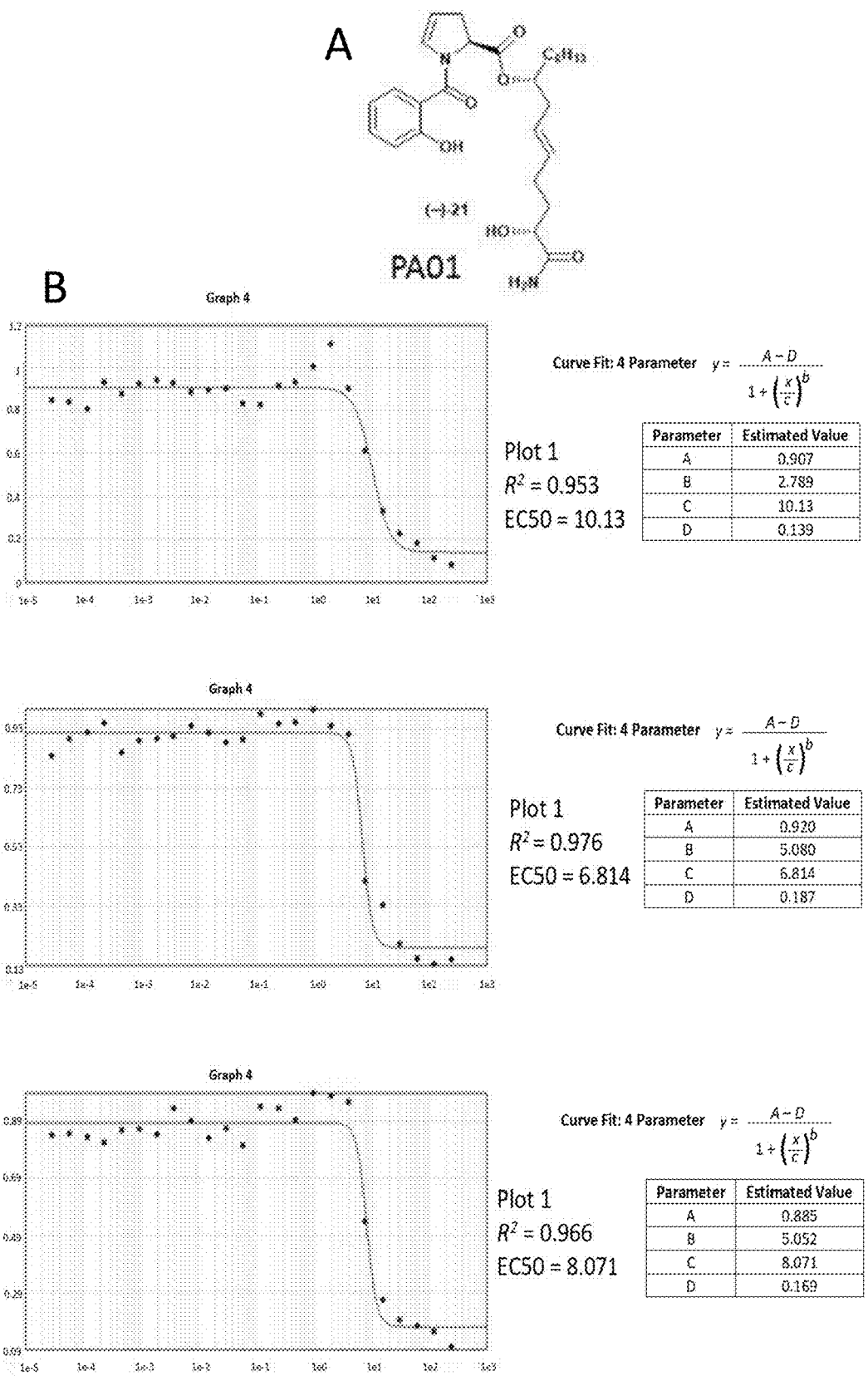
FIG. 26, comprising
Figure 27:
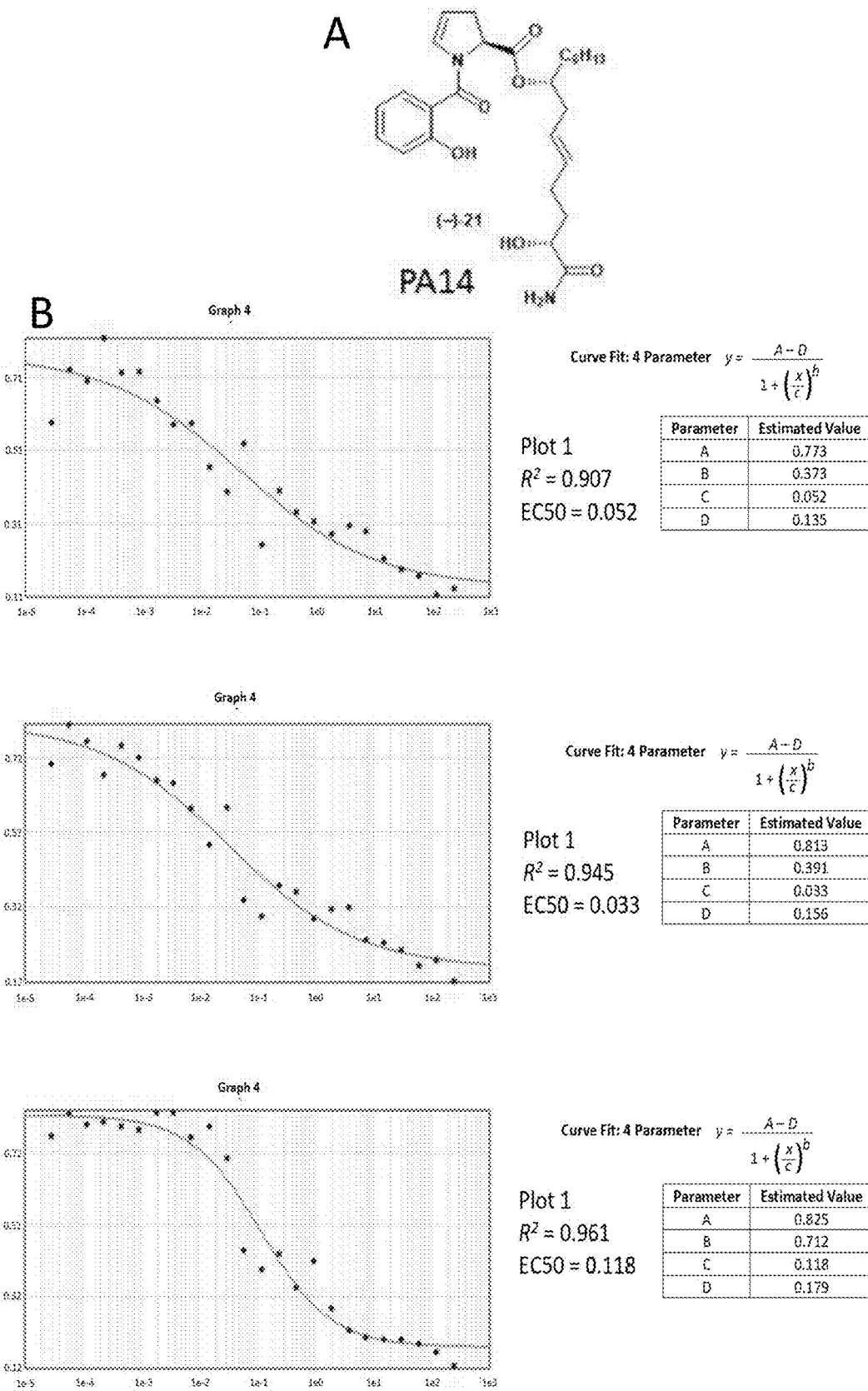
FIG. 27, comprising
Figure 28:
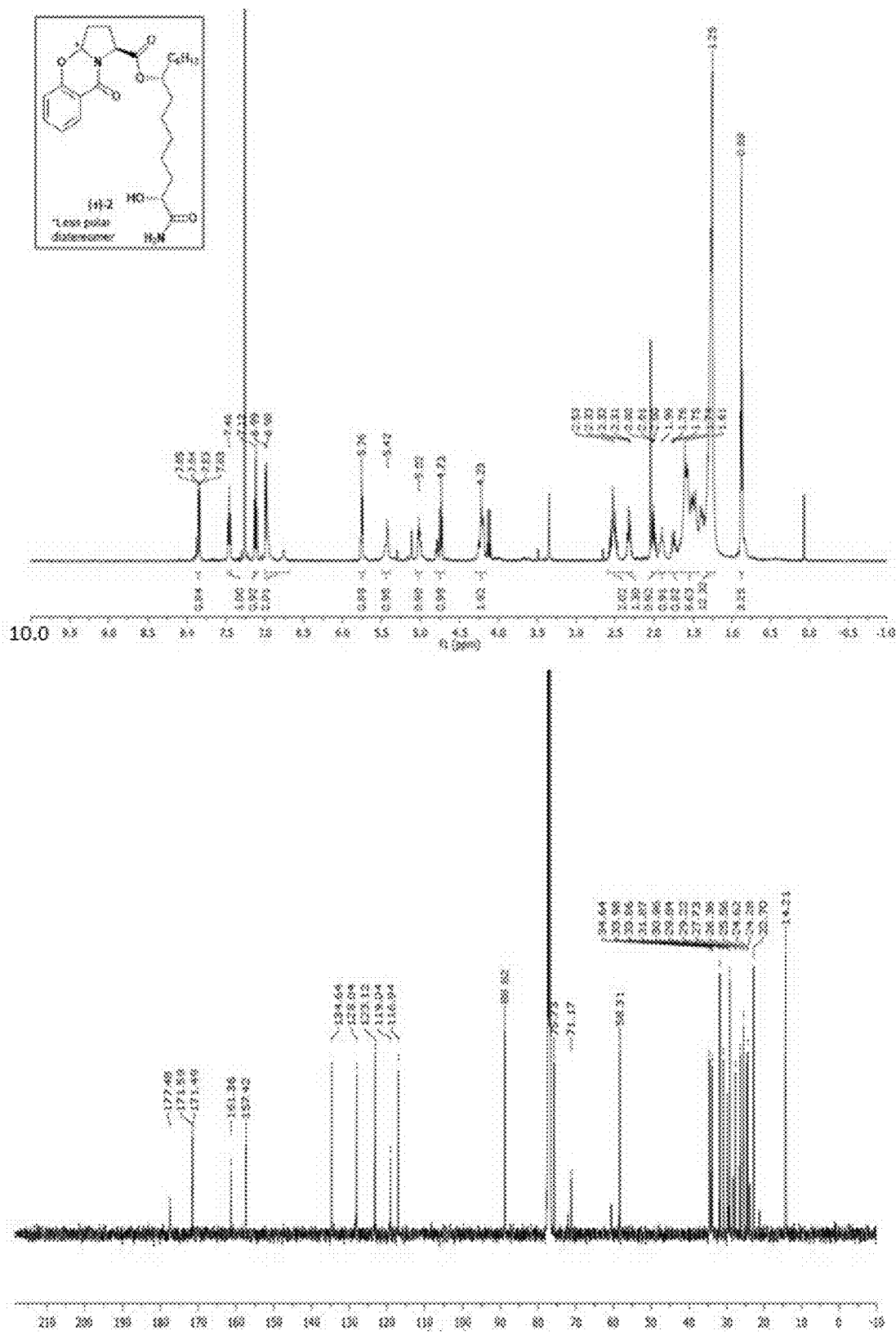
FIG. 28 depicts the proton ($^1$H) and carbon ($^{13}$C) NMR spectra of promysalin synthetic intermediate (+)-2.
Figure 29:
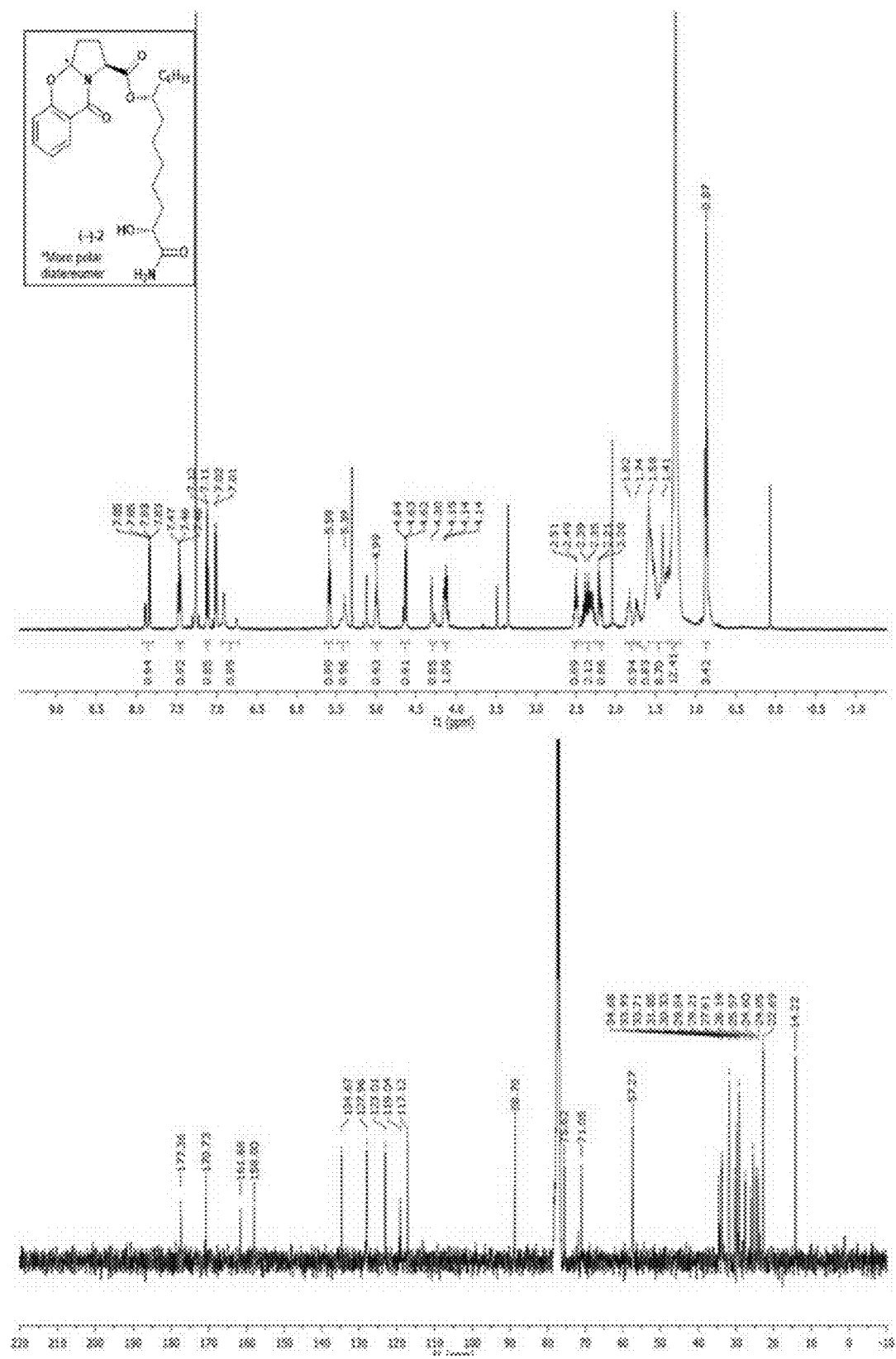
FIG. 29 depicts the proton ($^1$H) and carbon ($^{13}$C) NMR spectra of promysalin synthetic intermediate (−)-2.
Figure 30:
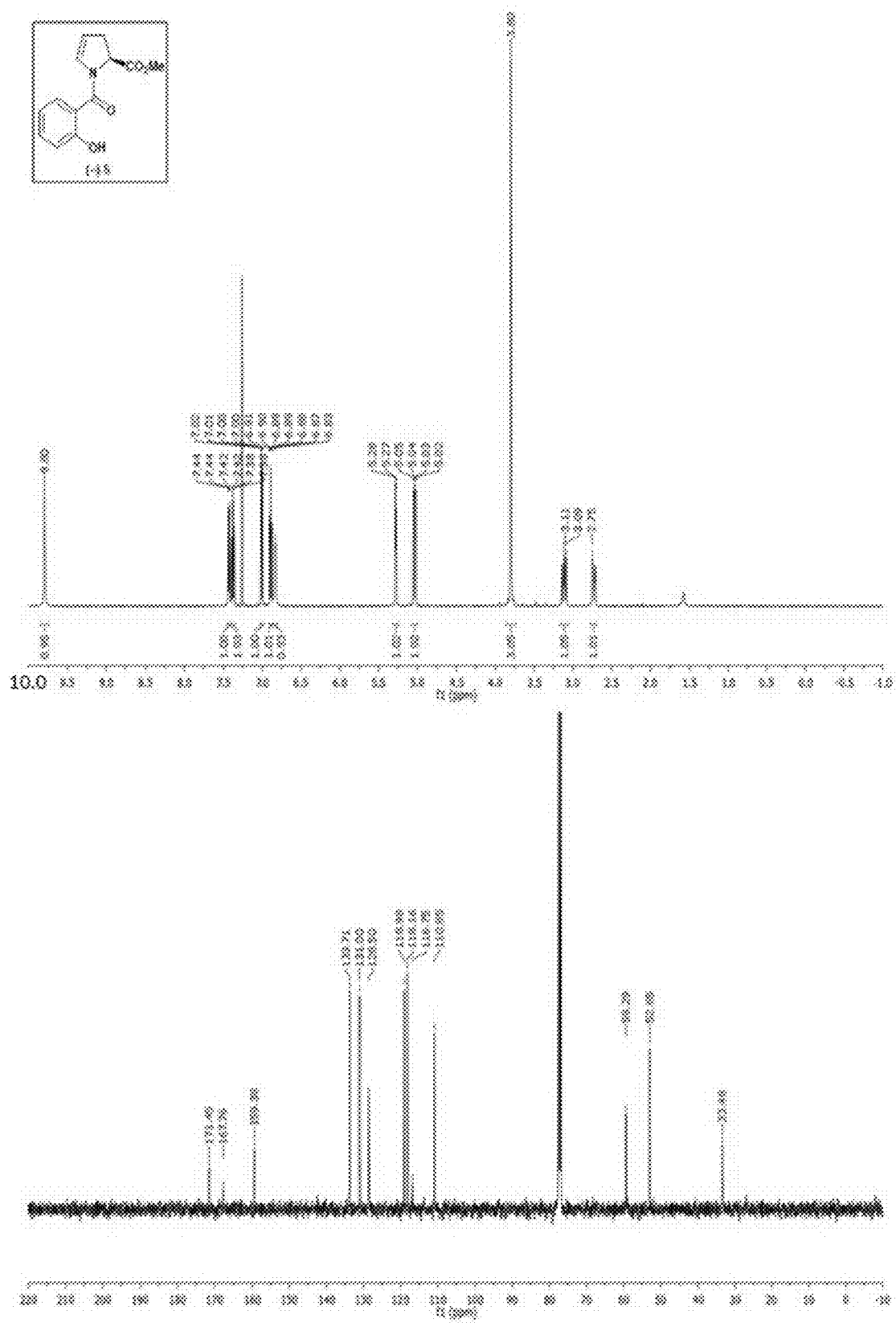
FIG. 30 depicts the proton ($^1$H) and carbon ($^{13}$C) NMR spectra of promysalin synthetic intermediate (−)-5.
Figure 31:
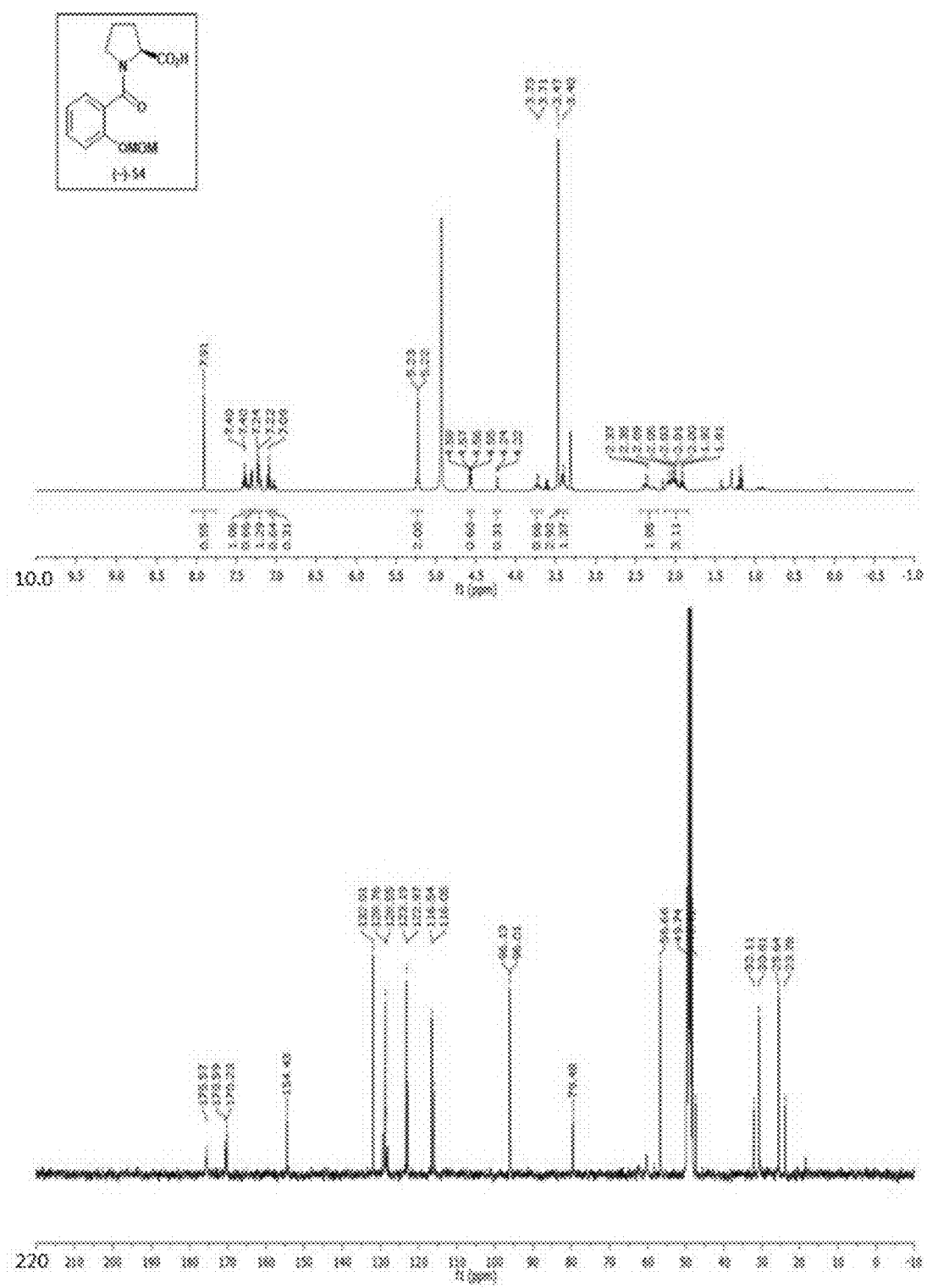
FIG. 31 depicts the proton ($^1$H) and carbon ($^{13}$C) NMR spectra of promysalin synthetic intermediate (−)-S4.
Figure 32:
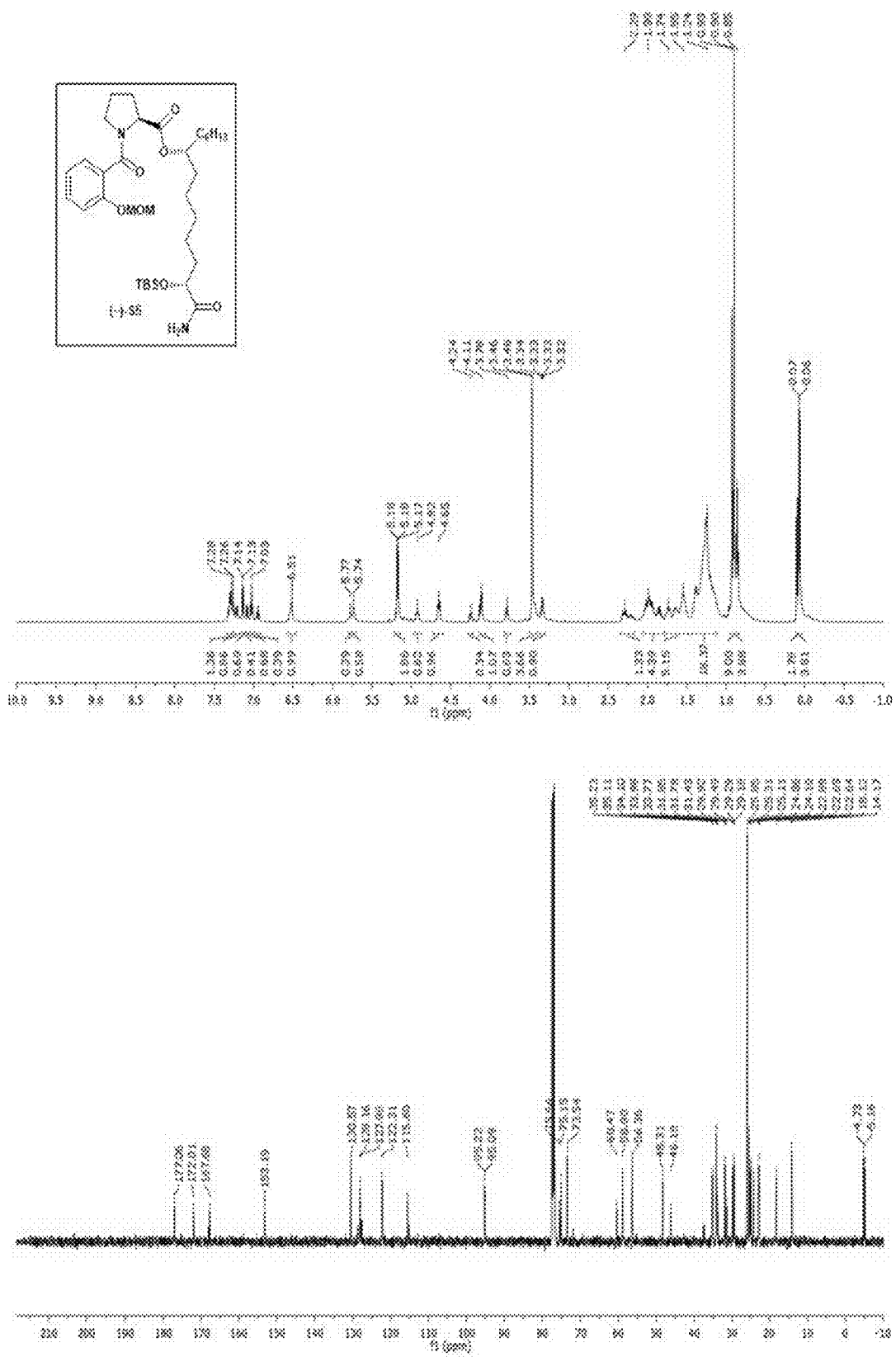
FIG. 32 depicts the proton ($^1$H) and carbon ($^{13}$C) NMR spectra of promysalin synthetic intermediate (−)-S5.
Figure 33:
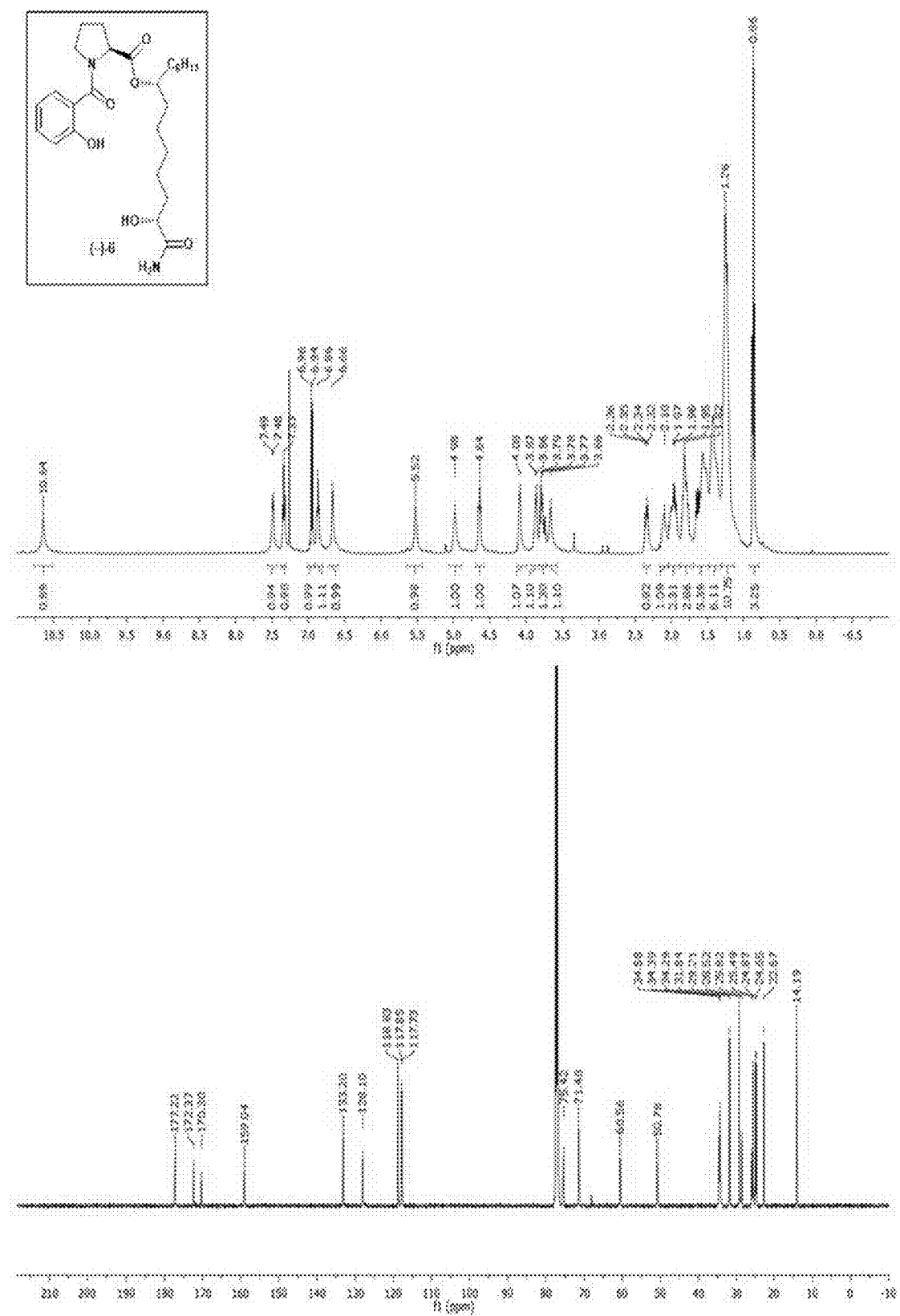
FIG. 33 depicts the proton ($^1$H) and carbon ($^{13}$C) NMR spectra of promysalin analog (−)-6.
Figure 34:
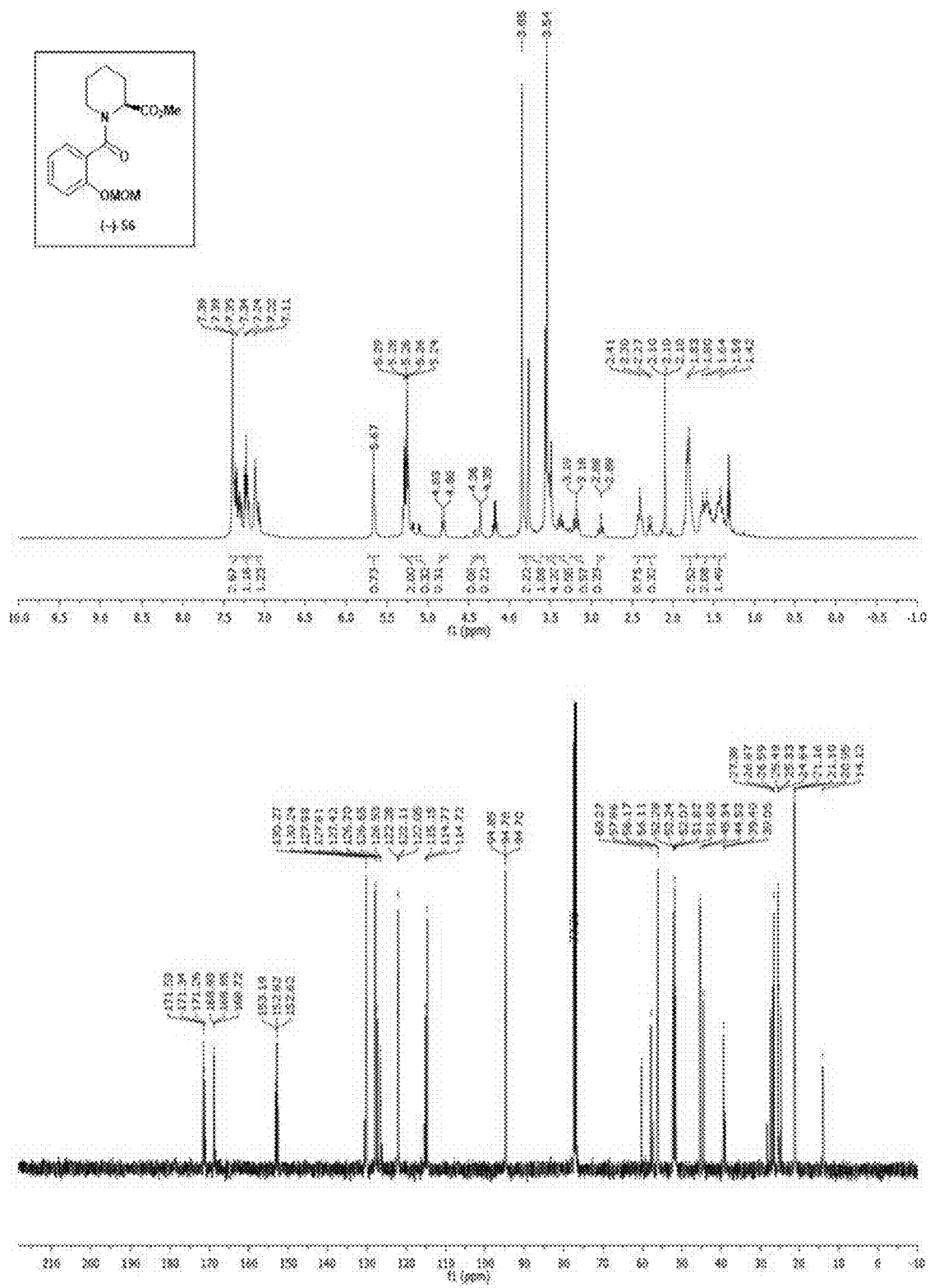
FIG. 34 depicts the proton ($^1$H) and carbon ($^{13}$C) NMR spectra of promysalin synthetic intermediate (−)-S6.
Figure 35:
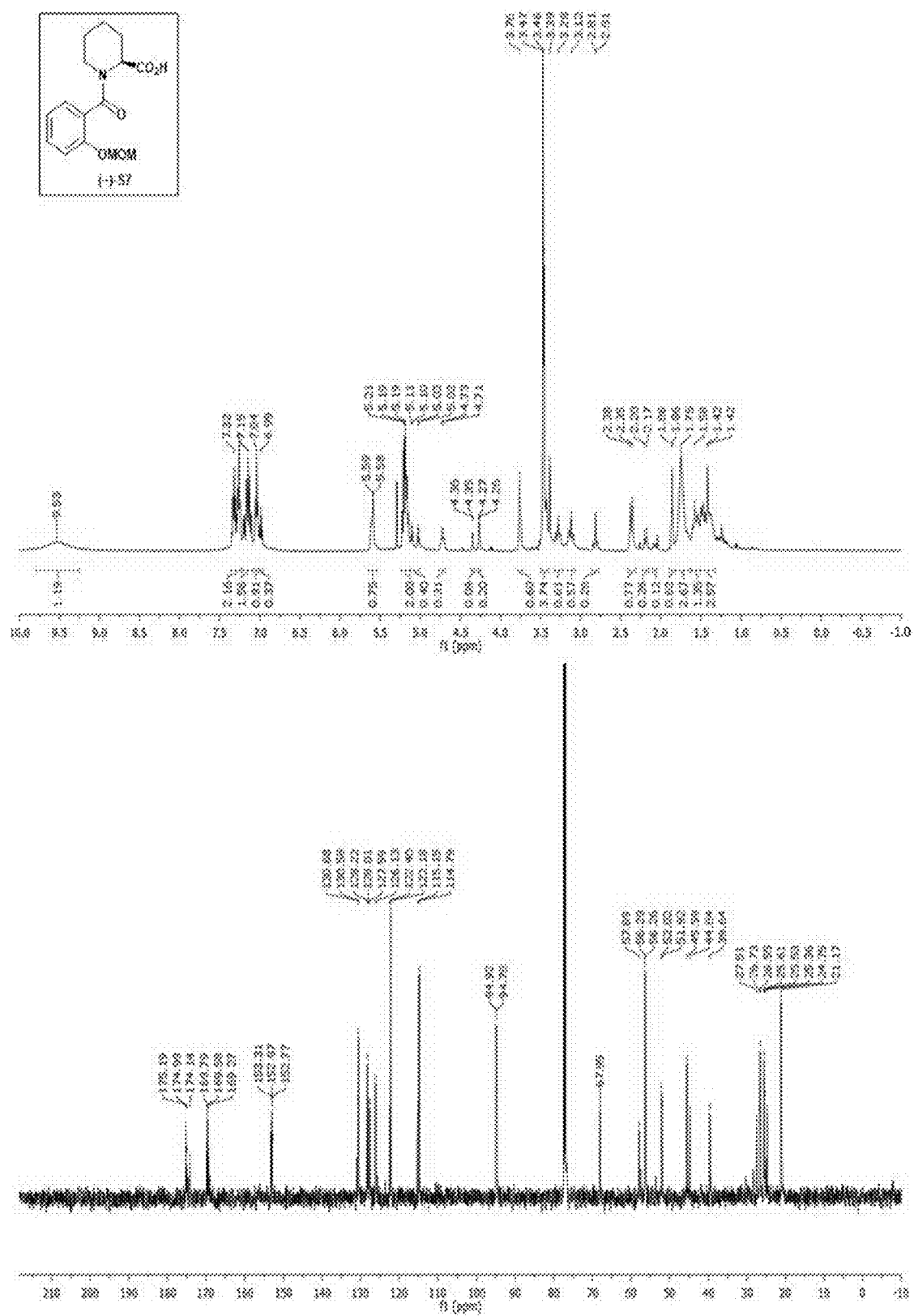
FIG. 35 depicts the proton ($^1$H) and carbon ($^{13}$C) NMR spectra of promysalin synthetic intermediate (−)-S7.
Figure 36:
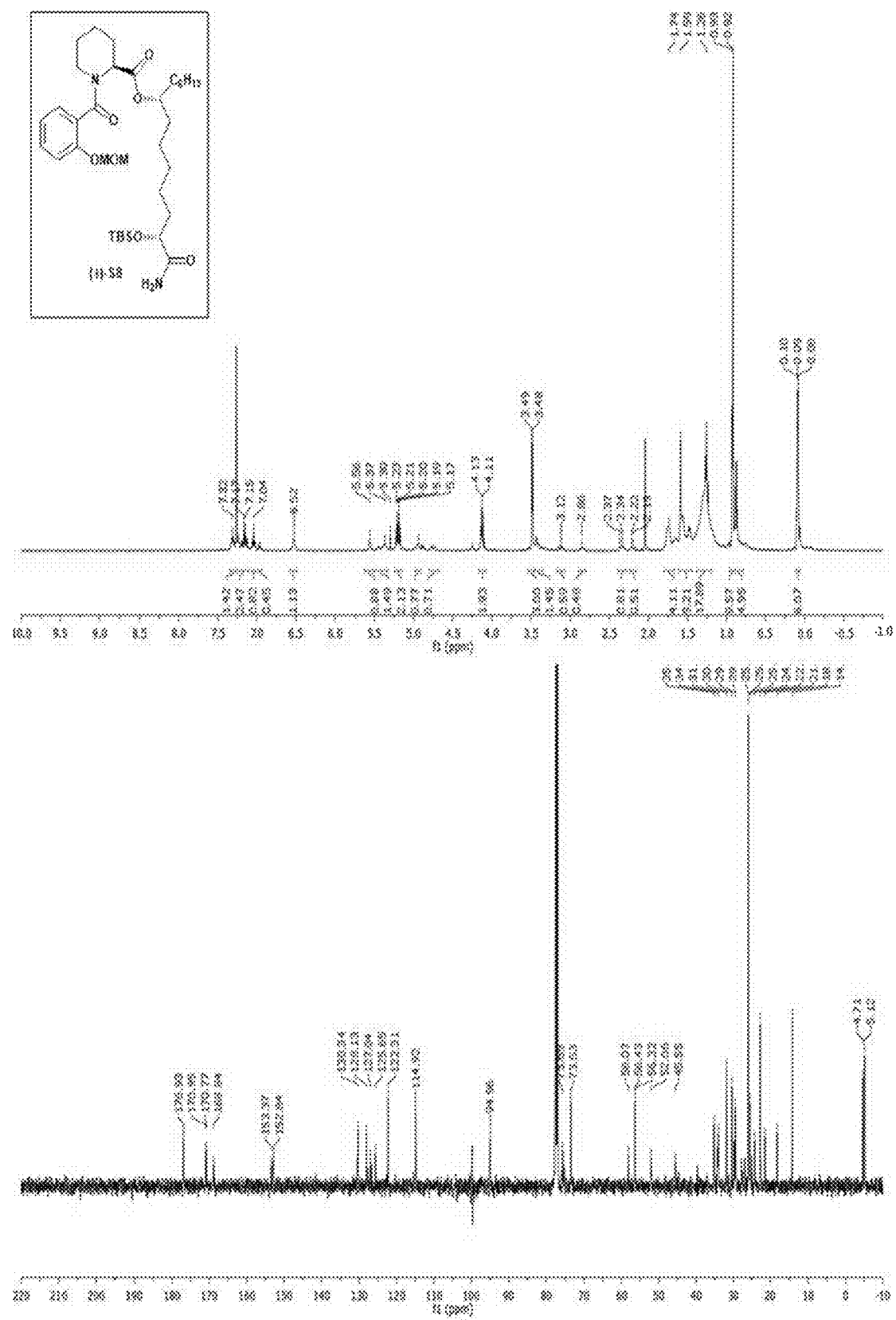
FIG. 36 depicts the proton ($^1$H) and carbon ($^{13}$C) NMR spectra of promysalin synthetic intermediate (+)-S8.
Figure 37:
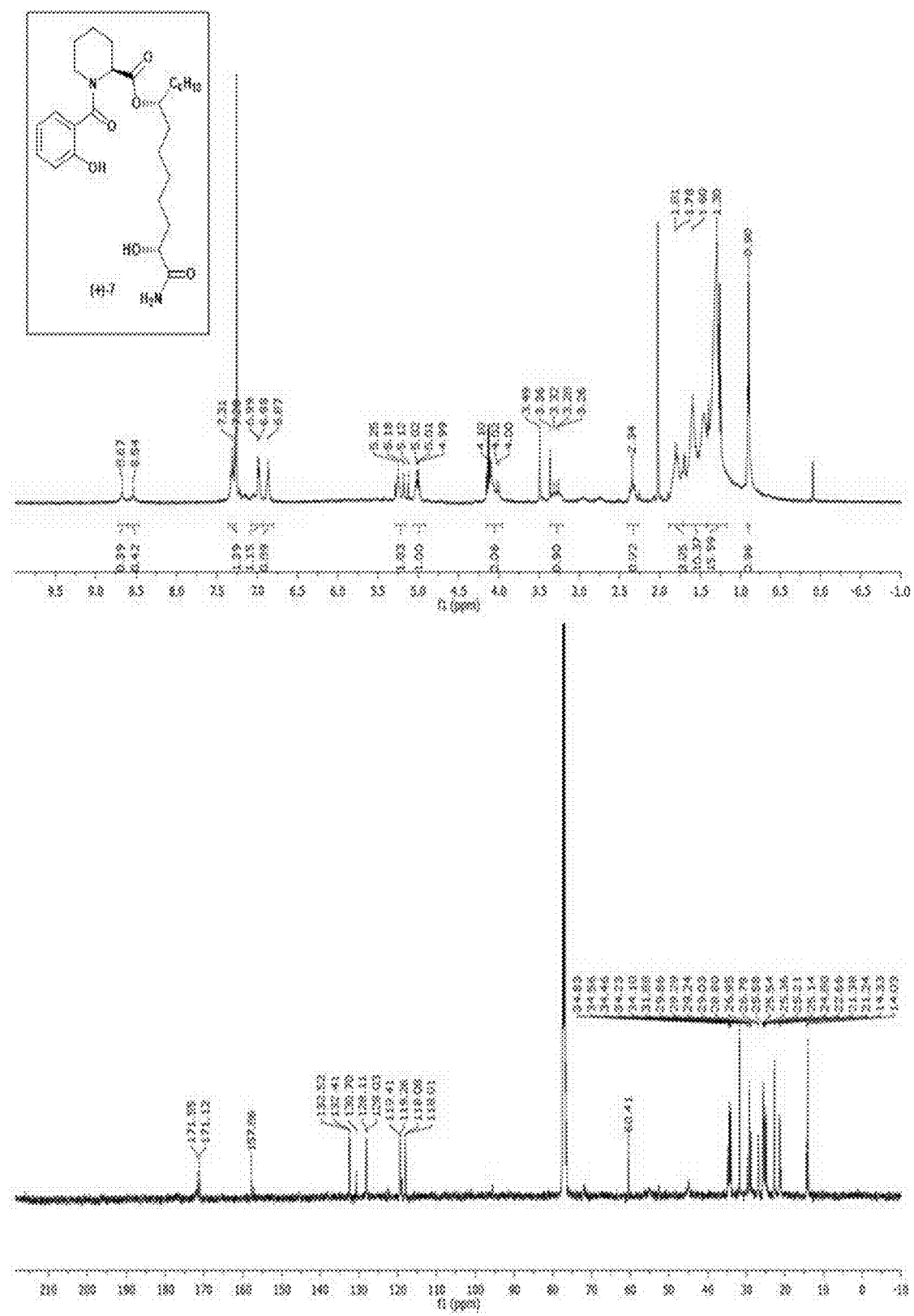
FIG. 37 depicts the proton ($^1$H) and carbon ($^{13}$C) NMR spectra of promysalin analog (+)-7.
Figure 38:
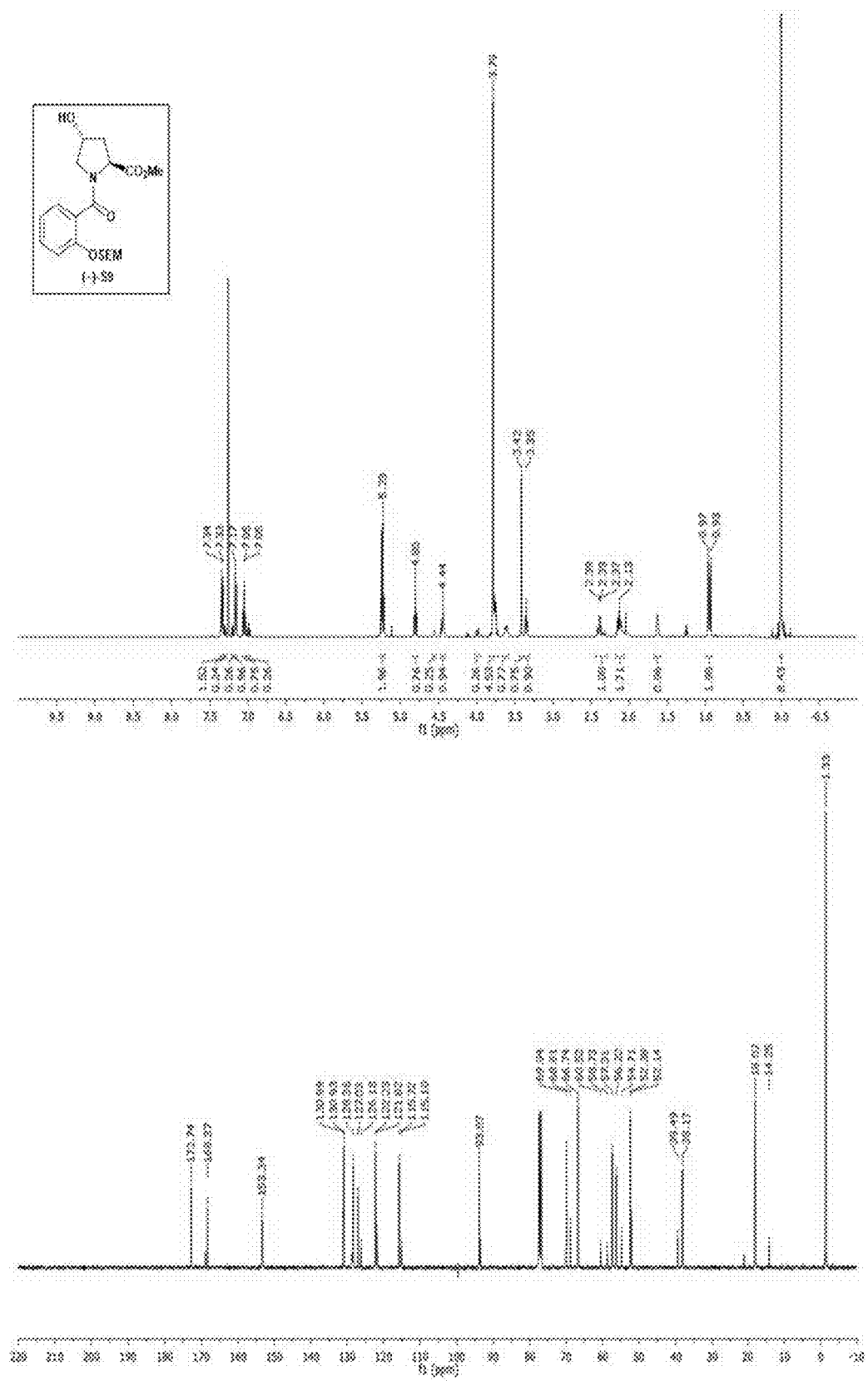
FIG. 38 depicts the proton ($^1$H) and carbon ($^{13}$C) NMR spectra of promysalin synthetic intermediate (−)-S9.
Figure 39:
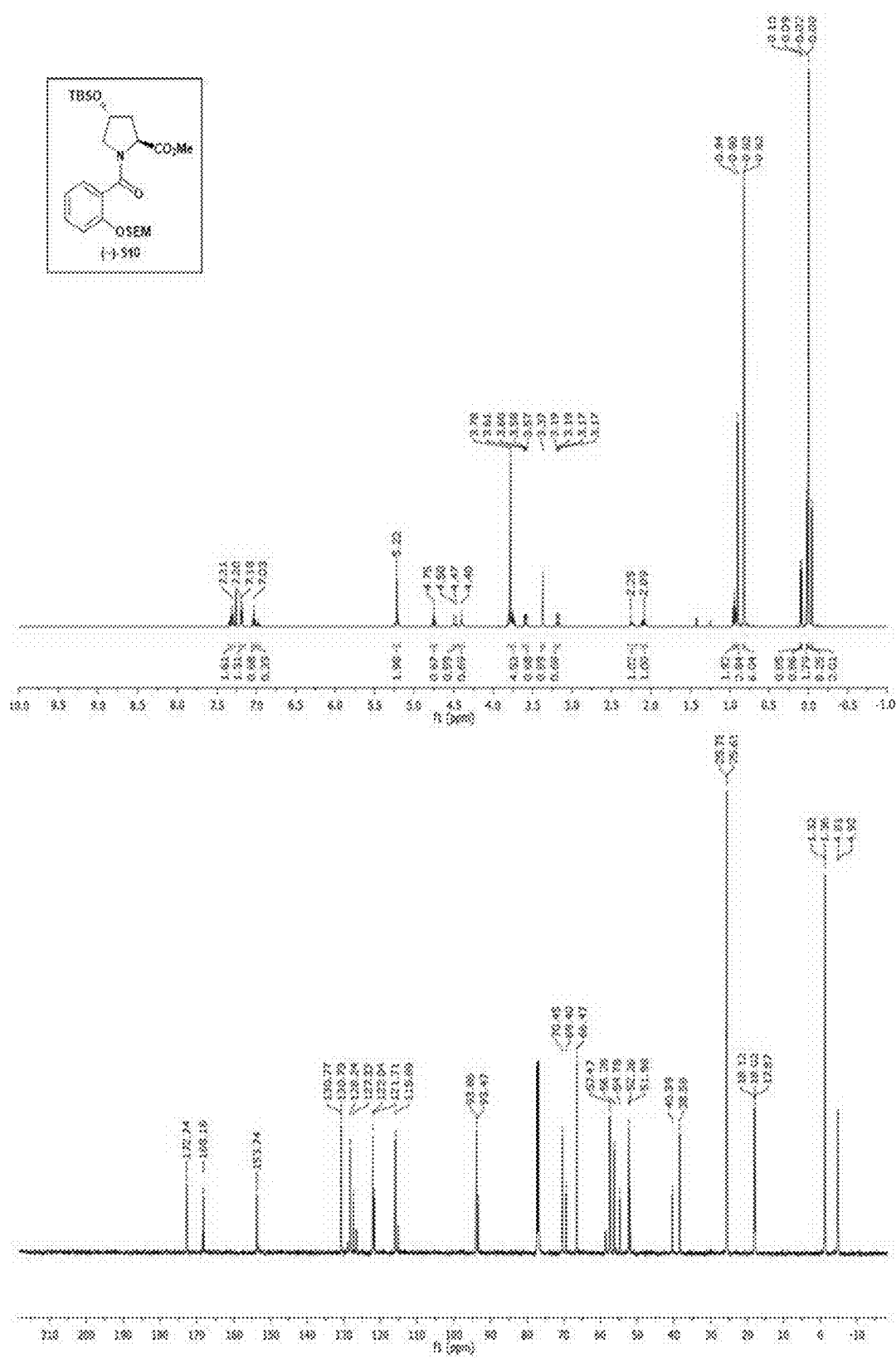
FIG. 39 depicts the proton ($^1$H) and carbon ($^{13}$C) NMR spectra of promysalin synthetic intermediate (−)-S10.
Figure 40:
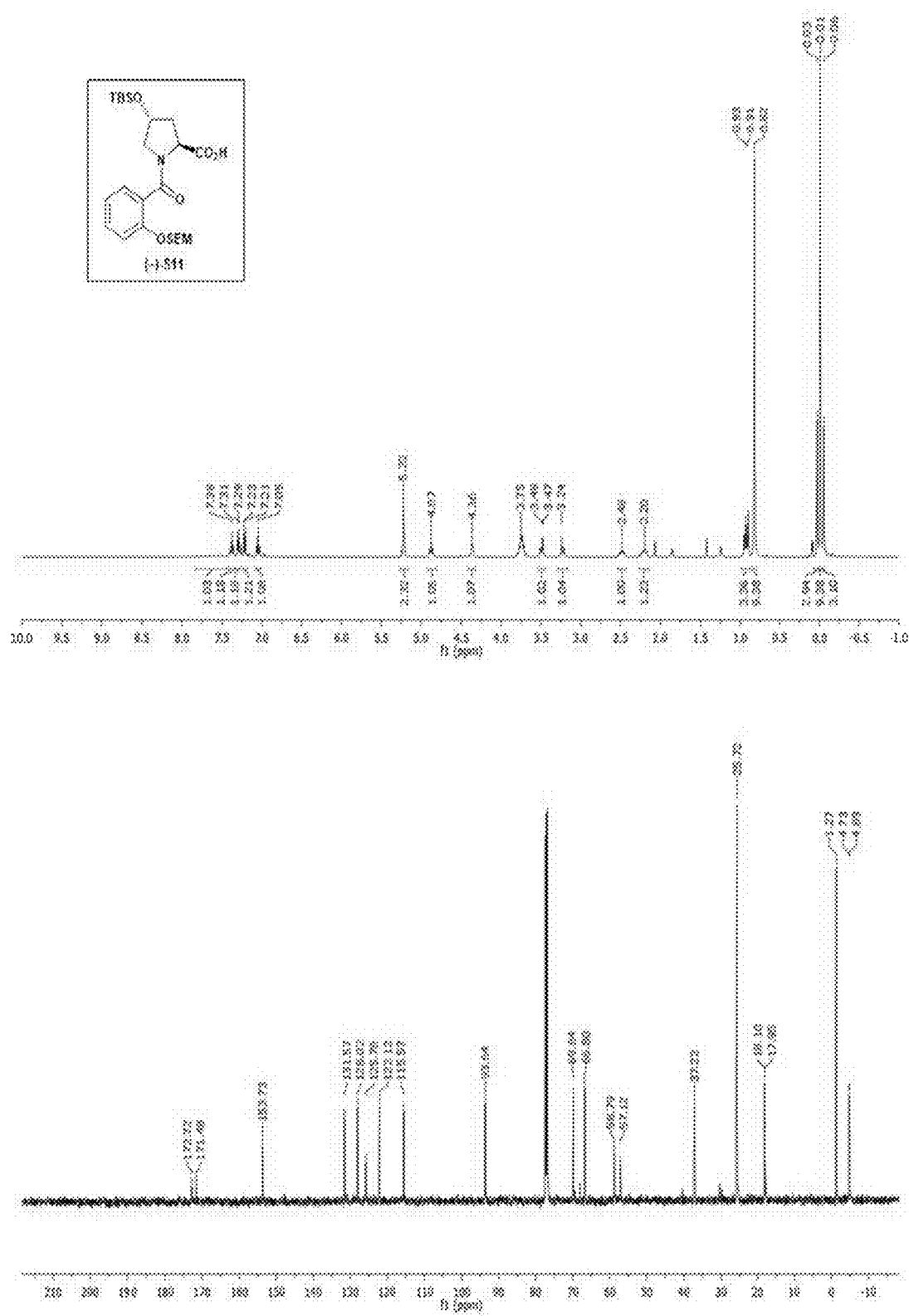
FIG. 40 depicts the proton ($^1$H) and carbon ($^{13}$C) NMR spectra of promysalin synthetic intermediate (−)-S11.
Figure 41:
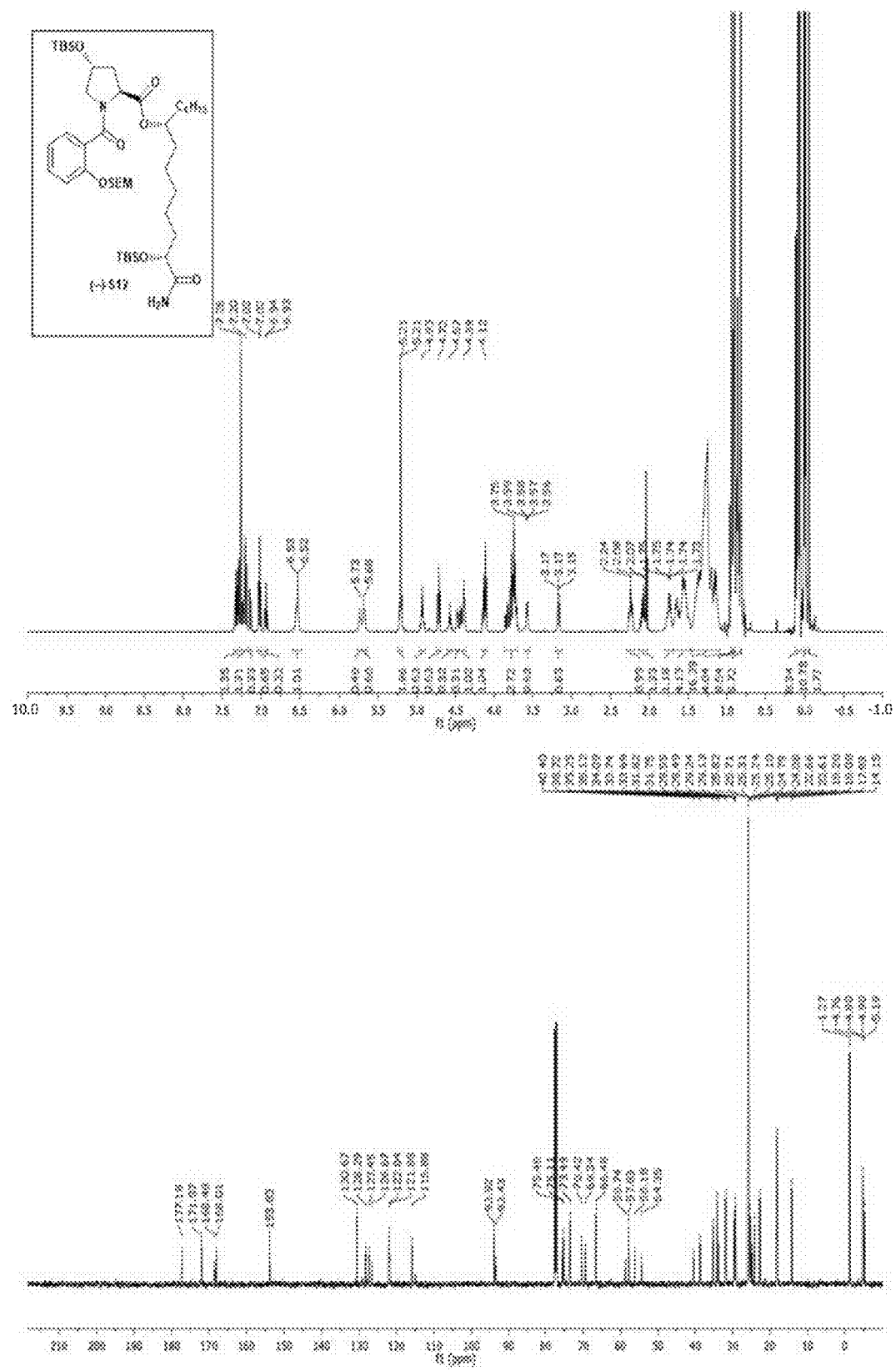
FIG. 41 depicts the proton ($^1$H) and carbon ($^{13}$C) NMR spectra of promysalin synthetic intermediate (−)-S12.
Figure 42:
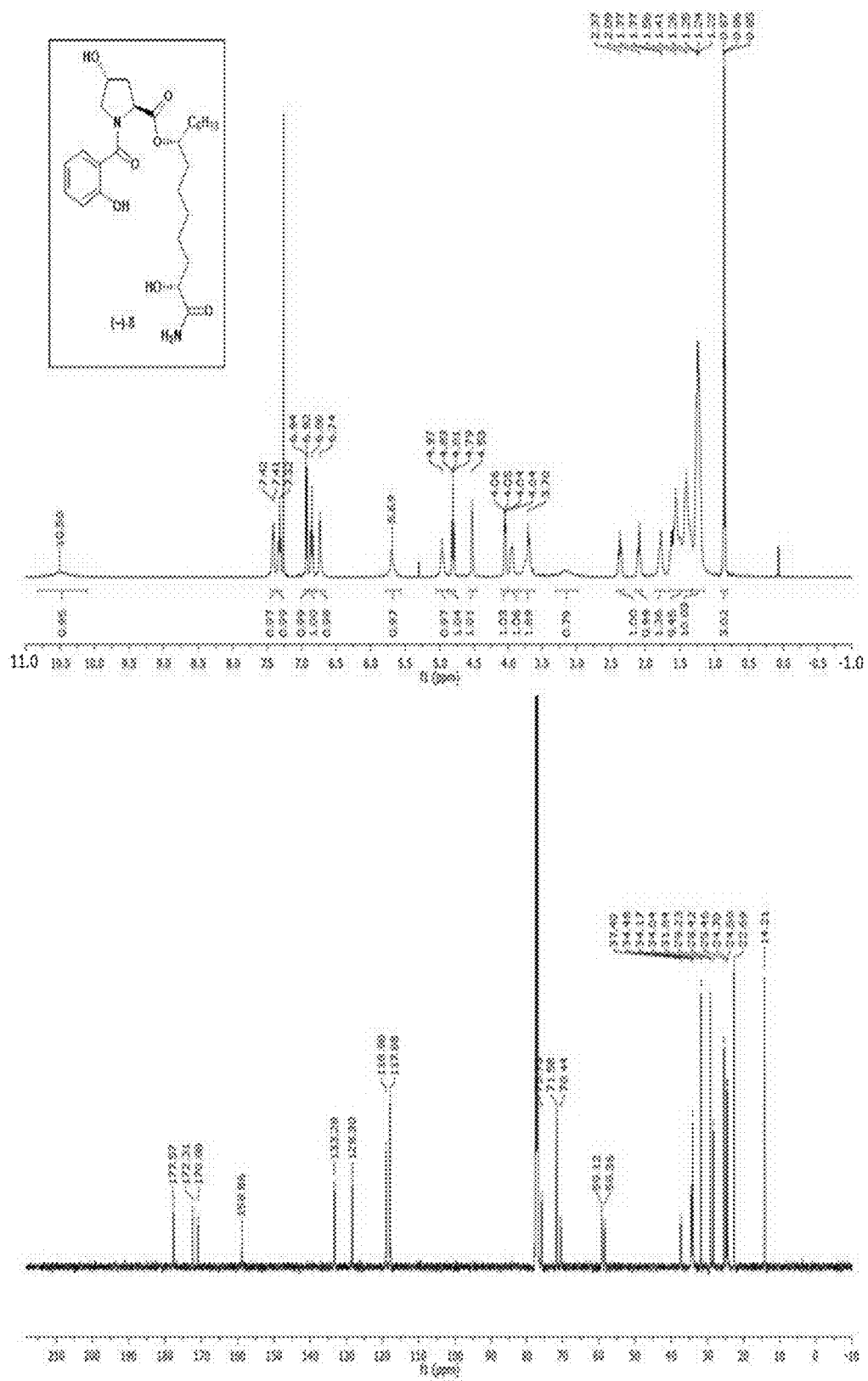
FIG. 42 depicts the proton ($^1$H) and carbon ($^{13}$C) NMR spectra of promysalin analog (−)-8.
Figure 43:
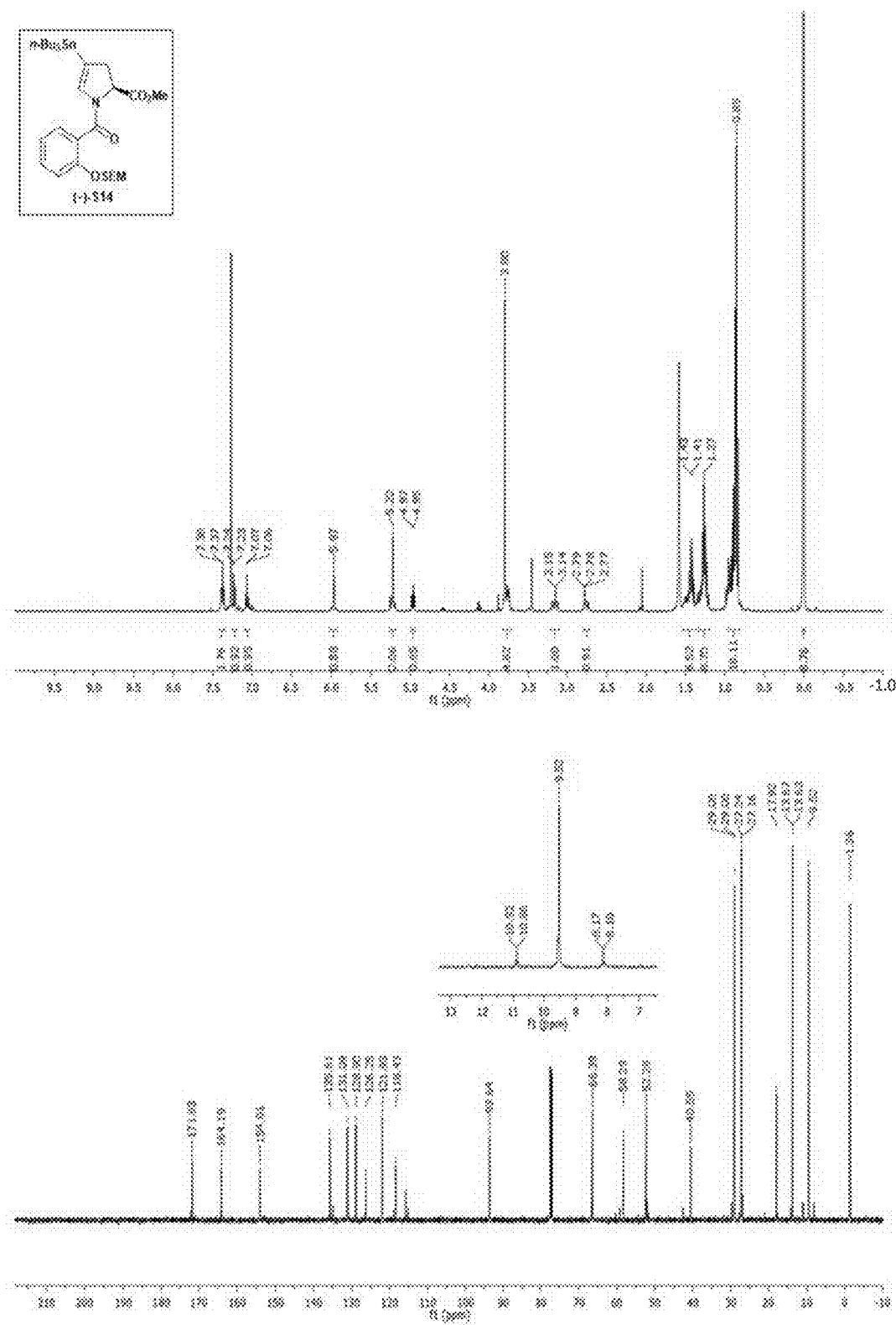
FIG. 43 depicts the proton ($^1$H) and carbon ($^{13}$C) NMR spectra of promysalin synthetic intermediate (−)-S14.
Figure 44:
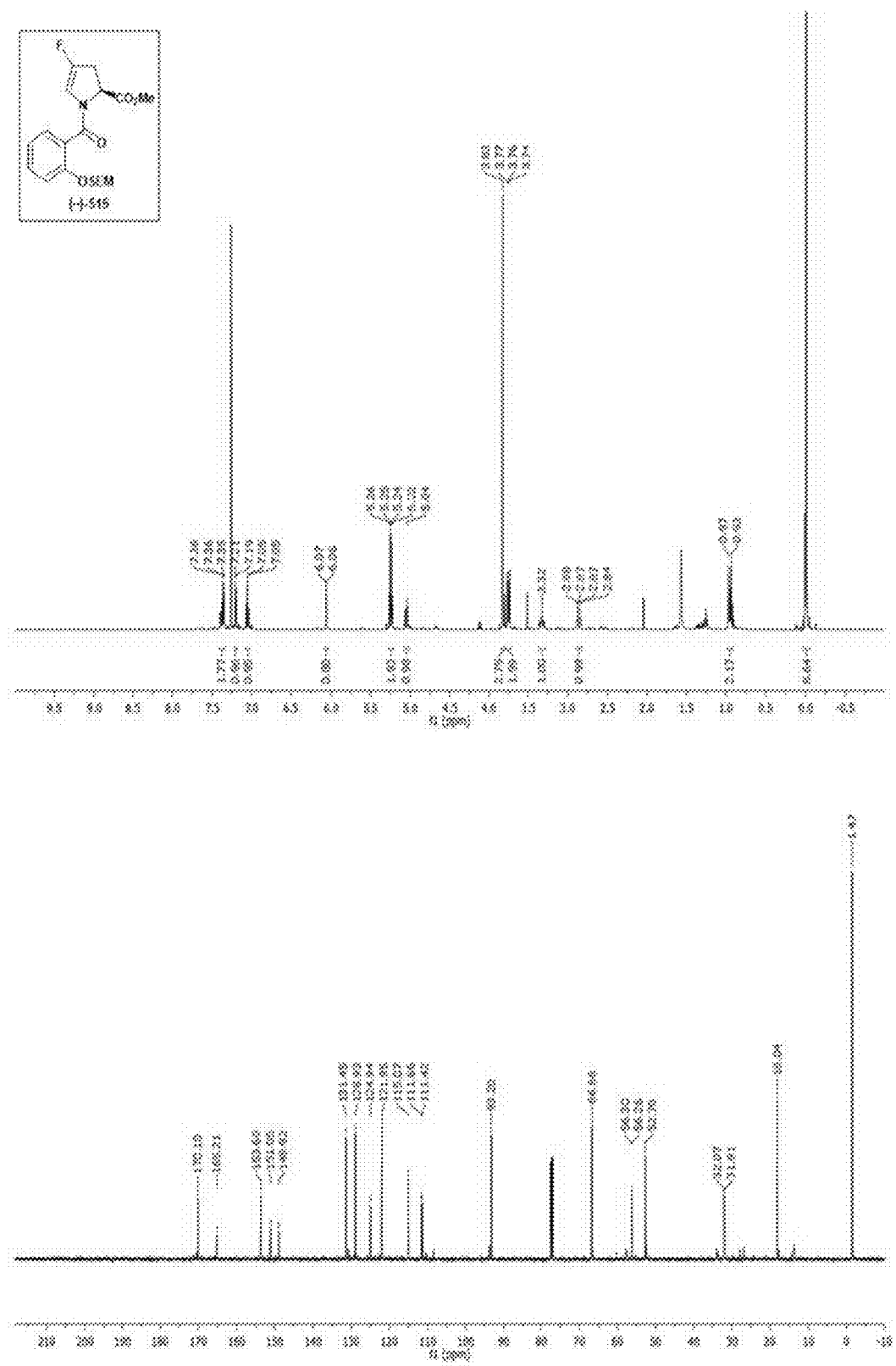
FIG. 44 depicts the proton ($^1$H) and carbon ($^{13}$C) NMR spectra of promysalin synthetic intermediate (−)-S15.
Figure 45:
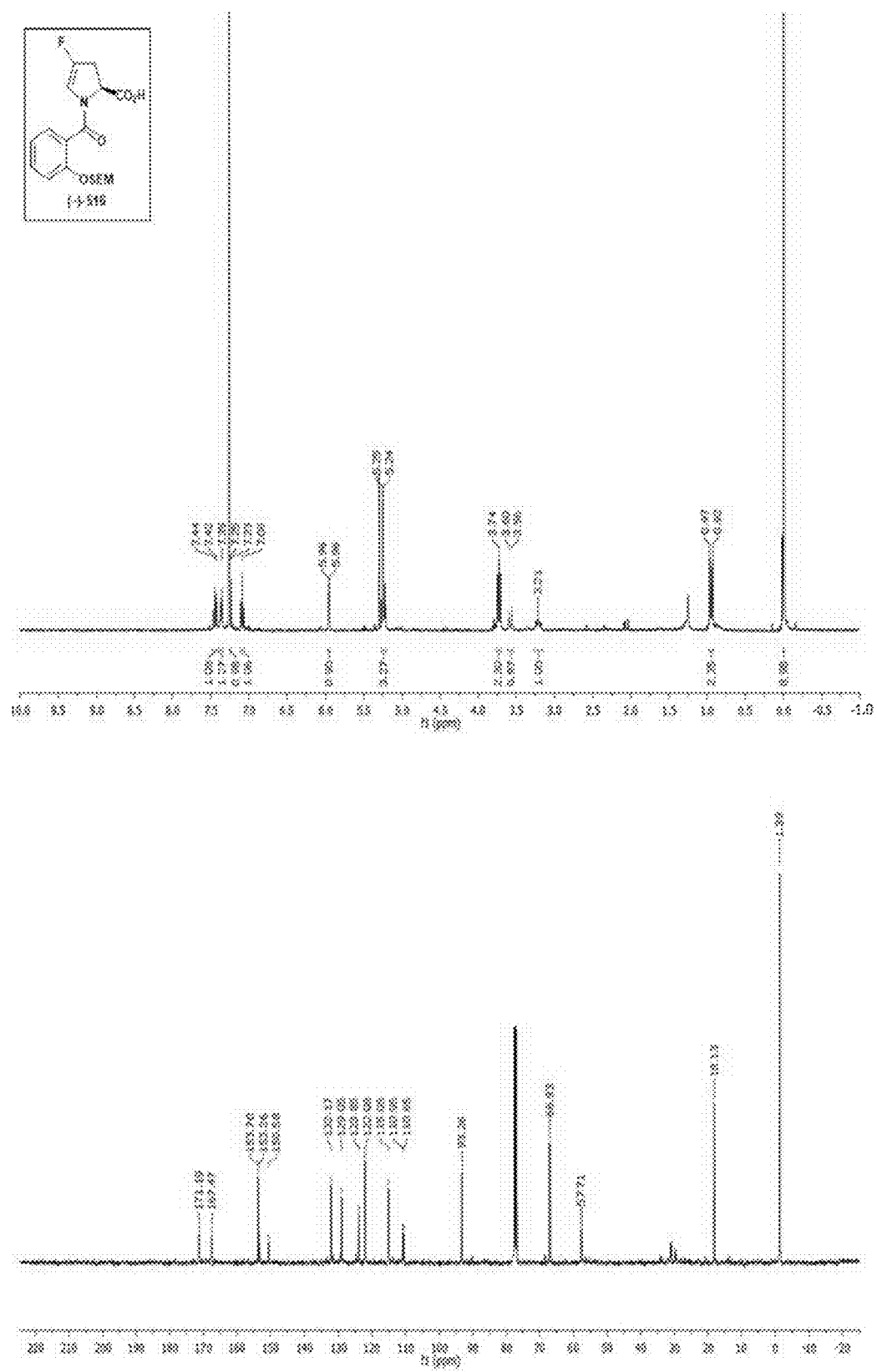
FIG. 45 depicts the proton ($^1$H) and carbon ($^{13}$C) NMR spectra of promysalin synthetic intermediate (−)-S16.
Figure 46:
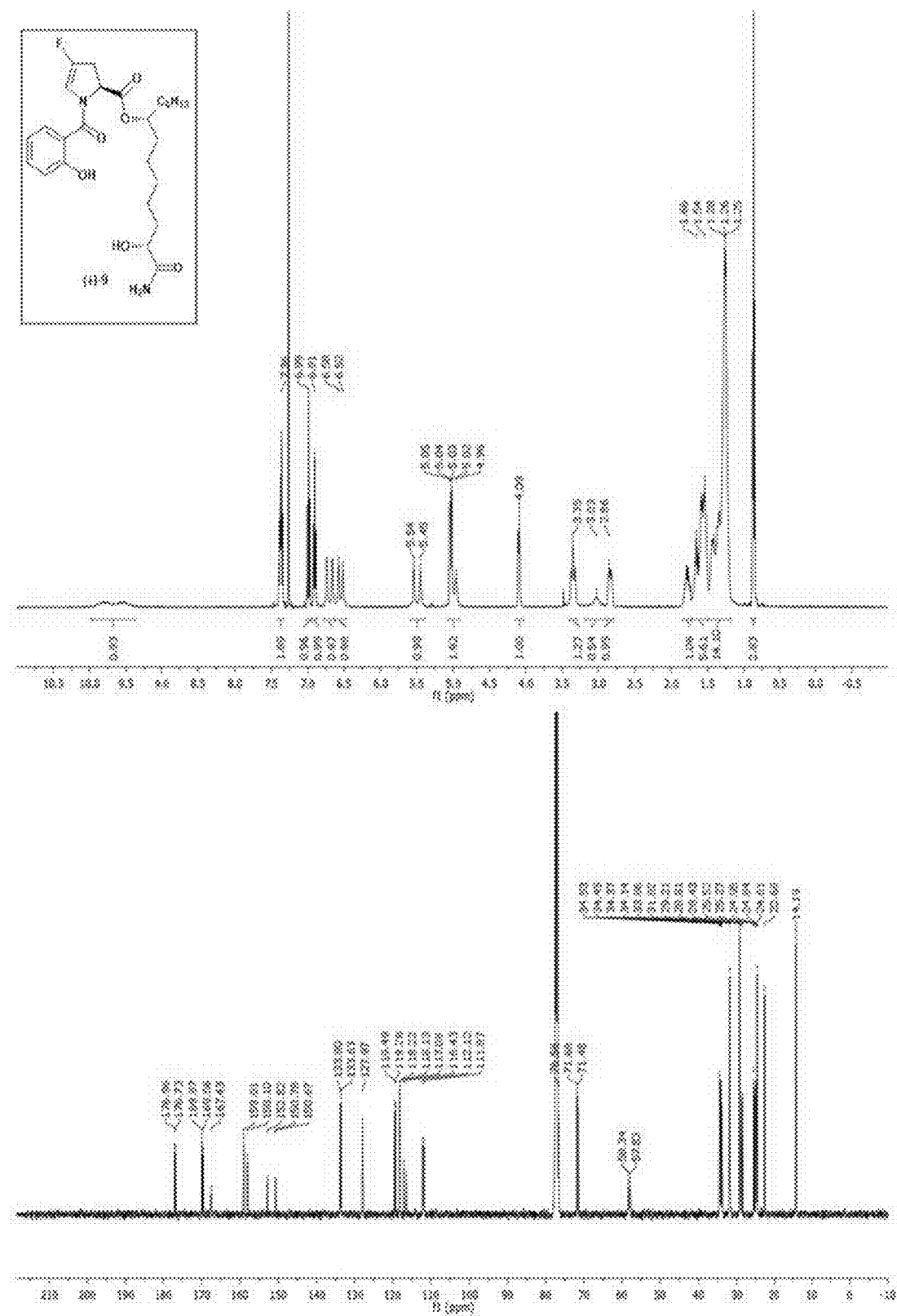
FIG. 46 depicts the proton ($^1$H) and carbon ($^{13}$C) NMR spectra of promysalin analog (+)-9.
Figure 47:
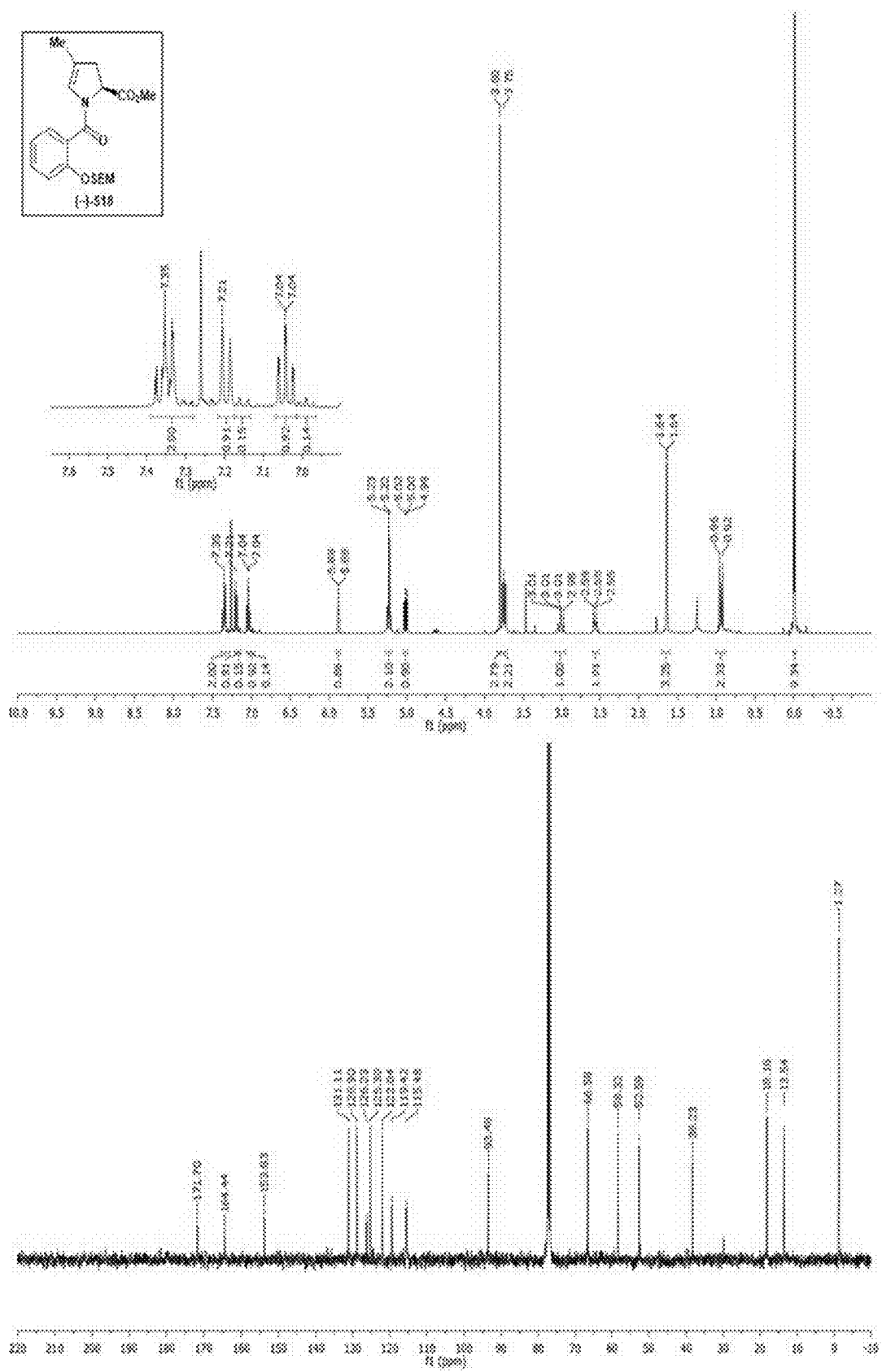
FIG. 47 depicts the proton ($^1$H) and carbon ($^{13}$C) NMR spectra of promysalin synthetic intermediate (−)-S18.
Figure 48:
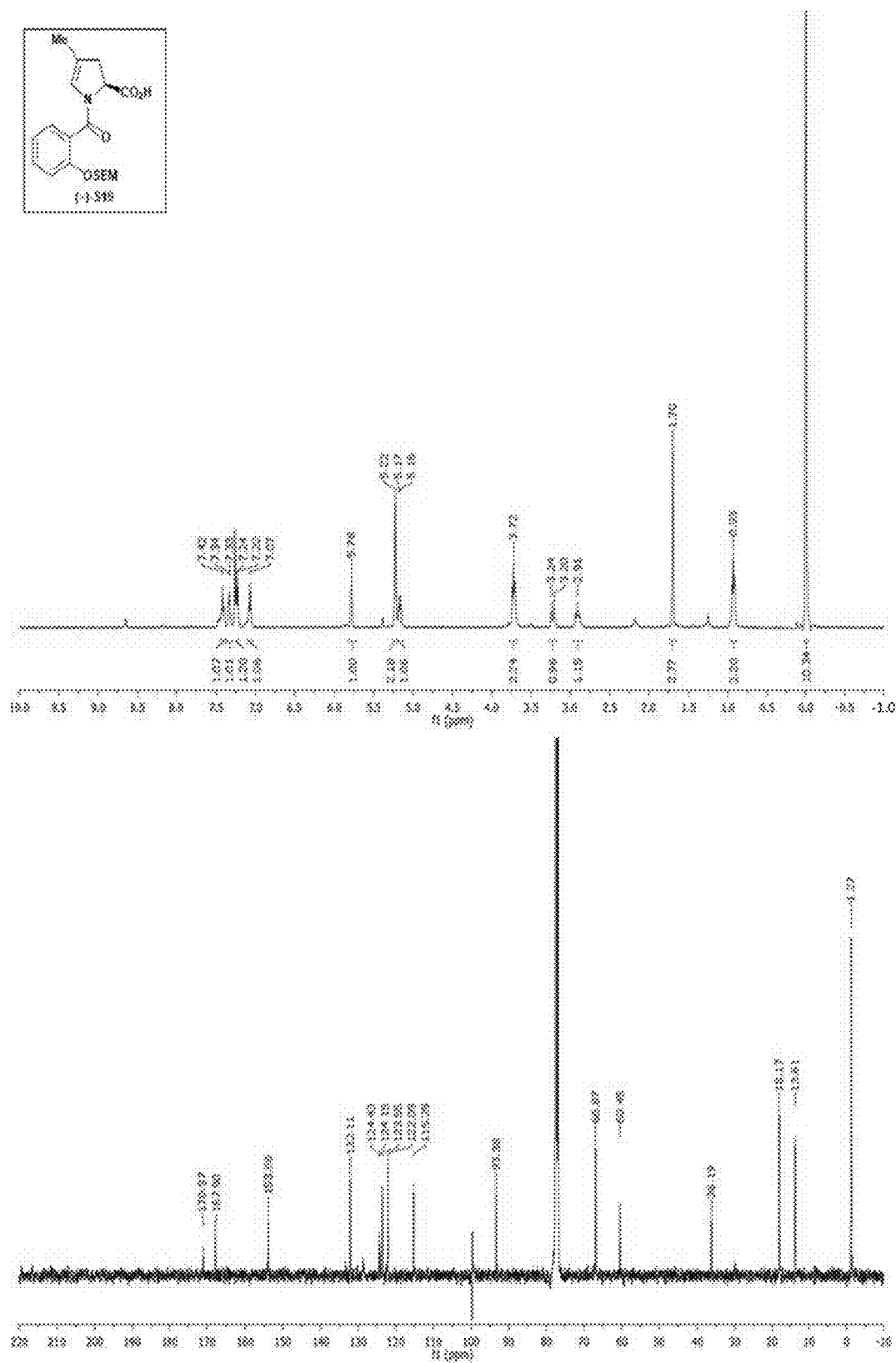
FIG. 48 depicts the proton ($^1$H) and carbon ($^{13}$C) NMR spectra of promysalin synthetic intermediate (−)-S19.
Figure 49:
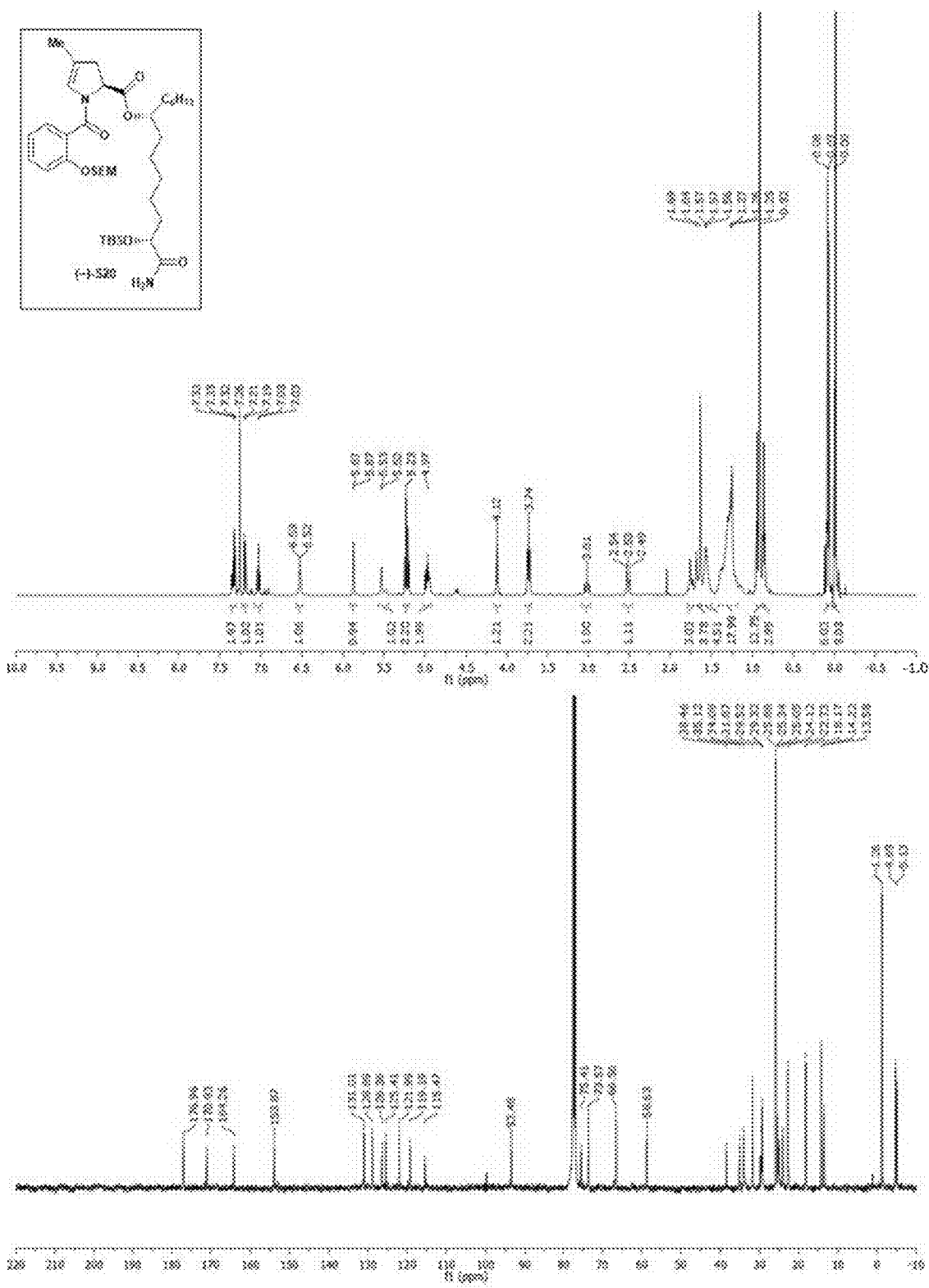
FIG. 49 depicts the proton ($^1$H) and carbon ($^{13}$C) NMR spectra of promysalin synthetic intermediate (−)-S20.
Figure 50:
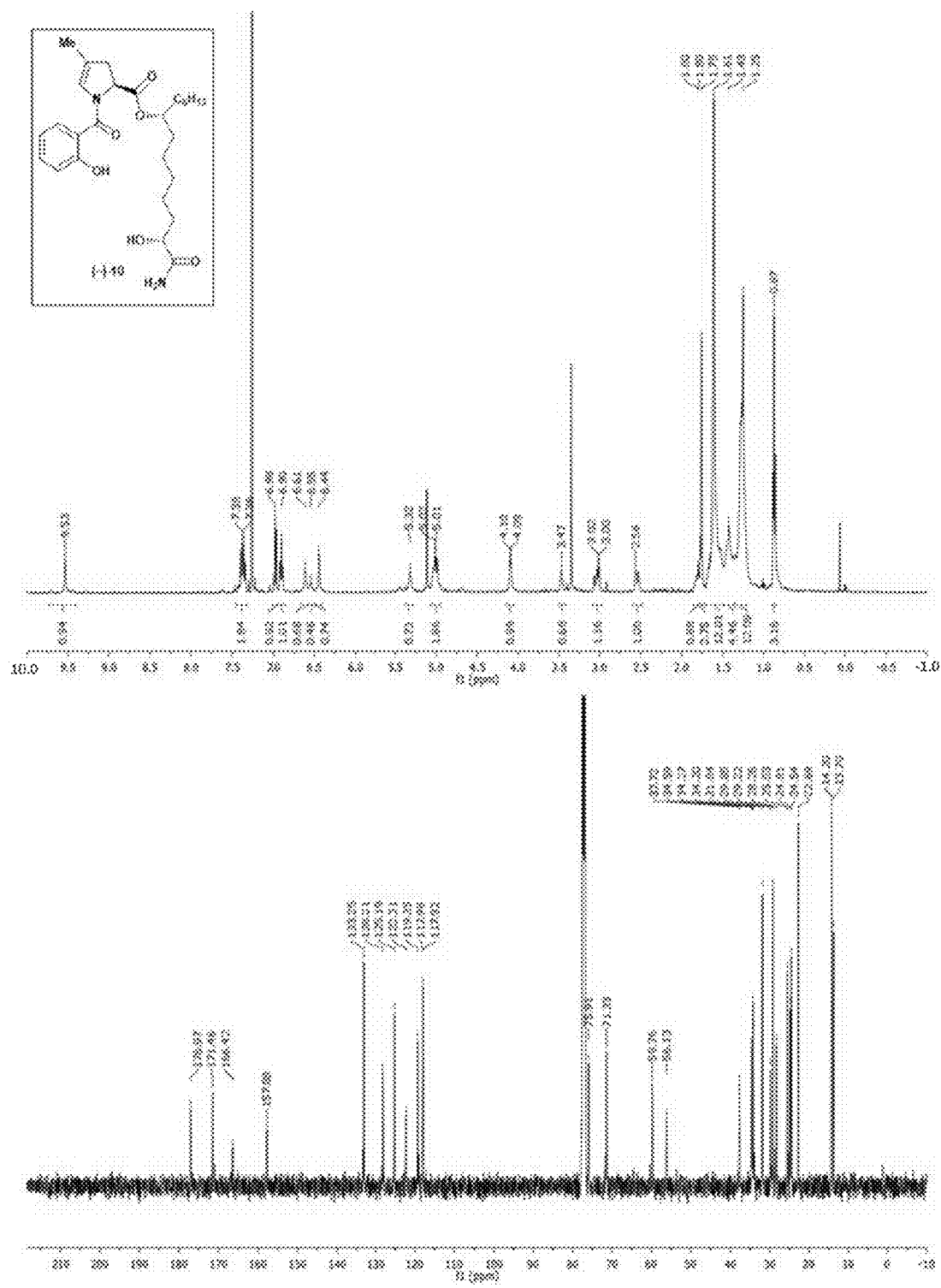
FIG. 50 depicts the proton ($^1$H) and carbon ($^{13}$C) NMR spectra of promysalin analog (−)-10.
Figure 51:
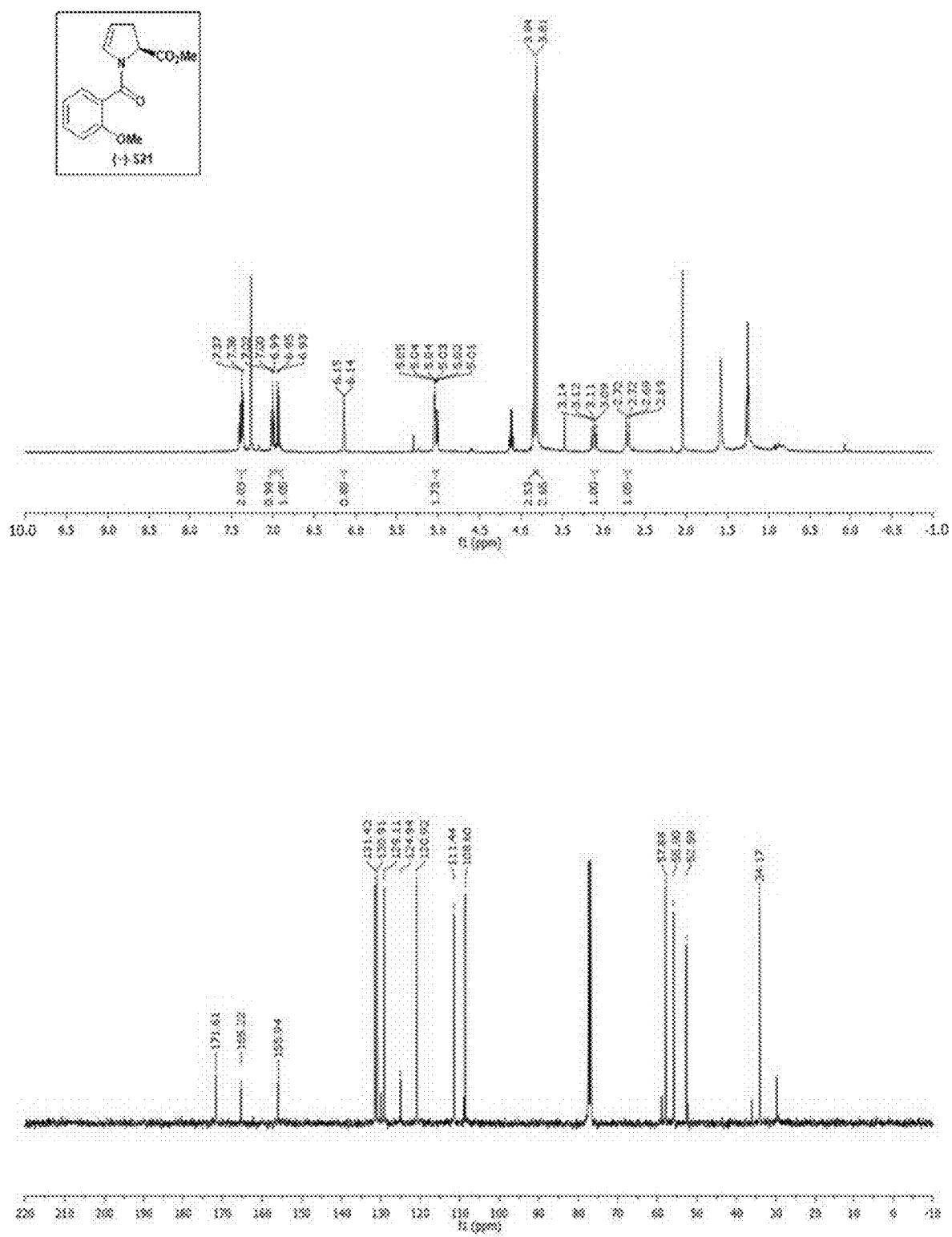
FIG. 51 depicts the proton ($^1$H) and carbon ($^{13}$C) NMR spectra of promysalin synthetic intermediate (−)-S21.
Figure 52:
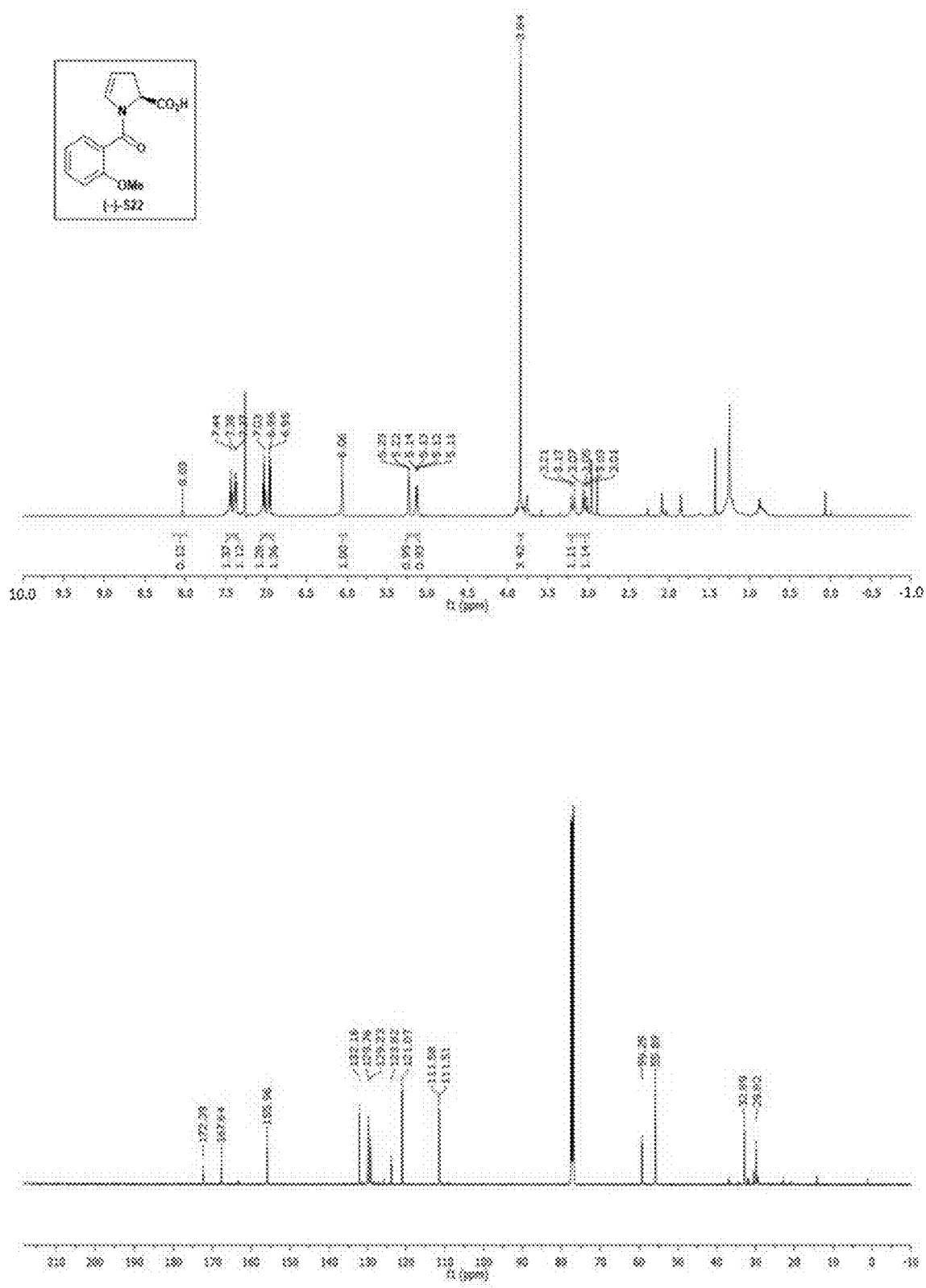
FIG. 52 depicts the proton ($^1$H) and carbon ($^{13}$C) NMR spectra of promysalin synthetic intermediate (−)-S22.
Figure 53:
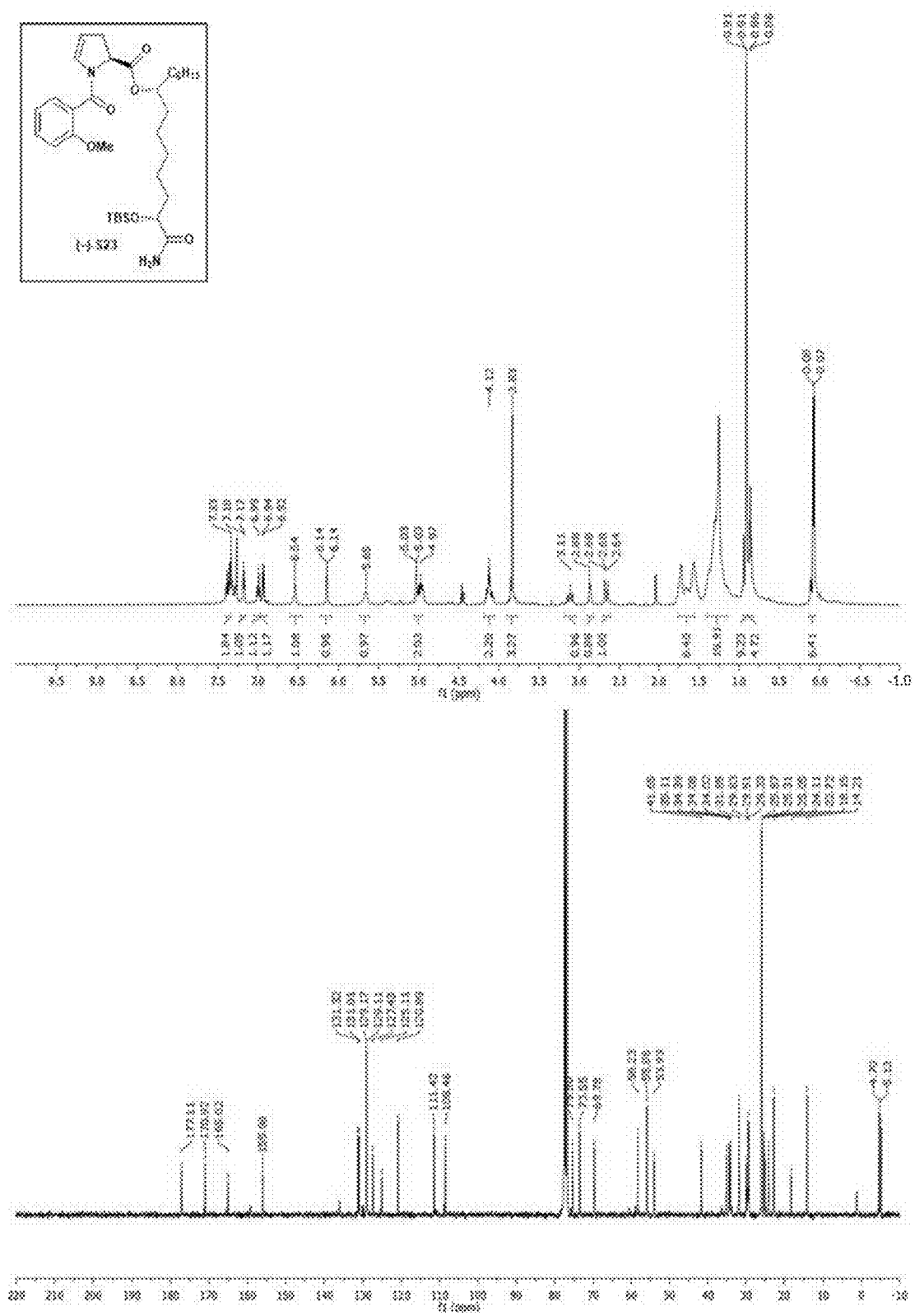
FIG. 53 depicts the proton ($^1$H) and carbon ($^{13}$C) NMR spectra of promysalin synthetic intermediate (−)-S23.
Figure 54:
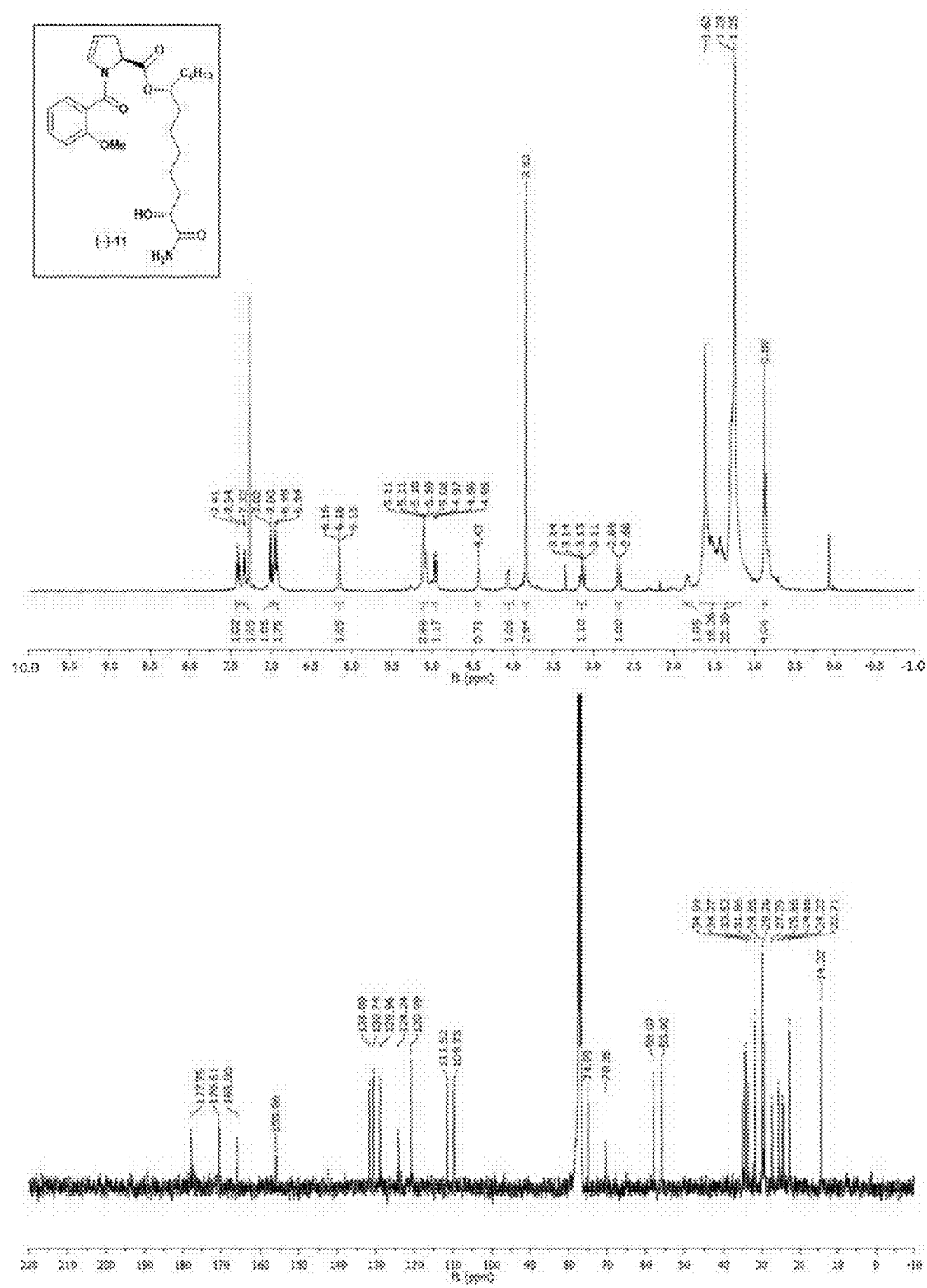
FIG. 54 depicts the proton ($^1$H) and carbon ($^{13}$C) NMR spectra of promysalin analog (−)-11.
Figure 55:
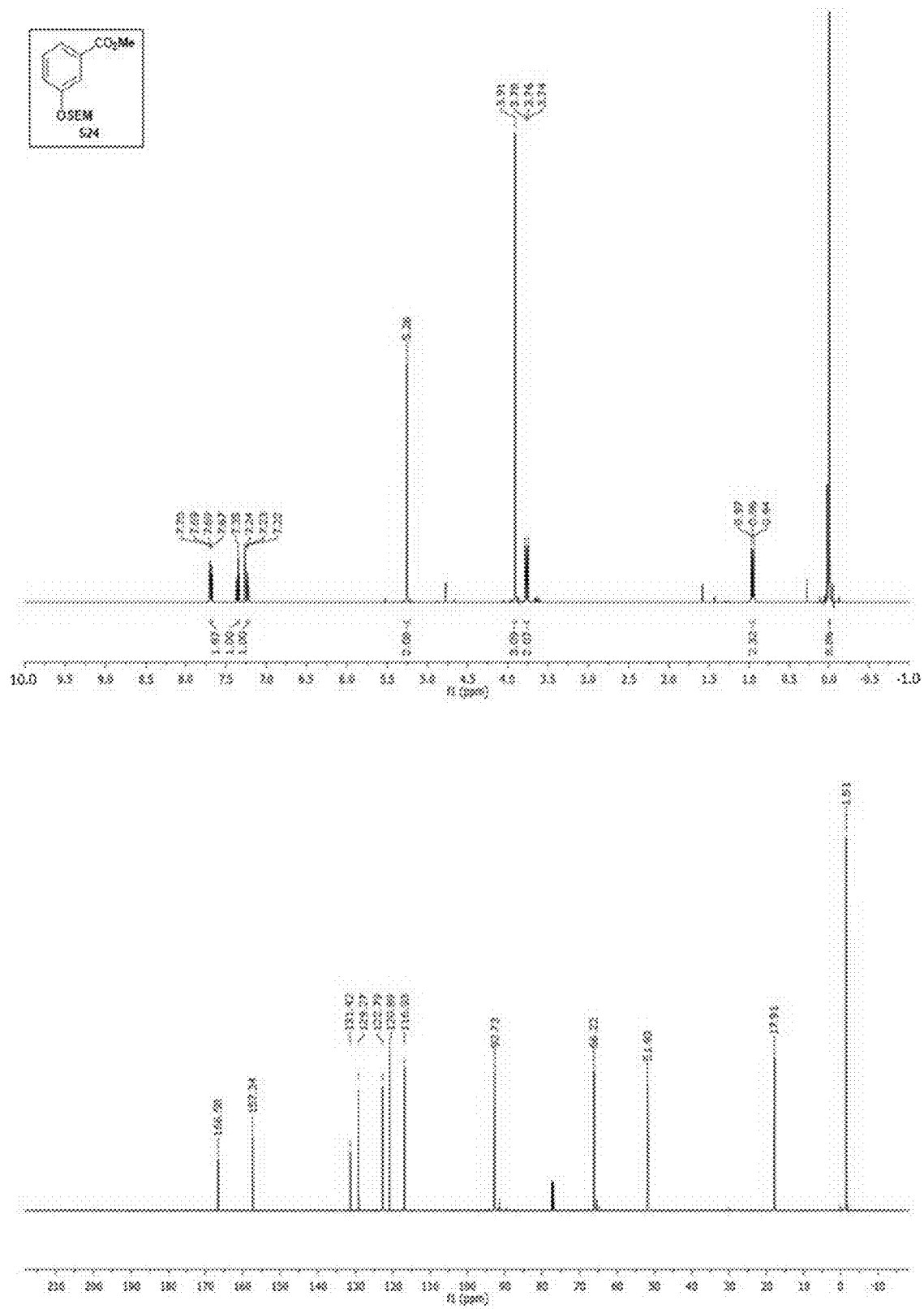
FIG. 55 depicts the proton ($^1$H) and carbon ($^{13}$C) NMR spectra of promysalin synthetic intermediate S24.
Figure 56:
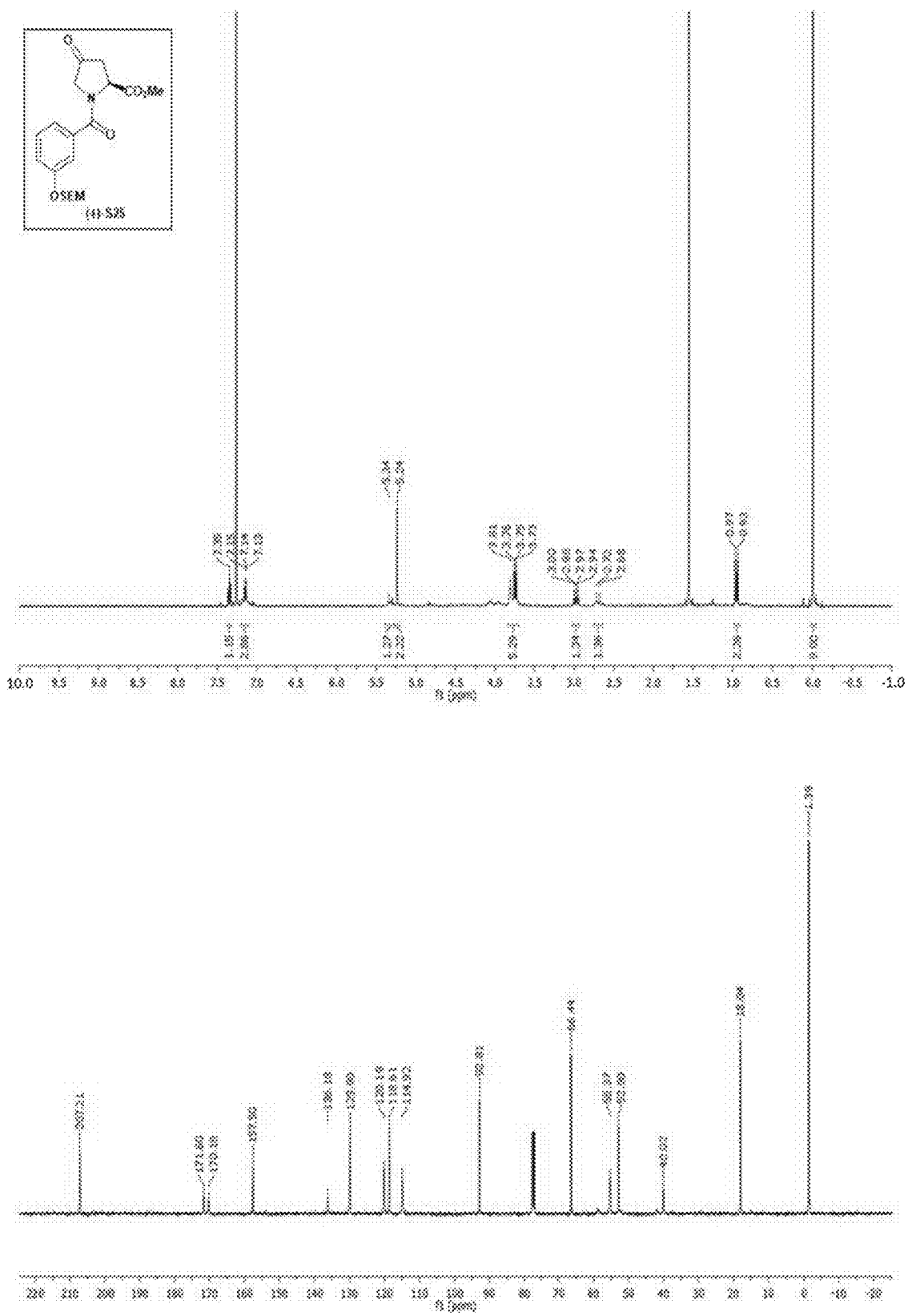
FIG. 56 depicts the proton ($^1$H) and carbon ($^{13}$C) NMR spectra of promysalin synthetic intermediate (+)-S25.
Figure 57:
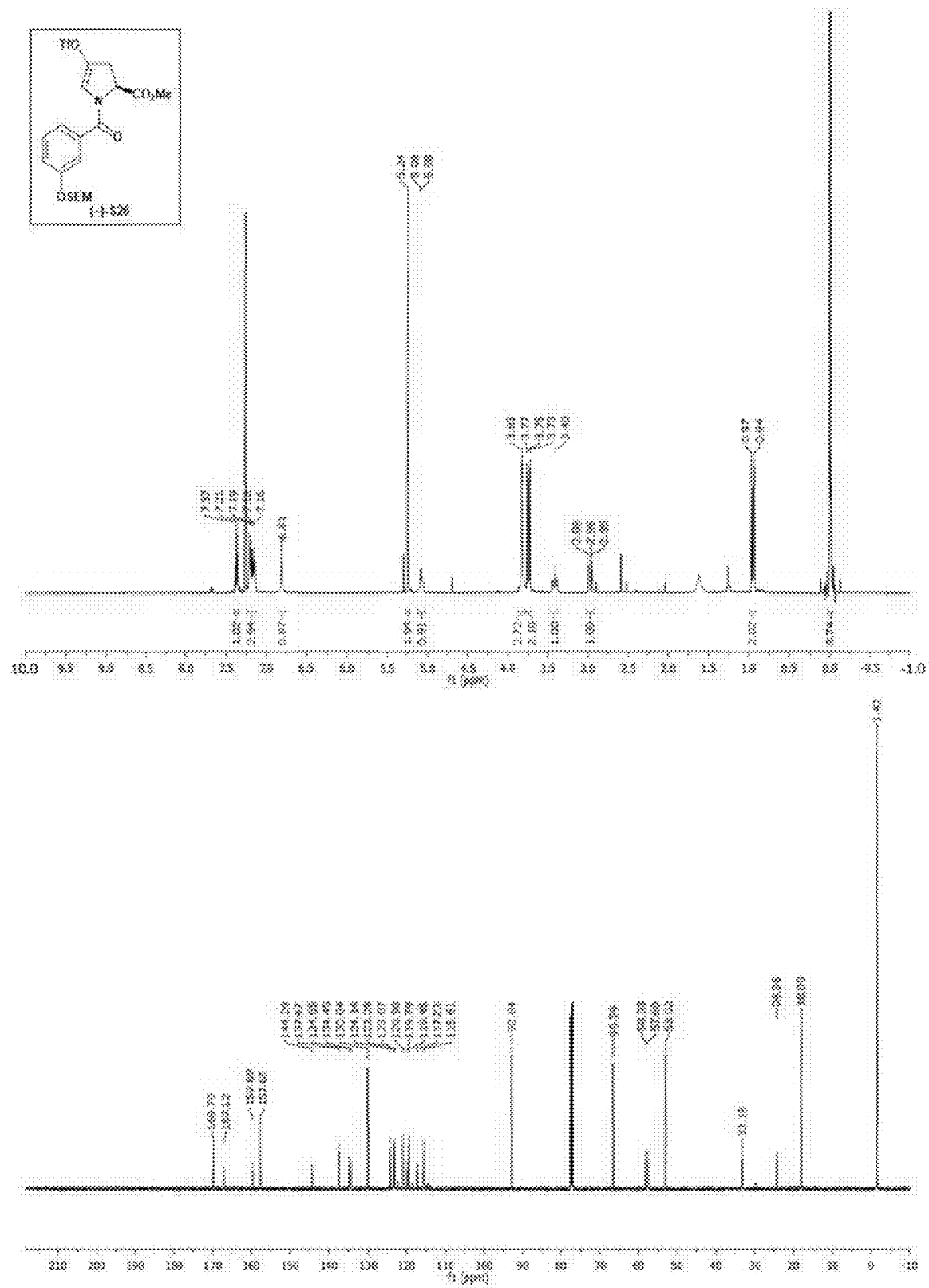
FIG. 57 depicts the proton ($^1$H) and carbon ($^{13}$C) NMR spectra of promysalin synthetic intermediate (−)-S26.
Figure 58:
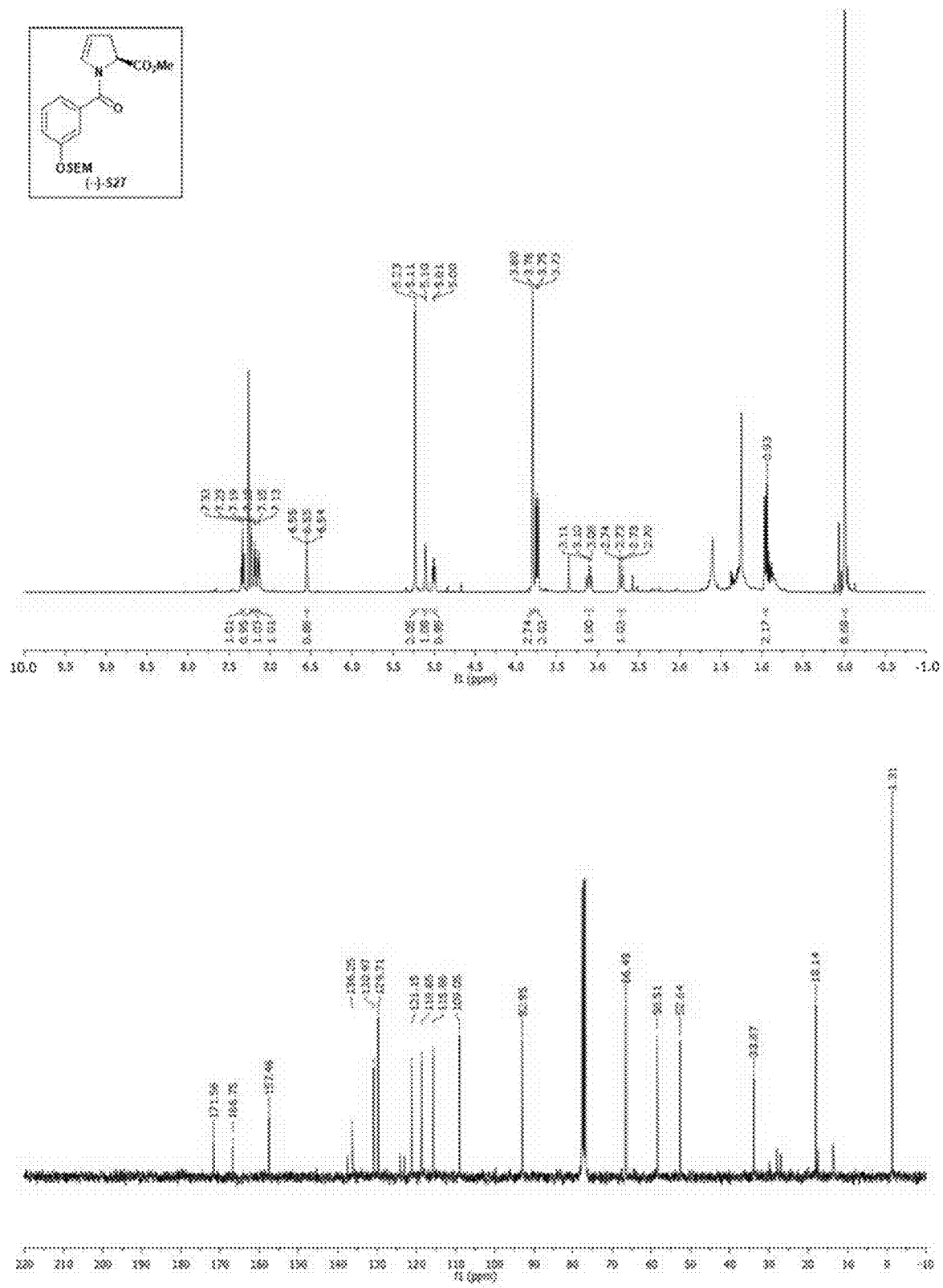
FIG. 58 depicts the proton ($^1$H) and carbon ($^{13}$C) NMR spectra of promysalin synthetic intermediate (−)-S27.
Figure 59:
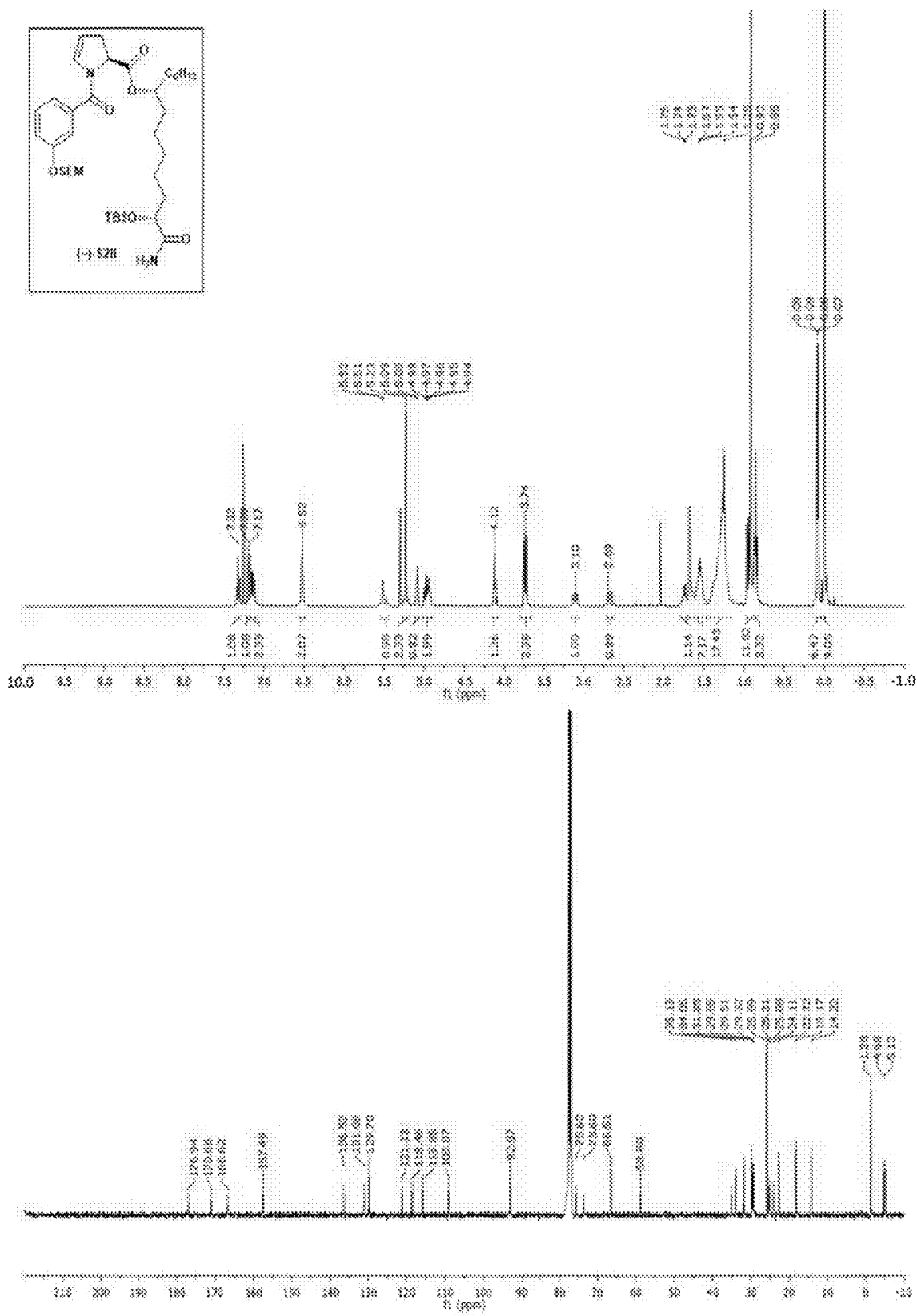
FIG. 59 depicts the proton ($^1$H) and carbon ($^{13}$C) NMR spectra of promysalin synthetic intermediate (−)-S28.
Figure 60:
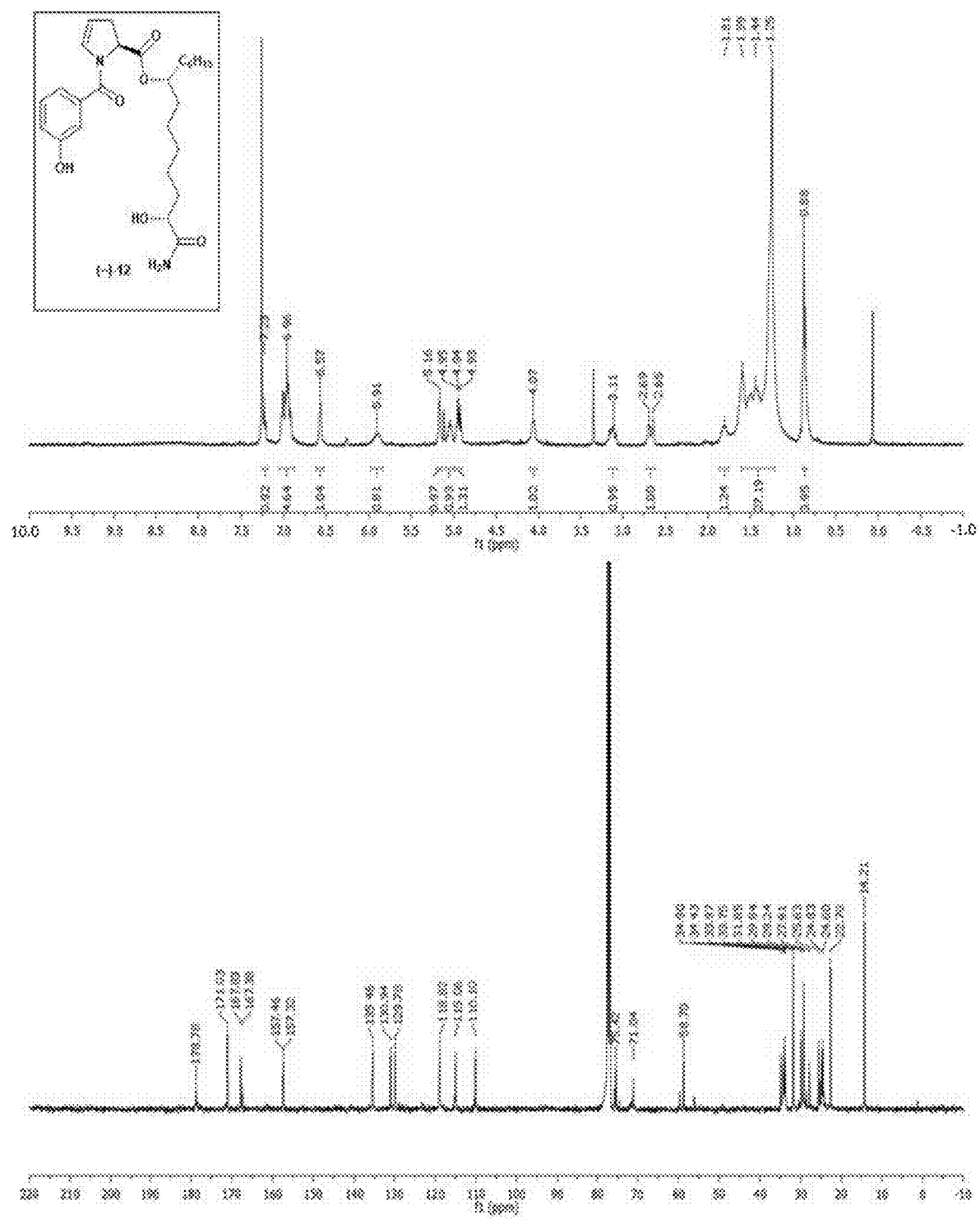
FIG. 60 depicts the proton ($^1$H) and carbon ($^{13}$C) NMR spectra of promysalin analog (−)-12.
Figure 61:
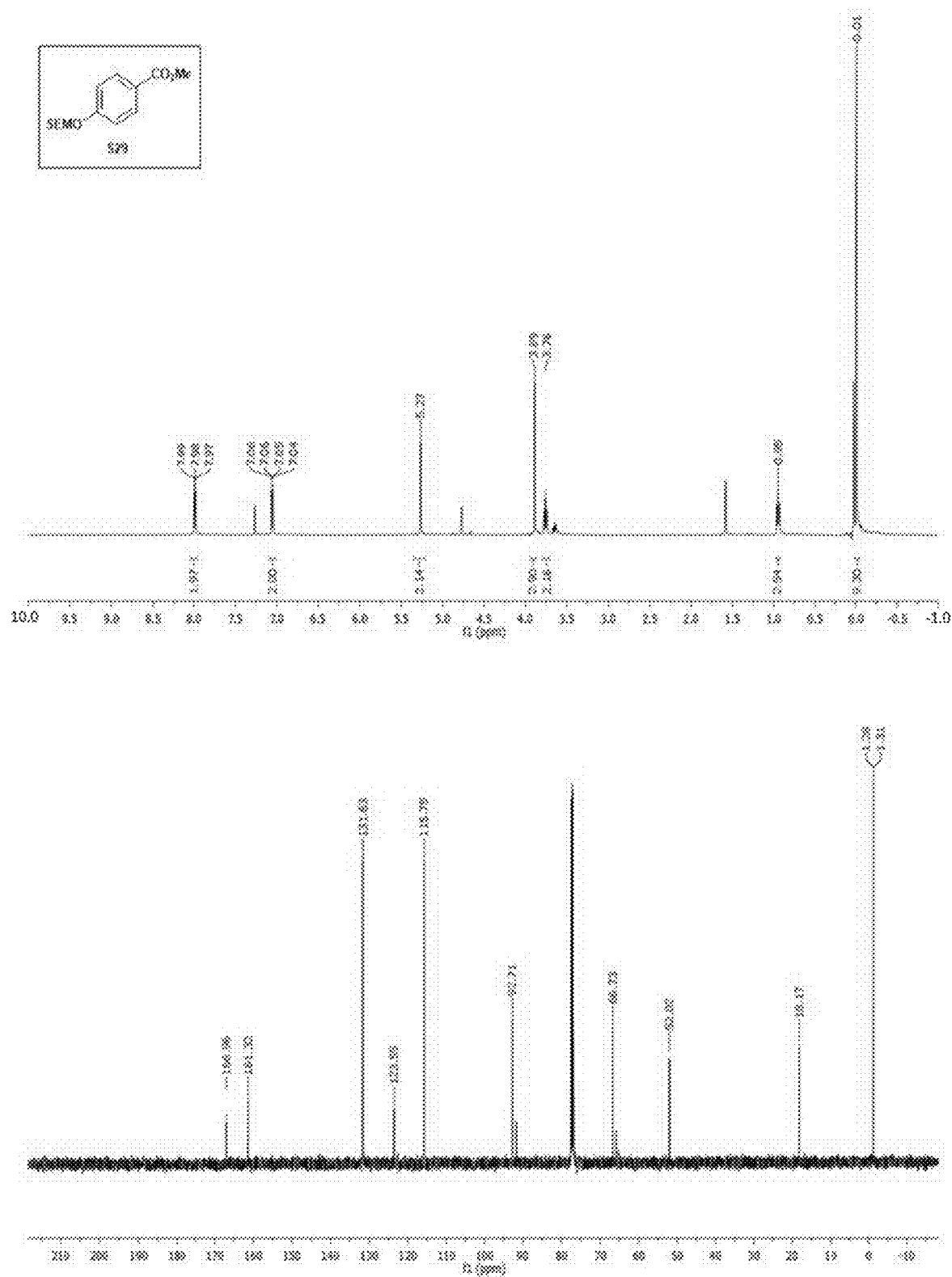
FIG. 61 depicts the proton ($^1$H) and carbon ($^{13}$C) NMR spectra of promysalin synthetic intermediate S29.
Figure 62:
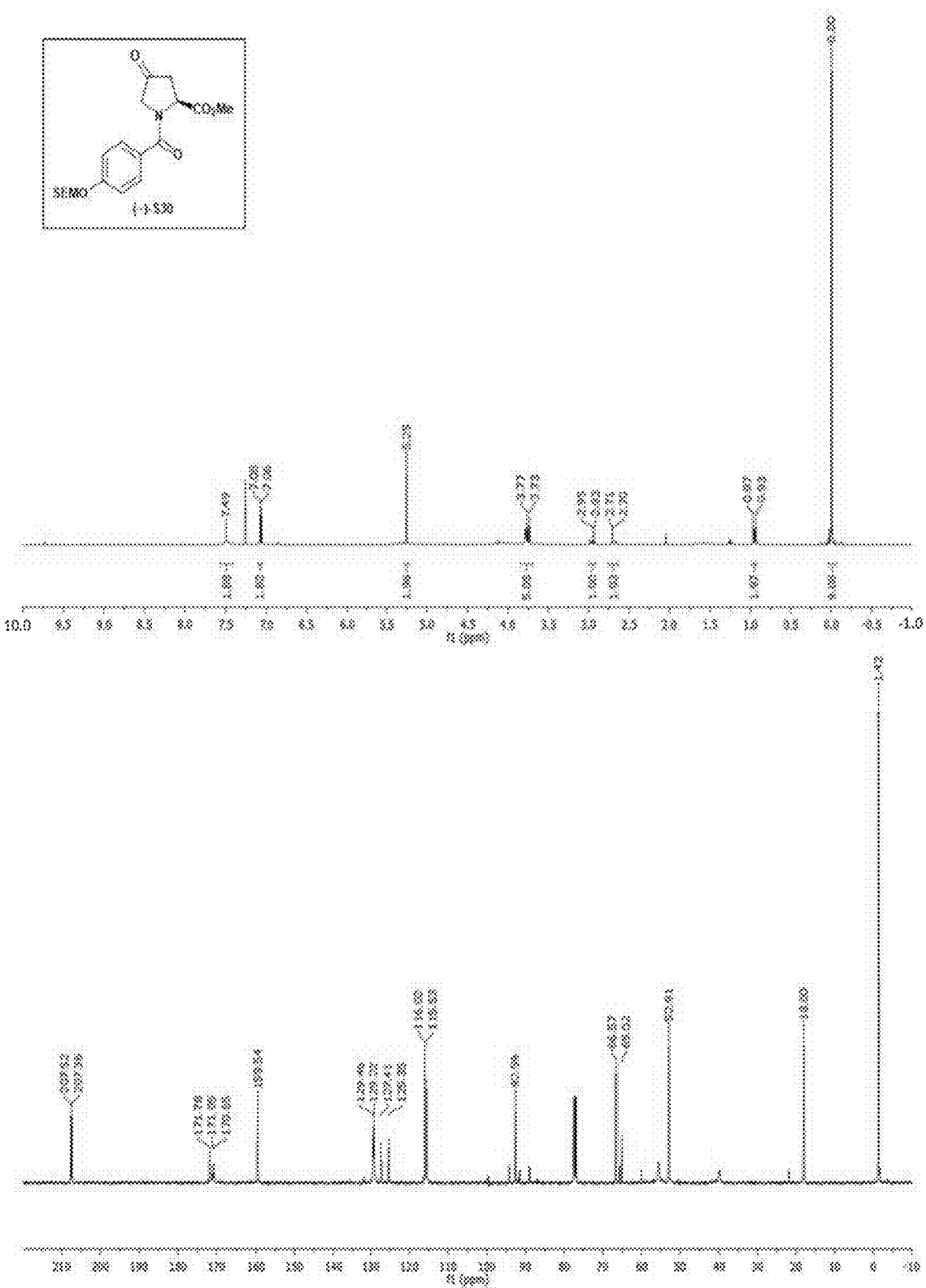
FIG. 62 depicts the proton ($^1$H) and carbon ($^{13}$C) NMR spectra of promysalin synthetic intermediate (−)-S30.
Figure 63:
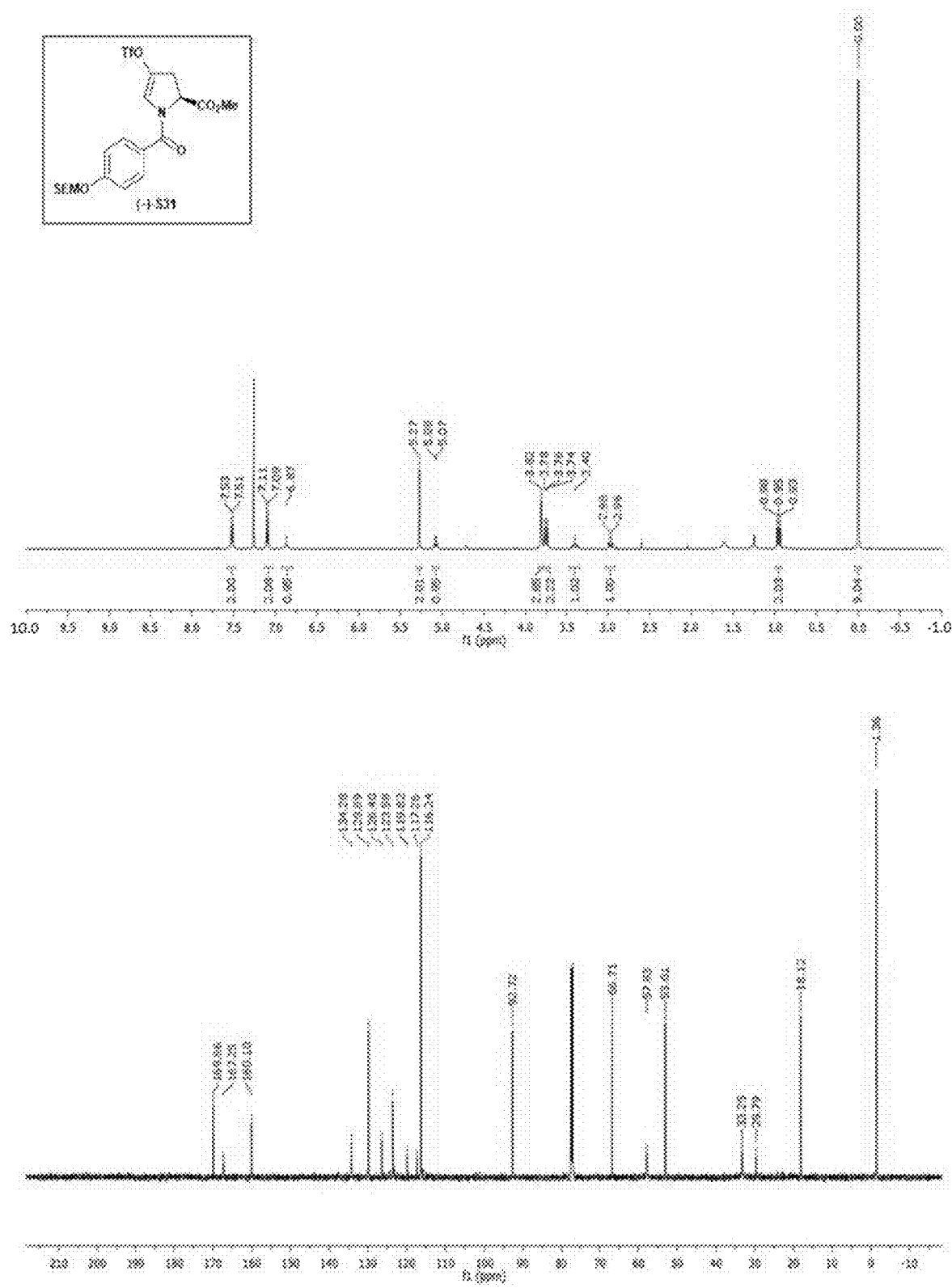
FIG. 63 depicts the proton ($^1$H) and carbon ($^{13}$C) NMR spectra of promysalin synthetic intermediate (−)-S31.
Figure 64:
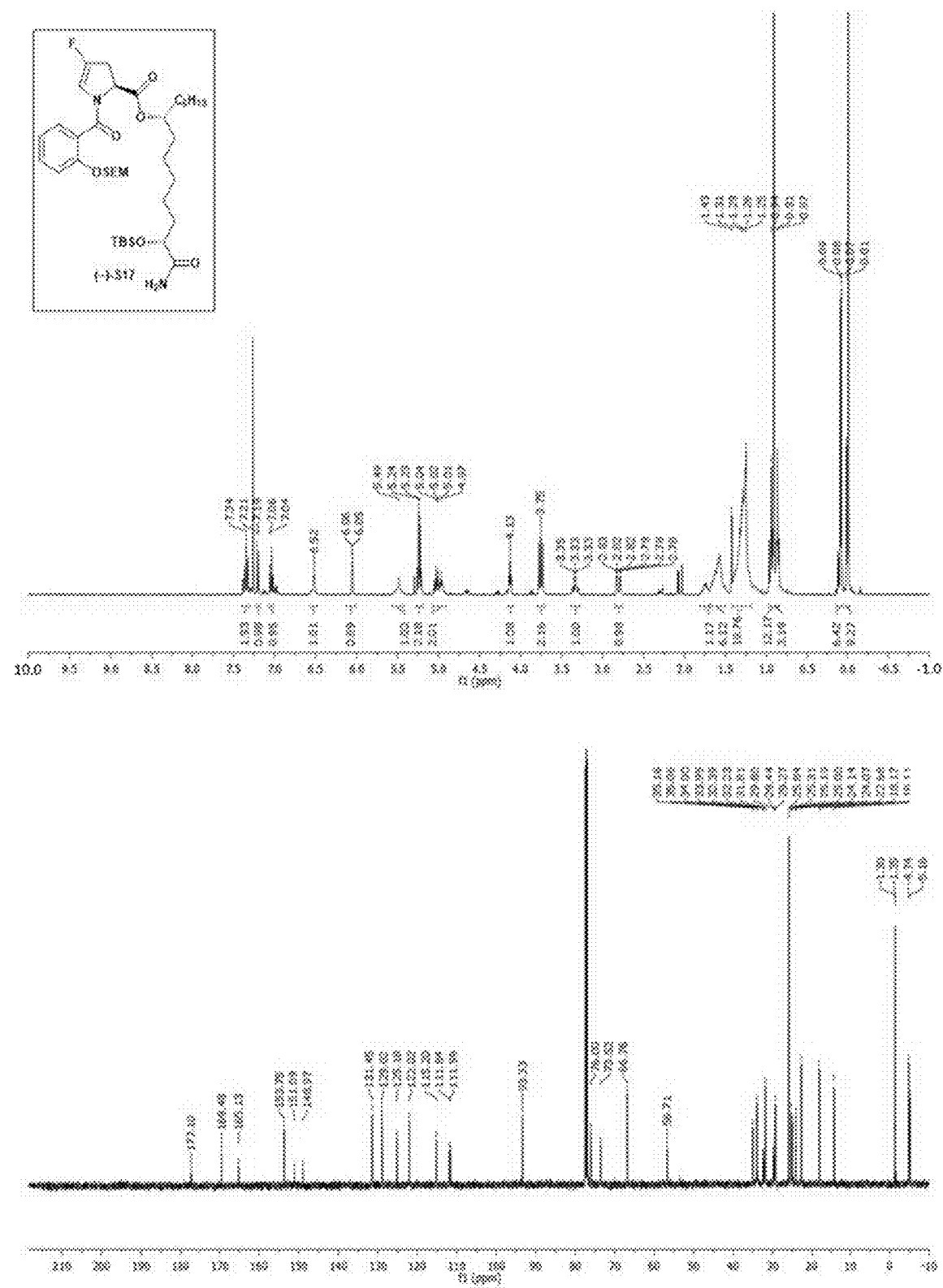
FIG. 64 depicts the proton ($^1$H) and carbon ($^{13}$C) NMR spectra of promysalin synthetic intermediate (−)-S17.
Figure 65:
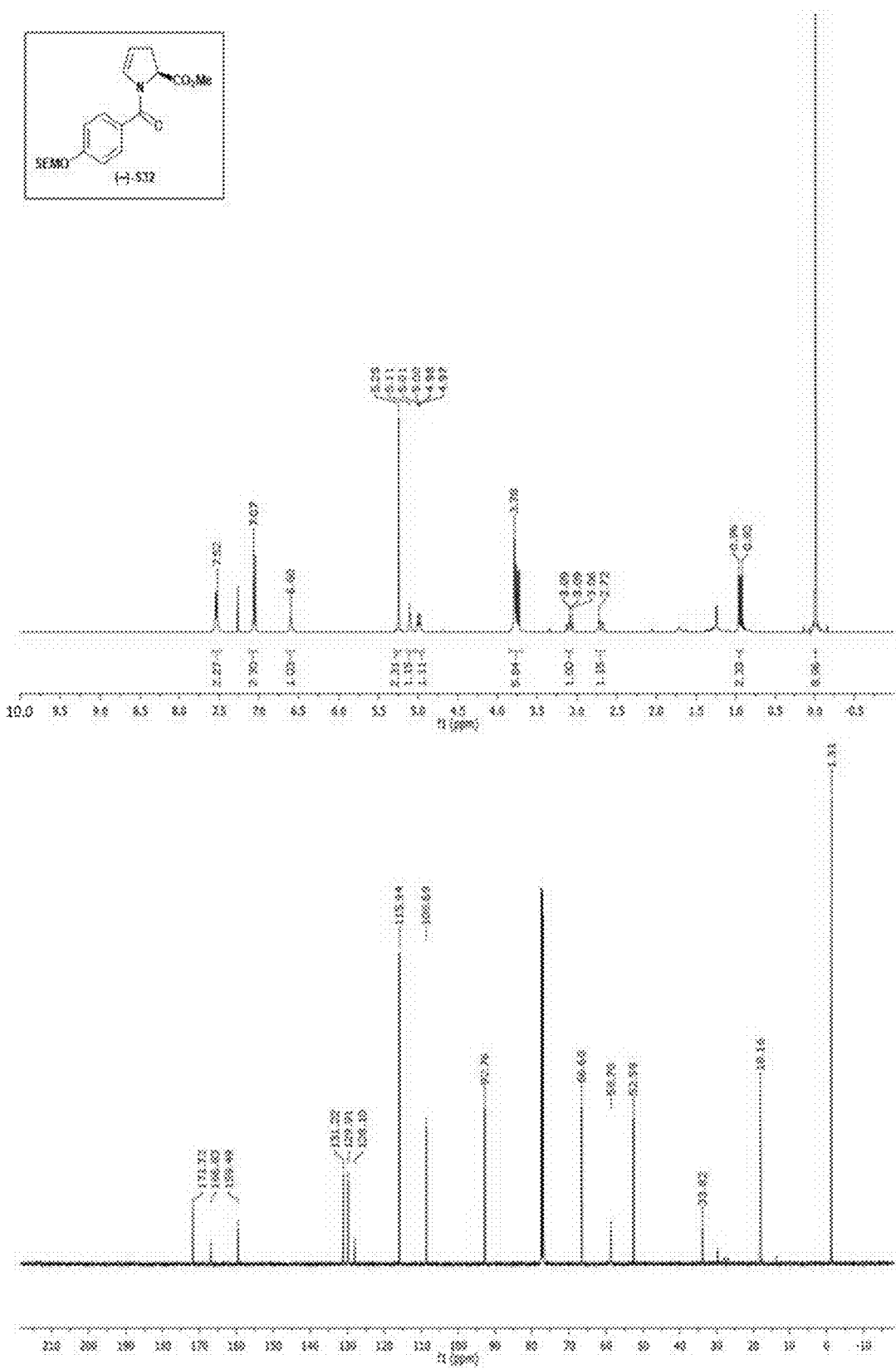
FIG. 65 depicts the proton ($^1$H) and carbon ($^{13}$C) NMR spectra of promysalin synthetic intermediate (−)-S32.
Figure 66:
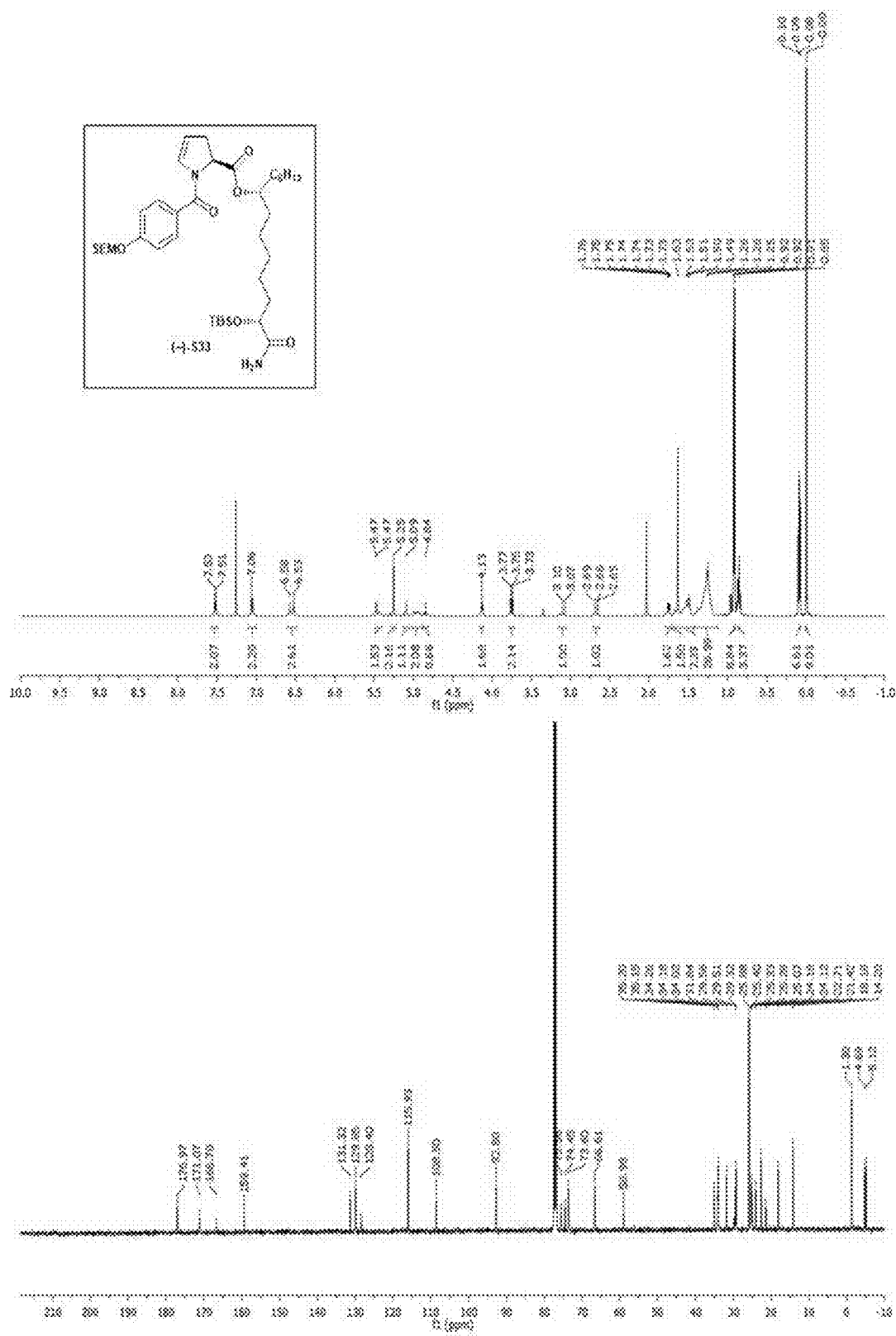
FIG. 66 depicts the proton ($^1$H) and carbon ($^{13}$C) NMR spectra of promysalin synthetic intermediate (−)-S33.
Figure 67:
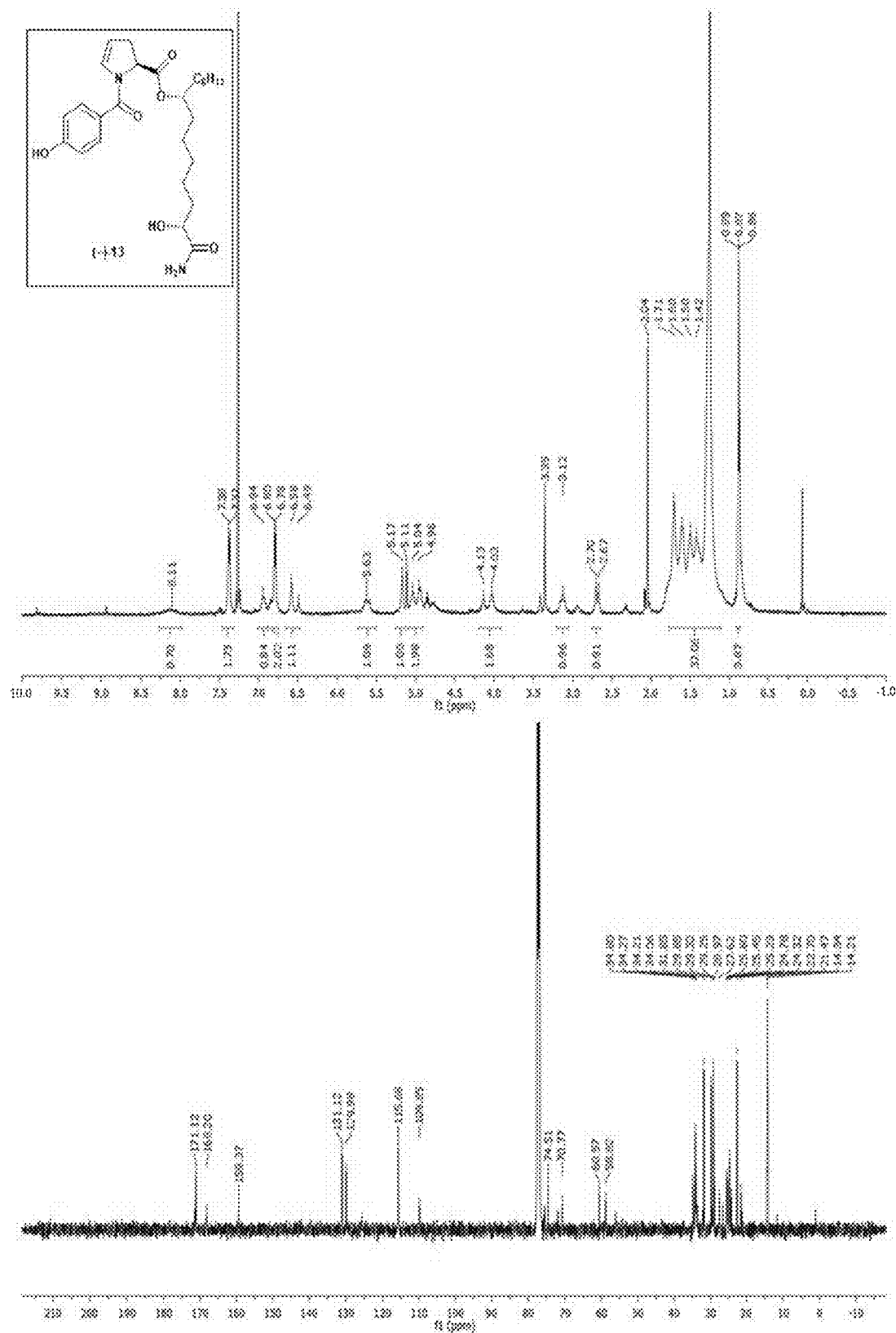
FIG. 67 depicts the proton ($^1$H) and carbon ($^{13}$C) NMR spectra of promysalin analog (−)-13.
Figure 68:
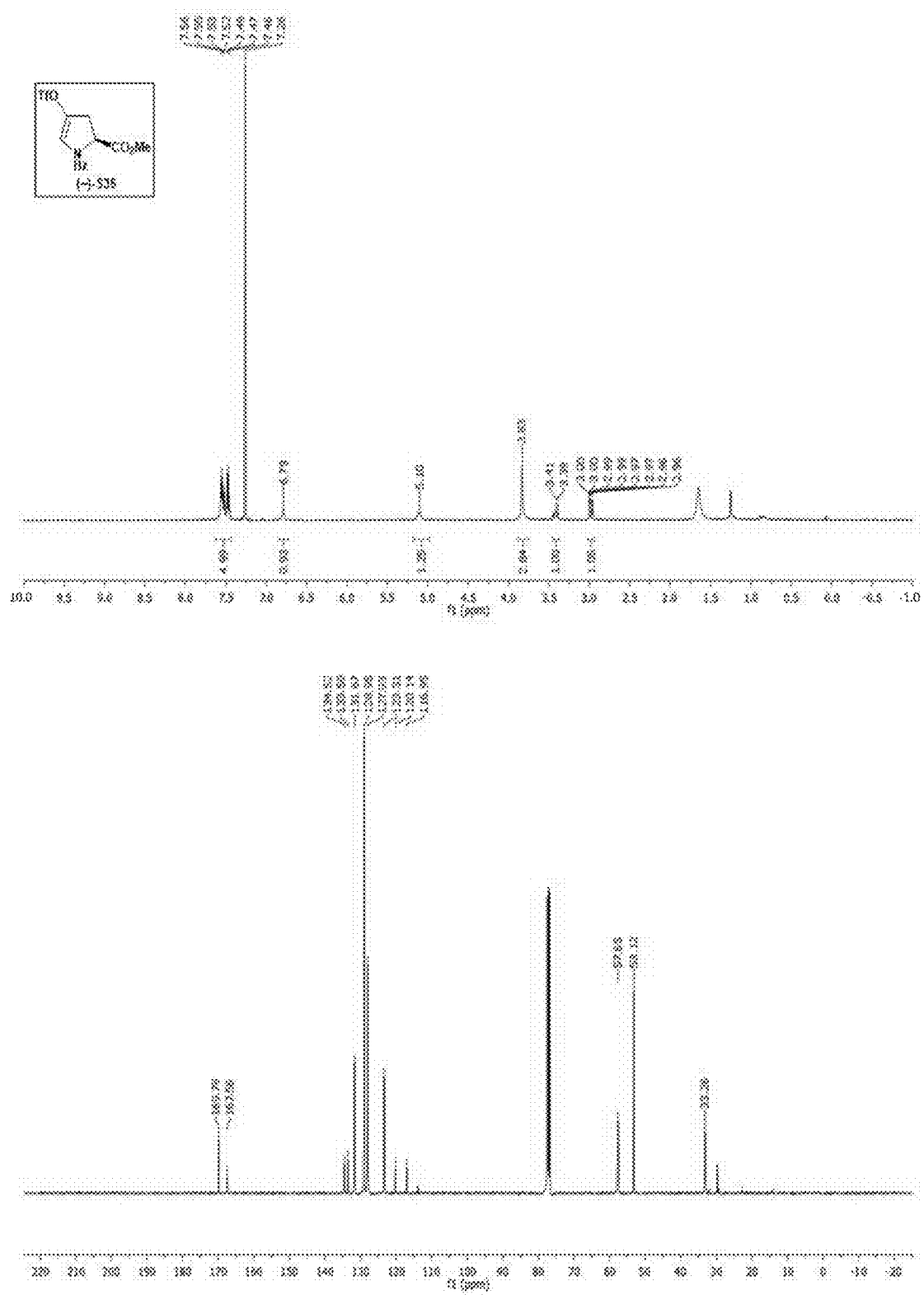
FIG. 68 depicts the proton ($^1$H) and carbon ($^{13}$C) NMR spectra of promysalin synthetic intermediate (−)-S35.
Figure 69:
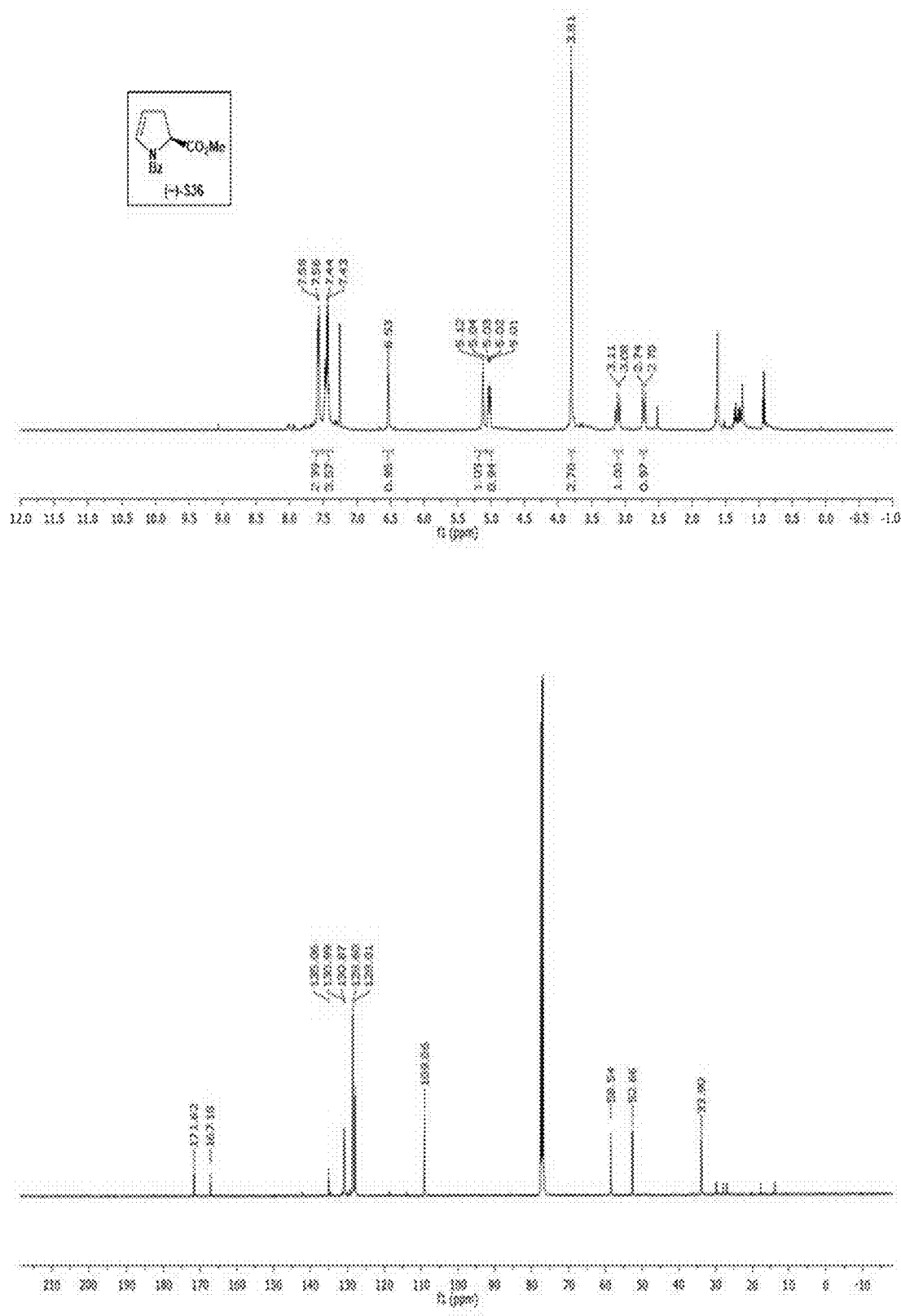
FIG. 69 depicts the proton ($^1$H) and carbon ($^{13}$C) NMR spectra of promysalin synthetic intermediate (−)-S36.
Figure 70:
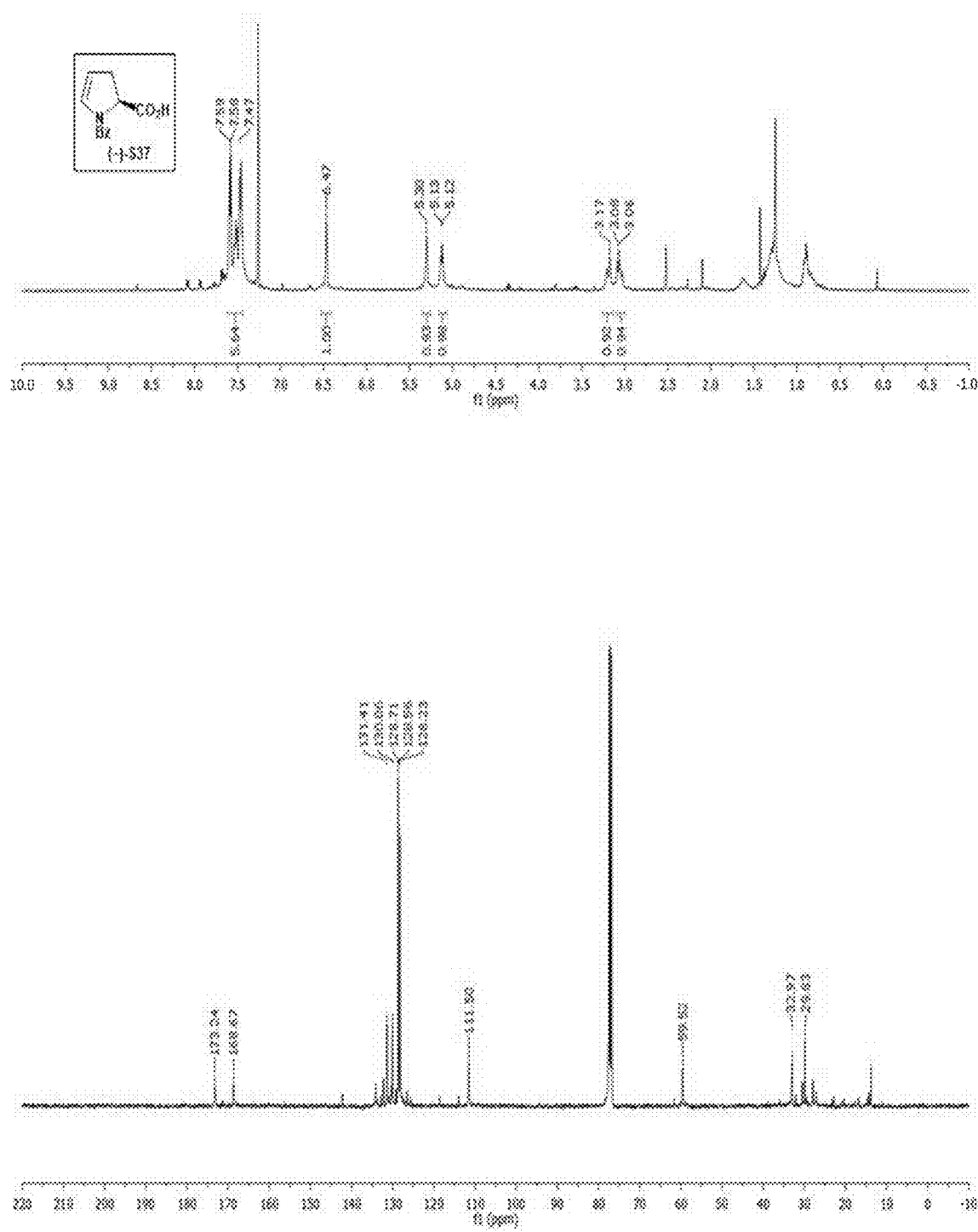
FIG. 70 depicts the proton ($^1$H) and carbon ($^{13}$C) NMR spectra of promysalin synthetic intermediate (−)-S37.
Figure 71:
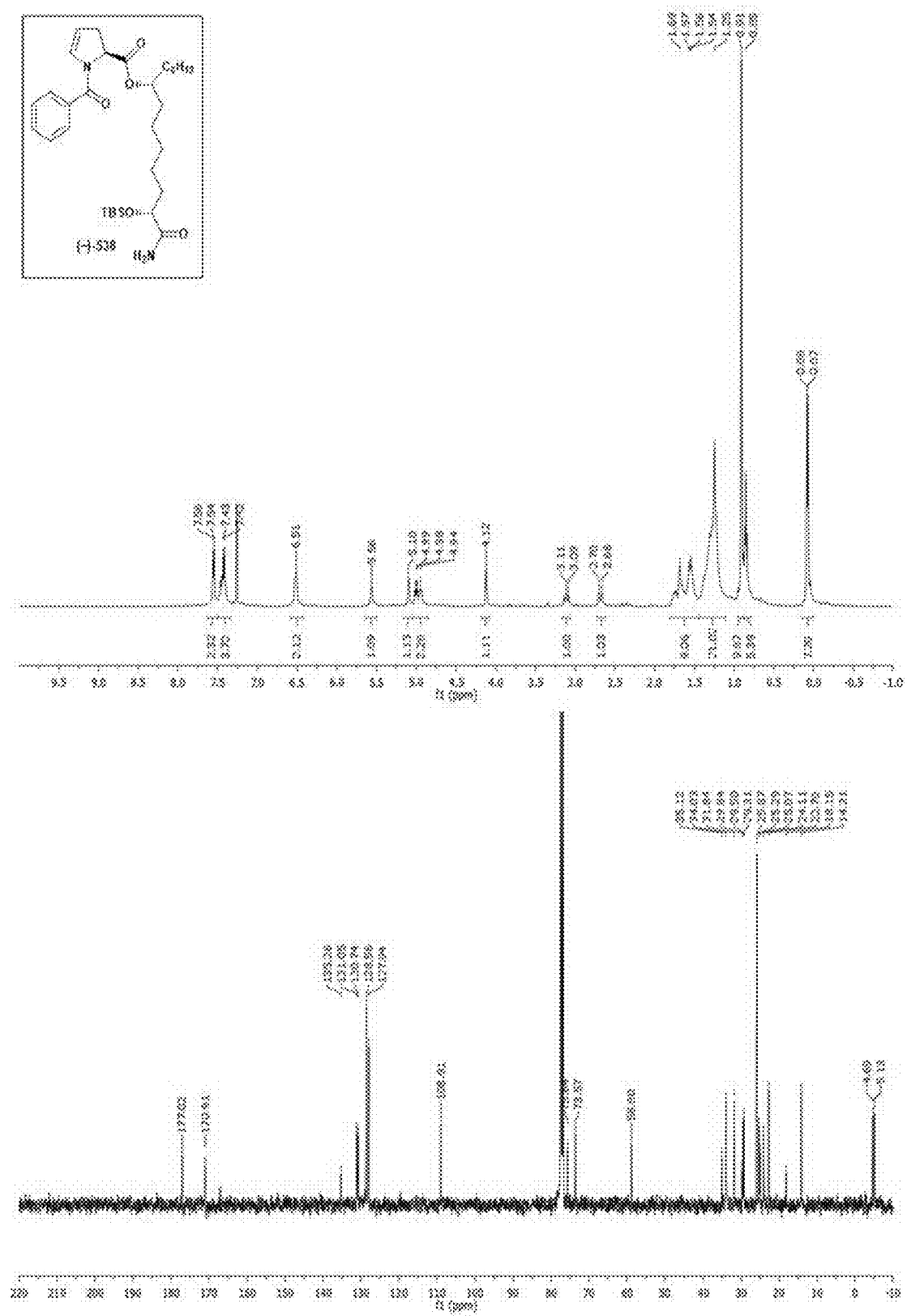
FIG. 71 depicts the proton ($^1$H) and carbon ($^{13}$C) NMR spectra of promysalin synthetic intermediate (−)-S38.
Figure 72:
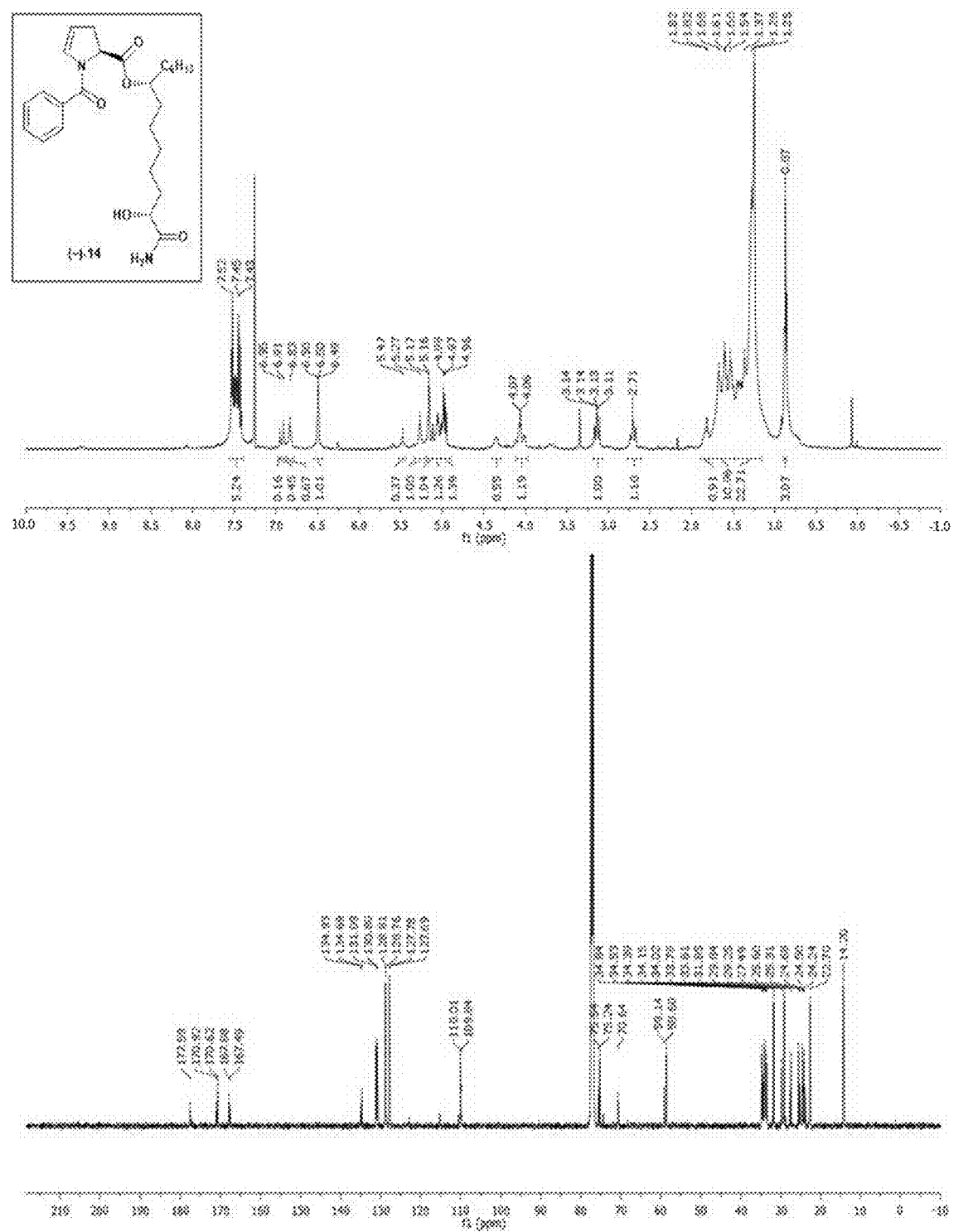
FIG. 72 depicts the proton ($^1$H) and carbon ($^{13}$C) NMR spectra of promysalin analog (−)-14.
Figure 73:
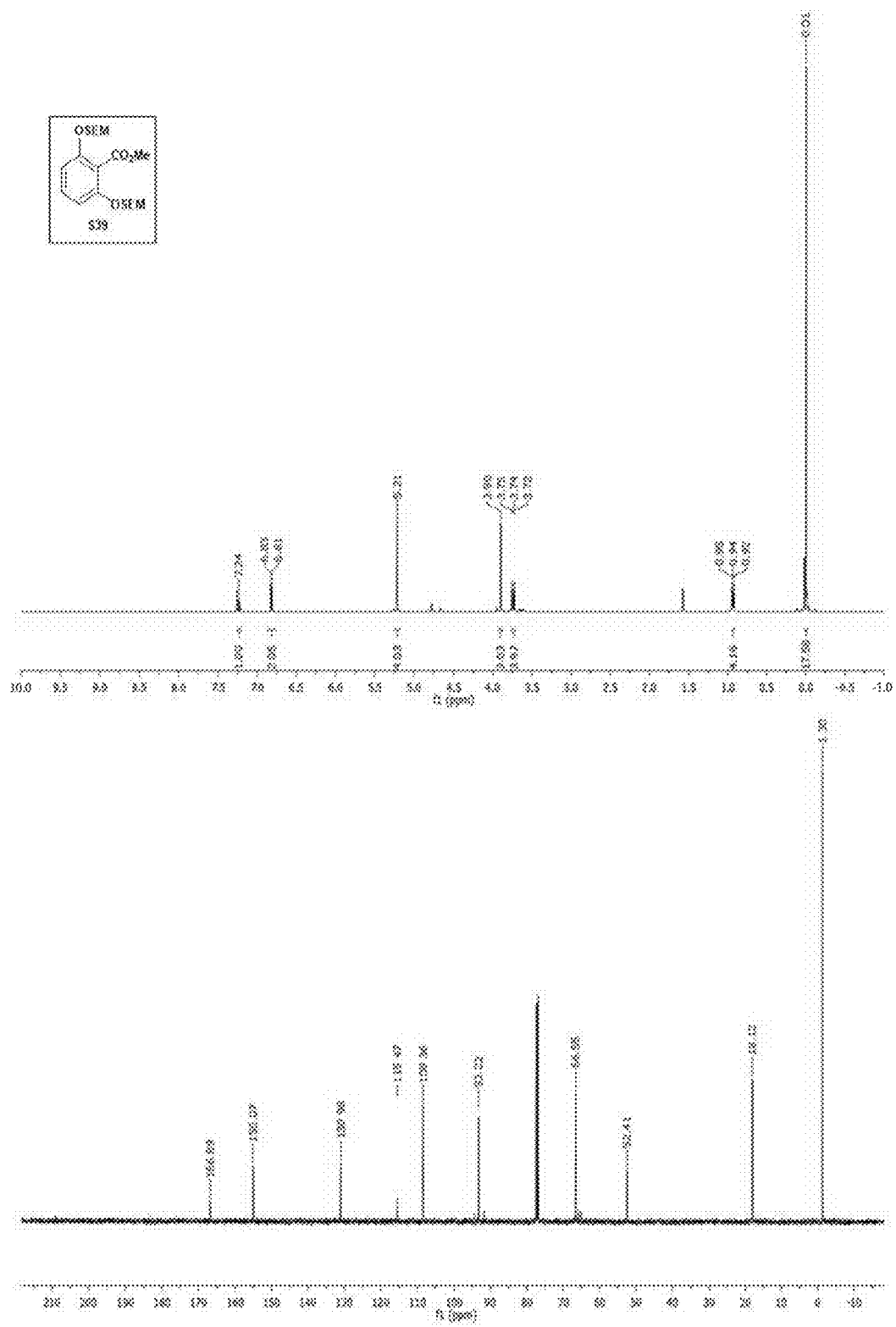
FIG. 73 depicts the proton ($^1$H) and carbon ($^{13}$C) NMR spectra of promysalin synthetic intermediate S39.
Figure 74:
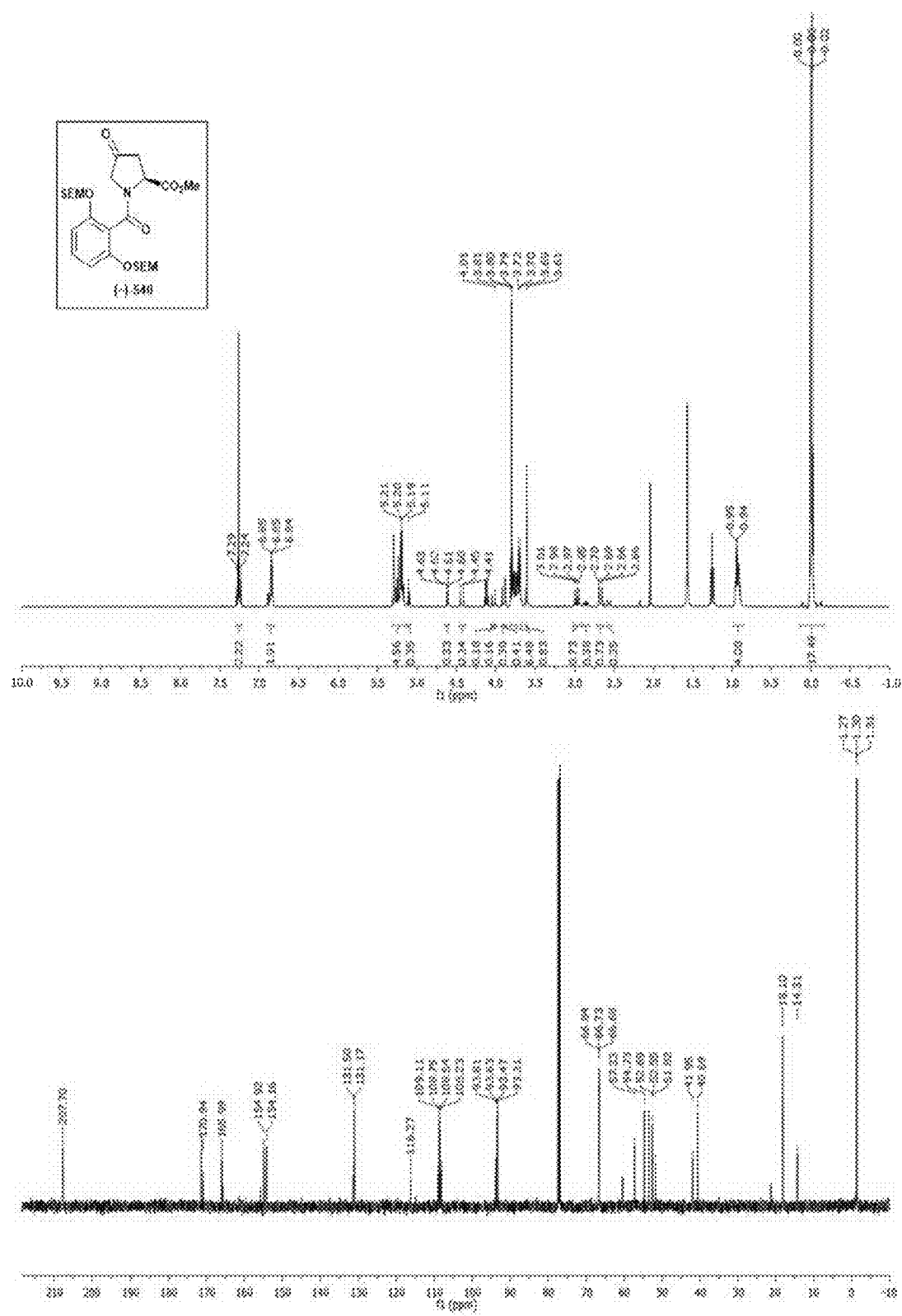
FIG. 74 depicts the proton ($^1$H) and carbon ($^{13}$C) NMR spectra of promysalin synthetic intermediate (−)-S40.
Figure 75:
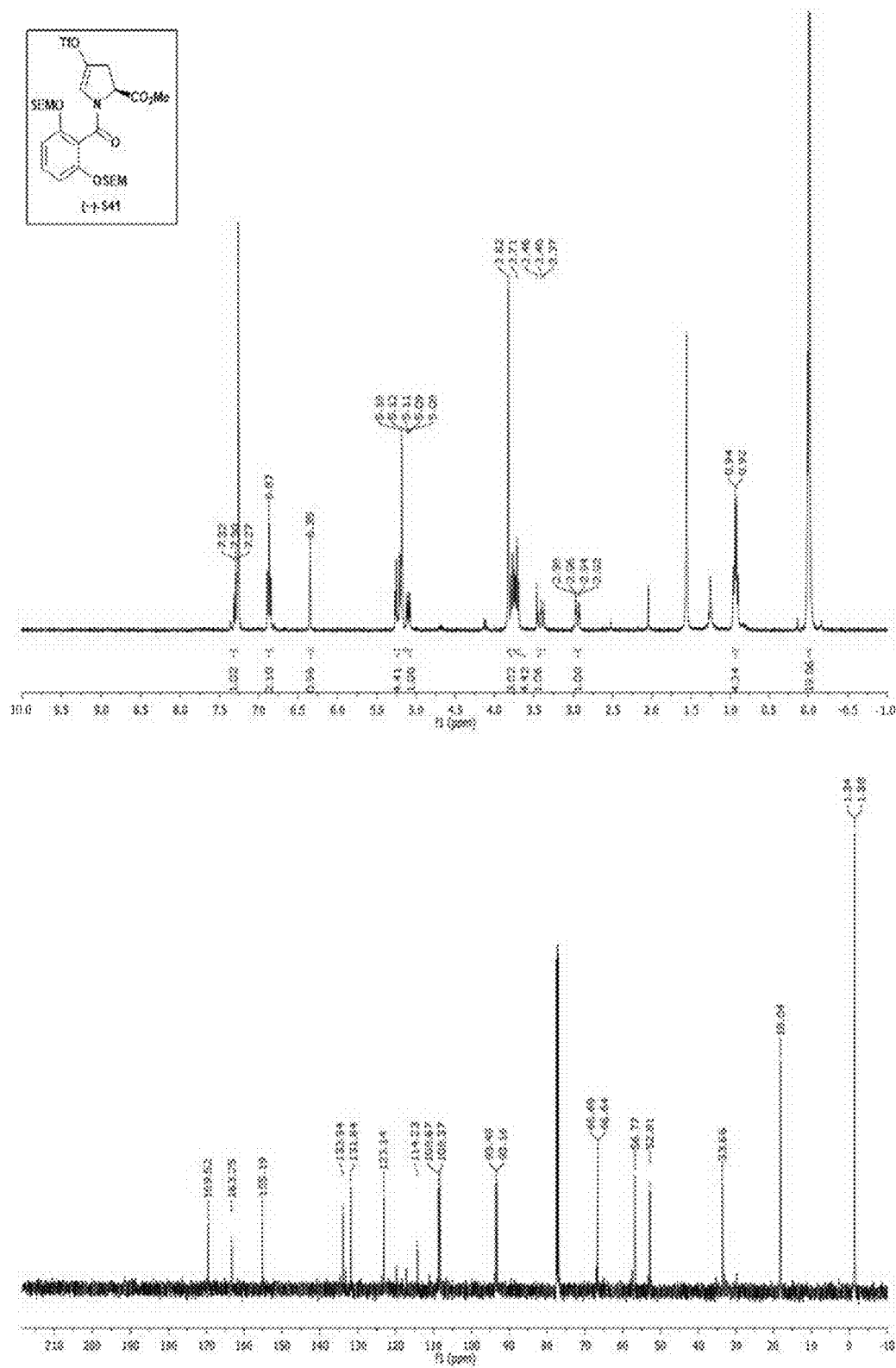
FIG. 75 depicts the proton ($^1$H) and carbon ($^{13}$C) NMR spectra of promysalin synthetic intermediate (−)-S41.
Figure 76:
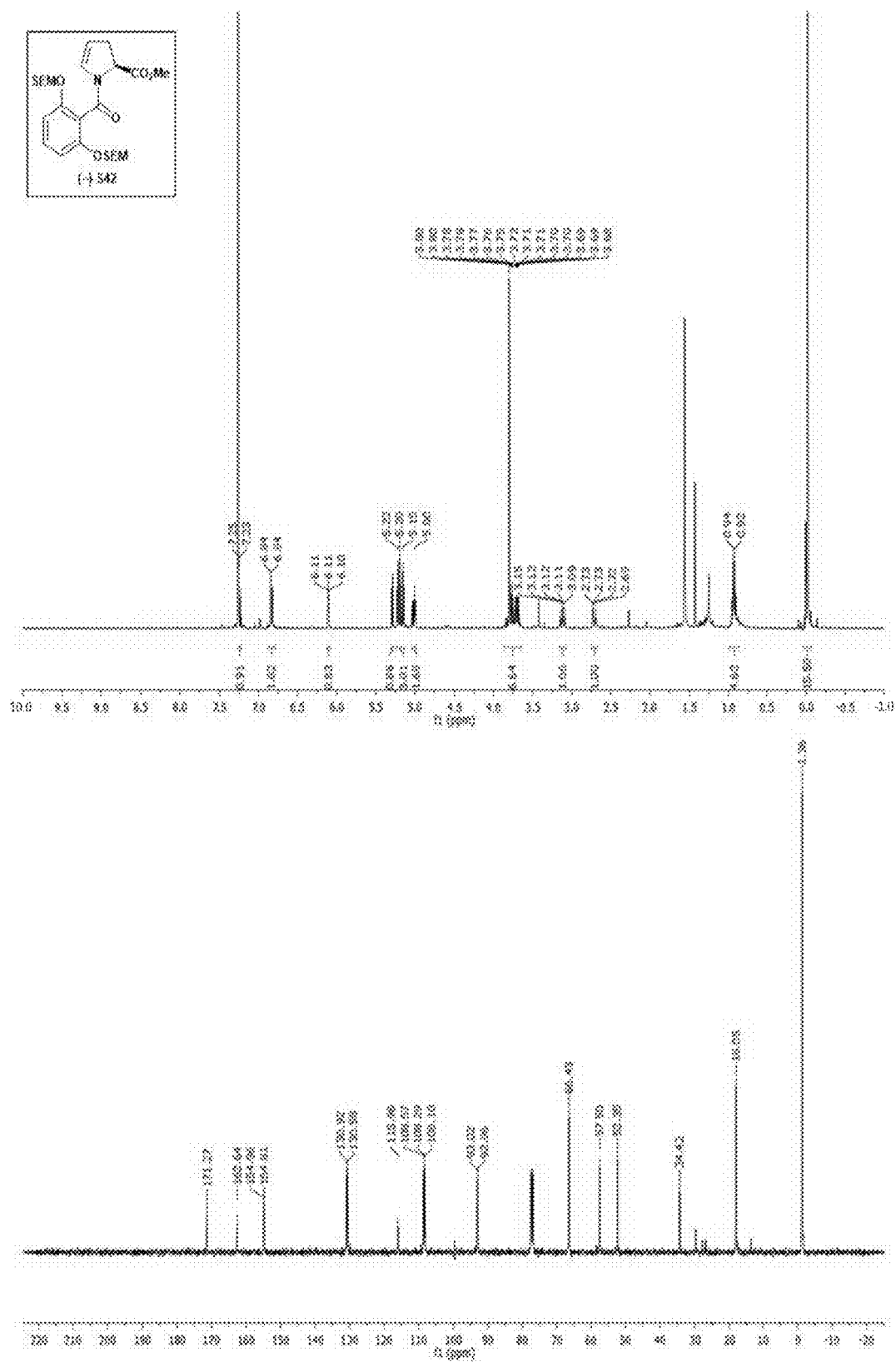
FIG. 76 depicts the proton ($^1$H) and carbon ($^{13}$C) NMR spectra of promysalin synthetic intermediate (−)-S42.
Figure 77:
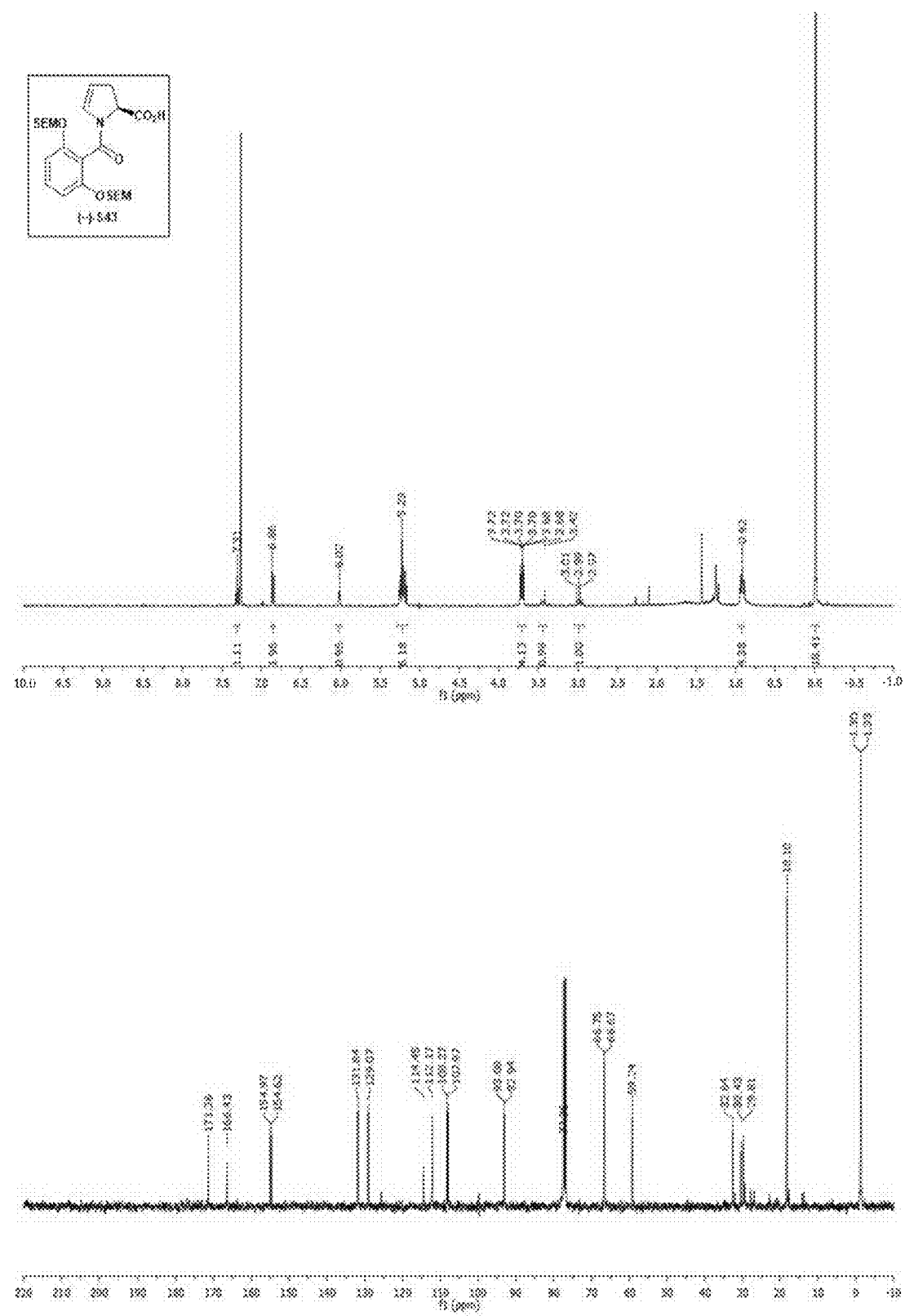
FIG. 77 depicts the proton ($^1$H) and carbon ($^{13}$C) NMR spectra of promysalin synthetic intermediate (−)-S43.
Figure 78:
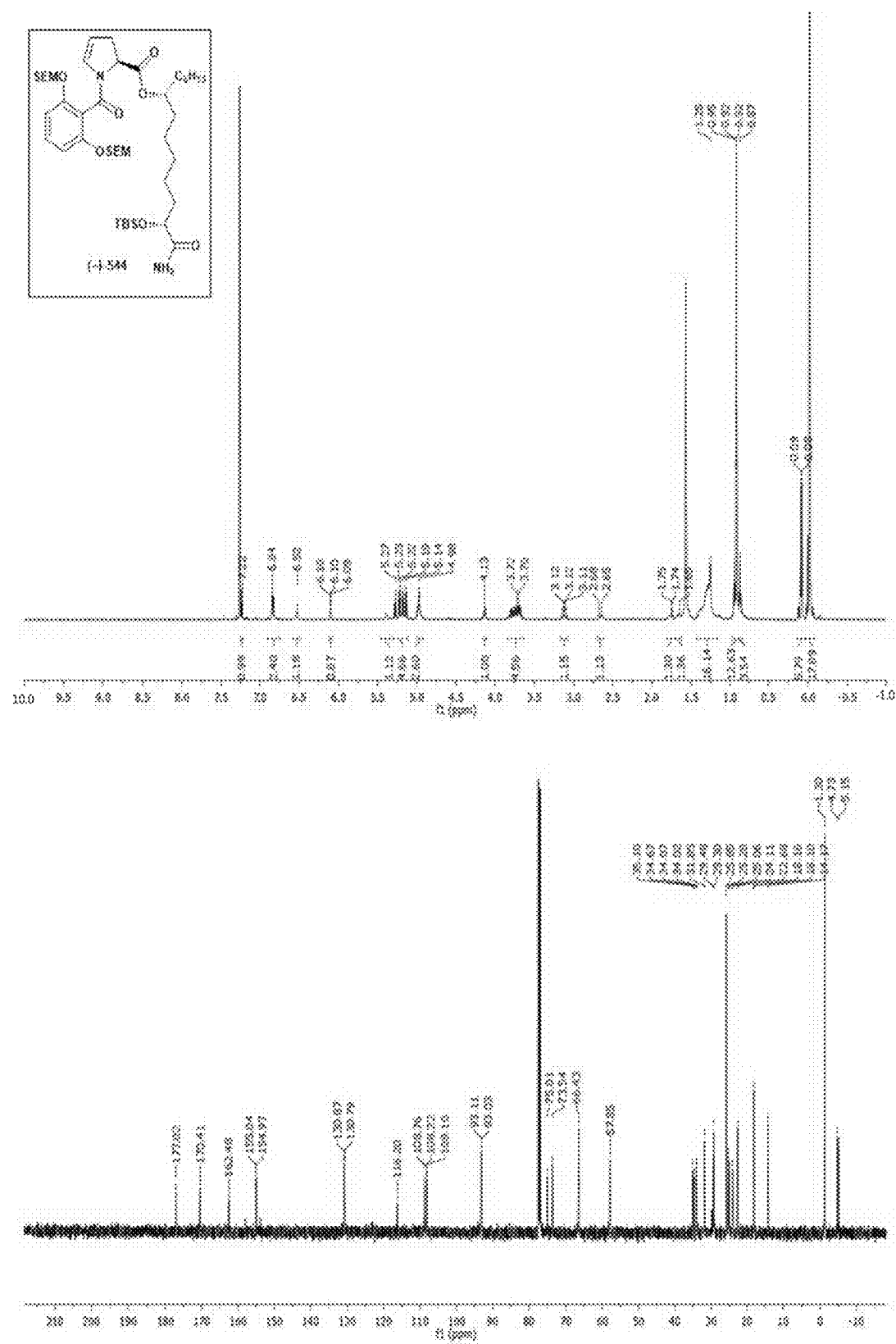
FIG. 78 depicts the proton ($^1$H) and carbon ($^{13}$C) NMR spectra of promysalin synthetic intermediate (−)-S44.
Figure 79:
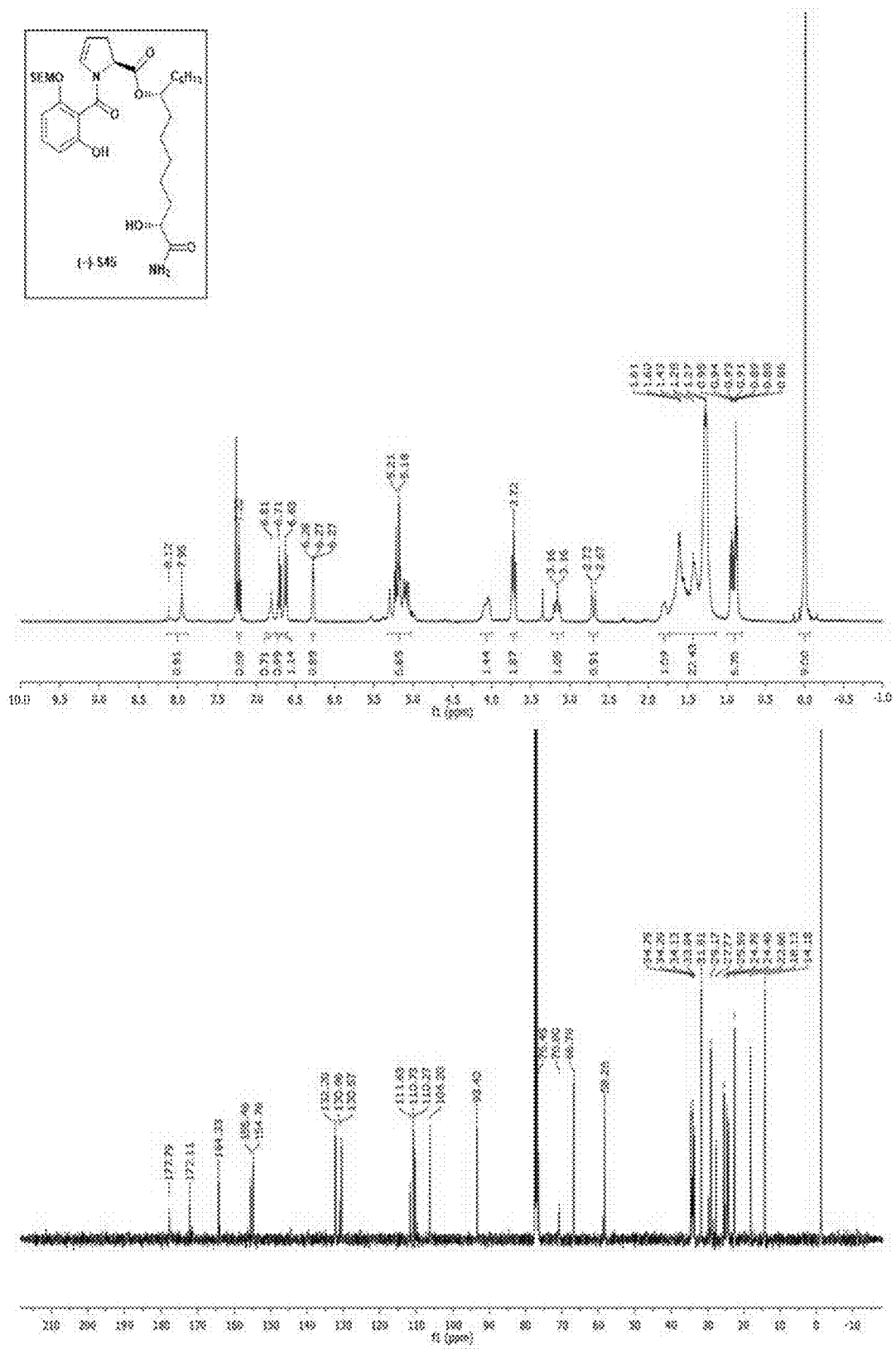
FIG. 79 depicts the proton ($^1$H) and carbon ($^{13}$C) NMR spectra of promysalin synthetic intermediate (−)-S45.
Figure 80:
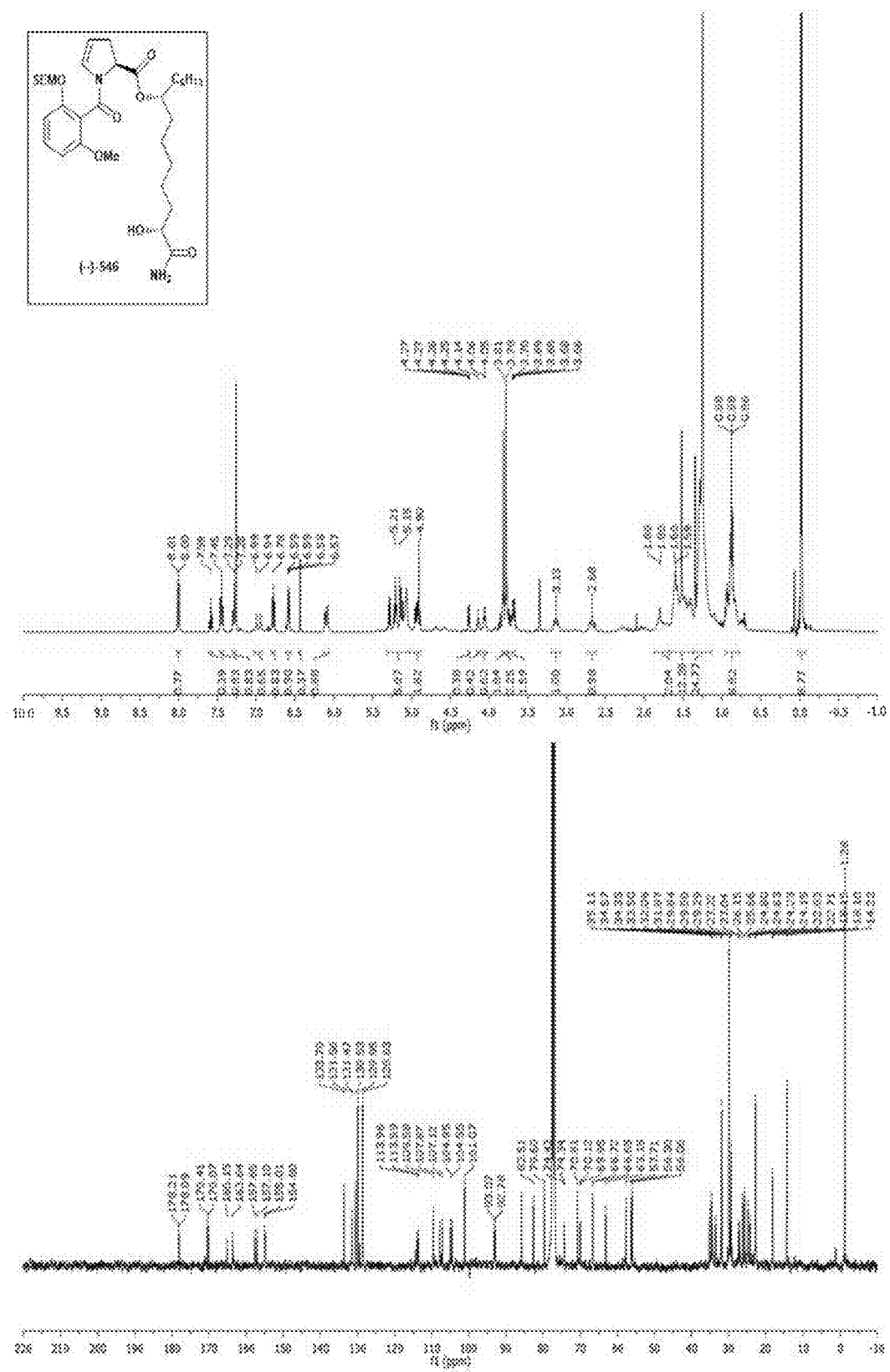
FIG. 80 depicts the proton ($^1$H) and carbon ($^{13}$C) NMR spectra of promysalin synthetic intermediate (−)-S46.
Figure 81:
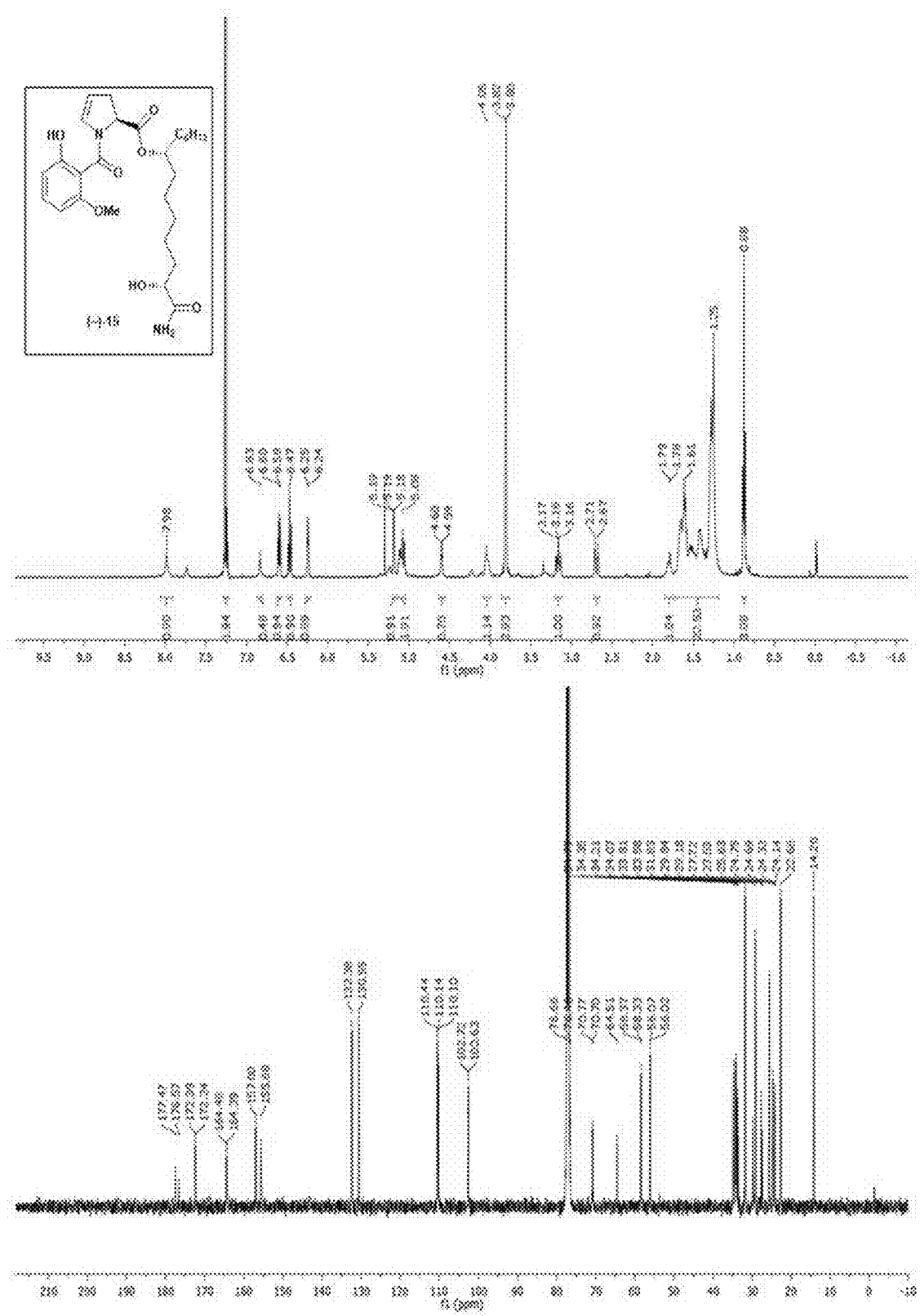
FIG. 81 depicts the proton ($^1$H) and carbon ($^{13}$C) NMR spectra of promysalin analog (−)-15.
Figure 82:
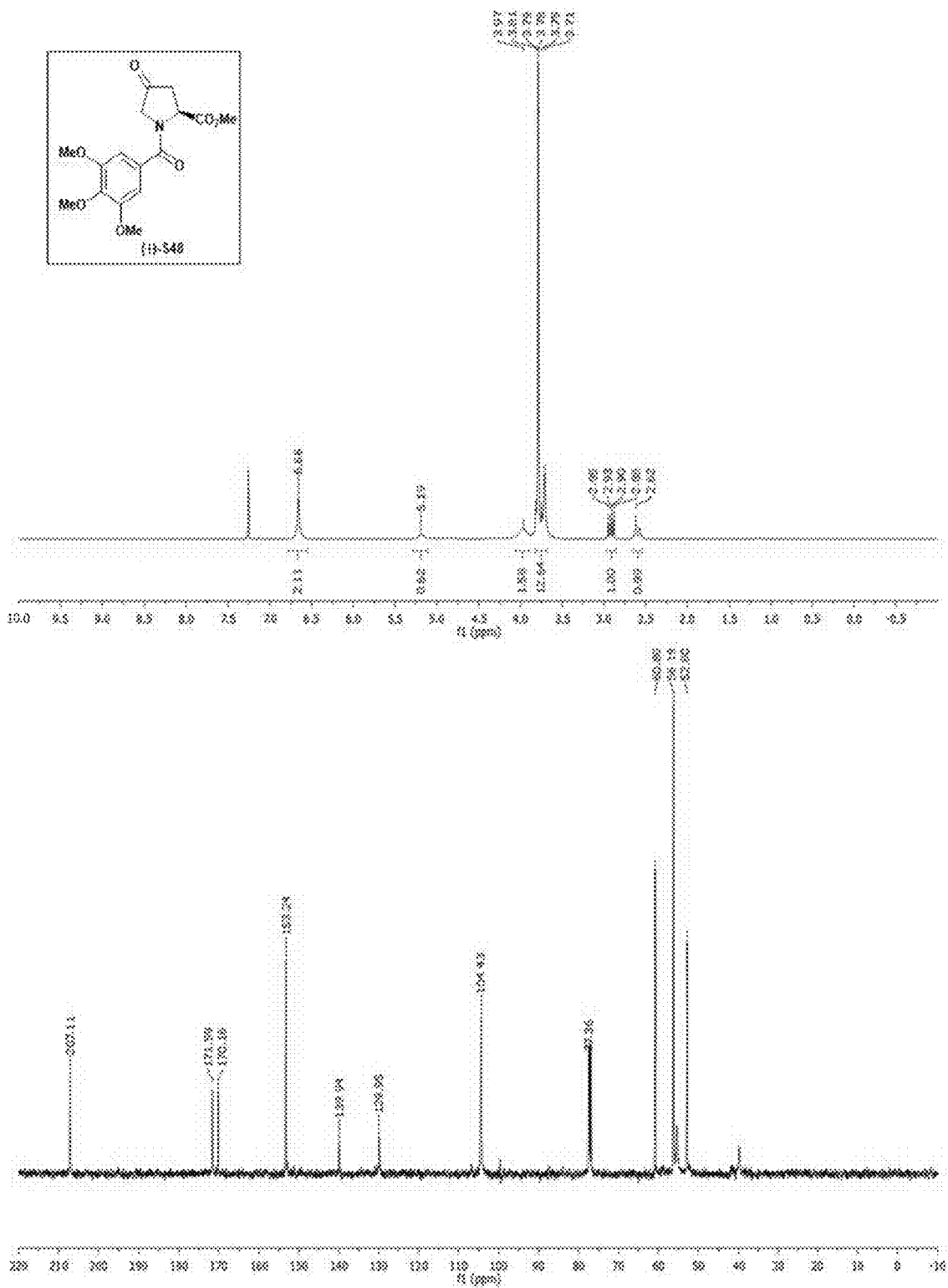
FIG. 82 depicts the proton ($^1$H) and carbon ($^{13}$C) NMR spectra of promysalin synthetic intermediate (+)-S48.
Figure 83:
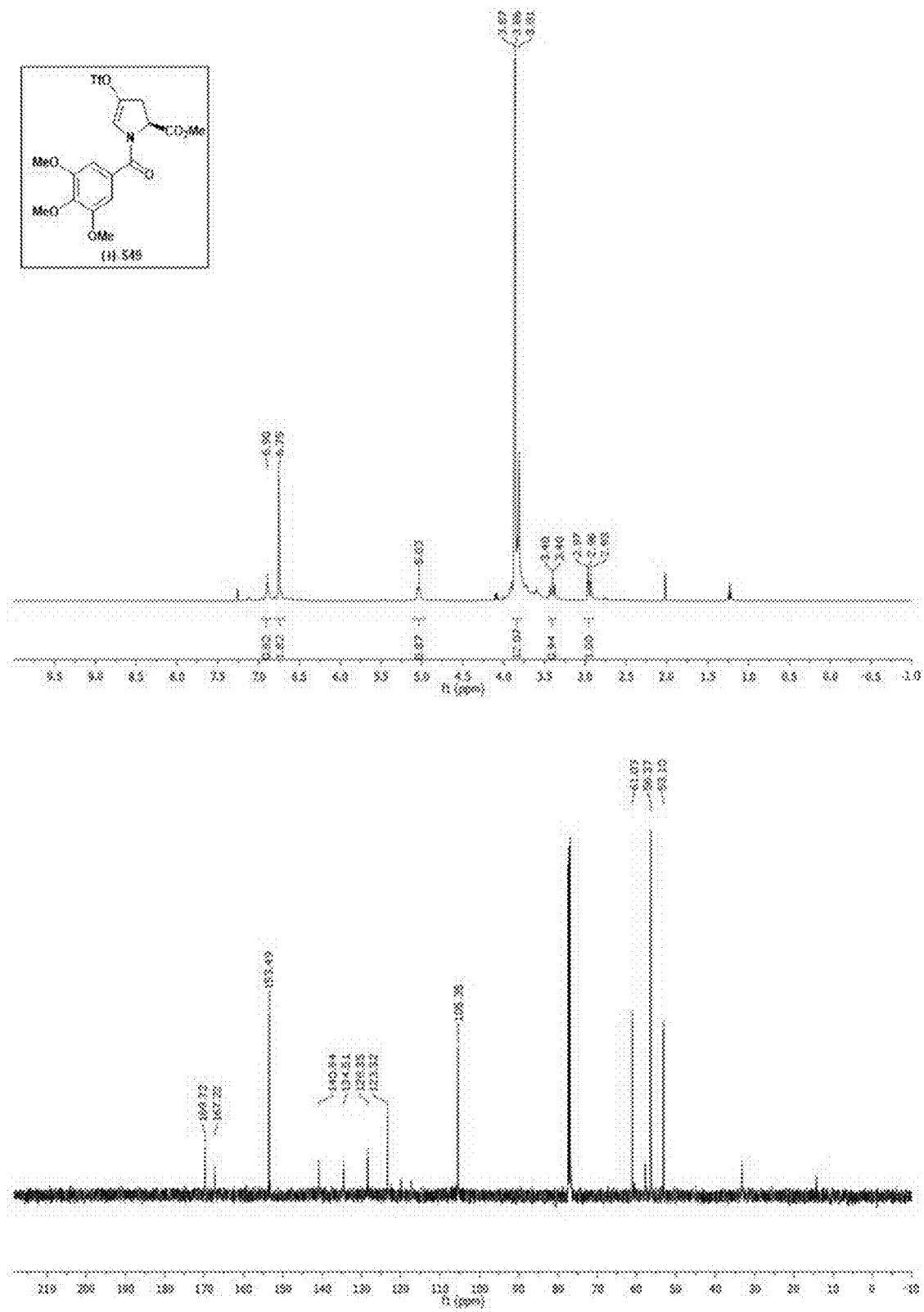
FIG. 83 depicts the proton ($^1$H) and carbon ($^{13}$C) NMR spectra of promysalin synthetic intermediate (+)-S49.
Figure 84:
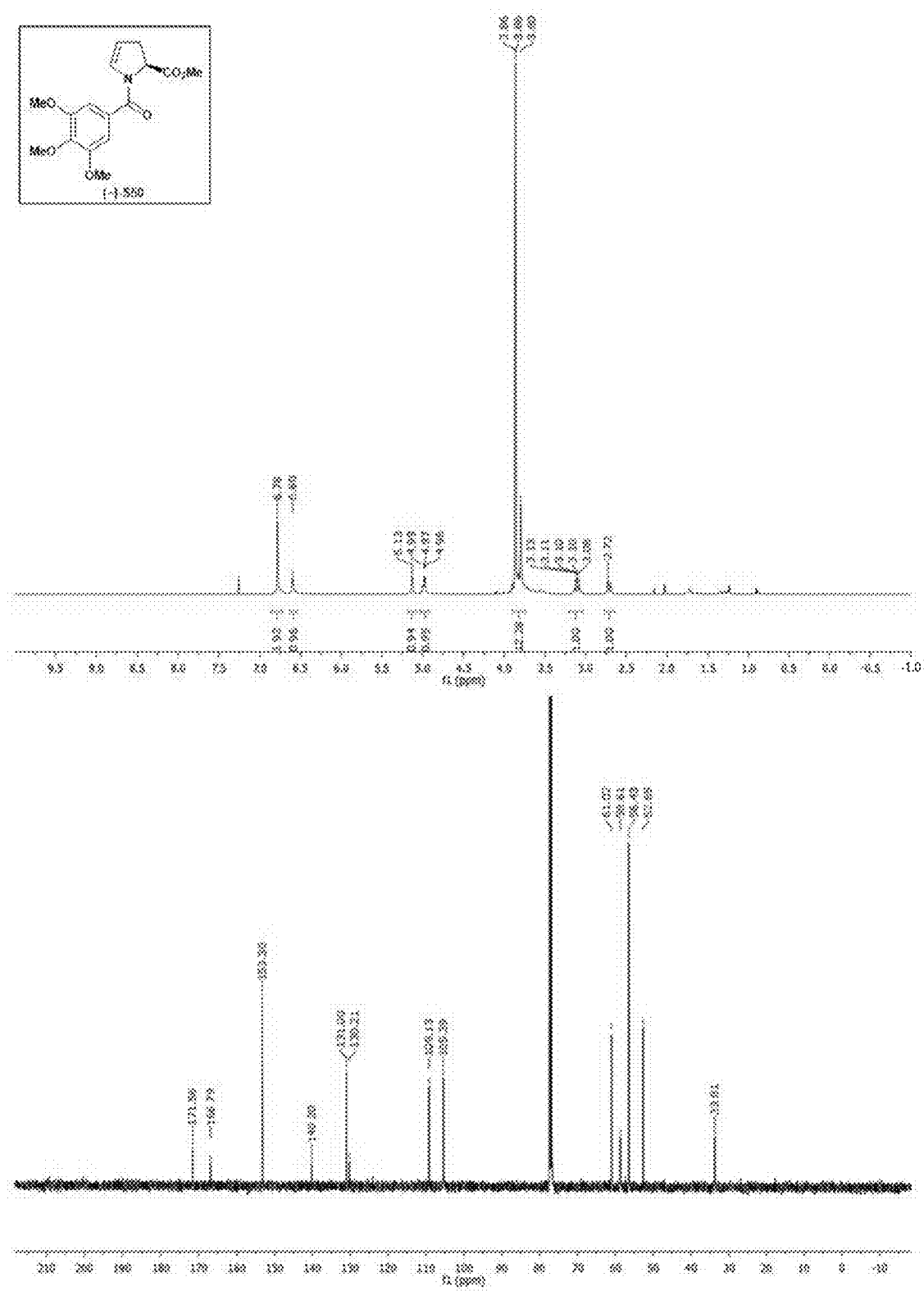
FIG. 84 depicts the proton ($^1$H) and carbon ($^{13}$C) NMR spectra of promysalin synthetic intermediate (−)-S50.
Figure 85:
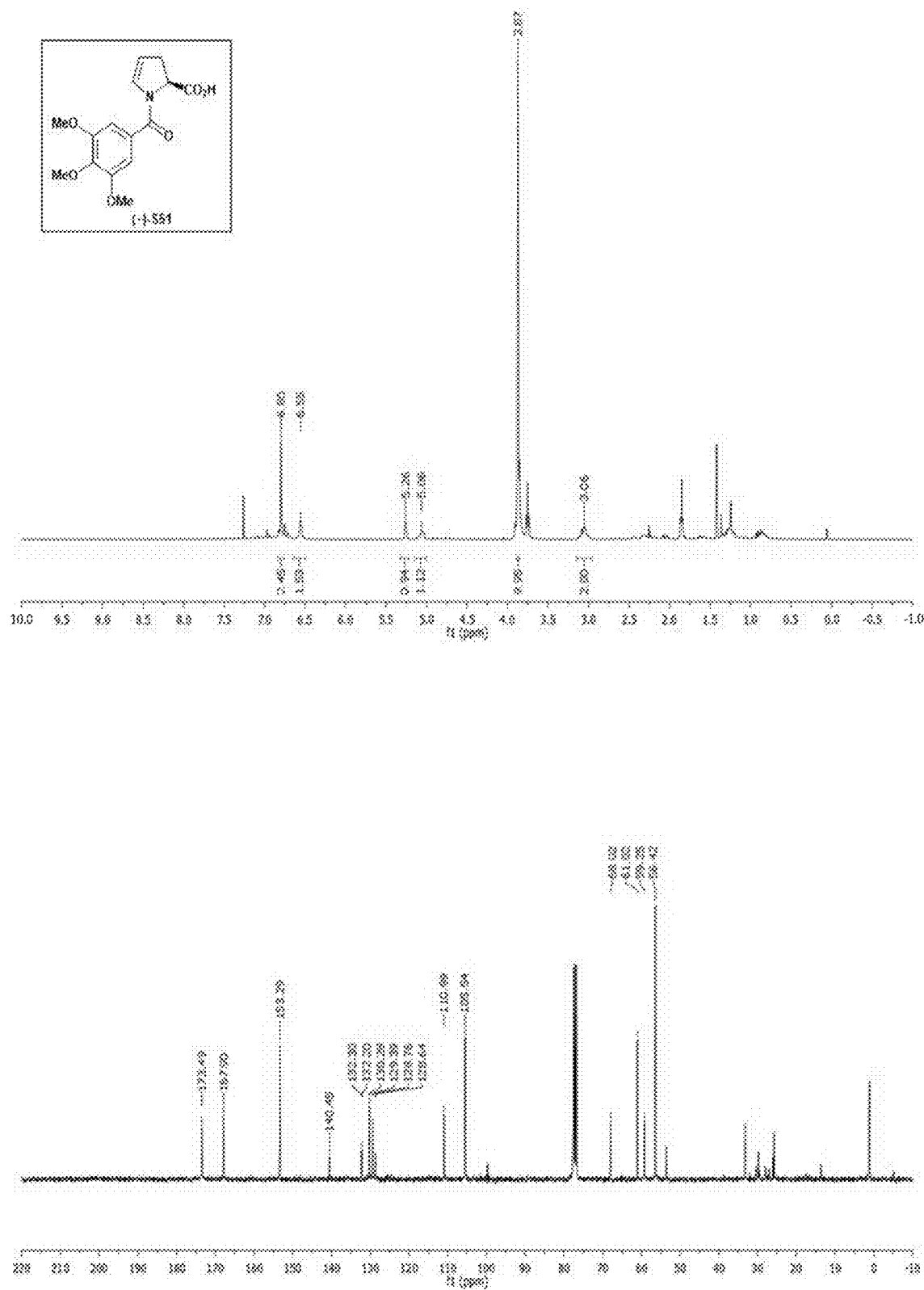
FIG. 85 depicts the proton ($^1$H) and carbon ($^{13}$C) NMR spectra of promysalin synthetic intermediate (−)-S51.
Figure 86:
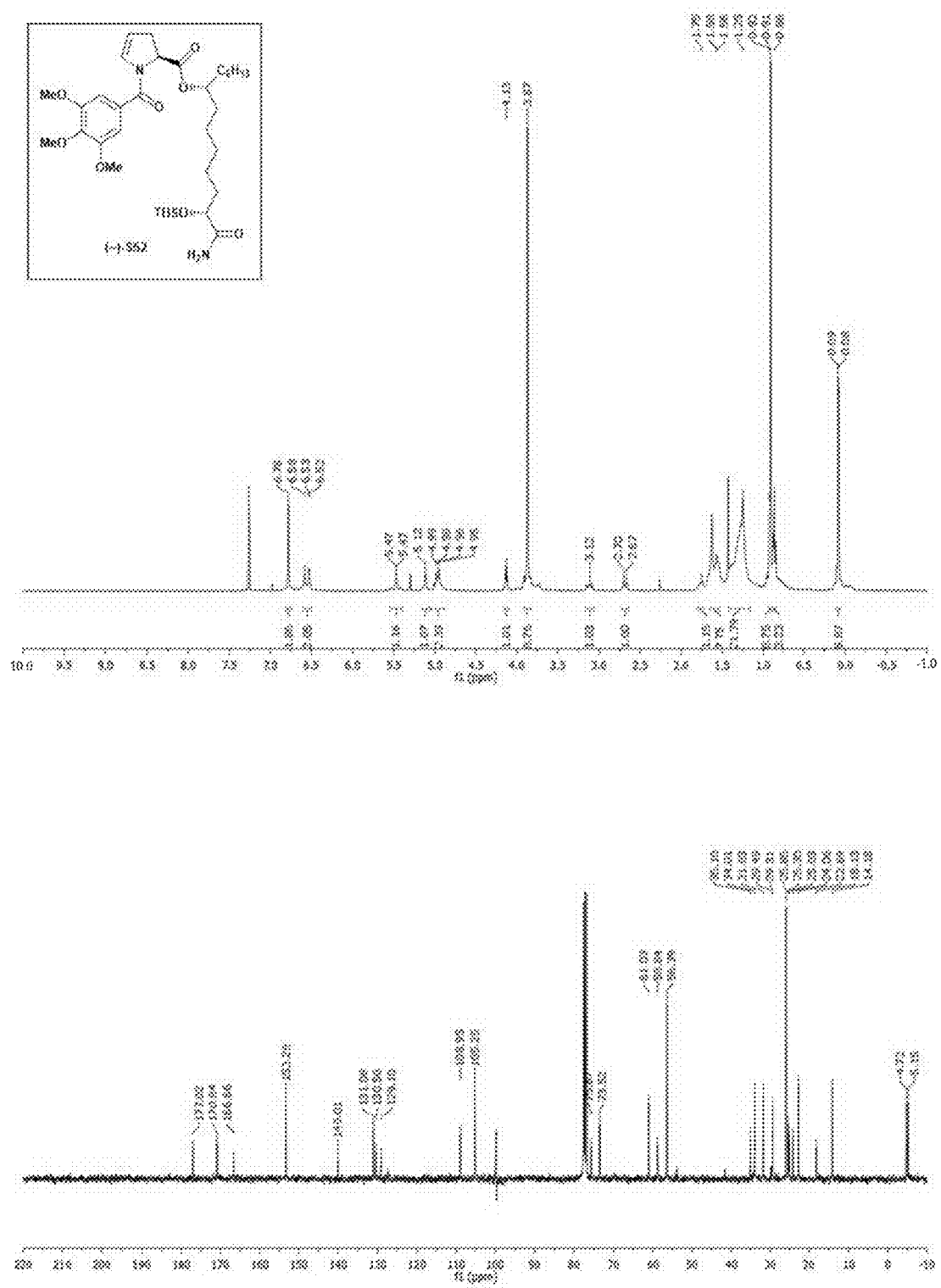
FIG. 86 depicts the proton ($^1$H) and carbon ($^{13}$C) NMR spectra of promysalin synthetic intermediate (−)-S52.
Figure 87:
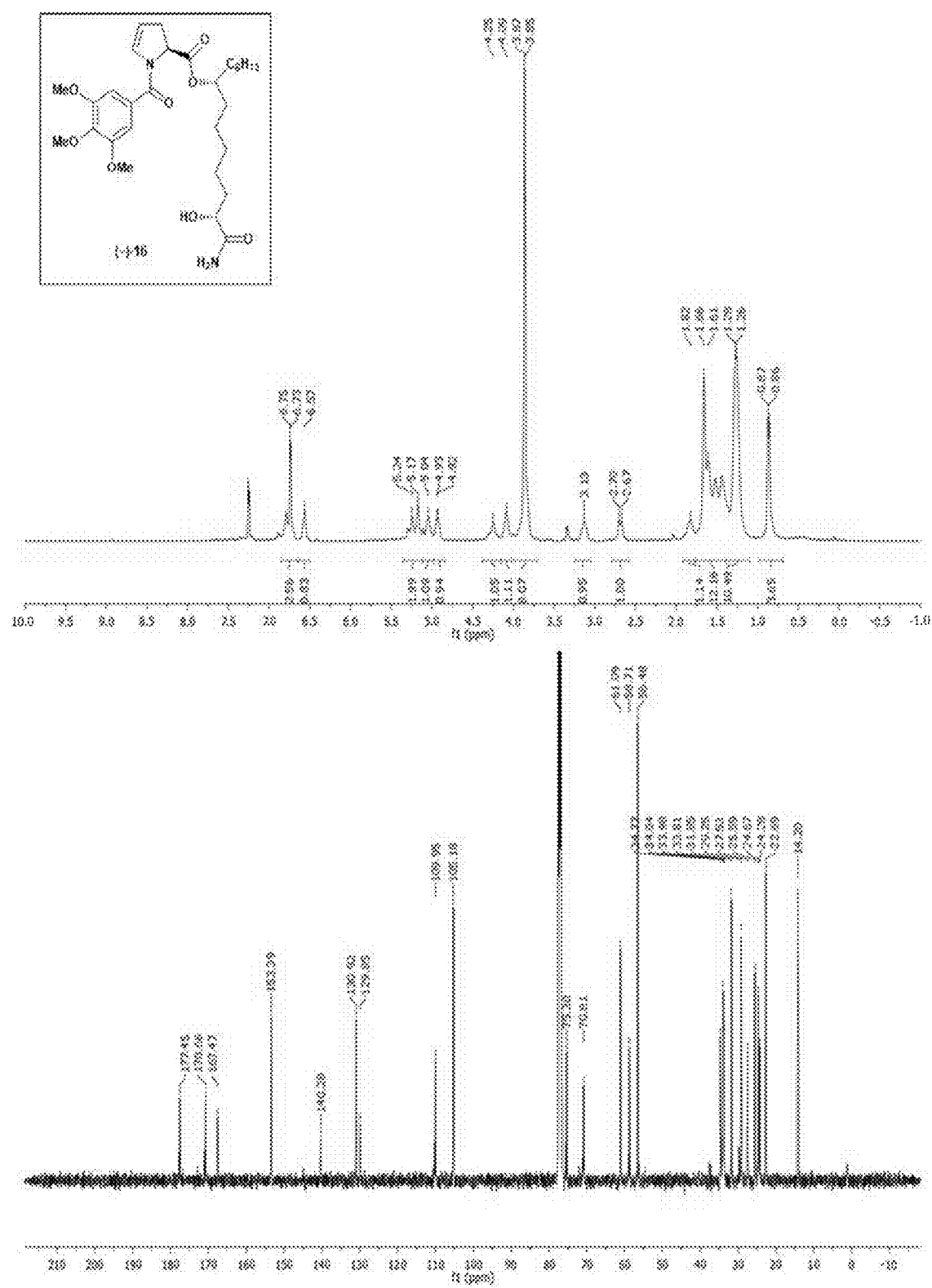
FIG. 87 depicts the proton ($^1$H) and carbon ($^{13}$C) NMR spectra of promysalin analog (−)-16.
Figure 88:
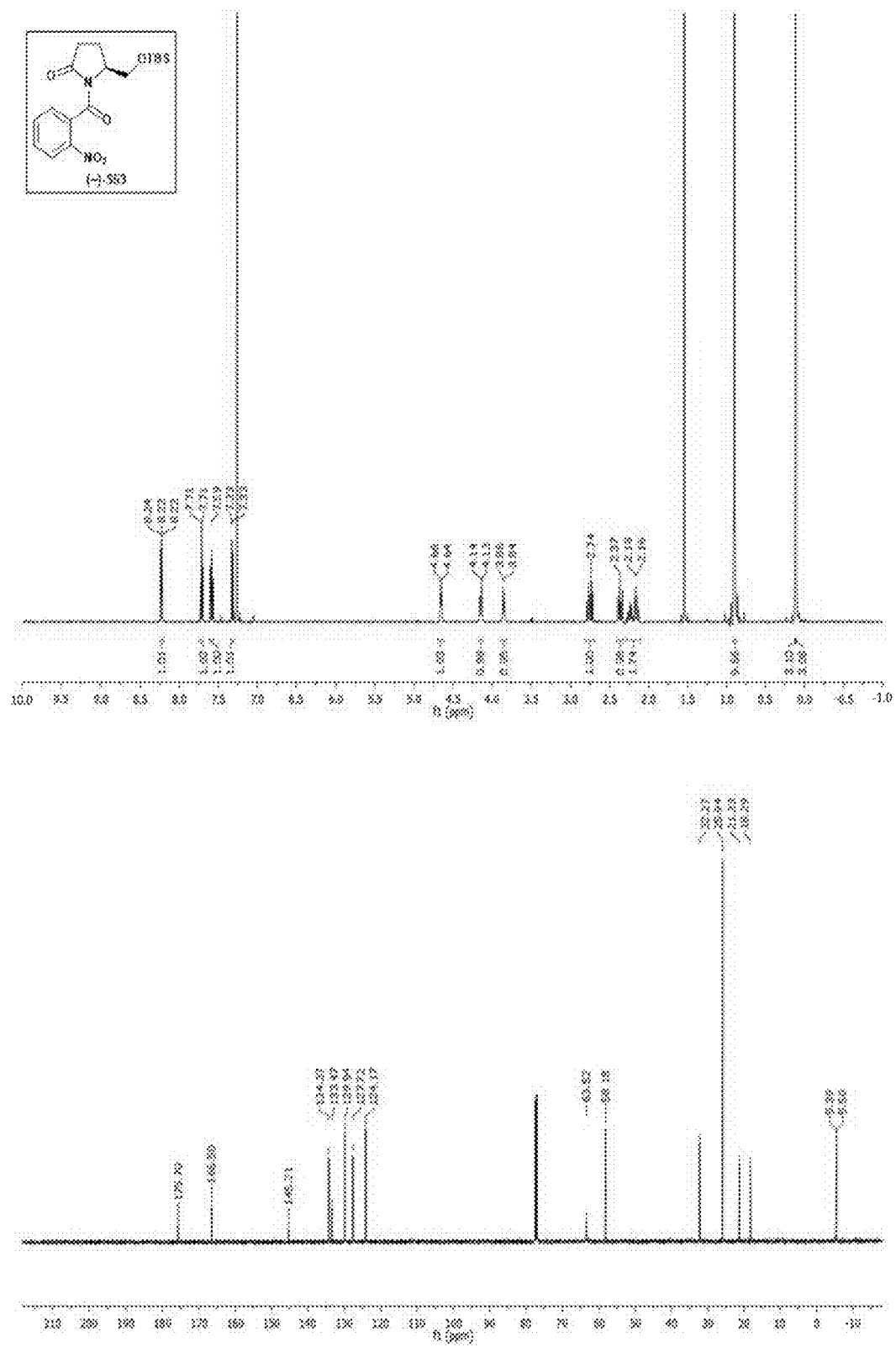
FIG. 88 depicts the proton ($^1$H) and carbon ($^{13}$C) NMR spectra of promysalin synthetic intermediate (−)-S53.
Figure 89:
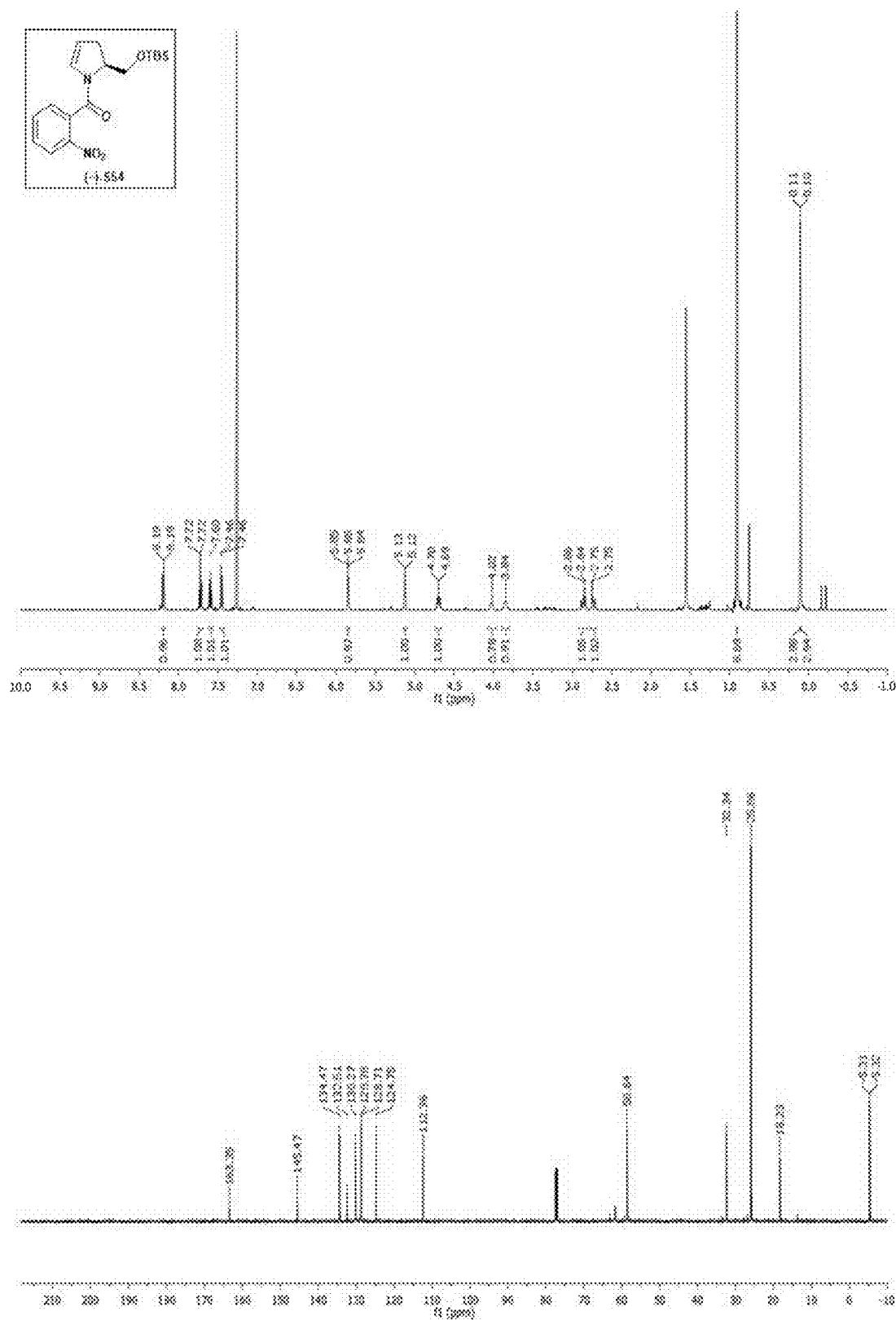
FIG. 89 depicts the proton ($^1$H) and carbon ($^{13}$C) NMR spectra of promysalin synthetic intermediate (−)-S54.
Figure 90:
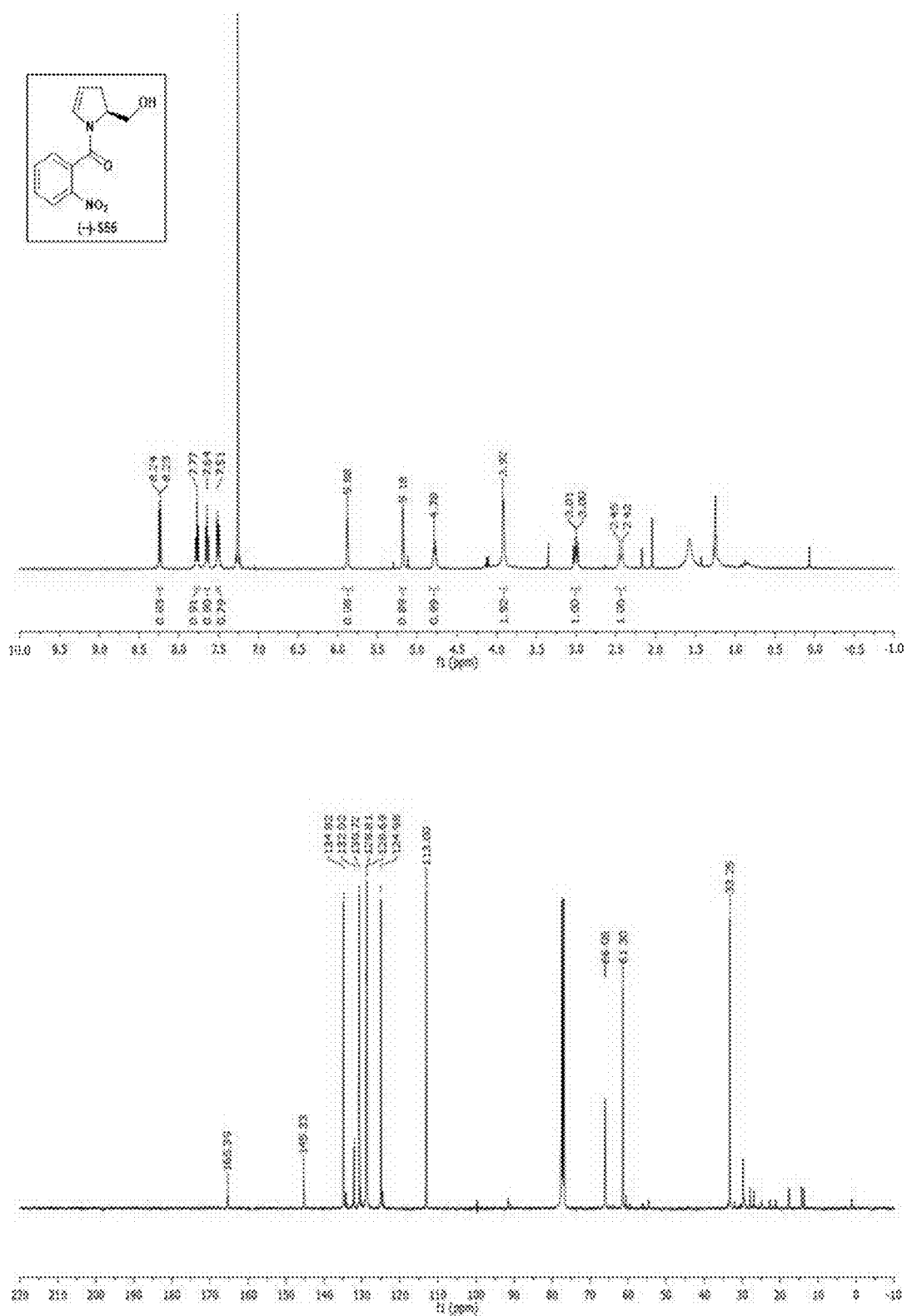
FIG. 90 depicts the proton ($^1$H) and carbon ($^{13}$C) NMR spectra of promysalin synthetic intermediate (−)-S55.
Figure 91:
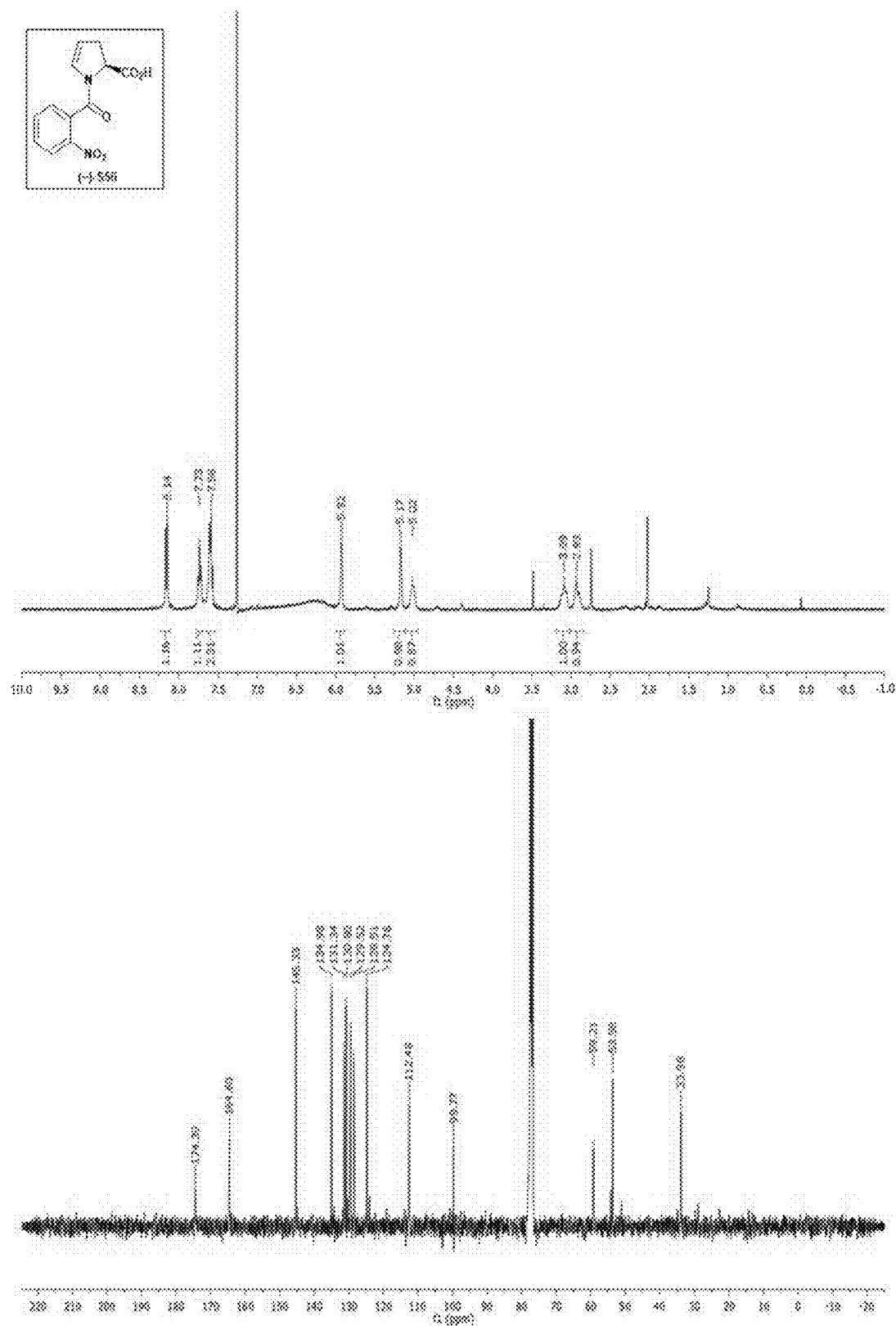
FIG. 91 depicts the proton ($^1$H) and carbon ($^{13}$C) NMR spectra of promysalin synthetic intermediate (−)-S56.
Figure 92:
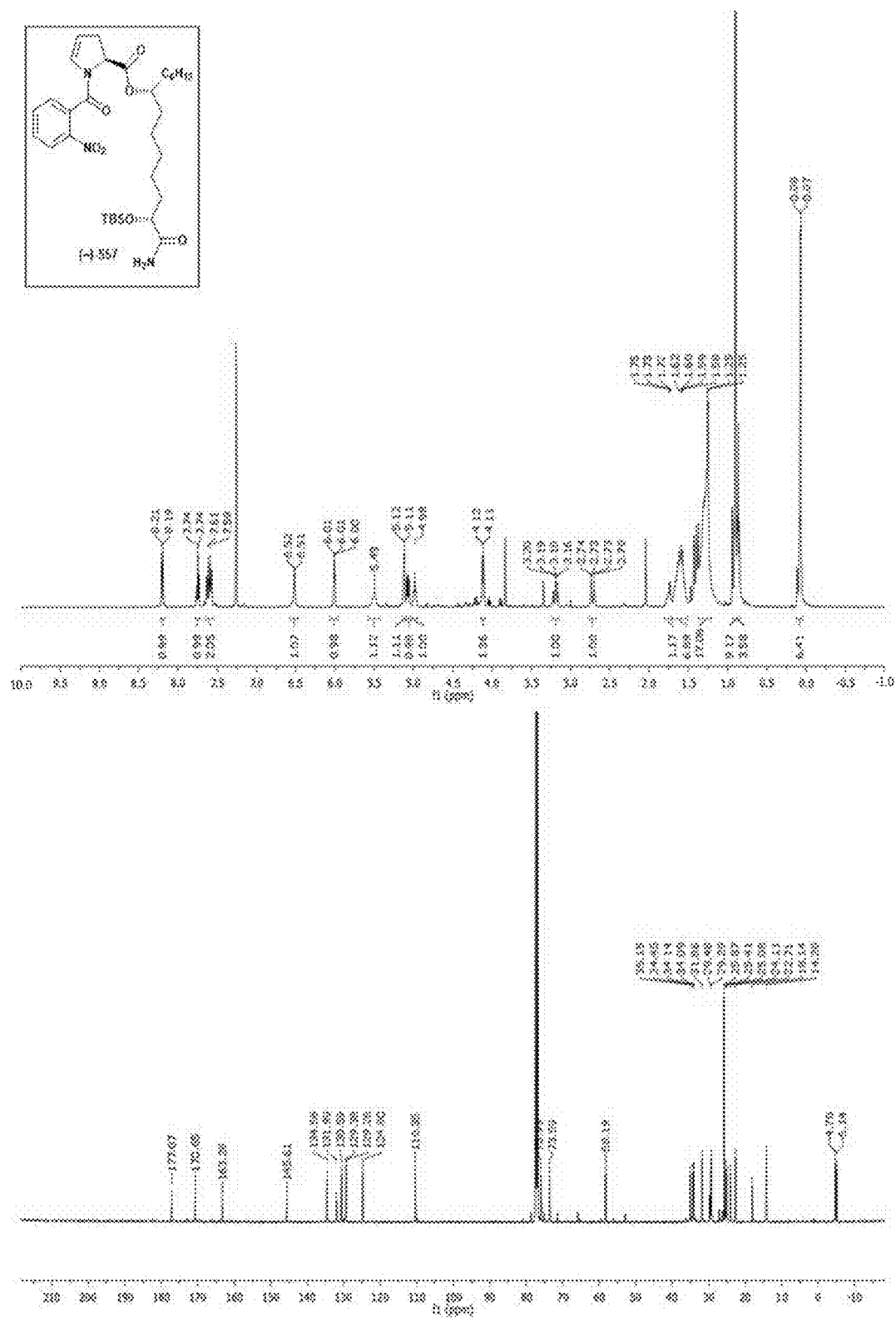
FIG. 92 depicts the proton ($^1$H) and carbon ($^{13}$C) NMR spectra of promysalin synthetic intermediate (−)-S57.
Figure 93:
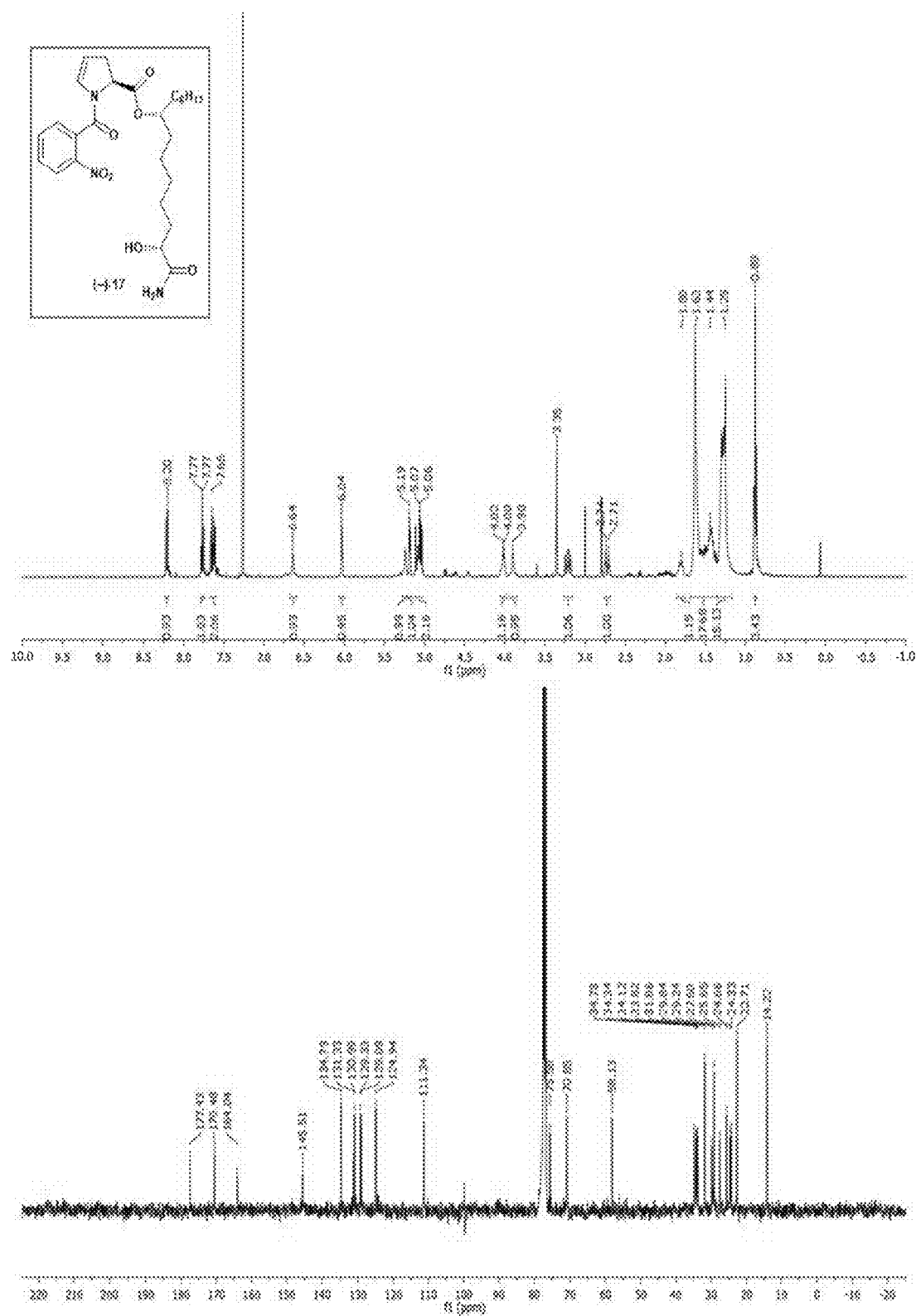
FIG. 93 depicts the proton ($^1$H) and carbon ($^{13}$C) NMR spectra of promysalin analog (−)-17.
Figure 94:
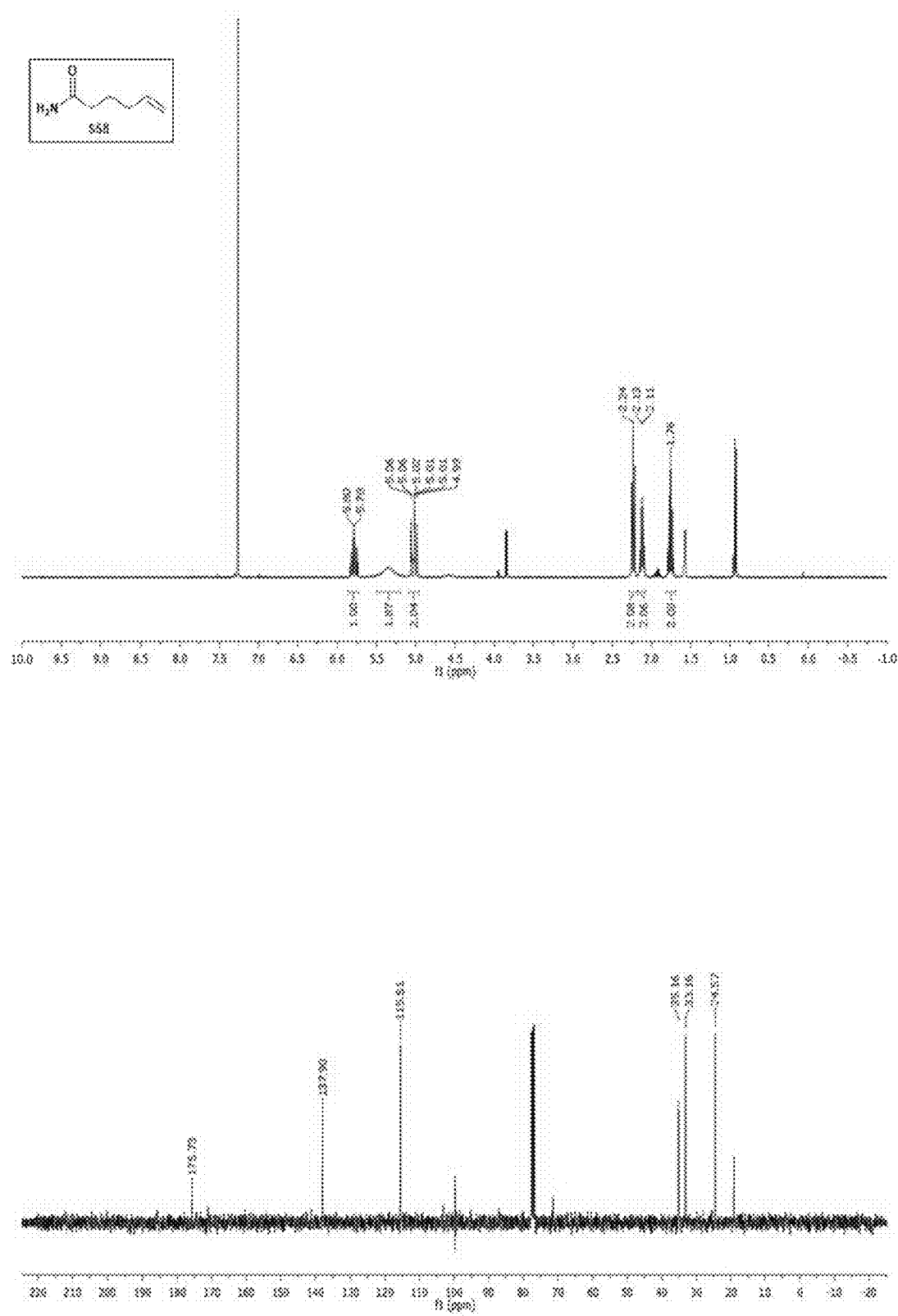
FIG. 94 depicts the proton ($^1$H) and carbon ($^{13}$C) NMR spectra of promysalin synthetic intermediate S58.
Figure 95:
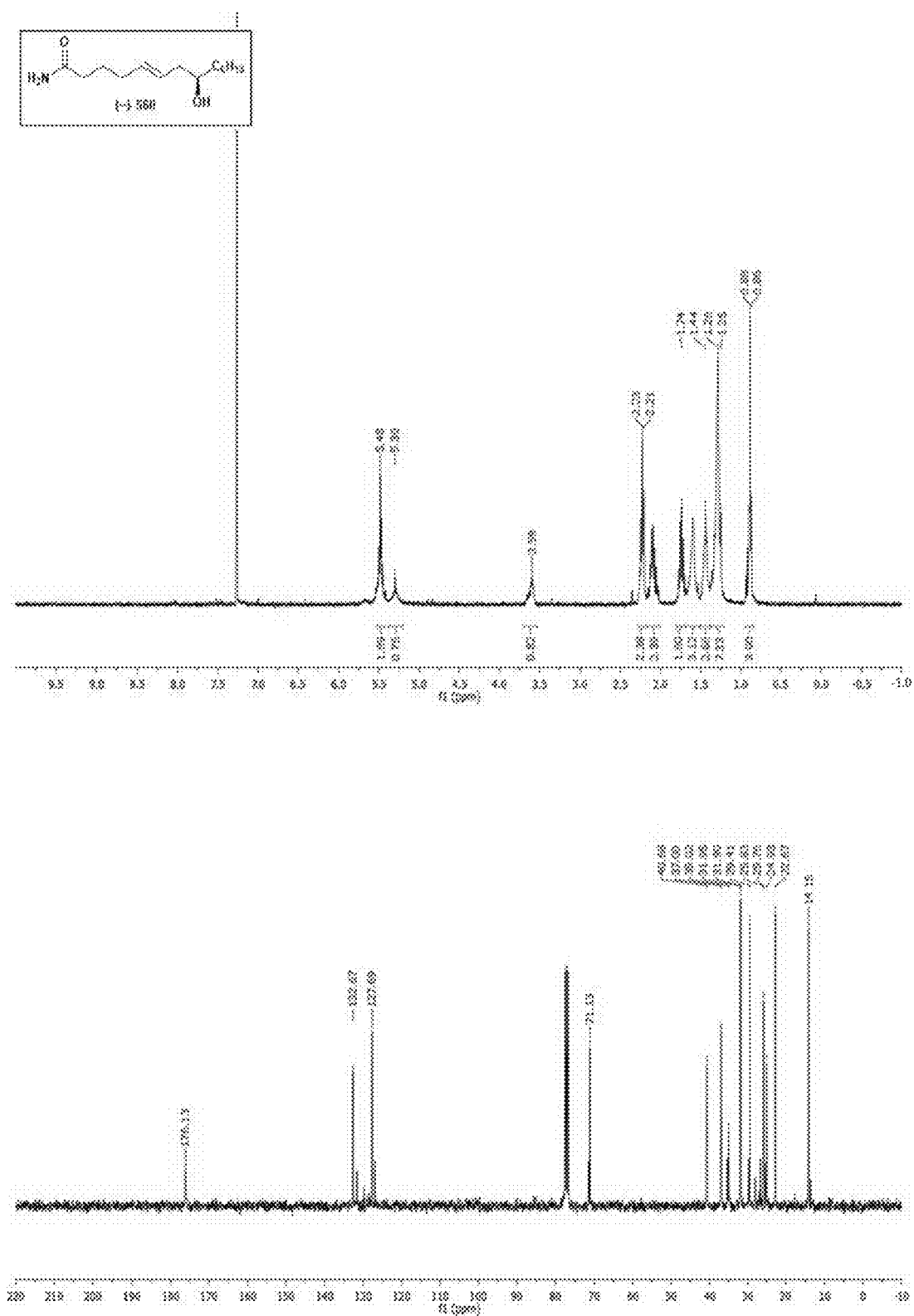
FIG. 95 depicts the proton ($^1$H) and carbon ($^{13}$C) NMR spectra of promysalin synthetic intermediate (−)-S60.
Figure 96:
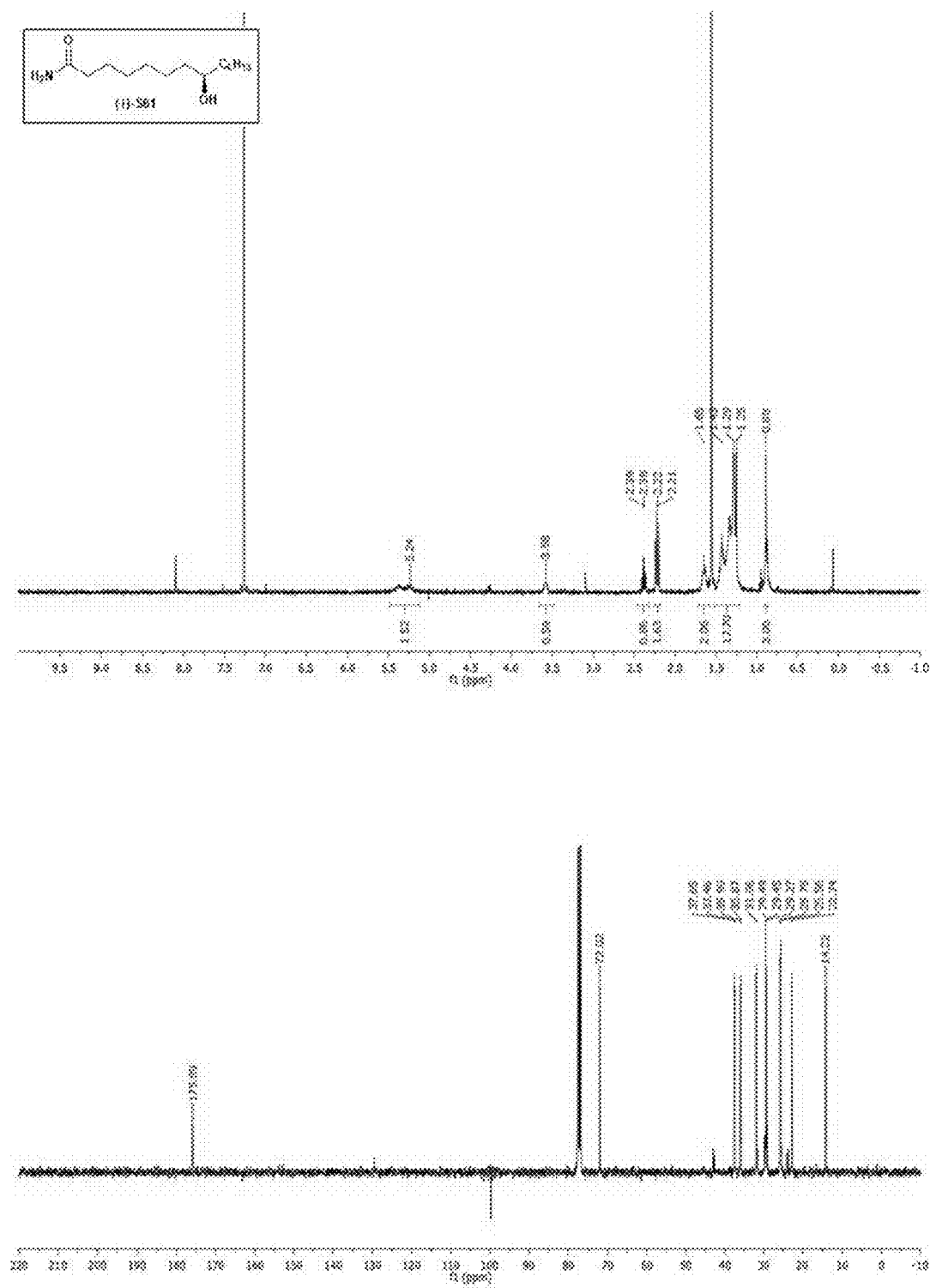
FIG. 96 depicts the proton ($^1$H) and carbon ($^{13}$C) NMR spectra of promysalin synthetic intermediate (+)-S61.
Figure 97:
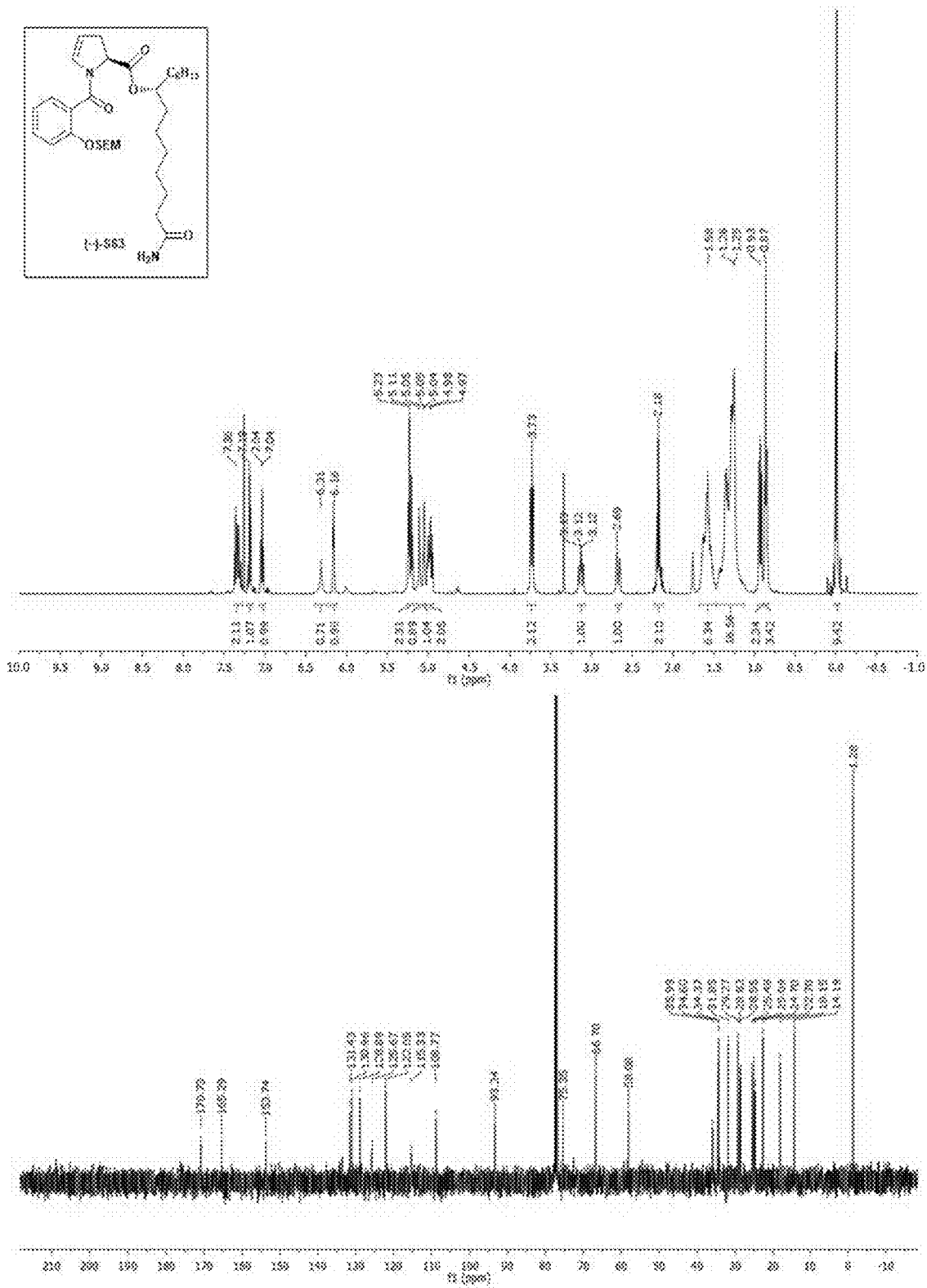
FIG. 97 depicts the proton ($^1$H) and carbon ($^{13}$C) NMR spectra of promysalin synthetic intermediate (−)-S63.
Figure 98:
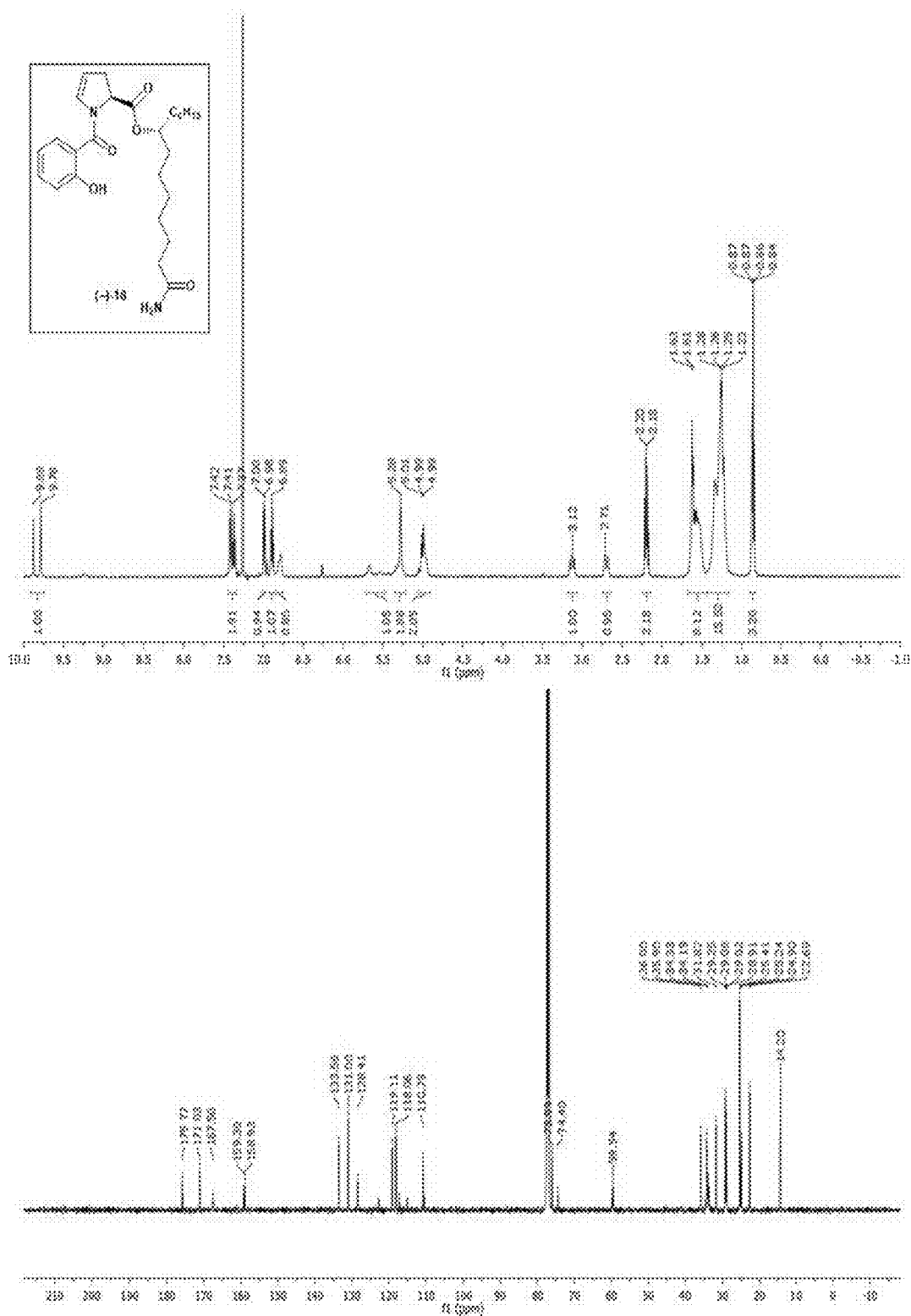
FIG. 98 depicts the proton ($^1$H) and carbon ($^{13}$C) NMR spectra of promysalin analog (−)-18.
Figure 99:
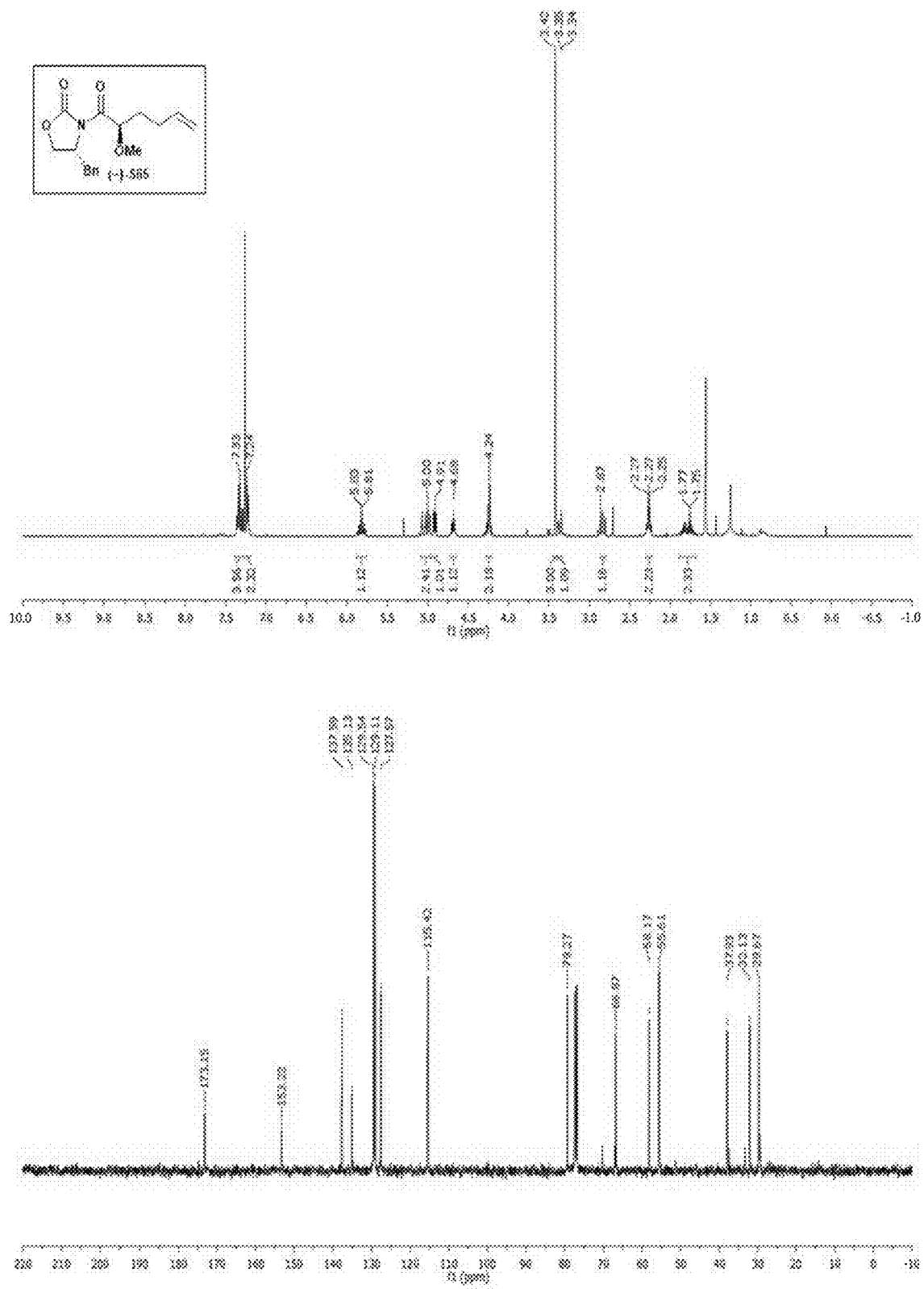
FIG. 99 depicts the proton ($^1$H) and carbon ($^{13}$C) NMR spectra of promysalin synthetic intermediate (−)-S65.
Figure 100:
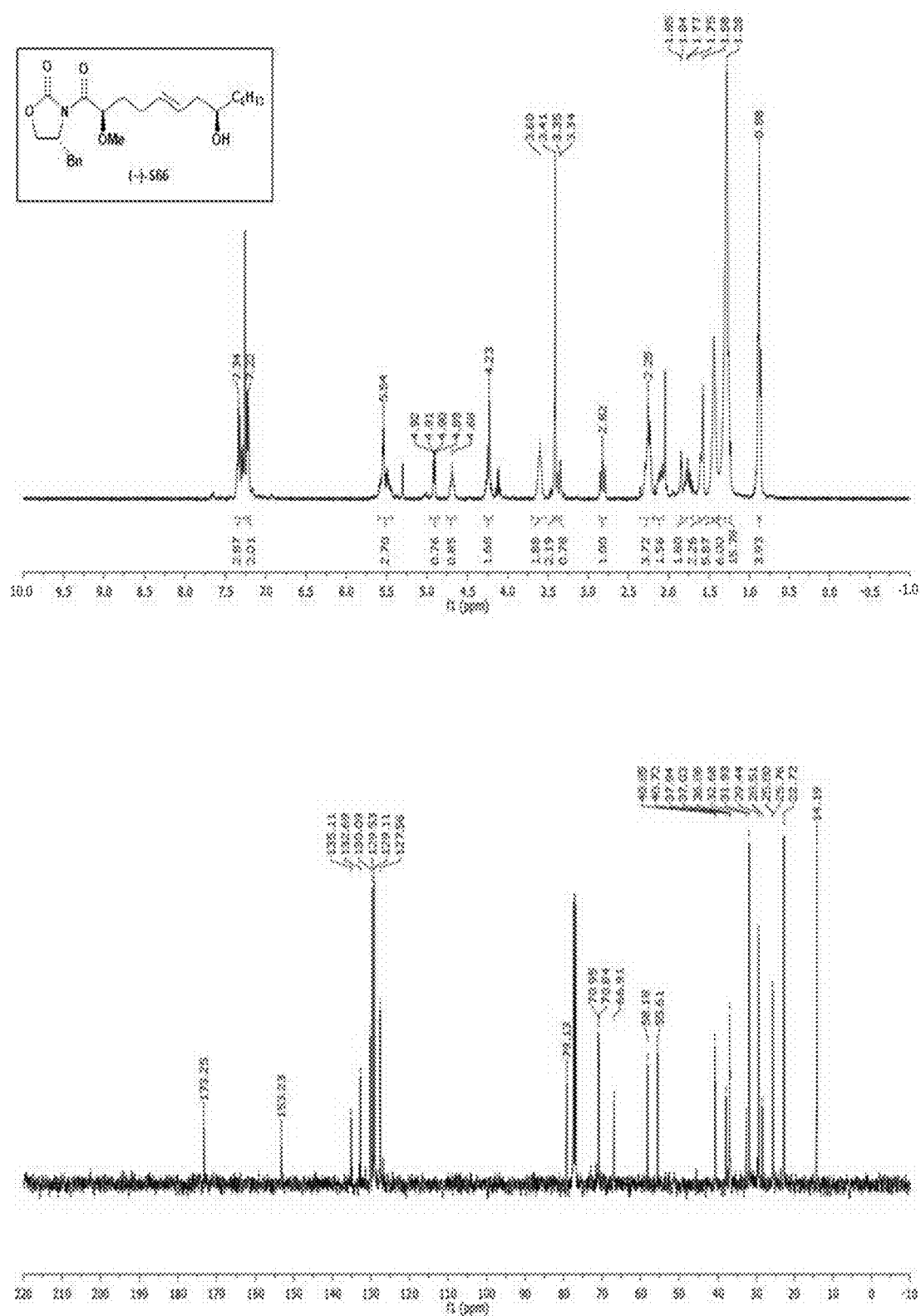
FIG. 100 depicts the proton ($^1$H) and carbon ($^{13}$C) NMR spectra of promysalin synthetic intermediate (−)-S66.
Figure 101:
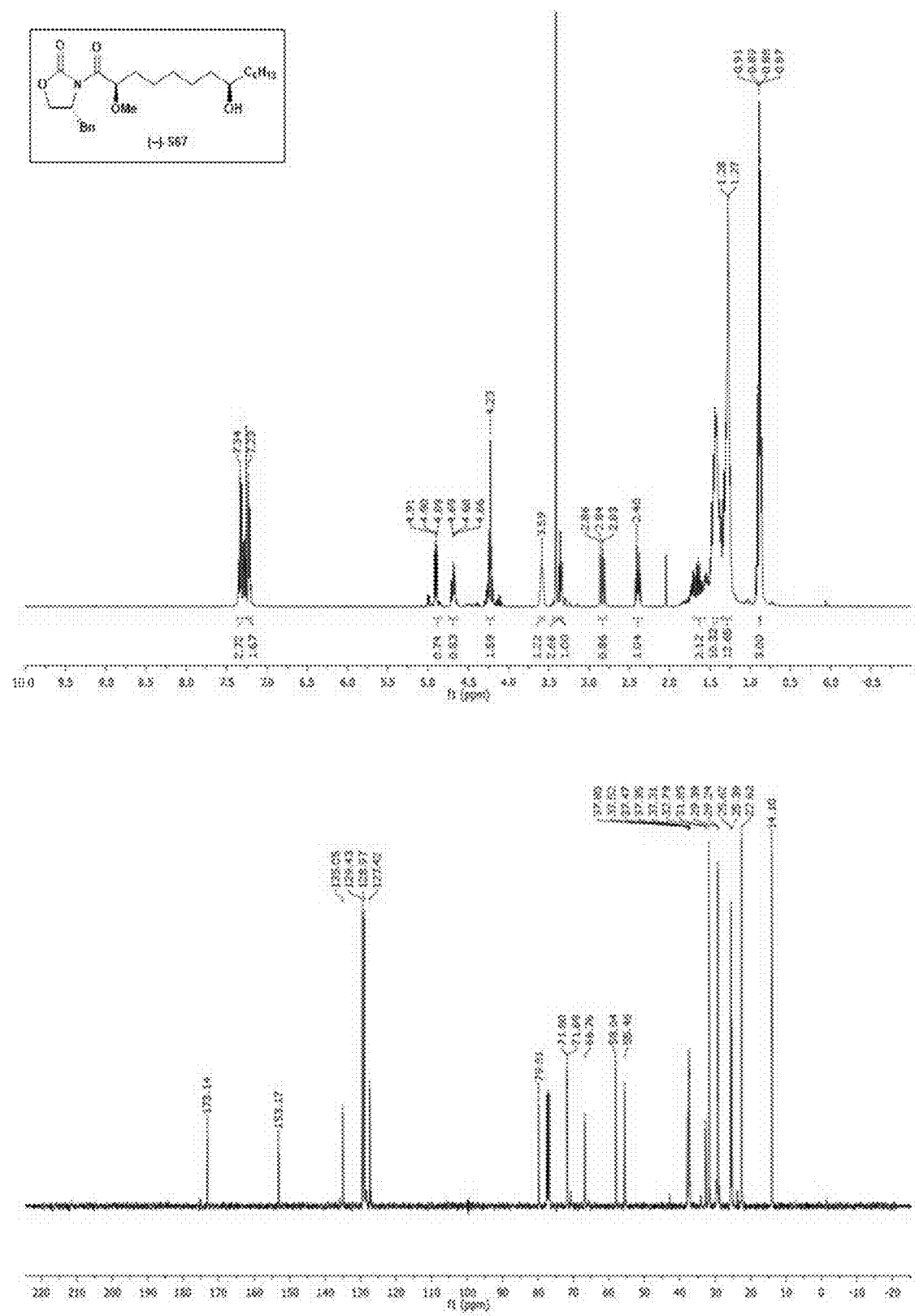
FIG. 101 depicts the proton ($^1$H) and carbon ($^{13}$C) NMR spectra of promysalin synthetic intermediate (−)-S67.
Figure 102:
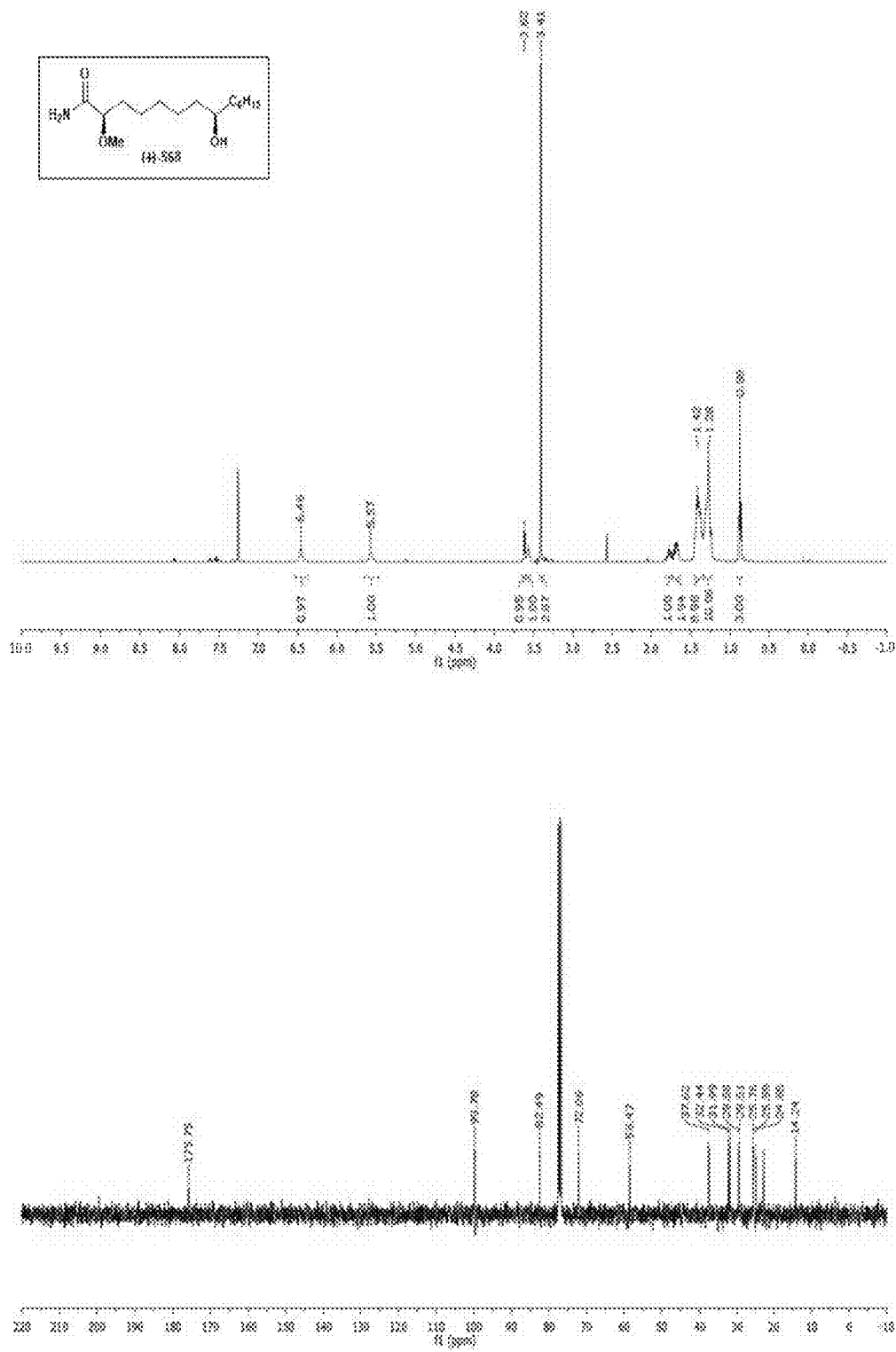
FIG. 102 depicts the proton ($^1$H) and carbon ($^{13}$C) NMR spectra of promysalin synthetic intermediate (+)-S68.
Figure 103:
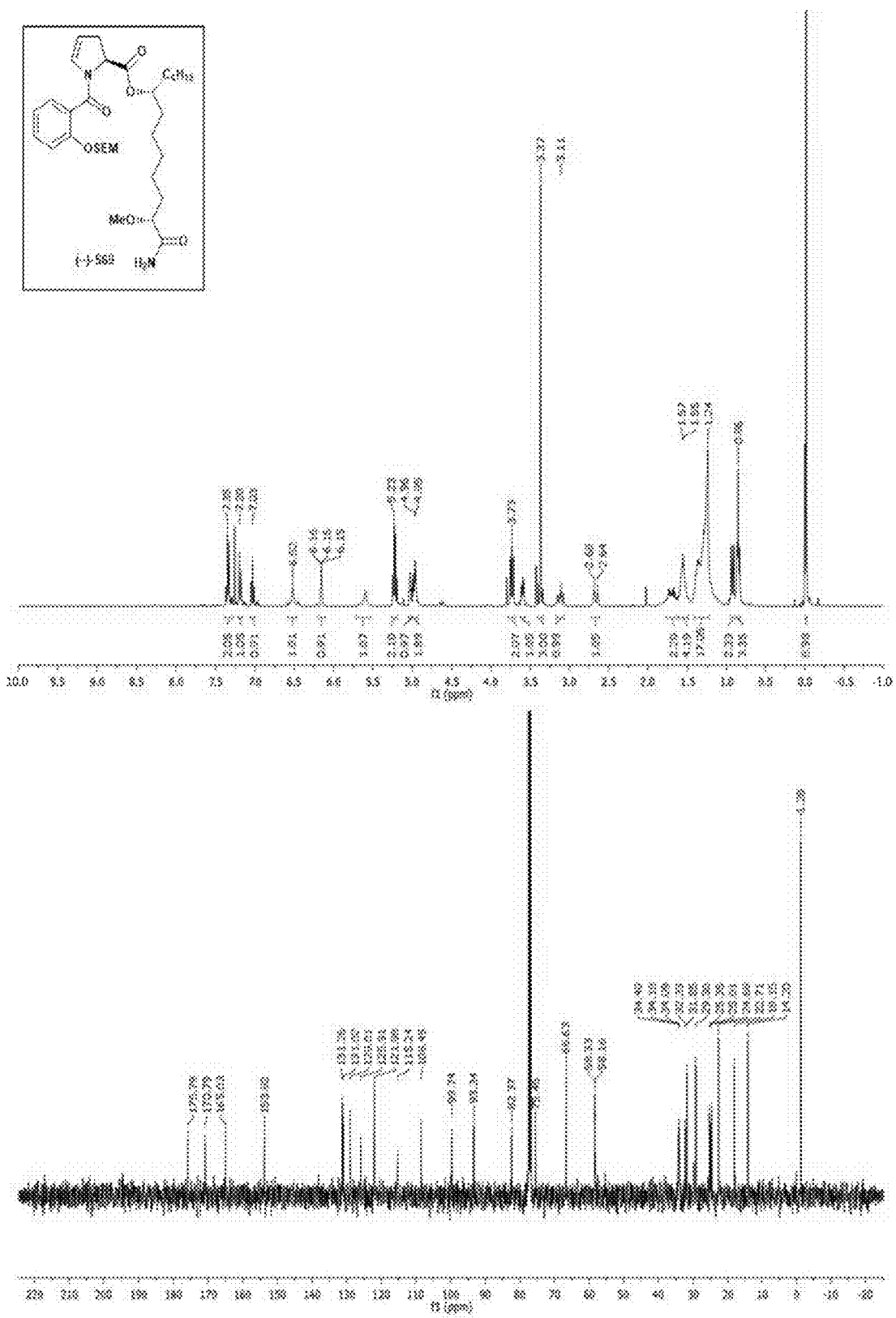
FIG. 103 depicts the proton ($^1$H) and carbon ($^{13}$C) NMR spectra of promysalin synthetic intermediate (−)-S69.
Figure 104:
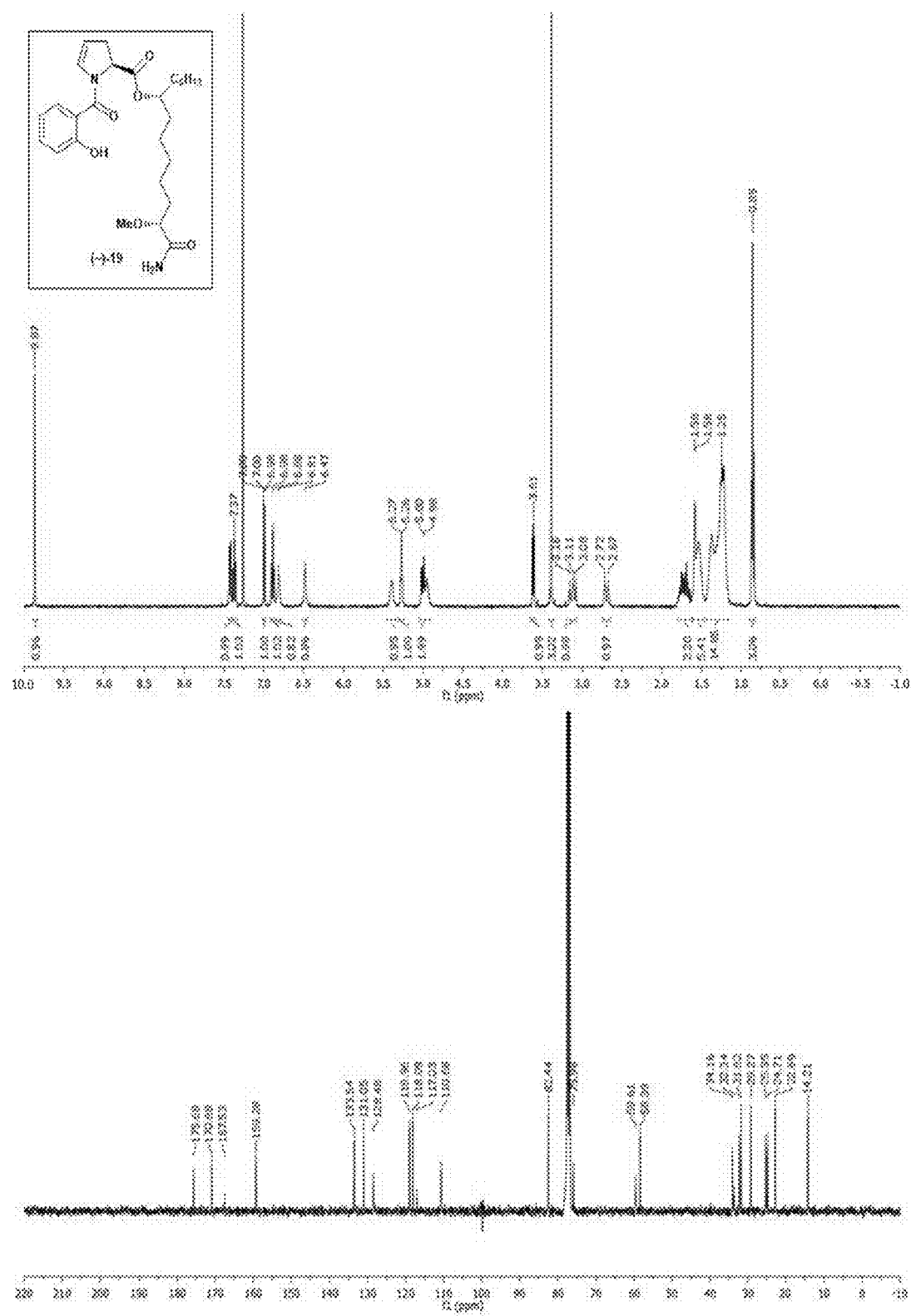
FIG. 104 depicts the proton ($^1$H) and carbon ($^{13}$C) NMR spectra of promysalin analog (−)-19.
Figure 105:
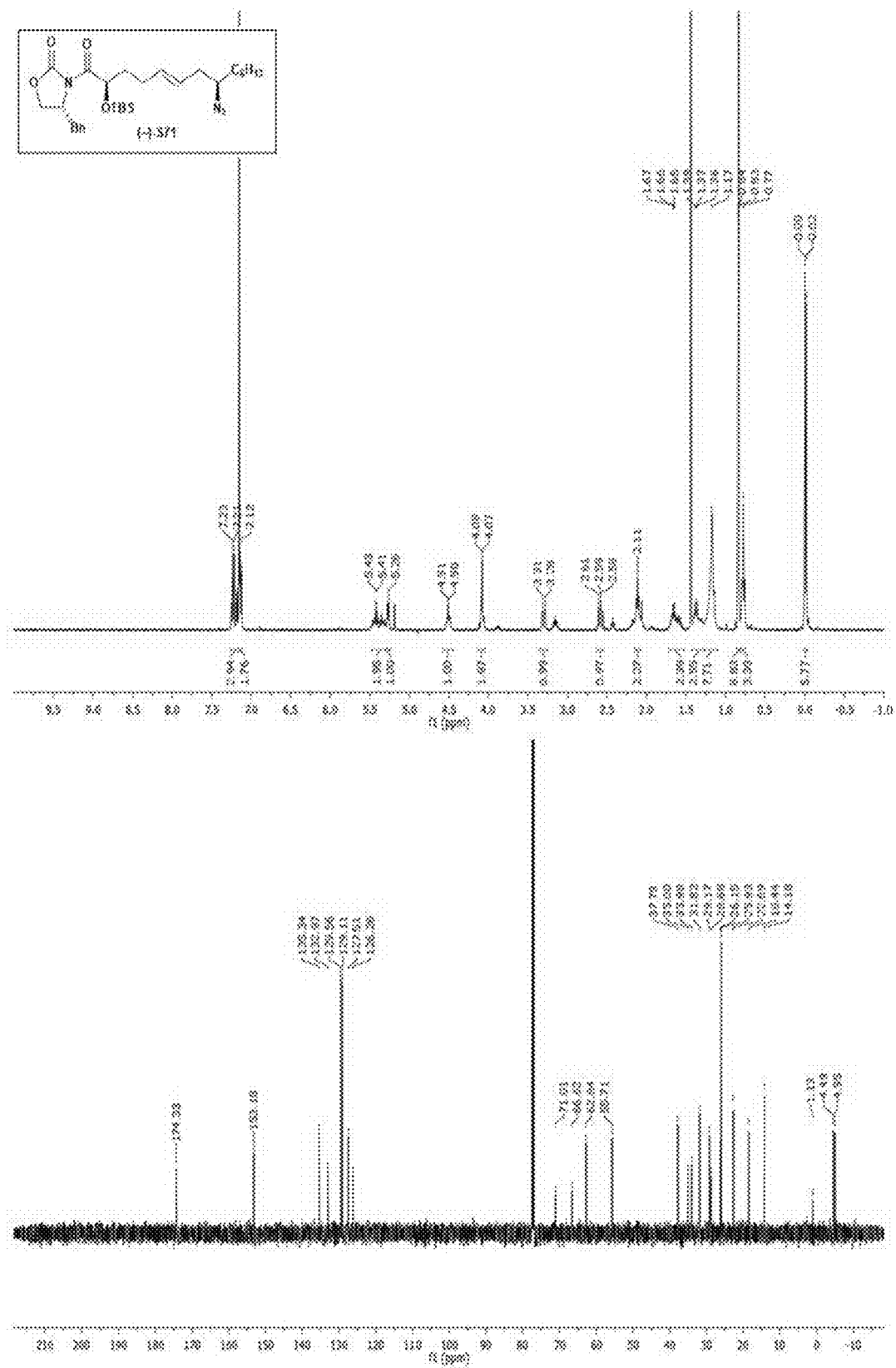
FIG. 105 depicts the proton ($^1$H) and carbon ($^{13}$C) NMR spectra of promysalin synthetic intermediate (−)-S71.
Figure 106:
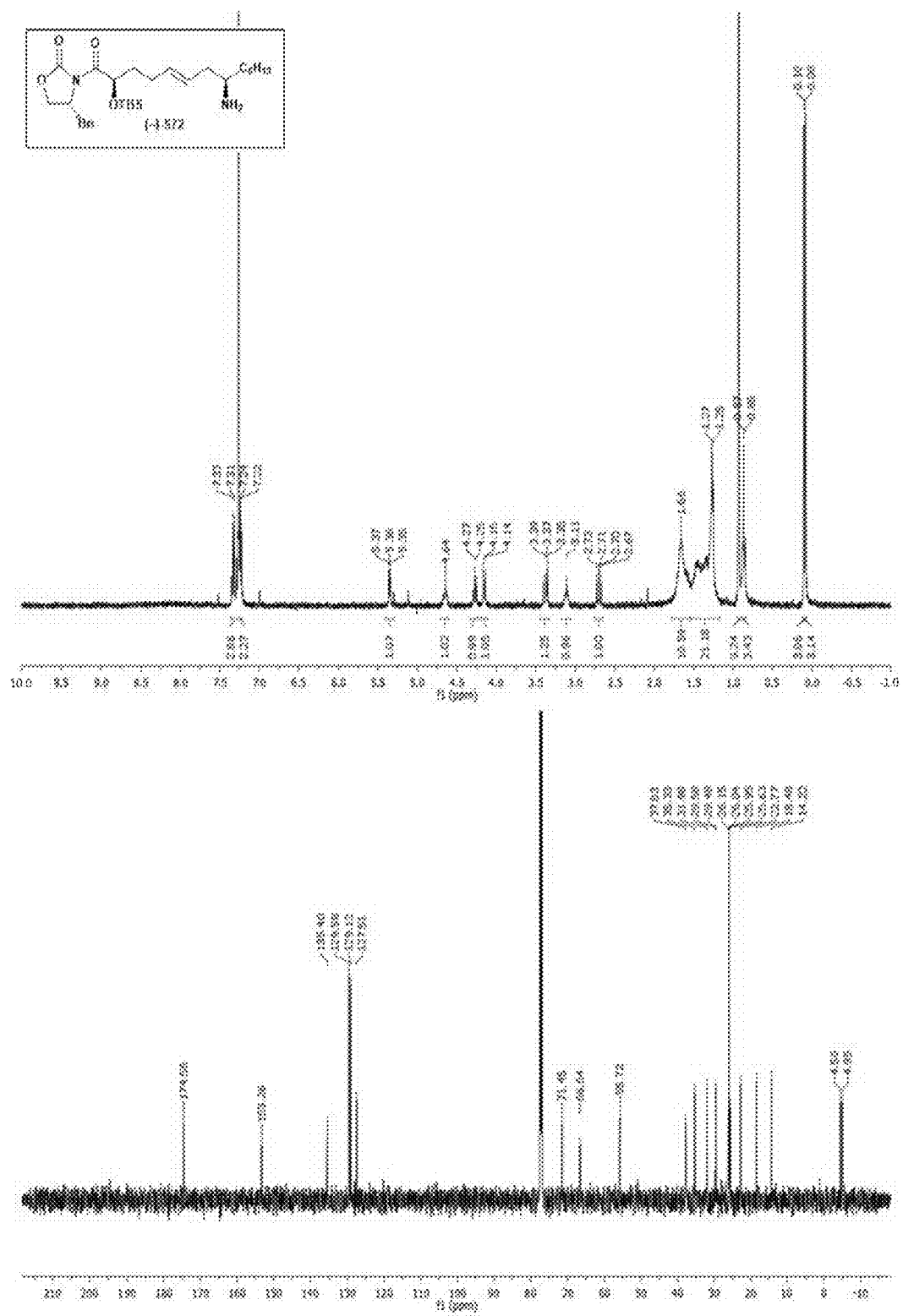
FIG. 106 depicts the proton ($^1$H) and carbon ($^{13}$C) NMR spectra of promysalin synthetic intermediate (−)-S72.
Figure 107:
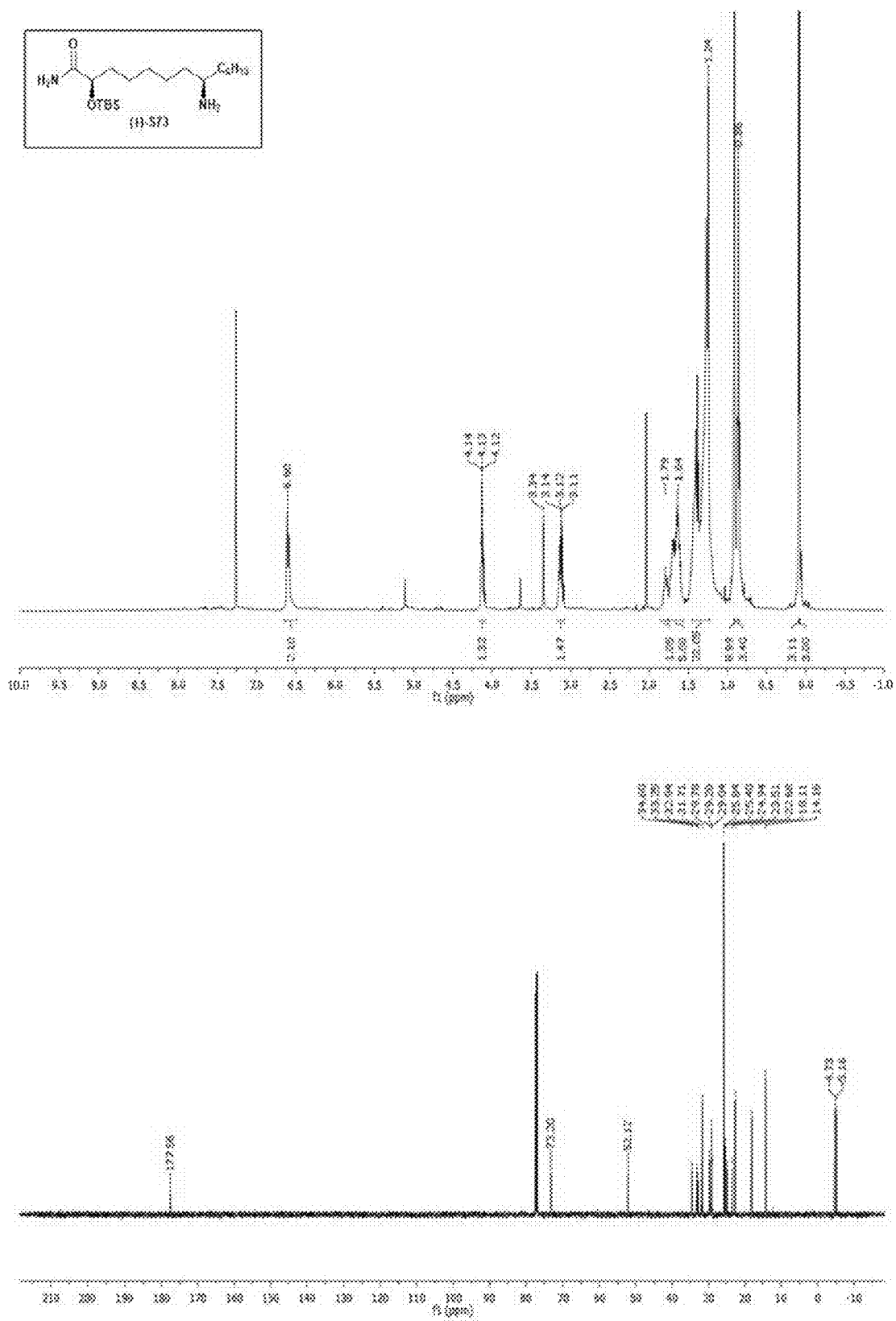
FIG. 107 depicts the proton ($^1$H) and carbon ($^{13}$C) NMR spectra of promysalin synthetic intermediate (+)-S73.
Figure 108:
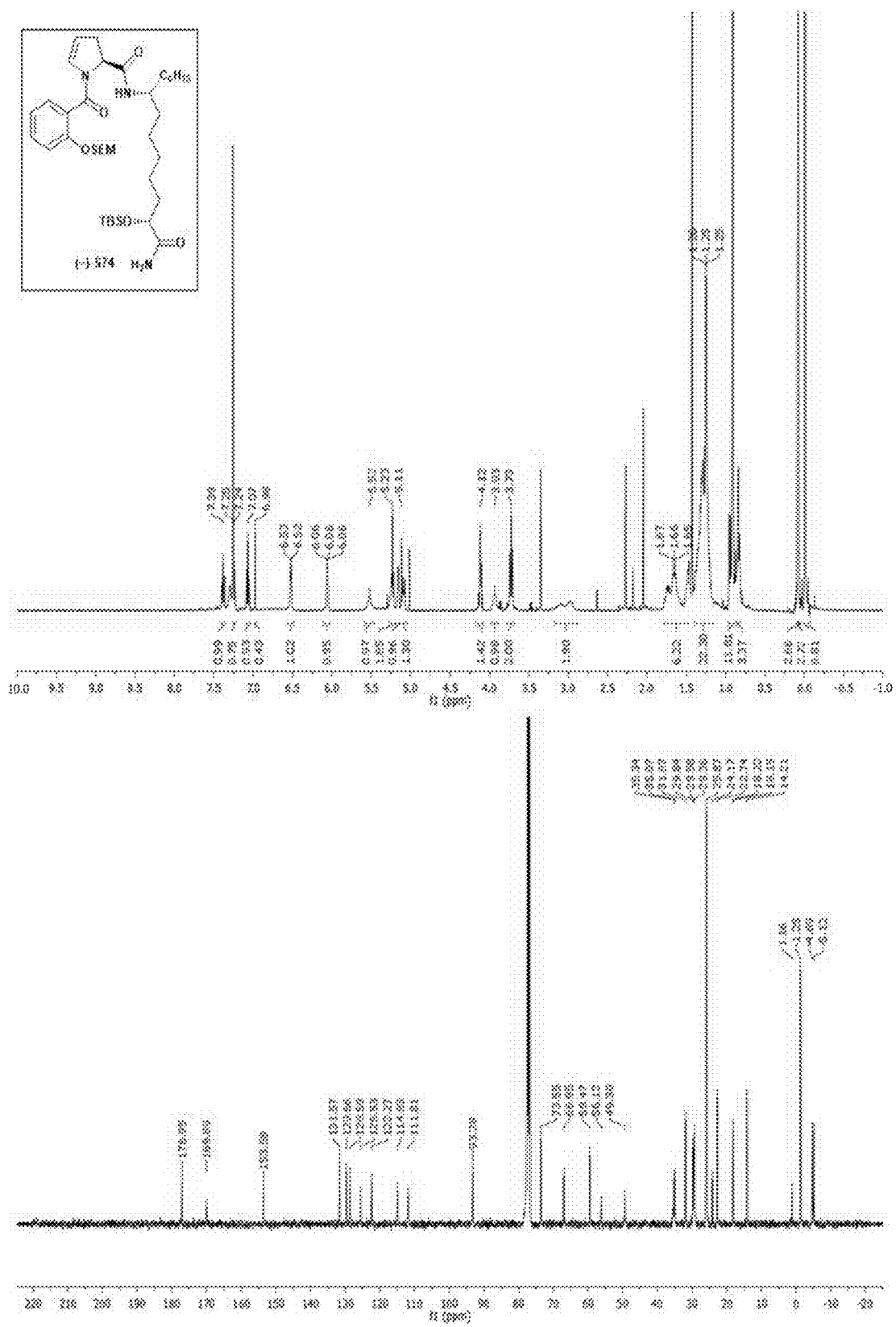
FIG. 108 depicts the proton ($^1$H) and carbon ($^{13}$C) NMR spectra of promysalin synthetic intermediate (−)-S74.
Figure 109:
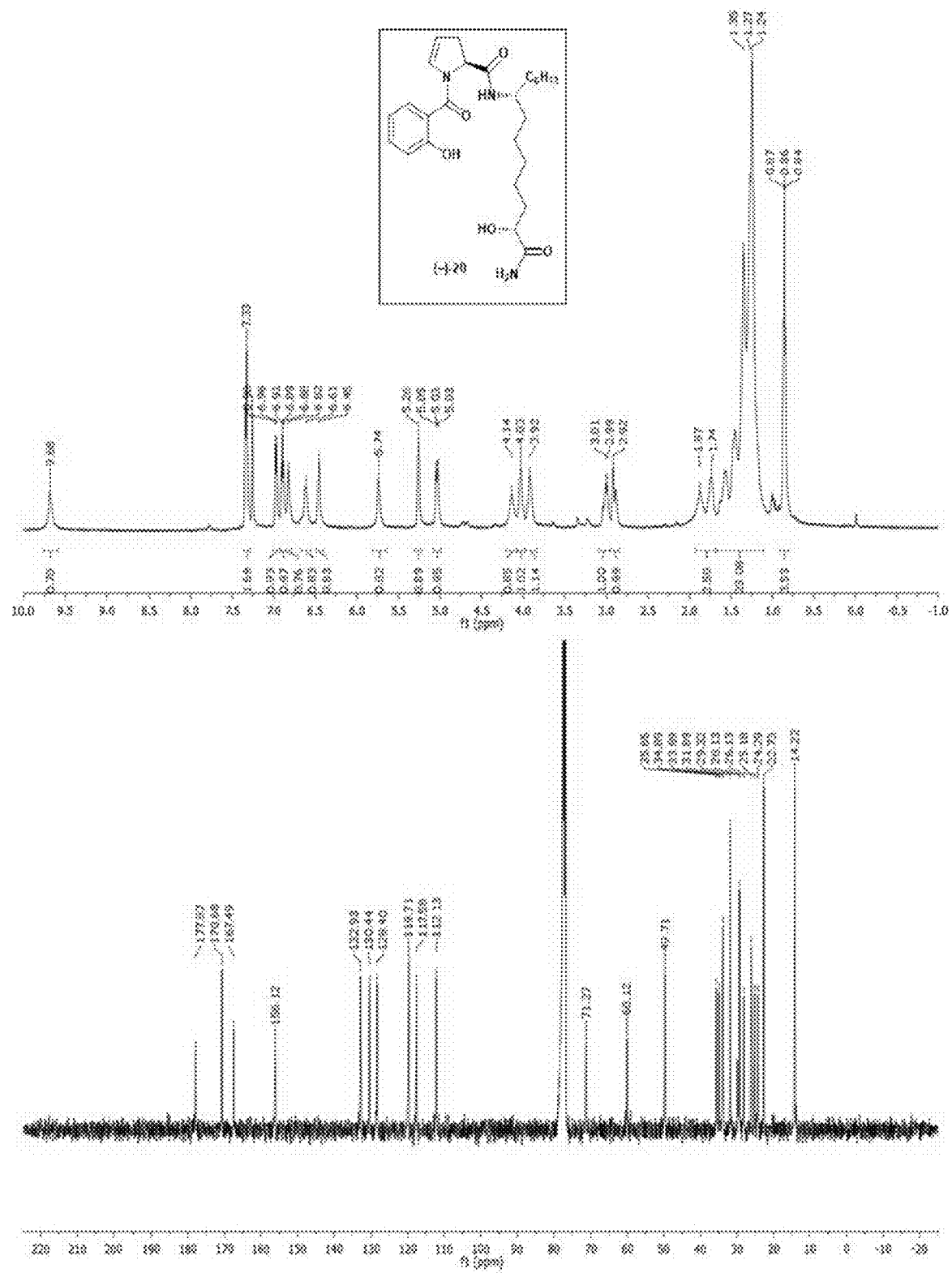
FIG. 109 depicts the proton ($^1$H) and carbon ($^{13}$C) NMR spectra of promysalin analog (−)-20.
Figure 110:
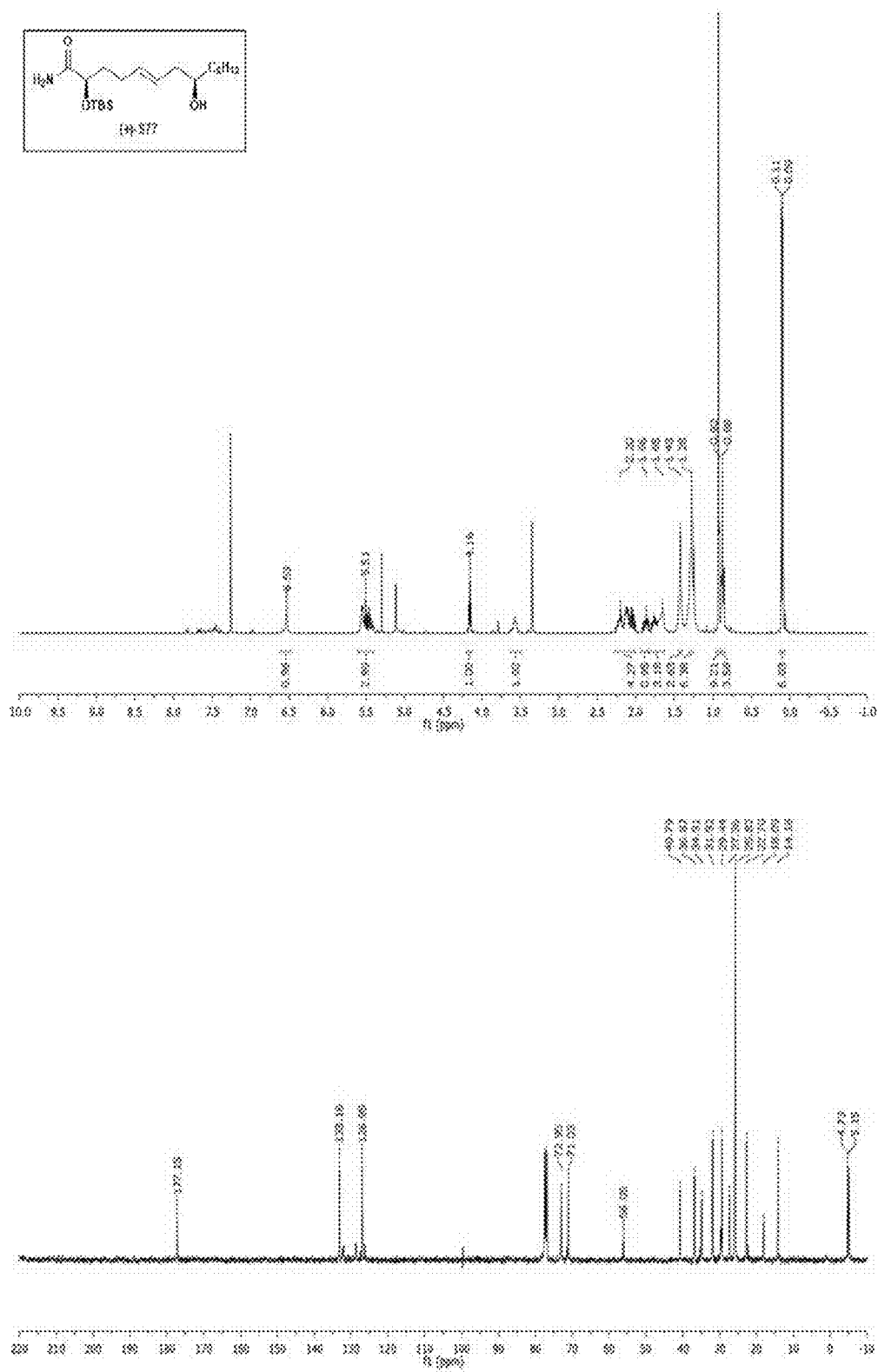
FIG. 110 depicts the proton ($^1$H) and carbon ($^{13}$C) NMR spectra of promysalin synthetic intermediate (+)-S77.
Figure 111:
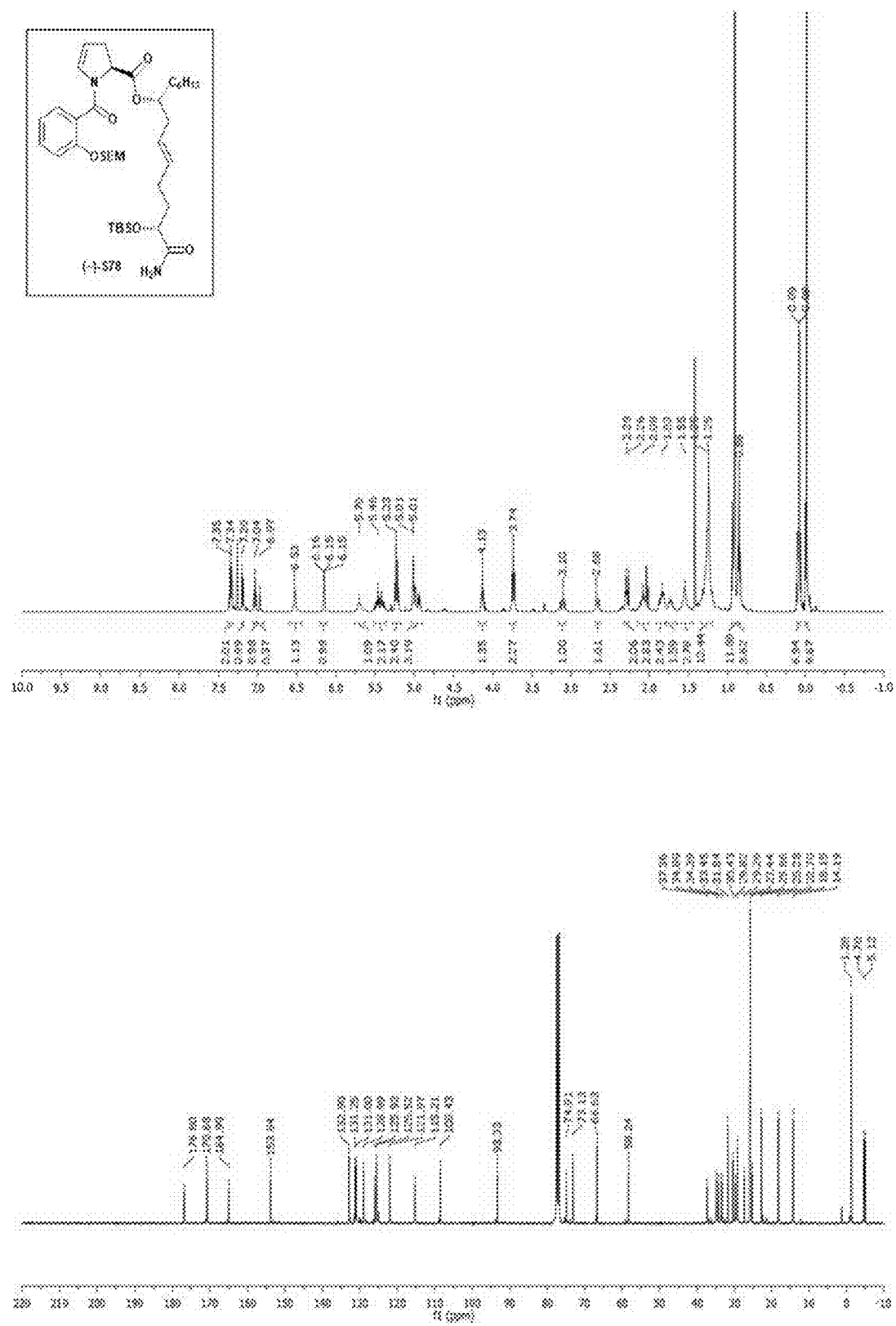
FIG. 111 depicts the proton ($^1$H) and carbon ($^{13}$C) NMR spectra of promysalin synthetic intermediate (−)-S78.
Figure 112:
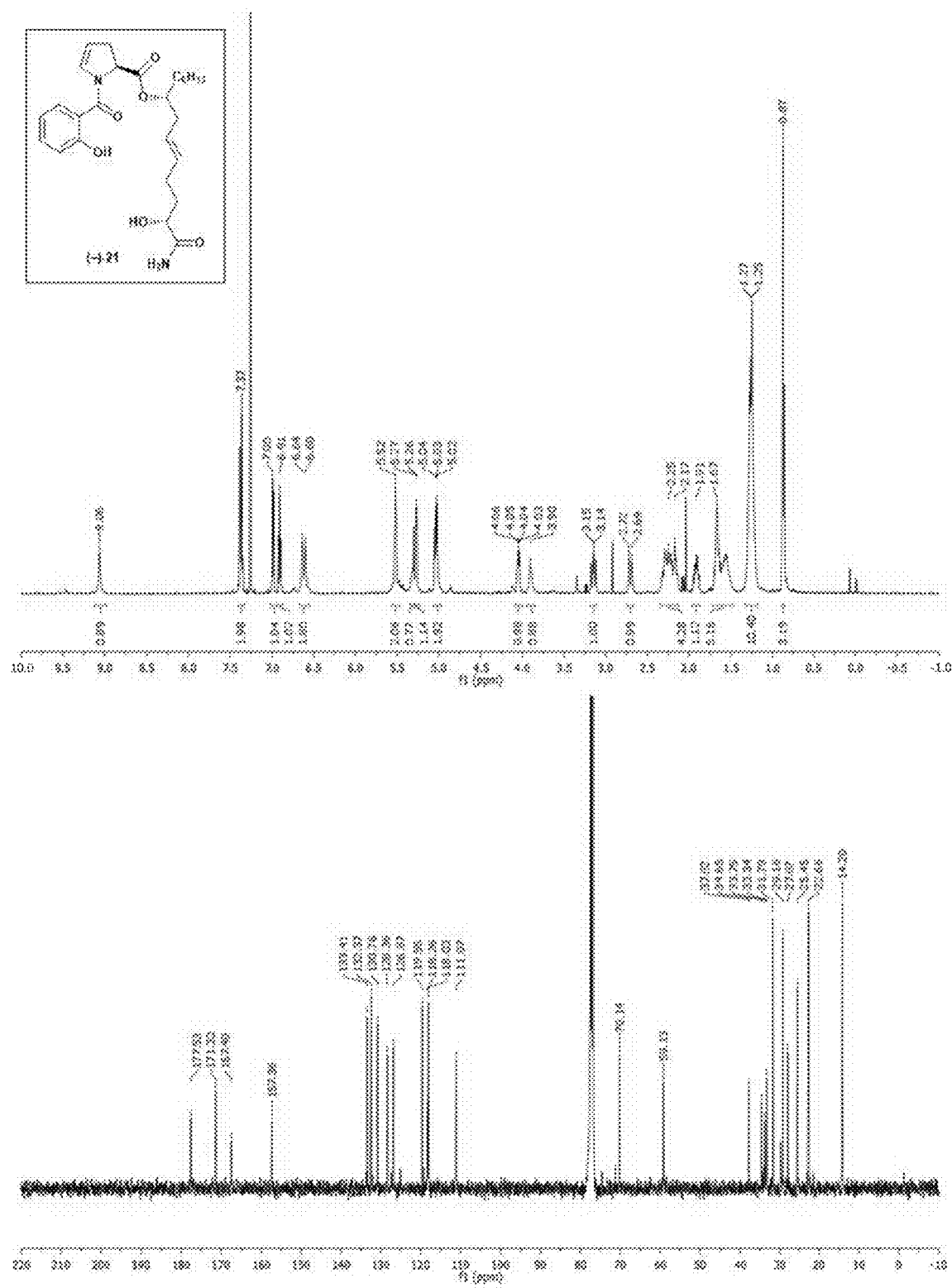
FIG. 112 depicts the proton ($^1$H) and carbon ($^{13}$C) NMR spectra of promysalin analog (−)-21.
Figure 113:
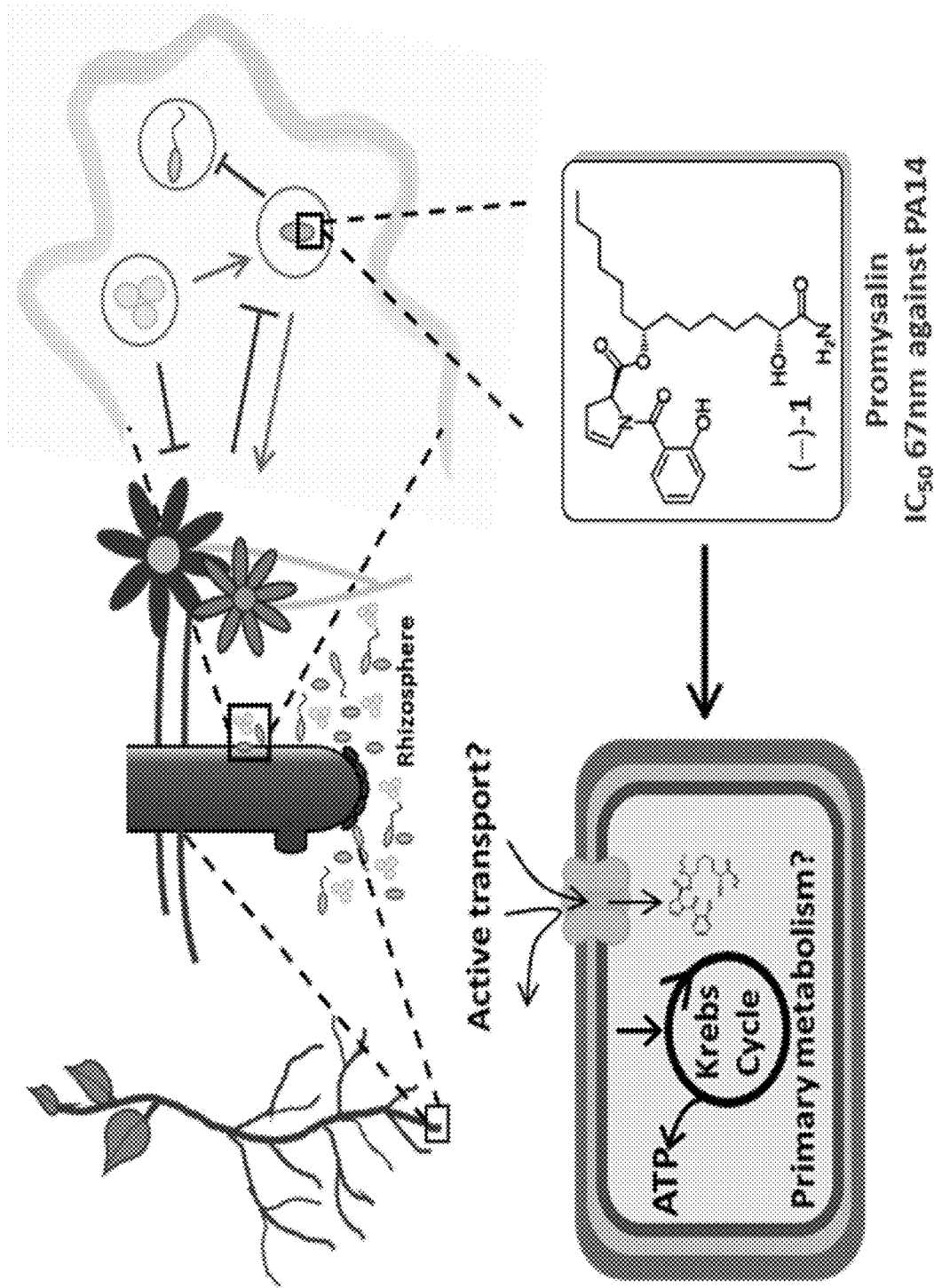
FIG. 113 is a schematic of the rhizosphere and the proposed mechanisms of action of promysalin.

P. aeruginosa PA01, and PA14 were gifts from Prof. George O'Toole (Dartmouth Medical School). Bacterial cultures were grown from freezer stocks overnight (16-24 hr) with shaking at 37° C. in Tryptic Soy Broth (TSB) media (10 mL). Growth curves were obtained for PA01 and PA14 to determine the OD of each strain in exponential growth; OD readings at 595 nm were taken every 10 minutes for 6 hours in a plate reader at 37° C. with shaking and repeated six times. (see FIGS. 6A and 6B)

IC50 Assay

Compounds were serially diluted in sterile DI water from a stock solution (1 mM in 10% DMSO/90% H$_2$O) to yield twenty-four test concentrations. Overnight cultures were diluted 1:100 in 5 mL fresh media and grown with shaking at 37° C. to an OD of 0.32 (see growth curves). Bacteria were diluted to a concentration of 0.004 using the following equation: (x μL O/N)(OD reading)=(0.004)(volume needed) and 100 μL was inoculated into each well of a flat-bottom 96-well plate (Corning 3370) containing 100 μL of compound solution. Plates were incubated statically at 37° C. for 24 hours, upon which time the OD at 595 nm was measured using a plate reader. IC$_{50}$ values were calculated by fitting the OD readings vs. concentration with a 4 parameter logistic model. Controls were prepared by serially diluting a 10% DMSO/90% H$_2$O the same as the compound stock solution. Compounds were tested in triplicate from separate O/N cultures and results averaged.

CAS Assay

CAS agar was prepared as described previously (Cordero, et al., PNAS, 2012, 109, 49, 29059). 10 μL of solution at given concentration were dosed onto plates and imaged after 24 hours. Stock solutions were made in 10% DMSO/H$_2$O.

The results of the experiments are now described

Sixteen promysalin analogs were synthesized utilizing diverted total synthesis (DTS) to better understand the mode of action of this natural product. The analog studies revealed that the bioactivity of promysalin is sensitive to changes within its hydrogen bond network whereby alteration has drastic biological consequences. The DTS library not only yielded three analogs that retained potency but also provided insights that resulted in the identification of a previously unknown ability of promysalin to bind iron. These findings suggest a complex multi-faceted role of the natural product within the rhizosphere. The structural diversity has shed light on the key structural features responsible for the bioactivity and highlights the importance of the key functionality in the hydrogen-bonding network. Although not wishing to be bound by any particular theory, these factors are presumably responsible for binding iron. Further, these findings have led to the discovery of the iron-binding ability of promysalin. Although not wishing to be bound by any particular theory, these results suggest a secondary role for the natural product as a rhizosphere siderophore. In light of these results, a potential mechanism of action via the inhibition of siderophore transport seems feasible.

Recently reported is the total synthesis and structural elucidation of promysalin, which is produced by Pseudomonas putida (PP), and inhibits the growth of PA at nM concentrations (Steele et al., 2015, J. Am. Chem. Soc. 137:7314), while Gram-positive bacteria show no susceptibility (Li et al., 2011, Chem. & Biol. 18:1320). Furthermore, during the biological studies it was found that promysalin inhibits the production of pyoverdine (a siderophore) in P. putida KT2440, and only one stereoisomer elicited this phenotype. Siderophores are essential for the growth of Pseudomonads as they actively chelate Fe$^{3+}$ for its end use in enzymatic processes. Siderophore production is closely linked to virulence; therefore, inhibiting such a process may yield novel anti-virulence therapies (Overhage et al., 2008, J. Bacteriol. 190:2671). These initial discoveries prompted let to a synthetic campaign to elucidate what chemical moieties are responsible for the species-specific nature of promysalin.

At the outset, two potential mechanisms of action were hypothesized. First, promysalin may be a "prodrug", whereby it would be activated by either an enzyme (i.e. an esterase) unique to PA or by the physical environment surrounding PA itself. A second alternative is that the chemical architecture of the molecule is exquisitely selective for a target harbored by PA but not present in other bacteria. Earlier synthetic studies suggested that the exact three-dimensional shape of the molecule was key to its biological activity as a 100-200-fold decrease in activity by altering either stereocenter on the fatty acid fragment was observed. To address these questions, a library of sixteen hypothesis-driven analogs was constructed via diverted total synthesis (DTS) (Wilson and Danishefsky, 2006, J. Org. Chem. 71:8329).

Figure 1:
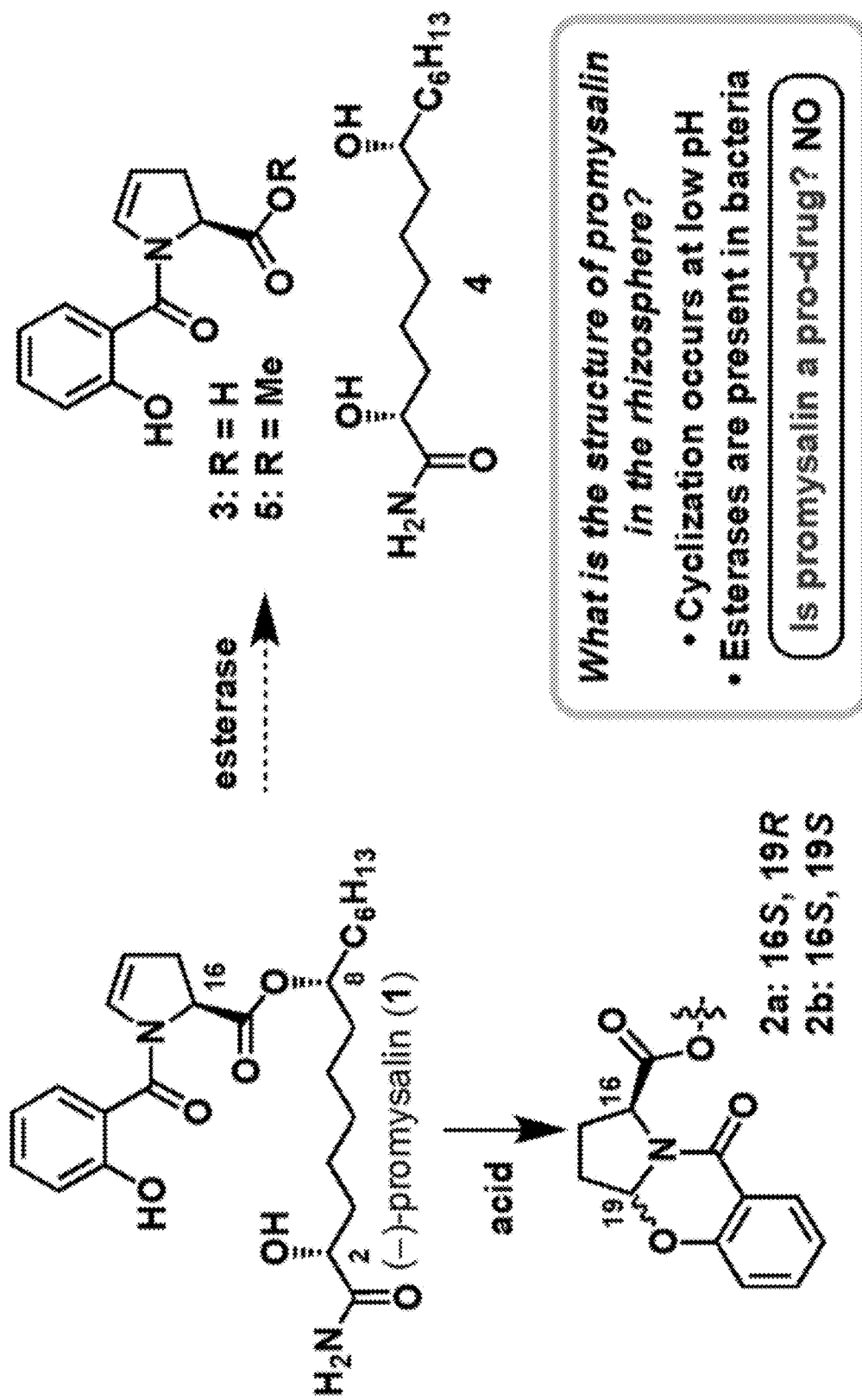
FIG. 1 depicts the structure of promysalin (1) and compounds 2-5 involved in the pro-drug hypothesis.

FIG. 1 depicts the structure of promysalin (1) and the structures involved in the current hypotheses. Enamines are quite susceptible to acid hydrolysis, and sought to examine the stability of promysalin in low pH environments. The instability of promysalin under mildly acidic conditions has been observed (Kaduskar et al., 2016, Tetrahedron), which could be attributed to the formation of cyclized products 2a/b. Whether this cyclization event was biologically relevant, whereby the compound would be dispensed by PP and would undergo cyclization in the known acidic environment present around PA (Hunter and Beveridge, 2005, Appl. Environ. Microbiol. 2501), was examined. However, the cyclized compounds showed no biological activity. Similarly, it is well known that bacteria possess enzymes capable of hydrolyzing esters. Therefore, whether the hydrolyzed fragments (3 and 4) would be active was examined. Methyl ester 5 was synthesized in lieu of the acid, for cell permeability purposes. Methyl ester 5 and diol 4 were both inactive up to concentrations of 250 µM. Additionally, it has also been recently shown that appending the acid fragment of promysalin to another myristate-derived natural product, lyngbic acid, yielded compounds devoid of activity against PA (Knouse and Wuest, 2016, J. Antibiotics). Although not wishing to be bound by any particular theory, these results suggest the cyclization and hydrolysis reactions are synthetic artifacts and not biologically relevant.

Based on these results DTS was used to access a library of analogs to build a structure-activity relationship (SAR) profile and further test the importance of the dehydroproline heterocycle. DTS has useful in previous natural product mechanistic studies (Szpilman and Carreira, 2010, Angew. Chem. Int. Ed. 49:9592), and in some cases has provided therapeutically useful analogs, exemplified by the development of fludelone (Rivken et al., 2995, Angew. Chem. Int. Ed. 44:2838). It should be noted that the analogs accessed from DTS presented here are inaccessible by enzymatic or chemical manipulation of the natural product directly, thus showcasing the power of organic synthesis.

Figure 2:
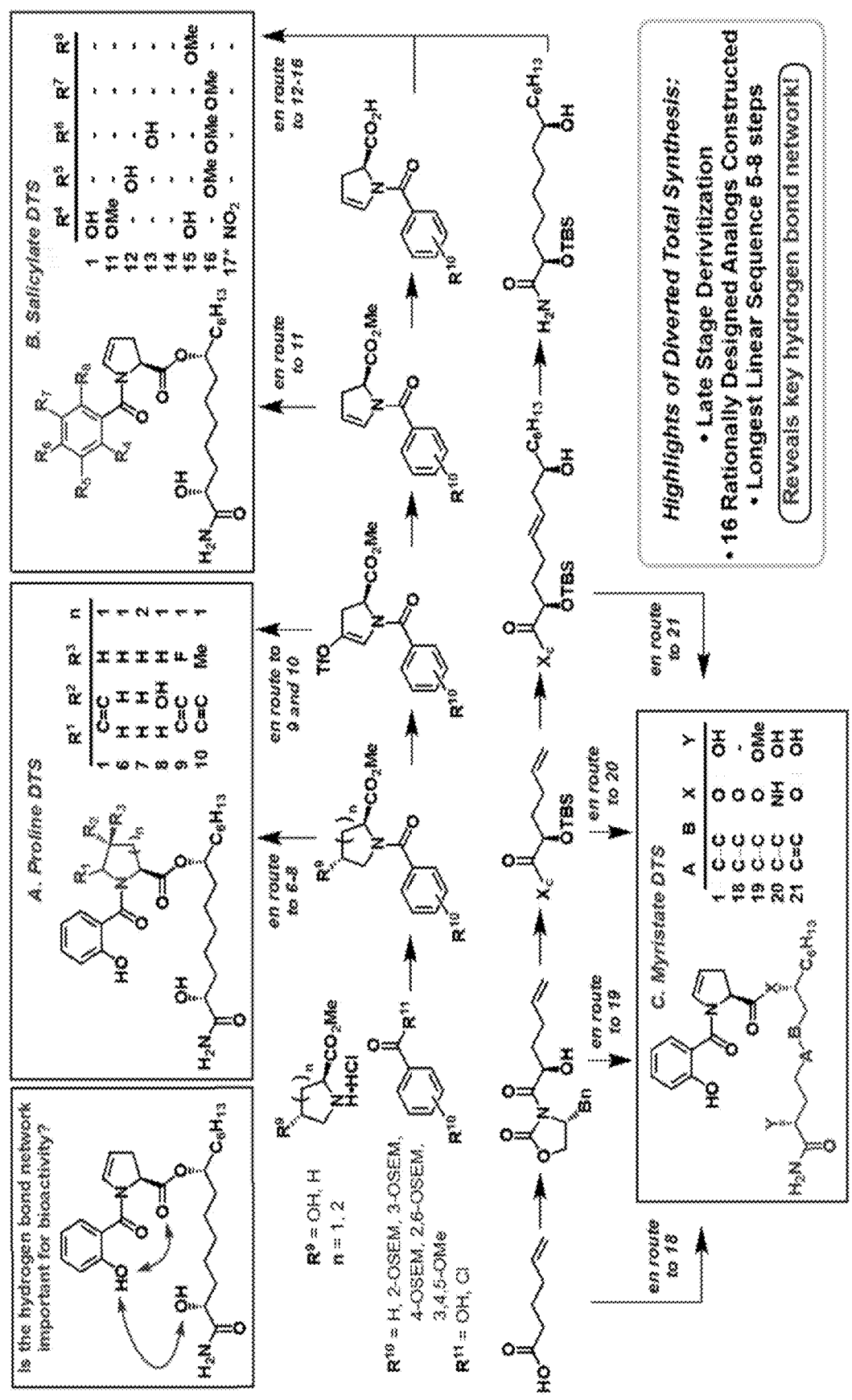
FIG. 2 is a scheme depicting the diverted total synthesis of promysalin analogs to probe the hydrogen-bonding network. Blue wording depicts the branching points from previously reported synthesis. Dashes in tables denote where hydrogens are present. *Compound 17 was prepared by a different route.
Figure 3:
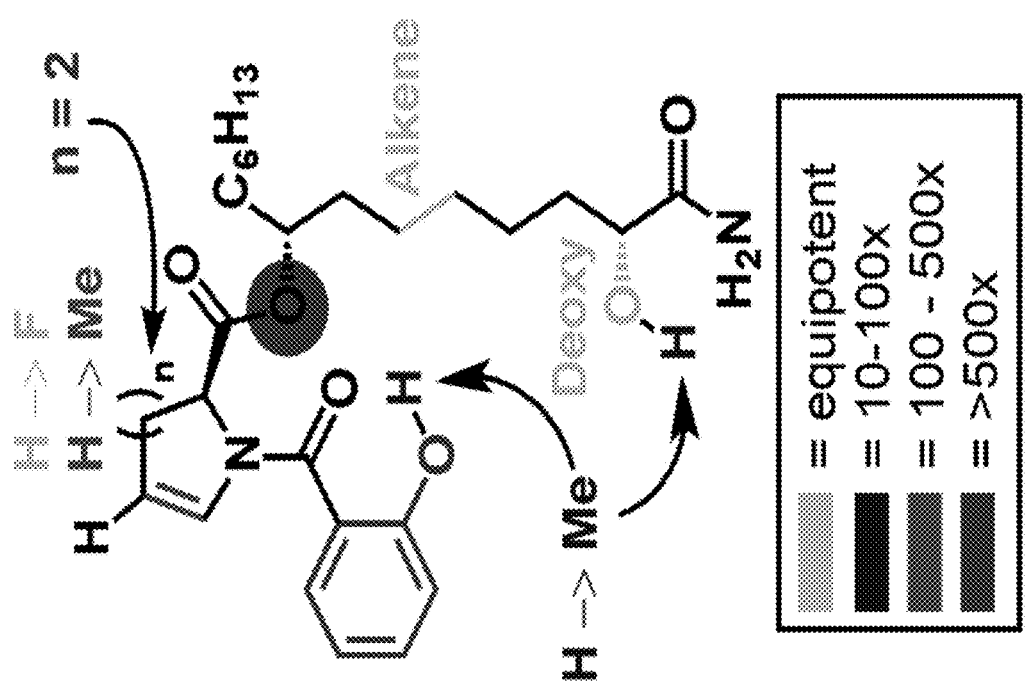
FIG. 3 depicts a color-coded SAR depicting the fold-decrease in activity.

It was initially hypothesized that the enamide moiety of promysalin was responsible for the bioactivity wherein it would covalently interact with its biological target; therefore, it was postulated that any modification would render the molecule inactive. DTS was utilized to access five specific dehydroproline derivatives (FIG. 2, Box A). The synthesis of the proline, piperidine, and hydroxyproline analogs 6-8 was straightforward using standard coupling reactions and protecting group manipulations. The inherent reactivity of the triflate intermediate via Pd-mediated coupling reactions was exploited to provide access to analogs 9 and 10.

Initial computational models of promysalin highlighted an intricate intramolecular hydrogen-bonding network resulting in a rigidified molecular framework. It was hypothesized that this network, composed of the phenol, hydroxyl, and ester moieties, were therefore critical for activity. To test this hypothesis, analogs varying these key functionalities were designed (FIG. 2, Box B). The salicylate fragment was systematically altered in three specific ways: 1) the position (12 and 13) and presence (14) of the phenol, 2) the substitution of the phenol with either the corresponding methyl ether (11) or nitro group (17), or 3) by increasing the electron density within the ring (15 and 16). In a similar fashion the role of ester linkage and secondary alcohol was probed (FIG. 2, Box C). For example, converting the ester to the corresponding amide (20) to create a hydrolytically more stable analog was envisioned, albeit one possessing a drastically altered hydrogen-bond network. Alkene analog 21 would add rigidity to the scaffold and potentially stabilize the active conformation. Finally, the importance of the hydroxyl group was probed by either methylation (19) or omission (18). The detailed synthetic route for the analogs library is presented in the Supporting Information (Scheme S1 and S2).

With a library of sixteen analogs in hand, all of the compounds were evaluated for inhibitory activity against *P. aeruginosa* strains PAO1 and PA14. The data for the active analogs ($IC_{50}$<250 µM) is shown in Table 1 along with the inhibitory data for the less potent diastereomers of promysalin (for numbering see FIG. 1) Table 2 shows the values of all $IC_{50}$ trials of active analogs against PAO1 and PA14; all $IC_{50}$ assays were run in triplicate. The inhibition data supported our initial hypothesis that the conformation of promysalin is exquisitely linked to its inhibition of PA. Of our modifications to the proline structure, fluorination (9)—being the smallest steric perturbation, was the only compound with equipotency to that of promysalin. Methylation (10) was slightly tolerated, while the piperidine (7) and hydroxyproline (8) derivatives were inactive. Proline derivative 6 was found to retain modest activity. Although not wishing to be bound by any particular theory, this result suggests an inhibitory mechanism that involves both structural recognition and covalent binding.

TABLE 1

$IC_{50}$ values of promysalin diastereomers and active compounds in µM (compounds with $IC_{50}$ > 250 µM are not shown). Values are averages of three independent experiments (see SI for graphs and experimental details).

|  | PAO1 | PA14 |
|---|---|---|
| 1 (2R,8R) | 4.1 | 0.067 |
| 1b (2R,8S) | 46 | 6.6 |
| 1c (2S,8S) | 90 | 22 |
| 1d (2S,8R) | 33 | 4.3 |
| 6 | 111 | 28 |
| 9 | 7.7 | 0.019 |
| 10 | 32 | 12 |
| 11 | 57 | 6.7 |
| 18 | 5.8 | 0.035 |
| 19 | 38 | 11 |
| 21 | 8.3 | 0.067 |

TABLE 2

Values of all IC50 trials of active analogs against PAO1 and PA14.

| | PAO1 | | | | | PA14 | | | | |
|---|---|---|---|---|---|---|---|---|---|---|
| | EXPT 1 (µM) | EXPT 2 (µM) | EXPT 3 (µM) | AVG (µM) | ST. DEV (µM) | EXPT 1 (µM) | EXPT 2 (µM) | EXPT 3 (µM) | AVG (µM) | ST. DEV (µM) |
| 11 | 59.28 | 55.37 | 55.49 | 56.71 | 2.22 | 6.98 | 5.86 | 7.39 | 6.74 | 0.791 |
| 6 | 112.6 | 98.88 | 121.1 | 110.86 | 11.21 | 24.28 | 27.05 | 33.66 | 28.33 | 4.82 |
| 10 | 32.26 | 32.53 | 31.07 | 31.95 | 0.78 | 10.83 | 11.18 | 12.18 | 11.4 | 0.7 |
| 21 | 10.13 | 8.07 | 6.81 | 8.34 | 1.67 | 0.12 | 0.05 | 0.03 | 0.067 | 0.044 |
| 19 | 29.15 | 49.29 | 47.56 | 38.34 | 11.69 | 12.78 | 5.72 | 15.03 | 11.18 | 4.86 |

TABLE 2-continued

Values of all IC50 trials of active analogs against PA01 and PA14.

| | PA01 | | | | | PA14 | | | | |
|---|---|---|---|---|---|---|---|---|---|---|
| | EXPT 1 (μM) | EXPT 2 (μM) | EXPT 3 (μM) | AVG (μM) | ST. DEV (μM) | EXPT 1 (μM) | EXPT 2 (μM) | EXPT 3 (μM) | AVG (μM) | ST. DEV (μM) |
| 9 | 8.11 | 8.57 | 6.41 | 7.7 | 1.14 | 0.04 | 0.01 | 0.01 | 0.019 | 0.019 |
| 18 | 4.78 | 5.64 | 7.12 | 5.85 | 1.18 | 0.02 | 0.09 | 0 | 0.035 | 0.048 |
| 1 (R,R) | 4.44 | 4.37 | 3.54 | 4.12 | 0.5 | 0.1 | 0.02 | 0.08 | 0.067 | 0.042 |
| 1b (R,S) | 44.44 | 46.88 | 47.67 | 46.33 | 1.68 | 6.64 | 7.02 | 6.1 | 6.59 | 0.46 |
| 1c (S,S) | 92.05 | 90.36 | 87.58 | 90 | 2.26 | 22.31 | 19.44 | 23.45 | 21.73 | 2.07 |
| 1d (S,R) | 32.72 | 29.25 | 37.85 | 33.27 | 4.33 | 3.88 | 5.01 | 4.08 | 4.32 | 0.6 |

The structure of the salicylate moiety was largely unforgiving in terms of the position (12, 13), substitution (17), or exclusion of the phenol (14). In addition, adding methoxy substituents in the presence (15) or absence (16) of the o-phenol was not tolerated. The only active salicylate analog was the methyl ether (11), albeit with of an order of magnitude less potency. In contrast, the side chain analogs all retained some, if not all activity, with the one exception being the amide (20). Methylation of the hydroxyl group (19) resulted in a decrease in potency on par with the methylated-phenol (11). Rigidifying the side chain by including the alkene (21) led to an equipotent analog. However, when the secondary alcohol was removed, providing compound 18, biological activity was fully retained. At first this result was particularly surprising, as it was postulated that the alcohol was integral to the hydrogen-bonding network, as evidenced by the difference in activity between 1 and 1b/c (10-100 fold decrease in potency). However, when considering the proposed macrocyclic structure, the implications of epimerization at a hydroxyl group can lead to drastic bond angle changes, in contrast, 18 can adopt a similar conformation simply by substituting the amide carbonyl as a Lewis base in place of the alcohol. Furthermore, the synthesis of 18 requires two less overall steps, and is more atom-economical, than that of promysalin as the use of a protecting group and chiral auxiliary is avoided.

Figure 4:
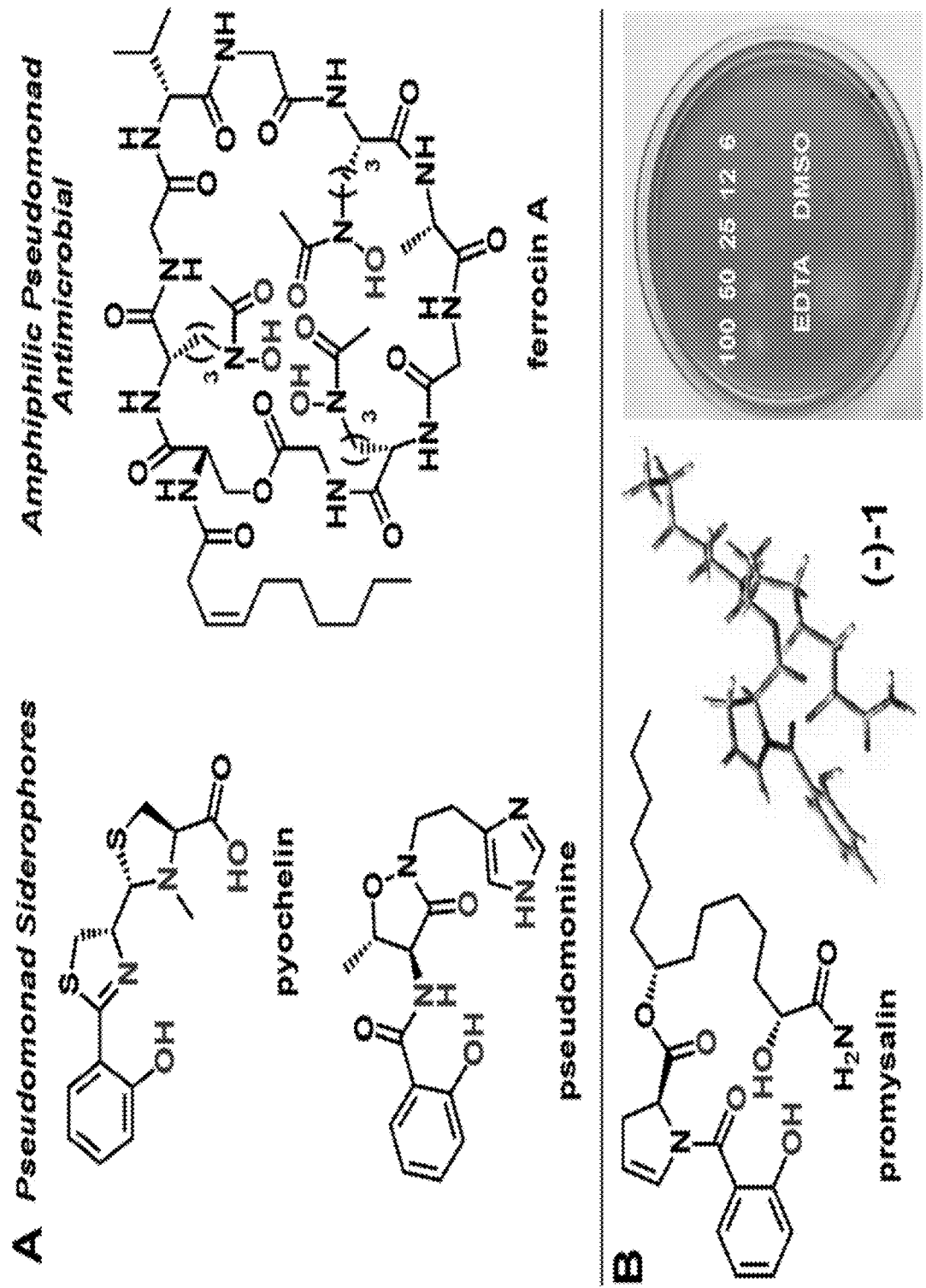
FIG. 4, comprising
Figure 5:
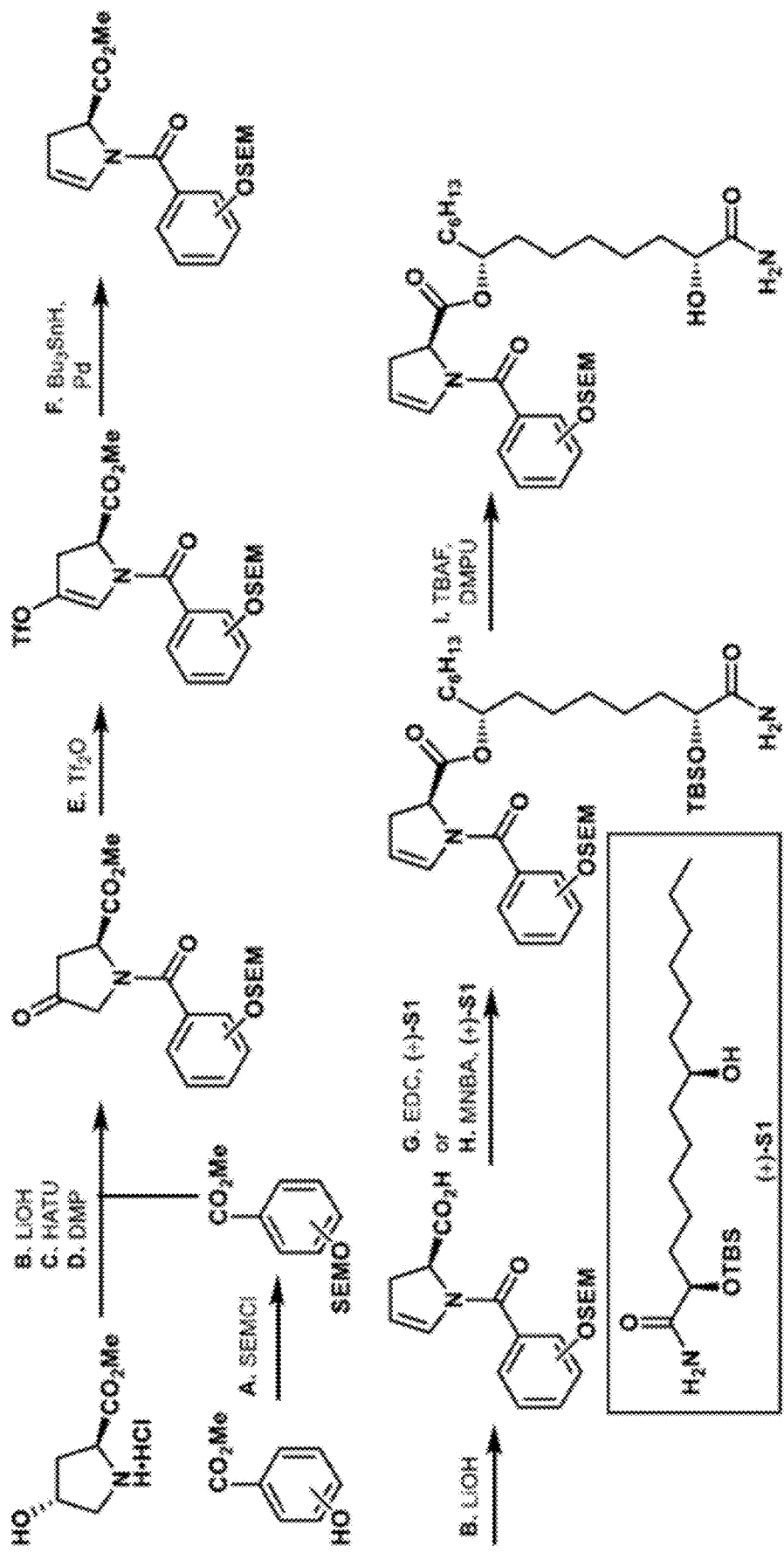
FIG. 5 is a scheme depicting a general synthetic route for promysalin analogs.

It was further hypothesized that promysalin might be capable of binding iron. This hypothesis was reinforced by earlier findings demonstrating that promysalin is capable of promoting swarming in PP and inhibiting pyoverdine production (FIG. 4A). With these questions in mind, the ability of promysalin to bind iron was tested. Indeed, promysalin tested positive for $Fe^{3+}$ chelation on CAS agar at concentrations ranging from 6-100 μM, albeit with reduced affinity when compared to the known iron chelator EDTA (FIG. 4B). Although not wishing to be bound by any particular theory, these suggest that promysalin has the ability to act as a siderophore in various *Pseudomonads*.

Example 2: Promysalin Elicits Species-Selective Inhibition of *Pseudomonas aeruginosa* by Targeting Succinate Dehydrogenase The results described herein demonstrate the use of activity-based protein profiling (ABPP) to identify the C-subunit of succinate dehydrogenase (Sdh) as the biological target of the natural product promysalin. The target was further validated both in silico via computational docking studies and in vivo through inhibition assays. Succinate dehydrogenase plays an essential role in primary metabolism of *Pseudomonas aeruginosa* as the only enzyme that is involved both in the tricarboxylic acid cycle (TCA) and in respiration via the electron transport chain. Although not wishing to be bound by any particular theory, these results suggest that the TCA cycle is an understudied target in the development of novel therapeutics to combat *P. aeruginosa*, a significant pathogen in clinical settings.

The materials and methods employed in these experiments are now described.

General

NMR spectra were recorded using the following spectrometers: Bruker Avance 500 (500/125 MHz) or Bruker Avance 400 (400/100 MHz). Chemical shifts are quoted in ppm relative to tetramethylsilane and with the indicated solvent as an internal reference. The following abbreviations are used to describe signal multiplicities: s (singlet), d (doublet), t (triplet), q (quartet), m (multiplet), br (broad), dd (doublet of doublets), dt (doublet of triplets), etc. Accurate mass spectra were recorded on an Agilent 6520 Accurate-Mass Q-TOF LC/MS, infrared spectra were obtained using a Thermo Nicolet Nexus 670 FTIR spectrophotometer and specific rotation measurements were made with a 1 dm path length using a Perkin Elmer 341 Polarimeter. Alternatively, accurate mass measurement data were acquired on a Waters LCT Premier XE by use of electrospray ionization with an internal lock mass reference of leucine enkephalin. Waters instruments are calibrated and report by use of neutral atom masses. Non-aqueous reactions were performed under an atmosphere of argon, in flame-dried glassware, with HPLC-grade solvents dried by passage through activated alumina. Amine bases were freshly distilled from $CaH_2$ prior to use. Brine refers to a saturated aqueous solution of sodium chloride. Products purified via flash chromatography using Biotage Isolera One Automated column. Reactions monitored via thin-layer chromatography (TLC) using EMD Millipore® TLC silica gel glass plates with $KMnO_4$ stain.

Bacterial strains (PA14, PAO1, KT2440, and RW10S1) were grown at 37° C. in TSB medium or on agar plates. Overnight cultures were diluted 1:100 in fresh media (TSB or M9 minimal media) and incubated (*P. aeruginosa* 37° C.; *P. putida* 30° C.; 200 rpm) until exponential growth, $OD_{600}$ reading of ~0.32.

Synthesis of Photoaffinity Probe

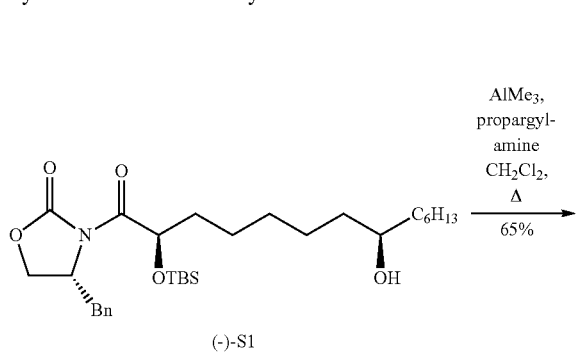

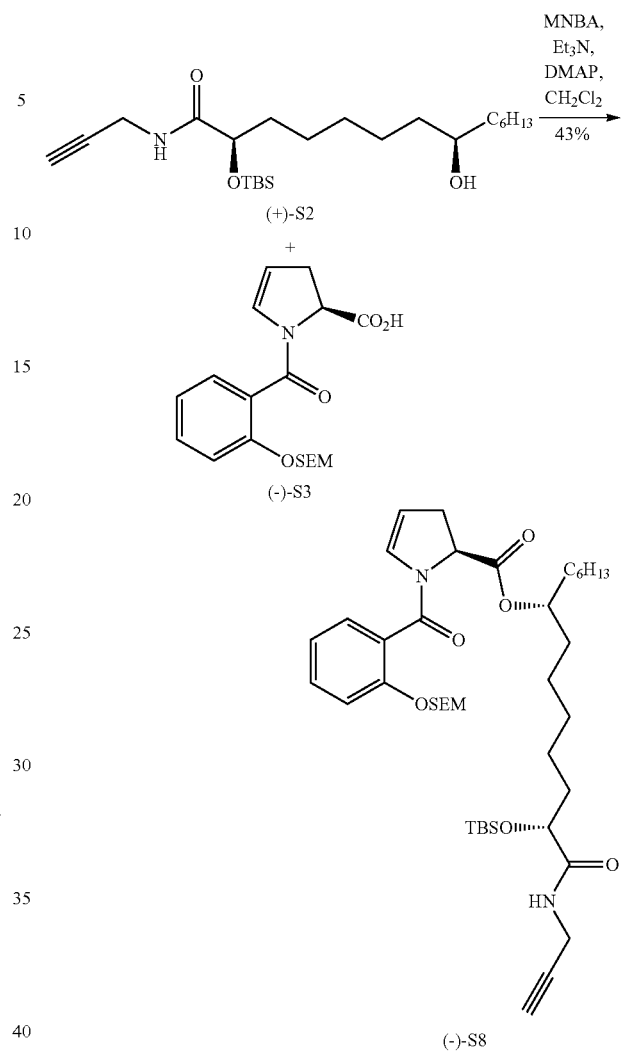

(2R,8R)-2-((tert-butyldimethylsilyl)oxy)-8-hydroxy-N-(prop-2-yn-1-yl)tetradecanamide (+)-S2. To a solution of propargylamine (0.020 mL, 0.310 mmol) dissolved in $CH_2Cl_2$ (1 mL) at 0° C. was added trimethylaluminum (2M in $CH_2Cl_2$, 0.155 mL, 0.310 mmol), and the solution was allowed to warm to room temperature. Oxazolidinone (−)-S1 (Steele, et al., J. Am. Chem. Soc., 2015, 137, 7314) (33 mg, 0.062 mmol) was added as a solution in $CH_2Cl_2$ (1 mL) and the reaction was heated to reflux overnight. The reaction was then quenched with water and filtered through Celite. The layers were separated and the aqueous was extracted further (2×) with $CH_2Cl_2$. The combined organic layers were washed with water and brine, dried over $MgSO_4$, filtered, concentrated, and purified by column chromatography, yielding the title compound as a clear oil (17 mg, 65% yield). $^1H$ NMR (500 MHz, $CDCl_3$) δ 6.74 (t, J=5.2 Hz, 1H), 4.17-4.08 (m, 2H), 3.97 (ddd, J=17.6, 4.8, 2.5 Hz, 1H), 3.61-3.50 (m, 1H), 2.22 (t, J=2.5 Hz, 1H), 1.74-1.65 (m, 2H), 1.46-1.16 (m, 28H), 0.93 (s, 9H), 0.87 (t, J=6.8 Hz, 3H), 0.09 (s, J=2.9 Hz, 3H), 0.08 (s, 3H); $^{13}C$ NMR (101 MHz, $CDCl_3$) δ 173.73, 125.65, 79.37, 73.59, 72.02, 71.73, 37.61, 37.47, 35.25, 31.97, 30.44, 29.66, 29.50, 28.76, 25.89, 25.75, 25.60, 24.28, 22.75, 18.17, 14.23, −4.68, −5.13; $[\alpha]^{25}_D$ +21.8 (c=1.00 in $CHCl_3$); HRMS Accurate mass (ES+): Found 434.3085 (+4.4 ppm), $C_{23}H_{45}NO_3SiNa$ (M+Na+) requires 434.3066; $R_f$ (2:1 hexanes:EtOAc)=0.44.

(7R,13R)-13-((tert-butyldimethylsilyl)oxy)-14-oxo-14-(prop-2-yn-1-ylamino)tetradecan-7-yl (S)-1-(2-((2-(trimethylsilyl)ethoxy)methoxy)benzoyl)-2,3-dihydro-1H-pyrrole-2-carboxylate (−)-S8. To a solution of acid (−)-S3 (Steele, et al., J. Am. Chem. Soc., 2015, 137, 7314) (25 mg, 0.068 mmol) in $CH_2Cl_2$ (1 mL) was added MNBA (44 mg, 0.126 mmol) and triethylamine (0.022 mL, 0.160 mmol). The solution was stirred at room temperature for 10 minutes, then a solution of alcohol (+)-S2 (20 mg, 0.049 mmol) and DMAP (1 mg, 0.012 mmol) in $CH_2Cl_2$ (1 mL) was added and the reaction was stirred at room temperature overnight. The following day, the reaction was poured into sat. $NH_4Cl$ and extracted with $CH_2Cl_2$ 3×. The combined organic layers were washed with brine, dried over $MgSO_4$, filtered, concentrated, and purified by column chromatography, yielding the title compound as a yellow oil (16 mg, 43% yield). $^1H$ NMR (500 MHz, $CDCl_3$) δ 7.36 (dd, J=12.2, 4.6 Hz, 2H), 7.20 (d, J=8.0 Hz, 1H), 7.07-7.00 (m, 1H), 6.74 (t, J=5.4 Hz, 1H), 6.16 (dt, J=4.2, 2.1 Hz, 1H), 5.22 (dd, J=17.4, 7.1 Hz, 2H), 5.02 (dt, J=4.8, 2.5 Hz, 1H), 4.99-4.91 (m, 2H), 4.16-4.08 (m, 2H), 3.97 (tt, J=4.9, 3.5 Hz, 1H), 3.75 (dd, J=16.5, 8.1 Hz, 2H), 3.11 (ddt, J=16.7, 11.6, 2.3 Hz, 1H), 2.69-2.63 (m, 1H), 2.23 (t, J=2.6 Hz, 1H), 1.76-1.48 (m, 7H), 1.41-1.19 (m, 17H), 0.96-0.90 (m, 11H), 0.86 (t, J=6.8 Hz, 3H), 0.09-0.05 (m, 6H), −0.01 (s, 9H); $^{13}C$ NMR (101

MHz, CDCl₃) δ 173.69, 170.79, 164.95, 153.85, 131.22, 131.06, 129.03, 125.96, 121.97, 115.21, 108.31, 93.34, 79.42, 75.50, 73.59, 71.72, 66.62, 58.19, 35.29, 34.41, 34.10, 31.86, 29.56, 29.33, 28.71, 25.90, 25.31, 25.13, 24.16, 22.72, 18.17, 14.21, −1.27, −4.68, −5.15; $[\alpha]^{25}_D$ −17.7 (c=1.00 in CHCl₃); HRMS Accurate mass (ES⁺): Found 757.4687 (+5.8 ppm), $C_{41}H_{69}N_2O_7Si_2$ (M+H+) requires 757.4643.

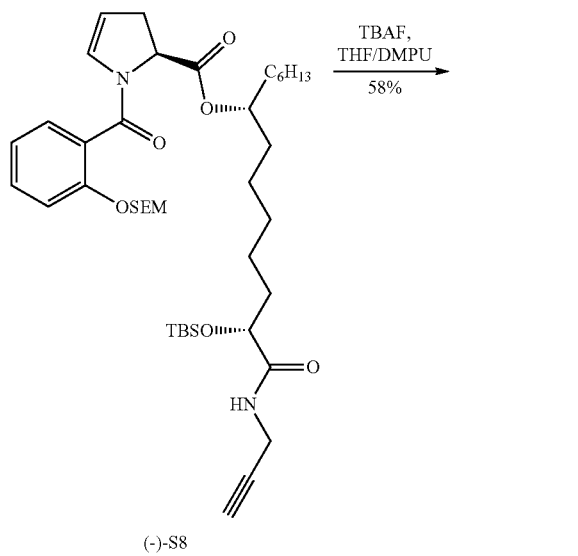

(7R,13R)-13-hydroxy-14-oxo-14-(prop-2-yn-1-ylamino) tetradecan-7-yl (S)-1-(2-hydroxybenzoyl)-2,3-dihydro-1H-pyrrole-2-carboxylate (−)-S4. To a solution of silyl ether (−)-S8 (14.9 mg, 0.0197 mmol) dissolved in DMPU (0.39 mL, dried over 3 Å molecular sieves prior to use) was added TBAF (1M in THF, 0.39 mL, 0.390 mmol, dried over 3 Å molecular sieves prior to use). After 30 minutes, the reaction was quenched with sat. NH₄Cl, and the mixture was extracted with Et₂O 5×. The combined organic layers were washed with 1M NH₄Cl 5× and brine, dried over MgSO₄, filtered, concentrated, and purified by column chromatography (3:1 EtOAc:hexanes), yielding the title compound as a clear oil (5.9 mg, 58% yield). ¹H NMR (500 MHz, CDCl₃) δ 9.53 (br s, 1H), 7.44-7.35 (m, 2H), 7.03-6.98 (m, 1H), 6.94-6.87 (m, 1H), 6.73 (s, 1H), 5.33-5.25 (m, 1H), 5.01 (dd, J=11.3, 4.6 Hz, 2H), 4.13-3.94 (m, 3H), 3.35 (br s, 1H), 3.19-3.08 (m, 1H), 2.70 (d, J=17.3 Hz, 1H), 2.19 (t, J=2.5 Hz, 1H), 1.87-1.76 (m, 1H), 1.71-1.48 (m, 6H), 1.32 (ddd, J=28.0, 17.2, 10.1 Hz, 15H), 0.87 (t, J=7.0 Hz, 3H); ¹³C NMR (126 MHz, CDCl₃) δ 173.87, 171.31, 167.45, 158.09, 133.52, 130.86, 128.33, 119.42, 118.06, 117.70, 111.12, 79.64, 75.98, 71.62, 71.53, 59.39, 34.54, 34.31, 34.11, 31.83, 29.22, 28.86, 28.27, 25.52, 24.84, 24.56, 22.68, 14.20; $[\alpha]^{25}_D$ −32.4 (c=0.38 in CHCl₃); HRMS Accurate mass (ES⁺): Found 513.2991 (+5.3 ppm), $C_{29}H_{41}N_2O_6$ (M+H⁺) requires 513.2964; $R_f$ (3:1 EtOAc:hexanes)=0.20.

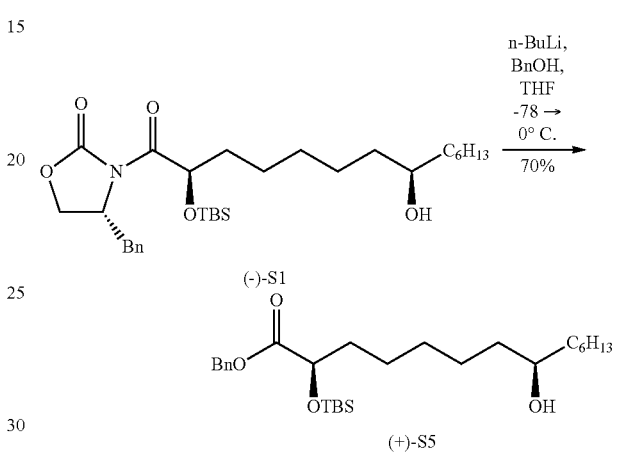

Benzyl (2R,8R)-2-((tert-butyldimethylsilyl)oxy)-8-hydroxytetradecanoate (+)-S5. To a solution of benzyl alcohol (0.040 mL, 0.388 mmol) dissolved in THF (3 mL) at −78° C. was added n-BuLi (2.25 M in hexanes, 0.140 mL, 0.323 mmol) dropwise. After 5 minutes, a solution of oxazolidinone (−)-S1 (69 mg, 0.129 mmol) was added dropwise to the reaction. The reaction was warmed to 0° C., after which time TLC indicated the consumption of starting material. The reaction was quenched with sat. NH₄Cl, extracted with EtOAc 3×, and the combined organic layers were washed with brine, dried over MgSO₄, filtered, concentrated, and purified by column chromatography, yielding the title compound as a clear oil (42 mg, 70% yield). ¹H NMR (500 MHz, CDCl₃) δ 7.37-7.30 (m, 5H), 5.15 (dd, J=27.9, 12.2 Hz, 2H), 4.22 (dd, J=6.7, 5.5 Hz, 1H), 3.56 (s, 1H), 1.74-1.67 (m, 2H), 1.46-1.22 (m, 22H), 0.88 (s, J=9H), 0.03 (s, 3H), 0.02 (s, 3H); ¹³C NMR (125 MHz, CDCl₃) δ 173.85, 135.86, 128.63, 128.54, 128.41, 72.38, 72.03, 66.54, 37.62, 37.46, 35.23, 31.97, 29.50, 25.83, 25.73, 25.60, 25.20, 22.75, 18.41, 14.22, −4.80, −5.24; $[\alpha]^{25}_D$+20.3 (c=1.00 in CHCl₃); HRMS Accurate mass (ES⁺): Found 465.3413 (2.8 ppm), $C_{27}H_{49}O_4Si$ (M+H⁺) requires 465.3400.

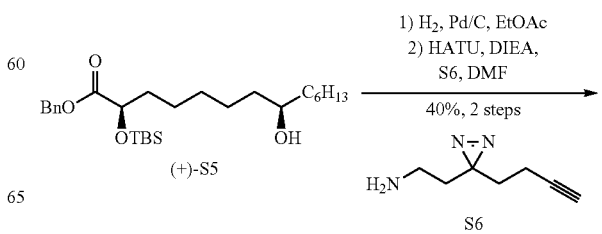

-continued

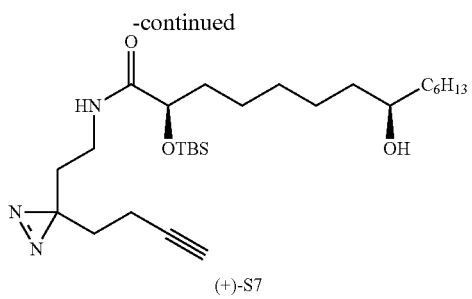

(+)-S7

-continued

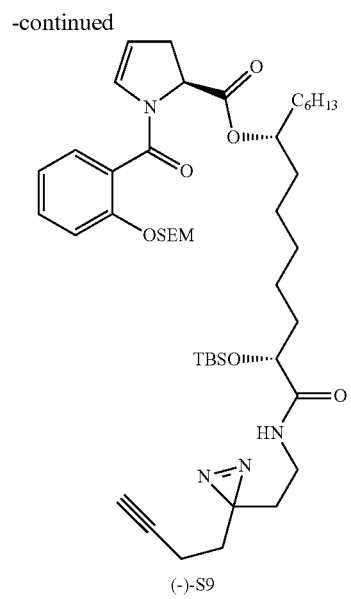

(-)-S9

(2R,8R)—N-(2-(3-(but-3-yn-1-yl)-3H-diazirin-3-yl)ethyl)-2-((tert-butyldimethylsilyl)oxy)-8-hydroxytetradecanamide (+)-S7. To a solution of benzyl ester (+)-S5 (43 mg, 0.093 mmol) dissolved in EtOAc (2 mL) was added 10% Pd/C (20 mg), and the reaction flask was vacuumed and backfilled 5× with a balloon of $H_2$. The reaction was closely monitored by TLC, and after 2 hours, the starting material was consumed. The reaction was filtered over Celite and concentrated (the acid intermediate, in particular the silyl ether moiety, was highly unstable, and cleavage was observed in as little as an hour) and immediately used in the next step. The acid was dissolved in DMF (1 mL), and HATU (42 mg, 0.112 mmol) was added as a solid, followed by a solution of amine S6 (Li, et al., Angew. Chem. Int. Ed. 2013, 52, 8551) (14 mg, 0.102 mmol) dissolved in DMF (1 mL), then DIEA (0.05 mL, 0.279 mmol) was added, and the reaction was stirred at room temperature overnight. The following day, the reaction was poured into water and EtOAc, and the layers were separated. The aqueous layer was extracted 2× more with EtOAc and the combined organic layers were washed with water and brine, concentrated, and purified by column chromatography, yielding the title compound as a yellow oil (18 mg, 40% over 2 steps). $^1$H NMR (500 MHz, CDCl$_3$) δ 6.63 (t, J=5.5 Hz, 1H), 4.15-4.09 (m, 1H), 3.56 (s, 1H), 3.16-3.06 (m, 2H), 2.06-1.95 (m, 3H), 1.79-1.61 (m, 6H), 1.47-1.21 (m, 19H), 0.94 (s, 9H), 0.88 (t, J=6.7 Hz, 3H), 0.10 (d, J=7.0 Hz, 6H); $[α]^{25}_D$ +12.2 (c=0.81 in CHCl$_3$); $^{13}$C NMR (100 MHz, CDCl$_3$) δ 173.99, 82.62, 73.48, 72.00, 69.49, 37.60, 37.48, 35.18, 33.80, 32.79, 32.35, 31.96, 29.70, 29.49, 26.84, 25.90, 25.74, 25.60, 24.13, 22.74, 18.16, 14.21, 13.38, −4.66, −5.04; HRMS Accurate mass (ES$^+$): Found 494.3801 (+4.7 ppm), $C_{27}H_{52}N_3O_3Si$ (M+H$^+$) requires 494.3778.

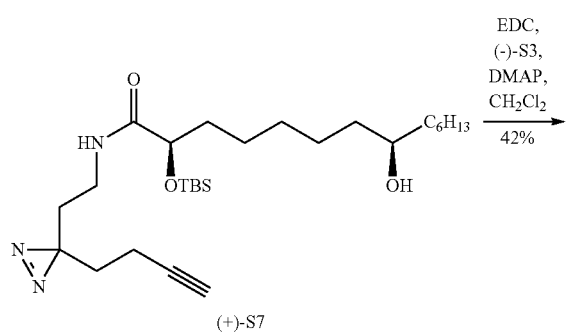

(+)-S7

EDC, (-)-S3, DMAP, CH$_2$Cl$_2$
42%

(7R,13R)-14-((2-(3-(but-3-yn-1-yl)-3H-diazirin-3-yl)ethyl)amino)-13-((tert-butyldimethylsilyl)oxy)-14-oxotetradecan-7-yl (S)-1-(2-((2-methoxyethoxy)methoxy)benzoyl)-2,3-dihydro-1H-pyrrole-2-carboxylate (-)-S9. To a solution of acid (-)-S3 (33 mg, 0.091 mmol), alcohol (+)-S7 (28 mg, 0.057 mmol), and EDC (20 mg, 0.114 mmol) in CH$_2$Cl$_2$ (2 mL) was added DMAP (3 mg, 0.029 mmol) and the reaction was stirred at room temperature overnight. The next day the reaction was poured into water and extracted with CH$_2$Cl$_2$ 3×. The combined organic layers were washed with brine, dried over MgSO$_4$, filtered, concentrated, and purified by column chromatography (0→20% EtOAc/hexanes), yielding the title compound as a yellow oil (20 mg, 42% yield). $^1$H NMR (500 MHz, CDCl$_3$) δ 7.37-7.32 (m, 2H), 7.19 (d, J=8.0 Hz, 1H), 7.03 (t, J=7.5 Hz, 1H), 6.64 (t, J=5.9 Hz, 1H), 6.16 (dt, J=4.2, 2.0 Hz, 1H), 5.22 (dd, J=18.2, 7.1 Hz, 2H), 5.01 (dt, J=4.7, 2.5 Hz, 1H), 4.99-4.91 (m, 2H), 4.12 (t, J=5.0 Hz, 1H), 3.76-3.70 (m, 2H), 3.18-3.02 (m, 3H), 2.70-2.61 (m, 1H), 2.02-1.96 (m, 3H), 1.78-1.16 (m, 26H), 0.92 (s, 9H), 0.86 (t, J=6.7 Hz, 3H), 0.08 (s, 3H), 0.07 (s, 3H), −0.02 (s, J=9H); $^{13}$C NMR (126 MHz, CDCl$_3$) δ 173.95, 170.78, 164.95, 153.86, 131.22, 131.08, 129.03, 126.02, 121.98, 115.25, 108.29, 93.37, 82.64, 75.50, 73.55, 69.49, 66.62, 58.22, 35.26, 34.42, 34.11, 33.82, 32.83, 32.35, 31.86, 29.82, 29.62, 29.33, 26.84, 25.93, 25.32, 25.14, 24.09, 22.72, 18.17, 14.20, 13.39, −1.27, −4.64, −5.03; $[α]^{25}_D$ −16.3 (c=1.00 in CHCl$_3$); HRMS Accurate mass (ES$^+$): Found 839.5166 (−1.0 ppm), $C_{45}H_{76}N_4O_7Si_2$ (M+H$^+$) requires 839.5174.

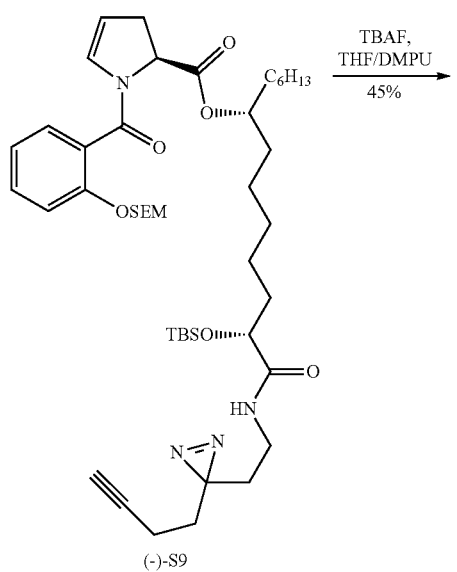

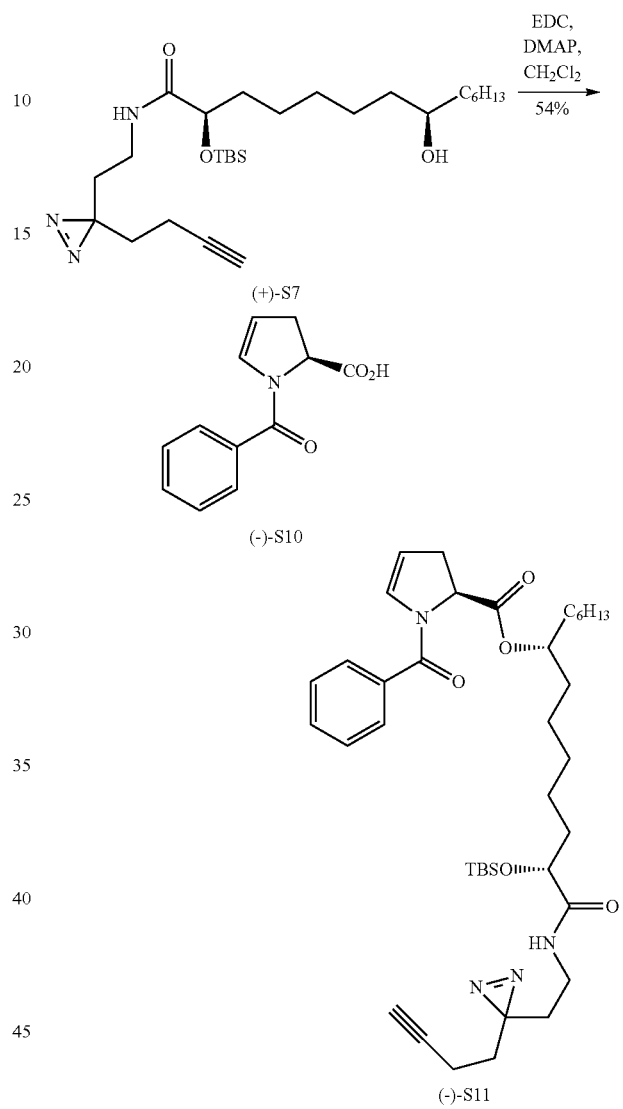

(7R,13R)-14-((2-(3-(but-3-yn-1-yl)-3H-diazirin-3-yl)ethyl)amino)-13-hydroxy-14-oxotetradecan-7-yl (S)-1-(2-hydroxybenzoyl)-2,3-dihydro-1H-pyrrole-2-carboxylate (−)-2. To a solution of silyl ether (−)-S9 (13 mg, 0.015 mmol) dissolved in DMPU (0.31 mL, dried over 3 Å molecular sieves prior to use) was added TBAF (1M in THF, 0.31 mL, 0.31 mmol, dried over 3 Å molecular sieves prior to use). After 30 minutes, the reaction was quenched with sat. $NH_4Cl$, and the mixture was extracted with $Et_2O$ 5×. The combined organic layers were washed with 1M $NH_4Cl$ 5× and brine, dried over $MgSO_4$, filtered, concentrated, and purified by column chromatography yielding the title compound as a clear oil (4.0 mg, 45% yield). $^1$H NMR (500 MHz, $CDCl_3$) δ 9.54 (br s, 1H), 7.43-7.35 (m, 2H), 6.98 (t, J=10.1 Hz, 1H), 6.91 (t, J=7.5 Hz, 1H), 6.73 (s, 1H), 5.31-5.25 (m, 1H), 5.01 (dd, J=11.2, 4.4 Hz, 1H), 4.07 (dd, J=8.0, 3.4 Hz, 1H), 3.30 (br s, 1H), 3.18-3.03 (m, 3H), 2.70 (d, J=17.0 Hz, 1H), 2.02-1.94 (m, 3H), 1.80 (s, 1H), 1.71-1.11 (m, 25H), 0.87 (t, J=6.9 Hz, 3H); $^{13}$C NMR (100 MHz, $CDCl_3$) δ 174.21, 171.24, 167.42, 158.14, 133.54, 130.86, 128.34, 119.41, 118.03, 117.65, 111.14, 82.80, 75.98, 71.60, 69.49, 59.39, 34.52, 34.33, 34.09, 32.77, 32.21, 31.83, 29.84, 29.22, 28.30, 26.89, 25.51, 24.84, 24.57, 22.69, 14.21, 13.38; $[α]^{25}_D$ −28.4 (c=0.52 in $CHCl_3$); HRMS Accurate mass (ES$^+$): Found 595.3523 (+4.5 ppm), $C_{33}H_{47}N_4O_6$ (M+H$^+$) requires 595.3496.

(7R,13R)-14-((2-(3-(but-3-yn-1-yl)-3H-diazirin-3-yl)ethyl)amino)-13-((tert-butyldimethylsilyl)oxy)-14-oxotetradecan-7-yl (S)-1-benzoyl-2,3-dihydro-1H-pyrrole-2-carboxylate (−)-S11. To a solution of acid (−)-S10 (Steele, et al., J. Am. Chem. Soc. 2016, 138, 5833) (22 mg, 0.101 mmol), alcohol (+)-S7 (25 mg, 0.051 mmol), and EDC (19 mg, 0.101 mmol) dissolved in $CH_2Cl_2$ (2 mL) was added DMAP (3 mg, 0.026 mmol), and the reaction was stirred at room temperature overnight. The following day, water was added and the aqueous layer was extracted with $CH_2Cl_2$ 3×. The combined organic layers were washed with brine, dried over $Na_2SO_4$, filtered, concentrated, and purified by column chromatography, yielding the title compound as a yellow oil (19 mg, 54% yield). $^1$H NMR (500 MHz, $CDCl_3$) δ 7.55 (d, J=6.9 Hz, 2H), 7.48-7.39 (m, 3H), 6.65 (t, J=6.0 Hz, 1H), 6.51 (s, 1H), 5.10 (s, 1H), 5.02-4.90 (m, 1H), 4.12 (t, J=4.9 Hz, 1H), 3.17-3.02 (m, 3H), 2.75-2.63 (m, 1H), 2.04-1.96 (m, 2H), 1.74-1.50 (m, 12H), 1.41-1.15 (m, 14H), 0.93 (s, 9H), 0.85 (t, J=6.8 Hz, 3H), 0.08 (d, J=5.8 Hz, 6H); $^{13}$C NMR (125 MHz, CDCl$_3$) δ 173.97, 170.88, 166.96, 135.27, 131.05, 130.72, 128.55, 127.93, 108.84, 82.63, 75.64, 73.53, 69.49, 58.80, 35.23, 34.07, 33.81, 32.81, 32.33, 31.83, 29.60, 29.30, 26.84, 25.92, 25.27, 25.13, 24.07, 22.69, 18.17, 14.19, 13.39, −4.65, −5.04; [α]$^{25}_D$ −26.6 (c=1.36 in CHCl$_3$); HRMS Accurate mass (ES$^+$): Found 693.4409 (−0.3 ppm), C$_{39}$H$_{61}$N$_4$O$_5$Si (M+H$^+$) requires 693.4411; R$_f$ (9:1 CH$_2$Cl$_2$:Et$_2$O)=0.50.

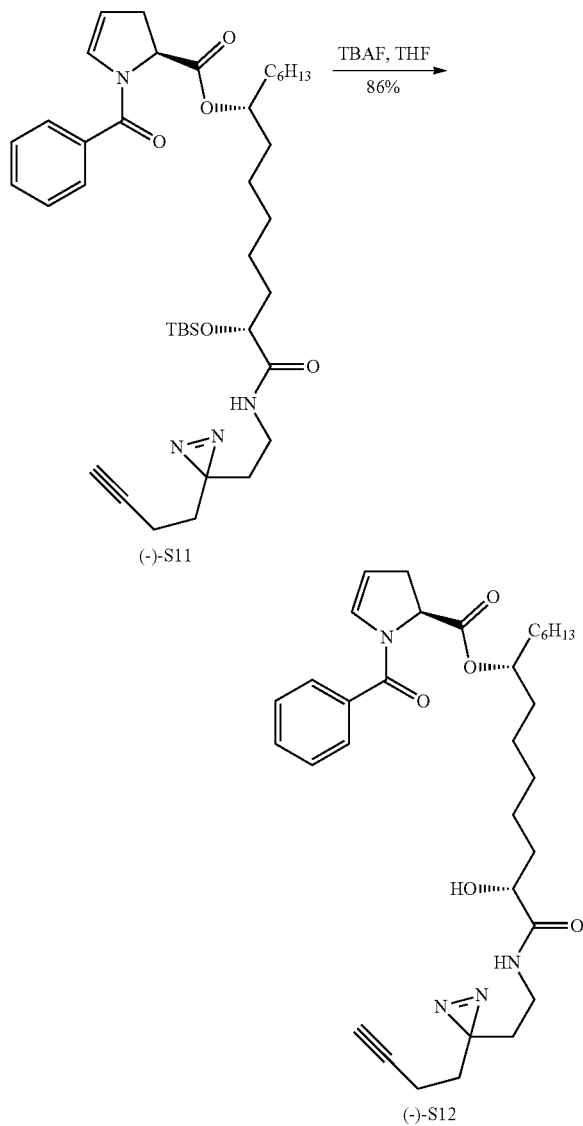

(7R,13R)-14-((2-(3-(but-3-yn-1-yl)-3H-diazirin-3-yl)ethyl)amino)-13-hydroxy-14-oxotetradecan-7-yl (S)-1-benzoyl-2,3-dihydro-1H-pyrrole-2-carboxylate (−)-S12. To a solution of silyl ether (−)-S11 (18 mg, 0.026 mmol) in THF (1 mL) was added TBAF (1M in THF, 0.03 mL, 0.03 mmol). After 15 minutes the reaction was quenched with sat. NH$_4$Cl, and the mixture was extracted with EtOAc 3×, washed with brine, dried over Na$_2$SO$_4$, filtered, concentrated, and purified by column chromatography, yielding the title compound as a clear oil (13 mg, 86% yield). $^1$H NMR (500 MHz, CDCl$_3$) δ 7.56-7.42 (m, 5H), 6.89 (t, J=5.9 Hz, 1H), 6.50 (dt, J=4.3, 2.1 Hz, 1H), 5.18-5.14 (m, 1H), 5.04 (qd, J=8.4, 4.2 Hz, 1H), 4.96 (dd, J=11.6, 5.0 Hz, 1H), 4.02 (dd, J=8.5, 3.3 Hz, 1H), 3.14 (ddt, J=16.7, 11.6, 2.4 Hz, 2H), 2.92 (dd, J=13.3, 7.1 Hz, 2H), 2.73-2.64 (m, 1H), 1.99-1.94 (m, 3H), 1.86-1.77 (m, 1H), 1.68-1.38 (m, 16H), 1.34-1.19 (m, 8H), 0.87 (t, J=7.0 Hz, 3H); $^{13}$C NMR (125 MHz, CDCl$_3$) δ 174.74, 170.53, 167.80, 134.73, 131.12, 130.81, 128.78, 127.83, 125.66, 110.03, 82.77, 75.19, 70.85, 69.42, 58.61, 34.77, 34.00, 33.91, 33.67, 32.79, 32.20, 31.84, 30.44, 29.25, 27.50, 26.82, 25.59, 24.67, 24.26, 22.69, 14.20, 13.37; [α]$^{25}_D$-25.1 (c=0.49 in CHCl$_3$); HRMS Accurate mass (ES$^+$): Found 579.3558 (+2.1 ppm), C$_{33}$H$_{47}$N$_4$O$_5$ (M+H$^+$) requires 579.3546.

UV-Visible Absorbance Spectra

Chelation of Fe$^{3+}$ by siderophore is usually characterized by a broad peak of absorbance around 500 nm. To test the ability of promysalin to act as a siderophore, a 65 µM solution of promysalin in buffer 200 mM sodium phosphate pH 8 has been incubated with 65 or 130 µM of either Fe(acac)3 (NH$_4$)$_5$[Fe(C$_6$H$_4$O$_7$)$_2$] or FeCl$_3$. Control have been done with a 65 µM solution of enterobactin incubated Tris(acetylacetonato)iron(III) (ration 1:1). Absorbance spectra were carried out with a varian cary 50 UV-visible spectrophotometer in a 100-µl cuvette.

Isothermal Microcalorimetry

The affinity of Promysalin for PaPiuA has been tested by isothermal titration calorimetry using a VP-ITC instrument (GE Healthcare) at 25° C. Titrations were performed using 5 µl injections of 164 µM (using ε$_{280}$=6 714 1 mol-1 cm-1 Li et al. Chemistry and Biology 2011) of the ligand in 17 µM of purified PaPiuA (Moynie et al. *Antimicrobial Agents and Chemotherapy* 2017) in the same buffer (50 mM sodium phosphate pH 7.5, 50 mM NaCl, 0.8% OctylPOE). The heats of dilution measured from injection of the ligands into the buffer were subtracted from the experimental data and titration curves were fitted to a single site binding using Origin software.

IC$_{50}$ Assay

Compounds were serially diluted in sterile DI water from a stock solution (10% DMSO/H$_2$O) yielding 24 test concentrations. Bacteria were diluted to a final concentration of 0.004 from regrown overnight culture according to the following equation: (xµL bacterial culture)(OD reading)= (0.004)(total volume needed) and 100 µL was inoculated into each well of a flat-bottom 96-well plate (Corning 3370) containing 100 µL of compound solution. Plates were incubated statically at 37° C. for 24 hours upon which time OD at 595 nm was measured using a plate reader (Spectra Max 190). IC$_{50}$ values were calculated using OD values and concentrations with a 4-parameter logistic model. Control experiments used a 10% DMSO/H$_2$O stock serially diluted to the same 24 concentrations. Compounds were tested in triplicate from three independent overnight cultures.

Affinity-Based Protein Profiling (ABPP)

Preparation of Samples 100 mL of TSB-Medium were inoculated 1:100 from an overnight culture of *P. aeruginosa* PAO1, *P. aeruginosa* PA14 or *P. putida* KT2440 and incubated (*P. aeruginosa* 37° C.; *P. putida* 30° C.; 200 rpm) until OD$_{600}$=1.0. The cultures were centrifuged (5 min, 6000 g), washed with 0.5 volumes PBS and resuspended in the same amount of PBS. Per sample 20 mL of washed culture were incubated (*P. aeruginosa* 37° C.; *P. putida* 30° C.; 30 min, 200 rpm) with either promysalin probe (3 µM), inactive promysalin probe (3 µM) or for competition experiments with promysalin (30 µM; 10 min pre-incubation) and promysalin probe (3 µM). The samples were poured in petri dishes (90 mm) and irradiated for 20 min (365 nm; Philips TL-D BLB 18W) without lids.

The cultures were centrifuged (10 min, 6000 g) and washed with the same amount of PBS. The pellets were resuspended in 1 mL PBS, transferred to a 1.5 mL tube, centrifuged again and stored at −80° C.

Click-Chemistry

Pellets were resuspended in 150 µL lysis buffer with EDTA-free protease inhibitors (PBS with 0.5% SDS and 1% Triton 100) and lysed using sonication (2×15 s, 60% intensity) with cooling on ice. Protein concentration was adjusted to 1 mg/mL using BCA assay. 500 µL of each sample were used for CuAAC reaction. All reagents for the click reaction were premixed and added to the samples at the indicated final concentrations: 100 µM biotin-azide (10 mM stock in DMSO), 1 mM $CuSO_4$ (50 mM stock in $ddH_2O$), 1 mM TCEP (50 mM stock in $ddH_2O$) and 100 µM TBTA (10 mM stock in DMSO). Samples were incubated at r.t. for one hour. 10 µL of EDTA (500 mM) were added and the whole sample was then transferred in a 15 mL tube containing 3 mL cold acetone (−80° C.). Proteins were allowed to precipitate overnight at −80° C.

Pulldown and Digestion

The precipitate was centrifuged (10 min, 18,000 g) and washed twice with 1 mL cold methanol (−80° C.) with resuspension (5 s ultrasonic bath) and centrifugation steps (10 min, 18,000 g) in between. All pellets were air-dried for 30 min at r.t. The washed pellets were resuspended in 500 µL PBS (containing 0.2% SDS and 1 mM DTT), centrifuged (20 min, 17,000 g), the supernatant transferred in low-bind tubes containing 50 µL washed avidin agarose beads and incubated (2 h, r.t.) with gentle rotation. Avidin beads were washed before five times with 700 µL PBS (containing 0.2% SDS). After incubation beads were washed (2×200 µL PBS+0.2% SDS; 3×200 µL 4 M Urea in PBS; 3×200 µL 50 mM TEAB) reconstituted in 50 µL 50 mM TEAB and 2 µL 250 mM DTT were added followed by incubation on a shaker (30 min, 55° C., 600 rpm). Beads were washed with 50 mM TEAB followed by addition of 50 µL TEAB and 2 µL 500 mM iodoacetamide with incubation on a shaker in the dark (30 min, 25° C., 600 rpm). After two more washed with TEAB beads were reconstituted in 50 µL 50 mM TEAB and 2 µL trypsin (0.5 µg/µL in 50 mM acetic acid) and incubated overnight (37° C. and 750 rpm).

Desalt and Dimethyl Label

The beads were centrifuged, the supernatant transferred in a new low-bind tube and digestion was stopped by addition of 0.7 µL formic acid (FA). Beads were washed two more times with 50 µL 0.1% FA in 50 mM TEAB and supernatants were combined.

Desalting of the samples was conducted on 50 mg SepPak C18 columns (Waters). Columns were equilibrated with 1 mL acetonitrile (ACN), 1 mL elution buffer (80% ACN, 0.5% FA) and 3 mL aqueous 0.5% FA solution. The acidified samples were loaded by gravity flow, washed five times with 1 mL 0.5% FA and then labeled with five times 1 mL of the respective dimethyl labeling agents (light (L): 30 mM $NaBH_3CN$, 0.2% $CH_2O$, 45 mM sodium phosphate buffer, pH 7.5; medium (M): 30 mM $NaBH_3CN$, 0.2% $CD_2O$, 45 mM sodium phosphate buffer, pH 7.5; heavy (H): 30 mM $NaBD_3CN$, 0.2% $^{13}CD_2O$, 45 mM sodium phosphate buffer, pH 7.5). Column bound peptides were washed two more times with 1 mL 0.5% FA and then eluted with two times 250 µL elution buffer. 900 µL of each sample were combined in a 15 mL tube, frozen in liquid nitrogen and lyophilized. Prior to LC-MS/MS measurement samples were dissolved in 40 µL 1% FA and filtered with 0.22 µm ultrafree centrifugal filters (Merck) equilibrated with 300 µL 1% FA. The filtrate was transferred into MS vials and queued for LC-MS/MS measurement.

LC/MS Data Analysis

44 µL of each sample were injected into the LC-MS/MS system. Samples were analyzed via HPLC-MS/MS using an UltiMate 3000 nano HPLC system (Dionex, Sunnyvale, Calif., USA) equipped with an Acclaim C18 PepMap100 75 µm ID×2 cm trap and an Acclaim Pepmap RSLC C18 separation column (75 µm ID×50 cm) in an EASY-spray setting coupled to a Thermo Fischer LTQ Orbitrap Fusion (Thermo Fisher Scientific Inc., Waltham, Mass., USA). Samples were loaded on the trap and washed with 0.1% TFA (at 5 µL/min), then transferred to the analytical column and separated using a non-linear 115 min gradient from 5% A to 32% B, then in 10 min to 90% B followed by another 10 min at 90% B (at 300 nL/min flow rate) (buffer A: $H_2O$ with 0.1% FA, buffer B: MeCN with 0.1% FA). LTQ Orbitrap Fusion was operated in a 3 second top speed data dependent mode. Full scan acquisition was performed in the orbitrap at a resolution of 120000 and an AGC target of 2e5 in a scan range of 300-1500 m/z. Monoisotopic precursor selection as well as dynamic exclusion for 60 s were enabled. Precursors with charge states of 2-7 and intensities greater than 5e3 were selected for fragmentation. Isolation was performed in the quadrupole using a window of 1.6 m/z. Precursors were collected to an AGC target of 1e4 for a maximum injection time of 50 ms with "inject ions for all available parallelizable time" enabled. Fragments were generated using higher-energy collisional dissociation (HCD, normalized collision energy: 30%) and detected in the ion trap at a rapid scan rate. Internal calibration was performed using the ion signal of fluoranthene cations (EASY-IC).

Raw files were analyzed using MaxQuant software (version 1.5.3.8) with the Andromeda search engine. The search included carbamidomethylation of cysteines as a fixed modification and oxidation of methionines and acetylation of protein N-termini as variable modifications. Light, medium and heavy labels (of lys and N-term) was set according to the samples, number of max. labeled AAs was set to 4. Trypsin wa specified as the proteolytic enzyme with N-terminal cleavage to proline and two missed cleavages allowed. Precursor mass tolerance was set to 4.5 ppm (main search) and fragment mass tolerance to 0.5 Da. Searches were performed against the Uniprot database for either *Pseudomonas aeruginosa* PAO1 (taxon identifier: 208964, including isoforms), *Pseudomonas aeruginosa* PA14 (taxon identifier: 208963, including isoforms) or *Pseudomonas putida* KT2440 (taxon identifier: 160488, including isoforms). The second peptide identification option was enabled. False discovery rate determination was carried out using a decoy database and thresholds were set to 1% FDR both at peptide-spectrum match and at protein levels. "I=L", "requantification" and "match between runs" (0.7 min match and 20 min alignment time windows) options were enabled.

Statistical analysis was performed with Perseus software (version 1.5.2.6). Putative contaminants, reverse sequences and only identified by site hits were filtered out. Ratios were logarithmized ($log_2$) and z-score normalized (within one replicate). Statistical evaluation was performed using "One-sample t-test" (both-sided; Benjamini-Hochberg FDR 0.05).

Computational Molecular Docking

Low-energy conformations of promysalin were built using OMEGA (Hawkins and Nicholls, 2012, J. Chem. Inf. Model 52:2919-2936), yielding 3,759 "conformers". Crystal structures of the *E. coli* Sdh complex bound to four different known ligands that engage the ubiquinone-binding site were aligned using ROCS (Hawkins and Skillman, 2007, 50:74-82), to a homology model of *P. aeruginosa* Sdh. Each of the promysalin conformers were aligned to each ligand using its position in the Sdh complex: this gave 15,036 crude models. Each of these models was refined by fullatom energy minimization in the Rosetta software (Leaver-Fay et al., 2011, 487:545-574), and ranked on the basis of protein-ligand interaction energy. The top-scoring 100 models were visually inspected to determine which were consistent with observations from SAR, as described above.

Homology Model of apo-SdhC

A model of the *P. aeruginosa* PAO1 Sdh complex was built using SWISS-MODEL (Arnold et al., Bioinformatics 2006, 22, 195) with the *E. coli* structure PDB ID 2ACZ$^2$ serving as the template.

Building Promysalin Conformer Library

To sample a wide range of promysalin conformers, the following promysalin SMILES string was used as an input to generate energetically favorable conformers in OMEGA (Hawkins et al., Journal of Chemical Information and Modeling 2010, 50, 572):
O=C(N1[C@H](C(O[C@H](CCCCCC)CCCCC[C@@H](O)C(N)=O)=O)CC=C1)C2=CC=CC=C2O.

Generating Bound Poses

The following command line was used, resulting in 3,759 conformers that passed the standard OMEGA scoring cutoff:
omega2-in input_file.smi-out output_file.sdf.gz-prefix ligand_name-warts-maxconfs 4000.

The generation of models promysalin bound to *P. aeruginosa* PAO1 Sdh, began with the structures of known ligands bound to *E. coli* Sdh. Four ligands were used in our study: ubiquinone, 2-[1-methylhexyl]-4,6-dinitrophenol, carboxin and carboxanilid; these correspond to PDB IDs 1NEK, 1NEN, 2WDQ and 2WU5, respectively (Ruprecht, et al., J. Biol. Chem. 2009, 284, 29836; Yankovskaya, et al., Science. 2003, 299, 700). In each case the PDB structure to was aligned to the homology model of *P. aeruginosa* PAO1 Sdh, then the protein components were removed: this operation transferred the known ligand into the appropriate location and orientation relative to the model.

Each of the 3,759 promysalin conformers was then aligned to the three-dimensional structures each known ligand using the following command in the ROCS program (Hawkins, et al., *J. Med. Chem.* 2007, 50, 74):
rocs-dbase promysalin_conformers.sdf.gz-query extracted_ligand.pdb-prefix structure_name-cutoff-1.0-oformat sdf-scdbase true-maxhits 4000-maxconfs 4000-outputquery false For the 4 known ligands, this approach yielded a total of 15,036 overlays. Because the known ligands had been pre-aligned with respect to our *P. aeruginosa* PAO1 homology model, these corresponded to crude models of the desired complex.

To refine these models, a gradient-based full atom minimization of each model was performed using the Rosetta energy function (Leaver-Fay, et al., Methods Enzymol. 2011, 487, 545). All native cofactors found in the *E. coli* crystal structure were included in these energy minimizations. After minimization, the 15,036 models were re-ranked on the basis of their protein-ligand interaction energy in Rosetta. The top-scoring 100 models were visually inspected to determine which were consistent with observations from SAR, as described below.

Zone of Inhibition

100 µL overnight culture was added to TSB or M9 agar plates and bacterial lawns were 'created' using Roll & Grow Plating Beads. Compound stock solution 20 µL of a 250 µM solution, 10 µL of a 10 mg/mL gentamicin solution, and 20 µL of a 250 µM DMSO control (stock=10% DMSO/H$_2$O) was absorbed into discs and allowed to dry. Discs were placed on the plates and incubated at 37° C. for 24 hours. Assay was run in triplicate from separate overnight cultures.

The results of the experiments are now described.

The Inhibitory Activity of Promysalin was not Affected by Iron Concentration

Previous reports have demonstrated that the inhibitory activity of sideromycins is correlated to iron-concentration as they rely on a chelation strategy to penetrate bacterial cells (Braun et al., 2009, Biometals 22:2-13). In an elegant display of chemical creativity, the Miller group used these molecules as inspiration and developed a second-generation of synthetic sideromycins, whereby established antibiotics were covalently tethered to known siderophores effectively creating a "Trojan Horse" strategy that was remarkably successful (Gorska et al., 2014, Trends Pharmacol. Sci. 35:442-449; Wencewicz and Miller, 2013, J. Med. Chem. 56:4044-4052; De Carvalho, 2016, Front. Microbiol. 7:470). This approach is best exemplified by BAL30072, a novel siderophore-sulfactam conjugate that entered Phase 1 clinical trials (Butler et al., 2017, J. Antibiot. 70:3-24). Similarly, these molecules also rely on iron-concentration and their activity can be enhanced by either the introduction of strong iron-chelators or prior removal of iron to the media. BT The bioactivity of promysalin against PAO1 and PA14 was probed over a range of iron concentrations. Under iron-limited conditions, it was expected transcriptional up-regulation of iron transport systems would facilitate the diffusion of promysalin into the cell and consequently increase its potency akin to sideromycins. However, the studies revealed that there was no identifiable effect of the available iron on efficacy as indicated by IC$_{50}$ values. Although not wishing to be bound by any particular theory, these results suggest that iron chelation is coincidental and separate from antibiotic activity.

Figure 117:
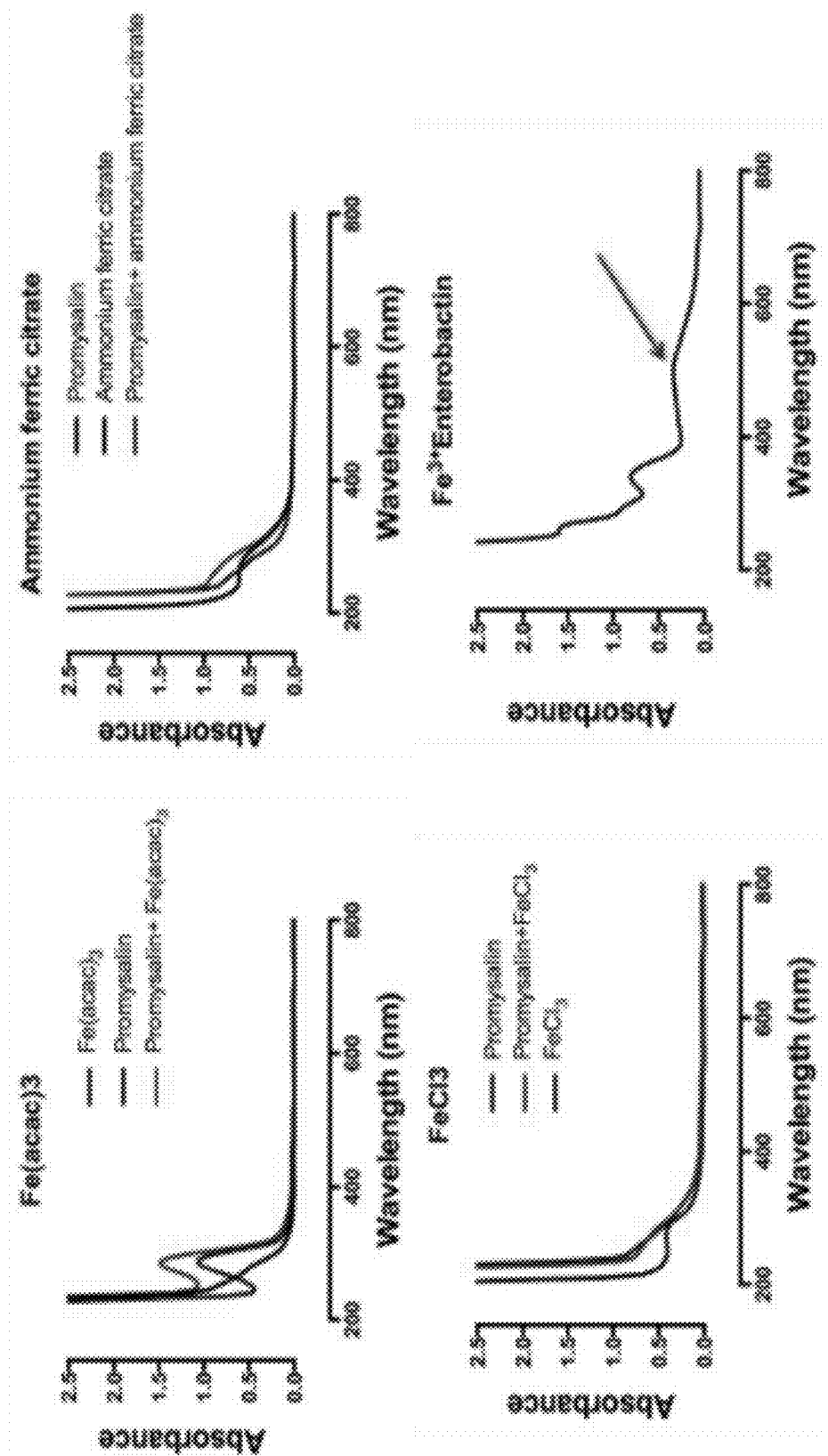
FIG. 117 depicts a series of graphs of experimental data demonstrating the UV-visible spectrum of different promysalin and iron solutions. Different Iron (III) solutions (Tris(acetylacetonato)iron(III), ammonium ferric (III) citrate, Iron (III) Chloride) were added to a 65 µM solution of Promysalin (200 mM NaP pH 8) (ration 2:1 and 1:1). No change in UV-visible spectra was observed. Chelation of iron (III) by siderophore is usually characterized by a broad peak between 400 and 600 nm (see control with $Fe^{3+}$-Enterobactin with similar concentration, Arrows)
Figure 118:
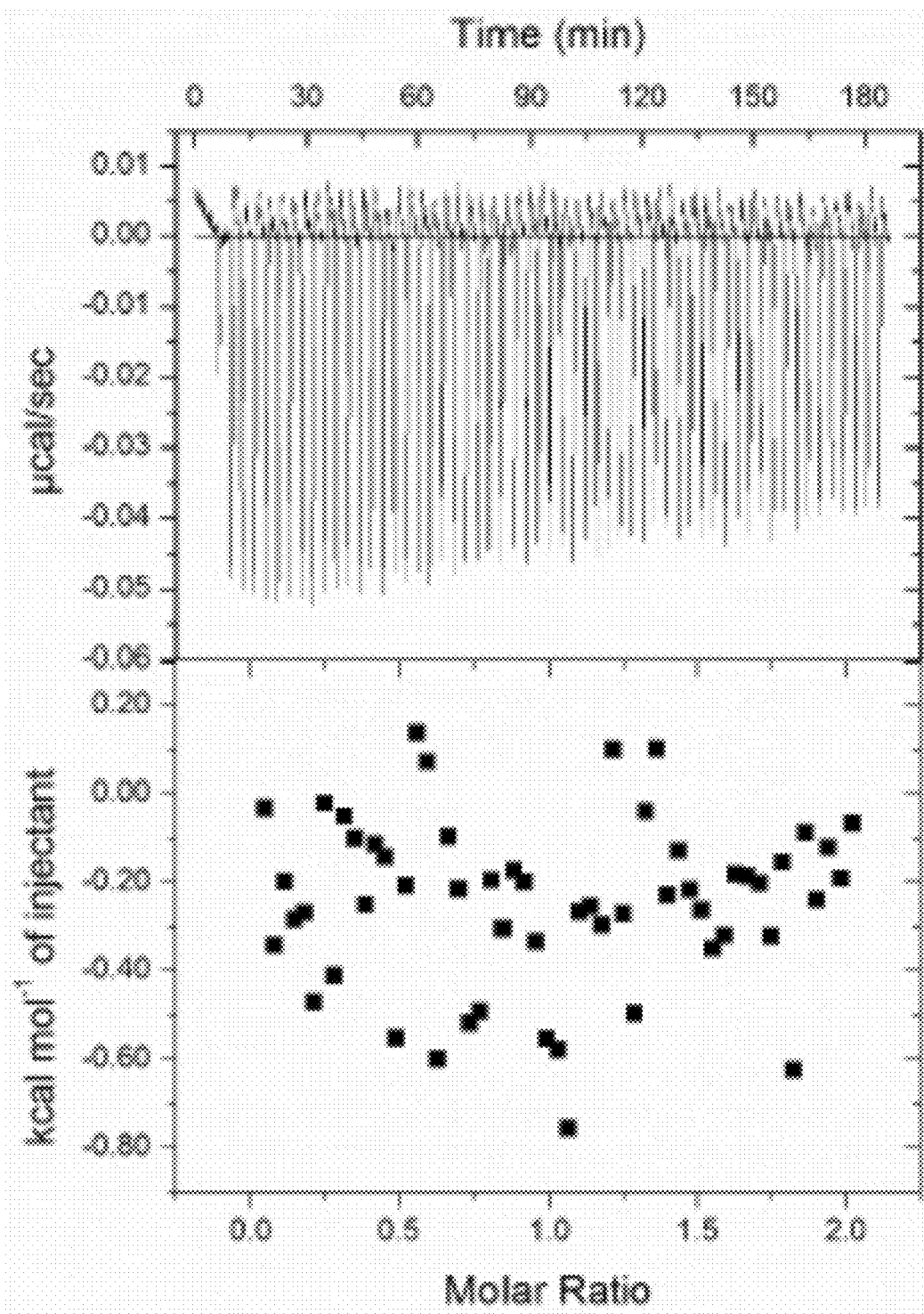
FIG. 118 depicts experimental data of isothermal calorimetry titration of Promysalin with PaPiuA. The top panel depicts raw titration data; the bottom panel depicts the isotherm after subtraction of the heats of dilution.

Previous work investigating the mechanism of action of BAL30072 identified the iron receptor PiuA as the active transporter responsible for the uptake of the molecule into PA (Delden et al., 2013, Antimicrob. Agents Chemother. 57:2095-2012). PiuA is a member of the TonB dependent transporter (TBT) family, which are membrane-bound proteins responsible for the active transport of siderophores by means of the proton motive force (Moynié, et al., Antimicrob. Agents Chemother. doi:10.1128/AAC.02531-16). Transcription of such systems is up-regulated in response to stress (Noinaj et al., 2010, Annu. Rev. Microbiol. 64:43-60) and conversely down-regulated when an equilibrium is met, as excess iron is toxic. Previous findings have shown that TBTs regulate pyoverdine production and also vary widely between *Pseudomonads*. Initially, the ability of promysalin to form an Fe$^{3+}$-bound complex with a variety of iron sources (Fe(acac)$_3$, (NH$_4$)$_5$[Fe(C$_6$H$_4$O$_7$)$_2$], and FeCl$_3$) was investigated by UV-Visible spectroscopy. In all instances, the characteristic Fe$^{3+}$-siderophore complex at ~500 nM seen in other systems like enterobactin was not observed (FIG. 117). Recently, the crystal structure of PiuA was solved and revealed the putative binding site of BAL30072 (Moynie, et al., Antimicrob. Agents Chemother. doi: 10.1128/AAC.02531-16). To further confirm that promysalin was not interacting via the PiuA system, isothermal microcalorimetry titration experiments were used to determine the extent at which the natural product binds. However, these studies showed no appreciable interaction (FIG. 118). Taken in sum, these findings demonstrate that although promysalin is capable of binding iron, it does not appear to be acting as a viable siderophore and/or using siderophore transport channels to elicit its response.

Activity-Based Protein Profiling Identifies the C-Subunit of Succinate Dehydrogenase as the Biological Target of Promysalin In view of the data demonstrating that promysalin does not appear to be acting as a viable siderophore and/or using siderophore transport channels to elicit its response, activity-based protein profiling (ABPP) was implemented to identify likely candidates. It was initially unclear if promysalin covalently modified its target; therefore a photoaffinity probe was installed to ensure capture of the biological moiety. The Yao group previously developed a concise route to a stand-alone diazirine photoprobe flanked on one end with an alkyne for ABPP and a primary amine on the other primed for amidation chemistry (Li et al., 2013, Angew. Chem. Int. Ed. 52:8551-8556). Initially, installing the diazirine photoprobe to the side chain hydroxyl group was envisioned, as that position was reactive based on the protecting group scheme from previous total synthesis; however, previous analog studies discouraged this modification (Steele et al., 2016, J. Am. Chem. Soc. 138:5833-5836). Instead, efforts were focused on the alkylation of the amide nitrogen, which can be easily accessed from earlier routes. For preliminary screening, a propargyl moiety was appended to the amide nitrogen (FIG. 120), which was only three-fold less active than the natural product (218 nM vs. 63 nM in PA14), thus permitting the strategy to synthesize the amide probe (full synthetic details are provided in the supporting information). Activity of the probe was confirmed, with an $IC_{50}$ value of 1.7 μM (in PA14), supporting its use for proteomic studies.

Figure 114:
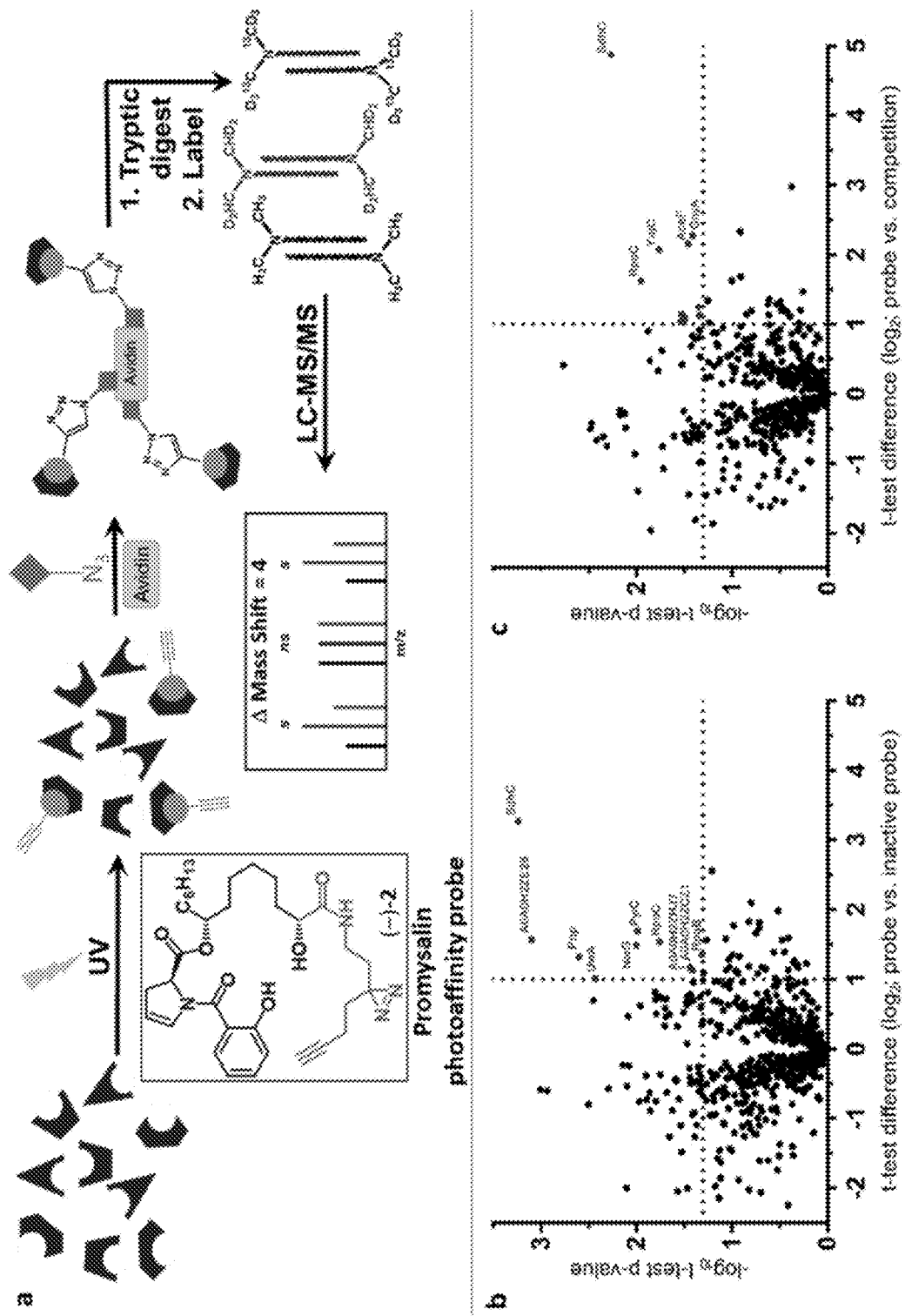
FIG. 114, comprising

With the probe in hand, ABPP was examined to elucidate the protein targets of promysalin. For each experiment, three different sample types were prepared for gel-free in situ proteomic analysis (FIG. 114A). Cultures of P. aeruginosa PAO1 and PA14 were grown to log phase and incubated with either 1) promysalin photoprobe, (−)-2, 2) inactive promysalin photoprobe, (−)-S12, or 3) promysalin (−)-1 followed by promysalin photoprobe (−)-2 (competitive inhibitor). After UV irradiation, cells were lysed, reacted in situ with biotin-azide, and enriched on avidin beads. Enriched proteins were subjected to a trypsin-digest and labeled with light, medium or heavy isotopes via dimethyl-isotope labeling (Boersema et al., 2009, Nat. Protoc. 4:484-494). Isotope labels were switched throughout biological replicates and samples with corresponding labels were pooled prior to LC-MS/MS measurement. Statistical analysis revealed only a small number of significantly (p-value≤0.05; $\log_2$-ratio≥1) enriched proteins (FIGS. 114A, 114B, and 119). The most prominent hit in both PA strains (PAO1 and PA14) as visualized by the volcano plot in FIG. 114 was the succinate dehydrogenase C-subunit (SdhC); furthermore, the enrichment could be outcompeted by promysalin thereby providing preliminary validation of SdhC as the biological target.

Computational Molecular Docking Supports SdhC as the Target of Promysalin

With consistent proteomic data in hand, the findings were validated by identifying a putative binding site with computational modeling. Because the Pseudomonas protein has not yet been crystallized, co-crystallizing promysalin with Sdh; was not performed. The homologous enzyme in E. coli has been structurally characterized (Yankovskaya et al., 2003, Science 5607:700-704), and thus this served as a starting point for modeling the Pseudomonas enzyme. Previous studies have also identified several small molecules that inhibit E. coli Sdh at the ubiquinone-binding site (FIG. 115A), and based on shared structural features of these compounds it was hypothesized that promysalin would bind at the analogous site (FIG. 115B) (Sierotzki and Scalliet, 2013, Phytopath. 103:880-887).

Each of these known inhibitors was aligned onto the Pseudomonas enzyme, and then these compounds were used as the basis for pharmacophoric matching using a broad range of possible promysalin three-dimensional conformations. Upon energy minimization, these yielded many bound poses with comparable predicted energetics; thus, leveraging existing SAR data to narrow down the possible models (Steele et al., 2016, J. Am. Chem. Soc. 138:5833-5836).

Figure 115:
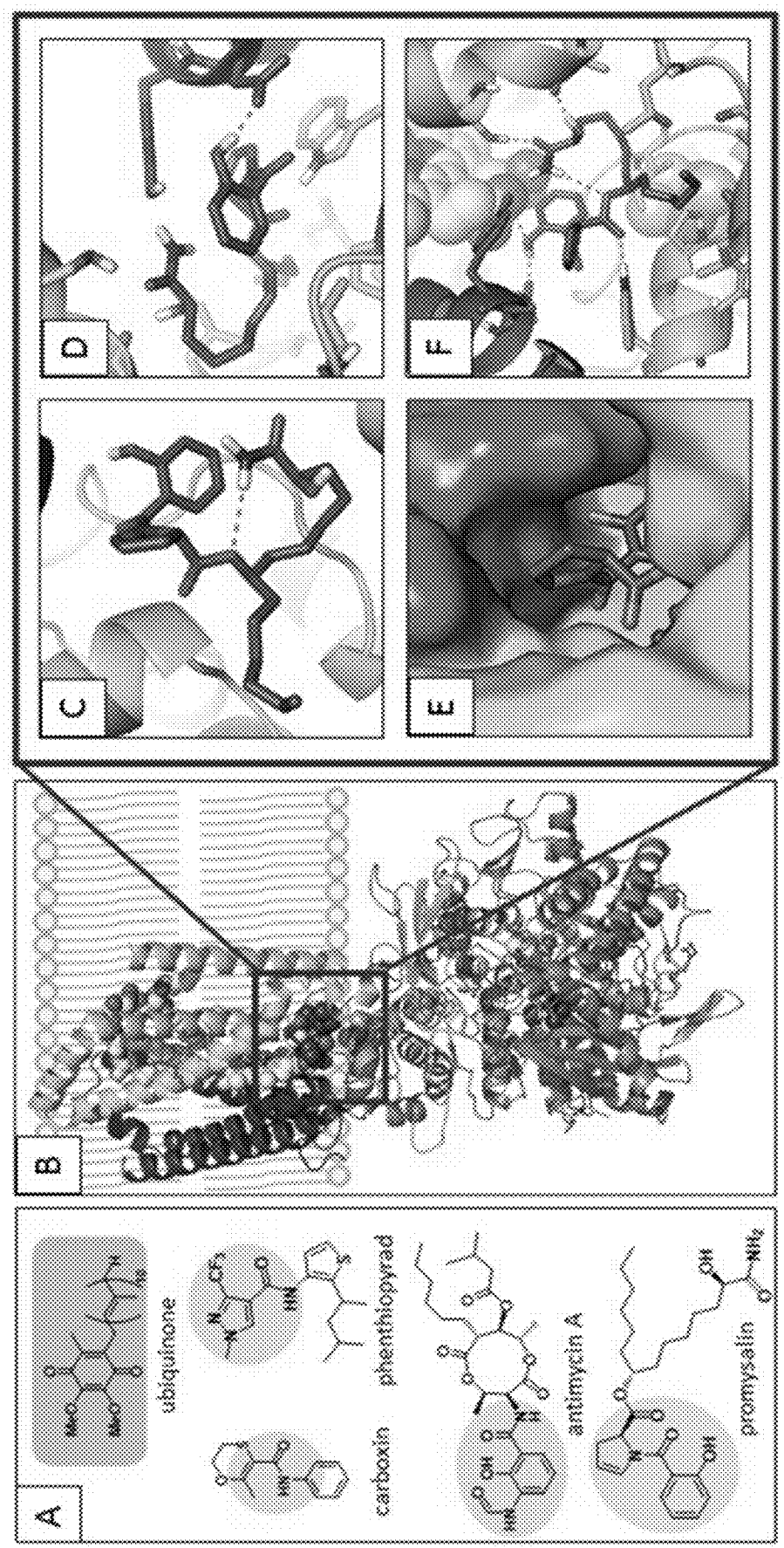
FIG. 115, comprising

It was found that the SAR was fully consistent with only one of these very diverse models. Although not wishing to be bound by any particular theory, this result suggests the stringency of the constraints that arise from this thorough SAR characterization and provides confidence in the final model. There are three key observations that led to the rejection of all possible models but this one. First, it was previously reported that the replacement of the ester linker with an amide abolished activity: in the docked model the ester adopts a conformation where the oxygen is engaged in intramolecular hydrogen bonding, whereas an amide substitution here would abolish this favorable interaction (FIG. 115C). Second, replacing the salicylate hydroxyl group with a methoxy group greatly reduced activity: in the docked model this hydroxyl group engages in hydrogen bonding with a nearby aspartate; alkylating the oxygen would render this interaction impossible (FIG. 115D). Finally, adding a methyl group to the dehydroproline heterocycle resulted in a compound with moderate activity; in the docked model this position points outward from the binding pocket. Although not wishing to be bound by any particular theory, this result suggests that incorporation of an extra substituent is tolerated (FIG. 115E).

This model is additionally consistent with information that was not part of the SAR used in its selection (FIG. 115F). The model includes a hydrogen bond between a backbone carbonyl of SdhC and the alcohol side chain on the myristate region: the modeled position and orientation of the side chain alcohol explains why its stereochemistry was important for activity (changing this stereochemistry would lead to a steric clash), and yet its removal was also tolerated. Separately, it was noted that promysalin must bind in a manner that can accommodate the diazirine photoprobe with only minimal effects on bioactivity (~10× less active): the terminal amide in this model engages in two hydrogen bonds with the enzyme, and still would allow the alkyne moiety of the photoprobe to project toward the hydrophobic groove occupied by the fatty acid side chain.

Another key consequence of this model relates to the strain-specific activity of promysalin. The sequences for each Sdh subunit for PAO1, PA14, and KT2440 were mapped back onto this model of binding: notably, there was not a single sequence difference among the three at this site. Although not wishing to be bound by any particular theory, this result suggests that the model implies that the observed differential activity is not based on binding preferences of promysalin for Sdh, but rather upon some other factor that distinguishes these strains.

Promysalin Leverages Differences in the Metabolic Flux of the TCA Cycle to Elicit Species-Specificity The Tricarboxylic Acid (TCA) cycle is an essential pathway in primary metabolism and facilitates the release of stored energy through a series of eight reactions (Akram, 2014, Cell Biochem. Biophys. 68:475-478). Succinate dehydrogenase is an enzyme within the TCA cycle and the electron transport chain (housed in membrane) (Hederstedt and Rutberg, 1981, Mictobiol. Rev. 45:542-555). Its specific function within the process is to catalyze the oxidation of succinate to fumarate with simultaneous reduction of the cofactor ubiquinone ($CoQ_{10}$) to ubiquinol. Under stress, however, the glyoxylate shunt pathway, consisting of four of the eight steps in the TCA, circumvents the other four steps for specific metabolic uses (Kornberg, 1966, J. Biochem. 99:1-11). In the glyoxylate pathway, isocitrate is converted to glyoxylate and sequentially converted to malate, thereby bypassing several transformations including the oxidation of succinate. Alternatively, isocitrate can also be directly converted to succinate. However, in this pathway, the succinate produced is often released for energy production and biosynthesis meaning metabolism and subsequent cellular function can persist without succinate dehydrogenase.

Figure 116:
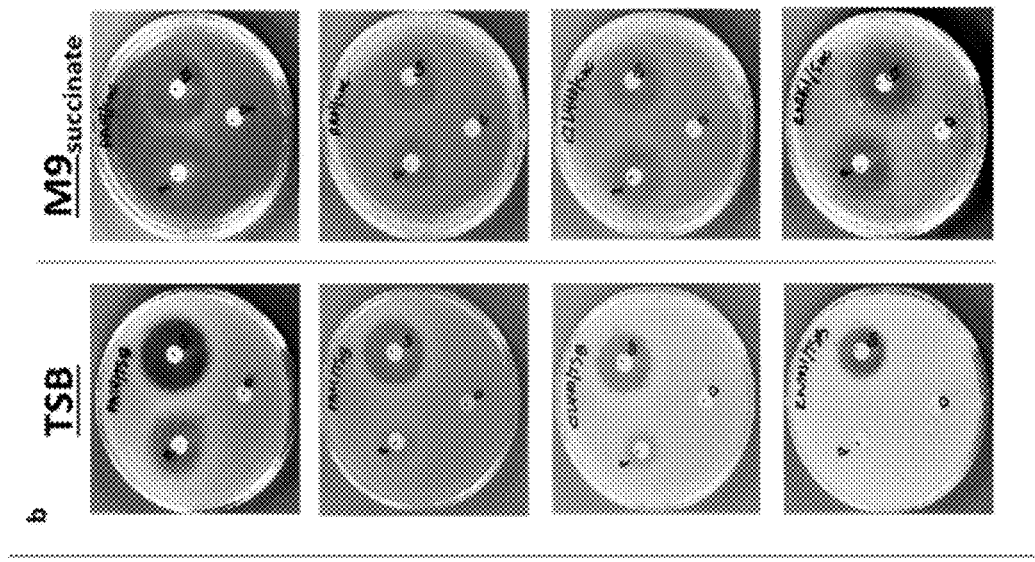
FIG. 116, comprising
Figure 116:
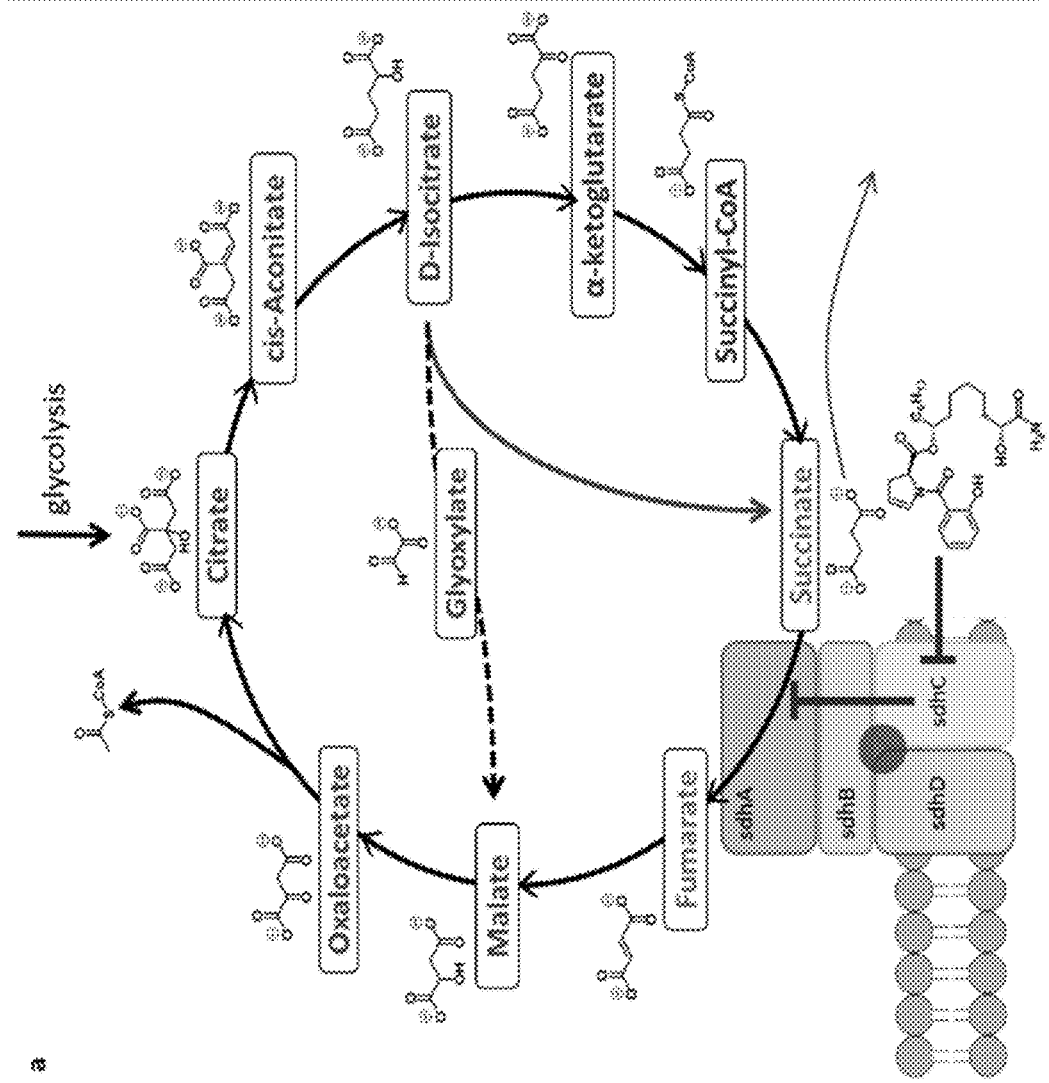

Based on this understanding of the TCA cycle, it was hypothesized that the proteomic findings could be validated with various microbiological growth assays. Toward this end, it was first attempted, albeit unsuccessfully, to rescue growth of *P. aeruginosa* through media supplementation of fumarate. Although not wishing to be bound by any particular theory, it was hypothesized that the method was unsuccessful due to the dual modality of Sdh, as this enzyme not only converts succinate to fumarate but also facilitates electron transport. Although the supplementation assay would rescue the former deficiency, it would not address the latter. It was next hypothesized that through purposefully selected feeding studies, any inherent species-specific preferences in primary metabolism could potentially be overrided and further confirm Sdh as the target. To begin, each strain was grown in both TSB and M9 media supplemented with either succinate or glucose, and optionally iron. Promysalin was found to be active only against *P. aeruginosa* and not *P. putida* in TSB and glucose+Fe media. Although not wishing to be bound by any particular theory, these results suggest that these carbon sources allowed the bacteria to utilize either the full TCA cycle or the shunt pathway in a fully aerobic process. In the initial isolation paper, it was observed that the natural product was produced in iron rich environments. Further, no transporter or resistance genes were reported; however, the gene cluster encoding the biosynthesis of the natural product is found immediately adjacent to the TCA genes (Li et al., 2011, Chem. Biol. 18:1320-1330. Based on this information, it was postulated that the natural product could inhibit the growth of PP if grown solely on succinate with iron-limiting conditions. As can be seen in FIG. 116B, a clear zone of inhibition is present in both PP strains (gentamicin shown as a control), including the producing organism. These results demonstrate that promysalin is capable of inhibiting the growth of PP in presumably non-environmental circumstances. Taken in sum, these results further validate the proteomic data and provide a rationale toward the selective nature of the natural product.

The results described herein demonstrate a multidisciplinary approach to identify the target of the *Pseudomonad* secondary metabolite promysalin. Based on the narrow-spectrum activity of the natural product, it was initially hypothesized to either identify a target unique to PA or a transporter specific to the natural product. Instead, a succinate dehydrogenase, an enzyme involved in primary metabolism, was uncovered as the biological target, and computational modeling and microbiological assays further validated these findings. Previous studies have shown that other rhizosphere natural products, like siccanin, a fungal natural product, also targets Sdh. This small molecule was "rediscovered" through an initial screen for PA membrane inhibitors but was later shown to be species-selective preferentially targeting PA, but not *E. coli* or *Corynebacterium glutamicum* (Mogi et al., 2009, J. Biochem. 146:383-387). When considering promysalin and siccanin, recent studies investigating the effect of growth conditions on essential functions of PA confirm SdhABCD as essential, regardless of growth media. These findings complement the siccanin data, as SdhABCD has been found to not be essential in corresponding *E. coli* investigations (Lee et al., 2015, Proc. Natl. Acad. Sci. 112:5189-5194). Although not wishing to be bound by any particular theory, this difference in activity may be understood via the duality of roles that Sdh serves both in metabolism via the TCA cycle and in respiration through the electron transport chain. While PA is able, under specific conditions, to grow and survive via fermentation, respiration is almost solely responsible for ATP production; consequently, unless in the proper environment, PA requires the electron transport chain to generate ATP and survive (Lee et al., 2015, Proc. Natl. Acad. Sci. 112:5189-5194; Wu et al., 2005, J. Bacteriol. 187:8185-8190). This facultative anaerobic behavior is a critical difference between PA and PP as PP possesses a highly versatile aerobic metabolism. Furthermore, recent work has demonstrated that metabolic flux in PA greatly varies between growth conditions (i.e. carbon sources), and that by targeting specific enzymes within the TCA cycle, one can potentiate antibiotic activity. Although not wishing to be bound by any particular theory, these findings may help to explain the differential activity between PAO1 and PA14 (Meylan et al., 2017, Cell Chem. Biol. 24:195-206). In a separate study looking at systems-level metabolic pathways, it has been postulated that PP may be able to interchangeably utilize the glyoxylate shunt pathway in lieu of the TCA cycle without sacrificing overall growth (Fahnoe et al., 2012, PLOS one 7: e51732).

The results described herein have identified the target of a species-selective antibiotic via proteomic studies. The success of these studies hinged on our previous analog findings thereby allowing for the chemical synthesis of a diazirine photoprobe retaining activity. Succinate dehydrogenase was identified using ABPP and was further validated with computational molecular docking as well as growth assays. Notably, the docking studies were able to not only validate the identified target but also rationalize previous SAR findings. Furthermore, it was show that under specific media conditions, promysalin is capable of inhibiting growth of its producing strain. These findings add to the emerging discoveries focusing on the targeting of the TCA cycle both to potentiate existing antibiotics and also develop narrow-spectrum therapies, which may be useful both in drug discovery and in deconvoluting multispecies microbiomes.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A compound of formula I, or a salt thereof:

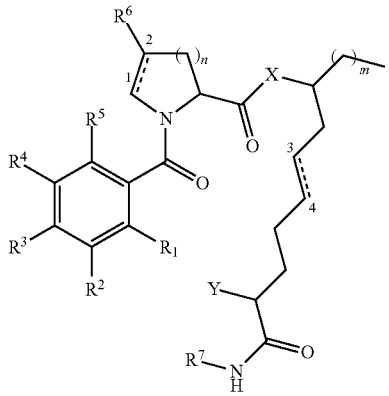

wherein in formula I:
- $R^1$, $R^2$, $R^3$, $R^4$, and $R^5$ are each independently selected from the group consisting of H, —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, —$OR^7$, —$SR^7$, —$S(=O)R^7$, —$S(=O)_2R^7$, —$NHS(=O)_2R^7$, —$C(=O)R^7$, —$OC(=O)R^7$, —$CO_2R^7$, —$OCO_2R^7$, —$CH(R^7)_2$, —$N(R^7)_2$, —$C(=O)N(R^7)_2$, —$OC(=O)N(R^7)_2$, —$NHC(=O)NH(R^7)$, —$NHC(=O)R^7$, —$NHC(=O)OR^7$, —$C(OH)(R^7)_2$, and —$C(NH_2)(R^7)_2$, wherein the alkyl, aryl, heteroaryl, cycloalkyl, heterocycloalkyl, and $C_1$-$C_6$ heteroalkyl group is optionally substituted;
- $R^6$ is selected from the group consisting of —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, —$OR^7$, —$SR^7$, —$S(=O)R^7$, —$S(=O)_2R^7$, —$NHS(=O)_2R^7$, —$C(=O)R^7$, —$OC(=O)R^7$, —$CO_2R^7$, —$OCO_2R^7$, —$CH(R^7)_2$, —$N(R^7)_2$, —$C(=O)N(R^7)_2$, —$OC(=O)N(R^7)_2$, —$NHC(=O)NH(R^7)$, —$NHC(=O)R^7$, —$NHC(=O)OR^7$, —$C(OH)(R^7)_2$, and —$C(NH_2)(R^7)_2$, wherein the alkyl, aryl, heteroaryl, cycloalkyl, heterocycloalkyl, and $C_1$-$C_6$ heteroalkyl group is optionally substituted;
- each occurrence of $R^7$ is independently selected from the group consisting of H and —$C_1$-$C_6$ alkyl, wherein the alkyl group is optionally substituted;
- the bond between carbons 1 and 2 and the bond between carbons 3 and 4 each independently represents a single or double bond;
- X is O or $NR^7$;
- Y is selected from the group consisting of H, $OR^7$, halogen, and —$NHR^7$;
- n is 1 or 2; and
- m is an integer from 0 to 8;
with the proviso that the compound of formula I is not:

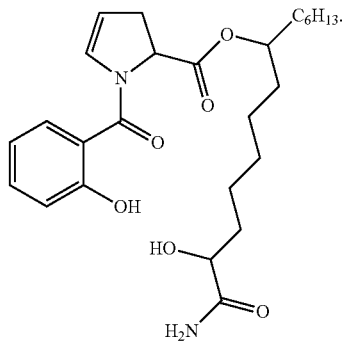

2. The compound of claim 1, wherein the compound of formula I is a compound of formula II, or a salt thereof:

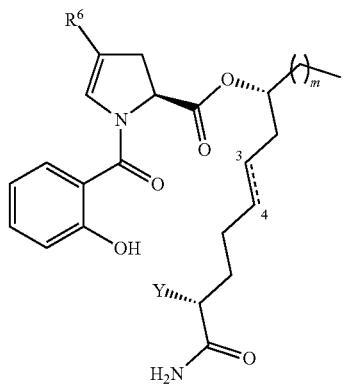

wherein in formula II:
- $R^6$ is selected from the group consisting of —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, —$OR^1$, —$SR^7$, —$S(=O)R^7$, —$S(=O)_2R^7$, —$NHS(=O)_2R^7$, —$C(=O)R^7$, —$OC(=O)R^7$, —$CO_2R^7$, —$OCO_2R^7$, —$CH(R^7)_2$, —$N(R^7)_2$, —$C(=O)N(R^7)_2$, —$OC(=O)N(R^7)_2$, —$NHC(=O)NH(R^7)$, —$NHC(=O)R^7$, —$NHC(=O)OR^7$, —$C(OH)(R^7)_2$, and —$C(NH_2)(R^7)_2$, wherein the alkyl, aryl, heteroaryl, cycloalkyl, heterocycloalkyl, and $C_1$-$C_6$ heteroalkyl group is optionally substituted;
- each occurrence of $R^7$ is independently selected from the group consisting of H and —$C_1$-$C_6$ alkyl, wherein the alkyl group is optionally substituted;
- the bond between carbons 3 and 4 represents a single or double bond;
- Y is H or $OR^7$; and
- m is an integer from 4 to 6;
with the proviso that the compound of formula II is not:

143

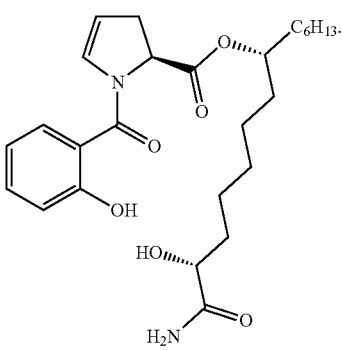

3. The compound of claim 1, wherein $R^6$ is F.

4. The compound of claim 1, wherein the bond between carbons 3 and 4 represents a single bond.

5. The compound of claim 1, wherein the bond between carbons 3 and 4 represents a double bond.

6. The compound of claim 1, wherein X is O.

7. The compound of claim 1, wherein Y is H.

8. The compound of claim 1, wherein Y is $OR^7$.

9. The compound of claim 1, wherein n is 1.

10. The compound of claim 1, wherein n is 2.

11. The compound of claim 1, wherein m is 5.

12. A compound selected from the group consisting of (1R,7R)-1-carbamoyl-1-hydroxytridecan-7-yl (2S)-1-(2-hydroxybenzoyl)piperidine-2-carboxylate, (1R,7R)-1-carbamoyl-1-hydroxytridecan-7-yl (2S,4R)-4-hydroxy-1-(2-hydroxybenzoyl)pyrrolidine-2-carboxylate, (7R,13R)-14-amino-13-hydroxy-14-oxotetradecan-7-yl (S)-4-fluoro-1-(2-hydroxybenzoyl)-2,3-dihydro-1H-pyrrole-2-carboxylate, (7R,13R)-14-amino-13-hydroxy-14-oxotetradecan-7-yl (S)-1-(2-hydroxybenzoyl)-4-methyl-2,3-dihydro-1H-pyrrole-2-carboxylate, (1R,7R)-1-carbamoyl-1-hydroxytridecan-7-yl (2S)-1-(2-methoxybenzoyl)-2,3-dihydro-1H-pyrrole-2-carboxylate, (7R,13R)-14-amino-13-hydroxy-14-oxotetradecan-7-yl (S)-1-(3-hydroxybenzoyl)-2,3-dihydro-1H-pyrrole-2-carboxylate, (1R,7R)-1-carbamoyl-1-hydroxytridecan-7-yl (2S)-1-(4-hydroxybenzoyl)-2,3-dihydro-1H-pyrrole-2-carboxylate, (1R,7R)-1-carbamoyl-1-hydroxytridecan-7-yl (2S)-1-benzoyl-2,3-dihydro-1H-pyrrole-2-carboxylate, (7R,13R)-14-amino-13-hydroxy-14-oxotetradecan-7-yl (S)-1-(2-hydroxy-6-methoxybenzoyl)-2,3-dihydro-1H-pyrrole-2-carboxylate, (1R,7R)-1-carbamoyl-1-hydroxytridecan-7-yl (2S)-1-(3,4,5-trimethoxybenzoyl)-2,3-dihydro-1H-pyrrole-2-carboxylate, (7R,13R)-14-amino-13-hydroxy-14-oxotetradecan-7-yl (S)-1-(2-nitrobenzoyl)-2,3-dihydro-1H-pyrrole-2-carboxylate, (7R,13R)-14-amino-13-methoxy-14-oxotetradecan-7-yl (S)-1-(2-hydroxybenzoyl)-2,3-dihydro-1H-pyrrole-2-carboxylate, (S)—N-((7R,13R)-14-amino-13-hydroxy-14-oxotetradecan-7-yl)-1-(2-hydroxybenzoyl)-2,3-dihydro-1H-pyrrole-2-carboxamide, and (7R,13R,E)-14-amino-13-hydroxy-14-oxotetradec-9-en-7-yl (S)-1-(2-hydroxybenzoyl)-2,3-dihydro-1H-pyrrole-2-carboxylate, or a salt thereof.

13. A pharmaceutical composition comprising a pharmaceutically acceptable carrier and at least one compound of claim 1.

14. A method of preventing or treating a *Psuedomonas* infection in a subject in need thereof, the method comprising administering to the subject an effective amount of a therapeutic composition comprising:

(a) at least one compound of formula I, or a salt thereof:

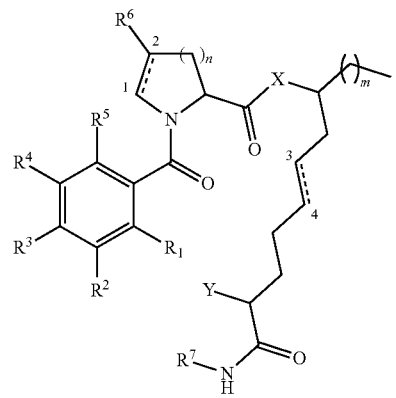

wherein in formula I:

$R^1$, $R^2$, $R^3$, $R^4$, and $R^5$ are each independently selected from the group consisting of H, —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, —$OR^7$, —$SR^7$, —S(=O)$R^7$, —S(=O)$_2$ $R^7$, —NHS(=O)$_2R^7$, —C(=O)$R^7$, —OC(=O)$R^7$, —$CO_2R^7$, —$OCO_2R^7$, —CH($R^7$)$_2$, —N($R^7$)$_2$, —C(=O)N($R^7$)$_2$, —OC(=O)N($R^7$)$_2$, —NHC(=O)NH($R^7$), —NHC(=O)$R^7$, —NHC(=O)$OR^7$, —C(OH)($R^7$)$_2$, and —C($NH_2$)($R^7$)$_2$, wherein the alkyl, aryl, heteroaryl, cycloalkyl, heterocycloalkyl, and $C_1$-$C_6$ heteroalkyl group is optionally substituted;

$R^6$ is selected from the group consisting of —$C_1$-$C_6$ alkyl, —$C_1$-$C_6$ fluoroalkyl, —$C_1$-$C_6$ heteroalkyl, aryl, heteroaryl, cycloalkyl, heterocycloalkyl, F, Cl, Br, I, —CN, —$NO_2$, —OH, —$OR^7$, —S(=O)$R^7$, —S(=O)$_2R^7$, —NHS(=O)$_2R^7$, —C(=O)$R^7$, —OC(=O)$R^7$, —$CO_2R^7$, —$OCO_2R^7$, —CH($R^7$)$_2$, —N($R^7$)$_2$, —C(=O)N($R^7$)$_2$, —OC(=O)N($R^7$)$_2$, —NHC(=O)NH($R^7$), —NHC(=O)$R^7$, —NHC(=O)$OR^7$, —C(OH)($R^7$)$_2$, and —C($NH_2$)($R^7$)$_2$, wherein the alkyl, aryl, heteroaryl, cycloalkyl, heterocycloalkyl, and $C_1$-$C_6$ heteroalkyl group is optionally substituted;

each occurrence of $R^7$ is independently selected from the group consisting of H and —$C_1$-$C_6$ alkyl, wherein the alkyl group is optionally substituted;

the bond between carbons 1 and 2 and the bond between carbons 3 and 4 each independently represents a single or double bond;

X is O or $NR^1$;

Y is selected from the group consisting of H, $OR^7$, halogen, and —$NHR^7$;

n is 1 or 2; and m is an integer from 0 to 8;

with the proviso that the compound of formula I is not:

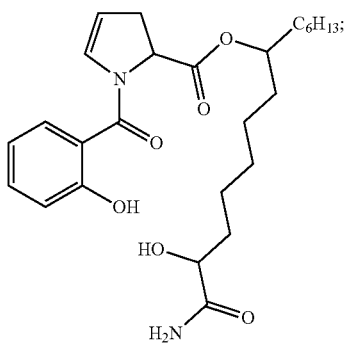

or (b) a compound selected from the group consisting of (1R,7R)-1-carbamoyl-1-hydroxytridecan-7-yl (2S)-1-(2-hydroxybenzoyl)piperidine-2-carboxylate, (1R,7R)-1-carbamoyl-1-hydroxytridecan-7-yl (2S)-1-(2-methoxybenzoyl)-2,3-dihydro-1H-pyrrole-2-carboxylate, (7R,13R)-14-amino-13-hydroxy-14-oxotetradecan-7-yl (S)-1-(3-hydroxybenzoyl)-2,3-dihydro-1H-pyrrole-2-carboxylate, (1R,7R)-1-carbamoyl-1-hydroxytridecan-7-yl (2S)-1-(4-hydroxybenzoyl)-2,3-dihydro-1H-pyrrole-2-carboxylate, (1R,7R)-1-carbamoyl-1-hydroxytridecan-7-yl (2S)-1-benzoyl-2,3-dihydro-1H-pyrrole-2-carboxylate, (7R,13R)-14-amino-13-hydroxy-14-oxotetradecan-7-yl (S)-1-(2-hydroxy-6-methoxybenzoyl)-2,3-dihydro-1H-pyrrole-2-carboxylate, (1R,7R)-1-carbamoyl-1-hydroxytridecan-7-yl (2S)-1-(3,4,5-trimethoxybenzoyl)-2,3-dihydro-1H-pyrrole-2-carboxylate, (7R,13R)-14-amino-13-hydroxy-14-oxotetradecan-7-yl (S)-1-(2-nitrobenzoyl)-2,3-dihydro-1H-pyrrole-2-carboxylate, (7R,13R)-14-amino-13-methoxy-14-oxotetradecan-7-yl (S)-1-(2-hydroxybenzoyl)-2,3-dihydro-1H-pyrrole-2-carboxylate, (S)—N-((7R,13R)-14-amino-13-hydroxy-14-oxotetradecan-7-yl)-1-(2-hydroxybenzoyl)-2,3-dihydro-1H-pyrrole-2-carboxamide, and (7R,13R,E)-14-amino-13-hydroxy-14-oxotetradec-9-en-7-yl (S)-1-(2-hydroxybenzoyl)-2,3-dihydro-1H-pyrrole-2-carboxylate, or a salt thereof.

15. The method of claim 14, wherein the compound is selected from the group consisting of (1R,7R)-1-carbamoyl-1-hydroxytridecan-7-yl (2S)-1-(2-hydroxybenzoyl)piperidine-2-carboxylate, (1R,7R)-1-carbamoyl-1-hydroxytridecan-7-yl (2S,4R)-4-hydroxy-1-(2-hydroxybenzoyl)pyrrolidine-2-carboxylate, (7R,13R)-14-amino-13-hydroxy-14-oxotetradecan-7-yl (S)-4-fluoro-1-(2-hydroxybenzoyl)-2,3-dihydro-1H-pyrrole-2-carboxylate, (7R,13R)-14-amino-13-hydroxy-14-oxotetradecan-7-yl (S)-1-(2-hydroxybenzoyl)-4-methyl-2,3-dihydro-1H-pyrrole-2-carboxylate, (1R,7R)-1-carbamoyl-1-hydroxytridecan-7-yl (2S)-1-(2-methoxybenzoyl)-2,3-dihydro-1H-pyrrole-2-carboxylate, (7R,13R)-14-amino-13-hydroxy-14-oxotetradecan-7-yl (S)-1-(3-hydroxybenzoyl)-2,3-dihydro-1H-pyrrole-2-carboxylate, (1R,7R)-1-carbamoyl-1-hydroxytridecan-7-yl (2S)-1-(4-hydroxybenzoyl)-2,3-dihydro-1H-pyrrole-2-carboxylate, (1R,7R)-1-carbamoyl-1-hydroxytridecan-7-yl (2S)-1-benzoyl-2,3-dihydro-1H-pyrrole-2-carboxylate, (7R,13R)-14-amino-13-hydroxy-14-oxotetradecan-7-yl (S)-1-(2-hydroxy-6-methoxybenzoyl)-2,3-dihydro-1H-pyrrole-2-carboxylate, (1R,7R)-1-carbamoyl-1-hydroxytridecan-7-yl (2S)-1-(3,4,5-trimethoxybenzoyl)-2,3-dihydro-1H-pyrrole-2-carboxylate, (7R,13R)-14-amino-13-hydroxy-14-oxotetradecan-7-yl (S)-1-(2-nitrobenzoyl)-2,3-dihydro-1H-pyrrole-2-carboxylate, (7R,13R)-14-amino-13-methoxy-14-oxotetradecan-7-yl (S)-1-(2-hydroxybenzoyl)-2,3-dihydro-1H-pyrrole-2-carboxylate, (S)—N-((7R,13R)-14-amino-13-hydroxy-14-oxotetradecan-7-yl)-1-(2-hydroxybenzoyl)-2,3-dihydro-1H-pyrrole-2-carboxamide, and (7R,13R,E)-14-amino-13-hydroxy-14-oxotetradec-9-en-7-yl (S)-1-(2-hydroxybenzoyl)-2,3-dihydro-1H-pyrrole-2-carboxylate, or a salt thereof.

16. The method of claim 14, wherein the *Psuedomonas* infection is a *Psuedomonas aeruginosa* (PA) infection.

17. The method of claim 14, wherein the compound is species-specific.

18. The method of claim 14, wherein the compound is administered in combination with an additional therapeutic agent wherein the therapeutic agent is an antibiotic.

19. The method of claim 18, wherein the compound and the therapeutic agent are co-administered and co-formulated to the subject.

20. A pharmaceutical composition comprising a pharmaceutically acceptable carrier and at least one compound of claim 12.

* * * * *

UNITED STATES PATENT AND TRADEMARK OFFICE
CERTIFICATE OF CORRECTION

| | | |
|---|---|---|
| PATENT NO. | : 10,647,671 B2 | |
| APPLICATION NO. | : 16/091685 | |
| DATED | : May 12, 2020 | |
| INVENTOR(S) | : William M. Wuest | |

It is certified that error appears in the above-identified patent and that said Letters Patent is hereby corrected as shown below:

In the Specification

On Column 1, Line 14, please replace the paragraph titled "STATEMENT REGARDING FEDERALLY SPONSORED RESEARCH OR DEVELOPMENT" with the following paragraph:
--STATEMENT REGARDING FEDERALLY SPONSORED RESEARCH
This invention was made with government support under R35 GM119426 awarded by the National Institutes of Health, and 1454116 awarded by the National Science Foundation. The government has certain rights in the invention.--

Signed and Sealed this
Second Day of January, 2024

*Katherine Kelly Vidal*

Katherine Kelly Vidal
*Director of the United States Patent and Trademark Office*